US006187777B1

(12) United States Patent
Norman et al.

(10) Patent No.: US 6,187,777 B1
(45) Date of Patent: Feb. 13, 2001

(54) COMPOUNDS AND METHODS WHICH MODULATE FEEDING BEHAVIOR AND RELATED DISEASES

(75) Inventors: Mark Henry Norman, Thousand Oaks; Clarence R. Hurt, Camarillo; Ning Chen, Thousand Oaks; Christopher H. Fotsch, Thousand Oaks; Nianhe Han, Thousand Oaks; Tracy J. Jenkins, Simi Valley; Longbin Liu, Thousand Oaks; Ofir A. Moreno, Ventura, all of CA (US)

(73) Assignee: Amgen Inc., Thousands Oaks, CA (US)

( * ) Notice: Under 35 U.S.C. 154(b), the term of this patent shall be extended for 0 days.

(21) Appl. No.: 09/246,775

(22) Filed: Feb. 4, 1999

Related U.S. Application Data

(60) Provisional application No. 60/073,927, filed on Feb. 6, 1998, provisional application No. 60/073,981, filed on Feb. 6, 1998, provisional application No. 60/093,482, filed on Jul. 20, 1998, and provisional application No. 60/093,577, filed on Jul. 20, 1998.

(51) Int. Cl.$^7$ ..................... A61K 31/519; C07D 487/02
(52) U.S. Cl. ............................ 514/258; 544/280
(58) Field of Search .............................. 544/280; 514/258

(56) References Cited

U.S. PATENT DOCUMENTS

| 3,661,908 | 5/1972 | Wotkun et al. | 260/256.5 |
|---|---|---|---|
| 3,763,156 | 10/1973 | Wotkun et al. | 260/247.1 |
| 3,838,121 | 9/1974 | Wotkun et al. | 260/247.1 |
| 3,883,651 | 5/1975 | Wotkun et al. | 424/248 |
| 3,888,851 | 6/1975 | Narr et al. | 260/243 |
| 4,731,368 | 3/1988 | Hoffman | 514/351 |
| 4,808,595 | 2/1989 | Hoffman | 514/302 |
| 5,338,849 | 8/1994 | Festal et al. | 546/113 |
| 5,439,923 | 8/1995 | Cullinan | 514/324 |
| 5,441,965 | 8/1995 | Sall et al. | 514/324 |
| 5,504,094 | 4/1996 | Burn et al. | 514/324 |
| 5,508,292 | 4/1996 | Sall et al. | 514/324 |
| 5,644,057 | * 7/1997 | Yuan et al. | 544/280 |
| 5,688,796 | 11/1997 | Cullinan | 514/253 |
| 5,688,812 | 11/1997 | Cullinan | 514/324 |
| 5,688,813 | 11/1997 | Sall et al. | 514/324 |
| 5,693,656 | 12/1997 | Black et al. | 514/324 |

FOREIGN PATENT DOCUMENTS

| 907618 | 8/1972 | (CA) . |
|---|---|---|
| 039051 | 11/1981 | (EP) . |
| 0 682 027 | 4/1995 | (EP) . |
| 0 729 758 | 9/1996 | (EP) . |
| 0 778 277 | 6/1997 | (EP) . |
| 0889034 | 1/1999 | (EP) . |
| 5-27391 | 2/1993 | (JP) . |
| WO 94/13676 | 6/1994 | (WO) . |
| WO 95/10506 | 4/1995 | (WO) . |
| WO 95/33748 | 12/1995 | (WO) . |
| WO 95/33750 | 12/1995 | (WO) . |
| WO 95/34563 | 12/1995 | (WO) . |
| WO 96/12489 | 5/1996 | (WO) . |
| WO 96/12490 | 5/1996 | (WO) . |
| WO 96/14307 | 5/1996 | (WO) . |
| WO 96/35689 | 11/1996 | (WO) . |
| WO 96/40142 | 12/1996 | (WO) . |
| WO 97/20820 | 6/1997 | (WO) . |
| WO 97/20821 | 6/1997 | (WO) . |
| WO 97/20822 | 6/1997 | (WO) . |
| WO 97/20823 | 6/1997 | (WO) . |
| WO 97/25041 | 7/1997 | (WO) . |
| WO 97/29110 | 8/1997 | (WO) . |
| WO 97/49706 | 12/1997 | (WO) . |
| WO 98/05661 | 2/1998 | (WO) . |
| WO 98/06703 | 2/1998 | (WO) . |
| WO 98/07726 | 2/1998 | (WO) . |
| WO 98/08846 | 3/1998 | (WO) . |
| WO 98/08847 | 3/1998 | (WO) . |
| WO 98/35944 | 8/1998 | (WO) . |
| WO 98/35957 | 8/1998 | (WO) . |
| WO 99/07703 | 2/1999 | (WO) . |

OTHER PUBLICATIONS

Akiyama et al., Science 232:1644 (1986) No Title.
Balasubramaniam, A., "Peptides", 18(3), 445 (1997) No Titel.
Berge et al., J. Pharm. Sci. 66:1 (1977) No Titel.
Boger, D. L. et al., M. J. Org. Chem. 1985, 50, 5782–5789 No Titel.
Bungaard, J. Med. Chem., vol. 32, 2503 (1989) No Titel.
Carpenter and Zendegni, J. Anal. Biochem. 153:279–282 (1985) No Titel.
Chaurasia, C., J. Med. Chem., 37, 2242 (1994) No Titel.
Coleman, Diabetologia, 9, 294 (1973) No Titel.
Criscione, et al., Society for Neuroscience, 23, Abstract No. 231.2, (1997) No Titel.
Doughty, M. B. et al., Eur. J. Pharmacol., 185, 113 (1990) No Titel.
Evans et al., Brit. J. Cancer 45:466–8 (1982) No Titel.
Falco et al., J. Am. Chem. Soc., 1952, 74, 4897–4902 No Titel.
Geissler et al., Cancer Research 52:4492–4498 (1992) No Titel.
Gerald et al., Nature, 382, 168 (1996) No Titel.
Gonda, "Critical Review in Therapeutic Drug Carrier Systems" 6 273–313 (1990) No Titel.
Gregory et al., J. Med. Chem. 1990, 33(9), 2569 No Titel.
Grigoriadis et al., Peptides 10:179–188 (1985) No Titel.
Grundemar, L. et al., "TiPS Reviews," vol. 15, p. 153, Elsevier Science Ltd. (1994) No Titel.
Harris et al., Int. J. Obes., 11, 275 (1987) No Titel.

(List continued on next page.)

Primary Examiner—Mukund J. Shah
Assistant Examiner—Sudhaker B. Patel
(74) Attorney, Agent, or Firm—Frank Ungemach; Steven M. Odre

(57) ABSTRACT

There are provided compounds, compositions and methods of use thereof in the modulation of feeding behavior, obesity, diabetes, cancer (tumor), inflammatory disorders, depression, stress related disorders, Alzheimer's disease and other disease conditions.

20 Claims, 5 Drawing Sheets

OTHER PUBLICATIONS

Harris, Diabetes Care, 14(3), 639 (1991) No Titel.
Hipskind, P. et al., "Annual Reports in Medicinal Chemistry," 31, pp. 1–10 (1996) No Titel.
House et al., Europ. J. Biochem. 140:363–367 (1984) No Titel.
Hu et al., J. Biol. Chem., 271, 26315 (1996) No Titel.
Tessel et al., J. Pharmacol. Exp. Ther., 265, 172 (1993) No Titel.
Lavastre, O et al., J. Tetrahedron, 1997, 53, 7595 No Title.
Lydon et al., Oncogene Research 5:161–173 (1990) No Title.
McGlynn et al., Europ. J. Biochem. 207:265–275 (1992) No Title.
Meyer et al., Int. J. Cancer 43:851 (1989) No Title.
Michalski and co–workers, Phosphorus and Sulfur 1986, 26, 321 No Title.
Modnikova et al., Pharm. Chem. J., 1988, 22, 185–191 (with translation pp. 135–141) No Title.
Munglani, R. et al., "Drugs," 52(3), 371 (1996) No Title.
Ozawa et al., Int. J. Cancer 40:706–710 (1987) No Title.
Raeburn et al. J. Pharmacol. Toxicol. Methods. 27 143–159 (1992) No Title.
Rudolf, K., et al., Eur. J. Pharmacol., 271, R11–R13 (1994) No Title.
Santon et al., Cancer Research 46:4701–4705 (1986) No Title.
Sautel, M., et al., Mol. Pharmacol., 50, 285 (1996) No Title.
Serradeil–Le Gal, C., et al., FEBS Lett., 362, 192 (1995) No Title.
Serradeil–Le Gal, C., et al., Soc. Neurosci. Abstr. 376.14 (1994) No Title.
Smith et al., Brain Research 745:248–256 (1997) No Title.
Svensson and Tunek, Drug Metabolism Reviews, 19(2), 165 (1988) No Title.
Tanaka et al., Chem. Pharm. Bull. 1964, 12, 1024–1030 No Title.
Tatemoto, et al. Nature, 296, 659 (1982) No Title.
Tatemoto, Proc. Natl. Acad. Sci USA, 79, 5485 (1982) No Title.
Trinks et al., J. Med. Chem. 37:7, 1015–1027 (1994) No Title.
Weissman and Aaronson, Cell 32:599 (1983) No Title.
Woldbye et al. Nat. Med., 3, 761 (1997) No Title.
Wright, J. L., et al., 211th ACS National Meeting, New Orleans, Louisiana (1996) No Title.
Wright, J. L., et al., Bioorg. Med. Chem. Lett., 6, 1809 (1996) No Title.
Wynn et al., Endocrinology 116:1653–1659 (1985) No Title.
Abramenko et al., Zh. Vses. Khim. Obshchest., 17(6), 695 (1972) No Title.
Aiello et al., J. Heterocyclic Chem., 15:537 (1978) No Title.
Artyomov et al., Tetrahedron, 52(3), 1011–1026 (1996) No Title.
Black, Scientific American Science & Medicine, p. 16–25 (1995) No Title.
Birnberg et al., J. Heterocyclic Chem., 32:1293 (1995) No Title.
Britten et al., Chemistry and Industry, p. 278 (1973) No Title.
Crane et al., J. Org. Chem., 45:3827–3831 (1980) No Title.
Glushkov et al., Pharmaceutical Chemistry Journal, 29(5), 316 (1995) No Title.
Kivokurtseva et al., Khimiko–farmatsevticheski Zhurnal, vol. 19, No. 7, pp. 847–848 (1985) (English version pp. 482–483) No Title.
Kravchenko et al., Farmakol Toksikol (Moscow), 42(6), pp. 659–65 (1979) (English version pp. 221–231) No Title.
Ogonor, Acta Polon. Pharm., XLII, Nr2, pp. 97–100 (1986) No Title.
Pershin et al., Farmakol. Toksikol. 35(4), p. 466 (1972) (English version pp. 181) No Title.
Ren et al., J. Heterocyclic Chem., 23:1757 (1986) No Title.
Shah et al., Indian Journal of Chemistry, 37B:73–77 (1998) No Title.
Sherif, Monatshefte fur Chemie, 127:955–962 (1996) No Title.
Shiotani et al., J. Heterocyclic Chem., 34:129 (1997) No Title.
Sobolov et al., Tetrahedron Letters, 39:5685–5688 (1998) No Title.
Sokolova et al., Khimiko–farmatsevticheskii Zhurnal, vol. 22, No. 6, pp. 656–660 (1988) (English version pp. 421–424) No Title.
Sokolova et al., Khimiko–farmatsevticheskii Zhurnal, vol. 7, No. 3, pp. 19–24 (1973) (English version pp. 150–154) No Title.
Sokolova et al., Khimiko–farmatsevticheskii Zhurnal, vol. 8, No. 1, pp. 14–17 (1974) (English version pp. 13–16) No Title.
Sokolova et al., Khimiko–farmatsevticheskii Zhurnal, vol. 13, No. 9, pp. 17–22 (1979) (English version pp. 902–906) No Title.
Torchilin et al., Proceed. Intern. Symp. Control. Rel. Bioact. Mater., 20:368 (1993) No Title.
Wallace, DDT, 2(11), p. 504 (1997) No Title.

* cited by examiner

COMPOUNDS AND METHODS WHICH MODULATE FEEDING BEHAVIOR AND RELATED DISEASES

This patent application claims priority to U.S. provisional patent applications serial nos. 60/073,927 (filed on Feb. 6, 1998); 60/073,981 (filed on Feb. 6, 1998); 60/093,482 (filed on Jul. 20, 1998); and 60/093,577 (filed on Jul. 20, 1998), each of which is incorporated herein by reference in its entirety.

BACKGROUND OF THE INVENTION

Neuropeptide Y ("NPY") is a 36 amino acid peptide related to and a member of the "PP" peptide family which includes peptide YY ("PYY") and pancreatic peptide ("PP") (See, Tatemoto, et al. Nature, 296, 659 (1982); Tatemoto, Proc. Natl. Acad. Sci USA, 79, 5485 (1982)). NPY is named for the presence of an N-terminal tyrosine and a C-terminal tyrosine amide and is the most abundant peptide neurotransmitter in the brain and central nervous system. NPY is found also in various parts of the peripheral nervous system. This peptide mediates several important biological activities through various receptors and receptor subtypes as discussed below.

In the brain, high NPY levels are found in the cerebral cortex, hippocampus, thalamus, hypothalamus and brainstem. Dense NPY staining occurs in the hypothalamic, brainstem and some limbic regions suggesting that NPY plays a role in somatic, sensory or cognitive brain function. Studies have suggested, also that NPY plays a role in the regulation of food intake, particularly in eating disorders including, for example, obesity, anorexia and bulimia, and memory retention and other cognitive functions, as well as anxiolysis and depression.

Additionally, NPY is found in both peripheral nerves and in the circulation. NPY appears to be a co-transmitter with norepinephrine, playing a role in vasoconstriction and hypertension, cardiac contractility, analgesia and hyperalgesia, as well as control of secretory activity in the intestine.

As noted, NPY and NPY analogs, mediate the noted biological functions through a family of closely related receptor and receptor subtypes. Presently, five receptor subtypes have been identified and are designated Y1 through Y5. Each receptor subtype generally is associated with different biological activities.

For example, the Y1 receptor is believed to be responsible for mediating many of the central and peripheral activities of NPY, including the anxiolytic and sedative effects, as well as the observed vasoconstrictive activities.

The Y2 receptor is predominant in the brain, particularly in the hippocampus. The Y2 receptor mediated effects are associated with inhibition of adenylate cyclase and inhibition of transmitter release. The Y2 receptor effects include vasoconstriction in some blood vessels, antisecretory effects in the intestine, enhanced memory retention, and inhibition of lipolysis.

The Y3 receptor effects are associated with inhibition of adenylate cyclase and elevation of intracellular calcium ion concentrations. Biological effects observed for Y3 include hypotension and bradycardia, inhibition of cardiac contractile force, inhibition of glutamate responsiveness and baroreceptor reflex, inhibition of catecholamine release and release of aldosterone.

The Y4 receptor(also referred to as "PP1" receptor) may be involved in pancreatic exocrine secretion and hormonal control and may be important in diabetes or conditions associated with diabetes.

The most recently identified receptor is Y5 (sometimes referred to as "Y1-like" or "Feeding" receptor) (See, Gerald et al., Nature, 382, 168 (1996) and Hu et al., J. Biol. Chem., 271, 26315 (1996)). This receptor is associated with food intake and may mediate eating disorders such as obesity, bulemia and anorexia. Recently, Y5 has been implicated in the mediation of epileptic states and thus, NPY may be an endogenous anticonvulsant agent (See, e.g. Woldbye et al. Nat. Med., 3, 761 (1997)).

For several articles describing NPY, NPY analogs and receptors, see, for example, Hipskind, P. and Gehler, D., "Annual Reports in Medicinal Chemistry," 31, pp. 1–10, Robertson ed., (1996); Grunemar, L. and Håkanson, R., "TiPS Reviews," Vol. 15, p. 153, Elsevier Science Ltd. (1994); Munglani, R. et al., "Drugs," 52(3), 371 (1996); and Balasubramaniam, A., "Peptides", 18(3), 445 (1997), and references cited therein.

Because of the biological importance of NPY and the receptors with which it interacts, researchers have sought mediators, particularly antagonists, as novel therapeutic agents. A variety of peptide derivatives and analogs have been prepared in which amino acid modifications, substitutions, and deletions have been made relative to NPY. See, e.g., Hipskind, supra.

Although it would be preferable to have an easily synthesized, physically and metabolically stable and perhaps orally active NPY modulating compound, only a few non-peptide antagonists have been prepared. For example, a few non-peptidyl antagonists include the following:

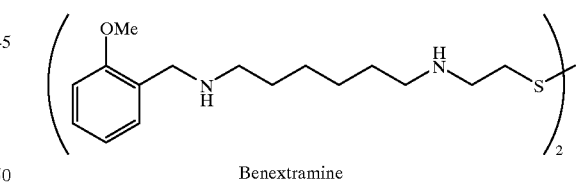

Benextramine

See Doughty, M. B. et al., Eur. J. Pharmacol., 185, 113 (1990); J. Pharmacol. Exp. Ther., 265, 172 (1993);

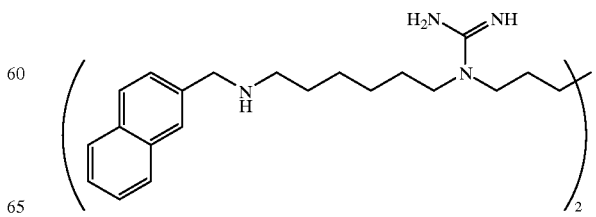

See, Chaurasia, C., *J. Med. Chem.*, 37, 2242 (1994);

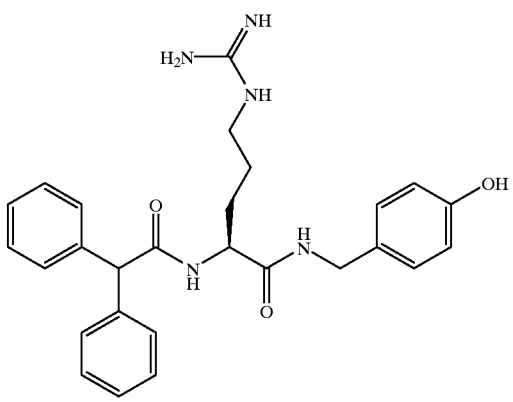

BIBP3226

See, Rudolf, K., et al., *Eur. J. Pharmacol.*, 271, R11–R13 (1994); Sautel, M., et al., *Mol. Pharmacol.*, 50, 285 (1996);

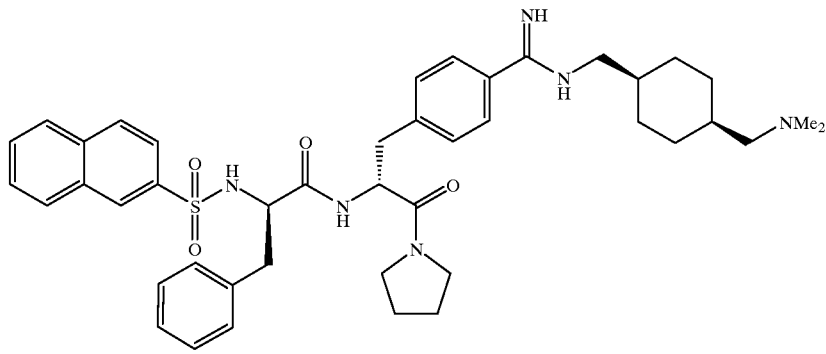

SR120819A

See, Serradeil-Le Gal, C., et al., *FEBS Lett.*, 362, 192 (1995); Serradeil-Le Gal, C., et al., *Soc. Neurosci. Abstr.* 376.14 (1994);

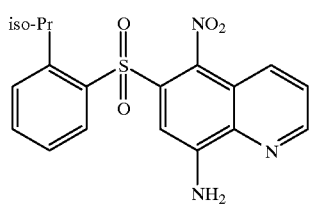

PD160170

See, Wright, J. L., et al., *Bioorg. Med. Chem. Lett.*, 6, 1809 (1996); Wright, J. L., et al., 211th ACS National Meeting, New Orleans, La. (1996);

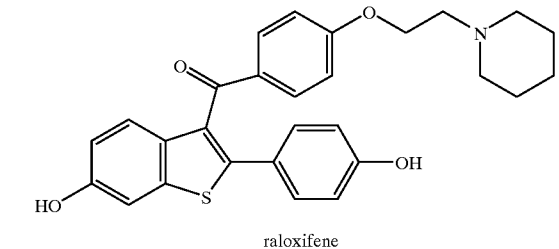

raloxifene

See, for example, Bruns, R. et al., PCT publications, WO 96/12489 and 96/12490; U.S. Pat. No. 5,504,094 (Apr. 2, 1996); and,

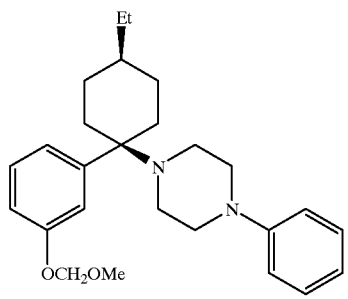

See Peterson, J. M., et al., PCT Publication WO 96/14307.

Additionally, compounds of the following general structure, described in PCT publication, WO 97/34873 (published Sep. 25, 1997), are noted to be useful in the treatment of hyperphagia, obesity or diabetes:

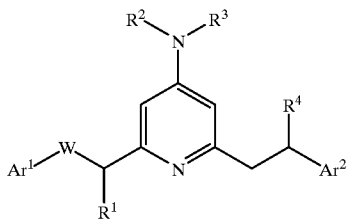

Further, the following compound and related compounds are noted to be useful in NPY5 associated disorders and are disclosed in PCT publications, WO 97/20823, WO 97/20820, WO 97/20821. and WO 97/20822:

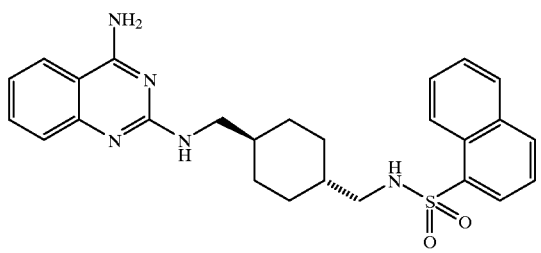

and WO 98/35944 and WO 98/35957 disclose substituted alkylamide NPY5 receptor antagonists.

See, also, L. Criscione, et al., Society for Neuroscience, 23, Abstract No. 231.2, (1997).

Other published compounds include the following general formulae:

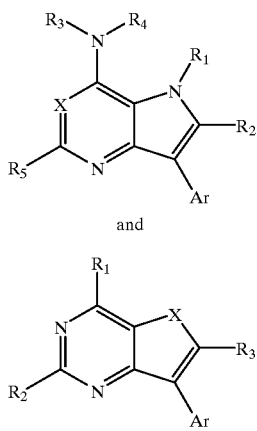

(See, respectively, PCT publication, WO 96/35689, published Nov. 14, 1996—CRF1 receptor agonist or antagonist compounds useful for treating and diagnosis of stress related disorders; and PCT publication, WO 97/29110, published Aug. 14, 1997—CRF receptor antagonist compounds useful for treating disorders relating to hypersecretion of CRF); and,

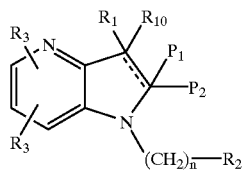

(See, PCT Publication, WO 95/33748, published Dec. 14, 1995—endothelin receptor antagonists).

Obesity, defined as an excess of body fat relative to lean body mass, is associated with important psychological and medical morbidities, the latter including hypertension, elevated blood lipids, and Type II or non-insulin dependent diabetes mellitus ("NIDDM"). There are over 6 million individuals with NIDDM in the United States, including approximately 20% of the population 65 years or older. See, Harris et al., Int. J. Obes., 11, 275 (1987). Approximately 45% of males and 70% of females with NIDDM are obese, and their diabetes is substantially improved or eliminated by weight reduction. See, Harris, Diabetes Care, 14(3), 639 (1991).

The assimilation, storage and utilization of nutrient energy is a complex system central to survival of a warm-blooded animal. Among land-dwelling mammals, storage in adipose tissue of large quantities of metabolic fuel as triglycerides is crucial for surviving through periods of food deprivation. The need to maintain a fixed level of energy stores without continual alteration in the size and shape of an organism requires the achievement of a balance between energy intake and expenditure.

Models of obesity which use animals with mutations in the ob and db gene indicate that the animals have an altered metabolism of carbohydrates resembling Type II diabetes in humans. These animals show effects which resemble other aspects of obesity. In particular, mice with these mutations eat more food and expend less energy than lean control animals. The phenotype is similar to that observed in animals with lesions of the ventromedial hypothalamus which indicates that the noted mutations may interfere with the ability to properly integrate or respond to nutritional information within the central nervous system. See, for example, Coleman, Diabetologia, 9, 294 (1973)

These studies and others related to NPY and NPY receptors show that there is an interaction of a variety of mechanisms involved in the development and maintenance of obesity, overeating and apparently related disease states such as diabetes, or even other NPY mediated disease states such as anxiety and depression. These may include a variety of genetic factors including modifications in the ob, db and NPY genes or receptors, or gene products which affect or modulate these receptors or gene products, including control mechanisms of these receptors or gene products, or control mechanisms of other receptors or targets either upstream or downstream in the signaling pathway from the noted genes, receptors or other target molecules.

Given the variety of clinical states associated with eating disorders, including hyperphagia, obesity, diabetes, and other disease states related to the various mechanisms involved including, for example, NPY pathways, a need exists for additional compounds capable of modulating such activities. In particular, there is a need to provide new approaches for the treatment or prophylaxis of obesity, overeating and diabetes and other diseases which are mediated by the same or related pathways associated with these diseases.

WO 98/06703 (incorporated herein in its entirety) discloses that compounds of the general formula

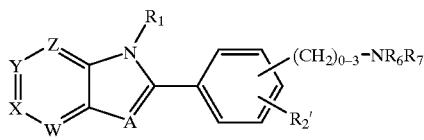

wherein A, W, X, Y, Z, $R_1$, $R_2'$, $R_6$ and $R_7$ are as defined therein, are monocyte chemoattractant protein 1 (MCP-1) receptor antagonists and are capable of inhibiting the binding of MCP-1 to its receptor. MCP-1, a chemokine (chemoattractant cytokine), appears to be involved in inflammation by acting on monocytes, activated memory T cells and on basophils. MCP-1 is a potent secretogogue of inflammatory mediators for monocytes and basophils and appears to have chemotactic activity for human monocytes and/or T cells. MCP-1 may also play a role in allergic hypersensitivity disease. Further, MCP-1 selectively activates the B1 integrin family of leukocyte adhesion molecule and may play a role in leukocyte interactions with the extracellular matrix. Thus, MCP-1 may not only trigger the initial arrest and adhesion of monocytes and T cells, but may also act to guide their migration in extravascular space.

WO 98/08847 (incorporated herein by reference in its entirety) discloses that compounds of the general formula

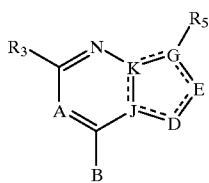

wherein $R_3$, $R_5$, A, B, D, E, G, J and K are as defined therein, are corticotropin releasing factor (CRF) antagonists, corticotropin releasing factor hormone (CRH) binding protein inhibitors and are also useful in the treatment of inflammatory disorders. The CRF antagonists were reported to be effective in the treatment of stress-related illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; cancer; infertility; muscular spasms; urinary incontinence; hypoglycemia and immune dysfunctions including stress induced immune dysfunctions, immune suppression and human immunodeficiency virus infections; and stress-induced infections in humans and animals. CRH binding protein inhibitors were reported to be effective in the treatment of Alzheimer's disease and obesity.

WO 98/05661 (incorporated herein by reference in its entirety) discloses that compounds of the general formula

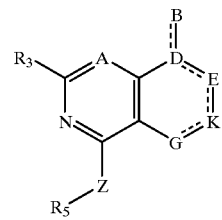

wherein $R_3$, R5, A, B, D, E, G, K and Z are as defined therein, are CRF antagonists, CRH binding protein inhibitors and are also useful in the treatment of inflammatory disorders.

WO 98/08846 (incorporated herein by reference in its entirety) discloses that compounds of the general formula

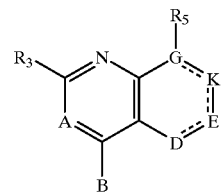

wherein $R_3$, $R_5$, A, B, D, E, G and K are as defined therein, are CRF antagonists, CRH binding protein inhibitors and are also useful in the treatment of inflammatory disorders.

WO 98/07726 (incorporated herein by reference in its entirety) discloses that compounds of the general formula

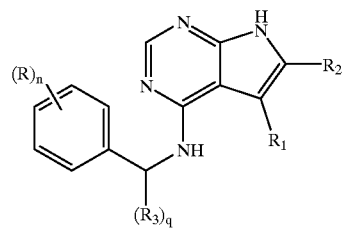

wherein R, $R_1$, $R_2$, $R_3$, n and q are as defined therein, are protein tyrosine kinase inhibitors and/or inhibitors of protein serine/threonine kinases. The compounds were reported to inhibit the tyrosine kinase activity of the receptor for the epidermal growth factor (EGF) and of c-erbB2 kinase. These receptor-specific enzyme activities play a key role in signal transmission in a large number of mammalian cells, including human cells, especially epithelial cells, cells of the immune system and cells of the central and peripheral nervous system. In various cell types, EGF-induced activation of receptor-associated protein tyrosine kinase (EGF-R-PTK) is a prerequisite for cell division and thus for the proliferation of the cell population. Inhibition of protein kinases, such as EGF-receptor-specific tyrosine kinase, inhibits the proliferation of the cells. The compounds were also reported to inhibit other protein tyrosine kinases that are involved in signal transmission mediated by trophic factors, for example abl kinase (such as v-abl kinase), kinases from the family of the src kinases (such as c-src kinase), lck, fyn, other kinases of the EGF family (such as c-erbB2 kinase (HER-2), c-erbB3 kinase, c-erbB4 kinase), members of the family of the PDGF receptor protein tyrosine kinases (such as PDGF receptor kinase, CSF-1 receptor kinase, Kit receptor kinase, VEGF receptor kinase and FGF receptor kinase), the receptor kinase of the insulin-like growth factor (IGF-1 kinase), and serine/threonine kinases (such as protein kinase C or cdc kinases), all of which play a part in growth regulation and transformation in mammalian cells, including human cells.

WO 97/49706 (incorporated herein by reference in its entirety) discloses that compounds of the general formula

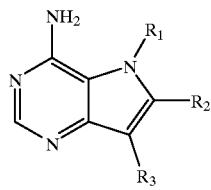

wherein $R_1$, $R_2$ and $R_3$ are as defined therein, are protein tyrosine kinase inhibitors.

SUMMARY OF THE INVENTION

There is a need to provide therapeutic and prophylactic methods for the modulation of feeding behavior, obesity, diabetes, cancer (tumor), inflammatory disorders, depression, stress related disorders, Alzheimer's disease and other disease conditions. Additionally, there is a need to provide therapeutic and prophylactic methods for the modulation of other disease states which result from the same or related biological pathways, including the biological pathways which are mediated by NPY and/or NPY receptors; CRF and/or CRH binding protein; protein tyrosine kinases and/or of protein serine/threonine kinases; MCP-1 and/or its receptor; and the like. The present invention provides compounds which can be used to modulate such activities. In particular, the present invention provides novel compounds and methods for modulating feeding behavior, obesity or diabetic conditions, as well as other disease states associated with the same pathways effecting the noted disease states, especially those modulated by NPY or NPY receptors and related pathways. Compounds useful in the various aspects of the invention are represented by the formula

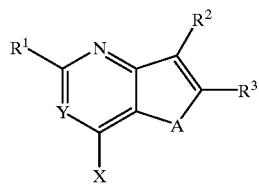

wherein A, X, Y, $R^1$, $R^2$ and $R^3$ are defined below.

Additionally, there are provided formulations which comprise a compound of this invention in combination with a pharmaceutically acceptable carrier, diluent or excipient therefor. These formulations may be used in the noted methods. Further, there are provided processes for preparing the compounds of this invention.

Figure 1A:
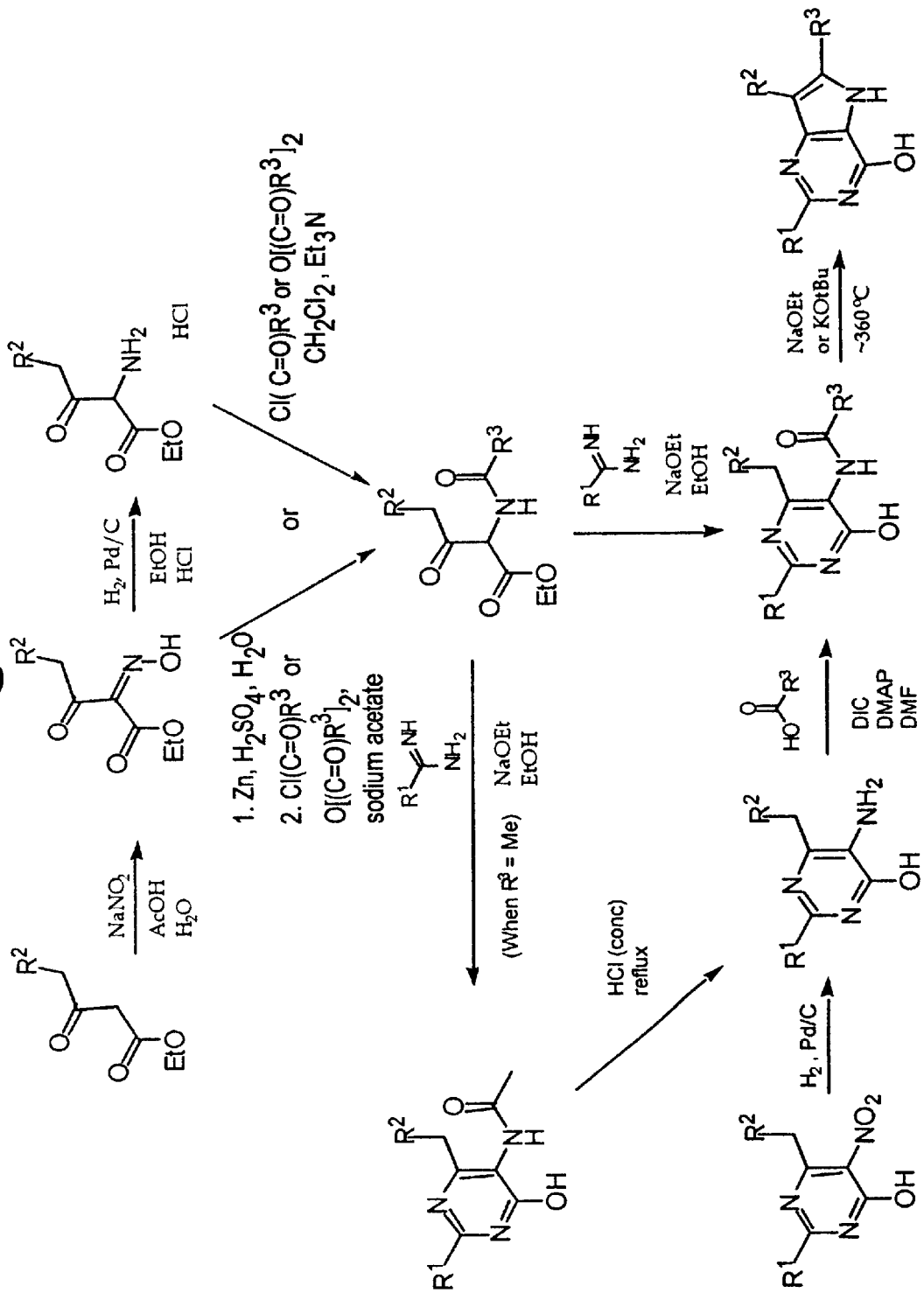
FIGS. 1A and 1B outlines a general reaction scheme for the synthesis of pyrrolo[3,2-d]pyrimidines of the invention.

In the drawings, L represents a leaving group familiar to one skilled in the art and E represents —$CO_2CH_3$, —C(O)X or —CN, wherein X is a halogen.

DETAILED DESCRIPTION OF THE INVENTION

In accordance with the present invention, there is provided compounds of the formula:

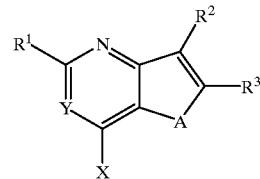

or a pharmaceutically acceptable salt, ester, solvate or N-oxide thereof, wherein Y is N or C($R^6$);

A is O, S, S(O), S(O)$_2$, N—H, N—$R^4$ or C$R^4R^7$; preferably, A is O, S, S(O)$_2$, N—H, N—$R^4$ or CH$R^4$; more preferably, A is O, S, N—H or N—$R^4$; more preferably, A is O, S or N—H; most preferably, A is N—H;

$R^6$ is a hydrogen, —OH, halo, —$CF_3$, —$OCF_3$, ($C_1$-$C_8$) alkoxy, —Z(aryl), —$NH_2$, —NH(($C_1$-$C_8$)alkyl), —N(($C_1$-$C_8$)alkyl)$_2$, ($C_1$-$C_8$)alkyl, ($C_3$-$C_{10}$) cycloalkyl or —Z(Q) radical; preferably, $R^6$ is a hydrogen, —OH, halo, —$CF_3$, —$OCF_3$, ($C_1$-$C_8$) alkoxy, aryl, —$NH_2$, —NH(($C_1$-$C_8$)alkyl), —N(($C_1$-$C_8$)alkyl)$_2$, ($C_1$-$C_8$)alkyl, ($C_3$-$C_{10}$) cycloalkyl or —Z(Q) radical; more preferably, $R^6$ is a hydrogen, —OH, halo, —$OF_3$, —$OCF_3$, ($C_1$-$C_8$) alkoxy, aryl, —$NH_2$, —NH(($C_1$-$C_8$)alkyl), —N(($C_1$-$C_8$)alkyl)$_2$, ($C_1$-$C_8$)alkyl, ($C_3$-$C_{10}$) cycloalkyl or —Z(Q) radical; more preferably, $R^6$ is a hydrogen, —OH, halo, —$CF_3$, —$OCF_3$, ($C_1$-$C_4$) alkoxy, —$NH_2$, —NH(($C_1$-$C_4$)alkyl), —N(($C_1$-$C_4$) alkyl)$_2$, ($C_1$-$C_4$)alkyl or ($C_3$-$C_6$)cycloalkyl radical; more preferably, $R^6$ is a hydrogen, —OH, chloro, fluoro, —$CF_3$, —$OCF_3$, ($C_1$-$C_2$)alkoxy, —$NH_2$, —NH (($C_1$-$C_2$)alkyl), —N(($C_1$-$C_2$)alkyl)$_2$ or ($C_1$-$C_4$)alkyl radical; more preferably, $R^6$ is a hydrogen, —OH, chloro, fluoro, —$CF_3$, —$OCF_3$, ($C_1$-$C_2$)alkoxy or ($C_1$-$C_2$)alkyl radical; most preferably, $R^6$ is a hydrogen radical;

$R^1$ is a hydrogen, halo, —OH, —$NO_2$, —NHOH, ($C_1$-$C_8$) alkyl, ($C_3$-$C_{10}$)cycloalkyl, —Z(($C_1$-$C_8$)alkoxy), —Z(aryloxy), —Z(aryl), —Z(heteroaryl), —Z(($C_3$-$C_{10}$)cycloalkyl), —Z($NR^5SO_2R^5$), —Z(CON ($R^5$)$_2$), —Z($CO_2R^5$), —Z(N($R^5$)$_2$), —Z($NR^5$CON ($R^5$)$_2$), —Z($NR^5$(CO)$R^5$), —Z($NR^5CO_2R^5$), —Z($COR^5$), —Z(S(O)$_p$$R^5$) or —Z(Q) radical; preferably, $R^1$ is a hydrogen, halo, —OH, —$NO_2$, —NHOH, —$CF_3$, —$OCF_3$, ($C_1$-$C_8$)alkyl, ($C_3$-$C_{10}$) cycloalkyl, —Z(($C_1$-$C_8$)alkoxy), —Z(aryloxy), —Z(aryl), —Z(heteroaryl), —Z(($C_3$-$C_{10}$)cycloalkyl), —Z($NR^5SO_2R^5$), —Z(CON($R^5$)$_2$), —Z($CO_2R^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; more preferably, R$^1$ is a hydrogen, halo, —OH, —NO$_2$, —NHOH, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; more preferably, R$^1$ is a hydrogen, halo, —OH, —NO$_2$, —NHOH, —CF$_3$, —OCF$_3$, (C$_1$–C$_8$)alkyl, (C$_3$–C$_6$)cycloalkyl, —Z((C$_1$–C$_8$)alkoxy), —Z((C$_3$–C$_6$)cycloalkyl), —Z(NR$^{10}$SO$_2$R$^5$), —Z(N(R$^5$)$_2$) or —Z(Q) radical; more preferably, R$^1$ is a hydrogen, halo, —OH, —NO$_2$, —NHOH, —CF$_3$, —OCF$_3$, (C$_1$–C$_4$)alkyl, (C$_1$–C$_4$)alkoxy, —(NR$^{10}$)$_k$((C$_1$–C$_2$)alkyl)$_k$-cyclopropyl or —(NR$^{10}$)$_k$((C$_1$–C$_2$)alkyl)$_k$-N(R$^{10}$)$_2$ radical; more preferably, R$^1$ is a bromo, chloro, fluoro, —OH, —NO$_2$, —NHOH, —CF$_3$, —OCF$_3$, (C$_1$–C$_2$)alkyl, (C$_1$–C$_2$)alkoxy, —(NR$^{10}$)$_k$((C$_1$–C$_2$)alkyl)$_k$-cyclopropyl, —NH$_2$ or —NH((C$_1$–C$_2$)alkyl) radical; most preferably, R$^1$ is a —CF$_3$, —OCF$_3$, methyl, methoxy, cyclopropyl, —NH$_2$ or —NH-methyl radical; alternatively, preferably, R$^1$ is not an optionally substituted aryl or heteroaryl radical;

X is a hydrogen, halo, —OH, —NO$_2$, —NHOH, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; preferably, X is a (C$_1$–C$_8$)alkyl, (C$_3$–C$_{10}$)cycloalkyl, —(NR$^5$)$_k$((C$_1$–C$_8$)alkyl)(C$_1$–C$_8$)alkoxy, —(NR$^5$)$_k$((C$_1$–C$_8$)alkyl)aryloxy, —(NR$^5$)((C$_1$–C$_8$)alkyl)$_k$S(O)$_p$R$^5$, —(NR$^5$)$_k$((C$_1$–C$_8$)alkyl)S(O)$_p$R$^5$, —(NR$^5$)D(C$_1$–C$_8$)alkoxy, —(NR$^5$)(CH$_2$)$_m$((C$_3$–C$_{10}$)cycloalkyl)$_k$(CH$_2$)(C$_1$–C$_8$)alkoxy, —(NR$^5$)$_k$(CH$_2$)((C$_3$–C$_{10}$)cycloalkyl)$_k$(CH$_2$)$_m$(C$_1$–C$_8$)alkoxy, —(NR$^5$)$_k$(CH$_2$)$_m$((C$_3$–C$_{10}$)cycloalkyl)(CH$_2$)$_m$(C$_1$–C$_8$)alkoxy, —(NR$^5$)(CH$_2$)$_m$((C$_3$–C$_{10}$)cycloalkyl)$_k$(CH$_2$)aryloxy, —(NR$^5$)$_k$(CH$_2$)((C$_3$–C$_{10}$)cycloalkyl)$_k$(CH$_2$)$_m$aryloxy, —(NR$^5$)$_k$(CH$_2$)$_m$((C$_3$–C$_{10}$)cycloalkyl)(CH$_2$)$_m$aryloxy, —Z(S(O)$_q$R$^5$), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$) or —Z(Q) radical; more preferably, X is a —(NR$^5$)$_k$((C$_1$–C$_8$)alkyl)(C$_1$–C$_8$)alkoxy, —(NR$^5$)$_k$((C$_1$–C$_8$)alkyl)aryloxy, —(NR$^5$)((C$_1$–C$_8$)alkyl)$_k$S(O)$_p$R$^5$, —(NR$^5$)$_k$((C$_1$–C$_8$)alkyl)S(O)$_p$R$^5$, —(NR$^5$)D(C$_1$–C$_8$)alkoxy, —(NR$^5$)(CH$_2$)$_m$((C$_3$–C$_{10}$)cycloalkyl)$_k$(CH$_2$)(C$_1$–C$_8$)alkoxy, —(NR$^5$)$_k$(CH$_2$)((C$_3$–C$_{10}$)cycloalkyl)$_k$(CH$_2$)$_m$(C$_1$–C$_8$)alkoxy, —(NR$^5$)$_k$(CH$_2$)$_m$((C$_3$–C$_{10}$)cycloalkyl)(CH$_2$)$_m$(C$_1$–C$_8$)alkoxy, —(NR$^5$)(CH$_2$)$_m$((C$_3$–C$_{10}$)cycloalkyl)$_k$(CH$_2$)aryloxy, —(NR$^5$)$_k$(CH$_2$)((C$_3$–C$_{10}$)cycloalkyl)$_k$(CH$_2$)$_m$aryloxy, —(NR$^5$)$_k$(CH$_2$)$_m$((C$_3$–C$_{10}$)cycloalkyl)(CH$_2$)$_m$aryloxy, —(NR$^{10}$)(CH$_2$)$_m$((C$_3$–C$_{10}$)cycloalkyl)$_k$(CH$_2$)(C$_1$–C$_8$)alkoxy, —(NR$^{10}$)(CH$_2$)$_m$((C$_3$–C$_{10}$)cycloalkyl)(CH$_2$)$_m$(C$_1$–C$_8$)alkoxy, —(NR$^{10}$)(CH$_2$)$_m$((C$_3$–C$_{10}$)cycloalkyl)$_k$(CH$_2$)aryloxy, —(NR$^{10}$)(CH$_2$)((C$_3$–C$_{10}$)cycloalkyl)$_k$(CH$_2$)$_m$aryloxy,—(NR$^{10}$)(CH$_2$)$_m$((C$_3$–C$_{10}$)cycloalkyl)(CH$_2$)$_m$aryloxy, —(NR$^{10}$)D(S(O)$_q$R$^5$), —(NR$^{10}$)D'(S(O)$_q$R$^5$), —(NR$^{10}$)D(aryl), —(NR$^{10}$)D'(aryl), —(NR$^{10}$)D(heteroaryl), —(NR$^{10}$)D'(heteroaryl), —(NR$^{10}$)D((C$_3$–C$_{10}$)cycloalkyl), —(NR$^{10}$)D'((C$_3$–C$_{10}$)cycloalkyl), —(NR$^{10}$)D(NR$^{10}$SO$_2$R$^5$), —(NR$^{10}$)D'(NR$^{10}$SO$_2$R$^5$), —(NR$^{10}$)D(CON(R$^5$)$_2$), —(NR$^{10}$)D'(CON(R$^5$)$_2$), —(NR$^{10}$)D(CO$_2$R$^5$), —(NR$^{10}$)D'(CO$_2$R$^5$), —(NR$^{10}$)D(N(R$^5$)$_2$), —N(R$^5$)$_2$, —(NR$^{10}$)D'(N(R$^5$)$_2$), —(NR$^{10}$)D(NR$^{10}$CON(R$^5$)$_2$), —(NR$^{10}$)D'(NR$^{10}$CON(R$^5$)$_2$), —(NR$^{10}$)D(NR$^{10}$(CO)R$^5$), —(NR$^{10}$)D'(NR$^{10}$(CO)R$^5$), —(NR$^{10}$)D(NR$^{10}$CO$_2$R$^5$), —(NR$^{10}$)D'(NR$^{10}$CO$_2$R$^5$), —(NR$^{10}$)D(COR$^5$), —(NR$^{10}$)D'(COR$^5$), —(NR$^{10}$)D—Q, —(NR$^{10}$)D'—Q or Q radical; more preferably, X is a —(N((C$_1$–C$_4$)alkyl))—((C$_1$–C$_4$)alkyl)aryloxy, —(N((C$_1$–C$_4$)alkyl))—(CH$_2$)$_m$((C$_3$–C$_6$)cycloalkyl)$_k$(CH$_2$)(C$_1$–C$_4$)alkoxy, —(N((C$_1$–C$_4$)alkyl))—(CH$_2$)((C$_3$–C$_6$)cycloalkyl)$_k$(CH$_2$)$_m$(C$_1$–C$_4$)alkoxy, —(N((C$_1$–C$_4$)alkyl))—(CH$_2$)$_m$((C$_3$–C$_6$)cycloalkyl)(CH$_2$)$_m$(C$_1$–C$_4$)alkoxy, —(N((C$_1$–C$_4$)alkyl))—(CH$_2$)$_m$((C$_3$–C$_6$)cycloalkyl)$_k$(CH$_2$)aryloxy, —(N((C$_1$–C$_4$)alkyl))—(CH$_2$)((C$_3$–C$_6$)cycloalkyl)$_k$(CH$_2$)$_m$aryloxy, —(N((C$_1$–C$_4$)alkyl))—(CH$_2$)$_m$((C$_3$–C$_6$)cycloalkyl)(CH$_2$)$_m$aryloxy, —(N((C$_1$–C$_4$)alkyl))—D(aryl), —(N((C$_1$–C$_4$)alkyl))—D'(aryl), —(N((C$_1$–C$_4$)alkyl))—D(heteroaryl), —(N((C$_1$–C$_4$)alkyl))—D'(heteroaryl), —(N((C$_1$–C$_4$)alkyl))—D(NR$^{10}$SO$_2$R$^5$), —(N((C$_1$–C$_4$)alkyl))—D(CON(R$^5$)$_2$), —(N((C$_1$–C$_4$)alkyl))—D(CO$_2$R$^5$), —(N((C$_1$–C$_4$)alkyl))—D(N(R$^5$)$_2$), —N(R$^5$)$_2$, —(N((C$_1$–C$_4$)alkyl))—D(NR$^{10}$CON(R$^5$)$_2$), —(N((C$_1$–C$_4$)alkyl))—D(NR$^{10}$(CO)R$^5$), —(N((C$_1$–C$_4$)alkyl))—D(NR$^{10}$CO$_2$R$^5$), —(N((C$_1$–C$_4$)alkyl))—D(COR$^5$), —(N((C$_1$–C$_4$)alkyl))—D—Q, —(N((C$_1$–C$_4$)alkyl))—D'—Q or Q radical; more preferably, X is a —N((C$_1$–C$_4$)alkyl)$_2$ or 4-membered to 10-membered heterocyclyl or heteroaryl ring, having a nitrogen atom ring member bonded directly to the carbon atom adjoining X, optionally substituted with 1–2 radicals of R$^8$; most preferably, 5-membered to 6-membered heterocyclyl ring, having a nitrogen atom ring member bonded directly to the carbon atom adjoining X and containing an additional 0–1 nitrogen, oxygen or sulfur atom ring member, which is optionally substituted with 1–2 radicals of R$^8$;

wherein each R$^{10}$ is independently a hydrogen or (C$_1$–C$_4$)alkyl radical; preferably, wherein each R$^{10}$ is independently a hydrogen or (C$_1$–C$_2$)alkyl radical; alternatively, X and A, when A is N or C, together with the adjoining carbon atoms form a 5-membered to 10-membered mono- or bicyclic carbocyclic or heterocyclic ring which is optionally substituted with 1–2 radicals of R$^8$; preferably, X and A, when A is N or C, together with the adjoining carbon atoms form a 5-membered to 10-membered mono- or bicyclic heterocyclic ring which is optionally substituted with 1–2 radicals of R$^8$; more preferably, X and A, when A is N or C, together with the adjoining carbon atoms form a 5-membered to 10-membered mono- or bicyclic heterocyclyl moiety which is optionally substituted with 1–2 radicals of R$^8$; more preferably, X and A, when A is N or C, together with the adjoining carbon atoms form a 8-membered to 10-membered bicyclic heterocyclyl moiety which is optionally substituted with 1–2 radicals of $R^8$; most preferably, X and A, when A is N or C, together with the adjoining carbon atoms form a 8-membered to 10-membered bicyclic heterocyclyl moiety containing 1–2 nitrogen atom and 0–1 oxygen or sulfur atom ring members and which is optionally substituted with 1–2 radicals of $R^8$ on ring carbon atoms;

$R^2$ is a hydrogen, halo, —OH, —NO$_2$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)R$^5$) or —Z(Q); preferably, $R^2$ is a hydrogen, halo, —OH, —NO$_2$, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; more preferably, $R^2$ is a hydrogen, halo, —OH, —NO$_2$, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(N(R$^5$)$_2$), —Z(NR$^5$CON(R$^5$)$_2$), —Z(NR$^5$(CO)R$^5$), —Z(NR$^5$CO$_2$R$^5$), —Z(S(O)$_p$R$^5$) or —Z(Q) radical; more preferably, $R^2$ is a hydrogen, halo, —OH, —NO$_2$, —CF$_3$, —OCF, (C$_1$–C$_{18}$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^{10}$SO$_2$R$^5$), —Z(CON(R$^5$)$_2$), —Z(N(R$^5$)$_2$), —Z(NR$^{10}$CON(R$^5$)$_2$), —Z(NR$^{10}$(CO)R$^5$), —Z(NR$^{10}$CO$_2$R$^5$), —Z(S(O)$_p$R$^5$) or —Z(Q) radical; more preferably, $R^2$ is a hydrogen, chloro, fluoro, —CF$_3$, —OCF$_3$, (C$_1$–C$_4$)alkyl, (C$_3$–C$_6$)cycloalkyl, —(NR$^{10}$)$_k$((C$_1$–C$_2$)alkyl)$_k$—(C$_1$–C$_4$)alkoxy), —(NR$^{10}$)$_k$((C$_1$–C$_2$)alkyl)$_k$—(CON(R$^5$)$_2$), —(NR$^{10}$)$_k$(C$_1$–C$_2$)alkyl)$_k$—(N(R$^5$)$_2$), —(NR$^{10}$)$_k$((C$_1$–C$_2$)alkyl)$_k$—(S(O)$_p$R$^5$) or —(NR$^{10}$)$_k$((C$_1$–C$_2$)alkyl)$_k$—Q radical; more preferably, $R^2$ is a hydrogen, chloro, fluoro, —CF$_3$, —OCF$_3$, (C$_1$–C$_2$)alkyl or (C$_1$–C$_2$) alkoxy radical; most preferably, $R^2$ is a hydrogen, —CF$_3$ or methyl radical;

$R^3$ is a hydrogen, halo, —OH, —NO$_2$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q); preferably, $R^3$ is a (C$_3$–C$_{10}$)cycloalkyl, (C$_1$–C$_8$)alkyl, —((C$_1$–C$_8$)alkyl)OH, (C$_1$–C$_8$)alkoxy-(C$_1$–C$_8$)alkyl-, —((C$_1$–C$_8$)alkyl)N(R$^5$)$_2$, —((C$_1$–C$_8$)alkyl)S(O)$_p$((C$_1$–C$_8$)alkyl), —(CH$_2$)((C$_3$–C$_{10}$)cycloalkyl)$_k$(CH$_2$)$_m$OH, —(CH$_2$)$_m$((C$_3$–C$_{10}$)cycloalkyl)(CH$_2$)$_m$OH, —(CH$_2$)$_m$((C$_3$–C$_{10}$)cycloalkyl)$_k$(CH$_2$)OH, —(CH$_2$)((C$_3$–C$_{10}$)cycloalkyl)$_k$(CH$_2$)$_m$(C$_1$–C$_8$)alkoxy, —(CH$_2$)$_m$((C$_3$–C$_{10}$)cycloalkyl)$_m$(C$_1$–C$_8$)alkoxy, —(CH$_2$)$_m$((C$_3$–C$_{10}$)cycloalkyl)$_k$(CH$_2$)(C$_1$–C$_8$)alkoxy, —(CH$_2$)((C$_3$–C$_{10}$)cycloalkyl)$_k$(CH$_2$)$_m$N(R$^5$)$_2$, —(CH$_2$)$_m$((C$_3$–C$_{10}$)cycloalkyl)(CH$_2$)$_m$N(R$^5$)$_2$, —(CH$_2$)$_m$((C$_3$–C$_{10}$)cycloalkyl)$_k$(CH$_2$)N(R$^5$)$_2$, —(CH$_2$)$_m$((C$_3$–C$_{10}$)cycloalkyl)(CH$_2$)$_m$S(O)$_p$R$^5$, —D'(S(O)R$^5$), —D'(aryloxy), —D'(aryl), —D'(heteroaryl), —D'((C$_3$–C$_{10}$)cycloalkyl), —D'(NR$^5$SO$_2$R$^5$), —D'(CON(R$^5$)$_2$), —D'(CO$_2$R$^5$), —D'(NR$^5$CON(R$^5$)$_2$), —D'(NR$^5$(CO)R$^5$) —D'(NR$^5$CO$_2$R$^5$), —D'(COR$^5$), —D'(Q), —D(aryloxy), —D(aryl), —D'(heteroaryl), —D((C$_3$–C$_{10}$)cycloalkyl), —D(NR$^5$SO$_2$R$^5$), —D(CON(R$^5$)$_2$), —D(CO$_2$R$^5$), —D(S(O)$_q$R$^5$), —D(NR$^5$CON(R$^5$)$_2$), —D(NR$^5$(CO)R$^5$), —D(NR$^5$CO$_2$R$^5$), —D(COR$^5$) or —(NR$^5$)$_k$—D—Q radical; more preferably, $R^3$ is a (C$_3$–C$_{10}$)cycloalkyl, (C$_3$–C$_8$)alkyl, —((C$_1$–C$_8$)alkyl)OH, (C$_1$–C$_8$)alkoxy-(C$_1$–C$_8$)alkyl-, —((C$_1$–C$_8$)alkyl)N(R$^5$)$_2$, —((C$_1$–C$_8$)alkyl)S(O)$_p$((C$_1$–C$_8$)alkyl), —(CH$_2$)((C$_3$–C$_{10}$)cycloalkyl)$_k$(CH$_2$)$_m$OH, —(CH$_2$)$_m$((C$_3$–C$_{10}$)cycloalkyl)(CH$_2$)$_m$OH, —(CH$_2$)$_m$((C$_3$–C$_{10}$)cycloalkyl)$_k$(CH$_2$)OH, —(CH$_2$)((C$_3$–C$_{10}$)cycloalkyl)$_k$(CH$_2$)$_m$(C$_1$–C$_8$)alkoxy, —(CH$_2$)$_m$((C$_3$–C$_{10}$)cycloalkyl)(CH$_2$)$_m$(C$_1$–C$_8$)alkoxy, —(CH$_2$)$_m$((C$_3$–C$_{10}$)cyclo- alkyl)$_k$(CH$_2$)(C$_1$–C$_8$)alkoxy, —(CH$_2$)((C$_3$–C$_{10}$)cyclo alkyl)$_k$(CH$_2$)$_m$N(R$^5$)$_2$, —(CH$_2$)$_m$((C$_3$–C$_{10}$)cycloalkyl)(CH$_2$)$_m$N(R$^5$)$_2$, —(CH$_2$)$_m$((C$_3$–C$_{10}$)cycloalkyl)$_k$(CH$_2$)N(R$^5$)$_2$, —(CH$_2$)$_m$((C$_3$–C$_{10}$)cycloalkyl)(CH$_2$)$_m$S(O)$_p$R$^5$, —(CH$_2$)$_m$((C$_3$–C$_{10}$)cycloalkyl)(CH$_2$)$_m$(CO$_2$R$^5$), —(CH$_2$)$_m$((C$_3$–C$_{10}$)cycloalkyl)(CH$_2$)$_m$(COR$^5$), —((C$_1$–C$_8$)alkyl)(CO$_2$R$^5$), —((C$_1$–C$_8$)alkyl)(COR$^5$), —D'(S(O)$_q$R$^5$), —D'(aryloxy), —D'(aryl), —D'(heteroaryl), —D'((C$_3$–C$_{10}$)cycloalkyl), —D'(NR$^5$SO$_2$R$^5$), —D'(CON(R$^5$)$_2$), —D'(NR$^5$CON(R$^5$)$_2$), —D'(NR$^5$(CO)R$^5$), —D'(NR$^5$CO$_2$R$^5$), —D'(Q), —D(aryloxy), —D(aryl), —D(heteroaryl), —D((C$_3$–C$_{10}$)cycloalkyl), —D(NR$^5$SO$_2$R$^5$), —D(CON(R$^5$)$_2$), —D(S(O)$_q$R$^5$), —D(NR$^5$CON(R$^5$)$_2$), —D(NR$^5$(CO)R$^5$), —D(NR$^5$CO$_2$R$^5$) or —(NR$^5$)$_k$—D—Q radical; more preferably, $R^3$ is a (C$_3$–C$_{10}$)cycloalkyl, (C$_3$–C$_8$)alkyl, —((C$_1$–C$_8$)alkyl)OH, (C$_1$–C$_8$)alkoxy-(C$_1$–C$_8$)alkyl-, —((C$_1$–C$_8$)alkyl)N(R$^5$)$_2$, —((C$_1$–C$_8$)alkyl)S(O)$_p$((C$_1$–C$_8$)alkyl), —(CH$_2$)((C$_3$–C$_{10}$)cycloalkyl)$_k$(CH$_2$)$_m$OH, —(CH$_2$)$_m$((C$_3$–C$_{10}$)cycloalkyl)(CH$_2$)$_m$OH, —(CH$_2$)$_m$((C$_3$–C$_{10}$)cycloalkyl)$_k$(CH$_2$)OH, —(CH$_2$)((C$_3$–C$_{10}$)cycloalkyl)$_k$(CH$_2$)$_m$(C$_1$–C$_8$)alkoxy, —(CH$_2$)$_m$((C$_3$–C$_{10}$)cycloalkyl)(CH$_2$)$_m$(C$_1$–C$_8$)alkoxy, —(CH$_2$)$_m$((C$_3$–C$_{10}$)cycloalkyl)$_k$(CH$_2$)(C$_1$–C$_8$)alkoxy, —(CH$_2$)((C$_3$–C$_{10}$)cycloalkyl)$_k$(CH$_2$)$_m$N(R$^5$)$_2$, —(CH$_2$)$_m$((C$_3$–C$_{10}$)cycloalkyl)(CH$_2$)$_m$N(R$^5$)$_2$, —(CH$_2$)$_m$((C$_3$–C$_{10}$)cycloalkyl)$_k$(CH$_2$)N(R$^5$)$_2$, —(CH$_2$)$_m$((C$_3$–C$_{10}$)cycloalkyl)(CH$_2$)$_m$S(O)$_p$R$^5$, —(CH$_2$)$_m$((C$_3$–C$_{10}$)cycloalkyl)(CH$_2$)$_m$(CO$_2$R$^5$), —(CH$_2$)$_m$((C$_3$–C$_{10}$)cycloalkyl)(CH$_2$)$_m$(COR$^5$), —((C$_1$–C$_8$)alkyl)(CO$_2$R$^5$), —((C$_1$–C$_8$)alkyl)(COR$^5$), —D'(S(O)$_q$R$^5$), —D'(aryloxy), —D'(aryl), —D'(heteroaryl), —D'((C$_3$–C$_{10}$)cycloalkyl), —D'(NR$^{10}$SO$_2$R$^5$), —D'(CON(R$^5$)$_2$), —D'(NR$^{10}$CON(R$^5$)$_2$), —D'(NR$^{10}$(CO)R$^5$) —D'(NR$^1$CO$_2$R$^5$), —D'(Q), —D(aryloxy), —D(aryl), —D(heteroaryl), —D((C$_3$–C$_{10}$)cycloalkyl), —D(NR$^{10}$SO$_2$R$^5$), —D(CON(R$^5$)$_2$), —D(S(O)$_q$R$^5$), —D(NR$^{10}$CON(R$^5$)$_2$), —D(NR$^{10}$(CO)R$^5$), —D(NR$^{10}$R$^5$), or —(NR$^{10}$)$_k$—D—Q radical; more preferably, $R^3$ is a (C$_3$–C$_6$)cycloalkyl, (C$_3$–C$_6$)alkyl, —((C$_1$–C$_4$)alkyl)OH, (C$_1$–C$_4$)alkoxy-(C$_1$–C$_4$)alkyl-, —((C$_1$–C$_4$)alkyl)N(R$^5$)$_2$, —(CH$_2$)((C$_3$–C$_6$)cycloalkyl)$_k$(CH$_2$)$_m$OH, —(CH$_2$)$_m$((C$_3$–C$_6$)cycloalkyl)(CH$_2$)$_m$OH, —(CH$_2$)$_m$((C$_3$–C$_6$)cycloalkyl)$_k$(CH$_2$)OH, —(CH$_2$)((C$_3$–C$_6$)cycloalkyl)$_k$(CH$_2$)$_m$(C$_1$–C$_4$)alkoxy, —(CH$_2$)$_m$((C$_3$–C$_6$)cycloalkyl)(CH$_2$)$_m$(C$_1$–C$_4$)alkoxy, —(CH$_2$)$_m$((C$_3$–C$_6$)cycloalkyl)$_k$(CH$_2$)(C$_1$–C$_4$)alkoxy, —(CH$_2$)((C$_3$–C$_6$)cycloalkyl)$_k$(CH$_2$)$_m$N(R$^5$)$_2$, —(CH$_2$)$_m$((C$_3$–C$_6$)cycloalkyl)(CH$_2$)$_m$N(R$^5$)$_2$, —(CH$_2$)$_m$((C$_3$–C$_6$)cycloalkyl)$_k$(CH$_2$)N(R$^5$)$_2$, —(CH$_2$)$_m$((C$_3$–C$_6$)cycloalkyl)(CH$_2$)$_m$S(O)$_p$R$^5$, —(CH$_2$)$_m$((C$_3$–C$_6$)cycloalkyl)(CH$_2$)$_m$(CO$_2$R$^5$), —(CH$_2$)$_m$((C$_3$–C$_6$)cycloalkyl)(CH$_2$)$_m$(COR$^5$), —D'(S(O)$_q$R$^5$), —D'(aryloxy), —D'(aryl), —D'(heteroaryl), —D'((C$_3$–C$_{10}$)cycloalkyl), —D'(Q), —D(aryloxy), —D(aryl), —D(heteroaryl), —D(NR$^{10}$SO$_2$R$^5$), —D(CON(R$^5$)$_2$), —D(S(O)$_q$R$^5$), —D(NR$^{10}$CON(R$^5$)$_2$), —D(NR$^{10}$(CO)R$^5$), —D(NR$^{10}$CO$_2$R$^5$) or —(NR$^{10}$)$_k$—D—Q radical; more preferably, R$^3$ is a (C$_3$–C$_6$)cycloalkyl, (C$_3$–C$_6$)alkyl, —((C$_1$–C$_4$)alkyl)OH, (C$_1$–C$_4$)alkoxy-(C$_1$–C$_4$)alkyl-, —((C$_1$–C$_4$)alkyl)N(R$^5$)$_2$, —(CH$_2$)((C$_5$–C$_6$)cycloalkyl)$_k$(CH$_2$)$_m$OH, —(CH$_2$)$_m$((C$_5$–C$_6$)cycloalkyl)(CH$_2$)$_m$OH, —(CH$_2$)$_m$((C$_5$–C$_6$)cycloalkyl)$_k$(CH$_2$)OH, —(CH$_2$)((C$_5$–C$_6$)cycloalkyl)$_k$(CH$_2$)$_m$(C$_1$–C$_2$)alkoxy, —(CH$_2$)$_m$((C$_5$–C$_6$)cycloalkyl)(CH$_2$)$_m$(C$_1$–C$_2$)alkoxy, —(CH$_2$)$_m$((C$_5$–C$_6$)cycloalkyl)$_k$(CH$_2$)(C$_1$–C$_2$)alkoxy, —(CH$_2$)((C$_5$–C$_6$)cycloalkyl)$_k$(CH$_2$)$_m$N(R$^5$)$_2$, —(CH$_2$)$_m$((C$_5$–C$_6$)cycloalkyl)(CH$_2$)$_m$N(R$^5$)$_2$, —(CH$_2$)$_m$((C$_5$–C$_6$)cycloalkyl)$_k$(CH$_2$)N(R$^5$)$_2$, —(CH$_2$)$_m$((C$_5$–C$_6$)cycloalkyl)(CH$_2$)$_m$S(O)$_p$R$^5$, —(CH$_2$)$_m$((C$_5$–C$_6$)cycloalkyl)(CH$_2$)$_m$(CO$_2$R$^5$), —(CH$_2$)$_m$((C$_5$–C$_6$)cycloalkyl)(CH$_2$)$_m$(COR$^5$), —D'(S(O)$_q$R$^5$), —D'(aryloxy), —D'(aryl), —D'(heteroaryl), —D'((C$_3$–C$_6$)cycloalkyl), —D'(Q), —D(aryloxy), —D(aryl), —D(heteroaryl), —D(NR$^{10}$SO$_2$R$^5$), —D(CON(R$^5$)$_2$), —D(S(O)$_q$R$^5$), —D(NR$^{10}$CON(R$^5$)$_2$), —D(NR$^{10}$(CO)R$^5$), —D(NR$^{10}$CO$_2$R$^5$) or —(NR$^{10}$)$_k$—D—Q radical; more preferably, R$^3$ is a (C$_5$–C$_6$)cycloalkyl, (C$_3$–C$_6$)alkyl, aryloxy-(C$_1$–C$_2$)alkyl-, aryl, heteroaryl, aryl-(C$_1$–C$_2$)alkyl-, heteroaryl-(C$_1$–C$_2$)alkyl- or (C$_5$–C$_6$)cycloalkyl-(C$_1$–C$_2$)alkyl- radical; and alternatively, preferably, R$^3$ is not —SO$_2$NH$_2$;

R$^4$ is a hydrogen, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; preferably, R$^4$ is a (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical; more preferably, R$^4$ is a (C$_1$–C$_4$)alkyl, (C$_3$–C$_6$)cycloalkyl, —N(R$^5$)$_2$ or —Z(Q) radical; more preferably, R$^4$ is a (C$_1$–C$_4$)alkyl radical; most preferably, R$^4$ is a methyl radical;

each R$^5$ is independently a hydrogen, —OH, (C$_1$–C$_8$)alkoxy, aryl, —NH$_2$, —NH((C$_1$–C$_8$)alkyl), —N((C$_1$–C$_8$)alkyl)$_2$, (C$_1$–C$_8$)alkyl or (C$_3$–C$_{10}$)cycloalkyl radical; preferably, each R$^5$ is independently a hydrogen, —OH, (C$_1$–C$_4$)alkoxy, —NH$_2$, —NH((C$_1$–C$_4$)alkyl), —N((C$_1$–C$_4$)alkyl)$_2$, (C$_1$–C$_4$)alkyl or (C$_3$–C$_6$)cycloalkyl radical; more preferably, each R$^5$ is independently a hydrogen, —OH, (C$_1$–C$_4$)alkoxy, —NH$_2$, —NH((C$_1$–C$_4$)alkyl), —N((C$_1$–C$_4$)alkyl)$_2$ or (C$_1$–C$_4$)alkyl radical; more preferably, each R$^5$ is independently a hydrogen, —OH, (C$_1$–C$_2$)alkoxy, —NH$_2$, —NH((C$_1$–C$_2$)alkyl), —N((C$_1$–C$_2$)alkyl)$_2$ or (C$_1$–C$_2$) alkyl radical; most preferably, each R$^5$ is independently a hydrogen, —OH, (C$_1$–C$_2$)alkoxy, —NH$_2$ or (C$_1$–C$_2$) alkyl radical;

R$^7$ is a hydrogen, —OH, (C$_1$–C$_8$)alkoxy, aryl, —NH$_2$, —NH((C$_1$–C$_8$)alkyl), —N((C$_1$–C$_8$)alkyl)$_2$, (C$_1$–C$_8$)alkyl or (C$_3$–C$_{10}$)cycloalkyl radical; preferably, R$^7$ is a hydrogen, —OH, (C$_1$–C$_4$)alkoxy, —NH$_2$, —NH((C$_1$–C$_4$)alkyl), —N((C$_1$–C$_4$)alkyl)$_2$, (C$_1$–C$_4$)alkyl or (C$_3$–C$_6$)cycloalkyl radical; more preferably, R$^7$ is a hydrogen, —OH, (C$_1$–C$_4$)alkoxy, —NH$_2$, —NH((C$_1$–C$_4$)alkyl), —N((C$_1$–C$_4$)alkyl)$_2$ or (C$_1$–C$_4$)alkyl radical; more preferably, R$_7$ is a hydrogen, —OH, —NH$_2$ or (C$_1$–C$_2$)alkyl radical; most preferably, R$^7$ is a hydrogen or methyl radical;

Q is a 4-membered to 10-membered heterocyclyl or heteroaryl ring optionally substituted with 1–2 radicals of R$^8$; preferably, 4-membered to 7-membered heterocyclyl or 5-membered, 6-membered, 9-membered or 10-membered heteroaryl ring, each of which is optionally substituted with 1–2 radicals of R$^8$;

each R$^8$ is independently a —OH, halo, —CF$_3$, —OCF$_3$, (C$_1$–C$_8$)alkoxy, —NH$_2$, —NH((C$_1$–C$_8$)alkyl), —N((C$_1$–C$_8$)alkyl)$_2$, or (C$_1$–C$_8$)alkyl radical; preferably, each R$^8$ is independently a —OH, halo, —CF$_3$, —OCF$_3$, (C$_1$–C$_4$)alkoxy, —NH$_2$, —NH((C$_1$–C$_4$)alkyl), —N((C$_1$–C$_4$)alkyl)$_2$, or (C$_1$–C$_4$)alkyl radical; more preferably, each R$^8$ is independently a —OH, halo, —CF$_3$, —OCF$_3$, (C$_1$–C$_2$)alkoxy, —NH$_2$, —NH((C$_1$–C$_2$)alkyl), —N((C$_1$–C$_2$)alkyl)$_2$, or (C$_1$–C$_2$) alkyl radical; most preferably, each R$^8$ is independently a —OH, —CF$_3$ or methyl radical;

Z is D(NR$^5$)$_k$, D'(NR$^5$)$_k$, (NR$^5$)$_k$D or (NR$^5$)$_k$D'; preferably, Z is D(NR$^{10}$)$_k$, D'(NR$^{10}$)$_k$, (NR$^{10}$)$_k$D or (NR$^{10}$)$_k$D'; more preferably, Z is (NR$^{10}$)$_k$D or (NR$^{10}$)$_k$D';

D is (CH$_2$)$_m$(C$_3$–C$_{10}$)cycloalkyl)$_k$(CH$_2$)$_m$—; preferably, D is —(CH$_2$)$_m$((C$_3$–C$_6$)cycloalkyl)$_k$(CH$_2$)$_m$—; more preferably, —(CH$_2$)$_m$((C$_5$–C$_6$)cycloalkyl)$_k$(CH$_2$)$_m$—;

D' is —((C$_1$–C$_8$)alkyl)$_k$—; preferably, D' is —((C$_1$–C$_4$)alkyl)$_k$—;

each k is independently 0 or 1; each m is independently an integer between 0 and 6, preferably, between 0 and 4, more preferably, between 0 and 3, and most preferably between 0 and 2; each p is independently an integer between 0 and 2; and each q is independently 1 or 2; and wherein each alkyl, aryl, heteroaryl, cycloalkyl, Q, alkoxy or aryloxy moiety of any of X, R$^1$, R$^2$, R$^3$, R$^4$, R$^5$, R$^6$, R$^7$ and R$^8$ is optionally substituted with one or more radicals of halo, —CF$_3$, —OCF$_3$, —Z(COOH), —Z(OH), —Z(NO$_2$), —Z(SH), —(C$_1$–C$_8$)alkyl, —(C$_1$–C$_8$)acyloxy, —(C$_3$–C$_{10}$)cycloalkyl, —S—((C$_1$–C$_8$)alkyl)$_k$—aryl, —((C$_1$–C$_8$)alkyl)$_k$-SO$_2$NH-aryl, —S—(C$_1$–C$_8$)alkyl, —Z((C$_1$–C$_8$)alkoxy), —Z(aryloxy), —Z(aryl), —Z(heteroaryl), —Z((C$_3$–C$_{10}$)cycloalkyl), —Z(NR$^9$SO$_2$R$^9$), —Z(CON(R$^9$)$_2$), —Z(CO$_2$R$^9$), —Z(N(R$^9$)$_2$), —Z(NR$^9$CON(R$^9$)$_2$), —Z(NR$^9$(CO)R$^9$), —Z(NR$^9$CO$_2$R$^9$), —Z(COR$^9$), —Z(S(O)$_p$R$^9$) or —Z(Q), wherein such aryl, heteroaryl, cycloalkyl and Q substitutents are optionally substituted with one or more radicals of halo, —NO$_2$, —CF$_3$, —OCF$_3$, —N(R$^9$)$_2$, —C(O)R$^9$, —CO$_2$R$^9$, —OR$^9$, —SR$^9$ or (C$_1$–C$_8$)alkyl; preferably, each alkyl, aryl, heteroaryl, cycloalkyl, Q, alkoxy or aryloxy moiety of any of X, R$^1$, R$^2$, R$^3$, R$^4$, R$^5$, R$^6$ and R$^7$ is optionally substituted with 1–3 radicals of halo and 1–2 radicals of —$CF_3$, —$OCF_3$ —Z(COOH), —Z(OH), —$Z(NO_2)$, —Z(SH), —($C_1$–$C_8$)alkyl, —($C_1$–$C_8$)acyloxy, —($C_3$–$C_{10}$) cycloalkyl, —S—(($C_1$–$C_8$)alkyl)$_k$—aryl, —(($C_1$–$C_8$) alkyl)$_k$—$SO_2$NH-aryl, —S—($C_1$–$C_8$)alkyl, —Z(($C_1$–$C_8$)alkoxy), —Z(aryloxy), —Z(aryl), —Z(heteroaryl), —Z(($C_3$–$C_{10}$)cycloalkyl), —Z($NR^9SO_2R^9$), —Z($CON(R^9)_2$), —Z($CO_2R^9$), —Z($N(R^9)_2$), —Z($NR^9CON(R^9)_2$), —Z($NR^9(CO)R^9$), —Z($NR^9CO_2R^9$), —Z($COR^9$), —Z($S(O)_pR^9$) or —Z(Q), wherein such aryl, heteroaryl, cycloalkyl and Q substituents are optionally substituted with 1–3 radicals of halo, —$NO_2$, —$CF_3$, —$OCF_3$, —$N(R^9)_2$, —$C(O)R^9$, —$CO_2R^9$, —$OR^9$, —$SR^9$ or ($C_1$–$C_8$)alkyl; more preferably, each alkyl, aryl, heteroaryl, cycloalkyl, Q, alkoxy or aryloxy moiety of any of X, $R^1$, $R^2$, $R^3$, $R^4$, $R^5$, $R^6$ and $R^7$ is optionally substituted with 1–3 radicals of halo and 1–2 radicals of —$CF_3$, —$OCF_3$, —$OR^9$, —$SR^9$, —$NO_2$, —(($C_1$–$C_4$)alkyl, —($C_1$–$C_4$)acyloxy, —($C_3$–$C_6$)cycloalkyl, —S—(($C_1$–$C_4$)alkyl)$_k$—aryl, —(($C_1$–$C_4$)alkyl)$_k$—$SO_2$NH-aryl, aryloxy, aryl, —$NR^9SO_2R^9$, —$CON(R^9)_2$, $CO_2R^9$, —$N(R^9)_2$, —$NR^9CON(R^9)_2$, —$NR^9(CO)R^9$, —$NR^9CO_2R^9$, —$COR^9$, —$S(O)_2(C_1$–$C_4)$alkyl or Q, wherein such aryl, heteroaryl, cycloalkyl and Q substituents are optionally substituted with 1–2 radicals of halo, —$NO_2$, —$CF_3$, —$OCF_3$, —$N(R^9)_2$, —$C(O)R^9$, —$CO_2R^9$, —$OR^9$, $SR^9$ or ($C_1$–$C_4$)alkyl; more preferably, each alkyl, aryl, heteroaryl, cycloalkyl, Q, alkoxy or aryloxy moiety of any of X, $R^1$, $R^2$, $R^3$, $R^4$, $R^5$, $R^6$ and $R^7$ is optionally substituted with 1–2 radicals of halo, —$CF_3$, —$OCF_3$, —$OR^9$, —$SR^9$, —$NO_2$, ($C_1$–$C_4$)alkyl, ($C_1$–$C_4$)acyloxy, —$NR^9SO_2R^9$, —CON($R^9$)$_2$, —$CO_2R^9$, —$N(R^9)_2$, —$NR^9CON(R^9)_2$, —$NR^9(CO)R^9$, —$NR^9CO_2R^9$, —$COR^9$ or —$S(O)_2(C_1$–$C_4)$ alkyl; more preferably, each alkyl, aryl, heteroaryl, cycloalkyl, Q, alkoxy or aryloxy moiety of any of X, $R^1$, $R^2$, $R^3$, $R^4$, $R^5$, $R^6$ and $R^7$ is optionally substituted with 1–2 radicals of halo, —$CF_3$, —$OCF_3$, —$OR^9$, —$SR^9$, ($C_1$–$C_2$)alkyl or —$N(R^9)_2$; and wherein each $R^9$ is independently a hydrogen or ($C_1$–$C_8$) alkyl radical; preferably, each $R^9$ is independently a hydrogen or ($C_1$–$C_4$)alkyl radical; more preferably, each $R^9$ is independently a hydrogen or ($C_1$–$C_2$)alkyl radical; and provided that the total number of aryl, heteroaryl, cycloalkyl, heterocyclyl and Q moieties in A, X, Y, $R^1$, $R^2$ and $R^3$ is 0–4, preferably, 0–3, more preferably 1–3; most preferably, 1–2.

The following preferred provisos relate to compounds and pharmaceutical compositions of the invention:

(a) when A is NH, Y is N, $R^1$ is H, methyl or phenyl, and $R^3$ is methyl, ethyl or phenyl, then (1) when $R^2$ is H, X is not —$NH_2$, —$N(CH_2CH_3)_2$, —$NHCH_2CH_2N$ $(CH_2CH_2)_2$, —$NHCH_2CH_2CH_2CO_2H$, —$NHCH_2CH_2OH$, —NH-phenyl, —$NHCH_2CH_2$-phenyl, —NH—CH($CH_3$)$CH_2$-phenyl, —NH—(methoxyphenyl), —$NHCH_2CH_2$—(dimethoxyphenyl), —$NHCH_2CH_2$-imidazolyl, —$NHCH_2CH_2$—(methylthioimidazolyl), —$NHCH_2CH_2$-cyclohexyl, —NH-cyclohexyl, piperidinyl, morpholinyl, —$NHNH_2$, —$NHCH(CH_3)_2$, —NH-butyl, —NH—CH($CH_3$) ($CH_2$)$_4CH_3$, —NH ($CH_2$)$_2$cyclohexenyl, —NH—($CH_2$)$_5CH_3$, —$NHCH_2CH=CH_2$, —NH—$CH_2$-phenyl, 4-methylpiperazine, —$NHSO_2$(4-aminophenyl) or —NH—(4-methylpiperazine); (2) when $R^2$ is —$CH_2N$ ($CH_2CH_3$)$_2$, —$CH_2$NH-butyl, —$CH_2NHCH_2CH_2$-cyclohexenyl or —$CH_2NHCH_2CH_2COOH$, X is not —NH($CH_2$)$_2$cyclohexenyl; and (3) when R2 is methyl, acetyl or —$COOCH_2CH_3$, X is not —$NH_2$ or —NH (C(O)$CH_3$);

(b) when $R^1$ is ethoxy, $R^2$ is H, $R^3$ is —$COOCH_2CH_3$, A is NH and Y is N, then X is not —$NH_2$;

(c) when A is N—H or N—$R^4$, Y is C—H and $R^1$ is hydrogen, halo, alkyl, cycloalkyl, alkoxy or alkylthio, then (1) when $R^3$ is methyl and $R^2$ is acetyl or —$COOCH_3$, X is not $NH_2$ or trifluoromethylphenyl; (2) when $R^3$ is methyl or —$COOCH_3$ and $R^2$ is H, X is not methyl; and (3) when one of $R^2$, $R^3$ or $R^4$ is optionally substituted -ethyl-$NR^5CONHR^5$, X is not alkyl or cycloalkyl;

(d) when A is N—$R^4$ and Y is C—H, then $R^3$ is not —$CO_2R^5$;

(e) when A is N—$C_1$–$C_6$ alkyl, Y is C—H or N, $R^1$ and $R^3$ are hydrogen, halo, alkyl, alkoxy or alkylthio, then $R^2$ is not thienyl optionally substituted with 1–3 halo, hydroxy, alkyl or alkoxy radicals;

(f) when A is $CH_2$, Y is C—H, $R^1$ is $NH_2$, $R^3$ is methyl and X is methyl, then $R^2$ is not C(O)$NH_2$;

(g) when A is N—H or N—$R^4$ and $R^3$ is aryl or heteroaryl, then $R^2$ is not aryl or heteroaryl;

(h) when A is N—$R^4$, Y is N, $R^1$ is H and $R^3$ is alkyl, then X is not —$NH_2$;

(i) when A is N—H or N—$R^4$ and $R^2$ is H, then $R^3$ is not optionally substituted phenyl which is substituted by —N($R^5$)—($C_2$–$C_6$ alkyl)—$N(R^5)_2$ or —N($R^5$)—($C_2$–$C_6$ alkyl)—Q;

(j) when A is S, Y is N, $R^2$ is H, $R^3$ is methyl or phenyl and $R^1$ is phenyl, $NH_2$, piperazinyl or methyl, then X is not $NH_2$, morpholinyl, 1-oxidothiomorpholinyl or thiomorpholinyl;

(k) when A is O, Y is C—H, $R^1$ is H, $R^2$ is H and $R^3$ is propyl, butyl or hydroxypropyl, then X is not methyl, benzyl or methoxyphenyl-$CH_2$—;

(l) when A is S, Y is N, $R^2$ is H or alkyl, $R^3$ is methyl, then $R^1$ is not nitro-furyl, —NH—($C_2$–$C_{10}$)alkyl-$NH_2$, —N(alkyl)-($C_2$–$C_{10}$)alkyl-$NH_2$ or —N(methyl)-ethyl-$NHSO_2$-tolyl;

(m) when A is S, Y is N, $R^2$ is H, halo, —$NO_2$ or alkyl, $R^3$ is alkyl or phenyl and X is Q, —N(alkyl-OH)2, —N(methyl)-ethyl-S-methyl or —N(methyl)-ethyl-S (O)-methyl, then $R^1$ is not Q, —N(alkyl-OH)2, —N(methyl)-ethyl-S-methyl or —N(methyl)-ethyl-S (O)-methyl;

(n) When A is O or S, Y is CH, $R^1$ is H and $R^2$ is H, then $R^3$ is not —$SO_2NH_2$;

(o) when A is S, Y is N, $R^1$ is H and $R^2$ is H, then (1) when $R^3$ is phenyl, X is not —NH—$NH_2$, optionally substituted indolylalkylamino, optionally substituted indolylamino, optionally substituted thiazolidinonylamino or optionally substituted azetidinonylamino, and (2) when $R^3$ is methyl, X is not piperidinyl;

(p) when A is O, Y is N, $R^1$ is optionally substituted phenyl, $R^2$ is H and $R^3$ is alkyl, then X is not optionally substituted phenyl; and (q) $R^2$ is not an optionally substituted phenyl, pyridyl, pyrazinyl, pyrimidyl or pyridazinyl radical; and more preferably, $R^2$ is not an optionally substituted aryl or heteroaryl radical.

Another aspect of this invention is a key synthetic intermediate of formula

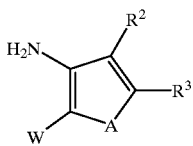

wherein A, R² and R³ are as defined above and W is —CN or —C(O)L; wherein L is a leaving group, such as a halo (preferably, bromo or chloro) or C1–C2 alkoxy radical.

In particular, in one aspect of the invention, there is provided a method for the therapeutic or prophylactic treatment of obesity in a warm-blooded animal which comprises administering to a warm blooded animal in need thereof a therapeutically or prophylactically effective amount of a compound of this invention.

In a related embodiment, there is provided a method for the treatment or prophylaxis of hyperphagia which comprises administering to a warm blooded animal in need thereof a therapeutically or prophylactically effective amount of a compound of of this invention or a pharmaceutically acceptable salt, ester or solvate thereof. Likewise, there is provided a method for the inhibition of the desire to eat which comprises administering to a warm blooded animal in need thereof an inhibition effective amount of a compound of this invention or a pharmaceutically acceptable salt, ester or solvate thereof.

In yet a further embodiment of the invention, given the relationship of obesity to diabetes, there is provided a method for the treatment or prophylaxis of diabetes which comprises administering to a warm blooded animal a therapeutically or prophylactically effective amount of a compound of this invention, or a pharmaceutically acceptable salt, ester or solvate thereof.

Given the apparent association of the NPY/NPY receptor signaling pathway, an additionally preferred embodiment of the invention includes a method for the therapeutic or prophylactic treatment of a NPY receptor mediated disease state in a warm-blooded animal which comprises administering to said animal a therapeutically or prophylactically effective amount of a compound of this invention, or a pharmaceutically acceptable salt, ester or solvate thereof. For example, the compounds of this invention may modulate a neuropeptide Y receptor mediated response, for example, by antagonizing the NPY receptor response. Especially preferred in this embodiment is the inhibition of an NPY5 receptor response.

The compounds and pharmacutical compositions of this invention are useful in the prophylaxis and/or treatment (comprising administering to a mammal, such as a human, an effective amount of such compound, a pharmaceutically acceptable salt thereof, or composition) of (1) diseases and disorders which can be effected or facilitated by modulating CRF, such as by antagonizing CRF, including but not limited to disorders induced or facilitated by CRF; (2) diseases and disorders which can be effected or facilitated by modulating CRH binding protein, such as by inhibiting CRH binding protein, including but not limited to disorders induced or facilitated by CRH binding protein; or (3) inflammatory disorders, such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfract dementia; amyotrophic lateral sclerosis; hypertension; tachycardia; congestive heart failure; osteoporosis; premature birth; and hypoglycemia in mammals, including humans.

CRF antagonists are effective in the prophylaxis and/or treatment of stress-related illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; cancer; infertility; muscular spasms; urinary incontinence; hypoglycemia and immune dysfunctions including stress induced immune dysfunctions, immune suppression and human immunodeficiency virus infections; and stress-induced infections in humans and animals.

CRH binding protein inhibitors are effective in the prophylaxis and/or treatment of Alzheimer's disease and obesity.

The compounds and pharmacutical compositions of this invention which inhibit the tyrosine kinase activity of the receptor for the epidermal growth factor (EGF) or of other protein tyrosine kinases are useful in the prophylaxis and/or treatment of benign or malignant tumors, effecting tumor regression, preventing the formation of tumor metastases and the growth of micrometastases, epidermal hyperproliferation (psoriasis), neoplasias of epithelial character (mammary carcinomas), and leukaemias. The compounds and pharmacutical compositions of this invention which inhibit one or more protein tyrosine kinases and/or protein serine/threonine kinases are useful in the prophylaxis and/or treatment of those disorders of the immune system in which one or more protein tyrosine kinases and/or protein serine/threonine kinases are involved and those disorders of the central or peripheral nervous system in which signal transmission by one or more protein tyrosine kinase and/or protein serine/threonine kinases are involved.

As utilized herein, the following terms shall have the following meanings:

"Alkyl", alone or in combination, means a saturated or partially unsaturated (provided there are at least two carbon atoms) straight-chain or branched-chain alkyl radical containing the designated number of carbon atoms; preferably 1–15 carbon atoms ($C_1$–$C_{15}$), more preferably 1–8 carbon atoms ($C_1$–$C_8$), more preferably 1–6 carbon atoms ($C_1$–$C_6$), more preferably 1–4 carbon atoms ($C_1$–$C_4$), more preferably 1–3 carbon atoms ($C_1$–$C_3$), and most preferably 1–2 carbon atoms ($C_1$–$C_2$). Examples of such radicals include methyl, ethyl, vinyl, n-propyl, allyl, isopropyl, n-butyl, 1-butenyl, 2-butenyl, 3-butenyl, sec-butyl, sec-butenyl, t-butyl, n-pentyl, 2-methylbutyl, 3-methylbutyl, 3-methylbutenyl, n-hexyl, 2-methylpentyl, 3-methylpentyl, 4-methylpentyl, 2,2-dimethylbutyl, 2,3-dimethylbutyl, and the like. A partially unsaturated alkyl preferably has at least one double or triple bond, more preferably 1–3 double or triple bonds, more preferably 1–2 double or triple bonds, and most preferably 1 double bond or 1 triple bond.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy, allyloxy and the like.

"Aryloxy-alkyl-", alone or in combination, means an alkyl radical as defined above wherein a hydrogen radical is replaced with a aryloxy radical, such as phenoxymethyl.

"Alkyl-aryloxy-", alone or in combination, means an aryloxy radical wherein a hydrogen radical of the aryl moiety is replaced with a alkyl radical, such as 4-methylphenoxy.

"Alkylthiol", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio, allylthio and the like.

The term "carbocyclic", alone or in combination, refers to an organic cyclic moiety in which the cyclic skeleton is comprised of only carbon atoms whereas the term "heterocyclic", alone or in combination, refers to an organic cyclic moiety in which the cyclic skeleton contains one or more, preferably 1–4, more preferably 1–3, most preferably 1–2, heteroatoms selected from nitrogen, oxygen, or sulfur and which may or may not include carbon atoms.

The term "cycloalkyl", alone or in combination, refers to a saturated or partially unsaturated (preferably 1–2 double bonds, more preferably 1 double bond) carbocyclic moiety containing the indicated number of carbon atoms. The term "$C_3$–$C_{10}$ cycloalkyl", therefore, refers to an organic cyclic substituent in which three to ten carbon atoms form a three, four, five, six, seven, eight, nine or ten-membered ring, including, for example, a cyclopropyl, cyclobutyl, cyclopentyl, cyclopentenyl, cyclohexenyl, cyclohexyl, cycloheptyl, cyclooctyl and the like ring. As used herein, "cycloalkyl" may also refer to two or more cyclic ring systems which are fused to form, for example, bicyclic, tricyclic, or other similar bridged compounds (e.g. adamantanyl).

"Aryl" refers to an aromatic carbocyclic group having a single ring, for example, a phenyl ring, multiple rings, for example, biphenyl, or multiple condensed rings in which at least one ring is aromatic, for example, naphthyl, 1,2,3,4,-tetrahydronaphthyl, anthryl, or phenanthryl, which can be unsubstituted or substituted with one or more (preferably 1–5, more preferably 1–4, more preferably 1–3, most preferably 1–2) other substituents as defined above. The substituents attached to a phenyl ring portion of an aryl moiety in the compounds of this invention may be configured in the ortho-, meta- or para-orientations. Examples of typical aryl moieties included in the scope of the present invention may include, but are not limited to, the following:

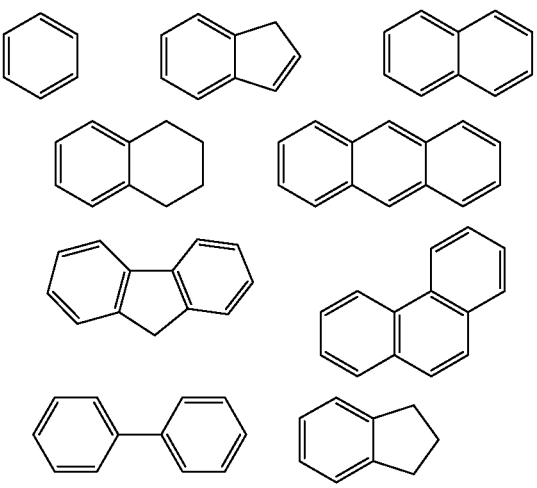

"Aryloxy" refers to an aryl group, as defined above, directly attached to an oxygen atom, which in turn is bonded to another atom. Thus, for example, benzyloxy, refers to a benzyl moiety linked through an oxygen atom to another substituent (e.g. —O—$CH_2$-phenyl).

"Heterocycle" or "heterocyclic" refers to a saturated, unsaturated or aromatic carbocyclic group having a single ring, multiple rings or multiple condensed rings, and having at least one hetero atom such as nitrogen, oxygen or sulfur within at least one of the rings. "Heteroaryl" refers to a heterocycle in which at least one ring is aromatic. Any of the heterocyclic or heteroaryl groups can be unsubstituted or optionally substituted with one or more groups as defined above and one or more, preferably 1–2, more preferably one, "oxo" group. Further, bi- or tri-cyclic heteroaryl moieties may comprise at least one ring which is either completely or partially saturated. "Heterocyclyl" refers to a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms.

As one skilled in the art will appreciate such heterocyclic moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

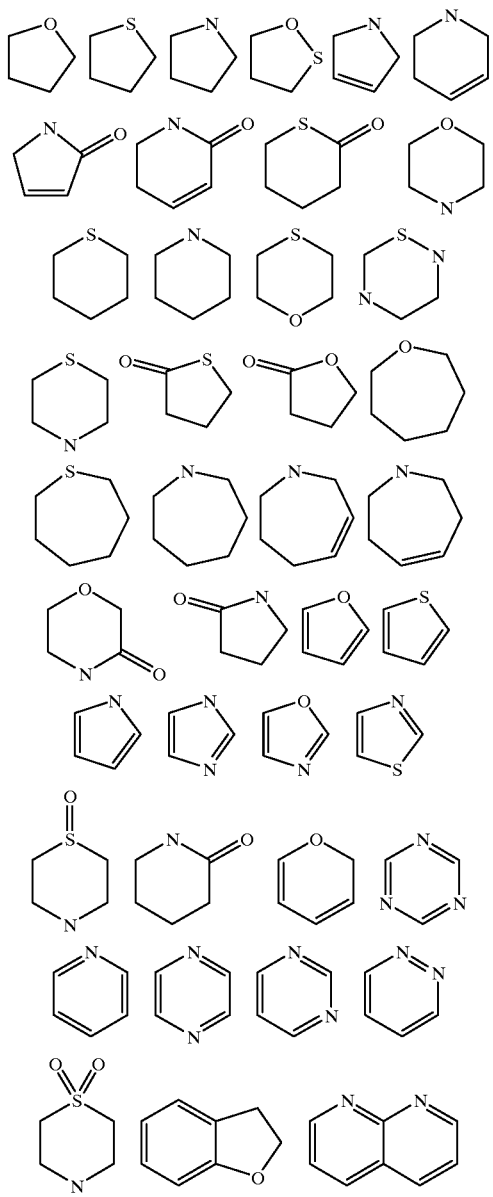

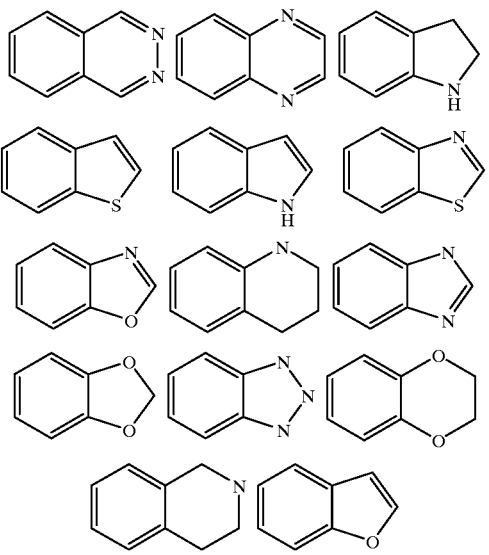

The term "halo" or "halogen" refers to a halogen atom which may include fluoro, chloro, bromo and iodo. Preferred halo groups include chloro, bromo and fluoro with chloro and fluoro being especially preferred.

The symbols used above have the following meanings:

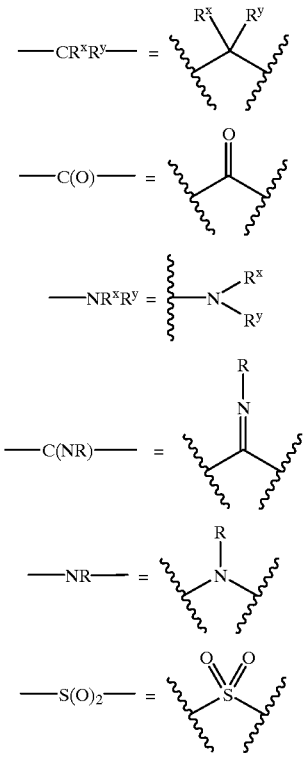

"modulate" as used herein refers to the ability of a compound of this invention to interact with a receptor, target gene or other gene product to (a) up-regulate the activity of that receptor, target gene or other gene product or biological effect (for example, as an agonist) or (b) down-regulating the receptor, target gene or other gene product or other biological effect, particularly by acting as an antagonist for the receptor, target gene or other gene product. Additionally, encompassed by "modulate" is the ability of a compound of the invention to effect a desired biological response, even if that response occurs upstream or downstream one or more steps in a signaling pathway from the receptor, target gene or other gene product in question. Thus, by way of example, the compounds of the invention may provide the desired effect by interacting with an NPY receptor, particularly an NPY5 receptor, to act as an agonist or antagonist to that receptor or at some point, either upstream or downstream, in the signaling pathway for the NPY receptor to effect the desired therapeutic or prophylactic response.

"Pharmaceutically acceptable salt", as used herein, refers to an organic or inorganic salt which is useful in the treatment of a warm-blooded animal. Such salts can be acid or basic addition salts, depending on the nature of the compound of this invention. For examples of "pharmacologically acceptable salts," see Berge et al., J. Pharm. Sci. 66:1 (1977). As used herein, "warm blooded animal" includes a mammal, including a member of the human, equine, porcine, bovine, murine, canine or feline species.

In the case of an acidic moiety in a compound of this invention, a salt may be formed by treatment of a compound of this invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine. An especially preferred salt is a sodium or potassium salt of a compound of this invention.

With respect to basic moieties, a salt is formed by the treatment of a compound of this invention with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic and the like organic acids. An especially preferred salt of this type is a hydrochloride or sulfate salt of a compound of this invention.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1, 3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the invention may have one or more asymmetric carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

While it may be possible to administer a compound of the invention alone, in the methods described, the compound administered normally will be present as an active ingredient in a pharmaceutical formulation. Thus, in one another embodiment of the invention, there is provided a formulation comprising a compound of this invention in combination with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilman's: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, e.g. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

The compounds of the invention may also be administered as an aerosol. The term "aerosol" includes any gasborne suspended phase of a compound of the invention which is capable of being inhaled into the bronchioles or nasal passages. Specifically, aerosol includes a gas-borne suspension of droplets of the desired compound, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the invention, the preferred range of concentration of the compounds of the invention is 0.1–100 milligrams (mg)/milliliter (mL), more preferably 0.1–30 mg/mL, and most preferably 1–10 mg/mL. Usually the solutions are buffered with a physiologically compatible buffer such as phosphate or bicarbonate. The usual pH range is from about 5 to about 9, preferably from about 6.5 to about 7.8, and more preferably from about 7.0 to about 7.6. Typically, sodium chloride is added to adjust the osmolarity to the physiological range, preferably within 10% of isotonic. Formulation of such solutions for creating aerosol inhalants is discussed, for example, in Remington's, supra; See, also, Ganderton and Johens, "Drug Delivery to the Respiratory Tract, Ellis Horwood (1987); Gonda, "Critical Review in Therapeutic Drug Carrier Systems" 6 273–313 (1990); and Raeburn et al. *J. Pharmacol. Toxicol. Methods*. 27 143–159 (1992).

Solutions of a compound of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the invention connected to or contained within any of the conventional means for creating aerosols in asthma medication, such as metered dose inhalers, jet nebulizers, or ultrasonic nebulizers. Optionally such devices may include a mouthpiece fitted around the orifice.

Further, there are provided a device which may comprise a solution of a compound of the instant invention in a nasal sprayer.

A dry powder comprising a compound of the invention, optionally with an excipient is another embodiment. This may be administered by a drug powder inhaler containing the described powder.

Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragées.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The preferred dosage for use in the methods of the invention, however, is in the range of about 0.01 mg/kg to about 100 mg/kg of body weight, preferably from about 0.1 mg/kg to about 50 mg/kg, up to 4 times per day. Whatever the dosage form, one skilled in the art will recognize that the dosage administered will be adjusted to factors such as the age, weight, and condition of the patient involved. The skilled practitioner will be familiar with how to adjust the dosage to accommodate these and other factors.

Figure 1B:
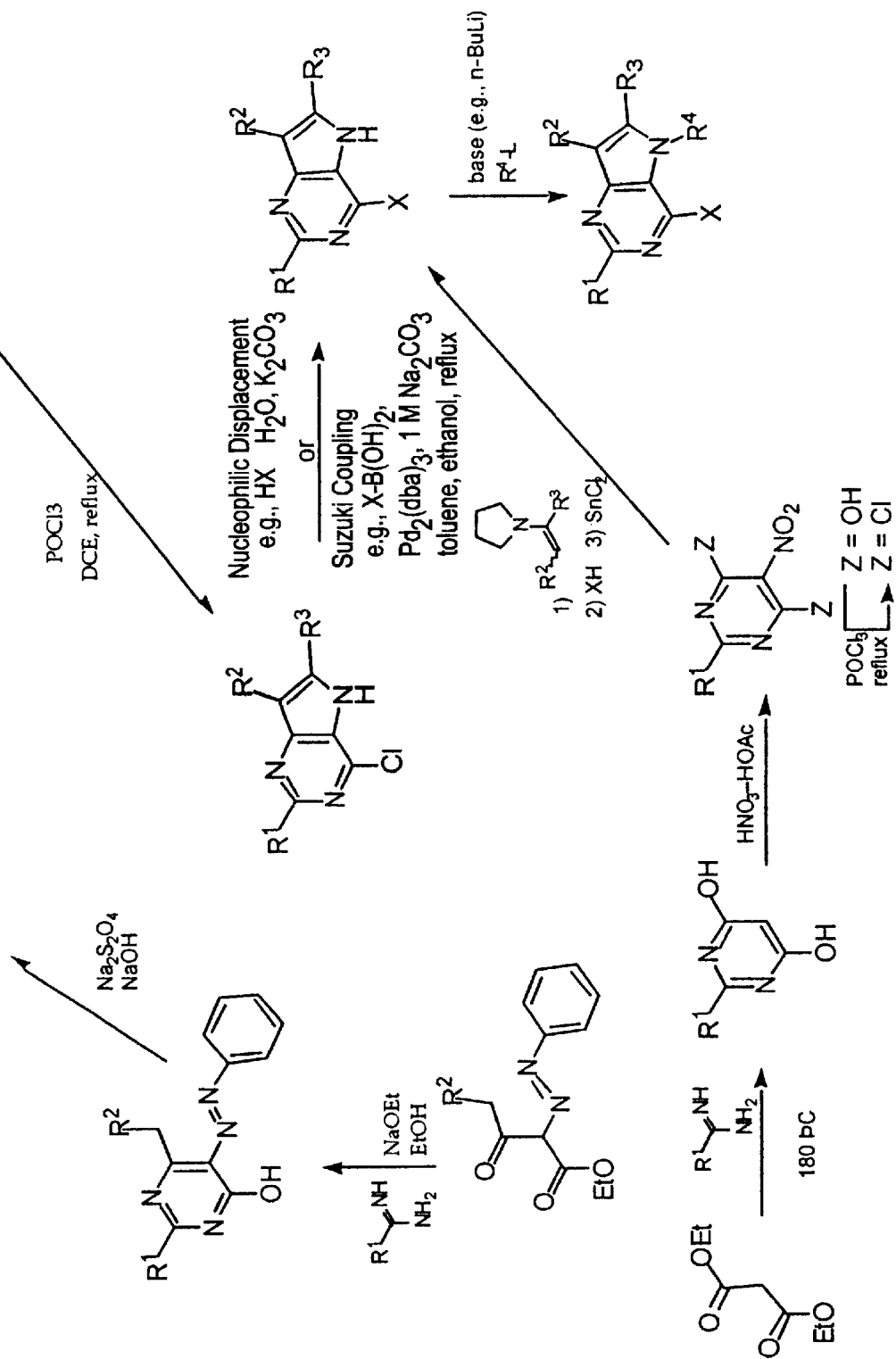
Figure 2:
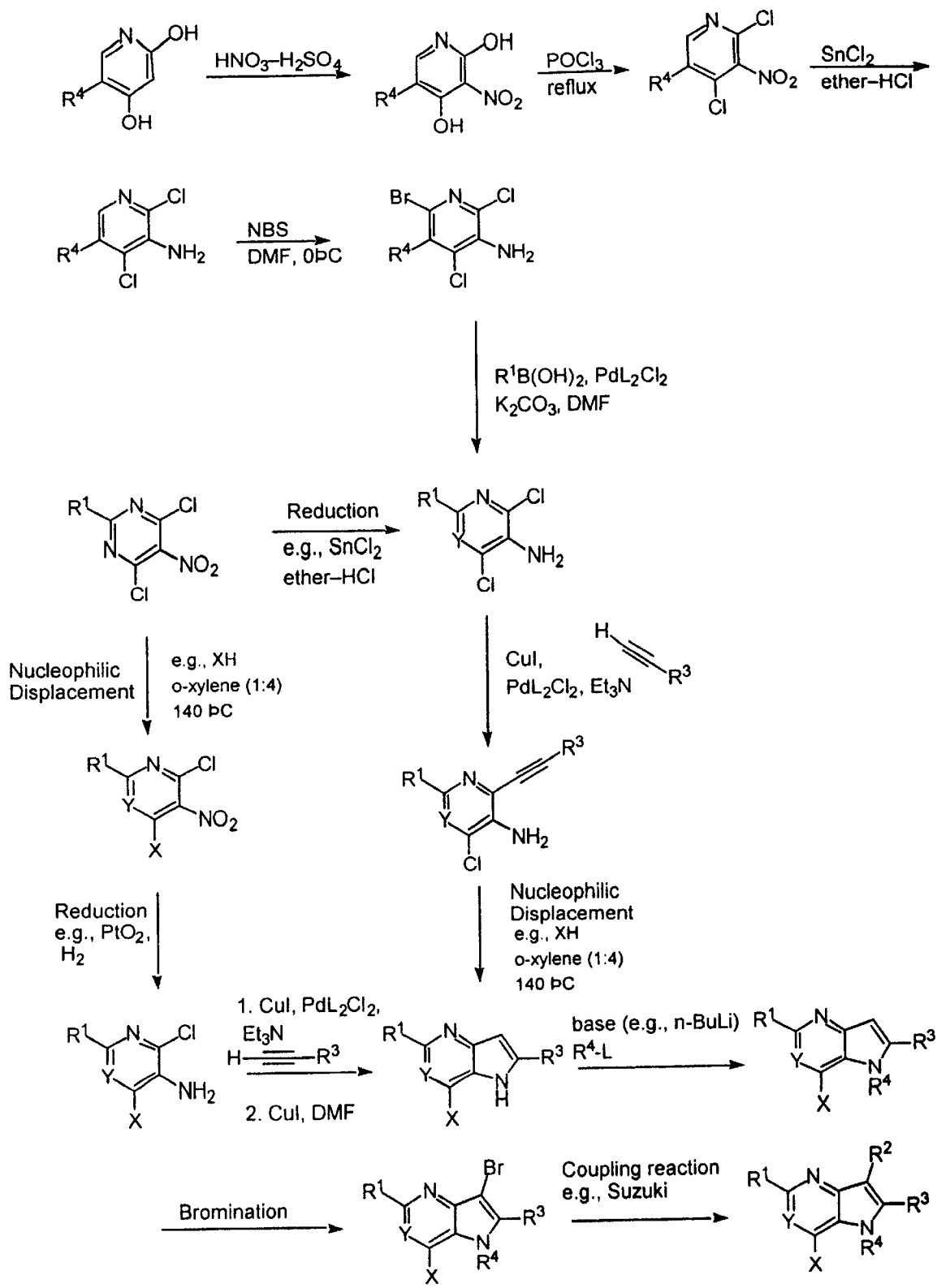
FIG. 2 outlines a general reaction scheme for the synthesis of pyrrolo[3,2-d]pyridines and pyrrolo[3,2-d]pyrimidines.
Figure 3:
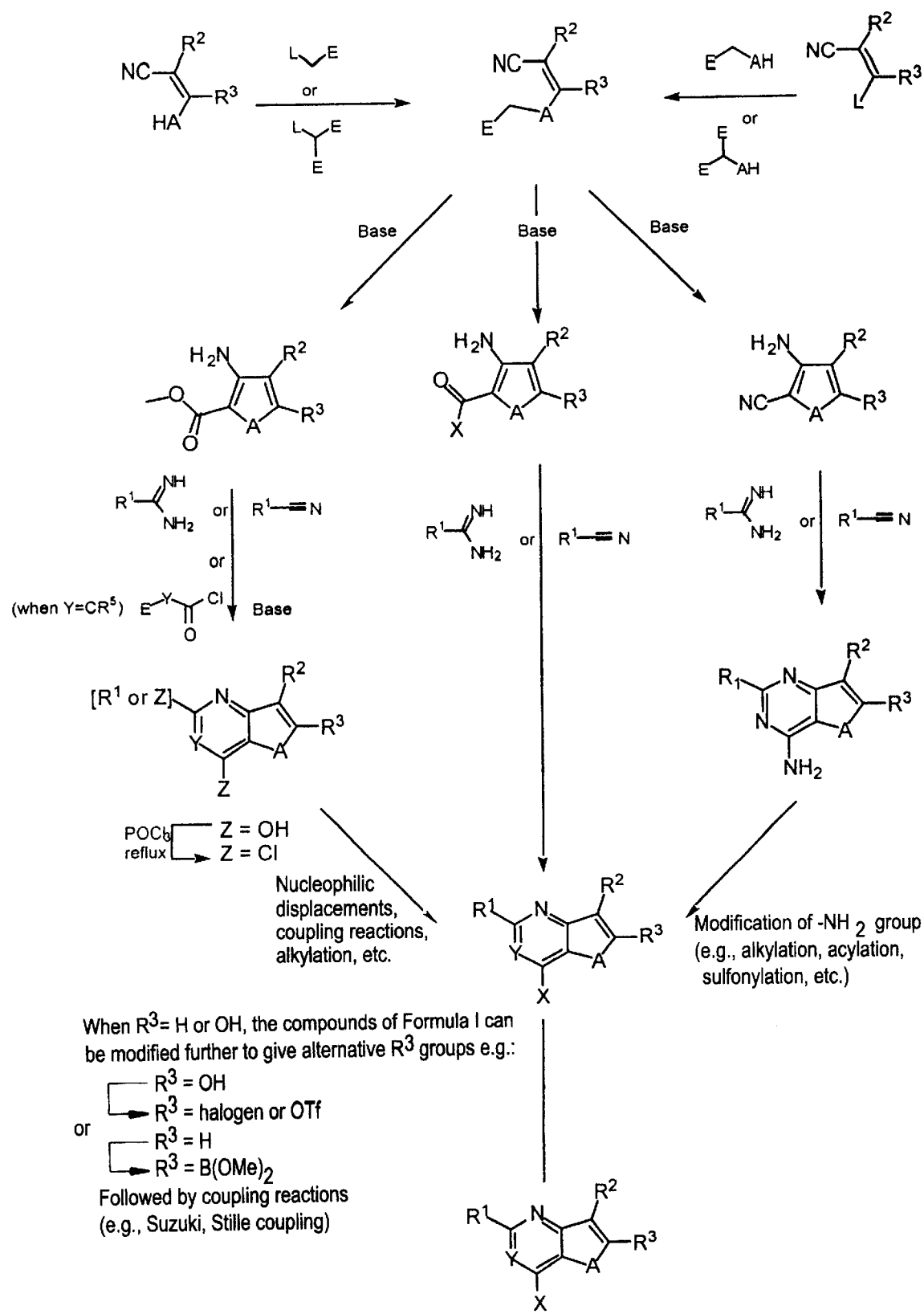
FIG. 3 provides a general process for the synthesis of thiopheno-, furano-, and pyrrolo-[3,2-d]-pyrimidines and -pyridines of the invention.
Figure 4:
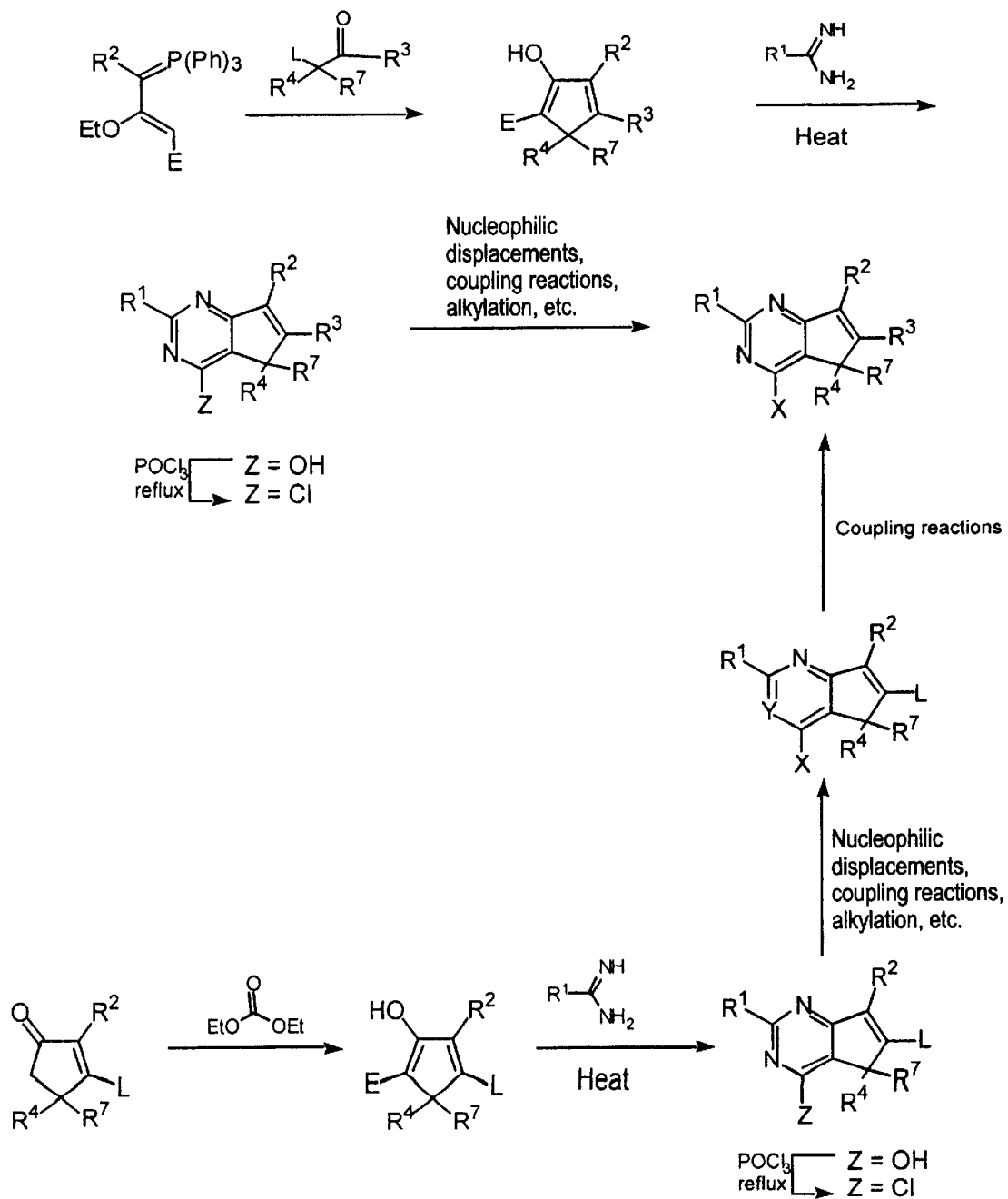
FIG. 4 provides a general process for the synthesis of 5-hydrocyclopenta[2,1-d]pyrimidines of the invention.

To better understand the synthesis of the compounds of this invention, FIG. 1 outlines a general reaction scheme for the synthesis of pyrrolo[3,2-d]pyrimidines of the invention. FIG. 2 also outlines a general reaction scheme for the synthesis of pyrrolo[3,2-d]pyridines and pyrrolo[3,2-d] pyrimidines while FIG. 3 provides a general process for the synthesis of thiopheno-, furano-, and pyrrolo-[3,2-d]-pyrimidines and -pyridines of the invention. Further, FIG. 4 provides a general process for the synthesis of 5-hydrocyclopenta-[2,1-d]pyrimidines of the invention.

The reactions described in the figures may be carried out in any number of solvents in which the reactants may be mutually soluble, including, for example, tetrahydrofuran, benzene, toluene, chloroform, dichloromethane, N,N-dimethylformamide, ethyl ether, dioxane, water, acetonitrile, or the like. Generally the reaction is carried out at a temperature of between −80° C. and 150° C., preferably, however, at room temperature. In certain cases, as noted in the examples provided herein, however, the temperature of the reaction may reach as high as or exceed about 360° C.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC using, for example, dilute trifluoroacetic acid in water, acetonitrile, or methanol mixtures as eluent), column chromatography, flash chromatography, radial chromatography, trituration, and the like.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, Ed., Plenum Press, New York, N.Y.; and "Protective Groups in Organic Synthesis," Greene, Ed., John Wiley & Sons, New York, N.Y. (1981) for the teaching of protective groups which may be useful in the preparation of compounds of the present invention.

Alternate means beyond those described above for preparing the compounds of the invention will be apparent to one skilled in the art and the noted general procedures are not to be construed as limiting the invention. To more fully understand the invention, including methods of preparing compounds of the invention, the following non-limiting examples are provided. The reader will appreciate that starting materials not otherwise described herein are either available commercially or can be prepared by methods generally known in the art.

Unless otherwise noted, all materials were obtained from commercial suppliers and used without further purification. Anhydrous solvents such as dimethylformamide (DMF), tetrahydrofuran (THF), dichloromethane ($CH_2Cl_2$), and toluene, dioxane were obtained from Aldrich Chemical Company in Sure/Seal bottles. All reactions involving air- or moisture-sensitive compounds were performed under a $N_2$ atmosphere. Flash chromatography was performed using ICN Biomedicals (SiliTech 32–63D 60A). Thin-layer chromatography (TLC) was performed with Analtech or Whatman silica gel TLC plates (250 $\mu$m). Preparatory TLC was performed with Whatman silica gel TLC plates (2000 $\mu$m). $^1$H NMR spectra were determined with superconducting FT NMR spectrometers operating at 400 and 500 MHz. Chemical shifts are expressed in ppm downfield from internal tetramethylsilane. Significant $^1$H NMR data are reported in the following order: multiplicity (s, singlet; d, doublet; t, triplet; q, quartet; m, multiplet; quin, quintet), number of protons, and coupling constants in Hz. Elemental analyses were performed by Atlantic Microlab, Inc., Norcross, Ga. Melting points were determined with a Buchi 535 capillary melting point apparatus and are uncorrected. Low resolution mass spectra (MS) were determined on a Perkin Elmer-SCIEX API 165 mass spectrometer using APCI or ES ionization modes (positive or negative). High resolution mass spectra (HRMS) were performed by Mass Consortium, San Diego, Calif. using FAB ionization.

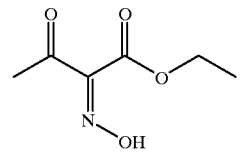

EXAMPLE 1

(a) Ethyl 2-(hydroxyimino)-3-oxybutyrate.

A solution of ethyl acetoacetate (Aldrich Chemical Company) (37.5 g, 0.279 mol) in acetic acid (55 mL) was cooled in an ice-water bath. A solution of sodium nitrite (26.5 g, 0.384 mol) in distilled $H_2O$ (60 mL) was added to the cooled reaction mixture over a 0.5 h period via a pressure-equalizing addition funnel. Upon this addition, the colorless reaction mixture turned a red-orange color. The cold bath was removed and the solution was allowed to stir at room temperature for 2 h. The red solution was transferred to a separatory funnel and extracted with $Et_2O$ (3×100 mL). The organic extracts were placed in a 1-L beaker equipped with a magnetic stirring bar. Saturated aqueous $NaHCO_3$ was added and the solution was stirred vigorously. Additional portions of solid $NaHCO_3$ were added to neutralize the solution. The aqueous layer was separated and extracted with ether. The organic layers were combined, washed with water and saturated NaCl, and dried over $MgSO_4$. The solution was filtered and concentrated with a rotary evaporator to give 42.5 g (95%) of the title compound as a pale yellow oil. $^1$H NMR ($CDCl_3$; 500 MHz): δ 1.36 (t, 3, J=7.1), 2.42 (s, 3), 4.39 (q, 2, J=7.1), 9.05 (m, 1). MS m/z: 160 (M+1). This material was used without further purification.

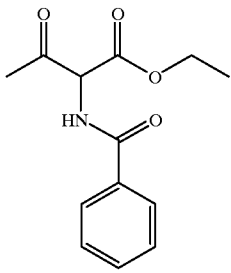

(b) Ethyl 3-oxo-2-(phenylcarbonylamino)butanoate.

To a 1-L, round-bottomed flask was added ethyl 2-(hydroxyimino)-3-oxybutyrate (25.0 g, 0.157 mol), $H_2SO_4$ (30% w/v) (230 mL) and crushed ice (250 g). This solution was cooled in an ice-salt-water bath and the internal temperature was monitored with an alcohol thermometer. Powdered zinc (100 mesh—Aldrich Chemical Company) (30.0 g, 0.459 mol, 2.9 equiv) was added to this cooled solution portionwise via a powder addition funnel. The temperature of the reaction was maintained between 0–10° C. After the addition of the zinc was complete the reaction mixture was allowed to stir at 0° C. for 0.5 h. The solution was filtered through a fritted funnel into a clean 1-L round-bottomed flask. This clear, colorless solution was cooled in an ice-water bath and sodium acetate trihydrate (Aldrich Chemical Company) (162.5 g, 1.19 mol) was added with stirring. Benzoyl chloride (Aldrich Chemical Company) (18.3 mL, 22.1 g, 0.157 mol) was slowly added to the resulting cloudy solution via a syringe. After the addition was complete, the cold bath was removed and the solution was allowed to stir at room temperature for 24 h. The yellow reaction mixture was extracted with $CH_2Cl_2$ (3×100 mL). The organic layers were washed with saturated aqueous $NaHCO_3$, dried over $MgSO_4$, filtered, and concentrated on a rotary evaporator to give 30.3 g of a yellow oil. This material was purified by flash chromatography on silica gel with 4:1 hexanes: EtOAc as eluant to give 20.0 g (51%) of the title compound as a viscous pale-yellow oil. $^1$H NMR (CDCl$_3$; 500 MHz): δ 1.33 (t, 3, J=7.1), 2.46 (s, 3), 4.31 (m, 2), 5.43 (d, 1, J=6.4), 7.28 (br m, 1), 7.46 (t, 2, J=7.6), 7.54 (m, 1), 7.85 (d, 2, J=7.2). MS m/z: 250 (M+1), 178 (base).

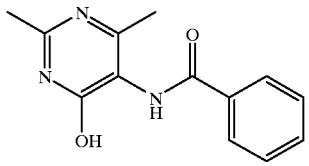

(c) 2,6-Dimethyl-4-hydroxy-5-benzamidopyrimidine.

Absolute EtOH (150 mL) was added to an oven-dried round-bottomed flask, and small pieces of sodium (4.95 g, 0.215 mol) were added portionwise. A reflux condenser was attached to the flask and the solution was allowed to stir at room temperature until all of the sodium was consumed. Acetamidine hydrochloride (Aldrich Chemical Company) (9.95 g, 0.105 mol) was added in one portion and the resulting creamy white solution was allowed to stir at room temperature for 0.5 h. In a separate flask ethyl 3-oxo-2-(phenyl carbonylamino)butanoate (23.8 g, 0.956 mol) was dissolved in absolute EtOH (30 mL). The acetamidine solution was filtered through a plug of celite into the ketoester solution. As this solution was added, the reaction mixture turned from an orange to a dark brown color. The mixture was placed under a $N_2$ atmosphere and allowed to stir at room temperature overnight. As the reaction proceeded solids precipitated out of solution to give a thick brown-orange mixture. The reaction mixture was filtered through a fritted funnel and the solids were washed with EtOH. The solids were dissolved in distilled $H_2O$ and HCl (conc.) was added to acidify the solution to a pH of 4–5 (pH paper). Upon acidification solids precipitated out of solution. The solution was cooled in an ice-water bath, the solids were filtered, washed with cold water and dried in a vacuum oven to give 7.59 g (33%) of the title compound as a white powder. The EtOH filtrate was concentrated with a rotary evaporator to give 13 g of a sticky orange oil. This material was purified by flash chromatography on silica gel with 95:5 $CH_2Cl_2$:MeOH as eluant to give an additional 2.61 g (11%) of the title compound as fluffy pale-yellow flakes (total yield 10.2 g (44%)). Mp: 279–281° C. (lit. mp=282° C.; (E. A. Falco et al., J. Am. Chem. Soc., 1952, 74, 4897–4902). $^1$H NMR (DMSO-d$_6$; 500 MHz): δ 2.09 (s, 3), 2.28 (s, 3), 7.51 (t, 2, J=7.1), 7.58 (t, 1, J=7.2), 7.96 (d, 2, J=7.4), 9.51 (s, 1), 12.51 (br s, 1). MS m/z: 244 (M+1). Anal. Calcd for $C_{13}H_{13}N_3O_2$: C, 64.19; H, 5.39; N, 17.27. Found: C, 64.10, H, 5.40, N, 17.19.

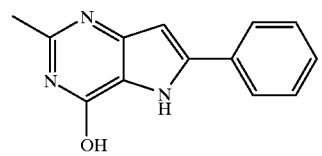

(d) 2-Methyl-6-phenylpyrrolo[3,2-d]pyrimidin-4-ol.

Method A: To an oven-dried, 250-mL, round-bottomed flask was added absolute EtOH (45 mL). Small pieces of sodium metal (2.87 g, 0.125 mol) were added portionwise. After all of the sodium was consumed, 2, 6-dimethyl-4-hydroxy-5-benzamidopyrimidine (10.1 g, 41.7 mol) was added in one portion via a powder addition funnel. An additional portion of EtOH (20 mL) was added to rinse the last portion of the amide from the funnel. The reaction mixture was heated at reflux for 0.25 h until all of the solids dissolved to give an orange solution. The condenser was replaced with a short-path distillation head and the EtOH was distilled off under a $N_2$ atmosphere. The resulting solids were scraped off the sides of the flask with a spatula and heated with a heating mantle at 360° C. for 20 min. The residue was allowed to cool to room temperature, dissolved in distilled $H_2O$ (35 mL), and HCl (conc.) was added portionwise to adjust the pH of the solution to 4–5 (pH paper). The resulting precipitate was filtered and dried in a vacuum oven to give 6.38 g of a tan solid. This material was dissolved in 3 N NaOH (~30 mL), and the resulting dark brown solution was filtered through a fritted funnel. Acetic acid was added to the filtrate with stirring. The resulting solids were filtered, washed with distilled $H_2O$, recrystallized from EtOH and dried in a vacuum oven to give 1.45 g (15%) of the title compound as a tan powder. Mp: >280° C. (lit mp=322(dec.); K. Tanaka et al., Chem. Pharm. Bull. 1964, 12, 1024–1030). $^1$H NMR (DMSO-d$_6$; 400 MHz): δ 2.31 (s, 3), 6.77 (d, 1, J=2.2), 6.77 (d, 1, J=2.2), 7.36 (tm, 1, J=6.5), 7.43 (t, 2, J=7.6), 7.93 (dd, 2, J=1.4, 7.2), 11.80 (s, 1), 12.28 (s, 1). MS m/z: 226 (M+1). Anal. Calcd for $C_{13}H_{11}N_3O$: C, 69.32; H, 4.92; N, 18.65. Found: C, 69.24; H, 5.97; N, 18.58.

Method B: To an oven-dried, 100-mL, round-bottomed flask equipped with a glass-covered magnetic stir bar was added absolute EtOH (35 mL). Small pieces of sodium metal (Aldrich Chemical Company) (1.89 g, 0.082 mol) where added portionwise. After all of the sodium was consumed, 2,6-dimethyl-4-hydroxy-5-benzamido pyrimidine (5.0 g, 0.02 mol) was added in one portion via a powder addition funnel. An additional portion of EtOH (2 mL) was added to rinse the last portion of the amide from the funnel. A reflux condenser was attached to the flask and the mixture was heated at reflux for 0.5 h until all of solid dissolved to give a yellow solution. The reflux condenser was replaced with a short-path distillation head and the EtOH was distilled off under a $N_2$ atmosphere. The resulting yellow solids were heated with a sand bath at 340° C. for 15–20 min. The residue was allowed to cool to room temperature and dissolved in distilled water (50 mL). The resulting brown solution, which contained black pieces of solids, was filtered through a Buchner funnel into a round-bottomed flask. An additional portion of water (50 mL) was added to rinse the reaction flask. The dark-brown solution (pH=12) was transferred to a 250-mL beaker. HCl (conc.) was added dropwise to adjust the pH of the solution to 4–5 (pH paper). Precipitate formed instantly upon acidification. The suspension was stirred for 2 h, filtered, washed by cold water and dried in a vacuum oven at 40° C. overnight to give 3.20 g (69%) of the title compound as a fine tan powder (98% pure by HPLC). $^1$H NMR of this material was identical to that obtained in Method A. This material was used without further purification.

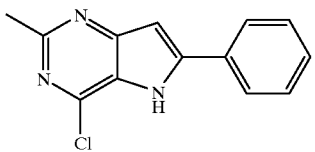

(e) 4-Chloro-2-methyl-6-phenylpyrrolo[3,2-d]pyrimidine.

Method A: Phosphorus oxychloride (Aldrich Chemical Company) (2.46 mL, 4.05 g, 26.4 mmol), N,N-diethylaniline (Aldrich Chemical Company) (1.2 mL, 1.12 g, 7.5 mmol), 1,2-dichloroethane (4 mL) and 2-methyl-6-phenylpyrrolo[3,2-d]pyrimidin-4-ol (0.50 g, 2.22 mmol) were added to a 50-mL, oven-dried, round-bottomed flask. The resulting dark-red solution was placed under $N_2$ and heated at reflux for 3 h. The solution was concentrated with a rotary evaporator to give a dark red oil. This material was cooled in an ice-water bath and distilled $H_2O$ was added. The solution was filtered through a fritted funnel, and the filtrate was concentrated with a rotary evaporator to give a wet solid. This crude material was free based by the addition of aqueous $NH_4OH$ and extracted into EtOAc. The organic layer was dried over $MgSO_4$, filtered and concentrated with a rotary evaporator to give 0.98 g of an orange oil. This material was purified by flash chromatography on silica gel with 4:1 hexanes:EtOAc followed by 1:1 hexanes:EtOAc as eluant to give 0.24 g (44%) of the title compound as a tan solid. $^1$H NMR (CDCl$_3$; 400 MHz): δ 2.76 (s, 3), 6.90 (s, 1), 7.43 (m, 3), 7.80 (dm, 2, J=6.5), 10.17 (br s, 1). MS m/z: 243 (M$^+$), 208 (base).

Method B: Phosphorus oxychloride (Aldrich Chemical Company) (30 mL, 0.322 mol) was added to a 100-mL, oven-dried, round-bottomed flask containing a magnetic stir bar and 2-methyl-6-phenylpyrrolo[3,2-d]pyrimidin-4-ol (2.8 g, 0.012 mol). The resulting dark-red solution was heated at 120° C. and the reaction was monitored by HPLC. When the starting material was totally consumed (~24 h) the solution was concentrated with a rotary evaporator to give a dark red oil. This material was cooled in an ice-water bath and 100 mL of ice-$NH_4OH$-$H_2O$ was added. HCl (conc.) was added dropwise to adjust the pH to 7–8 (pH paper). The neutralized solution was extracted into 200 mL of EtOAc. The organic layer was dried over $MgSO_4$, filtered, concentrated with a rotary evaporator and dried in a vacuum oven at 40° C. overnight to give 2.21 g (73%) of the title compound as a tan solid (94% pure by HPLC). $^1$H NMR of this material was identical to that obtained in Method A. This material was used without further purification.

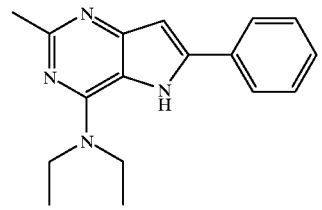

(f) Diethyl(2-methyl-6-phenylpyrrolo[2,3-e]pyrimidin-4-yl) amine.

Diethylamine (Aldrich Chemical Company) (0.66 mL, 0.47 g, 6.4 mmol), distilled $H_2O$ (15 mL), 4-chloro-2-methyl-6-phenylpyrrolo[3,2-d]pyrimidine (0.24 g, 0.98 mmol) and $K_2CO_3$ (0.68 g, 4.92 mmol) were added to a round-bottomed flask and placed under a $N_2$ atmosphere. The resulting suspension was heated at reflux for 6 h. Additional portions of diethylamine (1.32 mL, 13 equiv) and $K_2CO_3$ (0.68 g) were added and the reaction was heated at reflux overnight. The solution was allowed to cool to room temperature and $CH_2Cl_2$ was added. The organic layer was separated, dried over $MgSO_4$, filtered and concentrated with a rotary evaporator to give 0.24 g of a light orange solid. This material was purified by flash chromatography on silica gel with 1:1 hexanes:EtOAc as eluant to give 0.19 g (68%) of the title compound as an off-white powder. Mp: 184–185° C. (lit mp=183–185° C.; G. A. Modnikova et al., *Pharm. Chem. J.*, 1988, 22, 135–141). $^1$H NMR (CDCl$_3$; 500 MHz): δ 1.37 (t, 6, J=7.0), 2.57 (s, 3), 3.77 (q, 4, J=7.0), 6.75 (s, 1), 7.38 (t, 1, J=7.3), 7.47 (t, 2, J=7.5), 7.63 (d, 2, J=7.6), 8.13 (br s, 1). MS m/z: 281 (M+1). Anal Calcd for $C_{17}H_{20}N_4$: C, 72.83; H, 7.19; N, 19.98. Found: C, 73.02; H, 7.26; N, 19.76.

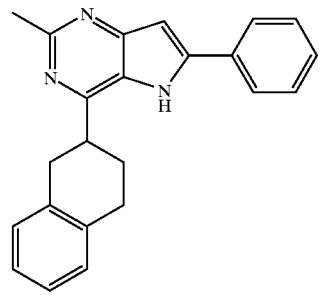

EXAMPLE 2

2-Methyl-6-phenyl-4-(2-1,2,3,4-tetrahydroquinolino-2-yl) pyrrolo[3,2-d]pyrimidine.

To a 5-mL Wheaton vial was added was added 4-chloro-2-methyl-6-phenylpyrrolo[3,2-d]pyrimidine (Example 1(e)) (100 mg, 0.41 mmol) and 1,2,3,4-tetrahydroquinoline (Aldrich Chemical Company) (0.26 mL, 2.05 mmol). A solution of $K_2CO_3$ (0.567 g, 4.1 mmol) in $H_2O$ (2.5 mL) was added, the vial was securely capped, and the reaction mixture was heated at 120° C. for 4 h. After cooling to room temperature, EtOAc (1 mL) was added. The resulting precipitate was collected by filtration, washed with distilled H$_2$O and EtOAc, and dried in a vacuum oven to give 105 mg (75%) of the title compound as an off-white solid. Mp: 251–253° C. (dec.). $^1$H NMR (CDCl$_3$; 400 MHz): δ 2.63 (s, 3), 3.09 (t, 2, J=5.9), 4.13 (t, 2, J=5.9), 5.02 (s, 2), 6.78 (s, 1), 7.21–7.25 (m, 4), 7.38–7.50 (m, 3), 7.66 (d, 2, J=7.3), 8.37 (br s, 1). MS m/z: 341 (M+1), 339 (M−1). Anal. Calcd for C$_{22}$H$_{20}$N$_4$: C, 77.62; H, 5.92; N, 16.46. Found: C, 77.55; H, 5.91; N, 16.42.

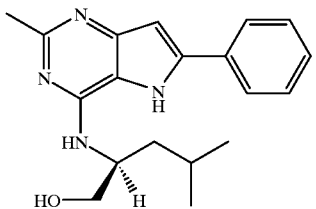

EXAMPLE 3
(S)-4-Methyl-2-[(2-methyl-6-phenylpyrrolo[2,3-e]pyrimidin-4-yl)amino]pentan-1-ol.

This compound was prepared according to the method described in Example 2 by employing 4-chloro-2-methyl-6-phenylpyrrolo[3,2-d]pyrimidine (Example 1(e)) (100 mg, 0.41 mmol), (S)-(+)-leucinol (Aldrich Chemical Company) (0.26 mL, 2.05 mmol) and K$_2$CO$_3$ (0.567 g, 4.1 mmol) in H$_2$O (2.5 mL) to give 75 mg (56%) of the title compound as shiny off-white crystals. Mp: 267–269° C. (dec.). $^1$H NMR (DMSO-d$_6$; 400 MHz): δ 0.91–0.95 (m, 6), 1.48–1.52 (m, 2), 1.66–1.70 (m, 1), 2.37 (s, 3), 3.50 (br s, 2), 4.39 (br s, 1), 4.90 (br s, 1), 6.65 (d, 1, J=8.4), 6.72 (s, 1), 7.36–7.52 (m, 3), 7.79 (d, 2, J=7.9), 11.35 (br s, 1). MS m/z: 325 (M+1), 323 (M−1). Anal. Calcd for C$_{19}$H$_{24}$N$_4$O: C, 70.34; H, 7.46; N, 17.27. Found: C, 70.14; H, 7.35; N, 17.13.

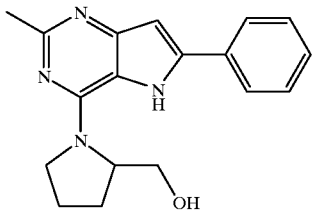

EXAMPLE 4
(S)-[1-(2-methyl-6-phenylpyrrolo[2,3-e]pyrimidin-4-yl)pyrrolidin-2-yl]methan-1-ol.

This compound was prepared according to the method described in Example 2 by employing 4-chloro-2-methyl-6-phenylpyrrolo[3,2-d]pyrimidine (Example 1(e)) (70 mg, 0.287 mmol), (S)-(+)-2-pyrrolidinemethanol (Aldrich Chemical Company) (0.14 mL, 1.44 mmol) and K$_2$CO$_3$ (0.397 g, 2.87 mmol) in H$_2$O (2 mL) to give 61.9 mg (70%) of the title compound as an off-white solid. An analytical sample was obtained by recrystallization from EtOH. Mp: 255–256° C. $^1$H NMR (CDCl$_3$; 500 MHz): δ 2.06–2.14 (m, 4), 2.54 (s, 3), 3.76 (d, 1, J=9.23), 3.84 (dd, 1, J=2.0, 11.1), 3.96–3.98 (m, 1), 4.11 (q, 1, J=7.6, 7.9), 4.55–4.57 (m, 1), 6.68 (s, 1), 7.35–7.45 (m, 3), 7.61 (d, 2, J=7.4), 9.17 (br s, 1). MS m/z: 167 (base), 307 (M−1). Anal. Calcd for C$_{18}$H$_{20}$N$_4$O: C, 70.11; H, 6.54; N, 18.17. Found: C, 70.00; H, 6.59; N, 18.11.

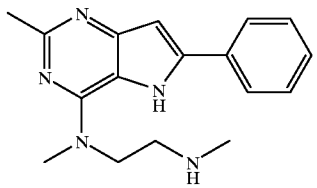

EXAMPLE 5

Methyl[2-(methylamino)ethyl](2-methyl-6-phenyl pyrrolo[2,3-e]pyrimidin-4-yl)amine.

This compound was prepared according to the method described in Example 2 by employing 4-chloro-2-methyl-6-phenylpyrrolo[3,2-d]pyrimidine (Example 1(e)) (70 mg, 0.29 mmol), N,N'-dimethylethylenediamine (Aldrich Chemical Company) (0.15 mL, 1.44 mmol) and K$_2$CO$_3$ (0.40 g, 2.87 mmol) in H$_2$O (2 mL). The crude material was purified by flash chromatography on silica gel with 9:1 CHCl$_3$:MeOH as eluant to give 18.5 mg (22%) of the title compound as an off-white solid. An analytical sample was obtained by recrystallization from EtOH. $^1$H NMR (CDCl$_3$; 400 MHz): δ 2.60 (s, 6), 3.04 (t, 2, J=4.5), 3.15 (s, 3), 3.75 (t, 2, J=4.5), 6.76 (s, 1), 7.31–7.42 (m, 3), 7.70 (d, 2, J=7.4). MS m/z: 296 (M+1), 294 (M−1). HRMS: Calcd for M+H: 296.1875. Found: 296.1884.

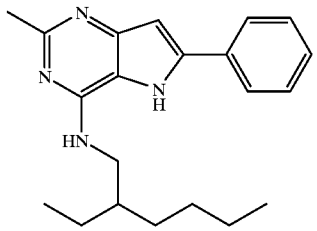

EXAMPLE 6

(2-Ethylhexyl)(2-methyl-6-phenylpyrrolo[2,3-e]pyrimidin-4-yl)amine.

This compound was prepared according to the method described in Example 2 by employing 4-chloro-2-methyl-6-phenylpyrrolo[3,2-d]pyrimidine (Example 1(e)) (70.0 mg, 0.29 mmol), 2-ethylhexylamine (Aldrich Chemical Company) (0.24 mL, 1.44 mmol) and K$_2$CO$_3$ (0.40 g, 2.87 mmol) in H$_2$O (2 mL) to give 61 mg (63%) of the title compound as a white solid. An analytical sample was obtained by recrystallization from i-PrOH. Mp: 288–289° C. (dec.). $^1$H NMR (CDCl$_3$; 500 MHz): δ 0.72–0.78 (m, 6), 1.15–1.34 (m, 9), 2.62 (s, 3), 3.56 (dd, 2, J=5.3, 7.6), 6.71 (s, 2), 7.17–7.24 (m, 3), 7.59 (d, 2, J=7.6), 12.78 (br s, 1). MS m/z: 337 (M+1), 335 (M−1). HRMS: Calcd for M+H: 337.2392. Found: 337.2397.

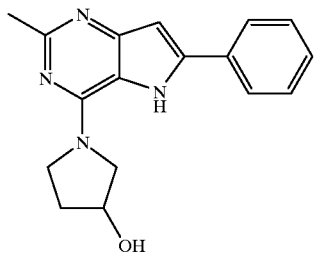

EXAMPLE 7

1-(2-methyl-6-phenylpyrrolo[2,3-e]pyrimidin-4-yl)pyrrolidin-3-ol.

This compound was prepared according to the method described in Example 2 by employing 4-chloro-2-methyl-6-phenylpyrrolo[3,2-d]pyrimidine (Example 1(e)) (70.0 mg, 0.29 mmol), 3-pyrrolidinol (Aldrich Chemical Company) (0.12 mL, 1.44 mmol) and $K_2CO_3$ (0.40 g, 2.87 mmol) in $H_2O$ (2 mL). The crude material was purified by flash chromatography on silica gel with 10:1 $CHCl_3$:MeOH as eluant to give 30.9 mg (37%) of the title compound as an off-white solid. An analytical sample was obtained by recrystallization from EtOH. Mp: 234–235° C. $^1$H NMR (DMSO-$d_6$; 500 MHz): δ 1.96–2.05 (m, 2), 2.39 (s, 3), 3.77–3.93 (m, 4), 4.43 (s, 1), 5.03 (s, 1), 6.71 (s, 1), 7.38–7.50 (m, 3), 7.88 (d, 2, J=7.6), 10.64 (br s, 1). MS m/z: 295 (M+1), 293 (M−1). HRMS: Calcd for M+H: 295.1923. Found: 295.1910.

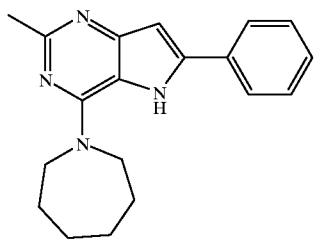

EXAMPLE 8

4-Homopiperidyl-2-methyl-6-phenylpyrrolo[3,2-d]pyrimidine.

This compound was prepared according to the method described in Example 2 by employing 4-chloro-2-methyl-6-phenylpyrrolo[3,2-d]pyrimidine (Example 1(e)) (70 mg, 0.287 mmol), hexamethyleneimine (Aldrich Chemical Company) (0.16 mL, 1.44 mmol) and $K_2CO_3$ (0.40 g, 2.87 mmol) in $H_2O$ (2 mL). The crude material was purified by preparative TLC on silica gel with 9:1 $CHCl_3$:MeOH as eluant to give 54.1 mg (62%) of the title compound as a white solid. An analytical sample was obtained by recrystallization from EtOAc. Mp: 209–210° C. $^1$H NMR (CDCl$_3$; 500 MHz): δ 1.65–1.68 (m, 4), 1.93–1.97 (m, 4), 2.57 (s, 3), 3.91 (t, 4, J=5.9), 6.75 (s, 1), 7.37–7.49 (m, 3), 7.63 (d, 2, J=7.43), 8.19 (br s, 1). MS m/z: 307 (M+1), 305 (M−1). HRMS: Calcd for M+H: 307.1923. Found: 307.1933.

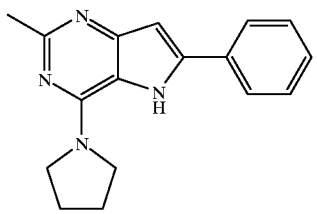

EXAMPLE 9

2-Methyl-6-phenyl-4-pyrrolidinylpyrrolo[3,2-d]pyrimidine.

This compound was prepared according to the method described in Example 2 by employing 4-chloro-2-methyl-6-phenylpyrrolo[3,2-d]pyrimidine (Example 1(e)) (70 mg, 0.287 mmol), pyrrolidine (Aldrich Chemical Company) (0.12 mL, 1.44 mmol) and $K_2CO_3$ (0.397 g, 2.87 mmol) in $H_2O$ (2 mL). The crude material was purified by flash chromatography on silica gel with 20:1 $CHCl_3$:MeOH as eluant to give 42.1 mg (53%) of the title compound as an off-white solid. An analytical sample was obtained by recrystallization from EtOH. $^1$H NMR (CDCl$_3$; 500 MHz): δ 2.07 (t, 4, J=6.3), 2.58 (s, 3), 3.88–3.90 (m, 4), 6.71 (s, 1), 7.36–7.46 (m, 3), 7.63 (d, 2, J=7.7). MS m/z: 279.5 (M+1), 277.5 (M−1). HRMS: Calcd for M+H: 279.1610. Found: 279.1613.

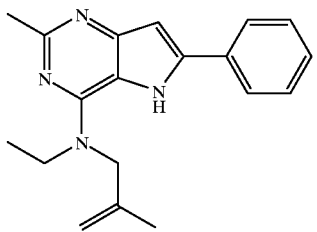

EXAMPLE 10

Ethyl(2-methyl-6-phenylpyrrolo[2,3-e]pyrimidin-4-yl)(2-methylprop-2-enyl)amine.

This compound was prepared according to the method described in Example 2 by employing 4-chloro-2-methyl-6-phenylpyrrolo[3,2-d]pyrimidine (Example 1(e)) (70 mg, 0.29 mmol), N-ethyl-2-methylallylamine (Aldrich Chemical Company) (0.19 mL, 1.44 mmol) and $K_2CO_3$ (0.397 g, 2.87 mmol) in $H_2O$ (2 mL). The crude material was purified by preparative TLC on silica gel with 1:1 EtOAc:hexanes as eluant to give 36.7 mg (42%) of the title compound as off-white solid. An analytical sample was obtained by recrystallization from EtOAc. Mp: 148–150° C. $^1$H NMR (CDCl$_3$; 500 MHz): δ 1.32 (t, 3, J=7.1), 1.95 (s, 3), 2.59 (s, 3), 3.78 (q, 2, J=7.1), 4.20 (s, 2), 5.18 (s, 1), 5.24 (s, 1), 6.74 (s, 1), 7.35–7.48 (m, 3), 7.55 (d, 2, J=7.4), 8.47 (br s, 1). MS m/z: 307 (M+1), 305 (M−1). Anal. Calcd for $C_{19}H_{22}N_4$: C, 74.48; H, 7.24; N, 18.28. Found: C, 74.36; H, 7.27; N, 18.19.

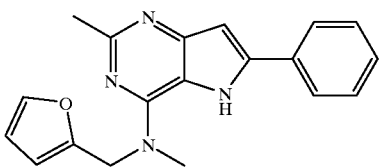

EXAMPLE 11

(2-Furylmethyl)methyl(2-methyl-6-phenylpyrrolo[2,3-e]pyrimidin-4-yl)amine.

This compound was prepared according to the method described in Example 2 by employing 4-chloro-2-methyl-6-phenylpyrrolo[3,2-d]pyrimidine (Example 1(e)) (70.0 mg, 0.29 mmol), N-methylfurfurylamine (The Sigma-Aldrich Library of Rare Chemicals) (0.16 g, 1.44 mmol) and $K_2CO_3$ (0.40 g, 2.87 mmol) in $H_2O$ (2 mL). The crude material was purified by preparative TLC on silica gel with 1:1 EtOAc:hexanes as eluant to give 53.6 mg (59%) of the title compound as an off-white solid. An analytical sample was obtained by recrystallization from EtOAc. Mp: 168–169° C. $^1$H NMR (CDCl$_3$; 500 MHz): δ 2.62 (s, 3), 3.35 (s, 3), 4.83 (s, 2), 6.42–6.44 (m, 2), 6.79 (s, 1), 7.36–7.48 (m, 4), 7.64 (d, 2, J=7.2), 8.91 (br s, 1). MS m/z: 319.5 (M+1), 317.0 (M−1). HRMS: Calcd for M+H: 319.1559. Found: 319.1566.

EXAMPLE 12

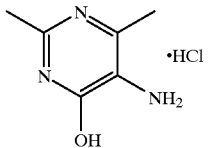

(a) 5-Amino-2,6-dimethyl-4-hydroxypyrimidine Hydrochloride.

To a 150-mL round-bottomed flask was added 5-acetamido-2,6-dimethyl-4-hydroxypyrimidine (Example 46 (b)) (6.0 g, 32.8 mmol) and HCl (conc.) (25 mL). The cloudy suspension was heated at reflux for 5 h. The solution became clear upon heating. The reaction mixture was allowed to cool to room temperature and then concentrated using the rotary evaporator. The white solid residue was triturated with acetone (25 mL) and the solid collected by vacuum filtration. The resulting solid was boiled in hot MeOH, hot filtered, and dried in a 60° C. vacuum oven to give 5.0 g (87%) of the title compound as a white solid. $^1$H NMR (DMSO-d$_6$; 400 MHz): δ 2.24 (s, 3), 2.48 (s, 3). MS m/z: 140 (M+1).

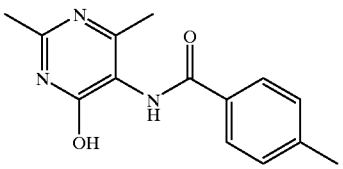

(b) 2,6-Dimethyl-4-hydroxy-5-(p-toluamido)pyrimidine.

4-Dimethylaminopyridine (DMAP) (2.69 g, 22.0 mmol) and 1,3-diisopropylcarbodiimide (DIC) (3.3 mL, 21.0 mmol) were added to a solution of p-toluic acid (2.72 g, 20 mmol) in $CH_2Cl_2$ (30 mL) and DMF (2 mL) at 0° C. under nitrogen. After stirring at 0° C. for 10 min, 5-amino-2,6-dimethyl-4-hydroxypyrimidine hydrochloride (3.51 g, 20.0 mmol) was added in one portion. The resulting mixture was stirred at 0° C. for 1 h and at room temperature for 16 h. The thick precipitate that formed was collected by filtration, washed with $CH_2Cl_2$ (20 mL), and EtOH (20 mL). This material was dried in a vacuum oven overnight to give 3.25 g (63%) of the title compound as a white solid. $^1$H NMR (DMSO-d$_6$; 500 MHz): δ 2.08 (s, 3). 2.29 (s, 3), 2.38 (s, 3), 7.31 (d, 2, J=7.9), 7.89 (d, 2, J=7.8), 9.51 (br s, 1),12.60 (br s, 1). This material was used without further purification.

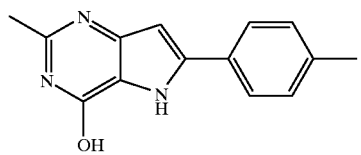

(c) 2-Methyl-6-(4-methylphenyl)pyrrolo[3,2-d]pyrimidin-4-ol.

This material was prepared according to the method described in Example 1(d) using 2,6-dimethyl-4-hydroxy-5-(p-toluamido)-pyrimidine (3.99 g, 15.5 mmol). The precipitate that formed upon acidification with HCl (conc.) was collected by filtration and dried in a vacuum oven overnight to give 0.60 g (16%) of the title compound as a tan solid. $^1$H NMR (DMSO-d$_6$; 400 MHz): δ 2.30 (s, 3), 2.33 (s, 3), 6.69 (s, 1), 7.24 (d, 2, J=7.8), 7.81 (d, 2, J=7.9), 11.79 (br s, 1), 12.18 (br s, 1). MS m/z: 240 (M+1), 238 (M−1). This material was used without further purification.

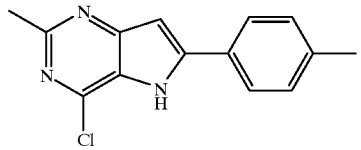

(d) 4-Chloro-2-methyl-6-(4-methylphenyl)pyrrolo[3,2-d]pyrimidine.

A mixture of 2-methyl-6-(4-methylphenyl) pyrrolo[3,2-d]pyrimidin-4-ol (0.565 g, 2.36 mmol) and POCl$_3$ (5.5 mL, 59.0 mmol) was heated at 120° C. for 21 h. POCl$_3$ was removed under reduced pressure to give a dark-red residue. The residue was diluted with ice-water and neutralized under stirring and cooling with ammonia water to pH 8 (pH paper). The resulting mixture was extracted three times with EtOAc. The combined organic layer was washed with brine, dried over MgSO$_4$ and concentrated in vacuo to give a brown solid. The solid was dried in vacuum oven overnight to give 0.392 g (64%) of the title compound. $^1$H NMR (CDCl$_3$; 500 MHz): δ 2.43 (s, 3), 2.78 (s, 3), 6.87 (s, 1), 7.32 (d, 2, J=7.89), 7.64 (d, 2, J=7.99), 8.72 (br s, 1). MS m/z: 240 (base), 256 (M−1). This material was used without further purification.

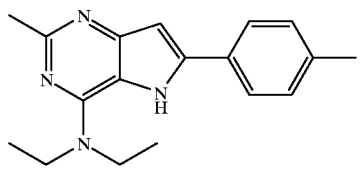

(e) Diethyl[2-methyl-6-(4-methylphenyl)pyrrolo[2,3-e]pyrimidin-4-yl]amine.

This compound was prepared according to the method described in Example 2 by employing 4-chloro-2-methyl-6-(4-methylphenyl)pyrrolo[3,2-d]pyrimidine (70 mg, 0.272 mmol), diethylamine (Aldrich Chemical Company) (0.14 mL, 1.36 mmol), and $K_2CO_3$ (0.376 g, 2.72 mmol) in $H_2O$ (2.5 mL). The crude solid was purified by flash chromatography on silica gel with 20:1 $CHCl_3$:MeOH as eluant to give 12.1 mg (15%) of the title compound as an off-white solid. $^1$H NMR ($CDCl_3$; 500 MHz): δ 1.37 (t, 6, J=7.0), 2.40 (s, 3), 2.56 (s, 3), 3.77 (q, 4, J=6.7, 7.0), 6.69 (s, 1), 7.24 (d, 2, J=7.8), 7.51 (d, 2, J=7.7). MS m/z: 295.5 (M+1), 293.0 (M−1). HRMS: Calcd for M+H: 295.1559. Found: 295.1559.

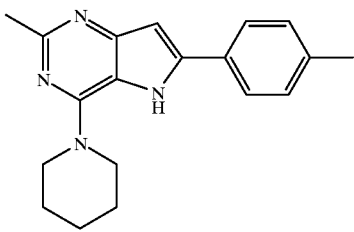

EXAMPLE 13
2-Methyl-6-(4-methylphenyl)-4-piperidylpyrrolo[3,2-d]pyrimidine.

This compound was prepared according to the method described in Example 2 by employing 2-methyl-4-chloro-6-(p-tolyl)-5H-pyrrolo[3,2-d]pyrimidine (Example 12(d)) (70 mg, 0.272 mmol), piperidine (Aldrich Chemical Company) (0.13 mL, 1.36 mmol), and $K_2CO_3$ (0.376 g, 2.72 mmol) in $H_2O$ (2.5 mL). The crude material was purified by flash chromatography on silica gel with 9:1 $CHCl_3$:MeOH as eluant to give 50.2 mg (60%) of the title compound as a tan solid. $^1$H NMR ($CDCl_3$; 500 MHz): δ 1.74–1.76 (m, 6), 2.40 (s, 3), 2.58 (s, 3), 3.79–3.81 (m, 4), 6.67 (s, 1), 7.25 (d, 2, J=7.8), 7.54 (d, 2, J=7.7). MS m/z: 307 (M+1), 305 (M−1). HRMS: Calcd for M+H: 307.1923. Found: 307.1910.

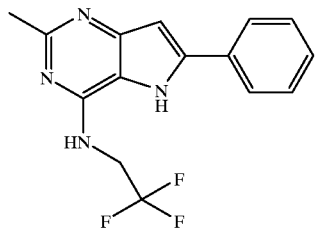

EXAMPLE 14
(2-Methyl-6-phenylpyrrolo[2,3-e]pyrimidin-4-yl)(2,2,2-trifluoroethyl)amine.

To a mixture of 4-chloro-2-methyl-6-phenylpyrrolo[3,2-d]pyrimidine (Example 1(e)) (55.9 mg, 0.23 mmol) and 2,2,2-trifluoroethylamine (Aldrich Chemical Company) (95 μL, 1.15 mmol) was added a solution of $K_2CO_3$ (0.13 g, 0.92 mmol) in $H_2O$ (1.5 mL). This mixture was stirred at 140° C. in a closed-capped Wheaton vial for 2.5 h. After cooling, $CH_2Cl_2$ (10 mL) and $H_2O$ (10 mL) were added. The organic solution was removed and the aqueous solution was washed with $CH_2Cl_2$ (10 mL). The combined organic solutions were washed with saturated aqueous NaCl (15 mL), dried over $MgSO_4$, filtered and concentrated under reduced pressure. The residue was washed with $CH_2Cl_2$ until all the color was removed. The remaining solid was recrystallized from hot MeOH to provide 21 mg (29%) of the title compound as a white solid. Mp: >310° C. MS m/z 307 (M+1), 294, 281, 226. $^1$H NMR (DMSO-$d_6$; 400 MHz): δ 2.31 (s, 3), 2.52 (s, 2), 6.74 (s, 1), 7.33 (t, 1, J=7.3), 7.43 (t, 2, J=7.8), 7.92 (d, 2, J=7.3), 11.74 (s, 1), 12.22 (s, 1). HRMS: Calcd for M+H, $C_{15}H_{13}F_3N_4$: 307.1168. Found: 307.1160.

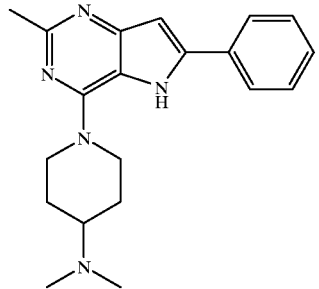

EXAMPLE 15
Dimethyl[1-(2-methyl-6-phenylpyrrolo[2,3-e]pyrimidin-4-yl)(4-piperidyl)]amine.

To a mixture of 4-chloro-2-methyl-6-phenylpyrrolo[3,2-d]pyrimidine (Example 1(e)) (96.7 mg, 0.40 mmol) and 4-dimethylamine piperidine (Salor Chemical Company) (0.25 g, 1.90 mmol) was added a solution of $K_2CO_3$ (0.35 g, 1.60 mmol) in $H_2O$ (2.5 mL). This mixture was stirred at 140° C. in a closed-capped Wheaton vial for 1 h. After cooling the precipitate was collected, washed with $H_2O$ (5×2 mL), ether (5×3 mL) and dried under vacuum to give a cream-colored solid. This material was recrystallized from MeOH/$CH_2Cl_2$ to give 59 mg (44%) of the title compound. Mp: 261.5–263° C. MS m/z: 336 (M+1), 291, 237. $^1$H NMR (DMSO-$D_6$; 400 MHz): δ 1.50 (br q, 2H, J=10.4), 1.86 (d, 2, J=11.8), 2.20 (s, 6), 2.42 (s, 3), 3.00 (br t, 1, J=11.2), 4.46 (br d, 2H, J=10.4), 6.76 (s, 1), 7.40 (br d, 1, J=6.4), 7.47 (t, 2, J=6.4), 7.90 (d, 2H, J=7.6), 11.02 (s, 1),. Anal. Calcd for $C_{20}H_{25}N_5.H_2O$: C, 67.99; H, 7.65; N, 19.83. Found: C, 67.81; H, 7.67; N, 19.75.

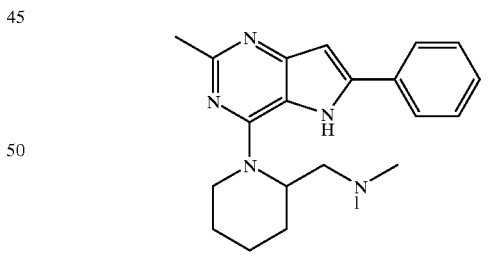

EXAMPLE 16
Dimethyl{[1-(2-methyl-6-phenylpyrrolo[2,3-e]pyrimidin-4-yl)(2-piperidyl)]methyl}amine.

To a mixture of 4-chloro-2-methyl-6-phenylpyrrolo[3,2-d]pyrimidine (Example 1(e)) (88.3 mg, 0.36 mmol) and N-(2-piperidylmethyl)-dimethylamine (Salor Chemical Company) (0.25 g, 1.72 mmol) was added a solution of $K_2CO_3$ (0.25 g, 1.60 mmol) in $H_2O$ (2.5 mL). This mixture was stirred at 140° C. in a closed-capped Wheaton vial for 2.5 h. After cooling, $CH_2Cl_2$ (10 ML) and $H_2O$ (10 mL) were added. The organic solution was removed and the aqueous solution was washed with CH$_2$Cl$_2$ (10 mL). The combined organic solutions were washed with saturated NaCl (15 mL), dried over MgSO$_4$, filtered and concentrated under reduced pressure. The residue was purified by flash chromatography (3% MeOH:CHCl$_3$ on silica gel) to give 43 mg (34%) of the title compound as a yellow oil. MS m/z: 350 (M+1), 305, 214. $^1$H NMR (DMSO-d$_6$; 400 MHz): δ 1.63 (m, 6), 2.29 (s, 6), 2.40 (s, 3), 2.81 (m, 2), 3.03 (br t, 1, J=11.8), 4.53–4.63 (m, 2), 6.75 (s, 1), 7.37 (m, 1), 7.50 (t, 2, J=7.5), 7.81 (d, 2, J=7.8), 12.47 (s, 1).

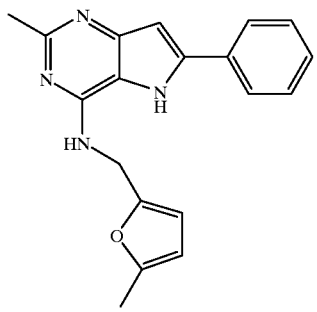

EXAMPLE 17
[(5-methyl(2-furyl)methyl](2-methyl-6-phenylpyrrolo[2,3-e]pyrimidin-4-yl)amine.

To a mixture of 4-chloro-2-methyl-6-phenylpyrrolo[3,2-d]pyrimidine (Example 1(e)) (47.6 mg, 0.19 mmol) and 5-methyl-2-furanmethanamine (Acros Chemical Company) (100 μL, 0.98 mmol) was added a solution of K$_2$CO$_3$ (0.11 g, 0.76 mmol) in H$_2$O (1.5 mL). This mixture was stirred at 140° C. in a closed-capped Wheaton vial for 2.5 h. After cooling, CH$_2$Cl$_2$ (10 mL) and H$_2$O (10 mL) were added. The organic solution was removed and the aqueous solution washed with CH$_2$Cl$_2$ (10 mL). The combined organic solutions were washed with saturated NaCl (15 mL), dried over MgSO$_4$, filtered and concentrated under reduced pressure. The residue was purified by flash chromatography (3% MeOH:CHCl$_3$ on silica gel) to give 37 mg (62%) of the title compound as a beige solid. Mp: 125–127.5° C. MS m/z: 319 (M+1), 294, 225, 195, 147. $^1$H NMR (CD$_3$OD, 400 MHz): δ 2.28 (s, 3), 2.53 (s, 3), 4.72 (s, 2), 5.97 (d, 1, J=3.0), 6.24 (d, 1, J=3.0), 6.66 (s, 1), 7.34 (m, 1), 7.43 (t, 2, J=7.7), 7.71 (dd, 2, J=7.1, 1.4). HRMS: Calcd for M+H, C$_{19}$H$_{18}$ON$_4$: 319.1555. Found: 319.1566.

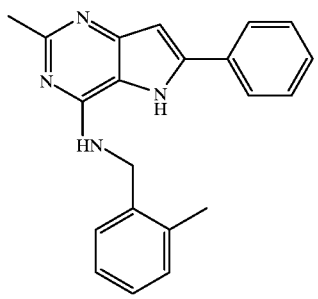

EXAMPLE 18
[(2-methylphenyl)methyl](2-methyl-6-phenylpyrrolo[2,3-e]pyrimidin-4-yl)amine.

To a mixture of 4-chloro-2-methyl-6-phenylpyrrolo[3,2-d]pyrimidine (Example 1(e)) (85.0 mg, 0.35 mmol) and 2-methylbenzyl amine (Aldrich Chemical Company) (2.2 mL, 17.4 mmol) was added a solution of K$_2$CO$_3$ (0.35 g, 2.54 mmol) in H$_2$O (2.5 mL). This mixture was stirred at 140° C. in a closed-capped Wheaton vial for 1.5 h. After cooling, CH$_2$Cl$_2$ (10 mL) and H$_2$O (10 mL) were added. The organic solution was removed and the aqueous solution washed with CH$_2$Cl$_2$ (10 mL). The combined organic solutions were washed with saturated NaCl (15 mL), dried over MgSO$_4$, filtered and concentrated under reduced pressure. The residue was purified by flash chromatography (3% MeOH:CHCl$_3$ on silica gel) and then recrystallized from MeOH/CH$_2$Cl$_2$ to give 42 mg (35%) of the title compound as a white solid. Mp: 277–281° C. MS m/z: 329 (M+1). $^1$H NMR (DMSO-d$_6$; 400 MHz): δ 2.38 (s, 3), 2.42 (s, 3), 4.69 (d, 2, J=4.8), 6.75 (s, 1), 6.98 (br t, 1), 7.19–7.25 (m, 3), 7.35–7.42 (m, 2), 7.49 (t, 2, J=7.8), 7.76 (d, 2, J=7.8), 11.27 (s, 1). Anal. Calcd for C$_{21}$H$_{20}$N$_4$: C, 76.83; H, 6.10; N, 17.07. Found: C, 76.58; H, 6.20; N, 16.94.

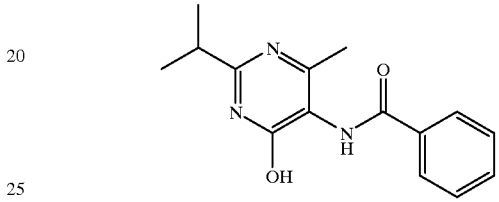

EXAMPLE 19
(a) 2-Isopropyl-6-methyl-4-hydroxy-5-benzamido-pyrimidine.

To a solution of sodium ethoxide (Aldrich Chemical Company) (3.30 g, 0.046 mol) in absolute ethanol (70 mL) was added isopropylcarbamidine hydrochloride (Maybridge Chemical Company) (2.70 g, 0.022 mol). After stirring at 25° C. for 0.5 h this slurry was filtered through a plug of celite into a solution of 2-benzoylamino-3-oxo-butyric acid ethyl ester (Example 1(b)) (5.01 g, 0.020 mol) in absolute EtOH (50 mL). The reaction mixture was placed under a N$_2$ atmosphere and allowed to stir at room temperature overnight. HCl (conc.) was added to acidify the solution to a pH of 4–5 (pH paper). The solids which precipitated out of solution were removed by filtration and the filtrate was concentrated under reduced pressure to give a gummy brown solid. This material was purified by recrystallization from acetone to give 1.6 g (29%) of the title compound as a white solid. Mp: 252.5–254° C. $^1$H NMR (DMSO-d$_6$; 500 MHz): δ 1.21 (d, 6, J=6.9), 2.12 (s, 3), 2.83 (septet, 1, J=6.9), 7.52 (t, 2, J=7.6), 7.59 (t, 1, J=7.4), 7.97 (d, 2, J=7.4), 9.56 (s, 1), 12.51 (s, 1). MS m/z: 272 (M+1). HRMS: Calcd for M+Na, C$_{15}$H$_{17}$ON$_4$: 319.1555. Found: 319.1566.

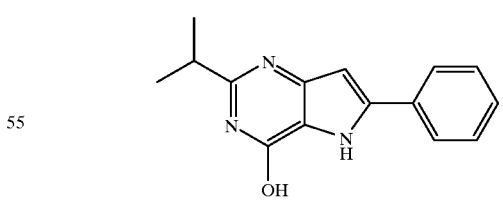

(b) 2-Isopropyl-6-phenylpyrrolo[3,2-d]pyrimidin-4-ol.

KOt-Bu (Aldrich Chemical Company) (2.5 g, 23.0 mmol) was added portionwise at room temperature to a slurry of 2-isopropyl-6-methyl-4-hydroxy-5-benzamidopyrimidine (0.62 g, 2.30 mmol) in t-BuOH (60 mL) in a round-bottomed flask equipped with a distillation head. The mixture was slowly heated to 180° C. under a slow steam of nitrogen until all the solvent was distilled off. The temperature was slowly increased with gas evolution until the solid cake had melted at 280° C. The temperature was kept at 280° C. for 10 min then raised to 300° C. for 10 min. The sand bath was removed allowing the reaction mixture to cool to room temperature. Distilled water (100 mL) was added and HCl (conc.) was added until the pH of the solution was 4–5 (pH paper). The resulting precipitate was collected by filtration and washed with $H_2O$ (3×10 mL). This material was purified by flash chromatography on silica gel with 98:2 $CHCl_3$:MeOH as eluant to give 97 mg (17%) of the title compound as a beige solid. Mp: >300° C. $^1$H NMR (DMSO-$d_6$; 400 MHz): δ 1.23 (d, 6, J=6.76), 2.88 (septet, 1, J=6.78), 6.81 (s, 1), 7.33 (t, 1, J=7.1), 7.44 (7.57), 7.92 (d, 2, J=7.8), 11.70 (s, 1), 12.26 (s, 1). MS m/z: 254 (M+1). Anal. Calcd for $C_{15}H_{15}N_3O$: C, 71.15; H, 5.93; N, 16.61. Found: C, 70.90; H, 5.95; N, 16.53.

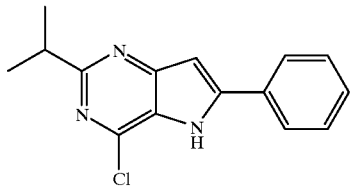

(c) 4-Chloro-2-isopropyl-6-phenylpyrrolo[3,2-d]pyrimidine.

Phosphorus oxychloride (Aldrich Chemical Company) (3.0 mL, 30.0 mmol) and 2-isopropyl-4-hydroxy-6-phenylpyrrolo[3,2-d]pyrimidin-4-ol (97.0 mg, 0.38 mmol) were added to a round-bottomed flask. The resulting mixture was heated at reflux overnight under $N_2$. After cooling the phosphorus oxychloride was removed under reduced pressure to provide a brown oil. This material was purified by flash chromatography on silica gel with 99:1 $CHCl_3$:MeOH as eluant to give 47 mg (46%) of the title compound as an off-white powder. $^1$H NMR (DMSO-$d_6$; 400 MHz): δ 1.31 (d, 6, J=6.9), 3.19 (septet, 1, J=6.8), 7.18 (s, 1), 7.47–7.57 (m, 3), 8.10 (d, 2, J=7.4), 12.53 (s, 1). MS m/z: 272 (M+1). HRMS Calcd for M+H, $C_{15}H_{14}N_3Cl$: 272.0951. Found: 272.0955.

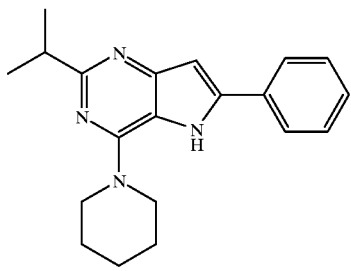

(d) 2-Isopropyl-6-phenyl-4-piperidylpyrrolo[3,2-d]pyrimidine.

To a mixture of 4-chloro-2-isopropyl-6-phenylpyrrolo[3,2-d]pyrimidine (46.0 mg, 0.17 mmol) and piperidine (Aldrich Chemical Company) (85 μL, 0.85 mmol) was added a solution of $K_2CO_3$ (0.10 g, 0.70 mmol) in $H_2O$ (1.0 mL). This mixture was stirred at 140° C. in a closed-capped Wheaton vial for 1 h. After cooling, the white precipitate was collected, washed with $H_2O$ (5×2 mL), ether (5×3 mL) and dried under vacuum to give 48 mg (88%) of the title compound as a cream colored solid. Mp: 269.5–272° C. MS m/z: 321 (M+1), 307, 240, 171. $^1$H NMR (DMSO-$d_6$; 500 MHz): δ 1.25 (d, 6, J=6.8), 1.66 (br s, 6), 2.95 (septet, 1, J=6.8), 3.73 (br s, 4), 6.78 (s, 1), 7.39 (m, 1), 7.48 (m, 2), 7.89 (d, 2, J=7.7), 11.06 (s, 1). Anal. Calcd for $C_{20}H_{24}N_4 \cdot 0.5H_2O$: C, 72.90; H, 7.65; N, 17.01. Found: C, 72.78; H, 7.26; N, 16.98.

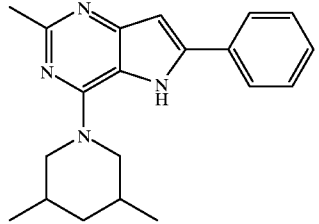

EXAMPLE 20 cis/trans-4-(3,5-dimethylpiperidinyl)-2-methyl-6-phenylpyrrolo[3,2-d]pyrimidine.

To a mixture of 4-chloro-2-methyl-6-phenylpyrrolo[3,2-d]pyrimidine (Example 1(e)) (83.8 mg, 0.34 mmol) and 3,5-dimethylpiperidine (cis/trans, Aldrich Chemical Company) (250 μL, 1.72 mmol) was added a solution of $K_2CO_3$ (0.19 g, 1.36 mmol) in $H_2O$ (2.0 mL). This mixture was stirred at 140° C. in a closed-capped Wheaton vial for 2.0 h. After cooling, $CH_2Cl_2$ (10 mL) and $H_2O$ (10 mL) were added. The organic solution was removed and the aqueous solution washed with $CH_2Cl_2$ (10 mL). The combined organic solutions were washed with saturated NaCl (15 mL), dried over $MgSO_4$, filtered and concentrated under reduced pressure. The residue was purified by flash chromatography (3% MeOH:$CHCl_3$ on silica gel) and then recrystallized from MeOH/$CH_2Cl_2$ to give 85 mg (78%) as a beige colored solid. This material was recrystallized from hot MeOH/$CH_2Cl_2$ to give 54 mg (50%) of the title compound as a 95:5 mixture of isomers as colorless crystals. Mp: 225.5–227° C. MS m/z: 321 (M+1). $^1$H NMR (DMSO-$d_6$; 400 MHz) (for major isomer): δ 0.90 (m, 2), 0.91 (d, 6, J=6.5), 1.73 (m, 2), 2.40 (s, 3), 2.42 (br s, 2), 4.42 (br d, 1, J=8.2), 6.74 (s, 1), 7.40 (m, 1), 7.49 (br s, 2), 7.89 (d, 2, J=7.4), 11.06 (s, 1). Anal. Calcd for $C_{20}H_{24}N_4$: C, 75.00; H, 7.50; N, 17.50. Found: C, 74.87; H, 7.56; N, 17.38.

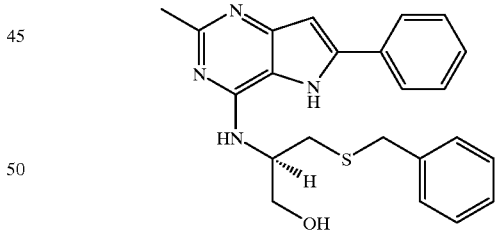

EXAMPLE 21

(S)-2-[(2-methyl-6-phenylpyrrolo[2,3-e]pyrimidin-4-yl)amino]-3-(phenylmethylthio)butan-1-ol.

To a mixture of 4-chloro-2-methyl-6-phenylpyrrolo[3,2-d]pyrimidine (Example 1(e)) (78.1 mg, 0.32 mmol) and S-benzyl-1-cysteinol (Aldrich Chemical Company) (0.32 g, 1.60 mmol) was added a solution of $K_2CO_3$ (0.35 g, 2.54 mmol) in $H_2O$ (2.5 mL). This mixture was stirred at 140° C. in a closed-capped Wheaton vial for 2.5 h. After cooling, $CH_2Cl_2$ (10 mL) and $H_2O$ (10 mL) were added. The organic solution was removed and the aqueous solution washed with $CH_2Cl_2$ (10 mL). The combined organic solutions were washed with saturated NaCl (15 mL), dried over $MgSO_4$, filtered and concentrated under reduced pressure. The residue was purified by flash chromatography (3% MeOH:CHCl₃ on silica gel) to give 51 mg (40%) of the title compound as a white solid. Mp: 220–221.5° C. MS m/z: 405 (M+1), 336, 203, 134. ¹H NMR (DMSO-d₆; 400 MHz): δ 2.41 (s, 3), 2.65–2.78 (m, 3), 3.63 (m, 1), 3.75 (m, 1), 3.86 (s, 2), 4.52 (br s, 1), 5.12 (br s, 1), 6.75 (d, 1, J=1.6), 6.99 (br d, 1, J=7.7), 7.20–7.40 (m, 6), 7.50 (t, 2, J=7.5), 7.82 (d, 2, J=7.5), 11.53 (s, 1). Anal. Calcd for C₂₃H₂₄N₄OS.H₂O: C, 65.40; H, 6.16; N, 13.27. Found: C, 65.05; H, 5.87; N, 13.07.

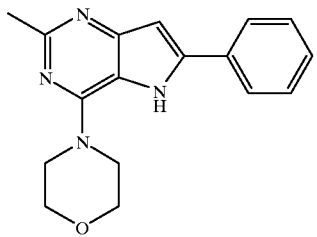

EXAMPLE 22

4-(2-Methyl-6-phenylpyrrolo[2,3-e]pyrimidin-4-yl) morpholine.

To a 5 mL Wheaton vial was added was added 4-chloro-2-methyl-6-phenylpyrrolo[3,2-d]pyrimidine (Example 1(e)) (100 mg, 0.41 mmol) and morpholine (Aldrich Chemical Company) (0.18 mL, 2.1 mmol). A solution of K₂CO₃ (0.37 g, 2.7 mmol) in H₂O (2.5 mL) was added, the vial was securely capped, and the reaction mixture was heated at 120° C. for 2 h. The reaction mixture was allowed to cool to room temperature and the resulting light-pink precipitate was collected by filtration, recrystallized from EtOAc and dried overnight in a 60° C. vacuum oven to give 0.04 g (33%) of the title compound as a white solid. Mp: 276° C. (dec.) ¹H NMR (CDCl₃; 500 MHz): δ 2.62 (s, 3), 3.87 (s, 4), 3.90 (s, 4), 6.79 (s, 1), 7.41 (t, 1, J=6.8), 7.48 (t, 2, J=7.4), 7.67 (d, 2, J=6.8), 8.17 (br s, 1). MS m/z: 295 (M+1). Anal. Calcd for C₁₇H₁₈N₄O.0.25 H₂O: C 68.32, H 6.24, N 18.75. Found: C 67.90, H 6.02, N 18.64.

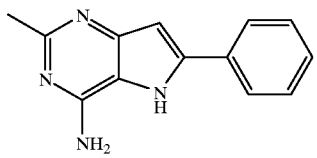

EXAMPLE 23

2-Methyl-6-phenylpyrrolo[3,2-d]pyrimidin-4-ylamine.

This compound was prepared according to the method described in Example 26 by employing 4-chloro-2-methyl-6-phenylpyrrolo[3,2-d]pyrimidine (Example 1(e)) (0.10 g, 0.41 mmol) with NH₄OH (Aldrich Chemical Company) (2.5 mL, 21.4 mmol) and K₂CO₃ (0.33 g, 2.4 mmol). The crude reaction mixture was concentrated to dryness and the residue extracted with hot MeOH and concentrated. The resulting yellow oil was purified by flash chromatography on silica gel (1:40 MeOH/CH₂Cl₂ followed by 1:20 MeOH/CH₂Cl₂) to give 0.005 g (5%) of the title compound as an off-white solid. Mp: >280° C. ¹H NMR (CD₃OD; 500 MHz): δ 2.53 (s, 3), 6.74 (s, 1), 7.44 (t, 1, J=7.2), 7.52 (t, 2, J=7.5), 7.82 (d, 2, J=7.5); MS m/z: 225 (M+1).

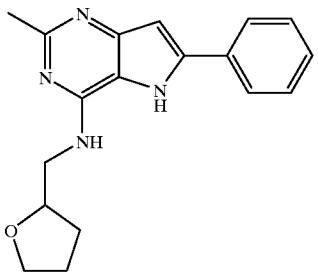

EXAMPLE 24

(2-Methyl-6-phenylpyrrolo[2,3-]pyrimidin-4-yl)(2-perhydrofurylmethyl)amine.

This compound was prepared according to the method described in Example 26 by employing 4-chloro-2-methyl-6-phenylpyrrolo[3,2-d]pyrimidine (Example 1(e)) (0.10 g, 0.41 mmol), tetrahydrofurfuryl amine (Aldrich Chemical Company) (0.212 mL, 2.05 mmol) and K₂CO₃ (0.34 g, 2.50 mmol) in H₂O (2.5 mL) to obtain crude pink solids. Recrystallization from EtOH/MeOH gave 0.044 g (35%) of the title compound as an off-white solid. Mp: 280° C. ¹H NMR (CDCl₃; 500 MHz): δ 1.59 (m, 1), 1.87 (m, 2), 2.00 (m, 1), 2.39 (s, 3), 3.48 (m, 1), 3.71 (m, 2), 3.86 (t, 1, J=7.3), 4.06 (m, 1), 6.74 (s, 1), 6.95 (s, 1), 7.38 (t, 1, J=7.1), 7.51 (t, 2, J=7.6), 7.80 (d, 2, J=8.0), 11.41 (s, 1). MS m/z: 309 (M+1). Anal. Calcd for C₁₈H₂₀N₄O: C 70.11, H 6.54, N 18.17. Found: C 69.88, H 6.51, N 18.03.

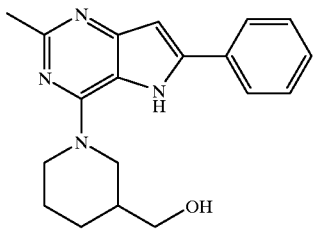

EXAMPLE 25

[1-(2-methyl-6-phenylpyrrolo[2,3-e]pyrimidin-4-yl)-3-piperidyl]methan-1-ol.

This compound was prepared according to the method described in Example 26 by employing 4-chloro-2-methyl-6-phenylpyrrolo[3,2-d]pyrimidine (Example 1(e)) (0.10 g, 0.41 mmol), 3-piperidinemethanol (Aldrich Chemical Company) (0.241 g, 2.09 mmol) and K₂CO₃ (0.34 g, 2.50 mmol) in H₂O (2.5 mL) to obtain crude pink solids. Recrystallization from EtOH/MeOH gave 0.040 g (30%) of the title compound as an off-white solid. Mp: 255–256° C. ¹H NMR (DMSO-d₆; 500 MHz): δ 1.45 (m, 1), 1.59 (m, 1), 1.67 (m, 1), 1.83 (m, 2), 2.42 (s, 3), 3.47 (m, 2), 3.55 (m, 1), 3.68 (m, 2), 3.86 (m, 1), 5.44 (br s, 1), 6.77 (s, 1), 7.38 (m, 1), 7.47 (m, 2), 7.87 (d, 2, J=7.2), 11.24 (br s, 1). MS m/z: 321 (M−1).

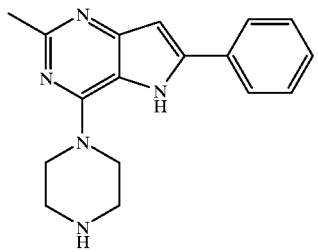

EXAMPLE 26

2-Methyl-6-phenyl-4-piperazinylpyrrolo[3,2-d]pyrimidine.

This compound was prepared according to the method described in Example 26 by employing 4-chloro-2-methyl-6-phenylpyrrolo[3,2-d]pyrimidine (Example 1(e)) (0.10 g, 0.41 mmol), piperazine (Aldrich Chemical Company) (0.382 g, 4.43 mmol) and $K_2CO_3$ (0.34 g, 2.50 mmol) in $H_2O$ (2.5 mL) to give crude pink solids. These solids were taken up in hot EtOAc, cooled to room temperature, and the impurities were removed by filtration. The filtrate was concentrated to give 0.035 g (29%) of the title compound as an off-white solid. Mp: 236° C. $^1$H NMR (DMSO-$d_6$; 500 MHz): δ 2.42 (s, 3), 2.85 (t, 4, J=5.2), 3.62 (t, 4, J=5.2), 6.77 (s, 1), 7.36 (m, 1), 7.45 (t, 2, J=7.8), 7.95 (d, 2, J=7.6), 10.96 (s, 1); MS m/z: 294 (M+1). Anal. Calcd for $C_{17}H_{19}N_5O.0.5$ $H_2O$: C 67.53, H 6.67, N 23.16. Found: C 67.35, H 6.59, N 23.01.

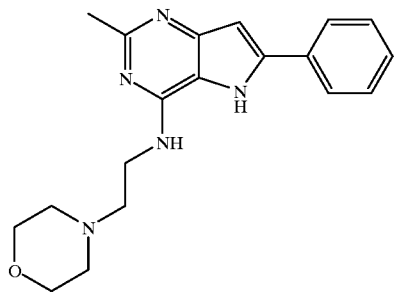

EXAMPLE 27

(2-methyl-6-phenylpyrrolo[2,3-e]pyrimidin-4-yl)(2-morpholin-4-ylethyl)amine.

This compound was prepared according to the method described in Example 26 by employing 4-chloro-2-methyl-6-phenylpyrrolo[3,2-d]pyrimidine (Example 1(e)) (0.10 g, 0.41 mmol), 4-(2-aminoethyl)morpholine (Aldrich Chemical Company) (0.270 g, 2.06 mmol) and $K_2CO_3$ (0.36 g, 2.60 mmol) in $H_2O$ (2.5 mL) to give crude pink solids. Recrystallization from EtOAc/MeOH gave 0.060 g (43%) of the title compound as a white solid. Mp: >280° C. $^1$H NMR (DMSO-$d_6$; 500 MHz): δ 2.39 (s, 3), 3.61 (t, 4, J=4.5), 3.65 (q, 2, J=6.1), 4.04 (s, 2), 6.75 (s, 1), 6.81 (br s, 1), 7.38 (t, 1, J=7.4), 7.51 (t, 2, J=7.6), 7.78 (d, 2, J=7.6), 11.39 (s, 1). $^{13}$C NMR (CD$_3$OD, 100 MHz): δ 26.3, 39.2, 55.9, 60.1, 68.8, 99.9, 127.3, 128.3, 130.6, 131.2, 134.0, 143.1, 149.8, 151.1, 161.5. MS m/z: 338 (M+1). Anal. Calcd for $C_{19}H_{23}N_5O.0.25H_2O$: C, 66.74; H, 6.93; N, 20.48. Found: C, 66.84; H, 6.83; N, 20.39.

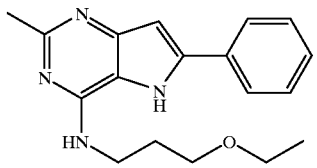

EXAMPLE 28

(3-Ethoxypropyl)(2-methyl-6-phenylpyrrolo[2,3-e]pyrimidin-4-yl) amine.

This compound was prepared according to the method described in Example 26 by employing 4-chloro-2-methyl-6-phenylpyrrolo[3,2-d]pyrimidine (Example 1(e)) (0.10 g, 0.41 mmol) with 3-ethoxypropylamine (Aldrich Chemical Company) (0.225 g, 2.18 mmol) and $K_2CO_3$ (0.34 g, 2.50 mmol) in $H_2O$ (2.5 mL) to give a biphasic reaction mixture, which was partitioned between $CH_2Cl_2$ and $H_2O$. The organic layers were separated, dried over $MgSO_4$ and concentrated. The resulting yellow oil was purified by flash chromatography on silica gel (1:40 MeOH/$CH_2Cl_2$ followed by 1:20 MeOH/$CH_2Cl_2$ as eluant) to give 0.056 g (44%) of the title compound as a light yellow oil that solidified upon standing. Mp: 208–209.5° C. $^1$H NMR (CDCl$_3$; 500 MHz): δ 1.16 (t, 3, J=7.0), 1.99 (quin, 2, J=5.8, 6.4), 2.58 (s, 3), 3.52 (q, 2, J=7.1), 3.63 (t, 2, J=5.6), 3.74 (t, 2, J=6.6), 5.95 (br s, 1), 6.67 (s, 1), 7.33 (t, 1, J=7.4), 7.40 (t, 2, J=7.6), 7.66 (d, 2, J=7.6); MS m/z: 311 (M+1).

EXAMPLE 29

(2-Methyl-6-phenylpyrrolo[2,3-e]pyrimidin-4-yl) benyzlamine.

This compound was prepared according to the method described in Example 26 by employing 4-chloro-2-methyl-6-phenylpyrrolo[3,2-d]pyrimidine (Example 1(e)) (0.20 g, 0.82 mmol), benzylamine (Aldrich Chemical Company) (0.45 mL, 4.11 mmol) and $K_2CO_3$ (0.71 g, 5.10 mmol) in $H_2O$ (5 mL) to obtain 0.24 g (93%) of the title compound as an off-white solid. Mp: 275–276.5° C. $^1$H NMR (DMSO-$d_6$, 500 MHz): δ 2.41 (s, 3), 4.73 (s, 2), 6.75 (s, 1), 7.30–7.49 (m, 9), 7.80 (d, 2, J=7.3), 11.50 (br s, 1); MS m/z: 315 (M+1).

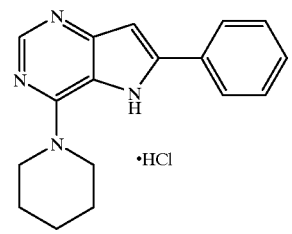

EXAMPLE 30

6-Phenyl-4-piperidylpyrrolo[3,2-d]pyrimidine Hydrochloride.

To a mixture of 1-(N-pyrrolyl)-1-phenyl ethylene (1.54 g, 8.90 mmol) [freshly prepared through TiCl$_4$ mediated condensation between acetophenone (Aldrich Chemical Company) and pyrrolidine (Aldrich Chemical Company) (1.70 g, 8.76 mmol) in ether by the method described by Boger, D. L.; Duff, S. R.; Panek, J. S.; Yasuda, M. *J. Org. Chem.* 1985, 50, 5782–5789)] and N,N-diisopropylethylamine (1.60 mL, 9.10 mmol) in toluene (15 mL) at room temperature was added 4,6-dichloro-5-nitro pyrimidine (Aldrich Chemical Company) (1.70 g, 8.76 mmol) slowly under a stream of N$_2$. The reaction mixture became hot upon mixing and was stirred at room temperature for 2.5 h. The solution was filtered through a fritted-funnel and the residue was washed with hot toluene (3×). The filtrate was concentrated in vacuo and the residue was dissolved in 1:2 toluene:dioxane (8.0–16.0 mL). Piperidine (Aldrich Chemical Company) (2.0 mL, 20 mmol) and Et$_3$N (2.0 mL) were slowly added (exothermic reaction). The mixture was stirred at 100° C. (sand bath temperature) for 1 h and cooled under a N$_2$ stream. To this solution was added SnCl$_2$ (32 mL of a 1.5 M solution in DMF) and the mixture was stirred at room temperature overnight. The reaction mixture was poured into a mixture of NaOH (3.80 g, 95.0 mmol) and ice (~100 mL) and stirred vigorously for 30 min. The resulting slurry (pH ~9) was filtered through a pad of celite, and the residue was washed exhaustively with 10:1 EtOAc:MeOH. The clear filtrate was separated and the organic phase was washed with H$_2$O (4×), saturated aqueous NaCl, dried over Na$_2$SO$_4$, filtered, and concentrated with a rotary evaporator. The residue was purified by flash chromatography on silica gel with a gradient eluant of 0.4:99.6 i-PrOH:CH$_2$Cl$_2$ to 5:95 i-PrOH:CH$_2$Cl$_2$ to afford 0.73 g (30%) of the title compound as a brown solid. A portion of this material was converted to it's corresponding HCl salt by treating a solution of the free base in CH$_2$Cl$_2$ with 1N ethereal HCl. The resulting solid was filtered and washed with hot EtOAc. MS m/z$^+$: 279 (M+1); m/z$^-$: 277 (M−1). $^1$H NMR (CD$_3$OD; 500 MHz): δ 2.12 (br s, 6), 4.53 (br s, 4), 8.01 (m, 2), 7.52 (s, 1), 7.85 (m, 3), 8.56 (s, 1). HRMS: Calcd for M+H, C$_{17}$H$_{19}$N$_4$: 279.1606. Found: 279.1606

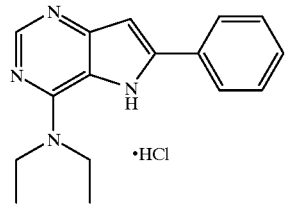

EXAMPLE 31

Diethyl(6-phenylpyrrolo[2,3-e]pyrimidin-4-yl)amine Hydrochloride.

To a mixture of 1-(N-pyrrolyl)-1-phenyl ethylene (2.0 g, 11.5 mmol) [freshly prepared through TiCl$_4$ mediated condensation between acetophenone (Aldrich Chemical Company) and pyrrolidine (Aldrich Chemical Company) (1.70 g, 8.76 mmol) in ether by the method described by Boger, D. L.; Duff, S. R.; Panek, J. S.; Yasuda, M. *J. Org. Chem.* 1985, 50, 5782–5789)] and Et$_3$N (1.7 mL, 12.2 mmol) in CH$_2$Cl$_2$ (15 mL) at room temperature was added 4,6-dichloro-5-nitro pyrimidine (Aldrich Chemical Company) (1.6 g, 8.2 mmol) slowly under a stream of N$_2$.

The reaction mixture became hot upon mixing and the solution was stirred at room temperature for 2.5 h. The solution was concentrated and the residue was treated with hot toluene, filtered, washed with hot toluene (3×), and the filtrate was concentrated in vacuo. Half of this material was dissolved in toluene (10 mL), and Et$_3$N (2.0 mL) followed by Et$_2$NH (Aldrich Chemical Company) (2.0 mL, 20 mmol) were added slowly, leading to an exothermic reaction. The mixture was stirred at 100° C. (sand bath temperature) overnight, cooled under a N$_2$ stream, and partitioned between H$_2$O and EtOAc. The organic layer was concentrated in vacuo. The residue was dissolved in i-PrOH-MeOH (5:1, ~20 mL) and hydrogenated with 10% Pd/C (0.5 g) and PtO$_2$ (0.1 g) as catalysts for 4 d at room temperature and atmospheric pressure. The solution was filtered through a plug of celite and concentrated with a rotary evaporator. The residue was purified by flash chromatography on silica gel with a gradient eluant of i-PrOH (0.4 to 5%):CH$_2$Cl$_2$ (99.6 to 95%) to afford the free base which was treated with 1N ethereal HCl to give 0.035 g (3.0%) of the title compound as a yellow solid. MS m/z$^+$267 (M+1); m/z$^-$265 (M−1). $^1$H NMR (CD$_3$OD; 500 MHz): δ 1.46 (t, 6, J=7.0), 4.26 (q, 4, J=7.0),. 7.61 (m, 3), 7.23 (s, 1), 8.30 (s, 1), 7.73 (m, 2). HRMS: Calcd for M+H, C$_{16}$H$_{19}$N$_4$: 267.1606. Found: 267.1598.

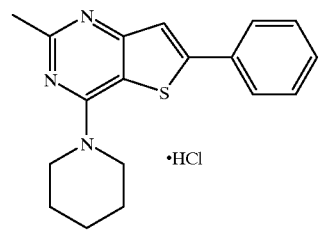

EXAMPLE 32

2-Methyl-6-phenyl-4-piperidylthiopheno[3,2-d]pyrimidine Hydrochloride.

A mixture of methyl 3-amino-5-phenylthiophene 2-carboxylate (Maybridge) (2.4 g, 10.6 mmol), acetamidine hydrogen chloride (Aldrich Chemical Company) (1.2 g, 12.3 mmol), and NaOMe (Aldrich Chemical Company) (1.0 g, 18.5 mmol) in polyethylene glycol (Aldrich Chemical Company) (20 mL) was heated at 120° C. for 2 d. The mixture was poured into aqueous 0.13 M HCl (50 mL, 6.4 mmol) and the resulting slurry was filtered. The solid was washed with distilled H$_2$O, dissolved in CH$_2$Cl$_2$ and DMF, and concentrated with a rotary evaporator. Toluene was added to the residue and the solution was concentrated to remove the residual H$_2$O (this process was repeated two additional times). To this material was added neat POCl$_3$ (15 mL) and the mixture was heated at 100° C. for 12 h. The solvent was evaporated in vacuo, and the residue was dissolved in toluene and concentrated (this process was repeated two additional times) to remove the residual POCl$_3$. The residue was dissolved in toluene (15 mL) and treated with piperidine (Aldrich Chemical Company) (5 mL). The mixture was heated at 100° C. for 12 h, cooled to room temperature, washed with aqueous. NaHCO$_3$, dried over Na$_2$SO$_4$, and concentrated with a rotary evaporator. This material was purified by flash chromatography on silica gel with 1:1 EtOAc:hexanes as eluant. Treatment of the free base with 1N ethereal HCl afforded 80 mg (2.2%) of the title compound as a yellow solid. MS m/z: 310 (M+1). $^1$H NMR (2:1 DMSO-$d_6$:CD$_3$OD-$d_6$; 400 MHz): δ 1.79 (br s, 6), 2.54 (s, 3), 4.16 (br s, 4), 7.56 (m, 3), 7.73 (s, 1), 7.91 (m, 2). HRMS: Calcd for M+H, $C_{18}H_{20}N_3S$: 310.1374. Found: 310.1377.

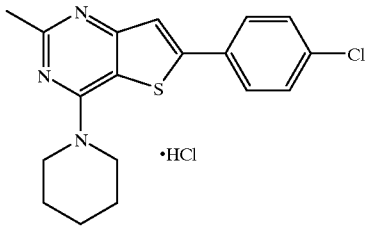

EXAMPLE 33
6-(4-Chlorophenyl)-2-methyl-4-piperidylthiopheno[3,2-d]pyrimidine Hydrochloride.

This compound was prepared by the method described in Example 32 by using methyl 3-amino-5-(4-chlorophenyl)thiophene 2-carboxylate (Maybridge) (1.30 g, 4.86 mmol) to give 170 mg (10%) of the title compound as a tan solid. MS m/z: 344 (M+1), 343. $^1$H NMR (DMSO-$d_6$; 500 MHz) : δ 1.75 (br s, 6), 2.62 (s, 3), 4.12 (br s, 4), 7.63 (d, 2, J=8.0), 7.84 (s, 1), 7.96 (d, 2, J=8.5). HRMS: Calcd for M+H, $C_{18}H_{19}ClN_3S$: 344.0984. Found: 344.0971.

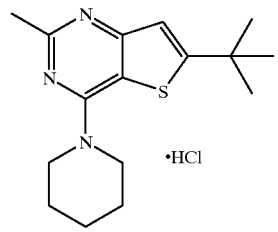

EXAMPLE 34
6-(tert-Butyl)-2-methyl-4-piperidylthiopheno[3,2-d]pyrimidine Hydrochloride.

This compound was prepared by the method described in Example 32 by using methyl 3-amino-5-tert-butylthiophene 2-carboxylate (Maybridge) (0.90 g, 4.22 mmol) to give 110 mg (8%) of the title compound as a white solid. MS m/z$^+$290.0 (M+1). $^1$H NMR (DMSO-$d_6$; 500 MHz): δ 1.45 (s, 15), 2.72 (s, 3), 4.07 (br s, 4), 7.43 (s, 1). HRMS: Calcd for M+H, $C_{16}H_{24}N_3S$: 290.1686. Found: 290.1686.

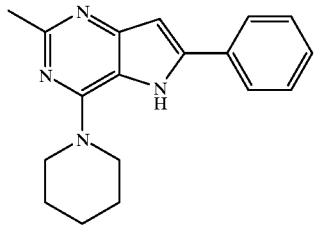

EXAMPLE 35
2-Methyl-6-phenyl-4-piperidylpyrrolo[3,2-d]pyrimidine Hydrochloride.

This compound was prepared according to the method described in Example 2 by employing 4-chloro-2-methyl-6-phenylpyrrolo[3,2-d]pyrimidine (Example 1(e)) (1.0 g, 4.1 mmol), piperidine (Aldrich Chemical Company) (2.0 mL, 20.52 mmol),and $K_2CO_3$ (2.84 g, 20.52 mmol) in $H_2O$ (30 mL). The precipitate that formed was collected by filtration, washed with water and hexane to give a brown solid as crude product. This material was purified by flash chromatography on silica gel with 2:1 EtOAc:hexanes as eluant to give 0.84 g (70%) of the free base as an off-white solid. $^1$H NMR (CDCl$_3$; 500 MHz): δ 1.74–1.76 (m, 6), 2.60 (s, 3), 3.79–3.81 (m, 4), 6.76 (s, 1), 7.38–7.49 (m, 3), 7.66 (d, 2, J=7.54). MS m/z: 293 (M+1), 291 (M−1). A portion of this free base (450 mg, 1.54 mmol) was dissolved in minimum amount of CHCl$_3$, and HCl (1.54 mL, 1.54 mmol, of a 1N solution in ether) was added dropwise. The mixture was stirred at room temperature for 20 min and the solvent was evaporated in vacuo to give a light-yellow foam. This material was recrystallized from MeOH-$H_2O$ to give 260 mg of the title compound as white needles. Mp: 293–294° C. $^1$H NMR (DMSO-$d_6$; 500 MHz): δ 1.71–1.72 (m, 6), 2.58 (s, 3), 4.06–4.07 (m, 4), 6.89 (s, 1), 7.50–7.57 (m, 3), 7.96 (d, 2, J=7.1), 12.0 (br s, 1), 14.4 (br s, 1). Anal. Calcd for $C_{18}H_{21}ClN_4.H_2O$: C, 62.33; H, 6.68; Cl, 10.22; N, 16.15. Found: C, 62.25; H, 6.64; N, 16.14; Cl, 10.34.

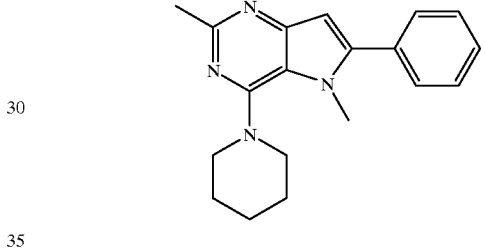

EXAMPLE 36
2,5-Dimethyl-6-phenyl-4-piperidylpyrrolo[3,2-d]pyrimidine.

A suspension of 2-methyl-6-phenyl-4-piperidylpyrrolo[3,2-d]pyridine (Example 35) (57 mg, 0.20 mmol) in THF (3 mL) was placed under a $N_2$ atmosphere and cooled with a dry-ice bath to −78° C. n-Butyl lithium (Aldrich Chemical Company) (360 μL, 0.90 mmol, 4.5 equiv of a 2.5 M solution in hexanes) was added slowly. The reaction mixture was stirred at −78° C. for 1 h and allowed to warmed to 0° C. Dimethyl sulfate (Eastman Kodak Company) (73.8 mg, 0.60 mmol, 3.0) was added slowly at 0° C. The solution was allowed to warm to room temperature and stir overnight. The reaction was quenched by the addition of 10% NH$_4$Cl (3 mL) and the THF was evaporated under reduced pressure. The solution was extracted with CHCl$_3$ (3×50 mL), and the combined organic layers were washed with saturated NaCl, dried over Na$_2$SO$_4$, filtered and concentrated with a rotary evaporator. The crude material was purified by flash chromatography on silica gel with a gradient eluant of EtOAc (0–20%):hexanes(100–80%) to provide 20 mg (34%) of the title compound as a white solid [30 mg (53%) of recovered starting material was also obtained]. Mp: 131–132° C. $^1$H NMR (acetone-$d_6$, 400 MHz): δ 7.68 (d, 2, J=7.0), 7.54 (t, 2, J=7.0), 7.47 (t, 1, J=7.0), 3.84 (s, 3), 3.40 (t, 4, J=4.9), 2.50 (s, 3), 1.78 (m, 4), 1.70 (m, 2). MS m/z: 307 (M+1).

EXAMPLE 37

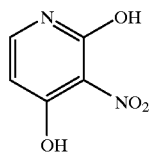

(a) 2,4-Dihydroxy-3-nitropyridine. Fuming HNO$_3$ (40 mL) was added to a stirring solution of 2,4-dihydroxypyridine (Aldrich Chemical Company) (9.0 g, 81 mmol) in H$_2$SO$_4$ (conc.) (40 mL) at 0° C. After 30 min, the solution was poured onto crushed ice (~80 mL) (caution: a non-violent exothermic reaction resulted), and the mixture was chilled in a freezer. The resulting precipitate was filtered, washed with cold water, and dried to constant weight in vacuo to afford 11.4 g (90%) of the title compound as a colorless solid. $^1$H NMR (DMSO-d$_6$; 400 MHz): δ 6.13 (d, 1, J=7.2), 7.48 (d, 1, J=7.0), 11.93 (s, 1), 12.42 (br s, 1). MS m/z: 157 (M+1).

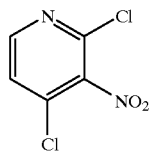

(b) 2,4-Dichloro-3-nitropyridine.

2,4-Dihydroxy-3-nitropyridine (1.56 g, 10 mmol) was taken up in POCl$_3$ (Aldrich Chemical Company) (20 mL) and the resulting black mixture was heated at reflux for 24 h. The volume of the solution was reduced by 70% in vacuo, and the cooled mixture was carefully poured onto crushed ice (caution: a violent exothermic reaction may result) and extracted with EtOAc (2×). The combined extracts were washed with brine, dried over MgSO$_4$, filtered and concentrated in vacuo. The residue was dissolved in 1:1 EtOAc:hexanes, filtered through a plug of silica gel, and concentrated in vacuo to afford 1.5 g (80%) of the title compound as a colorless crystalline solid. $^1$H NMR (DMSO-d$_6$; 400 MHz) δ 8.14 (d, 1, J=5.1), 8.72 (d, 1, J=5.2).

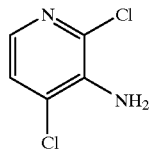

(c) 3-Amino-2,4-dichloropyridine. 2,4-Dichloro-3-nitropyridine (1.5 g, 8 mmol) was dissolved in Et$_2$O (8 mL). A solution of SnCl$_2$.2H$_2$O (18 g, 80 mmol) in HCl (conc.) (18 mL) was added cautiously. The reaction was exothermic upon this addition and the Et$_2$O boiled off of the solution. The reaction mixture was allowed to stir overnight at room temperature. The solution was cooled to 0° C. in an ice-water bath and the precipitate was collected via filtration. The resulting solid was suspended in distilled H$_2$O, and the mixture was adjusted to neutral pH by the addition of concentrated NH$_4$OH at 0° C. The resulting solution was extracted with EtOAc (2×). The combined extracts were washed with brine, dried over MgSO$_4$, filtered and concentrated in vacuo to afford 1.2 g (90%) of the title compound as a colorless crystalline solid. $^1$H NMR (DMSO-d$_6$; 500 MHz): δ 5.88 (s, 2) 7.35 (d, 1, J=5.1), 7.63 (d, 1, J=5.1). MS m/z: 163 (M+1).

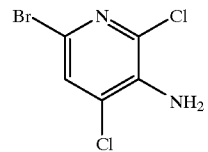

(d) 3-Amino-6-bromo-2,4,-dichloropyridine.

3-Amino-2,4-dichloropyridine (500 mg, 3.1 mmol) was dissolved in DMF (16 mL) and cooled to 0° C. in an ice-water bath. A solution of N-bromosuccinimide (660 mg, 3.7 mmol) in DMF (7 mL) was then added slowly. After 15 min, the solution was poured into H$_2$O and extracted with EtOAc (2×). The combined extracts were washed with H$_2$O and brine, dried over MgSO$_4$, filtered and concentrated in vacuo to obtain a red residue. This residue was dissolved in 1:1 EtOAc:hexanes, filtered through a plug of silica gel, and concentrated in vacuo to afford 0.68 g (90%) of the title compound as a colorless crystalline solid. $^1$H NMR (DMSO-d$_6$; 500 MHz): δ 6.10 (s, 2), 7.69 (s, 1). MS m/z: 243 (M+1; $^{81}$Br), 241 (M+1; $^{79}$Br).

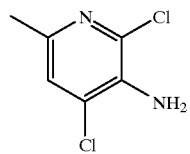

(e) 3-Amino-2,4-dichloro-6-methylpyridine.

3-Amino-6-bromo-2,4, -dichloropyridine (500 mg, 2.1 mmol) was dissolved in anhydrous DMF (10 mL), and MeB(OH)$_2$ (Aldrich Chemical Company) (380 mg, 6.3 mmol), K$_2$CO$_3$ (1.5 g, 10 mmol), and (PPh$_3$)$_2$PdCl$_2$ (150 mg, 0.21 mmol) were added. The mixture was heated to 100° C. for 24 h, then cooled to room temperature, poured into H$_2$O and extracted with EtOAc (2×). The combined extracts were washed with H$_2$O and brine, dried over MgSO$_4$, filtered and concentrated in vacuo. The crude material was purified by flash chromatography on silica gel with 1:4 EtOAc:hexanes to afford 0.31 g (85%) of the title compound as a colorless crystalline solid. $^1$H NMR (DMSO-d$_6$; 500 MHz): δ 2.28 (s, 3), 5.65 (s, 2), 7.34 (s, 1). MS m/z: 177 (M+1).

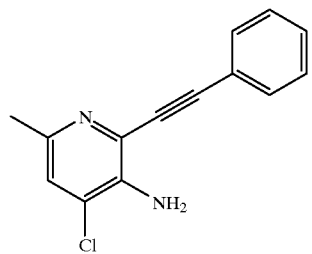

(f) 3-Amino-4-chloro-6-methyl-2-(2-phenylethynyl) pyridine.

To a solution of 3-amino-2,4-dichloro-6-methyl pyridine (220 mg, 1 mmol) in NEt$_3$ (5 mL), was added (PPh$_3$)$_2$PdCl$_2$ (35 mg, 0.05 mmol), and CuI (9.5 mg, 0.05 mmol). The mixture was cooled to 0° C. and phenyl acetylene (160 μl, 1.5 mmol) was added. The mixture was allowed to warm to room temperature then heated at 80° C. for 4 h. The mixture was cooled to room temperature and filtered through celite. The celite was rinsed with NEt$_3$, and the filtrate was concentrated in vacuo. The crude material was purified by flash chromatography on silica gel with 1:4 EtOAc:hexanes to afford 0.22 g (90%) of the title compound as a dark brown solid. $^1$H NMR (DMSO-d$_6$; 500 MHz): δ 2.31 (s, 3), 5.55 (br s, 2), 7.26 (s, 1), 7.44 (m, 3), 7.69 (m, 2). MS m/z: 243 (M+1)

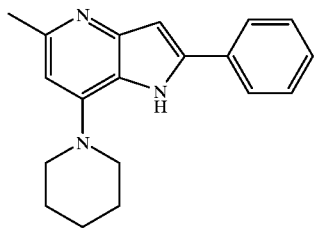

(g) 5-Methyl-2-phenyl-7-piperidylpyrrolo[3,2-b]pyridine.

Method A: 3-Amino-4-chloro-6-methyl-2-(2-phenyl ethynyl)pyridine (240 mg, 1 mmol) was taken up in 4:1 o-xylene/piperidine (10 mL) and heated to 140° C. in a Teflon-capped pressure tube for 7 d. The mixture was cooled to room temperature and the resulting precipitate was filtered and washed with o-xylene, followed by acetonitrile. The precipitate was dried to constant weight in vacuo to afford 0.23 g (80%) of the title compound as a pale yellow solid. $^1$H NMR (DMSO-d$_6$; 500 MHz): δ 1.65 (m, 2), 1.75 (m, 4), 2.42 (s, 3), 3.32 (br s, 4), 6.49 (s,l), 6.80 (s, 1), 7.33 (t, 1, J=7.2), 7.43 (m, 2), 7.90 (d, 2, J=7.2), 11.1 (br s, 1). MS m/z: 292 (M+1).

Method B: 3-Amino-4-chloro-6-methyl-2-(2-phenyl ethynyl)pyridine (1.24 g, 5.1 mmol) was dissolved in anhydrous DMF (90 mL), CuI (150 mg, 0.8 mmol) was added and the mixture was heated at 110° C. for 18 h. The cooled mixture was poured into H$_2$O (125 mL) and extracted with EtOAc (2×100 mL). The combined extracts were washed with H$_2$O and brine, dried over MgSO$_4$ and filtered through a plug of silica using CHCl$_3$. The crude product was triturated with 20:1 hexanes:EtOAc, filtered, and dried under high vacuum to afford 600 mg (48%) of 7-chloro-5-methyl-2-phenyl pyrrolo-[3,2-b]pyridine. $^1$H NMR (DMSO-d$_6$; 500 MHz): δ 2.40 (s, 3), 7.05 (s, 1), 7.16 (s,1), 7.38 (t, 1, J=5.2), 7.49 (m, 2), 8.02 (d, 2, J=7.2). MS m/z: 243 (M+H). This intermediate chloride (273 mg, 1.1 mmol) was taken up in 4:1 o-xylene/piperidine (10 mL) and heated to 140° C. in a Teflon-capped pressure tube for 7 d. The mixture was cooled to room temperature, diluted with H$_2$O (125 mL) and extracted with EtOAc (2×100 mL). The combined organic layers were washed with H$_2$O and brine, dried over MgSO$_4$ filtered, and concentrated in vacuo. Chromatography on silica gel eluting with 10:1 CHCl$_3$:MeOH afforded 244 mg (75%, 36% overall) of the title compound as a pale yellow solid. The product's $^1$H-NMR was identical to that obtained using Method A.

EXAMPLE 38

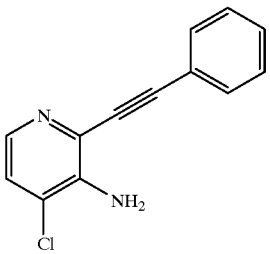

(a) 3-Amino-4-chloro-2-(2-phenylethynyl)pyridine.

This material was prepared according to the method described in Example 37(f) starting with 3-Amino-2,4-dichloropyridine (160 mg, 1.0 mmol) to give 0.20 g (90%) of the title compound as a tan solid. $^1$H NMR (DMSO-d$_6$; 500 MHz): δ 5.94 (s, 2), 7.39 (d, 1, J=5.0), 7.54 (m, 3), 7.75 (m, 2), 7.82 (d, 1, J=5.0). MS m/z: 229 (M+1).

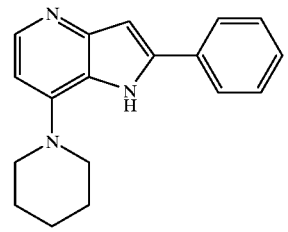

(b) 2-Phenyl-7-piperidylpyrrolo[3,2-b]pyridine.

This material was prepared according to Example 37(g) by employing 3-Amino-4-chloro-2-(2-phenylethynyl) pyridine (0.20 g 0.90 mmol). The crude material was purified by flash chromatography on silica gel with 1:9 MeOH:EtOAc as eluant to afford 0.20 g (80%) of the title compound as a colorless solid. $^1$H NMR (DMSO-d$_6$; 500 MHz): δ 1.77 (m, 6), 3.32 (m, 4), 6.63 (d, 1, J=5.2), 6.94 (s, 1), 7.36 (dd, 1, J=7.4, 7.2), 7.53 (dd, 2, J=7.6, 7.8), 7.94 (d, 2, J=8.1), 8.11 (br s, 1), 11.04 (br s, 1). MS m/z: 278 (M+1).

EXAMPLE 39

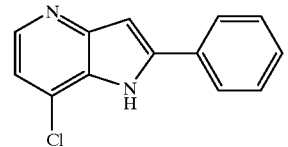

(a) 7-Chloro-2-phenylpyrrolo[3,2-b]pyridine.

3-Amino-4-chloro-2-(2-phenylethynyl)pyridine (Example 38(a)) (229 mg, 1 mmol) was dissolved in anhydrous DMF (10 mL), and CuI (9.5 mg, 0.05 mmol) was added, and the mixture was heated at 100° C. for 6 h. The cooled mixture was poured into H$_2$O and extracted with EtOAc (2×). The combined extracts were washed with H$_2$O and brine, dried over MgSO$_4$, filtered through a plug of silica gel, and concentrated in vacuo to afford 190 g (85%) of the title compound as a tan solid. $^1$H NMR (DMSO-d$_6$; 500 MHz): δ 7.18 (s, 1), 7.30 (d, 1, J=7.1), 7.43 (m, 1), 7.54 (m, 2), 8.04 (d, 2, J=7.7), 8.33 (d, 1, J=7.0), 10.91 (s, 1). MS m/z: 229 (M+H).

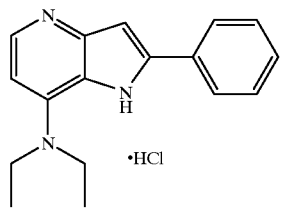

(b) Diethyl(2-phenylpyrrolo[3,2-b]pyridin-7-yl)amine Hydrochloride.

This material was prepared according to the method described in Example 37(g) by employing 7-chloro-2-phenylpyrrolo[3,2-b]pyridine (195 mg, 0.85 mmol) and 4:1 o-xylene:N,N-diethylamine (10 mL). This material was purified by flash chromatography on silica gel with 1:9 MeOH:EtOAc as eluant to give the free base as a tan solid. This material was dissolved in EtOAc and treated with excess 1N ethereal HCl. The resultant precipitate was collected via filtration and triturated with acetonitrile to afford 180 g (80%) of the title compound as a colorless solid. $^1$H NMR (DMSO-$d_6$; 500 MHz): δ 1.29 (t, 6, J=7.0), 3.94 (q, 4, J=7.0), 6.51 (d, 1, J=7.1), 7.30 (s, 1), 7.55 (m, 3), 7.92 (m, 2), 8.14 (d, 1, J=7.1), 11.30 (br s, 1). MS m/z: 266 (M+1).

EXAMPLE 40

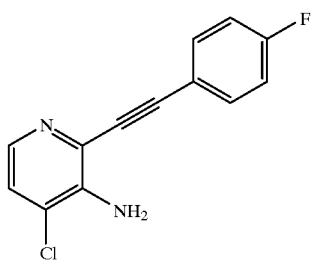

(a) 3-Amino-4-chloro-2-[2-(4-fluorophenyl)ethynyl]pyridine.

This material was prepared according to the method described in Example 37(f) by employing 3-Amino-2,4-dichloropyridine (Example 37(c)) (162 mg, 1.0 mmol) and 4-fluoroethynylbenzene (Aldrich Chemical Company) (180 mg, 1.5 mmol) to give 0.22 g (90%) of the title compound as an amber oil. MS m/z: 247 (M+1).

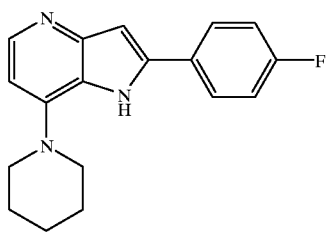

(b) 2-(4-Fluorophenyl)-7-piperidylpyrrolo[3,2-b]pyridine.

This material was prepared according to the method described in Example 37(g) by employing 3-Amino-4-chloro-2-3-amino-4-chloro-2-[2-(4-fluorophenyl)ethynyl]pyridine (0.22 g, 0.90 mmol). The crude material was purified by flash chromatography with 1:9 MeOH:EtOAc as eluant to give 0.21 g (80%) of the title compound as an off-white solid. $^1$H NMR (DMSO-$d_6$; 500 MHz): δ 1.67 (m, 6), 3.34 (m, 4), 6.66 (d, 1, J=5.3), 6.95 (s, 1), 7.31 (m, 2), 8.03 (m, 2), 8.11 (m, 1), 11.10 (br s, 1). MS m/z: 296 (M+1). Anal. Calcd for $C_{18}H_{18}FN_3 \cdot 0.8H_2O$: C, 69.79; H, 6.38; N, 13.56. Found: C, 69.55; H, 6.00; N, 13.32.

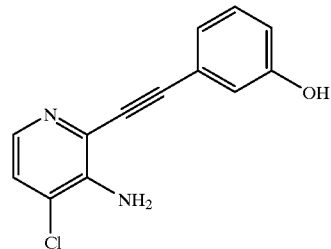

EXAMPLE 41

(a) 3-Amino-4-chloro-2-[2-(3-hydroxyphenyl)ethynyl]pyridine.

This material was prepared according to the method described in Example 37(f) by employing 3-Amino-2,4-dichloropyridine (Example 37(c)) (0.16 g, 1.0 mmol) and 3-hydroxyethynylbenzene (Aldrich Chemical Company) (0.15 g, 1.5 mol) to give 0.22 g (90%) of the title compound as a solid. $^1$H NMR (DMSO-$d_6$; 500 MHz): δ 5.82 (s, 2), 6.83 (m, 1), 7.00 (m, 1), 7.11 (m, 1), 7.20 (m, 1), 7.41 (m, 1), 7.83 (m, 1), 9.78 (s, 1). MS m/z: 245 (M+1).

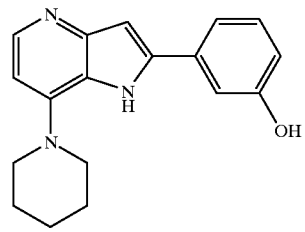

(b) 2-(3-Hydroxyphenyl)-7-piperidylpyrrolo[3,2-b]pyridine.

This material was prepared according to the method described in Example 37(g) by employing 3-Amino-4-chloro-2-[2-(3-hydroxyphenyl)ethynyl]pyridine (0.22 g, 0.90 mmol) and 4:1 o-xylene/piperidine (10 mL). The crude material was purified by flash chromatography on silica gel with 1:9 MeOH:EtOAc as eluant to give 0.18 g (70%) of the title compound as an off-white solid. $^1$H NMR (DMSO-$d_6$; 500 MHz): δ 1.69 (m, 6), 3.31 (m, 4), 6.58 (m, 1), 6.79 (m, 2), 7.31 (m, 3), 8.09 (br s, 1), 9.55 (br s, 1), 11.01 (br s, 1). MS m/z: 294 (M+1). Anal. Calcd for $C_{18}H_{19}N_3O \cdot 0.5CH_3OH$: C, 71.82; H, 6.84; N, 13.58. Found: C, 71.99; H, 6.99; N, 13.12.

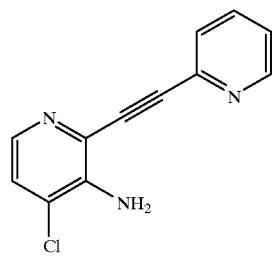

EXAMPLE 42

(a) 3-Amino-4-chloro-2-[2-(2-pyridyl)ethynyl]pyridine.

This material was prepared according to the method described in Example 37(f) by employing 3-amino-2,4-dichloropyridine (Example 37(c)) (0.16 g, 1.0 mmol) and 2-ethynylpyridine (Aldrich Chemical Company) (0.15 g, 1.5 mmol). The crude material was purified by flash chromatography on silica gel with 1:1 EtOAc:hexanes to afford 46 mg (20%) of the title compound as a tan solid. $^1$H NMR (DMSO-$d_6$; 500 MHz): δ 5.98 (s, 2), 7.41 (d, 1, J=5.0), 7.50 (m, 1), 7.63 (m, 1), 7.81 (d, 1, J=5.0), 7.87 (m, 1), 8.65 (d, 1, J=4.9). MS m/z: 230 (M+1).

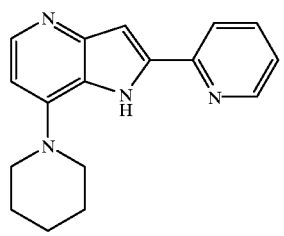

(b) 7-Piperidyl-2-(2-pyridyl)pyrrolo[3,2-b]pyridine.

This material was prepared according to the method described in Example 37(g) by employing 3-amino-4-chloro-2-[2-(2-pyridyl)ethynyl]pyridine (46 mg, 0.20 mmol). The crude material was purified by flash chromatography on silica gel with 1:9 MeOH:EtOAc as eluant to afford 50 mg (90%) of the title compound as a tan solid. $^1$H NMR (DMSO-$d_6$; 500 MHz): δ 1.75 (m, 6), 3.31 (m, 4), 6.62 (m, 1), 7.19 (m, 1), 7.42 (m, 1), 7.93 (m, 1), 8.10 (m, 2), 8.68 (m, 1), 11.01 (br s, 1). MS m/z: 279 (M+1).

EXAMPLE 43

(a) 3-Amino-4-chloro-2-[2-cyclohex-1-enylethynyl]pyridine.

This material was prepared according to the method described in Example 37(f) by employing 3-amino-2,4-dichloropyridine (Example 37(c)) (0.16 g, 1.0 mmol) and 1-ethynylcyclohexene (Aldrich Chemical Company) (0.16 g, 1.5 mol) to afford 0.23 g (99%) of the title compound as a viscous amber oil. $^1$H NMR (DMSO-$d_6$; 500 MHz): δ 1.63 (m, 4), 2.20 (m, 4), 5.65 (s, 2), 6.42 (m, 1), 7.27 (d, 1, J=5.0), 7.71 (d, 1, J=5.0). MS m/z: 233 (M+1).

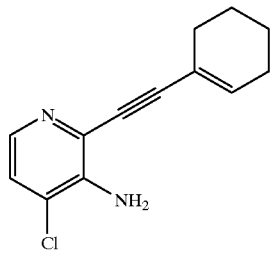

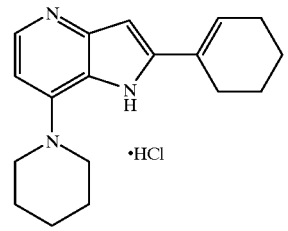

(b) 2-Cyclohex-1-enyl-7-piperidylpyrrolo[3,2-b]pyridine Hydrochloride.

This material was prepared according to the method described in Example 37(g) by employing 3-Amino-4-chloro-2-[2-cyclohex-1-enylethynyl]pyridine (0.23 g, 1.0 mmol). The free base was dissolved in EtOAc and treated with excess iN ethereal HCl. The resultant precipitate was collected via filtration and triturated with acetonitrile to afford 0.25 g (90%) of the title compound as an off-white solid. $^1$H NMR (DMSO-$d_6$; 500 MHz): δ 1.75 (m, 6), 2.30 (m, 4), 3.33 (m, 4), 3.71 (m, 4), 6.58 (s, 1), 6.72 (m, 1), 6.94 (d, 1, J=7.0), 8.11 (d, 1, J=7.0), 11.42 (s, 1), 13.80 (br s, 1). MS m/z: 282 (M+1), 254 (M+1–28). Anal. Calcd for $C_{18}H_{23}N_3 \cdot HCl \cdot 0.75H_2O$: C, 65.25; H, 7.75; N, 12.68. Found: C, 65.38; H, 7.39; N, 12.54.

EXAMPLE 44

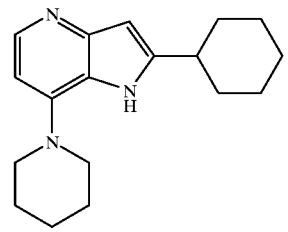

2-Cyclohexyl-7-piperidylpyrrolo[3,2-b]pyridine.

2–Cyclohex-1-enyl-7-piperidylpyrrolo[3,2-b]pyridine (Example 43(b)) (280 mg, 1 mmol) was dissolved in MeOH (5 mL), and 10% palladium on charcoal (28 mg) was added. The flask was purged with $H_2$ and a doubled-walled balloon filled with $H_2$ was attached to the flask (~30 psi $H_2$). After 16 h, the mixture was filtered through celite, and the filtrate was concentrated in vacuo. The crude material was purified by flash chromatography 1:9 MeOH:EtOAc to afford 0.28 g (99%) of the title compound as an off-white solid. $^1$H NMR (DMSO-$d_6$; 500 MHz): δ 2.0–1.2 (m, 16), 2.72 (m, 1), 3.18 (t, 4, J=5.2), 6.22 (s, 1), 6.55 (d, 1, J=5.3), 8.04 (d, 1, J=5.3), 10.61 (s, 1). MS m/z: 284 (M+1). Anal. Calcd for $C_{18}H_{25}N_3 \cdot 0.2H_2O$: C, 75.33; H, 8.92; N, 14.64. Found: C, 75.39; H, 8.64; N, 14.64.

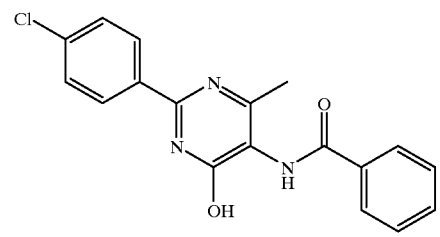

EXAMPLE 45

(a) 2-(4-Chlorophenyl)-4-hydroxy-6-methyl-5-benzamidopyrimidine.

To a solution of sodium ethoxide (Aldrich Chemical Company) (7.00 g, 0.099 mol) in absolute ethanol (70 mL) was added 4-chlorobenzamidine hydrochloride (Maybridge Chemical Company) (7.50 g, 0.040 mol). After stirring at 25° C. for 0.5 h this slurry was filtered through a plug of celite into a solution of 2-benzoylamino-3-oxo-butyric acid ethyl ester (Example 1(c)) (8.18 g, 0.033 mol). The mixture was placed under a $N_2$ atmosphere and allowed to stir at room temperature overnight. The precipitate was collected by filtration, washed with ethanol (3×20 mL) and dried under vacuum to provide 2.32 g (21%) of the title compound as a beige solid. Mp: >280° C. $^1$H NMR (DMSO-$d_6$; 400 MHz): δ 2.25 (s, 3), 7.51–7.62 (m, 5), 8.00 (d, 2, J=7.3), 8.15 (d, 2, J=7.6), 9.68 (s, 1), 12.96 (s, 1). MS m/z: 340 (M+1), 322 (M−$H_2O$).

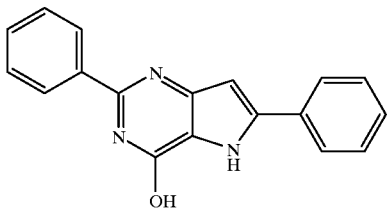

(b) 2,6-Diphenylpyrrolo[3,2-d]pyrimidin-4-ol.

This material was prepared according to the method described in Example 1(d) by employing 2-(4-chlorophenyl)-4-hydroxy-6-methyl-5-benzamidopyrimidine (Example 45(a)) (2.03 g, 24.0 mmol). The mixture was slowly heated to 180° C. under a slow steam of nitrogen until all the solvent was distilled off. The temperature was slowly increased to 340° C. The temperature was kept at 340° C. for 10 min then allowed to cool to room temperature. Water (50 mL) was added to the residue and HCl (conc.) was added until the pH of the solution was 4–5 (pH paper). The precipitate was collected by filtration and washed with $H_2O$ (3×10 mL). This material was purified by flash chromatography on silica gel with 99:1 $CHCl_3$:MeOH as eluant to give 420 mg (24%) of the title compound as a beige solid (Analytical data obtained for this product indicated that the para-chloro group in the starting material was reduced under the above reaction conditions). Mp: 227–231° C. $^1$H NMR (DMSO-$d_6$; 400 MHz): δ 6.95 (d, 1, J=2.1), 7.36 (t, 1, J=7.3), 7.44–7.52 (m, 5), 7.97 (d, 2, J=7.4), 8.11 (dd, 2, J=5.4, 7.6), 12.12 (s, 1), 12.46 (s, 1). MS m/z: 288 (M+1).

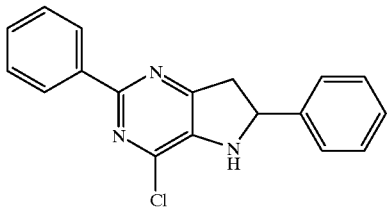

(c) 4-Chloro-2,6-diphenylpyrrolo[3,2-d]pyrimidine.

Phosphorus oxychloride (Aldrich Chemical Company) (15 mL) 2,6-diphenylpyrrolo[3,2-d]pyrimidin-4-ol (Example 45(b)) (0.40 g, 1.39 mmol) were added to a round-bottomed flask. The resulting mixture was heated at reflux under $N_2$ overnight. After cooling the phosphorus oxychloride was removed under reduced pressure to provide a brown oil. This material was purified by flash chromatography on silica gel with 99:1 $CHCl_3$:MeOH as eluant to give 200 mg (48%) of the title compound as a brown solid. Mp: 259–262° C. $^1$H NMR (DMSO-$d_6$; 400 MHz): δ 7.28 (d, 1, J=1.9), 7.47–7.58 (m, 6), 8.12 (d, 2, J=7.3), 8.40 (2, dd, J=1.6, 6.5), 12.53 (s, 1). MS m/z: 306 (M+1).

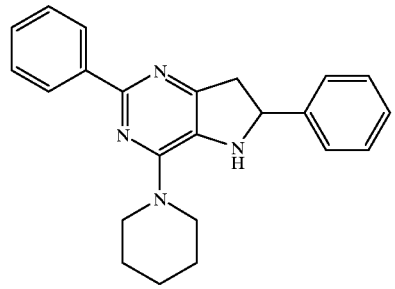

(d) 2,6-Diphenyl-4-piperidylpyrrolo[3,2-d]pyrimidine.

To a mixture of 4-chloro-2,6-diphenylpyrrolo[3,2-d]pyrimidine (Example 45(c)) (123.9 mg, 0.41 mmol) and piperidine (Aldrich Chemical Company) (200 μL, 2.03 mmol) was added a solution of $K_2CO_3$ (0.30 g, 2.18 mmol) in $H_2O$ (2.5 mL). This mixture was stirred at 140° C. in a closed-capped Wheaton vial for 2.0 h. After cooling, $CH_2Cl_2$ (10 mL) and $H_2O$ (10 mL) were added. The organic solution was removed and the aqueous solution washed with $CH_2Cl_2$ (10 mL). The combined organic solutions were washed with saturated NaCl (15 mL), dried over $MgSO_4$, filtered and concentrated under reduced pressure. The residue was purified by flash chromatography silica gel 1:99 MeOH:$CH_2Cl_2$ as eluant to give 61 mg (42%) of the title compound as a white solid. Mp: 259–261.5° C. $^1$H NMR (DMSO-$d_6$; 400 MHz): δ 1.71 (br s, 6), 3.85 (br s, 4), 6.94 (d, 1, J=1.6), 7.37–7.53 (m, 6), 7.94 (d, 2, J=8.3), 8.40 (2, dd, J=1.4, 8.3), 11.16 (s, 1). MS m/z: 355 (M+1). Anal. Calcd for $C_{23}H_{22}N_4 \cdot 0.5H_2O$: C, 76.03; H, 6.34; N, 15.43. Found: C, 76.27; H, 6.34; N, 15.34.

EXAMPLE 46

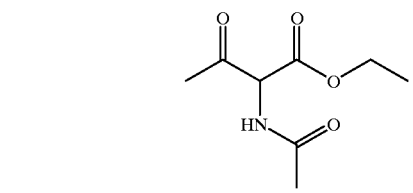

(a) Ethyl 2-(Acetylamino)-3-oxobutanoate.

This compound was prepared according to the method described in Example 1(b) by employing ethyl 2-hydroximino-3-oxybutyrate (25.2 g, 0.158 mol), $H_2SO_4$ (30% w/v) (230 g), crushed ice (240 g), and powdered zinc (100 mesh—Aldrich Chemical Company) (28.9 g). After filtration, the solution was treated with sodium acetate trihydrate (Aldrich Chemical Company) (148 g, 1.09 mol) and acetic anhydride (Aldrich Chemical Company) (18.2 g, 0.178 mol). The solution was stirred at room temperature for 0.25 h and worked-up as described in Example 1(b) to give 16.8 g (57%) of the title compound as a yellow oil after chromatography. $^1$H NMR ($CDCl_3$; 500 MHz): δ 1.32 (t, 3, J=7.0), 2.07 (s, 3), 2.40 (s, 3), 4.28 (q, 2, J=7.1), 5.25 (d, 1, J=6.5), 6.62 (br s, 1). MS m/z: 188 (M+1).

(b) 5-Acetamido-2,6-dimethyl-4-hydroxypyrimidine.

This compound was prepared according to the method described in Example 1(c) by mixing acetamidine hydrochloride (Aldrich Chemical Company) (5.1 g, 53.9 mmol) with a solution of sodium metal (2.2 g, 95.6 mmol) in absolute EtOH (95 mL). The suspension was filtered through celite and ethyl 2-(acetylamino)-3-oxobutanoate (8.4 g, 45.1 mmol) was added to the solution. After 18 hours, the reaction was concentrated to one half the original volume, $H_2O$ (25 mL) was added, and the solution treated with HCl (conc.) to a pH of 4 (pH paper). Solids precipitated out of solution and were collected by vacuum filtration. The wet solids were recrystallized from EtOH and dried in a vacuum oven to give 5.2 g (64%) of the title compound as a white solid. The filtrate was concentrated with a rotary evaporator and recrystallized from EtOH to give an additional 1.2 g (14%) of the title compound as a white solid (total yield 6.4 g (78%)). Mp: 280–281° C. $^1$H NMR (DMSO-$d_6$; 500 MHz): δ 1.98 (s, 3), 2.01 (s, 3), 2.24 (s, 3), 9.08 (s, 1), 12.46 (s, 1). MS m/z: 182 (M+1). Anal. Calcd for $C_8H_{11}N_3O_2 \cdot 0.75 H_2O$: C 49.35, H 6.47, N 21.58. Found: C 49.62, H 6.21, N 21.68.

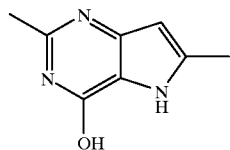

(c) 2,6-Dimethylpyrrolo[3,2-d]pyrimidin-4-ol.

This compound was prepared according to the method described in Example 1(d) by distilling to dryness a mixture of 5-acetamido-2,6-dimethyl-4-hydroxypyrimidine (4.8 g, 26.5 mmol) in a solution of sodium metal (1.82 g, 79.2 mmol) in absolute EtOH (40 mL). The white-yellow solids were scraped to the bottom of the flask and the residue heated at 360–400° C. for 20 min. $H_2O$ (100 mL) was added to the hot residue and the pH was adjusted with HCl (conc.) to pH 4 (pH paper). The solvent was removed using the rotary evaporator and the resulting brown residue was dissolved in 1 N HCl (35 mL), treated with charcoal, and filtered through a plug of celite. The filtrate was adjusted to pH 8 with 10% NaOH and light brown crystals formed in the solution. The solids were collected by filtration and dried in a vacuum oven to give 0.85 g (20%) of the title compound as a light brown solid. The filtrate was concentrated to half of its original volume and a second crop of crystals was collected by filtration to give an additional 0.40 g (9%) of the title compound (total yield 1.2 g (29%)). $^1$H NMR (DMSO-$d_6$; 500 MHz): δ 2.26 (s, 3), 2.29 (s, 3), 5.97 (s, 1), 11.57 (s, 1), 11.62 (s, 1). MS m/z: 164 (M+1). Anal. Calcd for $C_8H_9N_5O$: C, 58.89; H, 5.56; N 25.75. Found: C 58.62; H, 5.51; N, 25.56.

(d) 4-Chloro-2,6-dimethylpyrrolo[3,2-d]pyrimidine.

This compound was prepared according to the method described in Example 1(e) by employing 2,6-dimethylpyrrolo[3,2-d]pyrimidin-4-ol (1.1 g, 6.7 mmol), phosphorous oxychloride (Aldrich Chemical Company) (7.5 mL, 80.5 mmol), N,N-diethylaniline (Aldrich Chemical Company) (3.5 mL, 22.0 mmol), and 1,2-dichloroethane (10 mL) to give a brown oil. This crude material was purified by flash chromatography on silica gel with 5:1 hexanes:EtOAc followed by 1:1 hexanes:EtOAc to give 0.64 (52%) of the title compound as a clear glass. $^1$H NMR (DMSO-$d_6$; 400 MHz): δ 2.47 (s, 3), 2.57 (s, 3), 6.34 (s, 1), 12.04 (br s, 1). MS m/z: 182 (M+1).

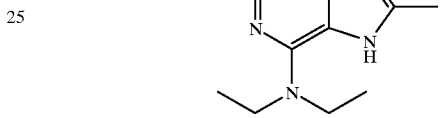

(e) (2,6-Dimethylpyrrolo [2,3-e]pyrimidin-4-yl) diethylamine.

To a 5-mL Wheaton vial was added 4-chloro-2,6-dimethylpyrrolo[3,2-d]pyrimidine (0.10 g, 0.55 mmol), diethylamine (Aldrich Chemical Company) (1.0 mL, 9.7 mmol), and absolute ethanol (1 mL). The reaction mixture was heated in the capped vial at reflux for 6 h. The reaction mixture was cooled to room temperature, diluted with $H_2O$ (5 mL), and extracted twice with $CH_2Cl_2$. The organic layers were dried over $MgSO_4$, filtered, and concentrated with a rotary evaporator. The resulting orange-brown oil was recrystallized from EtOAc to give 0.050 g (41%) of the title compound as a light brown solid. Mp: 212.5–213.5° C. $^1$H NMR (CDCl$_3$, 500 MHz): δ 1.31 (t, 6, J=7.2), 2.43 (s, 3), 2.54 (s, 3), 3.70 (q, 4, J=7.1), 6.19 (s, 1), 7.88 (br s, 1); MS m/z: 219 (M+1).

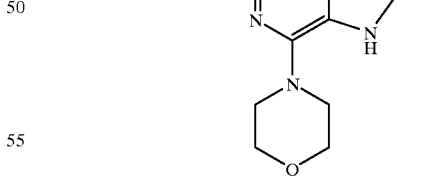

EXAMPLE 47

4-(2,6-Dimethylpyrrolo[2,3-e]pyrimidin-4-yl)morpholine.

To a 5-mL Wheaton vial was added 4-chloro-2,6-dimethylpyrrolo[3,2-d]pyrimidine (Example 46(d)) (0.10 g, 0.55 mmol) and morpholine (Aldrich Chemical Company) (0.24 mL, 2.7 mmol). A solution. of $K_2CO_3$ (0.35 g, 2.5 mmol) in water (2.5 mL) was added and the reaction mixture heated in the capped vial at reflux for 3.5 h. The reaction mixture was cooled to room temperature and the solution was filtered. The resulting precipitate was washed with H₂O and hexanes and dried in a 60° C. vacuum oven to give 0.083 g (65%) of the title compound as an off-white solid. Mp: 242–243° C. ¹H NMR (DMSO-d₆; 500 MHz): δ 2.39 (s, 6), 3.60 (s, 4), 3.74 (s, 4), 6.07 (s, 1), 10.90 (s, 1). MS m/z: 233 (M+1). Anal. Calcd for $C_{12}H_{16}N_4O$: C, 59.73; H, 7.10; N, 23.22. Found: C, 60.01; H, 6.84; N, 23.29.

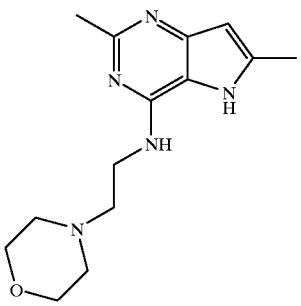

EXAMPLE 48
(2,6-Dimethylpyrrolo[2,3-e]pyrimidin-4-yl)(2-morpholin-4-ylethyl)amine.

This compound was prepared according to the method described in Example 46(e) by employing 4-chloro-2,6-dimethylpyrrolo[3,2-d]pyrimidine (Example 46(d)) (0.10 g, 0.55 mmol) with 4-(2-aminoethyl)morpholine (Aldrich Chemical Company) (0.388 mL, 2.95 mmol) and K₂CO₃ (0.36 g, 2.6 mmol) in water (2.5 mL) to give 0.038 g (25%) of the title compound as an off-white solid after recrystallization from EtOAc. Mp: 237–238.5° C. ¹H NMR (CDCl₃; 500 MHz): δ 2.43 (s, 3), 2.50 (t, 4, J=5.2), 2.58 (s, 3), 2.65 (t, 2, J=5.7), 3.67 (t, 4, J=4.6), 3.70 (q, 2, J=5.4), 5.55 (br s, 1), 6.18 (s, 1), 9.88 (br s, 1). MS m/z: 276 (M+1). Anal. Calcd for $C_{14}H_{21}N_5O$: C, 61.07; H, 7.69; N 25.43. Found: C, 61.19; H, 7.77; N, 25.39.

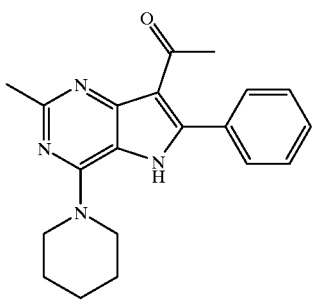

EXAMPLE 49
7-Acetyl-2-methyl-6-phenyl-4-piperidylpyrrolo[3,2-d]pyrimidine.

A mixture of 2-methyl-6-phenyl-4-piperidylpyrrolo[3,2-d]pyridine (Example 35) (50 mg, 0.17 mmol), acetic anhydride (Aldrich Chemical Company) (168 mg, 1.64 mmol, 9.7 eq), K₂CO₃ (227 mg, 1.64 mmol, 9.7 eq) and 4—N,N-dimethylaminopyridine (2.6 mg, 0.021 mmol, 0.12 eq) in anhydrous DMF (2.0 mL) was stirred under N₂ at 110° C. overnight. After cooling to the room temperature, the reaction was quenched by the addition of saturated NaHCO₃ (5 mL) and extracted with CHCl₃ (3×30 mL). The organic layers were washed with saturated NaCl, dried over Na₂SO₄ and concentrated with a rotary evaporator. The crude material was purified by flash chromatography on silica gel with a gradient eluant of EtOAc(0–25%):hexanes(100–75%) to afford 13 mg (22%) of the title compound as an off-white solid. Mp: 188–190° C. ¹H NMR (CDCl₃; 400 MHz): δ 11.43 (s, 1), 7.61 (d, 2, J=7.4), 7.43 (t, 2, J=7.4), 7.37 (t, 1, J=7.4), 4.88 (br s, 2), 4.06 (br s, 2), 2.58 (s, 3), 2.11 (s, 3), 1.73 (br s, 6). MS m/z: 335 (M+1), 333 (M−1). HRMS (NBA-NaI) m/z Calcd for M+H, $C_{20}H_{22}N_4O$: 335.1888. Found: 335.1872.

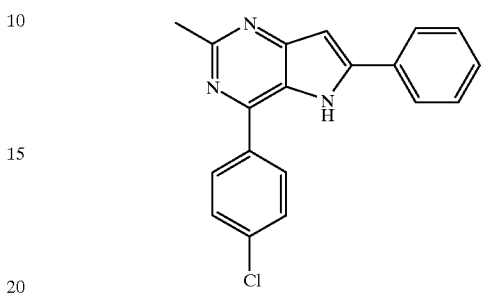

EXAMPLE 50
4-(4-Chlorophenyl)-2-methyl-6-phenylpyrrolo[3,2-d]pyrimidine.

A mixture of 4-chloro-2-methyl-6-phenylpyrrolo[3,2-d]pyrimidine (Example 1(e)) (50 mg, 0.21 mmol), 4-chlorophenylboronic acid (Aldrich Chemical Company) (39 mg, 0.25 mmol), tris(dibenzylide-neacetone)dipalladium(0) (Aldrich Chemical Company) (4.7 mg, 0.0051 mmol) and triphenylphosphine (Aldrich Chemical Company) (5.4 mg, 0.021 mmol) in a mixed solvent (600 μL of toluene, 300 μL of 1.0 M Na₂CO₃, and 150 μL of ethanol) was heated at reflux under N₂ for 20 h. Upon cooling to the room temperature, the reaction mixture was diluted with H₂O (20 mL) and extracted with CHCl₃ (3×15 mL), dried over Na₂SO₄ and concentrated with a rotary evaporator. The crude material was purified by flash chromatography on silica gel with a gradient eluant of EtOAc(0–25%):hexanes (100–75%) to afford 32 mg (49%) of the title compound as a yellow solid. Mp: 281–283° C. ¹H NMR (Acetone-d₆; 400 MHz): δ 10.89 (s, 1), 8.18 (d, 2, J=8.5), 8.02 (d, 2, J=7.4), 7.60 (d, 2, J=8.5), 7.53 (t, 2, J=7.4) 7.46 (t, 1, J=7.4), 7.01 (s, 1), 2.72 (s, 3). MS m/z: 320 (M+1), 318 (M−1). HRMS (NBA-NaI) m/z Calcd for M+H, $C_{19}H_{14}ClN_3$: 320.0955. Found: 320.0961.

EXAMPLE 51

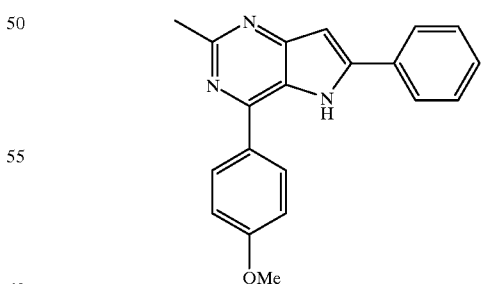

4-(4-Methoxyphenyl)-2-methyl-6-phenylpyrrolo[3,2-d]pyrimidine.

A mixture of 4-chloro-2-methyl-6-phenylpyrrolo-[3,2-d]pyrimidine (Example 1(e)) (50 mg, 0.21 mmol), 4-methoxyphenylboronic acid (Aldrich Chemical Company) (44 mg, 0.287 mmol), tris(dibenzylideneacetone)

dipalladium(0) (Aldrich Chemical Company) 4.7 mg, 0.0051 mmol, 0.025 eq) and triphenylphosphine (Aldrich Chemical Company) (10.8 mg, 0.041 mmol) in a mixed solvent (600 μL of toluene, 300 μL of 1.0 M $Na_2CO_3$, and 150 μL of ethanol) was heated at reflux under $N_2$ for 36 h. upon cooling to the room temperature, the reaction mixture was diluted with $H_2O$ (20 mL) and extracted with $CHCl_3$ (3×20 mL). The organic phase was dried over $Na_2SO_4$, filtered, and concentrated with a rotary evaporator. The crude material was purified by flash chromatography on silica gel with a gradient eluant of EtOAc(0–50%):hexanes (100–50%) to afford 57 mg (89%) of the title compound as a yellow solid. Mp: 225–227° C. $^1$H NMR (Acetone-$d_6$, 400 MHz): δ 10.72 (s, 1), 8.14 (d, 2, J=7.0), 8.00 (d, 2, J=8.0), 7.51 (t, 2, J=7.0), 7.44 (t, 1, J=7.0), 7.11 (d, 2, J=8.0), 6.95 (s, 1), 3.91 (s, 3), 2.70 (s, 3). MS m/z: 320 (M+1), 318 (M−1). HRMS (NBA-NaI) m/z Calcd for $M^+$+H, $C_{20}H_{17}N_3O$: 316.1450. Found: 316.1450.

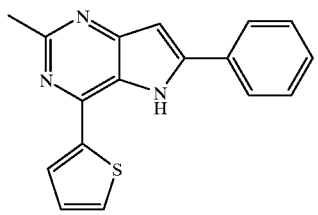

EXAMPLE 52
2-(2-Methyl-6-phenylpyrrolo[2,3-e]pyrimidin-4-yl) thiophene.

A mixture of 4-chloro-2-methyl-6-phenylpyrrolo-[3,2-d] pyrimidine (Example 1(e)) (50 mg, 0.21 mmol), thiophene-2-boronic acid (37 mg, 0.287 mmol), tris(dibenzylidene-acetone)dipalladium(0) (Aldrich Chemical Company) (4.7 mg, 0.0051 mmol) and triphenylphosphine (Aldrich Chemical Company) (10.8 mg, 0.041 mmol) in a mixed solvent (600 μL of toluene, 300 μL, 1.0 M $Na_2CO_3$ and 150 μL of ethanol) was heated at reflux under $N_2$ for 36 h. Upon cooling to the room temperature, the reaction mixture was diluted with $H_2O$ (20 mL) and extracted with $CHCl_3$ (3×20 mL). The organic phase was dried over $Na_2SO_4$, filtered, and concentrated with a rotary evaporator. The crude material was purified by flash chromatography on silica gel with a gradient eluant of EtOAc(0–25%):hexanes(100–75%) to afford 37.2 mg (62%) of the title compound as a yellow solid. Mp: 178–179° C. $^1$H NMR (Acetone-$d_6$; 400 MHz): δ 10.61 (s, 1), 8.21 (d, 1, J=4.5), 8.00 (d, 2, J=7.3), 7.73 (d, 2, J=4.5), 7.54 (t, 2, J=7.3), 7.48 (t, 1, J=7.3) 7.28 (t, 1, J=4.5), 6.96 (s, 1), 2.68 (s, 3). MS m/z: 292 (M+1), 290 (M−1). HRMS (NBA-NaI) m/z Calcd for M+H, $C_{17}H_{13}N_3S$: 292.0908. Found: 292.0900.

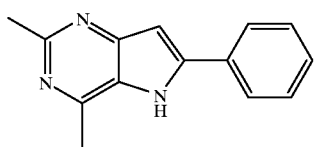

EXAMPLE 53
2,4-Dimethyl-6-phenylpyrrolo[3,2-d]pyrimidine.

A mixture of 4-chloro-2-methyl-6-phenylpyrrolo[3,2-d] pyrimidine (Example 1(e)) (80 mg, 0.33 mmol), methylboronic acid (Aldrich Chemical Company) (49 mg, 0.82 mmol), tris(dibenzylideneacetone) dipalladium(0) (Aldrich Chemical Company) (9.4 mg, 0.0103 mmol) and triphenylphosphine (Aldrich Chemical Company) (10.8 mg, 0.042 mmol) in a mixed solvent (1000 μL of toluene, 500 μL of 1.0 M $Na_2CO_3$, and 250 μL of ethanol) was heated at reflux under $N_2$ overnight. Upon cooling to the room temperature, the reaction mixture was diluted with $H_2O$ (20 mL) and extracted with $CHCl_3$ (4×40 mL). The organic extracts were dried over $Na_2SO_4$, filtered, and concentrated with a rotary evaporator. This material was purified by preparative thin layer chromatography on silica gel with 1:1 THF:hexanes as eluant to afford 30 mg (62%) of the title compound as a yellow solid. $^1$H NMR (CDCl$_3$; 400 MHz): δ 8.38 (s, 1), 7.74 (d, 2, J=7.0), 7.53 (t, 2, J=7.0), 7.45 (t, 1, J=7.0), 6.87 (d, 1, J=1.7), 2.79 (s, 3), 2.74 (s, 3). MS m/z: 224 (M+1), 222 (M−1).

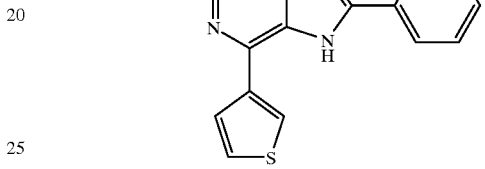

EXAMPLE 54
3-(2-Methyl-6-phenylpyrrolo[2,3-e]pyrimidin-4-yl) thiophene.

A mixture of 4-chloro-2-methyl-6-phenylpyrrolo[3,2-d] pyrimidine (Example 1(e)) (50 mg, 0.21 mmol), thiophene-3-boronic acid (37 mg, 0.287 mmol), tris(dibenzylideneacetone)dipalladium(0) (Aldrich Chemical Company) (4.7 mg, 0.0051 mmol, 0.025 eq) and triphenylphosphine (Aldrich Chemical Company) (10.8 mg, 0.041 mmol, 0.2 eq) in a mixed solvent (600 μL of toluene, 300 μL of 1.0 M $Na_2CO_3$, and 150 μL of ethanol) was heated at reflux under $N_2$ for 17 h. Upon cooling to the room temperature, the reaction mixture was diluted with $H_2O$ (20 mL) and extracted with $CHCl_3$ (3×20 mL). The organic phase was dried over $Na_2SO_4$, filtered and concentrated with a rotary evaporator. The crude material was purified by flash chromatography on silica gel a gradient eluant of EtOAc(0–25%):hexanes(100–75%) to afford 43.3 mg (73%) of an off-white solid. Mp: 232–233° C. $^1$H NMR (CDCl$_3$; 400 MHz): δ 8.57 (s, 1), 8.04 (dd, 1, J=1.2, 2.9), 7.66 (m, 3), 7.59 (dd, 1, J=2.9, 5.0), 7.52 (t, 2, J=7.7), 7.46 (t, 1, J=7.7), 6.94 (d, 1, J=2.0), 2.86 (s, 3). MS m/z: 292 (M+1), 290 (M−1).

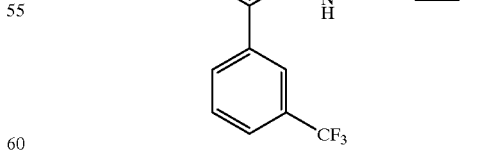

EXAMPLE 55
2-Methyl-6-phenyl-4-[3-(trifluoromethyl)phenyl]pyrrolo[3, 2-d]pyrimidine.

A mixture of 4-chloro-2-methyl-6-phenylpyrrolo[3,2-d] pyrimidine (Example 1(e)) (50 mg, 0.21 mmol), 3-(trifluoromethyl)phenylboronic acid (Fluka) (55 mg, 0.287 mmol, 1.4 eq), tris(dibenzylideneacetone)dipalladium (0) (Aldrich Chemical Company) (4.7 mg, 0.0051 mmol, 0.025 eq) and triphenylphosphine (Aldrich Chemical Company) (10.8 mg, 0.041 mmol, 0.2 eq) in a mixed solvent (600 μL of toluene, 300 μL of 1.0 M $Na_2CO_3$, and 150 μL of ethanol) was heated at reflux under $N_2$ for 19 h. Upon cooling to the room temperature, the reaction mixture was diluted with $H_2O$ (20 mL) and extracted with $CHCl_3$ (3×20 mL). The organic phase was dried over $Na_2SO_4$, filtered, and concentrated with a rotary evaporator. Mp: 206–208° C. $^1$H NMR (CDCl$_3$, 400 MHz): δ 8.58 (s, 1), 8.28 (s, 1), 8.18 (d, 1, J=7.6), 7.82 (d, 1, J=7.8), 7.77–7.72 (m, 3), 7.53 (t, 2, J=7.4), 7.46 (t, 1, J=7.4), 6.98(d, 1, J=2.0), 2.89 (s, 3). MS m/z: 354 (M+1), 352 (M−1).

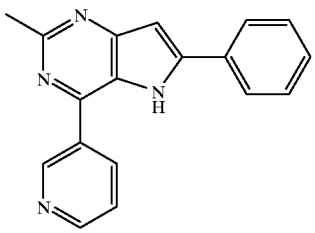

EXAMPLE 56

2-Methyl-6-phenyl-4-(3-pyridinyl)pyrrolo[3,2-d]pyrimidine.

A mixture of 4-chloro-2-methyl-6-phenylpyrrolo[3,2-d]pyrimidine (Example 1(e)) (230 mg, 0.94 mmol), 3-pyridinylboronic acid (Frontier Scientific) (139 mg, 1.13 mmol), tris(dibenzylideneacetone)dipalladium(0) (Aldrich Chemical Company) (22 mg, 0.024 mmol) and triphenylphosphine (Aldrich Chemical Company) (49 mg, 0.19 mmol) in a mixture of solvents (1.2 mL of toluene, 0.3 mL of 1.0 M $Na_2CO_3$ and 0.3 mL of ethanol) was heated at reflux under $N_2$ for 40 h. Upon cooling to the room temperature, the reaction mixture was diluted with $H_2O$ (20 mL), and the crude product was extracted with $CHCl_3$ (3×40 mL). The organic extracts were washed with $H_2O$ (50 mL), saturated NaCl (50 mL), dried over $Na_2SO_4$ and concentrated with a rotary evaporator. Chromatography on silica gel with a gradient eluant of MeOH (0–4%):$CH_2Cl_2$ (100–96%) afforded 171 mg (64%) of the title compound as a yellow solid. Mp: 252–254° C. $^1$H NMR (CDCl$_3$; 400 MHz): δ 2.89 (s, 3), 6.99 (s, 1), 7.46 (m, 4), 7.78 (d, 2, J=7.1), 8.37 (d, 1, J=7.7), 8.66 (d, 1, J=3.9), 9.31 (s, 1), 9.50 (s, 1). MS m/z: 287 (M+1), 285 (M−1). HRMS: Calcd for M+H: 287.1297. Found: 287.1288.

EXAMPLE 57

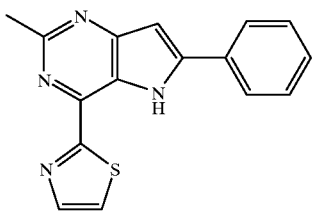

2-(2-Methyl-6-phenylpyrrolo[2,3-e]pyrimidin4-yl)-1,3-thiazole.

A mixture of 4-chloro-2-methyl-6-phenylpyrrolo[3,2-d]pyrimidine (Example 1(e)) (200 mg, 0.82 mmol), 2-tributylstannylthiazole (Frontier Scientific) (338 mg, 0.90 mmol), tris(dibenzylideneacetone)dipalladium(0) (Aldrich Chemical Company) (19 mg, 0.021 mmol) and triphenylphosphine (Aldrich Chemical Company) (43 mg, 0.16 mmol) in anhydrous toluene (2 mL) was refluxed under $N_2$ for 4 d. TLC showed that the reaction was not complete. Therefore, additional portions of 2-tributylstannylthiazole (338 mg, 0.90 mmol), tris(dibenzylideneacetone)dipalladium(0) (19 mg, 0.021 mmol) and triphenylphosphine (43 mg, 0.16 mmol) were added to the reaction mixture, and the mixture was stirred at 120° C. for 3 d. Upon cooling to the room temperature, the reaction was quenched with 5% HCl (50 mL) and the solution was extracted with $CHCl_3$ (3×100 mL). The organic extracts were washed with $H_2O$ (2×150 mL), filtered through a pad of Celite, washed with saturated NaCl (150 ml), dried over $Na_2SO_4$ and concentrated with a rotary evaporator. Chromatography on silica gel with a gradient eluant of MeOH (1–3%):$CH_2Cl_2$ (99–97%) afforded 119 mg (50%) of the title compound as a yellow solid. Mp: 248–250° C. $^1$H NMR (acetone-d$_6$; 400 MHz): δ 2.69 (s, 3), 7.01(s, 1), 7.57–7.47 (m, 3), 8.06 (d, 2, J=7.17), 8.97 (s, 1), 9.18 (s, 1), 10.76 (s, 1). MS m/z: 293 (M+1), 291 (M−1). HRMS: Calcd for M+H: 293.0861. Found: 293.0866.

EXAMPLE 58

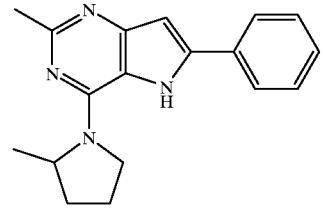

2-Methyl-4-(2-methylpyrrolidin-1-yl)-6-phenylpyrrolo[3,2-d]pyrimidine.

A mixture of 4-chloro-2-methyl-6-phenylpyrrolo[3,2-d]pyrimidine (Example 1(e)) (230 mg, 0.94 mmol), 2-methylpyrrolidine (Alfa) (799 mg, 9.4 mmol), $K_2CO_3$ (650 mg, 4.7 mmol) in $H_2O$ (1.5 mL) was stirred at 105° C. for 20 h. Upon cooling to room temperature, the reaction mixture was diluted with $H_2O$ (20 mL) and extracted with EtOAc (3×15 mL). The organic phase was washed with $H_2O$ (20 mL), saturated NaCl (20 mL), dried over $Na_2SO_4$, and concentrated with a rotary evaporator. Chromatography on silica gel with a gradient eluant of MeOH (0–10%):$CH_2Cl_2$ (100–90%) afforded 250 mg (93%) of the title compound as an off-white solid. Mp: 219–221° C. $^1$H NMR (CDCl$_3$; 400 MHz) δ 1.39 (d, 3, J=6.3), 1.79 (m, 1), 2.22–2.07 (m, 3), 2.58 (s, 3), 3.90 (m, 1), 4.04 (m, 1), 4.59 (m, 1), 6.74 (s, 1), 7.38 (t, 1, J=7.4), 7.46 (t, 2, J=7.4), 7.63 (d, 2, J=7.4), 8.31 (s, 1). MS m/z: 293 (M+1), 291 (M−1). HRMS: Calcd for M+H: 293.1766. Found: 293.1770.

EXAMPLE 59

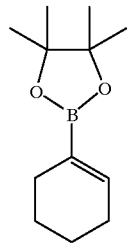

(a) 2-Cyclohex-1-enyl-4,4,5,5-tetra-ethyl-1,3,2-dioxaborolane.

A mixture of cyclohexenyl trifluoroacetate (1360 mg, 5.91 mmol, 1.0 eq), bis(pinacolacto)diboron (Ryan scietific) (1652 mg, 6.5 mmol, 1.1 eq), dichloro[1,1'-bis(diphenylphosphino)ferrocene]palladium (II) dichloromethane adduct [PdCl2(dppf)] (Aldrich Chemical Company) (145 mg, 0.177 mmol, 0.03 eq), potassium acetate (Aldrich Chemical Company) (1740 mg, 17.73 mmol, 3.0 eq) in anhydrous dimethyl sulfoxide (10 mL) was stirred under nitrogen at 70° C. for overnight. Upon cooling to the room temperature, the reaction mixture was diluted with $H_2O$ (30 mL), and the crude product was extracted with benzene (3×40 mL). The organic extracts were washed with $H_2O$ (3×40 mL), saturated NaCl (50 ml), and dried over $Na_2SO_4$ and concentrated in vacuo. Bulb-to-bulb distillation (oven temperature 90–100° C.) afforded 1065 mg (85%) of the title compound as a colorless oil. $^1$H NMR (CDCl$_3$; 400 MHz): δ 6.56 (s, 1), 2.09 (bs, 4), 1.59 (m, 4), 1.26 (s, 12).

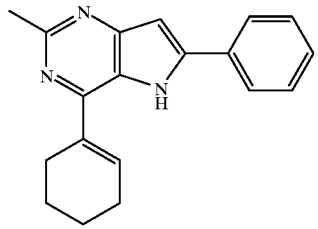

(b) 4-Cyclohex-1-enyl-2-methyl-6-phenylpyrrolo[3,2-d]pyrimidine.

A mixture of 4-chloro-2-methyl-6-phenylpyrrolo[3,2-d]pyrimidine (Example 1(e)) (261 mg, 1.03 mmol), 2-cyclohex-1-enyl-4,4,5,5-tetramethyl-1,3,2-dioxaborolane (Example 59(a)) (237 mg, 1.13 mmol, 1.04 eq), tris(dibenzylideneacetone)dipalladium(0) (Aldrich Chemical Company) (25 mg, 0.027 mmol) and triphenylphosphine (Aldrich Chemical Company) (56 mg, 0.21 mmol) in a mixture of solvents (1.2 mL of toluene, 0.3 mL of 1.0 M $Na_2CO_3$ and 0.3 mL of ethanol) was refluxed under $N_2$ for 2 d. Upon cooling to room temperature, the reaction mixture was diluted with $H_2O$ (40 mL) and the solution was extracted with CHCl$_3$ (4×40 mL). The organic extracts were washed with water (50 mL), saturated NaCl (50 mL), dried over $Na_2SO_4$ and concentrated with a rotary evaporator. Chromatography on silica gel with a gradient eluant of EtOAc (0–30%):hexanes (100–70%) afforded 153 mg (48%) of the title compound as an off-white solid. Mp: 247–249° C. $^1$H NMR (CDCl$_3$; 400 MHz): δ 1.79 (m, 2), 1.88 (m, 2), 2.36 (m, 2), 2.68 (m, 2), 2.79 (s, 3), 6.63 (m, 1), 6.87 (d, 1, J=2.0), 7.45 (t, 2, J=7.2), 7.49 (t, 2, J=7.2), 7.72 (d, 2, J=7.2), 8.47 (s, 1). MS m/z: 290 (M+1), 288 (M–1). HRMS: Calcd for M+H: 290.1657. Found: 290.1657.

EXAMPLE 60

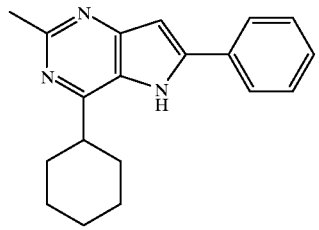

4-Cyclohexyl-2-methyl-6-phenylpyrrolo[3,2-d]pyrimidine.

A solution of 2-methyl-4-(1-cyclohexenyl)-5H-6-phenylpyrrolo[3,2-d]pyrimidine (Example 59) (96 mg, 0.33 mmol) in ethanol (5 mL) was agitated on a Parr Apparatus at room temperature in the presence of PtO$_2$ (Aldrich Chemical Company) (20 mg, 0.088 mmol) under $H_2$ (70 psi) for 30 h. The reaction mixture was filtered through a pad of Celite and concentrated on a rotary evaporator. Chromatography on silica gel with a gradient eluant of EtOAc (0–20%):hexanes (100–80%) afforded 55 mg (57%) of the title compoud as an off-white solid. Mp: >280° C. $^1$H NMR (CDCl$_3$; 400 MHz): δ 1.44–1.49 (m, 2), 1.81–1.88 (m, 4), 1.93–2.01 (m, 4), 2.99 (m, 1), 6.86 (d, 1, J=1.4), 7.44 (t, 1, J=6.1), 7.51 (t, 2, J=6.1), 7.74 (d, 2, J=6.1), 8.40 (s, 1). MS m/z: 292 (M+1), 290 (M–1). HRMS: Calcd for M+H: 292.1814. Found: 292.1806.

EXAMPLE 61

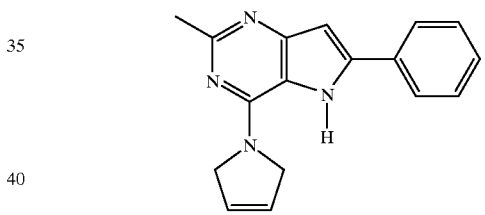

2-Methyl-6-phenyl-4-(pyrrolinyl)pyrrolo(3,2-d)pyrimidine Hydrochloride Monohydrate.

To a oven-dried, 50-mL, round-bottomed flask was added 4-chloro-2-methyl-6-phenylpyrrolo[3,2-d]pyrimidine (Example 1(e)) (250 mg, 1.03 mmol) and pyrroline (Aldrich Chemical Company) (1.00 mL, 13.1 mmol). The flask was purged with $N_2$ and the solution was heated at 180° C. for 2 h. The reaction was cooled to room temperature and the crude material was purified by flash chromatorgaphy on silica gel with 1:1 EtOAc:hexanes as eluant to give 283 mg (100%) of a light yellow solid. The product (282 mg, 1.03 mmol) was dissolved in MeOH (8 mL) and anhydrous etheral HCl (Aldrich Chemical Company) (1.05 mL of a 1 M soln, 1.05 mmol) was added dropwise. The mixture was stirred for 18 h at room temperature. The solvent was evaporated in vacuo, and the solid was recrystallized from EtOAc/MeOH to give 240 mg (85%) of the title compound as an off-white solid. Mp: 278–278.3° C. $^1$H NMR (DMSO-d$_6$; 400 MHz): δ 2.60 (s, 3), 4.59 (br s, 2), 5.05 (br s, 2), 6.12 (s, 2), 6.91 (s, 1), 7.49–7.58 (m, 3), 7.97 (d, 2, J=7.2), 11.62 (s, 1). MS m/z: 277(M+1), 275 (M–1). Anal. Calcd for $C_{17}H_{16}N_4 \cdot 1.1HCl \cdot H_2O$: C, 61.05; H, 5.76; N, 16.76; Cl, 11.66. Found: C, 60.92; H, 5.39; N, 16.36; Cl, 11.53.

EXAMPLE 62

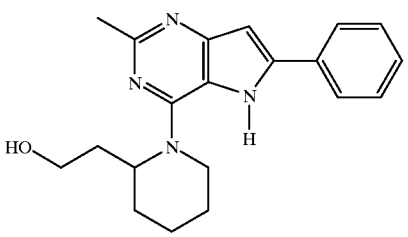

2-Methyl-6-phenyl-4-(2-piperidineethanolyl)pyrrolo(3,2-d) pyrimidine Hydrochloride.

To a oven-dried, 50-mL, round-bottomed flask was added 4-chloro-2-methyl-6-phenylpyrrolo[3,2-d]pyrimidine (Example 1(e)) (250 mg, 1.03 mmol) and 2-piperidine ethanol (Aldrich Chemical Company) (435 mg, 3.06 mmol). The flask was purged with $N_2$, and the solution was heated at 190° C. for 2 h. The reaction was cooled to room temperature and the crude material was purified by flash chromatography on silica gel with 1:1 EtOAc:hexanes as eluant to give 115 mg (33%) of a light-yellow solid. The product (43 mg, 0.128 mmol) was dissolved in $CH_2Cl_2$ (5 mL) and anhydrous etheral HCl (Aldrich Chemical Company) (0.128 mL of a 1M soln, 0.128 mmol) was added dropwise. The mixture was stirred for 18 h at room temperature. The solvent was evaporated and the solid was recrystallized from EtOAc/MeOH to give 39 mg (11%) of product. Mp: 273–273.5° C. $^1$H NMR (DMSO-$d_6$; 400 MHz): δ 1.34–2.12 (m, 6H); 2.38 (s, 3), 2.47–3.55 (m, 5), 4.67 (br d, 2), 6.76 (s, 1), 7.29–7.36, (m, 3), 7.72 (d, 2, J=6.72), 12.35 (br s, 1), 14.02 (br s, 1). MS m/z: 337(M+1), 335 (M−1). Anal. Calcd for $C_{20}H_{23}N_4$·HCl: C, 64.42; H, 6.76; N, 15.03. Found: C, 63.98; H, 6.76; N, 14.65.

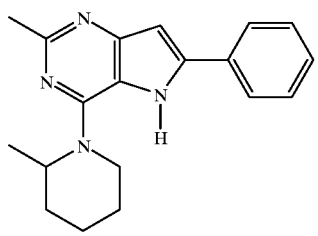

EXAMPLE 63

2-Methyl-6-phenyl-4-(2-methylpiperidinyl)pyrrolo(3,2-d) pyrimidine Hydrochloride Monohydrate.

To a oven dried, 50-mL, round-bottomed flask was added 4-chloro-2-methyl-6-phenylpyrrolo[3,2-d]pyrimidine (Example 1(e)) (250 mg, 1.03 mmol) and 2-methylpiperidine (Aldrich Chemical Company) (250 mg, 2.46 mmol). The flask was purged with $N_2$, and the solution was heated at 190° C. for 2 h. The reaction was cooled to room temperature and the crude material was purified by flash chromatorgaphy on silica gel with EtOAc as the eluant to give 214 mg (84% yield) of the free base as a white solid. The product (205 mg, 0.67 mmol) was dissolved in EtOAc (5 mL) and anhydrous etheral HCl (Aldrich Chemical Company) (0.67 mL of a 1 M soln, 0.67 mmol) was added dropwise. The mixture was stirred for 18 h at room temperature. The solvent was evaporated in vacuo and the solid was recrystallized from EtOAc/MeOH to give 200 mg (71%) of product. Mp: 268–269° C. $^1$H NMR (DMSO-$d_6$; 400 MHz): δ 1.17 (d, 3, J=6.8), 1.31–1.82 (m, 8), 2.41 (s, 3), 3.3 (br s, 1), 4.46 (br s, 1), 5.11 (br s, 1), 6.72 (s, 1), 7.34–7.42 (m, 3), 7.77 (d, 2, J=7.27), 11.71. MS m/z: 307 (M+1). Anal. Calcd for $C_{19}H_{22}N_4$·HCl·H$_2$O: C, 63.23; H, 6.98; N, 15.53; Cl, 9.82. Found: C, 62.82; H, 6.39; N, 15.38; Cl, 9.93.

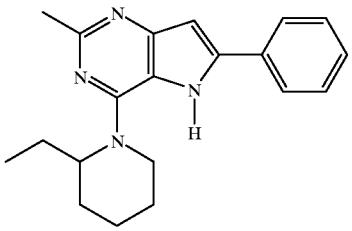

EXAMPLE 64

2-Methyl-6-phenyl-4-(2-ethylpiperidinyl)pyrrolo[3,2-d] pyrimidine Hydrochloride Hydrate.

To a oven-dried, 50-mL, round-bottomed flask was added 4-chloro-2-methyl-6-phenylpyrrolo[3,2-d]pyrimidine (Example 1(e)) (250 mg, 1.03 mmol) which was dissolved in 2-ethylpiperidine (Aldrich Chemical Company) (1.00 mL, 7.5 mmol). The flask was purged with nitrogen and the solution was heated at 190° C. for 2 h. The reaction was cooled to room temperature and chromatographed using EtOAc as the eluant afforded 307 mg (94%) of a light-yellow solid. The product (300 mg, 0.94 mmol) was dissolved in $CH_2Cl_2$ (7 mL) and anhydrous etheral HCl (Aldrich) (0.94 mL of a 1 M soln, 0.94 mmol) was added dropwise. The mixture was stirred for 18 h at room temperature. The solvent was evaporated in vacuo and the solid was recrystallized from EtOAc/MeOH to give 280 mg (74%) of product. Mp: 228–229° C. $^1$H NMR (DMSO-$d_6$; 400 MHz): δ 0.83 (t, 3, J=7.23), 1.63–1.95 (m, 8), 2.57 (s, 3); 3.37 (br s, 3), 4.56–5.13 (br d, 2), 6.89 (s, 1), 7.5–7.58 (m, 3), 7.94 (d, 2, J=7.3), 11.96 (br s, 1). MS m/z: 321 (M+1). Anal. Calcd for $C_{20}H_{24}N_4$·HCl·0.5H$_2$O: C, 65.6; H, 7.08; N, 15.14; Cl, 9.81. Found: C, 65.81; H, 6.86; N, 15.20; Cl, 9.61.

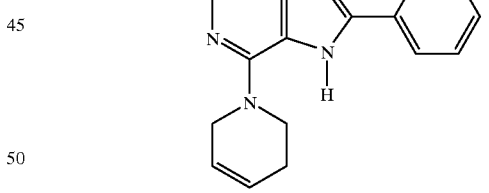

EXAMPLE 65

2-Methyl-6-phenyl-4-(1,2,3,6-tetrahydropyridinyl)pyrrolo [3,2-d]pyrimidine Hydrochloride.

To a oven-dried, 50-mL, round-bottomed flask was added 4-chloro-2-methyl-6-phenylpyrrolo[3,2-d]pyrimidine (Example 1(e)) (250 mg, 1.03 mmol) which was dissolved in 1,2,3,6-tetrahydropyridine (Aldrich Chemical Company) (580 mg, 7.00 mmol). The flask was purged with $N_2$ and heated at 190° C. for 2 h. After cooling to room temperature, the reaction mixture was chromatographed with 1:1 EtOAc:hexanes as the eluant to afford 310 mg (87%) of a light-yellow solid. The product (300 mg, 1.03 mmol) was dissolved in EtOAc:CHCl$_3$ (5:15 mL) and anhydrous etheral HCl (1.1 mL of a 1 M soln, 1.1 mmol) was added dropwise.

The mixture was stirred for 18 h at room temperature. The sample was concentrated in vacuo and the solid was recrystallized from EtOAc/MeOH to give 287 mg (74%) of product. Mp: 278–279° C. $^1$H NMR (DMSO-$d_6$; 400 MHz): δ 2.57 (s, 2), 2.8 (s, 3), 4.38 (t, 2, J=5.53), 4.86 (s, 2), 6.1 (d, 1, J=10.2), 6.2 (d, 2, J=10), 7.14 (s, 1), 7.72–7.81 (m, 3), 8.2 (d, 2, J=7.2), 12.18 (s, 1), 14.81 (br s, 1). MS m/z: 291(M+1), 289 (M−1). Anal. Calcd for $C_{18}H_{18}N_4$·HCl: C, 63.35; H, 6.09; N, 16.42. Found: C, 63.05; H, 5.64; N, 16.24.

EXAMPLE 66

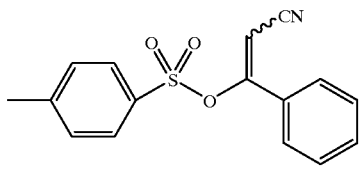

(a) 2-Cyano-1-phenylvinyl 4-methylbenzenesulfonate.

To a 100-mL, round-bottomed flask were added benzoyl acetonitrile (Aldrich Chemical Company) (3.4 g, 23 mmol), p-toluenesulfonyl chloride (Aldrich Chemical Company) (5.1 g, 27 mmol) and $CH_2Cl_2$ (50 mL). After colling the flask in an ice bath, $Et_3N$ (3.3 mL, 23 mmol) was added dropwise to the solution. The mixture was stirred for 1 h, and stirred at room temperature for 22 h. Water and $CH_2Cl_2$ were added, and the organic layer was separated, washed three times with water, dried over $Na_2SO_4$ and concentrated in vacuo to give an orange solid. Flash chromatography on silica gel using 10:1 hexane:EtOAc as eluant afforded 4.0 g (57%) of the title compound as a yellow solid. $^1$H NMR (CDCl$_3$; 400 MHz): δ 2.46 (d, 3), 5.57 (d, 1), 7.31–7.50 (m, 5), 7.58 (d, 1, J=7.93), 7.65 (d, 1, J=7.92), 7.76 (d, 1, J=8.22), 7.90 (d, 1, J=8.26). MS m/z: 300 (M+1), 298 (M−1).

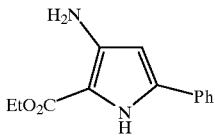

(b) Ethyl 3-amino-5-phenylpyrrole-2-carboxylate.

Sodium ethoxide was prepared freshly from Na (0.92 g, 40 mmol) and EtOH (25 mL). To the above solution was added a solution of 2-cyano-1-phenylvinyl 4-methylbenzenesulfonate (Example 66 (a)) (4.0 g, 13 mmol), aminodiethyl malonate hydrochloride (Aldrich Chemical Company) (2.8 g, 13 mmol) in EtOH (70 mL) and THF (6 mL) through a dropping funnel. After the addition was completed, the reaction mixture was stirred at room temperature for 2 h. A precipitate was then removed from the reaction mixture by filtration, and the filtrate was concentrated in vacuo to give an orange solid. Water was added and the mixture was extracted with EtOAc. The orgainc layer was separated, dried over $Na_2SO_4$ and concentrated in vacuo to give 3.0 g of crude product as an orange solid. This material was used directly in the following step without purification. An analytical sample was obtained as off-white crystals by recrystallization from toulene:cyclohexane. $^1$H NMR (DMSO-$d_6$; 400 MHz): δ 1.28 (t, 3, J=7.12), 4.22 (q, 2, J=7.20), 5.06 (br s, 2), 5.98–6.03 (m, 1), 7.16–7.38 (m, 3), 7.72–7.76 (m, 2), 10.68 (br s, 1); MS m/z: 231 (M+1), 229 (M−1).

The following compounds were also prepared using the method described in Example 66(b):

Ethyl 3-amino-5-(3-methylphenyl)pyrrole-2-carboxylate: MS (ESI) m/z: 244 (M+); Anal. Calcd for $C_{14}H_{16}N_2O_2$: C, 68.83; H, 6.60; N, 11.47. Found: C, 68.74; H, 6.72; N, 11.29;

Ethyl 3-amino-5-(2-chlorophenyl)pyrrole-2-carboxylate: MS (ESI) m/z: 265 (M+1); Anal. Calcd for $C_{13}H_{13}ClN_2O_2$: C, 58.99; H, 4.95; N, 10.58; Cl, 13.39. Found: C, 58.80; H, 5.08; N, 10.40; Cl, 13.17;

Ethyl 3-amino-5-(2-furyl)pyrrole-2-carboxylate: MS (ESI) m/z: 221 (M+1); Anal. Calcd for $C_{11}H_{12}N_2O_3$: C, 59.99; H, 5.49; N, 12.72. Found: C, 59.95; H, 5.55; N, 12.79;

Ethyl 3-amino-5-(2-thienyl)pyrrole-2-carboxylate: MS (ESI) m/z: 237 (M+1); Anal. Calcd for $C_{11}H_{12}N_2O_2S$: C, 55.92; H, 5.12; N, 11.86; S, 13.57. Found: C, 56.04; H, 5.04; N, 11.75; S, 13.60;

Ethyl 3-amino-5-(tert-butyl)pyrrole-2-carboxylate: MS (HRMS) m/z: 211.1446 (expected), 211.1443 (observed); and Ethyl 3-amino-4-methyl-5-phenylpyrrole-2-carboxylate: MS (ESI) m/z: 244 (M+); Anal. Calcd for $C_{14}H_{16}N_2O_2$: C, 68.83; H, 6.60; N, 11.47. Found: C, 69.06; H, 6.47; N, 11.54.).

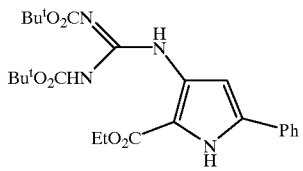

(c) tert-Butyl 2-aza-3-[(tert-butoxy)carbonylamino]-3-{[2-(ethoxycarbonyl)-5-phenylpyrrol-3-yl]amino}prop-2-enoate.

To a 25-mL, round-bottomed flask was added ethyl 3-amino-5-phenylpyrrole-2-carboxylate (Example 66(b)) (1.1 g) and MeOH (5 mL). To the reaction flask was added 1,3-bis(tertbutoxycarbonyl)-2-methyl-2-thiopseudourea (Aldrich Chemical Company) (1.6 g, 5.5 mmol), followed by glacial acetic acid (1.43 mL, 25 mmol). The reaction mixture was stirred at room temperature under $N_2$ for 28 h. A heavy precipitate formed and was collected by filtration, washed with $H_2O$ (3×10 mL) and dried in a vacuum oven overnight to give 0.71 g (32% from Example 66(a)) of the title compound as an off-white solid. $^1$H NMR (DMSO-$d_6$; 400 MHz): δ 1.38 (t, 3, J=7.00), 1.44 (s, 9), 1.46 (s, 9), 4.38 (q, 2, J=6.97), 7.31–7.46 (m, 3), 7.76 (d, 2, J=7.86), 11.06 (br s, 1), 11.25 (s, 1), 11.61 (s, 1), 11.95 (br s, 1); MS m/z: 473 (M+1), 471 (M−1).

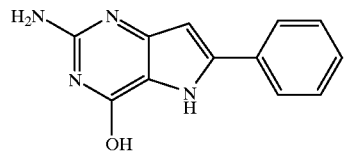

(d) 2-Amino-6-phenylpyrrolo[3,2-d]pyrimidin-4-ol.

To a round-bottomed flask was added a solution of tert-butyl 2-aza-3-[(tert-butoxy)carbonylamino]-3-{[2-(ethoxycarbonyl)-5-phenylpyrrol-3-yl]amino}prop-2-enoate (Example 66(c)) (0.679 g, 1.44 mmol) in $CH_2Cl_2$ (8 mL). Trifluoroacetic acid (2 mL) was added, and the reaction mixture was stirred at room temperature under $N_2$ for 4.5 h. After the solvent was evaporated in vacuo, the residue was heated in EtOH (8 mL) and 1N NaOH (4 mL) at reflux for 2 h. The reaction mixture was concentrated in vacuo to ca. 4 mL, and the pH of the resulting suspension was adjusted to pH 6 (pH paper) with 10% HCl. The precipitate that formed was collected by filtration, washed with water and dried in a vacuum oven overnight to give 0.2 g (61%) of the title compound as an off-white solid. $^1$H NMR (DMSO-$d_6$; 500 MHz): δ 5.81 (br s, 1), 6.56 (s, 1), 7.28–7.41 (m, 3), 7.87 (d, 1, J=7.44), 10.40 (br s, 1), 11.78 (br s, 1); MS m/z: 227 (M+1), 225 (M−1).

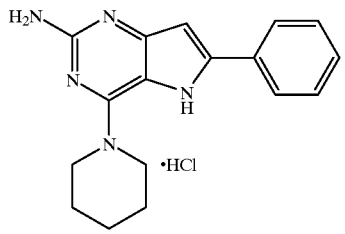

(e) 6-Phenyl-4-piperidylpyrrolo[3,2-d]pyrimidine-2-yl amine Hydrochloride Hydrate.

In a round-bottomed flask was added 2-amino-6-phenylpyrrolo[3,2-d]pyrimidin-4-ol (Example 66(d)) (0.26 g, 1.2 mmol) and phosphorus oxychloride (2.7 mL, 28.8 mmol). The mixture was heated in a 124° C. oil bath for 24 h, then excess POCl$_3$ was removed in vacuo to afford a brown residue. Ice-cold water was added and the pH of the solution was adjusted to pH 8 (pH paper) by adding aqueous Na$_2$CO$_3$. The resulting precipitate was collected by filtration, washed with water and then dried in a vacuum oven at 40° C. to give a brown solid. This material was transferred to a round-bottomed flask and heated with piperidine (0.57 mL, 5.75 mmol) and dioxane (8 mL) in a 110° C. oil bath for 15 h. Most of the solvent was then evaporated in vacuo. Chloroform was added to the residue, and the orgainc layer was separated, washed with water, dried over Na$_2$SO$_4$ and concentrated in vacuo to give a brown foam. Purification by flash chromatography on silica gel with 100:2:1 CHCl$_3$:MeOH:Et$_3$N as eluent afforded 92 mg (27%) of the title compound as a tan solid. The above material (78 mg, 0.27 mmol) was dissolved in a minimal amount of CHCl$_3$ and HCl (0.6 mL of a 1M soln in ether, 0.6 mmol) was added dropwise. The mixture was stirred at room temperature for 20 min, and the solvent was evaporated in vacuo to give a tan foam. Recrystallization from MeOH/H$_2$O gave 26 mg (6%) of the title compound as off-white crystals. Mp: >300° C. (dec). $^1$H NMR (DMSO-$d_6$; 500 MHz): δ 1.66–1.67 (m, 6), 3.97 (m, 4), 6.66 (s, 1), 7.32 (br s, 2), 7.45–7.53 (m, 3), 7.87 (d, 2, J=7.26), 11.53 (br s, 1), 12.51 (br s, 1); MS m/z: 294 (M+1), 292 (M−1). Anal. Calcd for C$_{17}$H$_{19}$N$_5$·HCl·0.2H$_2$O: C, 61.28%; H, 6.16%; N, 21.02%; Cl, 10.64%. Found: C, 61.28%; H, 6.15%; N, 21.06%; Cl, 10.78%.

EXAMPLE 67

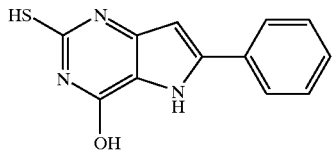

(a) 6-Phenyl-2-sulfanylpyrrolo[3,2-d]pyrimidin-4-ol.

To a solution of ethyl 3-amino-5-phenylpyrrole-2-carboxylate (Example 66(b)) (4.6 g) in dry benzene (100 mL) was added ethyl isothiocyanatoformate (Aldrich Chemical Company) (2.4 mL, 20 mmol). The reaction mixture was heated to 90° C. for 1 h. A precipitate formed and was filtered, washed with hexane to give 4.6 g of a brown solid. The crude solid was treated with 10 g of potassium hydroxide in water (160 mL), and heated at reflux for 15 h at 100° C. After cooling to ambient temperature, the pH of the solution was adjusted to pH 5 with 12 M HCl. A precipitate formed and was collected by filtration. This material was washed with water, and dried in a vacuum oven to give 1.2 g (32% from the tosylate) of the title compound as a brown solid. $^1$H NMR (DMSO-$d_6$; 400 MHz): δ 6.40 (s, 1), 7.35–7.54 (m, 3), 7.88 (d, 2, J=7.44), 12.04 (s, 1), 12.58 (s, 1), 12.68 (br s, 1). MS m/z: 244 (M+1), 242 (M−1).

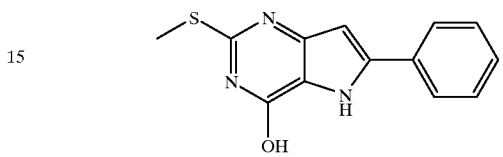

(b) 2-Methylthio-6-phenylpyrrolo[3,2-d]pyrimidin-4-ol.

To a solution of 6-phenyl-2-sulfanylpyrrolo[3,2-d]pyrimidin-4-ol (Example 67(a)) (1.1 g, 4.7 mmol) in acetone (100 mL) was added anhydrous potassium carbonate (0.52 g, 3.7 mmol), followed by iodomethane (0.47 mL, 7.5 mmol). The reaction mixture was stirred at room temperature for 1.5 h. Most of the solvent was evaporated in vacuo and the precipitate formed was collected by filtration, and dried in vacuum oven overnight to give 1.0 g (84%) of the title compound as a tan solid. $^1$H NMR (DMSO-$d_6$; 400 MHz): δ 2.32 (s, 3), 6.41 (s, 1), 7.18–7.36 (m, 3), 7.84 (d, 2, J=7.87), 11.01 (br s, 1). MS m/z: 258 (M+1); 256 (M−1).

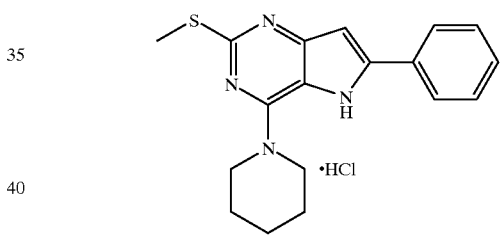

(c) 2-Methylthio-6-phenyl-4-piperidylpyrrolo[3,2-d] pyrimidine Hydrochloride Hydrate.

To a suspension of 2-methylthio-6-phenylpyrrolo [3,2-d] pyrimidin-4-ol (Example 67(b)) (1.3 g, 5.0 mmol) in CH$_2$Cl2 (50 mL) was added Et$_3$N (0.84 mL, 6 mmol), followed by methanesulfonyl chloride (Aldrich Chemical Company) (0.4 mL, 5.3 mmol) at 0° C. The reaction mixture was then warmed to room temperature over 3 h. Piperidine (1.5 mL, 15 mmol) was then added, and the reaction mixture was stirred for 15 h. A precipitate was then separated from the reaction mixture by filtration, and the filtrate was concentrated in vacuo to give an orange residue. Purification by flash chromatography on silica gel with a gradient of EtOAc (14–20%): hexane(86–80%) as eluant gave 0.1 g (6%) of a white solid. $^1$H NMR (CDCl$_3$; 500 MHz): δ 1.76 (m, 6), 2.60 (s, 3), 3.80 (m, 4), 6.74 (s, 1), 7.38–7.49 (m, 3), 7.64 (d, 2, J=7.11), 8.04 (br s, 1). The above material (90 mg, 0.28 mmol) was dissolved in minimum amount of CHCl$_3$, and HCl (0.3 mL of a 1M soln in ether, 0.3 mmol) was added dropwise. The mixture was stirred at room temperature for 20 min, and the solvent was then evaporated in vacuo to give a white foam that was recrystallized from CHCl$_3$/petroleum ether to give 55 mg (3%) of the title compound as white crystals. Mp: 281–283° C. (dec). $^1$H NMR (DMSO-$d_6$; 500

MHz): δ 1.73 (m, 6), 2.67 (s, 3), 4.05 (m, 4), 6.82 (s, 1), 7.49–7.57 (m, 3), 7.95 (d, 2, J=7.45), 11.92 (br s, 1). MS m/z: 325 (M+1), 323 (M−1). Anal. Calcd for $C_{18}H_{20}N_4S \cdot HCl \cdot 1.8H_2O$: C, 54.99%; H, 6.30%; N, 14.25%; Cl, 9.02%. Found: C, 54.99%; H, 5.93%; N, 14.09%; Cl, 9.09%.

EXAMPLE 68

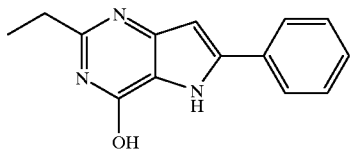

(a) 2-Ethyl-6-phenylpyrrolo[3,2-d]pyrimidine-4-ol.

Dry HCl gas was bubbled through a solution of ethyl 3-amino-5-phenylpyrrole-2-carboxylate (Example 66(b)) (3 g, 13 mmol) in propionitrile (Aldrich Chemical Company) (100 mL) at room temperature for 1.5 h. The reaction mixture was then capped and stirred at room temperature for 18 h. The solvent was evaporated in vacuo to give a solid that was dissolved in EtOH (80 mL) and 6% aqueous NaOH (50 mL) and the resulting solution was heated at reflux for 6 h. The solvent was concetrated in vacuo, and the resulting suspension was acidified with 12 M HCl to pH 5. Filtration of the reaction mixture lead to the isolation of a precipitate which was dried in a vacuum oven to give 2.6 g (85%) of the title compound as a tan solid. $^1$H NMR (DMSO-$d_6$; 500 MHz): δ 1.22 (t, 3, J=7.54), 2.60 (q, 2, J=7.52), 6.83 (s, 1), 7.32–7.42 (m, 3), 7.92 (d, 2, J=7.81), 11.7 (br s, 1), 12.1 (br s, 1). MS m/z: 240 (M+1), 238 (M−1).

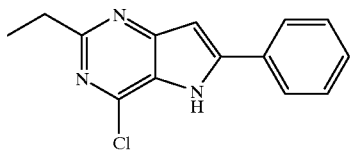

(b) 4-Chloro-2-ethyl-6-phenylpyrrolo[3,2-d]pyrimidine.

A mixture of 2-ethyl-6-phenylpyrrolo[3,2-d]pyrimidine-4-ol (Example 68(a)) (0.6 g, 2.5 mmol) and POCl$_3$ (5.8 mL, 62 mmol) was heated at 120° C. for 21 h. POCl$_3$ was removed in vacuo to give a dark-red residue. Ice-water was added, and the pH of the reaction mixture was adjusted to pH 8 by the addition of aq NH$_3$ at 0° C. The resulting mixture was extracted three times with EtOAc. Combined organic layer were washed with brine, dried over Na$_2$SO$_4$, concentrated in vacuo and dried in a vacuum oven overnight to give 0.31 g (47%) of the title compound as a tan solid. $^1$H NMR (DMSO-$d_6$; 400 MHz): δ 1.41 (t, 3, J=7.57), 3.04 (q, 2, J=7.60), 6.95 (s, 1), 7.45–7.54 (m, 3), 7.76 (d, 2, J=8.15), 8.94 (br s, 1). MS m/z: 258, 260 (M+1); 256, 258 (M−1).

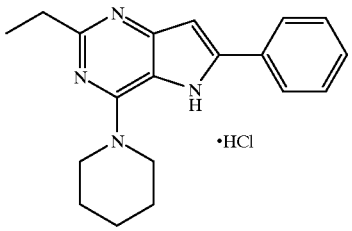

(c) 2-Ethyl-6-phenyl-4-piperidylpyrrolo[3,2-d]pyrimidine Hydrochloride Monohydrate.

To a 25-mL, round-bottomed flask were added 4-chloro-2-ethyl-6-phenylpyrrolo[3,2-d]pyrimidine (Example 68(b)) (0.31 g, 1.2 mmol) and piperidine (0.59 mL, 5.9 mmol), followed by addition of a solution of potassium carbonate (1.63 g, 11.8 mmol) in water (8 mL). The reaction mixture was stirred at 120° C. for 4 hr, cooled to room temperature and filtered. The precipitate was washed with water and hexane and dried in a vacuum oven to give 0.308 g (85%) of a tan solid. The above material (234 mg, 0.76 mmol) was dissolved in minimum amount of CHCl$_3$, and HCl (0.76 mL of a 1M soln in ether, 0.76 mmol) was added dropwise. After stirring for 20 min at room temperature, the solution was concentrated in vacuo to give a tan foam which was recrystallized from MeOH to give 114 mg (28%) of the title compound as light-tan crystals. Mp: 286–288° C. (dec). $^1$H NMR (DMSO-$d_6$; 500 MHz): δ 1.32 (t, 3, J=7.53), 1.72 (m, 6), 2.87 (q, 2, J=7.51), 4.08–4.09 (m, 4), 6.90 (s, 1), 7.51–7.57 (m, 3), 7.96 (d, 2, J=7.36), 12.01 (br s, 1), 14.36 (br s, 1). MS m/z: 307 (M+1), 305 (M−1). Anal. Calcd for $C_{19}H_{22}N_4 \cdot HCl \cdot H_2O$: C, 63.24; H, 6.98; N, 15.52; Cl, 9.82. Found: C, 63.25; H, 6.99; N, 15.50, Cl, 10.10.

EXAMPLE 69

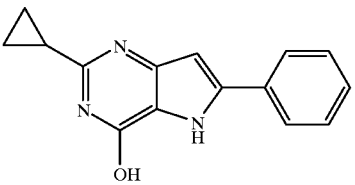

(a) 2-Cyclopropyl-6-phenylpyrrolo[3,2-d]pyrimidine-4-ol.

Dry HCl gas was bubbled through a suspension of ethyl 3-amino-5-phenylpyrrole-2-carboxylate (Example 66(b)) (2.48 g, 8.84 mmol) in cyclopropylcyanide (Aldrich Chemical Company) (75 g) at room temperature for 1.5 h. The reaction mixture was capped and stirred at room temperature overnight. The solvent was evaporated in vacuo to give a dark-red residue, which was dissolved in EtOH (70 mL) and 6% aqueous sodium hydroxide (50 mL). The reaction mixture was heated at reflux for 6 h. The solvent was evaporated in vacu and the resulting suspension was found to be pH 6. The aqueous layer was removed and the brownish residue was disolved in toluene and evaportated. The residue was again dissolved in toluene and evaporatied give a brown oil. The crude material was purified by flash chromatography on silica gel with 100:3 CHCl$_3$:MeOH as eluant to give 0.945 g (43%, 3 steps from tosylate) of the title compound as a tan solid. $^1$H NMR (DMSO-$d_6$; 500 MHz) δ 0.61–0.64 (m, 2), 0.93–0.95 (m, 1), 0.96–1.00 (m, 1), 1.93–1.98 (m, 1), 6.72 (s, 1), 7.31–7.44 (m, 3), 7.95 (d, 2, J=7.63), 11.99 (br s, 1), 12.21 (br s, 1); MS m/z: 252 (M+1), 250 (M−1).

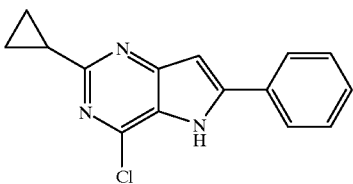

(b) 4-Chloro-2-cyclopropyl-6-phenylpyrrolo[3,2-d]pyrimidine.

A mixture of 2-cyclopropyl-6-phenylpyrrolo[3,2-d]pyrimidine-4-ol (Example 69(a)) (0.914 g, 3.64 mmol) and phosphorus oxychloride (Aldrich Chemical Company) (8.5 mL, 91 mmol) was heated at 120° C. for 24 h. The excess POCl$_3$ was removed under reduced pressure, and toluene was added. The toluene was evaporated to give a brown residue. The residue was diluted with ice-water and neutralized under stirring and cooling with ammonia water to pH 6. The resulting mixture was extracted three times with EtOAc. The combined organic layers were washed with brine, dried over Na$_2$SO$_4$, concentrated in vacuo, and dried in vacuum oven overnight to give 0.462 g (47%) of the title compound as a brown solid. $^1$H NMR (CDCl$_3$; 500 MHz): δ 1.01–1.07 (m, 2), 1.16–1.20 (m, 1), 1.24–1.27 (m, 1), 2.28–2.36 (m, 1), 6.88 (s, 1), 7.45–7.53 (m, 3), 7.74 (d, 2, J=7.31), 8.69 (br s, 1); MS m/z: 270, 272 (M+1); 268, 270 (M−1).

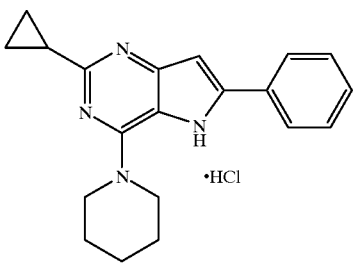

(c) 2-Cyclopropyl-6-phenyl-4-piperidylpyrrolo[3,2-d]pyrimidine Hydrochloride.

To a 25-mL, round-bottomed flask were added 4-chloro-2-cyclopropyl-6-phenylpyrrolo[3,2-d]pyrimidine (Example 69(b)) (0.311 g, 1.15 mmol) and piperidine (0.57 mL, 5.77 mmol), followed by addition of a solution of potassium carbonate (1.59 g, 11.5 mmol) in 8 mL of H$_2$O. The reaction mixture was stirred at 120° C. for 4 h. After cooling to room temperature, a precipitate formed and was collected by filtration. The solids were washed with H$_2$O and hexane, and dried in a vacuum oven to give 0.334 g of a brown solid. This material was purified by flash chromatography on silica gel with 1:1 EtOAc:hexane as eluant to give 0.078 g of a tan solid. The insoluble material on top of the column was isolated to give an additional 0.11 g of product as an off-white solid (total yield: 51%). The purified material (67 mg, 0.21 mmol) was dissolved in minimum amount of CHCl$_3$. Ethereal hydrogen chloride (1N, 0.21 mL, 0.21 mmol) was added dropwise. The mixture was stirred at room temperature for 20 min. Solvent was then evaporated in vacuo to give a tan foam, which was recrystallized from MeOH/H$_2$O to give 20 mg of the title compound as white needles. Mp: 285.4–286.0° C. (dec). $^1$H NMR (DMSO-d$_6$; 500 MHz): δ 1.14–1.21 (m, 4), 1.67–1.71 (m, 6), 2.20–2.24 (m, 1), 3.98–3.99 (m, 4), 6.88 (s, 1), 7.49–7.65 (m, 3), 7.95 (d, 2, J=7.78), 11.95 (br s, 1), 14.51 (br s, 1); MS m/z: 319 (M+1), 317 (M−1). Calcd for C$_{20}$H$_{23}$ClN$_4$·H$_2$O: C, 64.42; H, 6.76; N, 15.02; Cl, 9.51. Found: C, 64.40; H, 6.75; N, 14.93, Cl, 9.41.

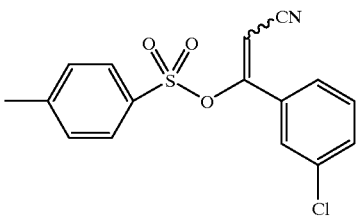

EXAMPLE 70

(a) 1-(3-Chlorophenyl)-2-cyanovinyl 4-methylbenzene sulfonate.

To a 100-mL, round-bottomed flask were added 3-chlorobenzoyl acetonitrile (Maybridge Chemical Company) (5.13 g, 28.5 mmol), p-toluenesulfonyl chloride (Aldrich Chemical Company) (6.53 g, 34.3 mmol) and CH$_2$Cl$_2$ (50 mL). To the above solution was added Et$_3$N (6 mL, 42.8 mmol) dropwise at 0° C. The mixture was stirred at 0° C. for 1 h, then at room temperature for 22 h. The cloudy reaction mixture was partitioned between H$_2$O and CH$_2$Cl$_2$. The organic layer was separated, washed three times with H$_2$O, dried over Na$_2$SO$_4$, and concentrated in vacuo to give a dark-red residue. This material was purified by flash chromatography on silica gel with 1:10 of EtOAc:hexane as eluent to give 8.79 g (92%) of the title compound as a yellow solid. $^1$H NMR (CDCl$_3$; 400 MHz): δ 2.45, 2.47 (d,3), 5.60, 5.62 (d, 1), 7.32–7.48 (m, 6), 7.74 (d, 1, J=8.37), 7.88 (d, 1, J=8.40). MS m/z: 351 (base peak), 332 (M−1).

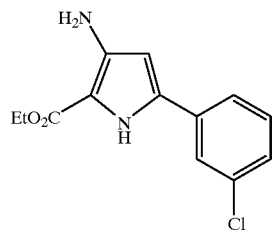

(b) Ethyl 3-amino-5-(3-chlorophenyl)pyrrole-2-carboxylate.

Sodium ethoxide was prepared fresh from Na (1.77 g, 77.1 mmol) and EtOH (30 mL). To the above solution was added a solution of 1-(3-chlorophenyl)-2-cyanovinyl 4-methylbenzenesulfonate (Example 70(a)) (8.56 g, 25.7 mmol), aminodiethyl malonate hydrochloride (Aldrich Chemical Company) (5.43 g, 25.7 mmol) in EtOH (70 mL) through a dropping funnel. After the addition was complete, the reaction mixture was stirred at room temperature for 2 h. The solvent was evaporated in vacuo and the residue was partitioned between EtOAc and H$_2$O. The organic layer was separated, dried over Na$_2$SO$_4$, and concentrated in vacuo to give 5.926 g of a brown solid (This material was used directly in the following step without further purification).

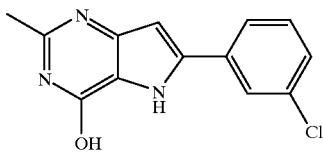

(c) 6-(3-Chlorophenyl)-2-methylpyrrolo [3,2-d]pyrimidine-4-ol.

Dry HCl gas was bubbled through a solution of ethyl 3-amino-5-(3-chlorophenyl)pyrrole-2-carboxylate (Example 70(b)) (3.5 g) in 120 mL of acetonitrile at room temperature for 1.5 h. The reaction mixture was capped, and stirred at room temperature overnight. The solvent was evaporated in vacuo to give a solid, which was dissolved in EtOH (70 mL) and 6% aqueous NaOH (23 mL). The reaction mixture was heated at reflux for 6 h. The precipitate that formed was filtered, and dried in a vacuum oven to give 1.17 g of a tan solid as pure product. The filtrate was concentrated and the resulting suspension was filtered to give a viscous solid. This material was purified by flash chromatography on silica gel with 100:5 of $CHCl_3$:MeOH as eluent to give 0.46 g (41% from the tosylate (70(a)) of the title compound as a tan solid. $^1$H NMR (DMSO-$d_6$; 500 MHz): δ 2.31 (s, 3), 6.86 (s, 1), 7.38 (d, 1, J=7.38), 7.45 (t, 1, J=7.89), 7.90 (d, 1, J=7.82), 8.06 (s, 1), 11.81 (br s, 1), 12.41 (br s, 1); MS m/z: 260, 262 (M+1), 258, 260 (M−1).

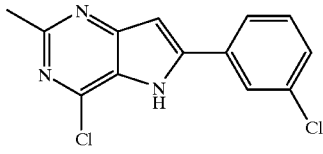

(d) 4-Chloro-6-(3-chlorophenyl)-2-methylpyrrolo[3,2-d]pyrimidine.

A mixture of 6-(3-chlorophenyl)-2-methylpyrrolo [3,2-d]pyrimidine-4-ol (Example 70(c)) (1.55 g, 5.97 mmol) and phosphorus oxychloride (14 mL, 149 mmol) was heated at 120° C. for 24 h. The excess $POCl_3$ was removed under reduced pressure to give a dark-red residue. The residue was diluted with ice-water and neutralized under stirring and cooling with ammonia water to pH 5. The resulting mixture was extracted three times with EtOAc. The combined organic layers were washed with brine, dried over $Na_2SO_4$ and concentrated in vacuo to give 1.42 g (85%) of the title compound as a brown solid. $^1$H NMR (DMSO-$d_6$; 400 MHz): δ 2.79 (s, 3), 6.92 (s, 1), 7.43–7.46 (m, 2), 7.66 (d, 1, J=6.5), 7.74 (s, 1), 9.10 (br s, 1). MS m/z: 278 (M+1); 276 (M−1).

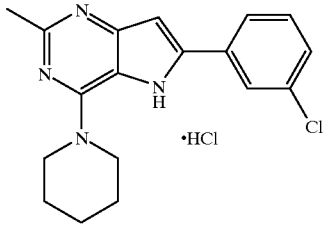

(e) 6-(3-Chlorophenyl)-2-methyl-4-piperidylpyrrolo [3,2-d] pyrimidine Hydrochloride Monohydrate.

To a 25-mL, round-bottomed flask were added 4-chloro-6-(3-chlorophenyl)-2-methylpyrrolo[3,2-d]pyrimidine (Example 70 (d)) (0.5 g, 1.8 mmol) and piperidine (Aldrich Chemical Company) (0.89 mL, 9 mmol), followed by addition of a solution of potassium carbonate (2.49 g, 18 mmol) in 10 mL of $H_2O$. The reaction mixture was stirred at 120° C. for 4 h. The mixture was allowed to cool to roomtemperature and was extracted with $CH_2Cl_2$. The organic layer was separated, dried over $Na_2SO_4$ and concentrated in vacuo to give a brown solid. This material was purified by flash chromatography on silica gel with 1:1 of EtOAc:hexane as eluent to give 0.42 g (71%) of a beige solid. A portion of this material (345 mg, 1.06 mmol) was dissolved in minimum amount of $CHCl_3$, and ethereal hydrogen chloride (1N, 1.1 mL, 1.1 mmol) was added dropwise. The mixture was stirred at room temperature for 20 min. Solvent was then evaporated in vacuo to give a light-yellow foam, which was recrystallized from MeOH to give 170 mg of the title compound as white crystals. MP: 244.5–246° C. (dec). $^1$H NMR (DMSO-$d_6$; 500 MHz): δ 1.72 (m, 6), 2.57 (s, 3), 4.06–4.07 (m, 4), 7.00 (s, 1), 7.56–7.58 (m, 2), 7.93–7.94 (m, 1), 8.10 (s, 1), 11.99 (br s, 1), 14.31 (br s, 1). MS m/z: 327, 329 (M+1), 325, 327 (M−1). Calcd for $C_{18}H_{20}Cl_2N_4H_2O$: C, 56.70; H, 5.82; N, 14.69; Cl, 18.60. Found: C, 56.75; H, 5.81; N, 14.62, Cl, 18.47.

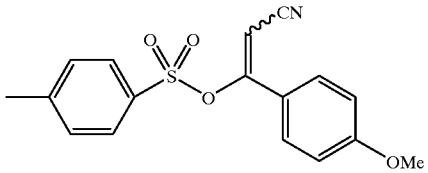

EXAMPLE 71

(a) 2-Cyano-1-(4-methoxyphenyl)vinyl 4-methylbenzene sulfonate.

To a 100-mL, round-bottomed flask were added 4-methoxybenzoyl acetonitrile (Maybridge Chemical Company) (5 g, 28.5 mmol), p-toluenesulfonyl chloride (Aldrich Chemical Company) (6.53 g, 34.3 mmol) and $CH_2Cl_2$ (50 mL). To the above solution was then added $Et_3N$ (6 mL, 42.8 mmol) dropwise at 0° C. The mixture was stirred at 0° C. for 1 h, and at room temperature for 48 h. The cloudy reaction mixture was partitioned between $H_2O$ and $CH_2Cl_2$. The organic layer was separated, washed three times with water, dried over $Na_2SO_4$, and concentrated in vacuo to give a dark-red residue. This material was purified by flash chromatography on silica gel with 1:10 to 1:8 of EtOAc:hexane as eluent to give 4.73 g (50%) of the title compound as a yellow solid. $^1$H NMR (CDCl$_3$; 400 MHz): δ 2.47 (s, 3), 3.86 (s, 3), 5.45 (s, 1), 6.91 (d, 2, J=8.9), 7.38 (d, 2, J=8.22), 7.55 (d, 2, J=8.95), 7.92 (d, 2, J=8.34) (for one isomer). MS m/z: 330 (M+1), 328 (M−1).

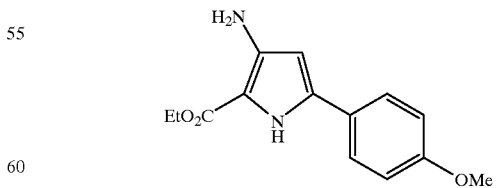

(b) Ethyl 3-amino-5-(4-methoxyphenyl)pyrrole-2-carboxylate.

Sodium ethoxide was prepared fresh from Na (0.97 g, 42.3 mmol) and EtOH (30 mL). To the above solution was added a solution of 2-cyano-1-(4-methoxyphenyl) vinyl 4-methylbenzenesulfonate (Example 71(a)) (4.64 g, 14.1 mmol), aminodiethyl malonate hydrochloride (Aldrich Chemical Company) (2.98 g, 14.1 mmol) in EtOH (40 mL) and THF (30 mL) through a dropping funnel. After the addition was complete, the reaction mixture was stirred at room temperature for 21 h. The solvent was evaporated in vacuo and the residue was partitioned between EtOAc and H$_2$O. The organic layer was separated, dried over Na$_2$SO$_4$, and concentrated in vacuo to give 2.98 g of an orange solid (This material was used directly in the following step without further purification).

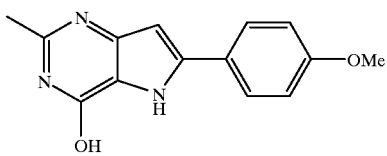

(c) 6-(4-Methoxyphenyl)-2-methylpyrrolo[3,2-d]pyrimidine-4-ol.

Dry HCl gas was bubbled through a solution of ethyl 3-amino-5-(4-methoxyphenyl)pyrrole-2-carboxylate (Example 71(b)) (2.75 g) in 90 mL of acetonitrile at room temperature for 1.5 h. The reaction mixture was then capped and stirred at room temperature overnight. The solvent was evaporated in vacuo to give a solid, which was dissolved in EtOH (50 mL) and 6% aqueous NaOH (16 mL). The reaction mixture was heated at reflux for 6 h. The EtOH was evaporated in vacuo to give a suspension. The precipitate that formed was filtered, washed with H$_2$O, and dried in a vacuum oven to give 1.69 g of a brown solid (This material was used directly in the following step without further purification).

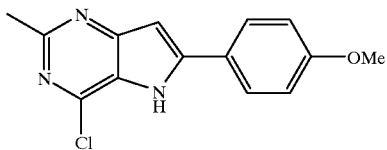

(d) 1-(4-Chloro-2-methylpyrrolo[4,5-d]pyrimidin-6-yl)-4-methoxybenzene.

A mixture of 6-(4-methoxyphenyl)-2-methylpyrrolo [3,2-d]pyrimidine-4-ol (Example 71(c)) (1.50 g, 5.89 mmol) and phosphorus oxychloride (14 mL, 149 mmol) was heated at 120° C. for 24 h. The excess POCl$_3$ was removed under reduced pressure to give a dark-red residue. This material was diluted with ice-water and neutralized under stirring and cooling with ammonia water to pH 7. The resulting mixture was extracted three times with EtOAc. The combined organic layers were washed with brine, dried over Na$_2$SO$_4$, and concentrated in vacuo to give a viscous oil. This material was purified by flash chromatography on silica gel with 1:4 to 1:1 of EtOAc:hexane as eluent to give 0.334 g (11% from the tosylate) of the title compound as a tan solid. $^1$H NMR (DMSO-d$_6$; 400 MHz): δ 2.78 (s, 3), 3.89 (s, 3), 6.82 (s, 1), 7.04 (d, 2, J=8.82), 7.70 (d, 2, J=8.74), 8.68 (br s, 1). MS m/z: 274 (M+1); 272 (M−1).

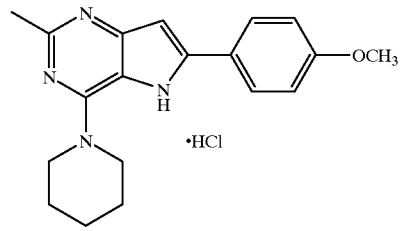

(e) 4-Methoxy-1-(2-methyl-4-piperidylpyrrolo[4,5-d]pyrimidin-6-yl)benzene Hydrochloride Monohydrate.

To a 15-mL, round-bottomed flask was added 1-(4-chloro-2-methylpyrrolo[4,5-d]pyrimidin-6-yl)-4-methoxy benzene (Example 71(d)) (0.3 g, 1.1 mmol) and piperidine (Aldrich Chemical Company) (0.54 mL, 5.5 mmol), followed by the addition of a solution of potassium carbonate (0.759 g, 5.5 mmol) in H$_2$O (5 mL)). The reaction mixture was stirred at 120° C. for 4 h. The precipitate that formed was collected by filtration, washed with H$_2$O and hexane, and dried in a vacuum oven to give 0.332 g (94%) of a tan solid. The above material (186 mg, 0.58 mmol) was dissolved in a minimum amount of CHCl$_3$, and ethereal hydrogen chloride (1N, 0.6 mL, 0.6 mmol) was added dropwise. The mixture was stirred at room temperature for 20 min. The solvent was then evaporated in vacuo to give a tan solid, which was recrystallized from MeOH to give 77 mg of the title compound as light-tan crystals. MP: 267.5–268° C. (dec). $^1$H NMR (DMSO-d$_6$; 500 MHz): δ 1.63–1.72 (m, 6), 2.54 (s, 3), 3.84 (s, 3), 4.00 (m, 4), 6.78 (s, 1), 7.10 (d, 2, J=8.67), 7.90 (d, 2, J=8.67), 8.56 (br s, 1), 11.73 (br s, 1). Calcd for C$_{19}$H$_{23}$ClN$_4$O.H$_2$O: C, 60.55; H, 6.69; N, 14.87; Cl, 9.41. Found: C, 60.77; H, 6.62; N, 14.84, Cl, 9.25.

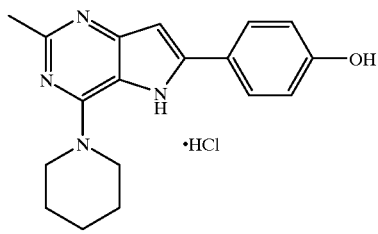

EXAMPLE 72

4-(2-Methyl-4-piperidylpyrrolo[4,5-d]pyrimidin-6-yl) phenol Hydrochloride Monohydrate.

The suspension of 4-methoxy-1-(2-methyl-4-piperidylpyrrolo[4,5-d]pyrimidin-6-yl)benzene (Example 71(e)) (0.138 g, 0.43 mmol) in anhydrous CH$_2$Cl$_2$ (12 mL) was cooled to −70° C. under nitrogen atmosphere. Boron tribromide (Aldrich Chemical Company) (0.41 mL, 4.3 mmol) in CH$_2$Cl$_2$ (4 mL) was added dropwise. The reaction mixture was stirred at −70° C. to room temperature for 16 h. The solution was poured into 40 mL of ice-water. The resulting mixture was basified with Et$_3$N to pH 10 and stirred for a period of 3 h. The precipitate that formed was collected by filtration, washed with H$_2$O, and dried in a vacuum oven to give 78.7 mg (60%) of a tan solid. A portion of this material (74 mg, 0.24 mmol) was dissolved in minimum amount of CHCl$_3$, and ethereal hydrogen chloride (1N, 0.26 mL, 0.26 mmol) was added dropwise. The mixture was stirred at room temperature for 20 min. Solvent was then evaporated in vacuo to give a brown solid, which was recrystallized from MeOH/H$_2$O to give 25 mg of the title compound as light-tan crystals. MP: >300° C. (dec). $^1$H NMR (DMSO-d$_6$; 400 MHz): δ 1.70 (m, 6), 2.55 (s, 3), 4.03 (m, 4), 6.73 (s, 1), 6.93 (d, 2, J=8.54), 7.79 (d, 2, J=8.54), 10.04 (s, 1), 11.75 (br s, 1), 14.15 (br s, 1); MS m/z: 309 (M+1), 307 (M−1). Calcd for C$_{18}$H$_{21}$ClN$_4$O.H$_2$O: C, 59.58; H, 6.39; N, 15.44. Found: C, 59.13; H, 6.33; N, 15.20.

EXAMPLE 73

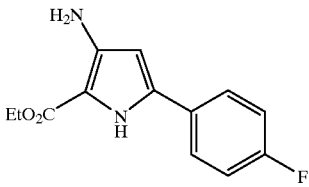

(a) Ethyl 3-amino-5-(4-fluorophenyl)pyrrole-2-carboxylate.

Sodium ethoxide was prepared fresh from Na (2.66 g, 116 mmol) and EtOH (40 mL). To this solution was added a solution of 3-chloro-3-(4-fluorophenyl)acrylo nitrile (Maybridge Chemical Company) (7.00 g, 38.5 mmol), aminodiethyl malonate hydrochloride (Aldrich Chemical Company) (8.16 g, 38.5 mmol) in EtOH (110 mL) through an addition funnel. After the addition was complete, the reaction mixture was stirred at room temperature for 21 h. The solvent was evaporated in vacuo and the residue was partitioned between EtOAc and H$_2$O. The organic layer was separated, dried over Na$_2$SO$_4$ and concentrated in vacuo to give 11.63 g of a dark-red solid (This material was used directly in the following step without further purification).

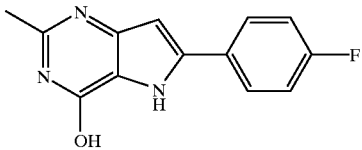

(b) 6-(4-Fluorophenyl)-2-methylpyrrolo[3,2-d]pyrimidine-4-ol.

Dry HCl gas was bubbled through a solution of ethyl 3-amino-5-(4-fluorophenyl)pyrrole-2-carboxylate (Example 73(a)) (8.78 g) in 250 mL of acetonitrile at room temperature for 1.5 h. The reaction mixture was then capped and stirred at room temperature overnight. The solvent was evaporated in vacuo to give a brownish residue, which was dissolved in EtOH (150 mL) and 6% aqueous NaOH (50 mL). The reaction mixture was heated at reflux for 6 h. The precipitate that formed was filtered, dried in a vacuum oven to give 1.25 g of a tan solid as a pure product. The filtrate was concentrated and the resulting suspension was filtered to give a viscous solid, which was purified by flash chromatography on silica gel with 100:5 of CHCl$_3$: MeOH as eluent to give 0.604 g (total yield 26% from the chloride) of the title compound as a tan solid. $^1$H NMR (DMSO-d$_6$; 400 MHz): δ 2.31 (s, 3), 6.72 (s, 1), 7.26–7.28 (m, 2), 7.96–7.97 (m, 2), 11.76 (br s, 1), 12.24 (br s, 1). MS m/z: 244 (M+1), 242 (M−1).

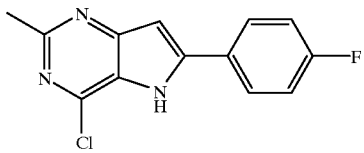

(c) 4-Chloro-6-(4-fluorophenyl)-2-methylpyrrolo[3,2-d]pyrimidine.

A mixture of 6-(4-fluorophenyl)-2-methylpyrrolo[3,2-d]pyrimidine-4-ol (Example 73(b)) (1.84 g, 7.58 mmol) and phosphorus oxychloride (18 mL, 189 mmol) was heated at 120° C. for 24 h. The excess POCl$_3$ was removed under reduced pressure to give a dark-brown residue. This material was diluted with ice-water and neutralized under stirring and cooling with ammonia water to pH 8. The resulting mixture was extracted three times with EtOAc. The combined organic layers were washed with brine, dried over Na$_2$SO$_4$ and concentrated in vacuo to give 1.22 g (62%) of product as a brown solid. $^1$H NMR (DMSO-d$_6$; 400 MHz): δ 2.79 (s, 3), 6.87 (s, 1), 7.19–7.23 (m, 2), 7.74–7.78 (m, 2), 9.17 (br s, 1). MS m/z: 262, 264 (M+1); 260, 262 (M−1).

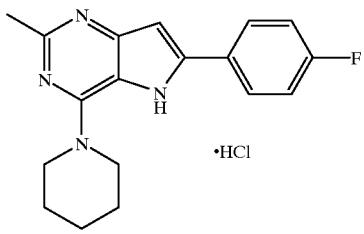

(d) 6-(4-Fluorophenyl)-2-methyl-4-piperidylpyrrolo[3,2-d]pyrimidine Hydrochloride.

To a 25-mL, round-bottomed flask were added 4-chloro-6-(4-fluorophenyl)-2-methylpyrrolo[3,2-d]pyrimidine (Example 73(c)) (0.5 g, 1.9 mmol) and piperidine (Aldrich Chemical Company) (0.95 mL, 9.6 mmol), followed by addition of a solution of potassium carbonate (2.64 g, 19 mmol) in 10 mL of water. The reaction mixture was stirred at 120° C. for 4 h. After cooling to room temperature, CH$_2$Cl$_2$ was added. The precipitate that formed was collected by filtration, and dried in a vacuum oven to give 0.168 g of an off-white solid as pure product. The filtrate was extracted with CH$_2$Cl$_2$, the organic layer was separated, dried over Na$_2$SO$_4$, and concentrated in vacuo to give a brown solid. This material was purified by flash chromatography on silica gel with 1:1 of EtOAc:hexane as eluent to give 0.196 g (61% total yield) of an off-white solid. This material (196 mg, 0.63 mmol) was dissolved in minimum amount of CHCl$_3$, and ethereal hydrogen chloride (1N, 0.65 mL, 0.65 mmol) was added dropwise. The mixture was stirred at room temperature for 20 min. The solvent was evaporated in vacuo to give an off-white solid, which was recrystallized from MeOH to give 67 mg of the title compound as off-white crystals. MP: 287–289° C. (dec). $^1$H NMR (DMSO-d$_6$; 500 MHz): δ 1.87–1.88 (m, 6), 2.74 (s, 3), 4.22–4.23 (m, 4), 7.05 (s, 1), 7.55–7.59 (m, 2), 8.19–8.22 (m, 2), 12.18 (br s, 1), 14.63 (br s, 1). MS m/z: 311 (M+1), 309 (M−1). Calcd for C$_{18}$H$_{20}$ClFN$_4$.H$_2$O: C, 59.26; H, 6.08; N, 15.36; Cl, 9.72. Found: C, 59.30; H, 6.10; N, 15.22, Cl, 9.67.

EXAMPLE 74

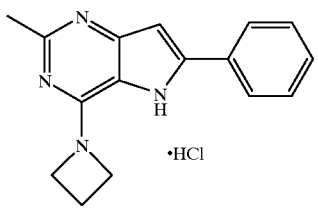

4-Azetidinyl-2-methyl-6-phenylpyrrolo[3,2-d]pyrimidine Hydrochloride Monohydrate.

This compound was prepared according to the method described in Example 73(d), by employing 2-methyl-4-chloro-6-phenyl-5H-pyrrolo[3,2-d]pyrimidine (Example 1(e)) (0.3 mg, 1.23 mmol), azetidine (Aldrich Chemical Company) (0.41 mL, 6.16 mmol) and potassium carbonate (1.7 g, 12.3 mmol) in $H_2O$ (8 mL) to give 0.322 g (99%) of an off-white solid. A portion of this material (298 mg, 1.13 mmol) was dissolved in minimum amount of $CHCl_3$ and MeOH, and ethereal hydrogen chloride (1N, 1.2 mL, 1.2 mmol) was added dropwise. The mixture was stirred at room temperature for 20 min. The precipitate that formed was filtered, recrystallized from MeOH/$H_2O$ to give 190 mg of the title compound as white crystals. MP: >300° C. (dec). $^1$H NMR (DMSO-$d_6$; 500 MHz): δ 2.48–2.52 (m, 2), 2.55 (s, 3), 4.46–4.63 (m, 4), 6.88 (s, 1), 7.49–7.57 (m, 3), 7.95 (d, 2, J=7.69), 11.78 (br s, 1), 14.32 (br s, 1). MS m/z: 265 (M+1), 263 (M−1). Calcd for $C_{16}H_{17}ClN_4 \cdot H_2O$: C, 60.28; H, 6.01; N, 17.57; Cl, 11.12. Found: C, 60.23; H, 5.96; N, 17.54, Cl, 11.18.

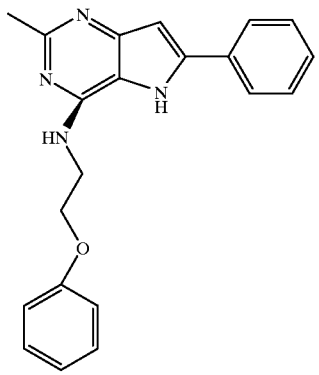

EXAMPLE 75

(2-Methyl-6-phenylpyrrolo[2,3-e]pyrimidin-4-yl)(2-phenoxyethyl)amine Hydrochloride.

This compound was prepared according to the method described in Example 2, by employing 2-methyl-4-chloro-6-phenyl-5H-pyrrolo[3,2-d]pyrimidine (Example 1(e)) (100 mg, 0.41 mmol), 2-phenoxyethylamine (Lancaster Synthesis Ltd.) (0.28 g, 2.05 mmol) and potassium carbonate (0.567 g, 4.1 mmol) in $H_2O$ (2.5 mL) to give 30.7 mg (22%) of the title compound as white crystals. MP: 266.9–267.4° C. (dec). $^1$H NMR (DMSO-$d_6$; 400 MHz): δ 2.43 (s, 3), 3.91–3.93 (m, 2), 4.22 (t, 2, J=5.3), 6.74 (s, 1), 6.93–7.07 (m, 4), 7.29–7.40 (m, 3), 7.49–7.52 (m, 2), 7.79 (d, 2, J=7.79), 11.33 (br s, 1). MS m/z: 345 (M+1), 343 (M−1). Anal. Calcd for $C_{19}H_{24}N_4O$: C, 70.34; H, 7.46; N, 17.27. Found: C, 70.14; H, 7.35; N, 17.13.

EXAMPLE 76

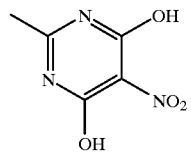

(a) 2-Methyl-4,6-dihydroxy-5-nitropyrimidine.

To a three-necked, round-bottomed flask equipped with an addition funnel, condenser, internal temperature probe and mechanical stirrer was added trifluoroacetic acid (Aldrich Chemical Company) (120 mL, 710 mmol) and powdered 2-methyl-4,6-dihydroxy pyrimidine (Aldrich Chemical Company) (20 g, 160 mmol). The suspension was stirred under a $N_2$ atmosphere for 15 min to allow complete dissolution of the solids. Nitric acid (9.7 mL, 210 mmol, 90% aq soln) was added over 25 min while maintaining the internal temperature between 13–21° C. by cooling the reaction flask in an ice bath. Stirring was continued for 12 h at room temperature. Water (100 mL) was added, and the resulting precipitate was collected by filtration and washed with $H_2O$. Recrystallization from $H_2O$ followed by drying in the vacuum oven provided 20 g (68%) of the title compound as a white crystalline solid. $^1$H NMR (DMSO-$d_6$; 400 MHz): δ 3.9 (s, 3). $^{13}$C NMR (DMSO-$d_6$; 100.6 MHz): δ 17.94, 118.0, 155.7, 161.7. MS m/z: 170 (M−1).

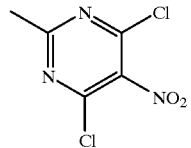

(b) 2-Methyl-4,6-dichloro-5-nitropyrimidine.

To a round-bottomed flask equipped with a Dean-Stark trap, reflux condenser, pressure-equalized addition funnel, magnetic stirrer, heating mantel and internal temperature probe was added 2-methyl-4,6-dihydroxy-5-nitropyrimidine (Example 76(a)) (2.0 g, 11 mmol) and toluene (16 mL). The Dean-Stark trap was filled with toluene (12 mL). For 3 h, the reaction mixture was heated at reflux during which time water collected in the Dean-Stark trap. Heat was removed from the reaction vessel, and after 20 min, diisopropylethylamine (Aldrich Chemical Company) (2.8 mL, 16 mmol) was poured into the reaction mixture through the reflux condenser. The reaction mixture was heated at reflux again, and $POCl_3$ (Aldrich Chemical Company) (7 mL, 74 mmol) was added through the addition funnel at such a rate as to maintain the internal temperature below 113° C. (8 min). Vigorous bubbling was observed during the addition of $POCl_3$. Following this addition, the reaction mixture was heated for an additional 3 h at reflux. Heat was then removed from the flask, and the reaction was stirred at room temperature for 18 h. The reaction mixture was then poured onto ice-water (100 mL), shaken in a separatory funnel, and filtered through a pad of Celite. The organic layer was collected from the filtrate, and the aqueous layer was extracted twice with ether. All organic fractions were combined, dried over $Na_2SO_4$, and concentrated in vacuo. Heptane was added to the residue, the contents were filtered through a pad of Celite, and concentrated in vacuo to give the title compound (1.1 g, 49%) as a brown rod-like crystals in sufficient purity for the next step. $^1$H NMR (DMSO-$d_6$;

400 MHz): δ 2.5 (s, 3). $^{13}$C NMR (DMSO-d$_6$; 100.6 MHz): δ 27.04, 127.0, 153.6, 170.8.

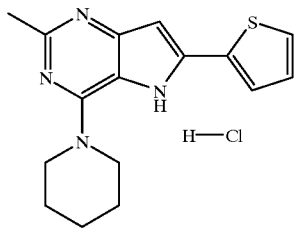

(c) 2-(2-Methyl-4-piperidylpyrrolo[4,5-d]pyrimidin-6-yl) thiophene Hydrochloride.

Using the method described in Example 30 by employing 2-(1-pyrrolidinylvinyl)thiophene (freshly prepared before use) (2.39 g, 13.4 mmol), 2-methyl-4,6-dichloro-5-nitropyrimidine (Example 76(b)) (2.76 g, 13.4 mmol), N,N-diisopropylethyl amine (Aldrich Chemical Company) (2.3 mL, 13.4 mmol), piperidine (2.1 mL, 21.4 mmol), NEt$_3$ (Aldrich Chemical Company) (2.0 mL) and SnCl$_2$ (40 mL of a 2M solution in DMF). The residue was purified by flash chromatography on silica gel with 95:5 CHCl$_3$:MeOH as elutant to give 540 mg (14%) of the free base as a cream colored solid. $^1$H NMR (DMSO-d$_6$; 400 MHz): δ 1.65 (s, 6), 2.41 (s, 3), 3.30 (s, 2), 3.71 (br s, 2), 6.49 (br s, 1), 7.14 (br s, 1), 7.62 (br s, 1), 11.09 (s, 1). MS m/z: 299 (M+1). To a solution of 2-(2-methyl-4-piperidyl pyrrolo[4,5-d] pyrimidin-6-yl)thiophene (0.54 g, 1.81 mmol) in 5:1 EtOAc: MeOH (30 mL) was added 1N etheral HCl (Aldrich Chemical Company) (1.80 mL, 1.80 mmol). The precipitate was collected by filtration, washed with EtOAc (2×10 mL), ether (3×15 mL) and dried under vacuum to give 550 mg (92%) of the title compound as a tan colored solid. Mp: >280° C. $^1$H NMR (DMSO-d$_6$; 400 MHz): δ 1.71 (s, 6), 2.56 (s, 3), 4.04 (br s, 4), 6.70 (s, 1), 7.26 (t, 1, J=4.2), 7.80 (d, 1, J=5.0), 7.89 (d, 1, J=3.0), 12.15 (s, 1), 14.44 (s, 1). MS m/z: 299 (M+1). Anal. Calcd for C$_{15}$H$_{18}$N$_4$S.HCl: C, 57.39; H, 5.72; N, 16.73; Cl, 10.59. Found C, 57.25; H, 5.75; N, 16.60; Cl, 10.73.

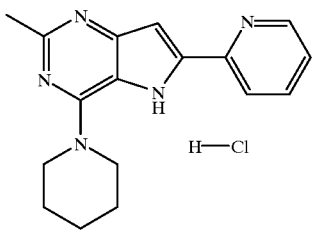

EXAMPLE 77
2-Methyl-4-piperidyl-6-(2-pyridyl)pyrrolo[3,2-d] pyrimidine Hydrochloride Hydrate.

Using the method described in Example 30 by employing 2-(1-pyrrolidinylvinyl)-2-pyridine (freshly prepared before use) (2.20 g, 12.6 mmol), 2-methyl-4,6-dichloro-5-nitropyrimidine (Example 76(b)) (2.61 g, 12.6 mmol), N,N-diisopropylethyl amine (Aldrich Chemical Company) (2.2 mL, 12.6 mmol), piperidine (2.0 mL, 20.2 mmol), NEt$_3$ (Aldrich Chemical Company) (2.0 mL) and SnCl$_2$ (Aldrich Chemical Company) (38 mL of a 2M solution in DMF). The residue was purified by flash chromatography on silica gel with 95:5 CHCl$_3$:MeOH as elutant to give 650 mg (18%) of the free base as a beige colored solid. $^1$H NMR (DMSO-d$_6$; 400 MHz): δ 1.66 (s, 6), 2.42 (s, 3), 3.74 (s, 4), 7.01 (br s, 1), 7.37 (br s, 1), 7.90 (br s, 1), 8.08 (d, 1, J=7.9), 8.67 (br s, 1), 11.18 (s, 1). MS m/z: 294 (M+1). To a solution of 2-methyl-4-piperidyl-6-(2-pyridyl)pyrrolo[3,2-d] pyrimidine (0.65 g, 2.22 mmol) in-EtOAc (30 mL) was added 1N etheral HCl (Aldrich Chemical Company) (2.20 mL, 2.22 mmol). The precipitate was collected by filtration, washed with EtOAc (2×10 mL), ether (3×15 mL) and dried under vacuum to give 621 mg (85%) of the title compound as a brown colored solid. Mp: >280° C. $^1$H NMR (DMSO-d$_6$; 400 MHz): δ 1.72 (s, 6), 2.58 (s, 3), 4.06 (br s, 4), 7.16 (s, 1), 7.51 (dd, 1, J=7.4, 7.4), 8.01 (dt, 1, J=1.4, 7.6), 8.24 (d, 1, J=7.9), 8.76 (d, 1, J=4.4), 12.19 (s, 1), 14.36 (s, 1). MS m/z: 294 (M+1). Anal. Calcd. for C$_{17}$H$_{19}$N$_5$.1.2HCl.0.4H$_2$O: C, 59.18; H, 6.14; N, 20.30; Cl, 12.53. Found C, 59.23; H, 6.14; N, 20.03; Cl, 12.56.

EXAMPLE 78

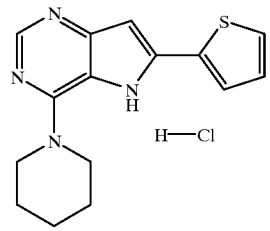

2-(4-Piperidylpyrrolo[4,5-d]pyrimidin-6-yl)thiophene Hydrochloride.

Using the method described in Example 30 by employing 2-(1-pyrrolidinylvinyl)thiophene (freshly prepared before use) (1.80 g, 10.1 mmol), 4,6-dichloro-5-nitropyrimidine (Aldrich Chemical Company) (1.95 g, 10.1 mmol), N,N-diisopropylethyl amine (Aldrich Chemical Company) (1.8 mL, 10.1 mmol), piperidine (2.0 mL, 20.3 mmol), NEt$_3$ (Aldrich Chemical Company) (2.0 mL) and SnCl$_2$ (30 mL of a 2M solution in DMF). The residue was purified by flash chromatography on silica gel with 97:3 CHCl$_3$:MeOH as elutant to give 460 mg (16%) of the free base as a beige colored solid. $^1$H NMR (DMSO-d$_6$; 400 MHz): δ 1.72 (s, 6), 3.83 (s, 4), 6.69 (br s, 1), 7.25 (t, 1, J=3.9), 7.69 (br s, 1), 7.75 (br s, 1), 8.30 (s, 1), 11.34 (s, 1). MS m/z: 285 (M+1). To a solution of 2-(4-Piperidylpyrrolo[4,5-d]pyrimidin-6-yl) thiophene (0.46 g, 1.63 mmol) in 10:1 EtOAc: MeOH (30 mL) was added 1N etheral HCl (Aldrich Chemical Company) (1.63 mL, 1.63 mmol). The precipitate was collected by filtration, washed with EtOAc (2×10 mL), ether (3×15 mL) and dried under vacuum to give 462 mg (88%) of the title compound as a beige colored solid. Mp: >280° C. $^1$H NMR (DMSO-d$_6$; 400 MHz): δ 1.71 (s, 6), 4.05 (br s, 4), 6.77 (s, 1), 7.26 (t, 1, J=4.6), 7.80 (d, 1, J=5.0), 7.89 (d, 1, J=3.6), 8.59 (s, 1), 12.45 (s, 1), 14.42 (s, 1). MS m/z: 285 (M+1 for free base). Anal. Calcd for C$_{15}$H$_{16}$N$_4$S.HCl: C, 56.15; H, 5.34; N, 17.46; Cl, 11.05. Found C, 55.86; H 5.32; N, 17.27; Cl, 11.29.

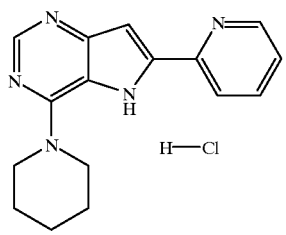

EXAMPLE 79
4-Piperidyl-6-(2-pyridyl)pyrrolo[3,2-d]pyrimidine Hydrochloride Hydrate.

Using the method described in Example 30 by employing 2-(1-pyrrolidinylvinyl)-2-pyridine (freshly prepared before use) (2.30 g, 13.2 mmol), 4,6-dichloro-5-nitropyrimidine (Aldrich Chemical Company) (2.55 g, 13.2 mmol), N,N-diisopropylethyl amine (Aldrich Chemical Company) (2.3 mL, 13.2 mmol), piperidine (2.1 mL, 21.1 mmol), NEt$_3$ (Aldrich Chemical Company) (2.0 mL) and SnCl$_2$ (Aldrich Chemical Company) (40 mL of a 2M solution in DMF). The residue was purified by flash chromatography on silica gel with 95:5 CHCl$_3$:MeOH as elutant to give 340 mg (9%) of the free base as a beige colored solid. $^1$H NMR (DMSO-d$_6$; 400 MHz): δ 1.66 (s, 6), 3.76 (s, 4), 7.13 (br s, 1), 7.41 (t, 1, J=4.8), 7.92 (t, 1, J=7.4), 8.10 (d, 1, J=8.0), 8.26 (br s, 1), 8.70 (br s, 1), 11.24 (s, 1). MS m/z: 280 (M+1). To a solution of 4-piperidyl-6-(2-pyridyl)pyrrolo[3,2-d]pyrimidine (0.34 g, 1.21 mmol) in 15:1 EtOAc:MeOH (30 mL) was added 1N etheral HCl (Aldrich Chemical Company) (1.20 mL, 1.21 mmol). The precipitate was collected by filtration, washed with EtOAc (2×10 mL), ether (3×15 mL) and dried under vacuum to give 300 mg (79%) of the title compound as a tan colored powder. Mp: 279–280° C. $^1$H NMR (DMSO-d$_6$; 400 MHz): δ 1.72 (s, 6), 4.0 (br s, 4), 7.24 (s, 1), 7.52 (dd, 1, J=7.4, 7.5), 8.01 (dt, 1, J=1.3, 7.7), 8.24 (d, 1, J=8.0), 8.64 (s, 1), 8.77 (d, 1, J=4.4), 12.21 (s, 1), 14.51 (s, 1). MS m/z: 280 (M+1). Anal. Calcd for C$_{16}$H$_{17}$N$_5$·1.2HCl·0.7H$_2$O: C, 56.91; H, 5.88; N, 20.75; Cl, 13.01. Found C, 56.91; H, 5.83; N, 20.54; Cl, 12.92.

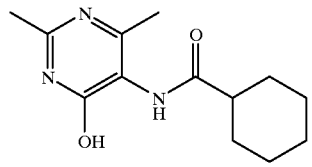

EXAMPLE 80
(a) 5-Cyclohexyl-2,6-dimethyl-4-hydroxypyrimidine.

To a slurry of 5-amino-2,6-dimethyl-4-hydroxy pyrimidine hydrochloride (Example 12(a)) (1.36 g, 7.77 mmol) in CH$_2$Cl$_2$ (20 mL) was added NEt$_3$ (Aldrich Chemical Company) (2.3 mL, 16.3 mmol). The slurry was stirred at 25° C. under a nitrogen atmosphere for 2–3 min at which time all material went into solution. To this clear solution was added cyclohexane carbonyl chloride (Aldrich Chemical Company) (1.4 mL, 10.1 mmol) and DMAP (Aldrich Chemical Company) (100 mg, catalytic). This mixture was stirred at 25° C. for 18 h. The precipitate was collected by filtration, washed with CH$_2$Cl$_2$ (3×15 mL) and dried under vacuum to provide 1.54 g (80%) of the title compound as a white solid. $^1$H NMR (DMSO-d$_6$; 400 MHz): δ 1.19–1.46 (m, 5), 1.66–1.84 (m,5), 2.04 (s, 3), 2.30 (s, 3), 2.39 (br s, 1), 5.80 (s, 1), 8.95 (s, 1). MS m/z: 250 (M+1).

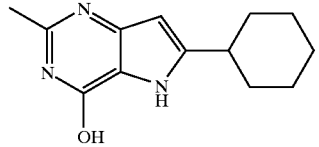

(b) 6-Cyclohexyl-2-methylpyrrolo[3,2-d]pyrimidine-4-ol.

Using the method described in Example 1(d) (Method B) by employing 5-cyclohexyl-2,6-dimethyl-4-hydroxypyrimidine (Example 80(a)) (1.00 g, 4.02 mmol) and Na (Aldrich Chemical Company) (0.37 g, 16.1 mmol). Following the work-up described in Example 1(d) the residue was purified by flash chromatography on silica gel with 98:2 CHCl$_3$:MeOH as elutant to give 355 mg (38%) of the title compound as a beige solid. $^{-1}$H NMR (DMSO-d$_6$; 400 MHz): δ 1.22–1.44 (m, 5), 1.67 (1, d, J=12.0), 1.76 (d, 2, J=12.5), 1.93 (d, 2, J=11.3), 2.26 (s, 3), 2.60 (tt, 1, J=3.5, 11.3), 5.98 (d, 1, J=2.1), 11.60 (s, 1). MS m/z: 232 (M+1).

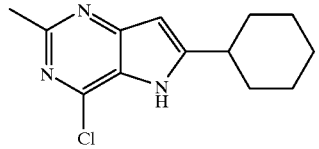

(c) 4-Chloro-6-cyclohexyl-2-methylpyrrolo[3,2-d]pyrimidine.

Using the method described for Example 45(c) by employing 6-cyclohexyl-2-methylpyrrolo[3,2-d]pyrimidine-4-ol (Example 80(b)) (0.33 g, 1.45 mmol) and POCl$_3$ (Aldrich Chemical Company) (15 mL). Following the work-up described in Example 45(c) the residue was purified by flash chromatography on silica gel with 98:2 CHCl$_3$:MeOH as elutant to give 257 mg (71%) of the title compound as a beige solid. $^1$H NMR (DMSO-d$_6$; 400 MHz): δ 1.37–1.70 (m, 5), 1.86 (d, 1, J=11.8), 1.94 (d, 2, J=12.5), 2.14 (d, 2, J=12.1), 2.73 (s, 3), 2.95 (tt, 1, J=3.5, 11.7), 6.51 (d, 1, J=1.5), 12.19 (s, 1). MS m/z: 250 (M+1).

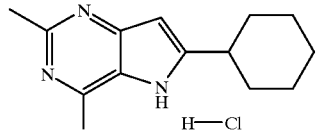

(d) 6-Cyclohexyl-2-methyl-4-piperidylpyrrolo[3,2-d]pyrimidine Hydrochloride Hydrate.

Using the method described for Example 45(d) by employing 4-chloro-6-cyclohexyl-2-methylpyrrolo[3,2-d]pyrimidine (Example 80(c)) (0.10 g, 0.40 mmol), piperidine (Aldrich Chemical Company) (100 mL, 1.00 mmol) and K$_2$CO$_3$ (Aldrich Chemical Company) (0.22 g, 1.60 mmol). Flash chromatography of the crude product on silica gel with 95:5 CHCl$_3$:MeOH as elutant gave 144 mg (48%) of the title compound as a beige solid. $^1$H NMR (DMSO-d$_6$; 400 MHz): δ 1.41 (m, 5), 1.63 (br s, 6), 1.71 (1, d, J=13.0), 1.80 (d, 2, J=9.2), 1.98 (d, 2, J=10.4), 2.37 (s, 3), 2.74 (m, 1), 3.64 (br s, 4), 6.00 (s, 1), 10.62 (s, 1). MS m/z: 299 (M+1). To a solution of 6-cyclohexyl-2-methyl-4-piperidylpyrrolo[3,2-d]pyrimidine (0.13 g, 0.46 mmol) in 10:1 EtOAc:MeOH (20 mL: 2 mL) was added 1N HCl in ether (460 mL, 0.46 mmol). After swirling for 5 min the solvent was removed under reduced pressure. The crude material was recrystallized from hot EtOAc to give 121 mg (79%) of the title compound as a beige sandy solid. Mp: >280° C. $^1$H NMR (DMSO-d$_6$; 400 MHz): δ 1.43–1.60 (m, 5), 1.79 (br s, 6), 1.92 (m, 3), 2.10 (br d, 2, J=10.9), 2.65 (s, 3), 3.01 (m, 1), 4.16 (br s, 4), 6.38 (s, 1), 11.90 (s, 1), 14.28 (s, 1). MS m/z: 299 (M+1). Anal. Calcd for $C_{18}H_{26}N_4$·HCl·0.1H$_2$O: C, 64.21; H, 8.14; N, 16.64; Cl, 10.53. Found C, 64.02; H, 8.09; N, 16.55; Cl, 10.87.

EXAMPLE 81

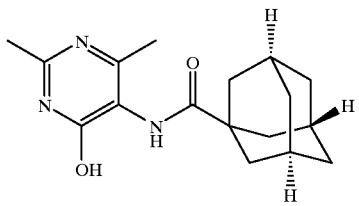

(a) 5-Adamantanyl-2,6-dimethyl-4-hydroxypyrimidine.

To a slurry of 5-amino-2,6-dimethyl-4-hydroxy pyrimidine hydrochloride (Example 12(a)) (0.94 g, 5.85 mmol) in CH$_2$Cl$_2$ (20 mL) was added NEt$_3$ (Aldrich Chemical Company) (1.7 mL, 12.3 mmol). The slurry was stirred at 25° C. under a nitrogen atmosphere for 2–3 min at which time all material went into solution. To this clear solution was added 1-adamantane carbonyl chloride (Aldrich Chemical Company) (1.5 g, 7.6 mmol) and DMAP (Aldrich Chemical Company) (100 mg, catalytic). This mixture was stirred at 25° C. for 18 h. The precipitate was collected by filtration, washed with CH$_2$Cl$_2$ (3×15 mL) and dried under vacuum to provide 1.15 g (65%) of the title compound as a white solid. $^1$H NMR (DMSO-d$_6$; 400 MHz): δ 1.73 (br s, 6), 1.92 (s, 6), 2.01 (s, 3), 2.03 (br s, 1), 2.27 (s, 3), 8.43 (s, 1), 12.47 (s, 1). MS m/z 302 (M+1).

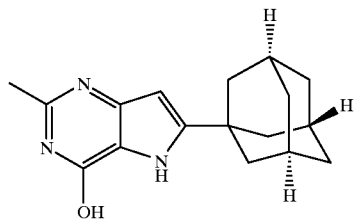

(b) 6-Adamantanyl-2-methylpyrrolo[3,2-d]pyrimidine-4-ol.

Using the method described in Example 1(d) (Method B) by employing 5-adamantanyl-2,6-dimethyl-4-hydroxypyrimidine (Example 81(a)) (0.82 g, 2.70 mmol) and Na (Aldrich Chemical Company) (0.25 g, 10.8 mmol). Following the work-up described in Example 1(d) the residue was purified by flash chromatography on silica gel with 97:3 CHCl$_3$:MeOH as elutant to give 120 mg (16%) of the title compound as a beige solid. $^1$H NMR (DMSO-d$_6$; 400 MHz): δ 1.72 (s, 6), 1.94 (s, 6), 2.02 (s, 3), 2.27 (s, 3), 5.95 (d, 1, J=2.1), 11.56 (s, 1), 11.62 (s, 1). MS m/z: 284 (M+1).

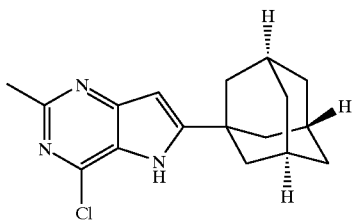

(c) 6-Adamantanyl-4-chloro-2-methylpyrrolo[3,2-d]pyrimidine.

Using the method described for Example 45(c) by employing 6-adamantanyl-2-methylpyrrolo[3,2-d]pyrimidine-4-ol (Example 81(b)) (0.10 g, 0.35 mmol) and POCl$_3$ (Aldrich Chemical Company) (10 mL). Following the work-up described in Example 45(c) the residue was purified by flash chromatography on silica gel with 98:2 CHCl$_3$:MeOH as elutant to give 67 mg (61%) of the title compound as a brown solid. $^1$H NMR (DMSO-d$_6$; 400 MHz): δ 1.76 (s, 6), 2.02 (s, 6), 2.08 (s, 3), 2.57 (s, 3), 6.31 (d, 1, J=1.8), 11.74 (s, 1). MS m/z: 302 (M+1).

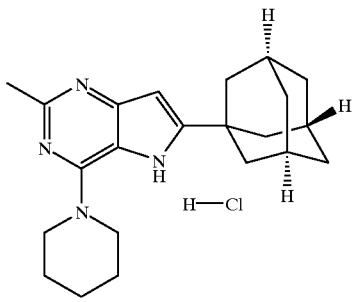

(d) 6-Adamantanyl-2-3ethyl-4-piperidylpyrrolo[3,2-d]pyrimidine Hydrochloride Monohydrate.

Using the method described for Example 45(d) by employing 6-adamantanyl-4-chloro-2-methylpyrrolo[3,2-d]pyrimidine (Example 81(c)) (65.0 mg, 0.22 mmol), piperidine (Aldrich Chemical Company) (110 mL, 1.08 mmol) and K$_2$CO$_3$ (Aldrich Chemical Company) (0.12 g, 0.90 mmol). Flash chromatography of the crude product on silica gel with 98:2 CHCl$_3$:MeOH as elutant gave 41 mg (53%) of the free base as a white solid. $^1$H NMR (DMSO-d$_6$; 400 MHz): δ 1.63 (s, 6), 1.76 (s, 6), 2.00 (s, 6), 2.06 (s, 3), 2.39 (s, 3), 3.62 (s, 4), 6.04 (s, 1), 10.17 (s, 1). MS m/z: 351 (M+1). To a solution of 6-adamantanyl-2-methyl-4-piperidylpyrrolo[3,2-d]pyrimidine (41.0 mg, 0.12 mmol) in EtOAc (10 mL) was added 1N HCl in ether (120 mL, 0.12 mmol). After swirling for 5 min the solvent was removed under reduced pressure to give 34 mg (74%) of the title compound as a beige solid. Mp: >280° C. $^1$H NMR (DMSO-d$_6$; 400 MHz): δ 1.49 (br s, 6), 1.60 (s, 6), 1.85 (s, 6), 1.90 (s, 3), 2.32 (s, 3), 3.80 (s, 4), 6.06 (s, 1), 10.83 (s, 1), 13.87 (s, 1). MS m/z: 351 (M+1). Anal. Calcd. for $C_{22}H_{30}N_4$·HCl·1.0H$_2$O: C, 65.24; H, 8.21; N, 13.84; Cl, 8.75. Found C, 65.06; H, 7.76; N, 13.69; Cl, 8.82.

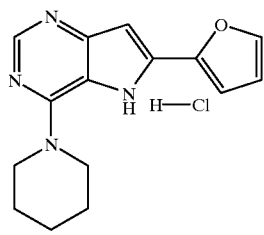

EXAMPLE 82

2-(4-Piperidylpyrrolo[4,5-d]pyrimidin-6-yl)furan Hydrochloride.

Using the method described in Example 30 by employing 2-(1-pyrrolidinylvinyl)furan (freshly prepared before use) (2.13 g, 13.1 mmol), 4,6-dichloro-5-nitropyrimidine (Aldrich Chemical Company) (2.51 g, 13.1 mmol), N,N-diisopropylethyl amine (Aldrich Chemical Company) (2.2 mL, 13.1 mmol), piperidine (Aldrich Chemical Company) (2.1 mL, 21.0 mmol), NEt$_3$ (Aldrich Chemical Company) (2.0 mL) and SnCl$_2$ (49 mL of a 2M solution in DMF). The residue was purified by flash chromatography on silica gel with 95:5 CHCl$_3$:MeOH as elutant to give 162 mg (5%) of the free base as a tan colored sandy solid. $^1$H NMR (DMSO-d$_6$; 400 MHz): δ 1.65 (br s, 6), 3.72 (br s, 4), 6.67 (br s, 2), 7.12 (s, 1), 7.83 (s, 1), 8.23 (s, 1), 11.27 (s, 1). MS m/z: 269 (M+1). To a solution of 2-(4-piperidylpyrrolo[4,5-d]pyrimidin-6-yl)furan (0.54 g, 1.81 mmol) in 5:1 EtOAc:MeOH (30 mL) was added 1M etheral HCl (Aldrich Chemical Company) (1.80 mL, 1.80 mmol). The precipitate was collected by filtration, washed with EtOAc (2×10 mL), ether (3×15 mL) and dried under vacuum to give 550 mg (92%) of the title compound as a beige colored solid. Mp: >280° C. $^1$H NMR (DMSO-D$_6$; 400 MHz): δ 1.71 (s, 6), 4.04 (br s, 4), 6.75 (dd, 1, J=3.1, 3.3), 6.83 (s, 1), 7.39 (s, 1), 7.96 (s, 1), 8.60 (s, 1), 12.27 (s, 1), 14.32 (s, 1). MS m/z: 269 (M+1). Anal. Calcd for C$_{15}$H$_{16}$N$_4$O.HCl: C, 59.11; H, 5.62; N, 18.38; Cl, 11.63. Found C, 58.84; H, 5.72; N, 18.16; Cl, 11.54.

EXAMPLE 83

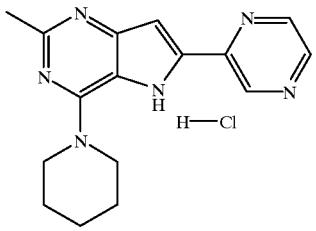

2-Methyl-4-piperidyl-6-pyrazin-2-ylpyrrolo[3,2-d]pyrimidine Hydrochloride Hydrate.

Using the method described in Example 30 by employing 2-(1-pyrrolidinylvinyl)pyrazine (freshly prepared before use) (2.15 g, 12.3 mmol), 2-methyl-4,6-dichloro-5-nitropyrimidine (Example 76(b)) (2.50 g, 12.3 mmol), N,N-diisopropylethyl amine (Aldrich Chemical Company) (2.1 mL, 12.3 mmol), piperidine (Aldrich Chemical Company) (1.9 mL, 19.7 mmol), NEt$_3$ (Aldrich Chemical Company) (2.0 mL) and SnCl$_2$ (37 mL of a 2M solution in DMF). The residue was purified by flash chromatography on silica gel with 95:5 CHCl$_3$:MeOH as elutant to give 116 mg (4%) of the free base as a brown colored solid. $^1$H NMR (DMSO-d$_6$; 400 MHz): δ 1.66 (br s, 6), 2.44 (s, 3), 3.30 (s, 2, under H$_2$O), 3.77 (br s, 2), 6.80–7.15 (m, 1), 8.91 (br s, 2), 9.33 (s, 1), 11.42 (s, 1). MS m/z: 295 (M+1). To a hot solution of 2-methyl-4-piperidyl-6-pyrazin-2-ylpyrrolo[3,2-d] pyrimidine (0.12 g, 0.39 mmol) in 10:1 EtOAc:MeOH (30 mL) was added 1N etheral HCl (Aldrich Chemical Company) (0.40 mL, 0.39 mmol). Cyrstallization occurred as the mixture cooled and the precipitate was collected by filtration, washed with Et$_2$O (3×10 mL), and dried under vacuum to give 68 mg (53%) of the title compound as a brown colored solid. Mp: 280–283.5° C. $^1$H NMR (DMSO-d$_6$; 400 MHz): δ 1.72 (s, 6), 2.59 (s, 3), 4.08 (br s, 4), 7.29 (s, 1), 8.74 (d, 1, J=2.4), 8.82 (br s, 1), 9.49 (s, 1), 12.41 (s, 1), 14.41 (s, 1). MS m/z: 295 (M+1 for free base). Anal. Calcd for C$_{16}$H$_{16}$N$_6$.HCl.1.4H$_2$O: C, 54.07; H, 5.64; N, 23.65; Cl, 10.19. Found C, 54.32; H, 5.69; N, 23.26; Cl, 10.18.

EXAMPLE 84

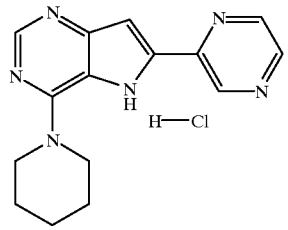

4-Piperidyl-6-pyrazin-2-ylpyrrolo[3,2-d]pyrimidine Hydrochloride Hydrate.

Using the method described in Example 30 by employing 2-(1-pyrrolidinylvinyl)pyrazine (freshly prepared before use) (2.39 g, 13.7 mmol), 4,6-dichloro-5-nitropyrimidine (Aldrich Chemical Company) (2.60 g, 13.7 mmol), N,N-diisopropylethyl amine (Aldrich Chemical Company) (2.4 mL, 13.7 mmol), piperidine (Aldrich Chemical Company) (2.2 mL, 21.9 mmol), NEt$_3$ (Aldrich Chemical Company) (2.0 mL) and SnCl$_2$ (41 mL of a 2M solution in DMF). The residue was purified by flash chromatography on silica gel with 95:5 CHCl$_3$:MeOH as elutant to give 143 mg (4%) of the free base as a beige colored solid. $^1$H NMR (DMSO-d$_6$; 400 MHz): δ 1.67 (br s, 6), 3.77 (s, 4), 7.28 (s, 1), 8.28 (s, 1), 8.63 (s, 1), 8.74 (s, 1), 9.36 (s, 1), 11.48 (s, 1). MS m/z: 281 (M+1). To a hot solution of 4-piperidyl-6-pyrazin-2-ylpyrrolo[3,2-d]pyrimidine (0.14 g, 0.51 mmol) in 10:1 EtOAc: MeOH (40 mL) was added 1M etheral HCl (Aldrich Chemical Company) (0.51 mL, 0.51 mmol). Cyrstallization occurred as the mixture cooled and the precipitate was collected by filtration. The crystals were washed with Et$_2$O (3×10 mL) and dried under vacuum to give 128 mg (80%) of the title compound as a beige colored solid. Mp: >280° C. $^1$H NMR (DMSO-d$_6$; 400 MHz): δ 1.73 (s, 6), 4.10 (s, 4), 7.37 (s, 1), 8.66 (s, 1), 8.75 (d, 1, J=2.5), 8.83 (t, 1, J=1.5), 9.49 (d, 1, J=1.2), 12.53 (s, 1), 14.56 (s, 1). MS m/z: 281 (M+1). Anal. Calcd for C$_{15}$H$_{16}$N$_6$.HCl.0.25H$_2$O: C, 56.00; H, 5.49; N, 26.13; Cl, 11.10. Found C, 56.00; H, 5.49; N, 26.11; Cl, 11.09.

EXAMPLE 85

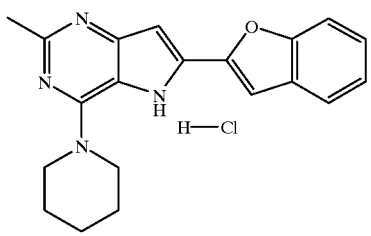

2-(2-Methyl-4-piperidylpyrrolo[4,5-d]pyrimidin-6-yl)benzo[b]furan Hydrochloride Monohydrate.

Using the method described in Example 30 by employing 2-(1-pyrrolidinylvinyl)benzo[b]furan (freshly prepared before use) (2.21 g, 10.4 mmol), 2-methyl-4,6-dichloro-5-nitropyrimidine (Example 76(b)) (2.10 g, 10.4 mmol), N,N-diisopropylethyl amine (Aldrich Chemical Company) (1.8 mL, 10.4 mmol), piperidine (Aldrich Chemical Company) (1.6 mL, 16.6 mmol), NEt$_3$ (Aldrich Chemical Company) (2.0 mL) and SnCl$_2$ (31 mL of a 2M solution in DMF). The residue was purified by flash chromatography on silica gel with 95:5 CHCL$_3$:MeOH as elutant to give 560 mg (16%) of the free base as a beige colored solid. $^1$H NMR (DMSO-d$_6$; 400 MHz): δ 1.67 (s, 6), 2.44 (s, 3), 3.30 (s, 2, under H$_2$0), 3.74 (s, 2), 6.83 (m, 1), 7.28 (br s, 3), 8.77 (br s, 2), 11.36 (s, 1). MS m/z: 333 (M+1). To a hot solution of 2-(2-methyl-4-piperidylpyrrolo[4,5-d]pyrimidin-6-yl)benzo[b]furan (Example 85(a)) (0.56 g, 1.69 mmol) in 5:1 EtOAc: MeOH (30 mL) was added 1M etheral HCl (Aldrich Chemical Company) (1.70 mL, 1.69 mmol). Upon cooling crystalliztion occurred and the solid was collected by filtration. This material was washed with Et$_2$O (2×10 mL) and dried under vacuum to give 588 mg (95%) of the title compound as a beige colored solid. Mp: >280° C. $^1$H NMR (DMSO-d$_6$; 400 MHz) δ 1.73 (s, 6), 2.58 (s, 3), 4.08 (s, 4), 7.00 (s, 1), 7.35 (t, 1, J=7.5), 7.44 (t, 1, J=8.0), 7.71 (d, 1, J=8.2), 7.79 (d, 1, J=7.7), 7.88 (s, 1), 12.48 (s, 1), 14.40 (s, 1). MS m/z: 333 (M+1). Anal. Calcd for C$_{20}$H$_{20}$N$_4$O.HCl.H$_2$O: C, 62.25; H, 5.71; N, 14.52; Cl, 9.19. Found C, 62.22; H, 5.94; N, 14.54; Cl, 9.22.

EXAMPLE 86

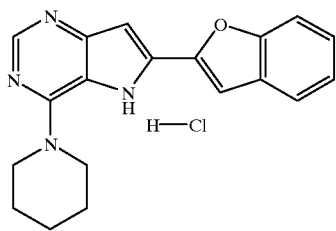

2-(4-Piperidylpyrrolo[4,5-d]pyrimidin-6-yl)benzo[b]furan Hydrochloride Hydrate.

Using the method described in Example 30 by employing 2-(1-pyrrolidinylvinyl) benzo[b]furan (freshly prepared before use) (2.29 g, 10.7 mmol), 4,6-dichloro-5-nitropyrimidine (Aldrich Chemical Company) (2.10 g, 10.7 mmol), N,N-diisopropylethyl amine (Aldrich Chemical Company) (1.9 mL, 10.7 mmol), piperidine (Aldrich Chemical Company) (1.7 mL, 17.1 mmol), NEt$_3$ (Aldrich Chemical Company) (2.0 mL) and SnCl$_2$ (32 mL of a 2M solution in DMF). The residue was purified by flash chromatography on silica gel with 95:5 CHCl$_3$:MeOH as elutant to give 612 mg (18%) of the free base as a tan colored solid. $^1$H NMR (DMSO-d$_6$; 400 MHz): δ 1.68 (s, 6), 3.77 (s, 4), 6.94 (s, 1), 7.32 (d, 2, J=18.9), 7.68 (t, 3, J=26.3), 8.28 (s, 1), 11.54 (s, 1). MS m/z: 319 (M+1). To a hot solution of 2-(4-piperidylpyrrolo[4,5-d]pyrimidin-6-yl)benzo[b]furan (0.61 g, 1.92 mmol) in 3:1 EtOAc: MeOH (50 mL) was added 1M etheral HCl (Aldrich Chemical Company) (1.90 mL, 1.92 mmol). Upon cooling crystalliztion occurred and the solid was collected by filtration. Thsi material was washed with Et$_2$O (2×10 mL) and dried under vacuum to give 612 mg (90%) of the title compound as a brown colored solid. Mp: 278.5–281° C. $^1$H NMR (DMSO-d$_6$; 400 MHz): δ 1.74 (s, 6), 4.10 (s, 4), 7.09 (s, 1), 7.36 (t, 1, J=7.5), 7.45 (t, 1, J=7.9), 7.72 (d, 1, J=8.3), 7.80 (d, 1, J=7.7), 7.93 (s, 1), 8.64 (s, 1), 12.76 (s, 1), 14.66 (s, 1). MS M/z : 319 (M+1). Anal. Calcd for C$_{19}$H$_{18}$N$_4$O.HCl.0.5H$_2$O: C, 62.80; H, 5.41; N, 15.42; Cl, 9.76. Found C, 62.89; H, 5.46; N, 15.36; Cl, 9.89.

EXAMPLE 87

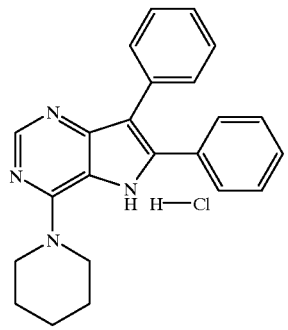

6,7-Diphenyl-4-piperidylpyrrolo[3,2-d]pyrimidine Hydrochloride Hydrate.

Using the method described in Example 30 by employing (1,2-diphenylvinyl)pyrrolidine (freshly prepared before use) (1.85 g, 7.43 mmol), 4,6-dichloro-5-nitropyrimidine (Aldrich Chemical Company) (1.40 g, 7.43 mmol), N,N-diisopropylethyl amine (Aldrich Chemical Company) (1.3 mL, 7.43 mmol), piperidine (1.2 mL, 11.9 mmol), NEt$_3$ (Aldrich Chemical Company) (2.0 mL) and SnCl$_2$ (Aldrich Chemical Company) (22 mL of a 2M solution in DMF). The residue was purified by flash chromatography on silica gel with 95:5 CHCl$_3$:MeOH as elutant to give 258 mg (10%) of the free base as a brown colored sandy solid. $^1$H NMR (DMSO-d$_6$; 400 MHz): δ 1.66 (br s, 6), 3.75 (br s, 4), 7.19 (t, 1, J=7.3), 7.29 (t, 2, J=7.7), 7.42–7.47 (m, 7), 8.30 (s, 1), 11.38 (s, 1). MS m/z: 355 (M+1). To a solution of 6,7-diphenyl-4-piperidylpyrrolo[3,2-d]pyrimidine (0.26 g, 0.73 mmol) in 4:1 EtOAc: MeOH (30 mL) was added 1M etheral HCl (Aldrich Chemical Company) (730 mL, 0.73 mmol). The precipitate was collected by filtration, washed with ether (3×15 mL) and dried under vacuum to give 258 mg (91%) of the title compound as a beige colored solid. Mp: 266–268.5° C. $^1$H NMR (DMSO-d$_6$; 400 MHz): δ 1.73 (br s, 6), 4.09 (br s, 4), 7.29 (d, 2, J=6.7), 7.37–7.44 (m, 8), 8.50 (s, 1), 12.42 (s, 1), 14.15 (s, 1). MS m/z: 355 (M+1). Anal. Calcd for C$_{23}$H$_{22}$N$_4$.HCl.0.25H$_2$O: C, 69.92; H, 5.99; N, 14.18; Cl, 8.97. Found C, 69.92; H, 6.01; N, 13.86; Cl, 9.37.

EXAMPLE 88

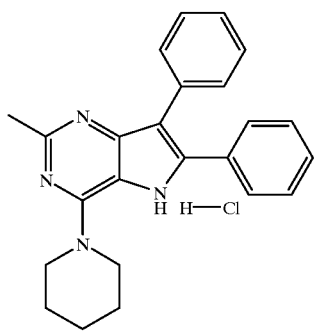

2-Methyl-6,7-diphenyl-4-piperidylpyrrolo[3,2-d]pyrimidine Hydrochloride Hydrate.

Using the method described in Example 30 by employing (1,2-diphenylvinyl)pyrrolidine (freshly prepared before use) (1.83 g, 7.35 mmol), 2-methyl-4,6-dichloro-5-nitropyrimidine (Example 76(b)) (1.50 g, 7.35 mmol), N,N-diisopropylethyl amine (Aldrich Chemical Company) (1.3 mL, 7.35 mmol), piperidine (1.2 mL, 11.8 mmol), NEt$_3$ (Aldrich Chemical Company) (2.0 mL) and SnCl$_2$ (Aldrich Chemical Company) (22 mL of a 2M solution in DMF). The residue was purified by flash chromatography on silica gel with 95:5 CHCl$_3$:MeOH as elutant to give 110 mg (4%) of the free base as a pale yellow colored solid. H NMR (DMSO-d$_6$; 400 MHz): δ 1.65 (br s, 6), 2.42 (s, 3), 3.72 (br s, 4), 7.19 (m, 1), 7.28 (m, 2), 7.39–7.44 (m, 7), 11.20 (s, 1). MS m/z: 369 (M+1). To a solution of 2-methyl-6,7-diphenyl-4-piperidylpyrrolo[3,2-d]pyrimidine (148 g, 0.40 mmol) in 1:1 EtOAc: MeOH (50 mL) was added 1M etheral HCl (Aldrich Chemical Company) (400 mL, 0.40 mmol). The solvent was removed under reduced pressure and then dried under vacuum to give 83 mg (51%) of the title compound as a beige colored solid. Mp: 169–171° C. $^1$H NMR (DMSO-d$_6$; 400 MHz): δ 1.72 (br s, 6), 2.56 (s, 3), 4.06 (br s, 4), 7.29 (dd, 2, J=1.7, 6.0), 7.37–7.45 (m, 8), 12.26 (s, 1), 13.40 (s, 1). MS m/z: 369 (M+1). Anal. Calcd. for C$_{24}$H$_{24}$N$_4$.HCl.H$_2$O: C, 68.25; H, 6.40; N, 13.27; Cl, 8.29. Found C, 68.33; H, 6.41; N, 13.15; Cl, 8.50.

EXAMPLE 89

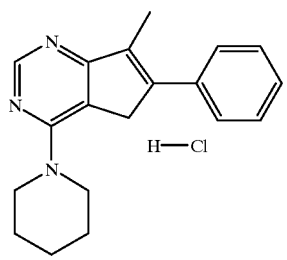

7-Methyl-6-phenyl-4-piperidylpyrrolo[3,2-d]pyrimidine Hydrochloride.

Using the method described in Example 30 by employing (1-phenylbut-1-enyl)pyrrolidine (freshly prepared before use) (2.10 g, 11.3 mmol), 4,6-dichloro-5-nitropyrimidine (Aldrich Chemical Company) (2.18 g, 11.3 mmol), N,N-diisopropylethyl amine (Aldrich Chemical Company) (2.0 mL, 11.3 mmol), piperidine (1.8 mL, 18.1 mmol), NEt$_3$ (Aldrich Chemical Company) (2.0 mL) and SnCl$_2$ (Aldrich Chemical Company) (34 mL of a 2M solution in DMF). The residue was purified by flash chromatography on silica gel with 95:5 CHCl$_3$:MeOH as elutant to give 407 mg (12%) of the product as a faint yellow colored solid. $^1$H NMR (DMSO-d$_6$; 400 MHz): δ 1.64 (br s, 6), 2.30 (s, 3), 3.72 (br s, 4), 7.44 (t, 1, J=7.3), 7.53 (t, 2, J=7.53), 7.66 (d, 2, J=7.3), 8.29 (s, 1), 10.95 (s, 1). MS m/z: 293 (M+1). To a solution of 7-methyl-6-phenyl- 4-piperidylpyrrolo[3,2-d]pyrimidine (0.22 g, 0.76 mmol) in 5:1 EtOAc: MeOH (30 mL) was added 1M etheral HCl (Aldrich Chemical Company) (760 mL, 0.73 mmol). The precipitate was collected by filtration, washed with ether (3×15 mL) and dried under vacuum to give 224 mg (90%) of the title compound as a white colored solid. Mp: 281–282.5° C. $^1$H NMR (DMSO-d$_6$; 400 MHz): δ 1.71 (br s, 6), 2.32 (s, 3), 4.04 (br s, 4), 7.52–7.61 (m, 3), 7.68 (d, 2, J=7.1), 8.56 (s, 1), 12.05 (s, 1), 14.67 (s, 1). MS m/z: 293 (M+1). Anal. Calcd. for C$_{24}$H$_{24}$N$_4$.HCl: C, 65.74; H, 6.44; N, 17.04; Cl, 10.78. Found C, 65.64; H, 6.51; N, 17.04; Cl, 10.71.

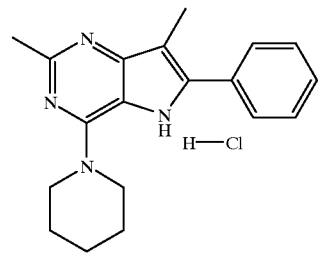

EXAMPLE 90

2,7-Dimethyl-6-phenyl-4-piperidylpyrrolo[3,2-d] pyrimidine Hydrochloride Monohydrate.

Using the method described in Example 30 by employing (1-phenylbut-1-enyl) pyrrolidine (freshly prepared before use) (2.13 g, 11.5 mmol), 4,6-dichloro-5-nitropyrimidine (Aldrich Chemical Company) (2.30 g, 11.5 mmol), N,N-diisopropylethyl amine (Aldrich Chemical Company) (2.0 mL, 11.5 mmol), piperidine (1.8 mL, 18.4 mmol), NEt$_3$ (Aldrich Chemical Company) (2.0 mL) and SnCl$_2$ (Aldrich Chemical Company) (35 mL of a 2M solution in DMF). The residue was purified by flash chromatography on silica gel with 95:5 CHCl$_3$:MeOH as elutant to give 304 mg (9%) of the free base as a beige colored fluffy solid. $^1$H NMR (DMSO-d$_6$; 400 MHz): δ 1.63 (br s, 6), 2.27 (s, 3), 2.44 (s, 3), 3.71 (br s, 4), 7.43 (t, 1, J=7.3), 7.52 (t, 2, J=7.6), 7.65 (d, 2, J=7.4), 10.79 (s, 1). MS m/z: 307 (M+1). To a solution of 2,7-dimethyl-6-phenyl-4-piperidylpyrrolo[3,2-d] pyrimidine (0.22 g, 0.76 mmol) in 5:1 EtOAc: MeOH (30 mL) was added 1M etheral HCl (Aldrich Chemical Company) (760 mL, 0.73 mmol). The precipitate was collected by filtration, washed with ether (3×15 mL) and dried under vacuum to give 224 mg (90%) of the title compound as a white colored solid. Mp: >280° C. $^1$H NMR (DMSO-d$_6$; 400 MHz): δ 1.69 (br s, 6), 2.35 (s, 3), 2.64 (s, 3), 4.03 (br s, 4), 7.52–7.60 (m, 3), 7.65–7.68 (m, 2), 11.94 (s, 1), 14.16 (s, 1). MS m/z: 307 (M+1). Anal. Calcd. for C$_{24}$H$_{24}$N$_4$.1.1HCl.H$_2$O: C, 62.74; H, 6.95; N, 15.41; Cl, 10.50. Found C, 63.09; H, 7.00; N, 15.39; Cl, 10.54.

EXAMPLE 91

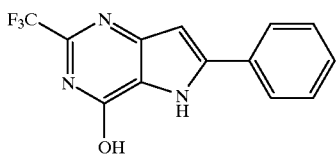

(a) 6-Phenyl-2-(trifluoromethyl)pyrrolo[3,2-d]pyrimidine-4-ol.

The mixture of ethyl 3-amino-5-phenylpyrrole-2-carboxylate (Example 66(b)) (2.3 g, 10 mmol) and trifluoromethylacetamidine (Aldrich Chemical Company) (1.457 g, 13 mmol) in 20 mL of o-xylene was heated under reflux for 15 h. The solvent was evaporated under reduced pressure to give a dark-red residue, and toluene was added. The precipitate that formed was collected by filtration, and dried in a vacuum oven overnight to give 1.847 g (66%) of the title compound as a tan solid. $^1$H NMR (DMSO-$d_6$; 500 MHz): δ 7.06 (s, 1), 7.38–7.49 (m, 3), 7.98 (d, 2, J=7.39), 12.74 (br s, 1); MS m/z: 280 (M+1), 278 (M−1).

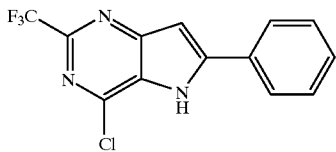

(b) 4-Chloro-6-phenyl-2-(trifluoromethyl)pyrrolo[3,2-d]pyrimidine.

A mixture of 6-phenyl-2-(trifluoromethyl)pyrrolo[3,2-d]pyrimidine-4-ol (Example 91(a)) (1.847 g, 6.62 mmol) and phosphoryl oxychloride (Aldrich Chemical Company) (15 mL, 166 mmol) was heated at 120° C. for 36 h. POCl$_3$ was removed under reduced pressure, and to the residue was added ice-water followed by ammonia water to pH 8. The resulting mixture was extracted three times with EtOAc. The combined organic layers were washed with brine, dried over Na$_2$SO$_4$, concentrated in vacuo, and dried in a vacuum oven overnight to give 1.249 g (63%) of the title compound as a brown solid. $^1$H NMR (CDCl$_3$; 500 MHz): δ 7.13 (s, 1), 7.51–7.58 (m, 3), 7.79 (d, 2, J=7.48), 9.15 (br s, 1). MS m/z: 298, 300 (M+1); 296, 298 (M−1).

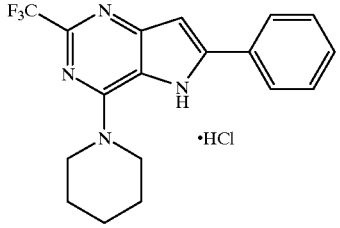

(c) 6-Phenyl-4-piperidyl-2-(trifluoromethyl)pyrrolo[3,2-d]pyrimidine Hydrochloride Monohydrate.

To a 25-mL, round-bottomed flask were added 4-chloro-6-phenyl-2-(trifluoromethyl)pyrrolo[3,2-d]pyrimidine (Example 91(b)) (0.4 g, 1.34 mmol) and piperidine (Aldrich Chemical Company) (0.66 mL, 6.72 mmol), followed by addition of a solution of potassium carbonate (1.85 g, 13.4 mmol) in 8 mL of water. The reaction mixture was stirred at 120° C. for 15 h. After cooling to room temperature, the precipitate formed was collected by filtration, washed with water and hexane to give a tan solid. The material was purified by flash chromatography on silica gel with 1:4 of EtOAc:hexane as eluent to give 0.361 g (78%) of a light-pink solid. This material (355 mg, 1.03 mmol) was dissolved in minimum amount of CHCl$_3$, and ethereal hydrogen chloride (1N, 1.1 mL, 1.1 mmol) was added dropwise. The mixture was stirred at room temperature for 20 min. Solvent was then evaporated in vacuo to give a foam, which was recrystallized from MeOH/H$_2$O to give 104 mg of the title compound as light-pink crystals. Mp: 235.1–237.5° C. (dec). $^1$H NMR (DMSO-$d_6$; 500 MHz): δ 1.68 (m, 6), 3.84–3.85 (m, 4), 7.02 (s, 1), 7.44–7.55 (m, 3), 7.93 (d, 2, J=7.68), 11.53 (br s, 1). MS m/z: 347 (M+1), 345 (M−1). Anal. Calcd for C$_{18}$H$_{18}$ClF$_3$N$_4$.H$_2$O: C, 53.94; H, 5.03; N, 13.98; Cl, 8.84. Found: C, 54.03; H, 5.02; N, 13.83, Cl, 8.98.

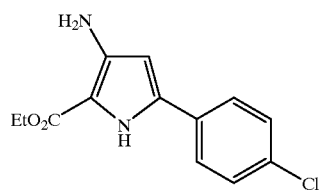

EXAMPLE 92

(a) Ethyl 3-amino-5-(4-chlorophenyl)pyrrole-2-carboxylate.

Sodium ethoxide was prepared freshly from Na (2.09 g, 91 mmol) and EtOH (25 mL). To this solution was added a solution of 3-chloro-3-(4-chlorophenyl)acrylonitrile (Maybridge Chemical Company) (6.00 g, 30.3 mmol), and aminodiethyl malonate hydrochloride (Aldrich Chemical Company) (6.41 g, 30.3 mmol) in EtOH (55 mL) through a dropping funnel. After the addition was completed, the reaction mixture was stirred at room temperature for 21 h. The solvent was evaporated in vacuo and the residue was partitioned between EtOAc and H$_2$O. The organic layer was separated, dried over Na$_2$SO$_4$ and concentrated in vacuo to give 4.266 g of a dark-red solid. It was used in the following step without purification.

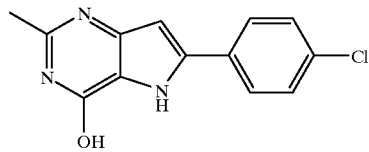

(b) 6-(4-Chlorophenyl)-2-methylpyrrolo[3,2-d]pyrimidin-4-ol.

Dry HCl gas was bubbled through a solution of ethyl 3-amino-5-(4-chlorophenyl)pyrrole-2-carboxylate (Example 92(a)) (3.78 g) in 90 mL of acetonitrile at room temperature for 1.5 h. The reaction mixture was then capped, and stirred at room temperature overnight. The solvent was evaporated in vacuo to give a brown residue, which was dissolved in 50 mL of EtOH and 25 mL of 6% aqueous sodium hydroxide. The reaction mixture was heated at reflux for 6 h. The that precipitate formed was filtered, and dried in a vacuum oven to give 0.657 g of the title compound as a brown solid. The filtrate was concentrated down and the resulting viscous solid was separated. Toluene was added and the solution evaportated in vacuo. CH$_2$Cl$_2$ was added to the residue. The precipitate formed was filtered, washed with water, and dried in a vacuum oven to give 0.693 g (total yield 19%) of the title compound as a tan solid. $^1$H NMR (DMSO-d$_6$; 500 MHz) δ 2.31 (s, 3), 6.79 (s, 1), 7.49 (d, 2, J=8.42), 7.95 (d, 2, J=8.58), 11.79 (br s, 1), 12.32 (br s, 1).

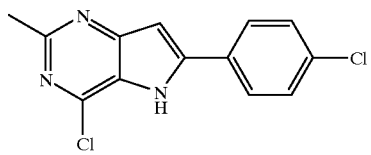

(c) 4-Chloro-6-(4-chlorophenyl)-2-methylpyrrolo[3,2-d] pyrimidine.

A mixture of 6-(4-chlorophenyl)-2-methylpyrrolo[3,2-d] pyrimidin-4-ol (Example 92(b)) (1.35 g, 5.2 mmol) and phosphorus oxychloride (Aldrich Chemical Company) (12 mL, 130 mmol) was heated at 120° C. for 24 h. The excess POCl$_3$ was removed under reduced pressure to give a dark-brown residue. The residue was diluted with ice-water and neutralized under stirring and cooling with ammonia water to pH 8. The resulting mixture was extracted three times with EtOAc. The combined organic layers were washed with brine, dried over Na$_2$SO$_4$ and concentrated in vacuo to give 0.654 g (45%) of the title compound as a brown solid. $^1$H NMR (DMSO-d$_6$; 500 MHz): δ 2.78 (s, 3), 6.90 (s, 1), 7.49 (d, 2, J=7.5), 7.69 (d, 2, J=7.22), 8.91 (br s, 1); MS m/z: 278, 280 (M+1); 276, 278 (M−1).

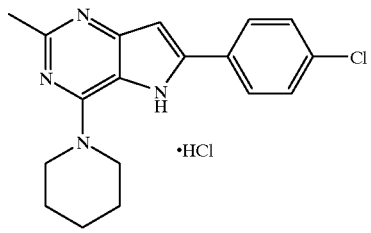

(d) 6-(4-Chlorophenyl)-2-methyl-4-piperidylpyrrolo[3,2-d] pyrimidine Hydrochloride.

To a 25-mL, round-bottomed flask were added 4-chloro-6-(4-chlorophenyl)-2-methylpyrrolo[3,2-d]pyrimidine (Example 92(c)) (0.3 g, 1.08 mmol) and piperidine (Aldrich Chemical Company) (0.53 mL, 5.4 mmol), followed by addition of a solution of potassium carbonate (1.49 g, 10.8 mmol) in 10 mL of water. The reaction mixture was stirred at 120° C. for 4 h. After cooling to room temperature, the precipitate that formed was collected by filtration, washed with water and hexane, and dried in a vacuum oven to give 0.355 g of a brown solid. This material (346 mg, 1.06 mmol) was dissolved in minimum amount of CHCl$_3$, ethereal hydrogen chloride (1N, 1.1 mL, 1.1 mmol) was added dropwise. The mixture was stirred at room temperature for 20 min. The solvent was then evaporated in vacuo to give a foam, which was recrystallized from MeOH/H$_2$O to give 138 mg of the title compound as tan crystals. Mp: 253.8–255.2 (dec). $^1$H NMR (DMSO-d$_6$; 500 MHz): δ 1.70–1.71 (m, 6), 2.57 (s, 3), 4.06–4.07 (m, 4), 6.94 (s, 1), 7.63 (d, 2, J=8.60), 8.01 (d, 2, J=8.6), 12.0 (br s, 1), 14.3 (br s, 1); MS m/z: 327, 329 (M+1), 325, 327 (M−1). Calcd for C$_{18}$H$_{20}$Cl$_2$N$_4$.H$_2$O: C, 56.70; H, 5.82; N, 14.69; Cl, 18.60. Found: C, 56.45; H, 5.79; N, 14.60, Cl, 18.42.

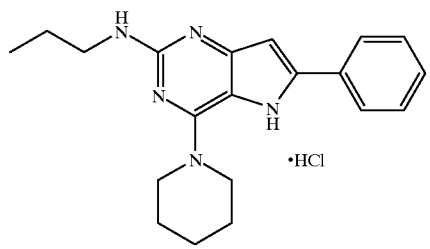

EXAMPLE 93

(6-Phenyl-4-piperidylpyrrolo[3,2-d]pyrimidine-2-yl) propylamine Hydrochloride.

To a solution of 6-phenyl-4-piperidylpyrrolo[3,2-d] pyrimidine-2-ylamine (Example 66(e)) (100 mg, 0.34 mmol) in MeOH (3.5 mL) in a 25-mL round-bottomed flask were added propionaldehyde (0.074 mL, 1.02 mmol) and sodium cyanoborohydride (Aldrich Chemical Company) (43 mg, 0.68 mmol). The pH of the reaction was adjusted to 6 by the addition of methanolic hydrogen chlroide. The reaction was heated at reflux for 40 h. The pH was lowered to 4 by addition of 10% HCl and the reaction was stirred for 1 h. The pH was raised to 10 by addition of saturated Na$_2$CO$_3$. The solvent was removed in vacuo and the residue was dissolved in water and extracted with CH$_2$Cl$_2$ three times. The combined organic layers were dried over Na$_2$SO$_4$, concentrated in vacuo to give an orange oil. The residue was purified by preparative TLC using 95:5 CHCl$_3$:MeOH as eluent to give 32 mg (28%) of a light-yellow solid. The above material was dissolved in CHCl$_3$ (2 mL). Ethereal hydrogen chloride (1N, 0.25 mL, 0.25 mmol) was added. The mixture was stirred at room temperature for 20 min. Solvent was evaporated to give 33 mg of the title compound as a light-yellow solid. $^1$H NMR (DMSO-d$_6$; 500 MHz): δ 0.93 (t, 3, J=7.22), 1.58–1.62 (m, 2), 1.68 (m, 6), 3.25 (m, 2), 3.96 (m, 4), 6.66 (s, 1), 7.45–7.54 (m, 3), 7.68 (br s, 1), 7.86 (d, 2, J=7.32), 11.54 (br s, 1), 12.23 (br s, 1). MS m/z: 336 (M+1), 334 (M−1). Anal. Calcd for C$_{20}$H$_{25}$N$_5$.HCl.0.5H$_2$O: C, 63.06; H, 7.14; N, 18.39. Found: C, 63.06; H, 6.93; N, 18.29.

EXAMPLE 94

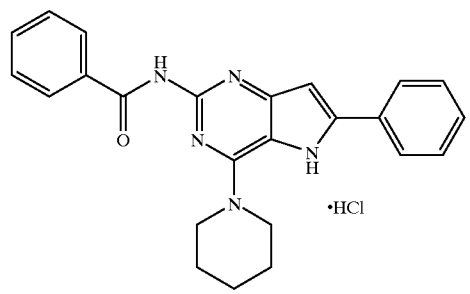

Phenyl-N-(6-phenyl-4-piperidylpyrrolo[3,2-d]pyrimidine-2-yl)formamide Hydrochloride Hydrate.

To a mixture of 6-phenyl-4-piperidylpyrrolo[3,2-d] pyrimidine-2-ylamine (Example (66(e)) (100 mg, 0.34 mmol) in pyridine (7 mL) in a 25-mL round-bottomed flask was added benzoic anhydride (81 mg, 0.36 mmol). The reaction was heated at reflux for 15 h. The solvent was removed in vacuo and 0.1 M NaOH (10 mL) was added to the residue. The precipitate that formed was filtered, washed with water, dired in a vacuum oven overnight to give 156 mg of an orange solid. The above material was dissolved in CHCl₃ (10 mL). Ethereal hydrogen chloride (1N, 0.35 mL, 0.35 mmol) was added. The mixture was stirred at room temperature for 20 min. The solvent was evaporated to give a foam, which was recrystallized from MeOH/H₂O to give 30 mg of the title compound as orange crystals. ¹H NMR (DMSO-d₆; 500 MHz): δ 1.74 (m, 6), 4.09 (m, 4), 7.07 (s, 1), 7.50–7.74 (m, 6), 7.89 (d, 2, J=7.63), 8.08 (d, 2, J=7.67), 11.85 (br s, 1), 11.94 (br s, 1), 13.61 (br s, 1). MS m/z: 398 (M+1), 396 (M−1). Anal. Calcd for C₂₄H₂₄ClN₄O.2.2H₂O: C, 60.88; H, 6.04; N, 14.80; Cl, 7.49. Found: C, 60.88; H, 5.77; N, 14.63, Cl, 7.38.

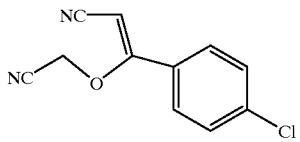

EXAMPLE 95

(a) 3-(4-Chlorophenyl)-3-(cyanomethoxy)-prop-2-ene nitrile.

Glycolonitrile (Aldrich Chemical Company) (5.0 g, 43.8 mmol, 55 wt. % in H₂O) was dissolved in THF (20 mL) and MgSO₄ was added. The mixture was stirred for 10 min and filtered into a 250-mL round-bottomed flask. The solution was cooled to 0° C. and NaH (Aldrich Chemical Company) (1.75 g, 43.8 mmol, 60%) was added in portions over 15 min with stirring. After this addition, the mixture was stirred for another 30 min at 0° C. and 30 min at room temperature. A solution of 4-chlorophenyl-acrylonitrile (4.34 g, 21.9 mmol, Maybridge) in THF (10 ml) was added dropwise over 5 min. The resulting solution was stirred at RT overnight. The reaction was poured onto ice (100 g) and extracted with Et₂O (3×100 mL). The combined organic layers were washed with brine (200 mL) and dried over MgSO₄, filtered, and evaporated to give a crude oil. Chromatography on flash silica gel (100% Hexanes to 20% EtOAc/Hexanes) gave 750 mg (15.7%) of a yellow solid. Mp: 87–88° C. ¹H NMR (CDCl₃, 400 MHz): δ 5.06 (s, 2), 5.23 (s, 2), 7.44–7.50 (m, 4).

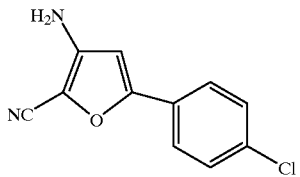

(b) 3-Amino-5-(4-chlorophenyl)-furan-2-carbonitrile.

The dinitrile (Example 95(a)) (500 mg, 2.29 mmol) was dissolved in THF (10 mL) and cooled to −78° C. with stirring under nitrogen. To this mixture was added a solution of NaOCH₃ (Aldrich Chemical Company) (0.53 mL, 2.30 mmol, 25 wt. %) dropwise over a 2 min. The reaction was stirred at −78° C. for 1 h, then allowed to warm to room temperature. At room temperature, the mixture was poured onto ice (50 g) and extracted with Et₂O (3×100 mL). The combined organic layers were washed with brine (200 mL) and dried over MgSO₄, filtered, and evaporated to give a crude oil. Chromatography on flash silica gel (33% EtOAc/Hexanes) gave 444 mg (89%) of a yellow solid. Mp: 147–148° C. ¹H NMR (CDCl₃, 400 MHz): δ 3.91 (s, 2), 6.34 (s, 1), 7.38 (d, 2, J=8.5), 7.58 (d, 2, J=8.5). The side product isolated in 10% yield resulted from the hydrolysis of the nitrile to give the methyl ester.

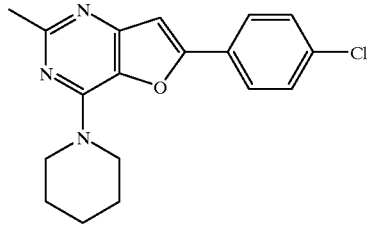

(c) 6-(4-Chlorophenyl)-2-methyl-4-piperidinylfurano-[3,2-d]-pyrimidine Hydrochloride Hydrate.

N,N-dimethylacetamide (Aldrich Chemical Company) (88 uL, 0.95 mmol) was added dropwise to POCl₃ (Aldrich Chemical Company) (10 mL) and stirred at room temperature under nitrogen for 1 h. To this solution was added the aminonitrile furan (Example 95(b)) (200 mg, 0.915 mmol), and the resulting solution was heated at reflux for 16 h. The reaction was allowed to cool to room temperature and the solvent was evaporated in vacuo to leave a residue. The residue was dissolved in piperidine (10 mL) and the mixture was heated at reflux for 16 h. The reaction was cooled to room temperature and taken up in EtOAc (150 mL). The organic layer was washed with saturated NaHCO₃ (3×100 mL), brine (100 mL) and dried over MgSO₄, filtered and evaporated at reduced pressure to give an oil. Chromatography on silica gel (50% EtOAc/Hexanes) gave 193 mg (64%) of a yellow solid. The furanyl pyrimidine (150 mg, 0.457 mmol) was dissolved in EtOAc (10 mL) and stirred rapidly as etheral HCl (0.46 mL, 0.46 mmol, 1.0 M) was added dropwise. The mixture immediately became cloudy. After 1 h, the product was filtered and dried in a vacuum oven at 60° C. to give 160 mg (97% yield). Mp: >288° C. ¹H NMR (CDCl₃, 400 MHz): δ 1.75 (br s,6), 2.59 (s, 3), 4.16 (br s, 4), 7.67 (br d, 3, J=6.4), 8.11 (br d, 2, J=7.1). MS m/z 328(M+1). Anal Calcd for C₁₈H₁₈ClN₃O.HCl.0.75H₂O: C, 57.24; H, 5.47; N, 11.13; Cl, 18.77. Found: C, 57.24; H, 5.41; N, 11.16; Cl, 18.65.

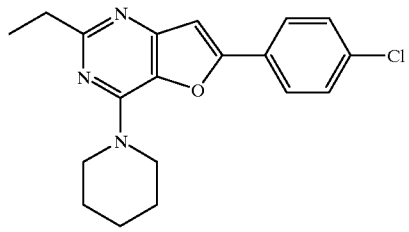

EXAMPLE 96

6-(4-Chlorophenyl)-2-ethyl-4-piperidinylfurano[3,2-d] pyrimidine.

N,N-Dimethylpropionamide (0.15 mL, 1.35 mmol) was added dropwise to POCl₃ (10 mL) and stirred at room temperature under nitrogen for 1 hour. To this solution was added the aminonitrile furan (Example 95(b)) (275 mg, 1.26 mmol), and the resulting solution was refluxed for 16 h. The reaction was allowed to cool to room temperature and the solvent was evaporated in vacuo to leave a residue. The residue was dissolved in piperidine (10 mL) and the mixture was heated at reflux for 16 h. The reaction was cooled to room temperature and taken up in EtOAc (150 mL). The organic layer was washed with saturated NaHCO₃ (3×100 mL), brine (100 mL) and dried over MgSO₄, filtered and evaporated at reduced pressure to give an oil. Chromatography on silica gel (25% EtOAc/Hexanes) gave 200 mg (47%) of a yellow solid. The furanylpyrimidine (150 mg, 0.432 mmol) was dissolved in EtOAc (10 mL) and stirred rapidly as etheral HCl (0.44 mL, 0.44 mmol, 1.0 M) was added dropwise, and the mixture immediately became cloudy. After 1 h, the product was filtered off and dried in a vacuum oven at 60° C. to give 160 mg (96% yield). Mp: >288° C. ¹H NMR (CDCl₃, 400 MHz): δ 1.31 (t, 3, J=7.52), 1.75 (6), 2.88 (q, J=7.5), 4.17 (s, 4), 7.52 (s, 1), 7.66 (d, 2, J=8.8), 8.11 (d, 2, J=8.5). MS m/z 342(M+1). Anal. Calcd for $C_{19}H_{21}Cl_2N_3O$: C, 60.32; H, 5.60; N, 11.11; Cl, 18.74. Found: C, 60.04; H, 5.63; N, 11.00; Cl, 18.61.

EXAMPLE 97

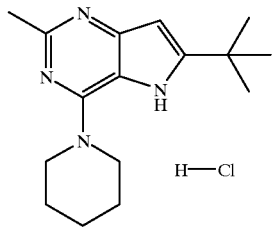

6-(tert-Butyl)-2-methyl-4-piperidylpyrrolo[3,2-d]pyrimidine Hydrochloride Hydrate Using the method described in Example 30 by employing 1-(tert-butyl)vinylpyrrolidine (freshly prepared before use) (1.20 g, 7.73 mmol), 2-methyl-4,6-dichloro-5-nitropyrimidine (Example 76(b)) (1.60 g, 7.73 mmol), N,N-diisopropylethyl amine (Aldrich Chemical Company) (1.3 mL, 7.73 mmol), piperidine (Aldrich Chemical Company) (1.2 mL, 12.4 mmol), NEt₃ (Aldrich Chemical Company) (2.0 mL) and SnCl₂ (23 mL of a 2M solution in DMF). The crude residue was purified by flash chromatography on silica gel with 95:5 CHCl₃:MeOH as elutant to give 448 mg (21%) of the free base as a cream colored solid. ¹H NMR (DMSO-d₆; 400 MHz): δ 1.36 (s, 9), 1.63 (br s, 6), 2.38 (s, 3), 3.60 (br s, 4), 6.05 (d, 1, J=1.6), 10.20 (s, 1). MS m/z: 273 (M+1). To a hot solution of 6-(tert-butyl)-2-methyl-4-piperidylpyrrolo[3,2-d]pyrimidine (0.45 g, 1.65 mmol) in 10:1 EtOAc:MeOH (30 mL) was added 1N etheral HCl (Aldrich Chemical Company) (1.70 mL, 1.65 mmol). Crystallization occurred as the mixture cooled and the precipitate was collected by filtration, washed with Et₂O (3×10 mL) and dried under vacuum to give 420 mg (83%) of the title compound as a white colored solid. Mp: 256–258° C. ¹H NMR (DMSO-d₆; 400 MHz): δ 1.41 (s, 9), 1.67 (m, 6), 2.54 (s, 3), 3.98 (t, 4, J=5.2), 6.26 (s, 1), 11.14 (s, 1), 14.32 (s, 2). MS m/z: 273 (M+1). Anal. Calcd for $C_{16}H_{25}ClN_4 \cdot 0.25H_2O$: C, 61.41; H, 8.20; N, 17.91; Cl, 11.33. Found C, 61.41; H, 8.11; N, 17.90; Cl, 11.39.

EXAMPLE 98

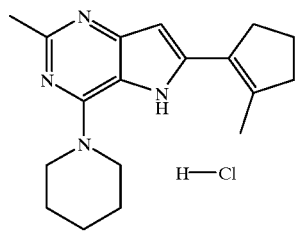

2-Methyl-6-(2-methylcyclopent-1-eneyl)-4-piperidyl pyrrolo[3,2-d]pyrimidine Hydrochloride.

Using the method described in Example 30 by employing [1-(2-methylcyclopent-1-enyl)vinyl]pyrrolidine (freshly prepared before use) (2.41 g, 13.6 mmol), 2-methyl-4,6-dichloro-5-nitropyrimidine (Example 76(b)) (2.80 g, 13.6 mmol), N,N-diisopropyl ethyl amine (Aldrich Chemical Company) (2.4 mL, 13.6 mmol), piperidine (Aldrich Chemical Company) (2.1 mL, 21.7 mmol), NEt₃ (Aldrich Chemical Company) (2.0 mL) and SnCl₂ (41 mL of a 2M solution in DMF). The residue was purified by flash chromatography on silica gel with 95:5 CHCl₃:MeOH as elutant to give 552 mg (14%) of the free base as a pale yellow colored solid. ¹H NMR (DMSO-d₆; 400 MHz): δ 1.62 (br s, 6), 1.85–1.90 (m, 2), 1.93 (s, 3), 2.39 (s, 3), 2.79 (br s, 2), 3.30 (br s, 2), 3.67 (br s, 4), 6.23 (s, 1), 10.36 (s, 1). MS m/z: 297 (M+1). To a hot solution of 2-methyl-6-(2-methylcyclopent-1-eneyl)-4-piperidylpyrrolo[3,2-d]pyrimidine (0.55 g, 1.86 mmol) in 5:1 EtOAc:MeOH (30 mL) was added 1M etheral HCl (Aldrich Chemical Company) (1.85 mL, 1.85 mmol). Crystallization occurred as the mixture cooled and the precipitate was collected by filtration, washed with EtOAc (1×5 mL), Et₂O (3×10 mL) and dried under vacuum to give 580 mg (94%) of the title compound as a white colored solid. Mp: 224.5–226° C. ¹H NMR (DMSO-d₆; 400 MHz): δ 1.69 (br s, 6), 1.89–1.93 (m, 5), 2.50 (s, 3), 2.82 (br s, 2), 3.31 (s, 2), 3.99 (br s, 4), 6.39 (s, 1), 11.49 (s, 1), 14.34 (s, 1). MS m/z: 297 (M+1). Anal. Calcd for $C_{18}H_{24}N_4 \cdot HCl$: C, 64.95; H, 7.57; N, 16.83; Cl, 10.65. Found C, 64.72; H, 7.63; N, 16.65; Cl, 10.37.

EXAMPLE 99

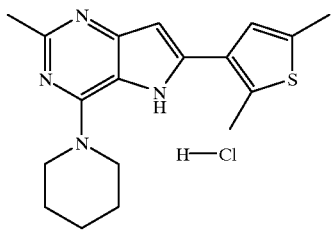

2,5-Dimethyl-3-(2-methyl-4-piperidylpyrrolo[4,5-d]pyrimidin-6-yl)thiophene Hydrochloride Hydrate.

Using the method described in Example 30 by employing 2,5-dimethyl-3-(1-pyrrolidinylvinyl) thiophene (freshly prepared before use) (1.40 g, 6.76 mmol), 2-methyl-4,6-dichloro-5-nitropyrimidine (Example 76(b)) (1.40 g, 6.76 mmol), N,N-diisopropyl ethyl amine (Aldrich Chemical Company) (1.2 mL, 6.76 mmol), piperidine (Aldrich Chemical Company) (1.1 mL, 10.8 mmol), NEt₃ (Aldrich Chemical Company) (1.0 mL) and SnCl₂ (20 mL of a 2M solution in DMF). The residue was purified by flash chromatography on silica gel with 95:5 CHCl$_3$:MeOH as elutant to give 335 mg (15%) of the free base as a beige colored solid. $^1$H NMR (DMSO-d$_6$; 400 MHz): δ 1.63 (br s, 6), 2.40 (s, 3), 2.42 (s, 3), 2.50 (s, 3), 3.70 (br s, 4), 6.36 (s, 1), 7.04 (s, 1), 10.82 (s, 1). MS m/z: 327 (M+1). To a hot solution of 2,5-dimethyl-3-(2-methyl-4-piperidyl pyrrolo[4,5-d]pyrimidin-6-yl)thiophene (0.35 g, 1.02 mmol) in 5:1 EtOAc:MeOH (40 mL) was added 1M etheral HCl (Aldrich Chemical Company) (1.00 mL, 1.00 mmol). Crystallization occurred as the mixture cooled and the precipitate was collected by filtration, washed with Et$_2$O (2×5 mL) and dried under vacuum to give 222 mg (60%) of the title compound as a beige colored solid. Mp: 240–241.5° C. $^1$H NMR (DMSO-d$_6$; 400 MHz): δ 1.70 (br s, 6), 2.44 (s, 3), 2.50 (s, 3), 2.55 (s, 3), 4.02 (br s, 4), 6.54 (s, 1), 7.06 (s, 1), 11.89 (s, 1), 14.15 (s, 1). MS m/z: 327 (M+1). Anal. Calcd for C$_{18}$H$_{22}$N$_4$S.HCl.1.5H$_2$O: C, 55.53; H, 6.68; N, 14.40; Cl, 9.00; S, 8.23. Found C, 55.62; H, 6.66; N, 14.31; Cl, 9.31; S, 8.28.

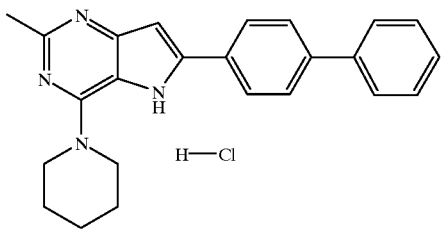

EXAMPLE 100

2-Methyl-6-(4-phenylphenyl)-4-piperidylpyrrolo[3,2-d]pyrimidine Hydrochloride Monohydrate.

Using the method described in Example 30 by employing [1-(4-phenylphenyl)vinyl]pyrrolidine (freshly prepared before use) (1.35 g, 5.42 mmol), 2-methyl-4,6-dichloro-5-nitropyrimidine (Example 76(b)) (1.21 g, 5.42 mmol), N,N-diisopropylethyl amine (Aldrich Chemical Company) (0.9 mL, 5.42 mmol), piperidine (Aldrich Chemical Company) (0.9 mL, 8.67 mmol), NEt$_3$ (Aldrich Chemical Company) (1.0 mL) and SnCl$_2$ (Aldrich Chemical Company) (16 mL of a 2M solution in DMF). The residue was purified by flash chromatography on silica gel with 95:5 CHCl$_3$:MeOH as elutant to give 220 mg (11%) of the free base as a beige colored solid. $^1$H NMR (DMSO-d$_6$; 400 MHz): δ 1.67 (br s, 6), 2.43 (s, 3), 3.74 (br s, 4), 6.80 (s, 1), 7.39 (t, 1, J=7.2), 7.50 (t, 2, J=7.7), 7.75 (d, 2, J=7.5), 7.78 (d, 2, J=7.6), 8.00 (d, 2, J=8.2), 11.01 (s, 1). MS m/z: 369 (M+1). To a hot solution of 2-methyl-6-(4-phenylphenyl)-4-piperidyl pyrrolo[3,2-d]pyrimidine (0.22 g, 0.59 mmol) in 10:1 EtOAc: MeOH (40 mL) was added 1N etheral HCl (Aldrich Chemical Company) (600 mL, 0.60 mmol). Crystallization occurred as the mixture cooled and the precipitate was collected by filtration, washed with Et$_2$O (3×5 mL) and dried under vacuum to give 205 mg (86%) of the title compound as a pale yellow colored solid. Mp: >280° C. $^1$H NMR (DMSO-d$_6$; 500 MHz): δ 1.72 (br s, 6), 2.58 (s, 3), 4.07 (br s, 4), 6.96 (s, 1), 7.43 (t, 1, J=7.2), 7.42 (t, 2, J=7.7), 7.77 (d, 2, J=7.9), 7.86 (d, 2, J=8.1), 8.06 (d, 2, J=8.1), 12.00 (s, 1), 14.29 (s, 1). MS m/z: 369 (M+1). Anal. Calcd for C$_{24}$H$_{24}$N$_4$.HCl.1.0H$_2$O: C, 67.92; H, 6.45; N, 13.21; Cl, 8.35. Found C, 67.92; H, 6.43; N, 13.17; Cl, 8.46.

EXAMPLE 101

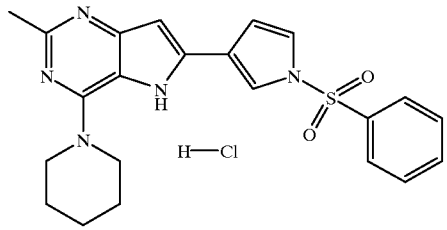

3-(2-Methyl-4-piperidylpyrrolo[4,5-d]pyrimidin-6-yl)-1-(phenylsulfonyl)pyrrole Hydrochloride Hydrate.

Using the method described in Example 30 by employing 1-(phenylsulfonyl)-3-(1-pyrrolidinylvinyl) pyrrole (freshly prepared before use) (0.97 g, 4.68 mmol), 2-methyl-4,6-dichloro-5-nitropyrimidine (Example 76(b)) (1.41 g, 4.68 mmol), N,N-diisopropyl ethyl amine (Aldrich Chemical Company) (0.8 mL, 4.68 mmol), piperidine (Aldrich Chemical Company) (0.7 mL, 7.5 mmol), NEt$_3$ (Aldrich Chemical Company) (1.0 mL) and SnCl$_2$ (Aldrich Chemical Company) (14 mL of a 2M solution in DMF). The residue was purified by flash chromatography on silica gel with 95:5 CHCl$_3$:MeOH as elutant to give 186 mg (9%) of the free base as a tan colored solid. $^1$H NMR (DMSO-d$_6$; 400 MHz): δ 1.64 (br s, 6), 2.38 (s, 3), 3.68 (br s, 4), 6.60 (s, 1), 6.92 (s, 1), 7.47 (s, 1), 7.68 (t, 2, J=7.5), 7.77 (t, 1, J=7.5), 8.00 (d, 2, J=7.6), 8.09 (br s, 1), 10.74 (s, 1). MS m/z: 422 (M+1). To a hot solution of 3-(2-methyl-4-piperidylpyrrolo[4,5-d]pyrimidin-6-yl)-1-(phenylsulfonyl)pyrrole (0.18 g, 0.43 mmol) in 5:1 EtOAc: MeOH (40 mL) was added 1N etheral HCl (Aldrich Chemical Company) (432 mL, 0.43 mmol). Crystallization occurred as the mixture cooled and the precipitate was collected by filtration, washed with Et$_2$O (2×5 mL) and dried under vacuum to give 166 mg (85%) of the title compound as a brown colored powder. Mp: 183–185.5° C. $^1$H NMR (DMSO-d$_6$; 500 MHz): δ 1.67–1.69 (m, 6), 2.54 (s, 3), 4.02 (s, 4), 6.79 (s, 1), 7.06 (s, 1), 7.56 (t, 1, J=2.7), 7.69 (t, 2, J=7.8), 7.79 (t, 1, J=7.6), 8.04 (d, 2, J=8.0), 8.31 (s, 1), 11.70 (s, 1), 14.14 (s, 1). MS m/z: 422 (M+1). Anal. Calcd for C$_{22}$H$_{23}$N$_5$O$_2$S.HCl.1.5H$_2$O: C, 54.26; H, 5.63; N, 14.39; Cl, 7.28. Found C, 54.31; H, 5.39; N, 13.99; Cl, 7.58.

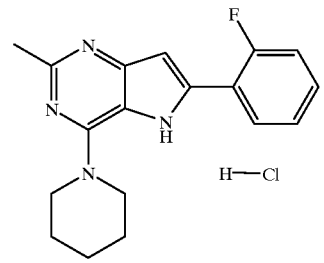

EXAMPLE 102

6-(2-Fluorophenyl)-2-methyl-4-piperidylpyrrolo[3,2-d]pyrimidine Hydrochloride Monohydrate.

Using the method described in Example 30 by employing [1-(2-fluorophenyl)vinyl]pyrrolidine (freshly prepared before use) (1.02 g, 5.34 mmol), 2-methyl-4,6-dichloro-5-nitropyrimidine (Example 76(b)) (1.10 g, 5.34 mmol), N,N-diisopropylethyl amine (Aldrich Chemical Company) (1.3 mL, 7.73 mmol), piperidine (Aldrich Chemical Company) (0.9 mL, 5.34 mmol), NEt$_3$ (Aldrich Chemical Company)

(1.0 mL) and SnCl₂ (Aldrich Chemical Company) (16 mL of a 2M solution in DMF). The residue was purified by flash chromatography on silica gel with 95:5 CHCl₃:MeOH as elutant to give 142 mg (9%) of the free base as a cream colored solid. ¹H NMR (DMSO-d₆; 400 MHz): δ 1.65 (br s, 6), 2.43 (s, 3), 3.73 (br s, 4), 6.63 (s, 1), 7.33 (br s, 3), 7.44 (br s, 1), 7.87 (s, 1), 11.04 (s, 1). MS m/z: 311 (M+1). To a hot solution of 6-(2-fluorophenyl)-2-methyl-4-piperidylpyrrolo[3,2-d]pyrimidine (0.14 g, 0.46 mmol) in 5:1 EtOAc:MeOH (30 mL) was added 1N etheral HCl (Aldrich Chemical Company) (460 mL, 0.46 mmol). Crystallization occurred as the mixture cooled and the precipitate was collected by filtration, washed with Et₂O (3×10 mL) and dried under vacuum to give 140 mg (88%) of the title compound as white colored long needles. Mp: 287–289° C. ¹H NMR (DMSO-d₆; 400 MHz): δ 1.72 (br s, 6), 2.58 (s, 3), 4.05 (br s, 4), 6.80 (d, 1, J=1.6), 7.39–7.46 (m, 2), 7.57 (q, 1, J=7.1), 7.89 (t, 1, J=7.7), 12.13 (s, 1), 14.37 (s, 1). MS m/z: 311 (M+1). Anal. Calcd for C₁₈H₁₉FN₄.HCl.H₂O: C, 59.28; H, 6.08; N, 15.37; Cl, 9.72. Found C, 59.28; H, 6.02; N, 15.39; Cl, 9.77.

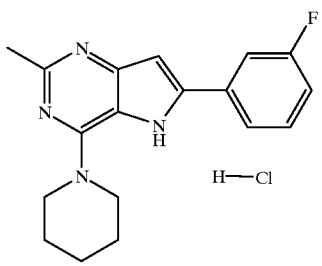

EXAMPLE 103

6-(3-Fluorophenyl)-2-methyl-4-piperidylpyrrolo[3,2-d]pyrimidine Hydrochloride Monohydrate.

Using the method described in Example 30 by employing [1-(3-fluorophenyl)vinyl]pyrrolidine (freshly prepared before use) (1.10 g, 5.81 mmol), 2-methyl-4,6-dichloro-5-nitropyrimidine (Example 76(b)) (1.21 g, 5.81 mmol), N,N-diisopropylethyl amine (Aldrich Chemical Company) (0.9 mL, 5.81 mmol), piperidine (Aldrich Chemical Company) (0.9 mL, 9.3 mmol), NEt₃ (Aldrich Chemical Company) (1.0 mL) and SnCl₂ (Aldrich Chemical Company) (17 mL of a 2M solution in DMF). The residue was purified by flash chromatography on silica gel with 95:5 CHCl₃:MeOH as elutant to give 82 mg (5%) of the free base as a beige colored solid. ¹H NMR (DMSO-d₆; 400 MHz): δ 1.65 (br s, 4), 2.42 (s, 3), 3.72 (br s, 4), 6.85 (s, 1), 7.22 (m, 1), 7.51 (m, 1), 7.75–7.81 (m, 2), 10.97 (s, 1). MS m/z: 311 (M+1). To a hot (near boiling) solution of 6-(3-fluorophenyl)-2-methyl-4-piperidylpyrrolo[3,2-d]pyrimidine (82.0 mg, 0.26 mmol) in 10:1 EtOAc: MeOH (30 mL) was added 1M etheral HCl (Aldrich Chemical Company) (265 mL, 0.26 mmol). Crystallization occurred as the mixture cooled and the precipitate was collected by filtration, washed with Et₂O (2×5 mL) and dried under vacuum to give 82 mg (91%) of the title compound as beige colored small needles. Mp: >285° C. ¹H NMR (DMSO-d₆; 400 MHz): δ 1.71 (br s, 6), 2.57 (s, 3), 4.06 (br s, 4), 6.99 (s, 1), 7.35 (t, 1, J=8.5), 7.60 (q, 1, J=7.7), 7.83 (d, 1, J=7.6), 7.91 (d, 1, J=10.2), 11.99 (s, 1), 14.34 (s, 1). MS m/z: 311 (M+1). Anal. Calcd for C₁₈H₁₉FN₄.HCl.H₂O: C, 59.17; H, 6.09; N, 15.34; Cl 9.70. Found C, 59.17; H, 6.09; N, 15.21; Cl, 9.81.

EXAMPLE 104

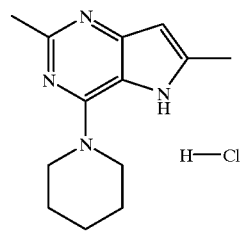

2,6-Dimethyl-4-piperidylpyrrolo[3,2-d]pyrimidine Hydrochloride Hydrate.

This compound was prepared according to the method described in Example 46(e) by employing 2,6-dimethyl-4-chloro-5H-pyrrolo[3,2-d]pyrimidine (Example 46(d)) (0.29 g, 1.60 mmol) with piperidine (Aldrich Chemical Company) (0.80 mL, 8.1 mmol) and K₂CO₃ (0.58 g, 4.7 mmol) in H₂O (6.0 mL). The hydrochloride salt was formed by treating a CH₂Cl₂ solution of the crude product with ethereal HCl (1.0 M, 1.1 mL, 1.1 mmol). Recrystallization from MeOH gave 0.090 g (21%) of the title compound as a hygroscopic beige solid. Mp: 244–245.5° C. ¹H NMR (DMSO-d₆; 500 MHz): δ 1.67 (m, 4), 1.72 (m, 2), 2.48 (s, 3), 2.52 (s, 3), 3.97 (t, 4), 6.30 (s, 1), 6.18 (s, 1), 11.92 (s, 1), 14.00 (s, 1); MS m/z: 231 (M+1). Anal. Calcd for C₁₃H₁₈N₄.1.05HCl.0.86H₂O: C, 54.94; H, 7.37; N, 19.72; Cl, 13.11. Found: C, 54.94; H, 7.57; N, 19.36; Cl, 13.14.

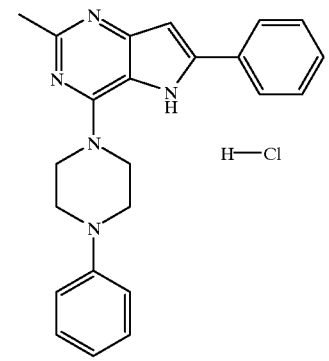

EXAMPLE 105

2-Methyl-6-phenyl-4-(4-phenylpiperazinyl)pyrrolo[3,2-d]pyrimidine Hydrochloride Hydrate.

A mixture of 2-methyl-4-chloro-6-phenyl-5H-pyrrolo[3,2-d]pyrimidine (Example 1(e)) (0.51 g, 2.45 mmol) and 1-phenylpiperazine (Aldrich Chemical Company) (10 mL) was stirred at 140° C. for 4 h under a N₂ atmosphere. After cooling the precipitate was removed by filtration and the filtrate was poured onto a mixture of CH₂Cl₂ (30 mL) and H₂O (40 mL). The mixture was transferred to a separatory funnel where the organic solution was collected, washed with H₂O (3×40 mL), saturated NaCl (50 mL), dried (MgSO₄), filtered and concentrated under reduced pressure. The residue was purified by flash chromatography on silica gel with 97:3 CHCl₃/MeOH as eluant to give 483 mg (54%) of 2-methyl-6-phenyl-4-(4-phenylpiperazinyl)pyrrolo[3,2-d]pyrimidine as a tan colored solid. This compound (483 mg, 1.31 mmol) was dissolved in 5:1 EtOAc/MeOH (30 mL) and heated to boiling. To the hot solution was added 1 M ethereal HCl (1.30 mL, 1.30 mmol). The solution was allowed to cool to room temperature. The resulting solid was collected by filtration, washed with EtOAc (2×5 mL), Et$_2$O (2×5 mL) and dried under vacuum at 60° C. to give 404 mg (41%) of the title compound as a beige powder. Mp: 232–234.5° C. $^1$H NMR (DMSO-d$_6$; 500 MHz): δ 2.55 (s, 3), 3.36 (br s, 4), 4.21 (br s, 4), 6.80 (t, 1, J=7.2), 6.88 (s, 1), 6.99 (d, 2, J=7.8), 7.22 (t, 2, J=7.5), 7.46 (q, 1, J=7.1), 7.51 (t, 2, J=7.3), 7.93 (d, 2, J=7.7), 12.06 (s, 1), 14.46 (s, 1). MS m/z: 370 (M+1 for free base). Anal. Calcd for C$_{23}$H$_{23}$N$_5$.2.0HCl.2.5H$_2$O: C, 56.67; H, 6.20; N, 14.37; Cl, 14.55. Found: C, 56.67; H, 6.23; N, 14.19; Cl, 14.34.

EXAMPLE 106

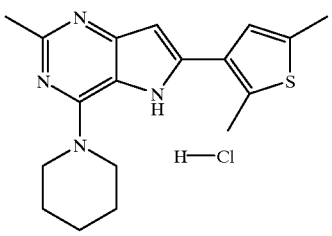

2,5-Dimethyl-3-[2-methyl-4-piperidylpyrrolo[4,5-d] pyrimidin-6-yl]thiophene Hydrochloride Hydrate.

Using the method described in Example 30 by employing 2,5-dimethyl-3-(1-pyrrolidinylvinyl)thiophene (freshly prepared from 3-acetyl-2,5-dimethylthiophene (Aldrich Chemical Company), pyrrolidine and TiCl$_4$ (1.40 g, 6.76 mmol), 2-methyl-4,6-dichloro-5-nitropyrimidine (Example 76(b)) (1.40 g, 6.76 mmol), N,N-diisopropyl ethylamine (1.2 mL, 6.76 mmol), piperidine (1.1 mL, 10.8 mmol), NEt$_3$ (1.2 mL) and SnCl$_2$ (20 mL of a 2 M soln in DMF). The residue was purified by flash chromatography on silica gel with 95:5 CHCl$_3$/MeOH as eluant to give 335 mg (15%) of 2,5-dimethyl-3-[2-methyl-4-piperidylpyrrolo[4,5-d]pyrimidin-6-yl]thiophene as a tan colored solid. This material (335 mg, 1.00 mmol) was dissolved in 5:1 EtOAc/MeOH (30 mL) and heated to boiling. To the hot solution was added 1 M ethereal HCl (1.00 mL, 1.00 mmol). The solution was left to cool to room temperature. The resulting crystals were collected by filtration, washed with EtOAc (2×10 mL), Et$_2$O (3×15 mL) and dried under vacuum at 60° C. to give 222 mg (9%) of the title compound as a beige colored solid. Mp: 240–241.5° C. $^1$H NMR (DMSO-d$_5$; 400 MHz): δ 1.70 (br s, 6), 2.44 (s, 3), 2.50 (s, 3), 2.55 (s, 3), 4.02 (br s, 4), 6.54 (s, 1), 7.06 (s, 1), 11.89 (s, 1), 14.15 (s, 1). MS m/z: 327 (M+1 for free base). Anal. Calcd for C$_{18}$H$_{22}$N$_4$S.HCl.1.5H$_2$O: C, 55.53; H, 6.68; N, 14.40; Cl, 9.00; S, 8.23. Found: C, 55.62; H, 6.66; N, 14.31; Cl, 9.13; S, 8.28.

EXAMPLE 107

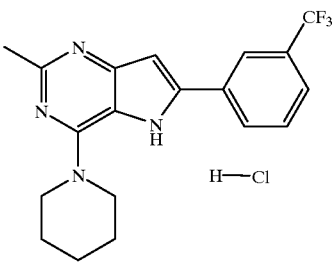

2-Methyl-4-piperidyl-6-[3-(trifluoromethyl)phenyl]pyrrolo [3,2-d]pyrimidine Hydrochloride Monohydrate.

Using the method described in Example 30 by employing [1-(3-(trifluoromethyl)phenyl)vinyl]pyrrolidine (freshly prepared before use from 3-(trifluoromethyl)acetophenone (Aldrich Chemical Company), pyrrolidine and TiCl$_4$ (1.97 g, 8.17 mmol), 2-methyl-4,6-dichloro-5-nitropyrimidine (Example 76(b)) (1.70 g, 8.17 mmol), N,N-diisopropylethylamine (1.4 mL, 8.17 mmol), piperidine (1.3 mL, 13.1 mmol), NEt$_3$ (1.3 mL) and SnCl$_2$ (25 mL of a 2 M soln in DMF). The residue was purified by flash chromatography on silica gel with 95:5 CHCl$_3$/MeOH as eluant to give 500 mg (17%) of 2-methyl-4-piperidyl-6-[3-(trifluoromethyl)phenyl]pyrrolo[3,2-d]pyrimidine as a beige colored solid. This material (500 mg, 1.39 mmol) was dissolved in 5:1 EtOAc/MeOH (30 mL) and heated to boiling. To the hot solution was added 1 M ethereal HCl (1.40 mL, 1.40 mmol). The solution was left to cool to room temperature. The resulting crystals were collected by filtration, washed with EtOAc (2×10 mL), Et$_2$O (3×15 mL) and dried under vacuum at 60° C. to give 493 mg (15%) of the title compound as a white colored solid. Mp: 241–243° C. $^1$H NMR (DMSO-d$_6$; 400 MHz): δ 1.72 (br s, 6), 2.59 (s, 3), 4.08 (s, 4), 7.14 (s, 1), 7.79 (t, 1, J=7.6), 7.85 (d, 1, J=7.5), 8.30 (d, 1, J=7.6), 8.34 (s, 1), 12.92 (s, 1), 14.53 (s, 1). MS m/z: 361 (M+1 for free base). Anal. Calcd for C$_{19}$H$_{19}$F$_3$N$_4$.HCl.1.0H$_2$O: C, 55.00; H, 5.35; N, 13.51; Cl, 8.55. Found: C, 54.99; H, 5.20; N, 13.39; Cl, 8.60.

EXAMPLE 108

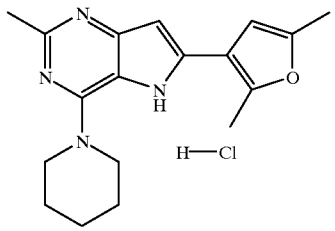

2,5-Dimethyl-3-(2-methyl-4-piperidylpyrrolo[4,5-d] pyrimidin-6-yl)furan Hydrochloride Monohydrate.

Using the method described in Example 30 by employing 2,5-dimethyl-3-[1-pyrrolidinyl]furan (freshly prepared before use from 3-acetyl-2,5-dimethylfuran (Aldrich Chemical Company), pyrrolidine and TiCl$_4$ (4.88 g, 25.5 mmol), 2-methyl-4,6-dichloro-5-nitropyrimidine (Example 76(b)) (5.30 g, 25.5 mmol), N,N-diisopropyl ethylamine (4.5 mL, 25.5 mmol), piperidine (4.0 mL, 40.8 mmol), NEt$_3$ (4.0 mL) and SnCl$_2$ (77 mL of a 2 M soln in DMF). Note because of the increase in scale, the workup involved NaOH (15 g) and crushed ice (300 mL). The residue was purified by flash chromatography on silica gel with 95:5 CHCl$_3$/MeOH as eluant to give 1.01 g (13%) of 2,5-dimethyl-3-(2-methyl-4-piperidylpyrrolo[4,5-d]pyrimidin-6-yl)furan as a beige colored powder. This material (1.01 g, 3.22 mmol) was dissolved in 2:1 EtOAc/MeOH (100 mL) and heated to boiling. To the hot solution was added 1 M ethereal HCl (3.25 mL, 3.25 mmol). The solution was left to cool to room temperature. The resulting crystals were collected by filtration, washed with EtOAc (2×10 mL), Et$_2$O (3×15 mL) and dried under vacuum at 60° C. to give 878 mg (10%) of the title compound as a white colored solid. Mp: 238–240° C. $^1$H NMR (DMSO-d$_6$; 400 MHz): δ 1.69 (br s, 6), 2.29 (s, 3), 2.44 (s, 3), 2.55 (s, 3), 4.01 (s, 4), 6.47 (s, 1), 6.55 (s, 1), 11.67 (s, 1), 14.18 (s, 1). MS m/z: 311 (M+1 for free base). Anal. Calcd for C$_{18}$H$_{22}$N$_4$O.HCl.1.0H$_2$O: C, 59.25; H, 6.91; N, 15.36; Cl, 9.72. Found: C, 59.19; H, 6.80; N, 15.30; Cl, 9.88.

EXAMPLE 109

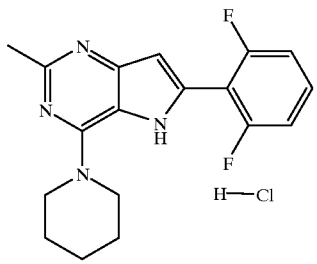

6-(2,6-Difluorophenyl)-2-methyl-4-piperidylpyrrolo[3,2-d]pyrimidine Hydrochloride Hydrate.

Using the method described in Example 30 by employing [1-(2,6-difluorophenyl)vinyl]pyrrolidine (freshly prepared before use from 2',6'-difluoro acetophenone (Aldrich Chemical Company), pyrrolidine and $TiCl_4$ (1.51 g, 7.22 mmol), 2-methyl-4,6-dichloro-5-nitropyrimidine (Example 76(b)) (1.20 g, 5.79 mmol), N,N-diisopropylethylamine (1.3 mL, 7.22 mmol), piperidine (1.2 mL, 11.6 mmol), $NEt_3$ (1.2 mL) and $SnCl_2$ (22 mL of a 2 M soln in DMF). The residue was purified by flash chromatography on silica gel with 95:5 $CHCl_3$/MeOH as eluant to give 199 mg (11%) of 6-(2,6-difluorophenyl)-2-methyl-4-piperidylpyrrolo[3,2-d]pyrimidine as a beige colored powder. This material (199 mg, 0.61 mmol) was dissolved in 5:1 EtOAc/MeOH (20 mL) and heated to boiling. To the hot solution was added 1 M ethereal HCl (0.60 mL, 0.60 mmol). The solution was left to cool to room temperature. The resulting crystals were collected by filtration, washed with EtOAc (2×10 mL), $Et_2O$ (3×15 mL) and dried under vacuum at 60° C. to give 33 mg (2%) of the title compound as a pale yellow colored sandy solid. Mp: >280° C. $^1H$ NMR (DMSO-$d_6$; 400 MHz): δ 1.71 (br s, 6), 2.58 (s, 3), 4.02 (s, 4), 6.77 (s, 1), 7.35 (t, 2, J=8.3), 7.67 (dquintet, 1, J=1.4, 6.8), 12.41 (s, 1), 14.51 (s, 1). MS m/z: 329 (M+1 for free base). Anal. Calcd for $C_{18}H_{18}F_2N_4$·HCl·1.2$H_2O$: C, 55.99; H, 5.58; N, 14.51; Cl, 9.18. Found: C, 55.99; H, 5.61; N, 14.41; Cl, 9.08.

EXAMPLE 110

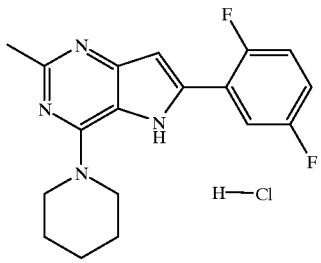

6-(2,5-Difluorophenyl)-2-methyl-4-piperidylpyrrolo[3,2-d]pyrimidine Hydrochloride Monohydrate.

Using the method described in Example 30 by employing [1-(2,5-difluorophenyl)vinyl]pyrrolidine (freshly prepared before use from 2',5'-difluoro acetophenone (Aldrich Chemical Company), pyrrolidine and $TiCl_4$ (1.45 g, 6.94 mmol), 2-methyl-4,6-dichloro-5-nitropyrimidine (Example 76(b)) (1.00 g, 4.83 mmol), N,N-diisopropylethylamine (1.2 mL, 6.94 mmol), piperidine (1.1 mL, 11.1 mmol), $NEt_3$ (1.2 mL) and $SnCl_2$ (21 mL of a 2 M soln in DMF). The residue was purified by flash chromatography on silica gel with 95:5 $CHCl_3$/MeOH as eluant to give 417 mg (26%) of 6-(2,5-difluorophenyl)-2-methyl-4-piperidylpyrrolo[3,2-d]pyrimidine as a tan colored foam. This material (415 mg, 1.25 mmol) was dissolved in 5:1 EtOAc/MeOH (30 mL) and heated to boiling. To the hot solution was added 1 M ethereal HCl (1.30 mL, 1.30 mmol). The solution was left to cool to room temperature. The resulting crystals were collected by filtration, washed with EtOAc (2×10 mL), $Et_2O$ (3×15 mL) and dried under vacuum at 60° C. to give 337 mg (19%) of the title compound as white colored needles. Mp: 279–281° C. $^1H$ NMR (DMSO-$d_6$; 400 MHz): δ 1.71 (br s, 6), 2.58 (s, 3), 4.06 (s, 4), 6.85 (s, 1), 7.42–7.55 (m, 2), 7.86–7.91 (m, 1), 12.13 (s, 1), 14.41 (s, 1). MS m/z: 329 (M+1 for free base). Anal. Calcd for $C_{18}H_{18}F_2N_4$·HCl·1.0$H_2O$: C, 56.54; H, 5.50; N, 14.65. Found: C, 56.29; H, 5.61; N, 14.53.

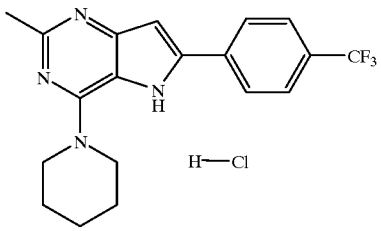

EXAMPLE 111

2-Methyl-4-piperidyl-6-[4-(trifluoromethyl)phenyl]pyrrolo[3,2-d]pyrimidine hydrochloride Hydrate.

Using the method described in Example 30 by employing [1-[4-(trifluoromethyl)phenyl]vinyl]pyrrolidine (freshly prepared before use from 4-(trifluoromethyl) acetophenone (Aldrich Chemical Company), pyrrolidine and $TiCl_4$ (1.21 g, 5.02 mmol), 2-methyl-4,6-dichloro-5-nitropyrimidine (Example 76(b)) (1.00 g, 5.02 mmol), N,N-diisopropylethylamine (0.9 mL, 5.02 mmol), piperidine (0.8 mL, 8.0 mmol), $NEt_3$ (1.0 mL) and $SnCl_2$ (15 mL of a 2 M soln in DMF). The residue was purified by flash chromatography on silica gel with 95:5 $CHCL_3$/MeOH as eluant to give 248 mg (14%) of 2-methyl-4-piperidyl-6-[4-(trifluoromethyl)phenyl]pyrrolo[3,2-d]pyrimidine as a beige colored solid. This material (245 mg, 0.69 mmol) was dissolved in 5:1 EtOAc/MeOH (30 mL) and heated to boiling. To the hot solution was added 1 M ethereal HCl (0.70 mL, 0.70 mmol). The solution was left to cool to room temperature. The resulting crystals were collected by filtration, washed with EtOAc (2×10 mL), $Et_2O$ (3×15 mL) and dried under vacuum at 60° C. to give 187 mg (10%) of the title compound as a beige colored solid. Mp: 278–280° C. $^1H$ NMR (DMSO-$d_6$; 400 MHz): δ 1.72 (br s, 6), 2.58 (s, 3), 4.08 (s, 4), 7.05 (s, 1), 7.93 (d, 2, J=8.3), 8.20 (d, 2, J=8.2), 12.16 (s, 1), 14.32 (s, 1). MS m/z: 361 (M+1 for free base). Anal. Calcd for $C_{19}H_{19}F_3N_4$·HCl·1.5$H_2O$: C, 53.79; H, 5.43; N, 13.21; Cl, 8.26. Found: C, 54.01; H, 5.40; N, 13.18; Cl, 8.60.

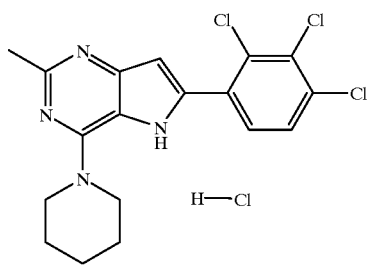

EXAMPLE 112
2-Methyl-4-piperidyl-6-(2,3,4-trichlorophenyl)pyrrolo[3,2-d]pyrimidine Hydrochloride Hydrate.

Using the method described in Example 30 by employing [1-(2,3,4-trichlorophenyl)vinyl]pyrrolidine (freshly prepared before use from 2',3',4'-trichloro acetophenone (Aldrich Chemical Company), pyrrolidine and TiCl$_4$ (1.00 g, 3.64 mmol), 2-methyl-4,6-dichloro-5-nitropyrimidine (Example 76(b)) (0.80 g, 3.64 mmol), N,N-diisopropylethylamine (0.6 mL, 3.64 mmol), piperidine (0.6 mL, 5.80 mmol), NEt$_3$ (0.7 mL) and SnCl$_2$ (11 mL of a 2 M soln in DMF). The residue was purified by flash chromatography on silica gel with 95:5 CHCl$_3$/MeOH as eluant to give 125 mg (9%) of 2-methyl-4-piperidyl-6-(2,3,4-trichlorophenyl)pyrrolo[3,2-d]pyrimidine as a brown colored oil. This material (125 mg, 0.32 mmol) was dissolved in 5:1 EtOAc/MeOH (15 mL) and heated to boiling. To the hot solution was added 1 M ethereal HCl (0.40 mL, 0.40 mmol). The solution was left to cool to room temperature. The resulting crystals were collected by filtration, washed with EtOAc (2×10 mL), Et$_2$O (3×15 mL) and dried under vacuum at 60° C. to give 55 mg (4%) of the title compound as beige colored needles. Mp: 264–266° C. $^1$H NMR (DMSO-d$_6$; 400 MHz): δ 1.71 (br s, 6), 2.58 (s, 3), 4.03 (s, 4), 6.78 (s, 1), 7.71 (d, 2, J=8.4), 7.88 (d, 2, J=8.5), 12.40 (s, 1), 14.39 (s, 1). MS m/z: 396 (M+1 for free base). Anal. Calcd for C$_{18}$H$_{17}$Cl$_3$N$_4$.HCl.1.75H$_2$O: C, 46.59; H, 4.67; N, 12.09; Cl, 30.59. Found: C, 46.64; H, 4.60; N, 11.93; Cl, 30.48.

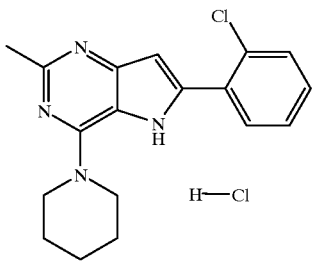

EXAMPLE 113
2-Methyl-4-piperidyl-6-(2-chlorophenyl)pyrrolo[3,2-d]pyrimidine Hydrochloride Monohydrate.

Using the method described in Example 30 by employing [1-(2-chlorophenyl)vinyl]pyrrolidine (freshly prepared before use from 2'-chloro acetophenone (Aldrich Chemical Company), pyrrolidine and TiCl$_4$ (1.06 g, 5.12 mmol), 2-methyl-4,6-dichloro-5-nitropyrimidine (Example 76(b)) (1.10 g, 5.12 mmol), N,N-diisopropylethylamine (0.9 mL, 5.12 mmol), piperidine (0.8 mL, 8.2 mmol), NEt$_3$ (0.9 mL) and SnCl$_2$ (15 mL of a 2 M soln in DMF). The residue was purified by flash chromatography on silica gel with 95:5 CHCl$_3$/MeOH as eluant to give 442 mg (25%) of 2-methyl-4-piperidyl-6-(2-chlorophenyl)pyrrolo[3,2-d]pyrimidine as a brown colored solid. This material (450 mg, 1.37 mmol) was dissolved in 5:1 EtOAc/MeOH (35 mL) and heated to boiling. To the hot solution was added 1 M ethereal HCl (1.40 mL, 1.40 mmol). The solution was left to cool to room temperature. The resulting crystals were collected by filtration, washed with EtOAc (2×10 mL), Et$_2$O (3×15 mL) and dried under vacuum at 60° C. to give 343 mg (17%) of the title compound as brown colored needles. Mp: 240–241.5° C. $^1$H NMR (DMSO-d$_6$; 400 MHz): δ 1.71 (br s, 6), 2.59 (s, 3), 4.03 (s, 4), 6.74 (s, 1), 7.55 (dquintet, 2, J=1.3, 7.8), 7.70 (dt, 2, J=0.9, 8.2), 12.34 (s, 1), 14.64 (s, 1). MS m/z: 327 (M+1 for free base). Anal. Calcd for C$_{18}$H$_{19}$ClN$_4$.HCl.H$_2$O: C, 56.70; H, 5.82; N, 14.70; Cl, 18.59. Found: C, 56.93; H, 5.91; N, 14.63; Cl, 18.70.

EXAMPLE 114

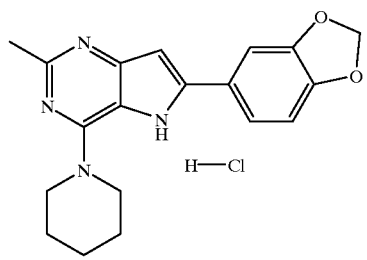

5-[2-Methyl-4-piperidylpyrrolo[4,5-d]pyrimidin-6-yl]-2H-benzo[d]1,3-dioxolane Hydrochloride Monohydrate.

Using the method described in Example 30 by employing 5-[1-pyrrolidinylvinyl]-2H-benzo[d]1,3-dioxane (freshly prepared before use from 3',4'-(methylenedioxyl) acetophenone (Aldrich Chemical Company), pyrrolidine and TiCl$_4$ (1.17 g, 5.39 mmol), 2-methyl-4,6-dichloro-5-nitropyrimidine (Example 76(b)) (1.10 g, 5.40 mmol), N,N-diisopropylethylamine (1.0 mL, 5.40 mmol), piperidine (0.9 mL, 8.6 mmol), NEt$_3$ (0.9 mL) and SnCl$_2$ (16 mL of a 2 M soln in DMF). The residue was purified by flash chromatography on silica gel with 95:5 CHCl$_3$/MeOH as eluant to give 397 mg (22%) of 5-[2-methyl-4-piperidylpyrrolo[4,5-d]pyrimidin-6-yl]-2H-benzo[d]1,3-dioxolane as a beige colored solid. This material (398 mg, 1.18 mmol) was dissolved in 5:1 EtOAc/MeOH (40 mL) and heated to boiling. To the hot solution was added 1 M ethereal HCl (1.20 mL, 1.20 mmol). The solution was left to cool to room temperature. The resulting crystals were collected by filtration, washed with EtOAc (2×10 mL), Et$_2$O (3×15 mL) and dried under vacuum at 60° C. to give 266 mg (13%) of the title compound as a beige colored powder. Mp: >280° C. $^1$H NMR (DMSO-d$_6$; 400 MHz): δ 1.71 (br s, 6), 2.56 (s, 3), 4.04 (s, 4), 6.14 (s, 2), 6.83 (s, 1), 7.11 (d, 1, J=8.2), 7.52 (d, 1, J=8.2), 7.61 (s, 1), 11.82 (s, 1), 14.37 (s, 1). MS m/z: 337 (M+1 for free base). Anal. Calcd for C$_{19}$H$_{20}$N$_4$O$_2$.HCl.H$_2$O: C, 58.38; H, 5.93; N, 14.34; Cl, 9.07. Found: C, 58.01; H, 6.00; N, 14.19; Cl, 8.94.

EXAMPLE 115

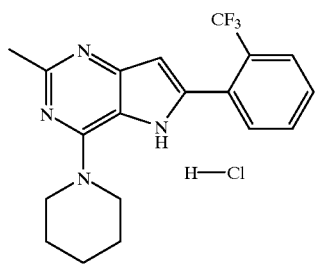

2-Methyl-4-piperidyl-6-[2-(trifluoromethyl)phenyl]pyrrolo[3,2-d]pyrimidine Hydrochloride Monohydrate.

Using the method described in Example 30 by employing [1-(2-(trifluoromethyl)phenyl)vinyl]pyrrolidine (freshly prepared before use from 2-(trifluoromethyl)acetophenone (Aldrich Chemical Company), pyrrolidine and $TiCl_4$ (1.19 g, 4.94 mmol), 2-methyl-4,6-dichloro-5-nitropyrimidine (Example 76(b)) (1.00 g, 4.94 mmol), N,N-diisopropylethylamine (0.9 mL, 4.94 mmol), piperidine (0.8 mL, 7.9 mmol), $NEt_3$ (0.9 mL) and $SnCl_2$ (15 mL of a 2 M soln in DMF). The residue was purified by flash chromatography on silica gel with 95:5 $CHCl_3$/MeOH as eluant to give 330 mg (19%) of 2-methyl-4-piperidyl-6-[2-(trifluoromethyl)phenyl]pyrrolo[3,2-d]pyrimidine as a tan colored solid. This material (330 mg, 0.90 mmol) was dissolved in 5:1 EtOAc/MeOH (40 mL) and heated to boiling. To the hot solution was added 1 M ethereal HCl (0.90 mL, 0.90 mmol). The solution was left to cool to room temperature. The resulting crystals were collected by filtration, washed with EtOAc (2×10 mL), $Et_2O$ (3×15 mL) and dried under vacuum at 60° C. to give 202 mg (11%) of the title compound as beige colored cube shaped crystals. Mp: >280° C. $^1H$ NMR (DMSO-$d_6$; 400 MHz): δ 1.70 (br s, 6), 2.58 (s, 3), 4.01 (s, 4), 6.62 (s, 1), 7.74 (d, 1, J=7.5), 7.79 (t, 1, J=7.5), 7.86 (t, 1, J=7.4), 7.97 (d, 1, J=7.8), 12.45 (s, 1), 14.43 (s, 1). MS m/z: 361 (H+1 for free base). Anal. Calcd for $C_{19}H_{19}F_3N_4 \cdot HCl \cdot H_2O$: C, 55.00; H, 5.35; N, 13.51; Cl, 8.55. Found: C, 55.25; H, 5.41; N, 13.31; Cl, 8.76.

EXAMPLE 116

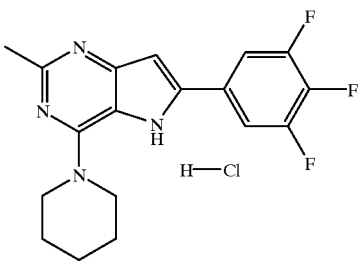

2-Methyl-4-piperidyl-6-(3,4,5-trifluorophenyl)pyrrolo[3,2-d]pyrimidine Hydrochloride Hydrate.

Using the method described in Example 30 by employing [1-(3,4,5-trifluorophenyl)vinyl]pyrrolidine (freshly prepared before use from 3,4,5-trifluoro acetophenone (Oakwood Products Inc.), pyrrolidine and $TiCl_4$ (1.58 g, 6.96 mmol), 2-methyl-4,6-dichloro-5-nitropyrimidine (Example 76(b)) (1.40 g, 6.96 mmol), N,N-diisopropylethylamine (1.2 mL, 6.96 mmol), piperidine (1.1 mL, 11.1 mmol), $NEt_3$ (1.1 mL) and $SnCl_2$ (21 mL of a 2 M soln in DMF). In this example the 2 M $SnCl_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 $CHCl_3$/MeOH as eluant to give 620 mg (26%) of 2-methyl-4-piperidyl-6-(3,4,5-trifluoro phenyl)pyrrolo[3,2-d]pyrimidine as a beige colored gummy solid. This compound (621 mg, 1.80 mmol) was dissolved in 3:1 EtOAc/MeOH (50 mL) and heated to boiling. To the hot solution was added 1 M ethereal HCl (1.80 mL, 1.80 mmol). The solution was allowed to cool to room temperature. The resulting crystals were collected by filtration, washed with EtOAc (2×10 mL), $Et_2O$ (3×15 mL) and dried under vacuum at 60° C. to give 426 mg (16%) of the title compound as a white colored fluffy solid. Mp: >280° C. $^1H$ NMR (DMSO-$d_6$; 500 MHz): δ 1.71 (br s, 6), 2.58 (s, 3), 4.07 (s, 4), 7.07 (s, 1), 8.14 (m, 2), 12.04 (s, 1), 14.45 (s, 1). MS m/z: 347 (M+1 for free base). Anal. Calcd for $C_{18}H_{17}F_3N_4 \cdot HCl \cdot 0.5H_2O$: C, 55.23; H, 4.88; N, 14.32; Cl, 9.06. Found: C, 55.23; H, 4.86; N, 14.11; Cl, 9.06.

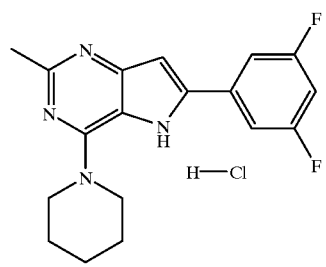

EXAMPLE 117

6-(3,5-Difluorophenyl)-2-methyl-4-piperidylpyrrolo[3,2-d]pyrimidine Hydrochloride Monohydrate.

Using the method described in Example 30 by employing [1-(3,5-difluorophenyl)vinyl]pyrrolidine (freshly prepared before use from 3,5-difluoro acetophenone (Oakwood Products Inc.), pyrrolidine and $TiCl_4$ (1.32 g, 6.32 mmol), 2-methyl-4,6-dichloro-5-nitropyrimidine (Example 76(b)) (1.30 g, 6.32 mmol), N,N-diisopropylethylamine (1.1 mL, 6.32 mmol), piperidine (1.0 mL, 10.1 mmol), $NEt_3$ (1.1 mL) and $SnCl_2$ (19 mL of a 2 M soln in DMF). In this example the 2 M $SnCl_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 $CHCl_3$/MeOH as eluant to give 820 mg (40%) of 6-(3,5-difluorophenyl)-2-methyl-4-piperidylpyrrolo[3,2-d]pyrimidine as a brown colored gummy solid. This compound (820 mg, 2.52 mmol) was dissolved in 5:1 EtOAc/MeOH (40 mL) and heated to boiling. To the hot solution was added 1 M ethereal HCl (2.50 mL, 2.50 mmol). The solution was allowed to cool to room temperature. The resulting crystals were collected by filtration, washed with EtOAc (2×10 mL), $Et_2O$ (3×15 mL) and dried under vacuum at 60° C. to give 440 mg (19%) of the title compound as pale yellow colored needles. Mp: >280° C. $^1H$ NMR (DMSO-$d_6$; 500 MHz): δ 1.61 (br s, 6), 2.47 (s, 3), 3.97 (br s, 4), 6.97 (s, 1), 7.28 (tt, 1, J=2.1, 7.1), 7.74 (d, 2, J=6.6), 11.93 (s, 1), 14.35 (s, 1). MS m/z: 329 (M+1 for free base). Anal. Calcd for $C_{18}H_{18}F_2N_4 \cdot HCl \cdot H_2O$: C, 56.47; H, 5.53; N, 14.64; Cl, 9.26. Found: C, 56.52; H, 5.54; N, 14.74; Cl, 9.38.

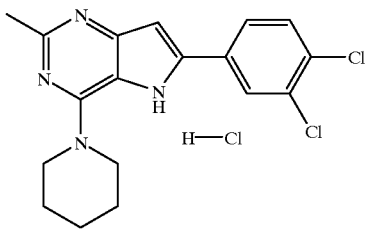

EXAMPLE 118
6-(3,4-Dichlorophenyl)-2-methyl-4-piperidylpyrrolo[3,2-d]pyrimidine Hydrochloride Monohydrate.

Using the method described in Example 30 by employing [1-(3,5-dichlorophenyl)vinyl]pyrrolidine (freshly prepared before use from 3',4'-dichloro acetophenone (Aldrich Chemical Company), pyrrolidine and TiCl$_4$ (1.09 g, 4.50 mmol), 2-methyl-4,6-dichloro-5-nitropyrimidine (Example 76(b)) (0.90 g, 4.50 mmol), N,N-diisopropylethylamine (0.8 mL, 4.50 mmol), piperidine (0.7 mL, 7.2 mmol), NEt$_3$ (0.7 mL) and SnCl$_2$ (14 mL of a 2 M soln in DMF). The residue was purified by flash chromatography on silica gel with 95:5 CHCl$_3$/MeOH as eluant to give 86 mg (5%) of 6-(3,4-dichlorophenyl)-2-methyl-4-piperidylpyrrolo[3,2-d]pyrimidine as a tan colored oil. This material (86 mg, 0.24 mmol) was dissolved in 5:1 EtOAc/MeOH (40 mL) and heated to boiling. To the hot solution was added 1 M ethereal HCl (250 mL, 0.24 mmol). The solution was left to cool to room temperature. The resulting crystals were collected by filtration, washed with EtOAc (2×10 mL), Et$_2$O (3×15 mL) and dried under vacuum at 60° C. to give 31 mg (2%) of the title compound as a brown colored solid. Mp: 265–268° C. $^1$H NMR (DMSO-d$_6$; 500 MHz): δ 1.71 (br s, 6), 2.57 (s, 3), 4.02 (s, 4), 7.06 (s, 1), 7.83 (d, 1, J=8.3), 8.00 (dd, 1, J=1.7, 8.5), 8.34 (d, 1, J=1.7), 12.04 (s, 1), 14.32 (s, 1). MS m/z: 361 (M+1 for free base). Anal. Calcd for C$_{18}$H$_{18}$Cl$_2$N$_4$.HCl.H$_2$O: C, 52.00; H, 5.09; N, 13.48; Cl, 25.58. Found: C, 51.65; H, 5.00; N, 13.24; Cl, 25.49.

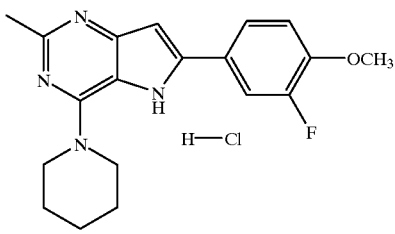

EXAMPLE 119
2-Fluoro-1-methoxy-4-[2-methyl-4-piperidylpyrrolo[4,5-d]pyrimidin-6-yl]benzene Hydrochloride Hydrate.

Using the method described in Example 30 by employing 2-fluoro-1-methoxy-4-(1-pyrrolidinylvinyl) benzene (freshly prepared before use from 3-fluoro-4-methoxyacetophenone (Aldrich Chemical Company), pyrrolidine and TiCl$_4$ (1.37 g, 6.19 mmol), 2-methyl-4,6-dichloro-5-nitropyrimidine (Example 76(b)) (1.30 g, 6.19 mmol), N,N-diisopropylethylamine (1.1 mL, 6.19 mmol), piperidine (1.0 mL, 9.9 mmol), NEt$_3$ (1.1 mL) and SnCl$_2$ (19 mL of a 2 M soln in DMF). In this example the 2 M SnCl$_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 CHCl$_3$/MeOH as eluant to give 481 mg (23%) of 2-fluoro-1-methoxy-4-[2-methyl-4-piperidylpyrrolo[4,5-d]pyrimidin-6-yl]benzene as a beige colored solid. This compound (481 mg, 1.41 mmol) was dissolved in 4:1 EtOAc/MeOH (30 mL) and heated to boiling. To the hot solution was added 1 M ethereal HCl (1.40 mL, 1.40 mmol). The solution was allowed to cool to room temperature. The resulting crystals were collected by filtration, washed with EtOAc (2×10 mL), Et$_2$O (3×15 mL) and dried under vacuum at 60° C. to give 372 mg (16%) of the title compound as a beige colored solid. Mp: 262–264° C. $^1$H NMR (DMSO-d$_6$; 500 MHz): δ 1.69 (br s, 6), 2.56 (s, 3), 3.92 (s, 3), 4.05 (br t, 4, J=5.4), 6.59 (s, 1), 7.33 (t, 1, J=8.8), 7.80 (d, 1, J=8.6), 7.96 (dd, 1, J=2.0, 12.7), 11.82 (s, 1), 14.20 (s, 1). MS m/z: 341 (M+1 for free base). Anal. Calcd for C$_{19}$H$_{21}$FN$_4$O.HCl.0.5H$_2$O: C, 59.08; H, 5.96; N, 14.51; Cl, 9.08. Found: C, 58.90; H, 5.89; N, 14.46; Cl, 9.30.

EXAMPLE 120

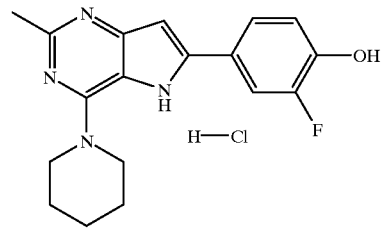

2-Fluoro-4-[2-methyl-4-pyridylpyrrolo[4,5-d]pyrimidin-6-yl]phenol Hydrochloride Hydrate.

To a −78° C. solution of 2-fluoro-1-methoxy-4-[2-methyl-4-piperidylpyrrolo[4,5-d]pyrimidin-6-yl]benzene (Example 119) (0.80 g, 2.35 mmol) in CH$_2$Cl$_2$ (40 mL) under a N$_2$ atmosphere was added 1 M BBr$_3$ (4.7 mL, 4.70 mmol). The reaction mixture was allowed to warm to room temperature. The mixture was stirred at room temperature for an additional 20 h. The reaction mixture was then poured onto ice-water (200 mL) and the pH of the aqueous solution was adjusted to pH 9 with the addition of NEt$_3$ (4 mL). The resulting mixture was stirred at room temperature for 2 h. The solid which formed was removed by filtration and dicarded. The remaining solution was transferred to a separatory funnel. The organic solution was separated, washed with H$_2$O (100 mL), saturated NaCl (100 mL), dried (MgSO$_4$), filtered and concentrated under reduced pressure to afford 483 mg (62%) of 2-fluoro-4-(2-methyl-4-pyridylpyrrolo[4,5-d]pyrimidin-6-yl)phenol as a pale yellow colored solid. This compound (481 mg, 1.50 mmol) was dissolved in 4:2:1 EtOAc/MeOH/CH$_2$Cl$_2$ (50 mL) and heated to boiling. To the hot solution was added 1 M ethereal HCl (1.50 mL, 1.50 mmol). The solution was allowed to cool to room temperature. The resulting solid was collected by filtration, washed with EtOAc (2×10 mL), Et$_2$O (3×15 mL) and dried under vacuum at 60° C. to give 315 mg (37%) of the title compound as a pale yellow colored solid. Mp: >280° C. $^1$H NMR (DMSO-d$_6$; 400 MHz): δ 1.63 (br s, 6), 2.49 (s, 3), 3.96 (br s, 4), 6.76 (s, 1), 7.06 (dt, 1, J=1.9, 8.7), 7.58 (d, 1, J=8.5), 7.83 (dd, 1, J=1.9, 12.5), 10.47 (s, 1), 11.79 (s, 1), 14.12 (s, 1). MS m/z: 327 (M+1 for free base). Anal. Calcd for C$_{18}$H$_{19}$FN$_4$O.HCl.1.5H$_2$O: C, 55.45; H, 5.95; N, 14.37; Cl, 9.09. Found: C, 55.49; H, 5.87; N, 14.07; Cl, 9.03.

EXAMPLE 121

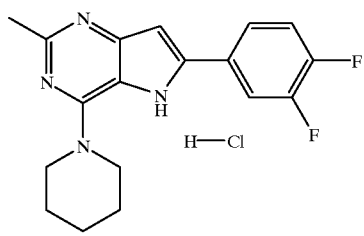

6-(3,4-Difluorophenyl)-2-methyl-4-piperidylpyrrolo[3,2-d]pyrimidine Hydrochloride Hydrate.

Using the method described in Example 30 by employing [1-(3,4-difluorophenyl)vinyl]pyrrolidine (freshly prepared before use from 3',4'-difluoro acetophenone (Aldrich Chemical Company), pyrrolidine and TiCl$_4$ (1.38 g, 6.60 mmol), 2-methyl-4,6-dichloro-5-nitropyrimidine (Example 76(b)) (1.40 g, 6.60 mmol), N,N-diisopropylethylamine (1.1 mL, 6.60 mmol), piperidine (1.0 mL, 10.6 mmol), NEt$_3$ (1.1 mL) and SnCl$_2$ (20 mL of a 2 M soln in DMF). The residue was purified by flash chromatography on silica gel with 95:5 CHCl$_3$/MeOH as eluant to give 395 mg (18%) of 6-(3,4-difluorophenyl)-2-methyl-4-piperidylpyrrolo[3,2-d]pyrimidine as a beige colored solid. This material (395 mg, 1.20 mmol) was dissolved in 10:1 EtOAc/MeOH (40 mL) and heated to boiling. To the hot solution was added 1 M ethereal HCl (1.20 mL, 1.20 mmol). The solution was left to cool to room temperature. The resulting solid was collected by filtration, washed with EtOAc (2×10 mL), Et$_2$O (3×15 mL) and dried under vacuum at 60° C. to give 159 mg (6%) of the title compound as beige colored solid. Mp: 243–245° C. $^1$H NMR (DMSO-d$_6$; 500 MHz): δ 1.71 (br s, 6), 2.57 (s, 3), 4.06 (t, 4, J=5.0), 6.85 (s, 1), 7.63 (q, 1, J=10.0), 7.89 (d, 1, J=8.1), 8.19 (dt, 1, J=1.3, 9.5), 12.01 (s, 1), 14.39 (s, 1). MS m/z: 329 (M+1 for free base). Anal. Calcd for C$_{18}$H$_{18}$F$_2$N$_4$.HCl.1.25H$_2$O: C, 55.81; H, 5.60; N, 14.47; Cl, 9.15. Found: C, 55.95; H, 5.25; N, 14.62; Cl, 9.26.

EXAMPLE 122

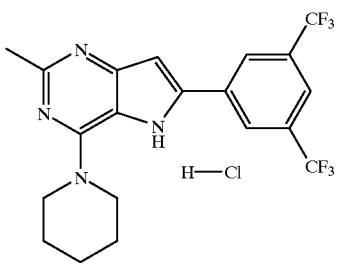

6-((3,5-bis(Trifluoromethyl)phenyl)-2-methyl-4-piperidylpyrrolo[3,2-d]pyrimidine Hydrochloride.

Using the method described in Example 30 by employing [1-(3,5-bis(trifluoromethyl)phenyl)vinyl]pyrrolidine (freshly prepared before use from 3',5'-bis(trifluoromethyl) acetophenone (Aldrich Chemical Company), pyrrolidine and TiCl$_4$ (1.33 g, 4.30 mmol), 2-methyl-4,6-dichloro-5-nitropyrimidine (Example 76(b)) (0.90 g, 4.30 mmol), N,N-diisopropylethylamine (0.7 mL, 4.30 mmol), piperidine (0.7 mL, 6.90 mmol), NEt$_3$ (1.0 mL) and SnCl$_2$ (13 mL of a 2 M soln in DMF). The residue was purified by flash chromatography on silica gel with 95:5 CHCl$_3$/MeOH as eluant to give 232 mg (13%) of 6-((3,5-bis(trifluoromethyl)phenyl)-2-methyl-4-piperidylpyrrolo[3,2-d]pyrimidine as a brown colored oil. This material (232 mg, 0.54 mmol) was dissolved in 10:1 EtOAc/MeOH (30 mL) and heated to boiling. To the hot solution was added 1 M ethereal HCl (0.60 mL, 0.60 mmol). The solution was left to cool to room temperature. The resulting solid was collected by filtration, washed with EtOAc (2×10 mL), Et$_2$O (3×15 mL) and dried under vacuum at 60° C. to give 57 mg (3%) of the title compound as a beige colored solid. Mp: >280° C. $^1$H NMR (DMSO-d$_6$; 500 MHz): δ 1.73 (br s, 6), 2.60 (s, 3), 4.10 (s, 4), 7.30 (s, 1), 8.22 (s, 1), 8.68 (s, 2), 12.27 (s, 1), 14.43 (s, 1). MS m/z: 429 (M+1 for free base). Anal. Calcd for C$_{20}$H$_{18}$F$_6$N$_4$.HCl: C, 51.68; H, 4.12; N, 12.05; Cl, 7.63. Found: C, 51.51; H, 4.17; N, 11.96; Cl, 7.82.

EXAMPLE 123

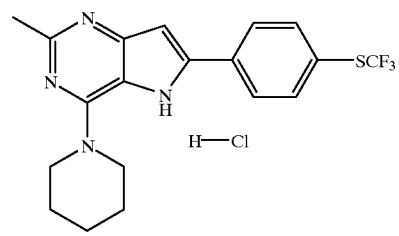

Trifluoro[4-(2-methyl-4-piperidylpyrrolo[4,5-d]pyrimidin-6-yl)phenylthio]methane Hydrochloride Monohydrate.

Using the method described in Example 30 by employing trifluoro[4-(1-pyrrolidinylvinyl)phenylthio]methane (freshly prepared before use from 4'-(trifluoro methylthio) acetophenone (Oakwood Products Inc.), pyrrolidine and TiCl$_4$ (1.96 g, 7.17 mmol), 2-methyl-4,6-dichloro-5-nitropyrimidine (Example 76(b)) (1.50 g, 7.17 mmol), N,N-diisopropylethylamine (1.2 mL, 7.17 mmol), piperidine (1.1 mL, 11.5 mmol), NEt$_3$ (1.1 mL) and SnCl$_2$ (21 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 742 mg (26%) of trifluoro[4-(2-methyl-4-piperidylpyrrolo[4,5-d]pyrimidin-6-yl)phenylthio]methane as a beige colored foam. This compound (741 mg, 1.90 mmol) was dissolved in 10:1 EtOAc/MeOH (60 mL) and heated to boiling. To the hot solution was added 1 M ethereal HCl (1.90 mL, 1.90 mmol). The solution was allowed to cool to room temperature. The resulting crystals were collected by filtration, washed with EtOAc (2×10 mL), Et$_2$O (3×15 mL) and dried under vacuum at 60° C. to give 418 mg (13%) of the title compound as white colored needles. Mp: 270–272° C. $^1$H NMR (DMSO-d$_6$; 400 MHz): δ 1.65 (br s, 6), 2.51 (s, 3), 4.00 (br s, 4), 6.96 (s, 1), 7.84 (d, 2, J=8.1), 8.06 (d, 2, J=8.2), 12.12 (s, 1), 14.39 (s, 1). MS m/z: 393 (M+1 for free base). Anal. Calcd for C$_{19}$H$_{19}$F$_3$N$_4$S.HCl.H$_2$O: C, 51.06; H, 4.96; N, 12.54; Cl, 7.93. Found: C, 51.02; H, 4.98; N, 12.46; Cl, 8.02.

EXAMPLE 124

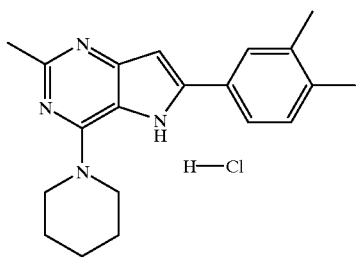

6-(3,4-Dimethylphenyl)-2-methyl-4-piperidylpyrrolo[3,2-d]pyrimidine Hydrochloride Hydrate.

Using the method described in Example 30 by employing [1-(3,4-dimethylphenyl)vinyl]pyrrolidine (freshly prepared before use from 3,4-dimethyl acetophenone (Aldrich Chemical Company), pyrrolidine and $TiCl_4$ (1.22 g, 6.07 mmol), 2-methyl-4,6-dichloro-5-nitropyrimidine (Example 76(b)) (1.30 g, 6.07 mmol), N,N-diisopropylethylamine (1.1 mL, 6.07 mmol), piperidine (1.0 mL, 9.7 mmol), $NEt_3$ (1.1 mL) and $SnCl_2$ (18 mL of a 2 M soln in DMF). In this example the reaction mixture was stirred at room temperature for 48 h after the addition of 2 M $SnCl_2$. The residue was mpurified by flash chromatography on silica gel with 95:5 $CHCl_3$/MeOH as eluant to give 605 mg (31%) of 6-(3,4-dimethylphenyl)-2-methyl-4-piperidylpyrrolo[3,2-d]pyrimidine as a beige colored solid. This material (605 mg, 1.88 mmol) was dissolved in 5:1 EtOAc/MeOH (35 mL) and heated to boiling. To the hot solution was added 1 M ethereal HCl (1.90 mL, 1.90 mmol). The solution was left to cool to room temperature. The resulting crystals were collected by filtration, washed with EtOAc (2×10 mL), $Et_2O$ (3×15 mL) and dried under vacuum at 60° C. to give 518 mg (24%) of the title compound as a beige colored powder. Mp: 198–201° C. $^1H$ NMR (DMSO-$D_6$; 400 MHz): δ 1.70 (br s, 6), 2.30 (s, 3), 2.33 (s, 3), 2.56 (s, 3), 4.05 (s, 4), 6.84 (s, 1), 7.32 (d, 1, J=7.9), 7.70 (d, 1, J=7.8), 7.74 (s, 1), 11.91 (s, 1), 14.38 (s, 1). MS m/z: 321 (M+1 for free base). Anal. Calcd for $C_{20}H_{24}N_4$·HCl·0.75$H_2O$: C, 64.95; H, 7.17; N, 15.15; Cl, 9.47. Found: C, 65.13; H, 7.11; N, 14.98; Cl, 9.54.

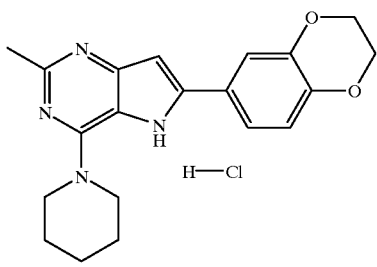

EXAMPLE 125

6-(2-Methyl-4-piperidylpyrrolo[4,5-d]pyrimidin-6-yl)-2H,3H-benzo[e]1,4-dioxane Hydrochloride Monohydrate.

Using the method described in Example 30 by employing 6-(1-pyrrolidinylvinyl)-2H,3H-benzo[e]1,4-dioxane (freshly prepared before use from 1,4-benzodioxan-6-yl methyl ketone (Aldrich Chemical Company), pyrrolidine and $TiCl_4$ (1.75 g, 7.58 mmol), 2-methyl-4,6-dichloro-5-nitropyrimidine (Example 76(b)) (1.62 g, 7.58 mmol), N,N-diisopropylethylamine (1.3 mL, 7.58 mmol), piperidine (1.2 mL, 12.2 mmol), $NEt_3$ (1.3 mL) and $SnCl_2$ (23 mL of a 2 M soln in DMF). In this example the reaction mixture was stirred at room temperature for 48 h after the addition of 2 M $SnCl_2$. The residue was purified by flash chromatography on silica gel with 95:5 $CHCl_3$/MeOH as eluant to give 781 mg (29%) of 6-(2-methyl-4-piperidylpyrrolo[4,5-d]pyrimidin-6-yl)-2H,3H-benzo[e]1,4-dioxane as a beige colored solid. This material (780 mg, 2.25 mmol) was dissolved in 5:1 EtOAc/MeOH (70 mL) and heated to boiling. To the hot solution was added 1 M ethereal HCl (2.30 mL, 2.30 mmol). The solution was left to cool to room temperature. The resulting crystals were collected by filtration, washed with EtOAc (2×10 mL), $Et_2O$ (3×15 mL) and dried under vacuum at 60° C. to give 690 mg (23%) of the title compound as a beige colored powder. Mp: >280° C. $^1H$ NMR (DMSO-$d_6$; 400 MHz): δ 1.70 (br s, 6), 2.56 (s, 3), 4.03 (s, 4), 4.32 (s, 4), 6.81 (s, 1), 7.03 (d, 1, J=8.5), 7.46 (dd, 1, J=2.2, 8.5), 7.55 (d, 1, J=2.1), 11.81 (s, 1), 14.37 (s, 1). MS m/z: 351 (M+1 for free base). Anal. Calcd for $C_{20}H_{22}N_4O_2$·HCl·$H_2O$: C, 59.32; H, 6.22; N, 13.84; Cl, 8.76. Found: C, 59.23; H, 6.28; N, 13.74; Cl, 8.65.

EXAMPLE 126

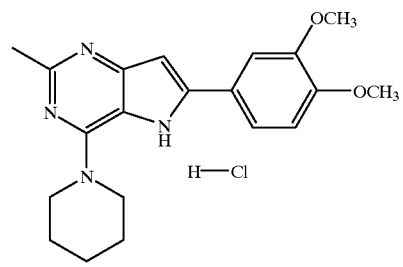

1,2-Dimethoxy-4-(2-methyl-4-piperidylpyrrolo[4,5-d]pyrimidin-6-yl)benzene Hydrochloride Hydrate.

Using the method described in Example 30 by employing 1,2-dimethoxy-4-(1-pyrrolidinylvinyl)benzene (freshly prepared before use from 3,4-dimethoxy acetophenone (Aldrich Chemical Company), pyrrolidine and $TiCl_4$ (1.71 g, 7.34 mmol), 2-methyl-4,6-dichloro-5-nitropyrimidine (Example 76(b)) (1.50 g, 7.34 mmol), N,N-diisopropylethylamine (1.3 mL, 7.34 mmol), piperidine (1.2 mL, 11.7 mmol), $NEt_3$ (1.3 mL) and $SnCl_2$ (22 mL of a 2 M soln in DMF). In this example the reaction mixture was stirred at room temperature for 48 h after the addition of 2 M $SnCl_2$. The residue was purified by flash chromatography on silica gel with 95:5 $CHCl_3$/MeOH as eluant to give 1.51 g (59%) of 1,2-dimethoxy-4-(2-methyl-4-piperidylpyrrolo[4,5-d]pyrimidin-6-yl)benzene as a brown colored solid. This material (1.51 g, 4.25 mmol) was dissolved in 5:1 EtOAc/MeOH (90 mL) and heated to boiling. To the hot solution was added 1 M ethereal HCl (4.30 mL, 4.30 mmol). The solution was left to cool to room temperature. The resulting crystals were collected by filtration, washed with EtOAC (2×10 mL), $Et_2O$ (3×15 mL) and dried under vacuum at 60° C. to give 0.95 g (34%) of the title compound as a white colored solid. Mp: 268–270° C. $^1H$ NMR (DMSO-$d_6$; 400 MHz): δ 1.71 (br s, 6), 2.57 (s, 3), 3.83 (se 3), 3.89 (s, 3), 4.05 (s, 4), 6.85 (s, 1), 7.13 (d, 1, J=8.4), 7.50–7.54 (m, 2), 11.90 (s, 1), 14.30 (s, 1). MS m/z: 353 (M+1 for free base). Anal. Calcd for $C_{20}H_{24}N_4O_2$·HCl·1.25$H_2O$: C, 58.33; H, 6.68; N, 13.61; Cl, 8.51. Found: C, 58.31; H, 6.70; N, 13.54; Cl, 8.49.

EXAMPLE 127

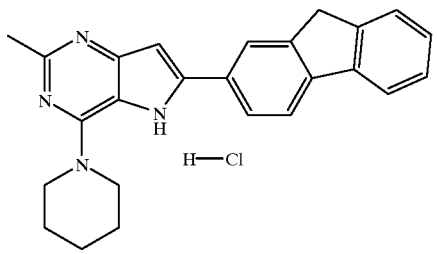

6-Fluoren-2-yl-2-methyl-4-piperidylpyrrolo[3,2-d]pyrimldine Hydrochloride Hydrate.

Using the method described in Example 30 by employing (1-fluoren-2-ylvinyl)pyrrolidine (freshly prepared before use from 2-acetylfluorene (Aldrich Chemical Company), pyrrolidine and TiCl$_4$ (1.27 g, 4.86 mmol), 2-methyl-4,6-dichloro-5-nitropyrimidine (Example 76(b)) (1.01 g, 4.86 mmol), N,N-diisopropylethylamine (0.9 mL, 4.86 mmol), piperidine (0.8 mL, 7.8 mmol), NEt$_3$ (1.0 mL) and SnCl$_2$ (15 mL of a 2 M soln in DMF). In this example the reaction mixture was stirred at room temperature for 48 h after the addition of 2 M SnCl$_2$. The residue was purified by flash chromatography on silica gel with 95:5 CHCl$_3$/MeOH as eluant to give 325 mg (18%) of 6-fluoren-2-yl-2-methyl-4-piperidylpyrrolo[3,2-d]pyrimidine as a beige colored solid. This material (321 mg, 0.86 mmol) was dissolved in 1:10 EtOAc/MeOH (60 mL) and heated to boiling. To the hot solution was added 1 M ethereal HCl (0.90 mL, 0.90 mmol). The solution was left to cool to room temperature. The resulting crystals were collected by filtration, washed with EtOAc (2×10 mL), Et$_2$O (3×15 mL) and dried under vacuum at 60° C. to give 138 mg (7%) of the title compound as a beige colored solid. Mp: >280° C. $^1$H NMR (DMSO-d$_6$; 400 MHz): δ 1.73 (br s, 6), 2.57 (s, 3), 4.05 (s, 2), 4.08 (br s, 4), 6.97 (s, 1), 7.39 (t, 1, J=7.2), 7.44 (t, 1, J=7.0), 7.66 (d, 1, J=7.2), 8.02 (d, 2, J=7.7), 8.10 (d, 1, J=8.0), 8.21 (s, 1), 12.01 (s, 1), 14.27 (s, 1). MS m/z: 381 (M+1 for free base). Anal. Calcd for C$_{25}$H$_{24}$N$_4$.HCl.1.5H$_2$O: C, 67.58; H, 6.31; N, 12.61; Cl, 7.88. Found: C, 67.77; H, 6.25; N, 12.54; Cl, 8.06.

EXAMPLE 128

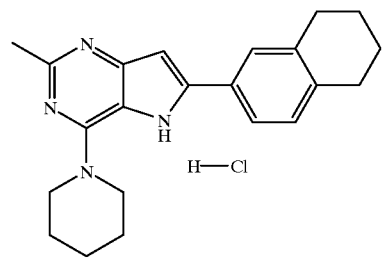

2-Methyl-4-piperidyl-6-(2-5,6,7,8-tetrahydronaphthyl)pyrrolo[3,2-d]pyrimidine Hydrochloride Dihydrate.

Using the method described in Example 30 by employing ((1-(2-5,6,7,8-tetrahydronaphthyl)vinyl) pyrrolidine (freshly prepared before use from 6-acetyltetralin (Lancaster Chemical Company), pyrrolidine and TiCl$_4$ (1.37 g, 6.03 mmol), 2-methyl-4,6-dichloro-5-nitropyrimidine (Example 76(b)) (1.20 g, 6.03 mmol), N,N-diisopropylethylamine (1.0 mL, 6.03 mmol), piperidine (1.0 mL, 9.6 mmol), NEt$_3$ (1.0 mL) and SnCl$_2$ (18 mL of a 2 M soln in DMF). In this example the reaction mixture was stirred at room tempera-ture for 48 h after the addition of 2 M SnCl$_2$. The residue was purified by flash chromatography on silica gel with 95:5 CHCl$_3$/MeOH as eluant to give 692 mg (33%) of 2-methyl-4-piperidyl-6-(2-5,6,7,8-tetrahydronaphthyl) pyrrolo[3,2-d]pyrimidine as a white-colored solid. This material (692 mg, 2.00 mmol) was dissolved in 5:1 EtOAc/MeOH (40 mL) and heated to boiling. To the hot solution was added 1 M ethereal HCl (2.00 mL, 2.00 mmol). The solution was left to cool to room temperature. The resulting crystals were collected by filtration, washed with EtOAc (2×10 mL), Et$_2$O (3×15 mL) and dried under vacuum at 60° C. to give 563 mg (24%) of the title compound as a faint yellow colored solid. Mp: 175–177° C. $^1$H NMR (DMSO-d$_6$; 400 MHz): δ 1.71 (br s, 6), 1.78 (m, 4), 2.57 (s, 3), 2.82 (d, 4, J=16.0), 4.06 (br s, 4), 6.93 (s, 1), 7.23 (d, 1, J=8.6), 7.65–7.67 (m, 2), 11.92 (s, 1), 14.45 (s, 1). MS m/z: 347 (M+1 for free base). Anal. Calcd for C$_{22}$H$_{26}$N$_4$.HCl.2.0H$_2$O: C, 63.02; H, 7.40; N, 13.37; Cl, 8.35. Found: C, 63.18; H, 7.43; N, 13.41; Cl, 8.62.

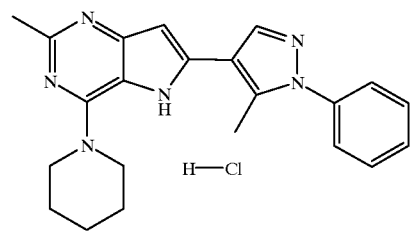

EXAMPLE 129

2-Methyl-6-(5-methyl-1-phenylpyrazol-4-yl)-4-piperidyl pyrrolo[3,2-d]pyrimidine Hydrochloride Hydrate.

Using the method described in Example 30 by employing 5-methyl-1-phenyl-4-(1-pyrrolidinylvinyl) pyrazole (freshly prepared before use from 4-acetyl-5-methyl-1-phenylpyrazole (Maybridge Chemical Company), pyrrolidine and TiCl$_4$ (1.30 g, 5.14 mmol), 2-methyl-4,6-dichloro-5-nitropyrimidine (Example 76(b)) (1.00 g, 5.14 mmol), N,N-diisopropylethylamine (1.0 mL, 5.14 mmol), piperidine (0.8 mL, 8.2 mmol), NEt$_3$ (1.0 mL) and SnCl$_2$ (15 mL of a 2 M soln in DMF). In this example the reaction mixture was stirred at room temperature for 48 h after the addition of 2 M SnCl$_2$. The residue was purified by flash chromatography on silica gel with 95:5 CHCl$_3$/MeOH as eluant to give 701 mg (37%) of 2-methyl-6-(5-methyl-1-phenylpyrazol-4-yl)-4-piperidyl pyrrolo[3,2-d]pyrimidine as a cream colored solid. This material (700 mg, 1.89 mmol) was dissolved in 4:1 EtOAc/MeOH (40 mL) and heated to boiling. To the hot solution was added 1 M ethereal HCl (1.90 mL, 1.90 mmol). The solution was left to cool to room temperature. The resulting crystals were collected by filtration, washed with EtOAc (2×10 mL), Et$_2$O (3×15 mL) and dried under vacuum at 60° C. to give 637 mg (31%) of the title compound as white colored long needles. Mp: >280° C. $^1$H NMR (DMSO-d$_6$; 400 MHz): δ 1.71 (br s, 6), 2.48 (s, 3), 2.57 (s, 3), 4.04 (br s, 4), 6.57 (s, 1), 7.48–7.62 (m, 5), 8.16 (s, 1), 11.89 (s, 1), 14.13 (s, 1). MS m/z: 373 (M+1 for free base). Anal. Calcd for C$_{22}$H$_{24}$N$_6$.HCl.0.25H$_2$O: C, 63.86; H, 6.17; N, 20.32; Cl, 8.47. Found: C, 64.11; H, 6.18; N, 20.43; Cl, 8.57.

EXAMPLE 130

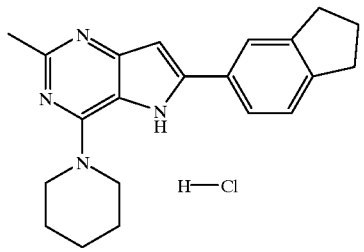

6-Indan-5-yl-2-methyl-4-piperidylpyrrolo[3,2-d]pyrimidine Hydrochloride Monohydrate.

Using the method described in Example 30 by employing (1-indan-5-ylvinyl)pyrrolidine (freshly prepared before use from 5-acetylindane (Avocado Chemical Company), pyrrolidine and TiCl$_4$ (1.35 g, 6.34 mmol), 2-methyl-4,6-dichloro-5-nitropyrimidine (Example 76(b)) (1.35 g, 6.34 mmol), N,N-diisopropylethylamine (1.1 mL, 6.34 mmol), piperidine (1.0 mL, 10.1 mmol), NEt$_3$ (1.1 mL) and SnCl$_2$ (19 mL of a 2 M soln in DMF). In this example the 2 M SnCl$_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 CHCl$_3$/MeOH as eluant to give 913 mg (43%) of 6-indan-5-yl-2-methyl-4-piperidylpyrrolo[3,2-d]pyrimidine as a beige colored solid. This compound (909 mg, 2.75 mmol) was dissolved in 5:1 EtOAc/MeOH (50 mL) and heated to boiling. To the hot solution was added 1 M ethereal HCl (2.80 mL, 2.80 mmol). The solution was allowed to cool to room temperature. The resulting solid was collected by filtration, washed with EtOAc (2×10 mL), Et$_2$O (3×15 mL) and dried under vacuum at 60° C. to give 601 mg (26%) of the title compound as a beige colored solid. Mp: 164–167° C. $^1$H NMR (DMSO-d$_6$; 500 MHz): δ 1.71 (br s, 6), 2.07 (quintet, 2, J=7.4), 2.56 (s, 3), 2.94 (quintet, 4, J=7.4), 4.05 (br s, 4), 6.83 (s, 1), 7.41 (d, 1, J=7.8), 7.72 (d, 1, J=8.0), 7.81 (s, 1), 11.88 (s, 1), 14.31 (s, 1). MS m/z: 333 (M+1 for free base). Anal. Calcd for C$_{21}$H$_{24}$N$_4$.HCl.H$_2$O: C, 65.18; H, 7.03; N, 14.48; Cl, 9.16. Found: C, 64.91; H, 6.96; N, 14.35; Cl, 9.22.

EXAMPLE 131

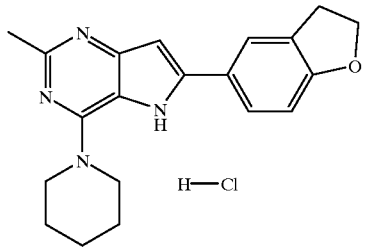

5-[2-Methyl-4-piperidylpyrrolo[4,5-d]pyrimidin-6-yl]-2,3-dihydrobenzo[b]furan Hydrochloride Hydrate.

Using the method described in Example 30 by employing 5-(1-pyrrolidinylvinyl)-2,3-dihydrobenzo[b]furan (freshly prepared before use from 5-acetyl-2,3-dihydrobenzo[b]furan (Avocado Chemical Company), pyrrolidine and TiCl$_4$ (1.20 g, 5.58 mmol), 2-methyl-4,6-dichloro-5-nitropyrimidine (Example 76(b)) (1.20 g, 5.58 mmol), N,N-diisopropylethylamine (1.0 mL, 5.58 mmol), piperidine (0.9 mL, 8.9 mmol), NEt$_3$ (1.1 mL) and SnCl$_2$ (17 mL of a 2 M soln in DMF). In this example the 2 M SnCl$_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 CHCl$_3$/MeOH as eluant to give 686 mg (37%) of 5-[2-methyl-4-piperidyl pyrrolo[4,5-d]pyrimidin-6-yl]-2,3-dihydrobenzo[b]furan as a beige colored solid. This compound (686 mg, 2.05 mmol) was dissolved in 3:1 EtOAc/MeOH (50 mL) and heated to boiling. To the hot solution was added 1 M ethereal HCl (2.10 mL, 2.10 mmol). The solution was allowed to cool to room temperature. The resulting solid was collected by filtration, washed with EtOAc (2×10 mL), Et$_2$O (3×15 mL) and dried under vacuum at 60° C. to give 591 mg (29%) of the title compound as a beige colored powder. Mp: 170–172° C. $^1$H NMR (DMSO-d$_6$; 500 MHz): δ 1.69 (br s, 6), 2.56 (s, 3), 3.29 (t, 2, J=8.7), 4.04 (br t, 4, J=5.4), 4.63 (t, 2, J=8.7), 6.76 (s, 1), 6.94 (d, 1, J=8.3), 7.74 (d, 1, J=8.3), 7.85 (s, 1), 11.78 (s, 1), 14.21 (s, 1). MS m/z: 335 (M+1 for free base). Anal. Calcd for C$_{20}$H$_{22}$N$_4$.HCl.1.25H$_2$O: C, 61.01; H, 6.48; N, 14.23; Cl, 8.90. Found: C, 61.17; H, 6.64; N, 14.19; Cl, 8.89.

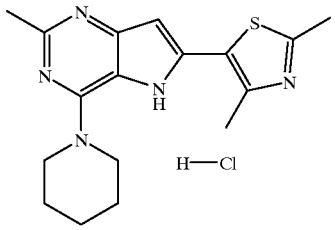

EXAMPLE 132

2,4-Dimethyl-5-[2-methyl-4-piperidylpyrrolo[4,5-d]pyrimidin-6-yl]-1,3-thiazole Hydrochloride Hydrate.

Using the method described in Example 30 by employing 2,4-dimethyl-5-(1-pyrrolidinylvinyl)-1,3-thiazole (freshly prepared before use from 5-acetyl-2,4-dimethylthiazole (Acros Chemical Company), pyrrolidine and TiCl$_4$ (1.35 g, 6.45 mmol), 2-methyl-4,6-dichloro-5-nitropyrimidine (Example 76(b)) (1.32 g, 6.45 mmol), N,N-diisopropylethylamine (1.1 mL, 6.45 mmol), piperidine (1.0 mL, 10.3 mmol), NEt$_3$ (1.1 mL) and SnCl$_2$ (19 mL of a 2 M soln in DMF). In this example the 2 M SnCl$_2$ solution was added to the reaction mixture at 140° C. Heating was then discontinued and the mixture was allowed to cool to room temperature. The mixture was stirred at room temperature for an additional 48 h. The residue was purified by flash chromatography on silica gel with 95:5 CHCl$_3$/MeOH as eluant to give 356 mg (17%) of 2,4-dimethyl-5-[2-methyl-4-piperidylpyrrolo[4,5-d]pyrimidin-6-yl]-1,3-thiazole as a beige colored solid. This compound (356 mg, 1.10 mmol) was dissolved in 4:1 EtOAc/MeOH (20 mL) and heated to boiling. To the hot solution was added 1 M ethereal HCl (1.10 mL, 1.10 mmol). The solution was allowed to cool to room temperature. The resulting solid was collected by filtration, washed with EtOAc (2×10 mL), Et$_2$O (3×15 mL) and dried under vacuum at 60° C. to give 332 mg (16%) of the title compound as a cream colored solid. Mp: 272–273.5° C. $^1$H NMR (DMSO-d$_6$; 500 MHz): δ 1.63 (br d, 6, J=5.4), 2.37 (s, 3), 2.50 (s, 3), 2.62 (s, 3), 3.96 (br t, 4, J=4.7), 6.56 (s, 1), 12.22 (s, 1), 14.44 (s, 1). MS m/z: 328 (M+1 for free base). Anal. Calcd for $C_{17}H_{21}N_5S \cdot 1.2HCl \cdot 1.5H_2O$: C, 51.27; H, 6.38; N, 17.59; Cl, 1041. Found: C, 51.59; H, 6.35; N, 17.48; Cl, 10.68.

EXAMPLE 133

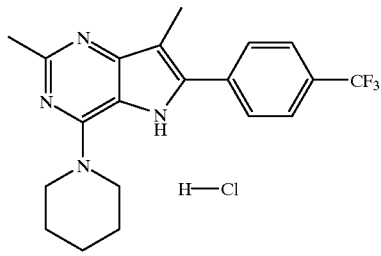

2,7-Dimethyl-4-piperidyl-6-[(4-trifluoromethyl)phenyl]pyrrolo[3,2-d]pyrimidine Hydrochloride.

Using the method described in Example 30 by employing [(1-(4-trifluoromethyl)phenyl)prop-1-enyl]pyrrolidine (freshly prepared before use from 4'-(trifluoromethyl)propiophenone (Aldrich Chemical Company), pyrrolidine and $TiCl_4$ (1.82 g, 7.13 mmol), 2-methyl-4,6-dichloro-5-nitropyrimidine (Example 76(b)) (1.51 g, 7.13 mmol), N,N-diisopropylethylamine (1.1 mL, 7.13 mmol), piperidine (1.1 mL, 11.4 mmol), $NEt_3$ (1.1 mL) and $SnCl_2$ (21 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 382 mg (14%) of 2,7-dimethyl-4-piperidyl-6-[(4-trifluoromethyl)phenyl]pyrrolo[3,2-d]pyrimidine as a beige colored solid. This compound (382 mg, 1.02 mmol) was dissolved in 10:1 EtOAc/MeOH (30 mL) and heated to boiling. To the hot solution was added 1 M ethereal HCl (1.00 mL, 1.00 mmol). The solution was allowed to cool to room temperature. The resulting crystals were collected by filtration, washed with EtOAc (2×10 mL), $Et_2O$ (3×15 mL) and dried under vacuum at 60° C. to give 199 mg (7%) of the title compound as a beige colored powder. Mp: >280° C. $^1H$ NMR (DMSO-$d_6$; 500 MHz): 5 1.69 (br s, 6), 2.35 (s, 3), 2.63 (s, 3), 4.04 (br s, 4), 7.91 (d, 2, J=8.1), 7.96 (d, 2, J=8.2), 12.03 (s, 1), 13.97 (s, 1). MS m/z: 375 (M+1 for free base). Anal. Calcd for $C_{20}H_{21}F_3N_4 \cdot HCl$: C, 58.47; H, 5.40; N, 13.64; Cl, 8.63. Found: C, 58.23; H, 5.38; N, 13.53; Cl, 8.76.

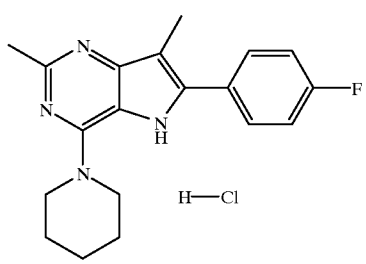

EXAMPLE 134
6-(4-Fluorophenyl)-2,7-dimethyl-4-piperidylpyrrolo[3,2-d]pyrimidine Hydrochloride Hydrate.

Using the method described in Example 30 by employing [(1-(4-fluorophenyl)prop-1-enyl]pyrrolidine (freshly prepared before use from 4'-fluoropropio phenone (Aldrich Chemical Company), pyrrolidine and $TiCl_4$ (1.65 g, 8.04 mmol), 2-methyl-4,6-dichloro-5-nitropyrimidine (Example 76(b)) (1.70 g, 8.04 mmol), N,N-diisopropylethylamine (1.4 mL, 8.04 mmol), piperidine (1.3 mL, 12.9 mmol), $NEt_3$ (1.4 mL) and $SnCl_2$ (24 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCL_3$/MeOH as eluant to give 608 mg (23%) of 6-(4-fluorophenyl)-2,7-dimethyl-4-piperidylpyrrolo[3,2-d]pyrimidine as a brown colored gummy solid. This compound (601 mg, 1.85 mmol) was dissolved in 5:1 EtOAc/MeOH (30 mL) and heated to boiling. To the hot solution was added 1 M ethereal HCl (1.90 mL, 1.90 mmol). The solution was allowed to cool to room temperature. The resulting crystals were collected by filtration, washed with EtOAc (2×10 mL), $Et_2O$ (3×15 mL) and dried under vacuum at 60° C. to give 285 mg (10%) of the title compound as a beige colored powder. Mp: >280° C. $^1H$ NMR (DMSO-$d_6$; 500 MHz): δ 1.68 (br s, 6), 2.32 (s, 3), 2.63 (s, 3), 4.04 (br t, 4, J=5.1), 7.43 (t, 2, J=8.7), 7.72 (dd, 2, J=7.8, 8.1), 11.93 (s, 1), 14.10 (s, 1). MS m/z: 325 (M+1 for free base). Anal. Calcd for $C_{19}H_{21}FN_4 \cdot HCl \cdot 0.3H_2O$: C, 62.30; H, 6.22; N, 15.30; Cl, 9.68. Found: C, 62.14; H, 6.11; N, 15.24; Cl, 9.66.

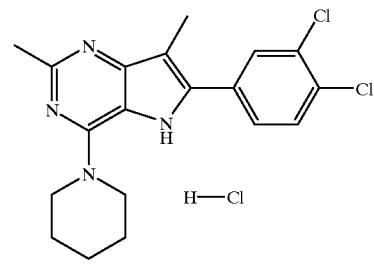

EXAMPLE 135
6-(3,4-Dichlorophenyl)-2,7-dimethyl-4-piperidylpyrrolo[3,2-d]pyrimidine Hydrochloride Hydrate.

Using the method described in Example 30 by employing [(1-(3,4-dichlorophenyl)prop-1-enyl]pyrrolidine (freshly prepared before use from 3',4'-dichloropropiophenone (Aldrich Chemical Company), pyrrolidine and $TiCl_4$ (1.64 g, 6.40 mmol), 2-methyl-4,6-dichloro-5-nitropyrimidine (Example 76(b)) (1.30 g, 6.40 mmol), N,N-diisopropylethylamine (1.1 mL, 6.40 mmol), piperidine (1.0 mL, 10.2 mmol), $NEt_3$ (1.1 mL) and $SnCl_2$ (19 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 511 mg (21%) of 6-(3,4-dichlorophenyl)-2,7-dimethyl-4-piperidylpyrrolo[3,2-d]pyrimidine as a brown colored oil. This compound (511 mg, 1.38 mmol) was dissolved in 5:1 EtOAc/MeOH (30 mL) and heated to boiling. To the hot solution was added 1 M ethereal HCl (1.40 mL, 1.40 mmol). The solution was allowed to cool to room temperature. The resulting crystals were collected by filtration, washed with EtOAc (2×10 mL), $Et_2O$ (3×15 mL) and dried under vacuum at 60° C. to give 90 mg (3%) of the title compound as beige colored needles. Mp: >280° C. $^1H$ NMR (DMSO-$d_6$; 400 MHz): δ 1.64 (br s, 6), 2.27 (s, 3), 2.56 (s, 3), 3.98 (br t, 4, J=5.4), 7.60 (dd, 1, J=2.0, 8.4), 7.78 (d, 1, J=8.4), 7.91 (d, 1, J=2.0), 11.93 (s, 1), 13.97 (s, 1). MS m/z: 375 (M+1 for free base). Anal. Calcd for $C_{19}H_{20}Cl_2N_4 \cdot HCl \cdot 0.5H_2O$: C, 54.23; H, 5.27; N, 13.32; Cl, 25.28. Found: C, 54.35; H, 5.23; N, 13.29; Cl, 25.54.

EXAMPLE 136

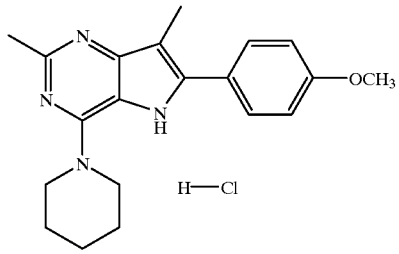

1-[2,7-Dimethyl-4-piperidylpyrrolo[4,5-d]pyrimidin-6-yl]-4-methoxybenzene Hydrochloride.

Using the method described in Example 30 by employing 4-(1-pyrrolidinylprop-1-enyl)-1-methoxy benzene (freshly prepared before use from 4'-methoxy propiophenone (Aldrich Chemical Company), pyrrolidine and $TiCl_4$ (1.77 g, 8.16 mmol), 2-methyl-4,6-dichloro-5-nitropyrimidine (Example 76(b)) (1.70 g, 8.20 mmol), N,N-diisopropylethylamine (1.4 mL, 8.20 mmol), piperidine (1.3 mL, 13.1 mmol), $NEt_3$ (1.4 mL) and $SnCl_2$ (25 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 894 mg (33%) of 1-[2,7-dimethyl-4-piperidylpyrrolo[4,5-d]pyrimidin-6-yl]-4-methoxybenzene as a brown colored foam. This compound (440 mg, 1.31 mmol) was dissolved in 5:1 EtOAc/MeOH (20 mL) and heated to boiling. To the hot solution was added 1 M ethereal HCl (1.30 mL, 1.30 mmol). The solution was allowed to cool to room temperature. The resulting crystals were collected by filtration, washed with EtOAc (2×10 mL), $Et_2O$ (3×15 mL) and dried under vacuum at 60° C. to give 202 mg (14%) of the title compound as a beige colored sandy solid. Mp: >280° C. $^1$H NMR (DMSO-$d_6$; 400 MHz): δ 1.62 (br s, 6), 2.24 (s, 3), 2.55 (s, 3), 3.94 (br s, 4), 7.08 (d, 2, J=8.7), 7.55 (d, 2, J=8.7), 11.76 (s, 1), 13.77 (s, 1). MS m/z: 337 (M+1 for free base). Anal. Calcd for $C_{20}H_{24}N_4O \cdot HCl$: C, 64.42; H, 6.76; N, 15.03; Cl, 9.51. Found: C, 64.40; H, 6.68; N, 15.03; Cl, 9.60.

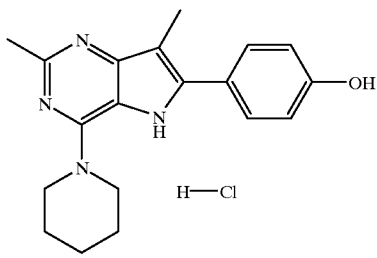

EXAMPLE 137

4-[2,7-Dimethyl-4-piperidylpyrrolo[4,5-d]pyrimidin-6-yl] phenol Hydrochloride Hydrate.

To a -78° C. solution of 1-[2,7-dimethyl-4-piperidylpyrrolo[4,5-d]pyrimidin-6-yl]-4-methoxybenzene (Example 136) (0.45 g, 1.34 mmol) in $CH_2Cl_2$ (20 mL) under a $N_2$ atmosphere was added 1 M $BBr_3$ (2.6 mL, 2.60 mmol). The reaction mixture was allowed to warm to room temperature. The mixture was stirred at room temperature for an additional 20 h. The reaction mixture was then poured onto ice-water (200 mL) and the pH of the aqueous solution was adjusted to pH 9 with the addition of $NEt_3$ (2 mL). The resulting mixture was stirred at room temperature for 2 h. The mixture was transferred to a separatory funnel. The organic solution was separated, washed with $H_2O$ (100 mL), saturated NaCl (100 mL), dried ($MgSO_4$), filtered and concentrated under reduced pressure to afford 272 mg (64%) of 4-[2,7-dimethyl-4-piperidylpyrrolo[4,5-d]pyrimidin-6-yl]phenol as a beige colored solid. This compound (272 mg, 0.80 mmol) was dissolved in 4:2:1 EtOAc/MeOH/$CH_2Cl_2$ (20 mL) and heated to boiling. To the hot solution was added 1 M ethereal HCl (0.80 mL, 0.80 mmol). The solution was allowed to cool to room temperature. The resulting solid was collected by filtration, washed with EtOAc (2×10 mL), $Et_2O$ (3×5 mL) and dried under vacuum at 60° C. to give 107 mg (23%) of the title compound as brown colored crystals. Mp: >280° C. $^1$H NMR (DMSO-$d_6$; 400 MHz): δ 1.61 (br s, 6), 2.24 (s, 3), 2.54 (s, 3), 3.93 (br s, 4), 6.91 (d, 2, J=8.1), 7.43 (d, 2, J=8.4), 9.96 (s, 1), 11.70 (s, 1), 13.94 (s, 1). MS m/z: 323 (M+1 for free base). Anal. Calcd for $C_{19}H_{22}N_4O \cdot HCl \cdot 0.75H_2O$: C, 61.28; H, 6.63; N, 15.05; Cl, 9.52. Found: C, 61.32; H, 6.62; N, 14.96; Cl, 9.45.

EXAMPLE 138

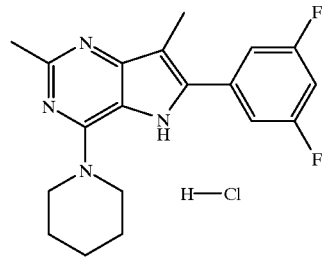

6-(3,5-Difluorophenyl)-2,7-dimethyl-4-piperidylpyrrolo[3,2-d]pyrimidine Hydrochloride Hydrate.

Using the method described in Example 30 by employing (1-(3,5-difluorophenyl)prop-1-enyl) pyrrolidine (freshly prepared before use from 3,5-difluoropropiophenone (Lancaster Chemical Company), pyrrolidine and $TiCl_4$ (2.29 g, 10.3 mmol), 2-methyl-4,6-dichloro-5-nitropyrimidine (Example 76(b)) (2.10 g, 10.3 mmol), N,N-diisopropylethylamine (1.8 mL, 10.3 mmol), piperidine (1.6 mL, 16.4 mmol), $NEt_3$ (1.6 mL) and $SnCl_2$ (31 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 605 mg (17%) of 6-(3,5-difluorophenyl)-2,7-dimethyl-4-piperidylpyrrolo[3,2-d]pyrimidine as a beige colored foam. This compound (600 mg, 1.75 mmol) was dissolved in 10:1 EtOAc/MeOH (20 mL) and heated to boiling. To the hot solution was added 1 M ethereal HCl (1.80 mL, 1.80 mmol). The solution was allowed to cool to room temperature. The resulting crystals were collected by filtration, washed with EtOAc (2×10 mL), $Et_2O$ (3×15 mL) and dried under vacuum at 60° C. to give 291 mg (7%) of the title compound as a beige colored solid. Mp: 242–245° C. $^1$H NMR (DMSO-$d_6$;

400 MHz): δ 1.52 (br s, 6), 2.28 (s, 3), 2.55 (s, 3), 3.97 (br s, 4), 7.36–7.41 (m, 3), 11.89 (s, 1), 13.82 (s, 1). MS m/z: 343 (M+1 for free base). Anal. Calcd for $C_{19}H_{20}F_2N_4 \cdot HCl \cdot 0.5H_2O$: C, 58.83; H, 5.72; N, 14.45; Cl, 9.24. Found: C, 58.86; H, 5.72; N, 14.50; Cl, 9.29.

EXAMPLE 139

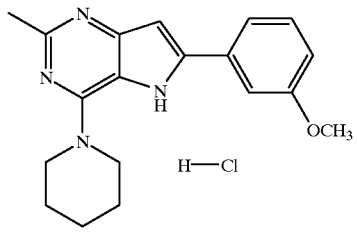

1-[2,7-Dimethyl-4-piperidylpyrrolo[4,5-d]pyrimidin-6-yl]-3-methoxybenzene Hydrochloride.

Using the method described in Example 30 by employing 1-methoxy-3-(1-pyrrolidinylvinyl)benzene (freshly prepared before use from 3-methoxyacetophenone (Aldrich Chemical Company), pyrrolidine and $TiCl_4$ (2.49 g, 12.3 mmol), 2-methyl-4,6-dichloro-5-nitropyrimidine (Example 76(b)) (2.52 g, 12.3 mmol), N,N-diisopropylethylamine (2.1 mL, 12.3 mmol), piperidine (1.9 mL, 19.7 mmol), $NEt_3$ (2.0 mL) and $SnCl_2$ (37 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 1.35 g (34%) of 1-[2,7-dimethyl-4-piperidylpyrrolo[4,5-d]pyrimidin- 6-yl]-3-methoxybenzene as a beige colored solid. This compound (463 mg, 1.43 mmol) was dissolved in 5:1 EtOAc/MeOH (40 mL) and heated to boiling. To the hot solution was added 1 M ethereal HCl (1.50 mL, 1.50 mmol). The solution was allowed to cool to room temperature. The resulting crystals were collected by filtration, washed with EtOAc (2×10 mL), $Et_2O$ (3×15 mL) and dried under vacuum at 60° C. to give 485 mg (32%) of the title compound as a white colored solid. Mp: 241–243° C. $^1H$ NMR (DMSO-$d_6$; 400 MHz): δ 1.64 (br s, 6), 2.50 (s, 3), 3.79 (s, 3), 3.98 (br s, 4), 6.84 (s, 1), 7.03 (dd, 1, J=1.0, 8.3), 7.38 (t, 1, J=3.9), 7.44–7.46 (m, 2), 11.91 (s, 1), 14.36 (s, 1). MS m/z: 323 (M+1 for free base). Anal. Calcd for $C_{19}H_{22}N_4O \cdot HCl \cdot 0.5H_2O$: C, 62.03; H, 6.58; N, 15.23; Cl, 9.64. Found: C, 62.08; H, 6.56; N, 15.17; Cl, 9.75.

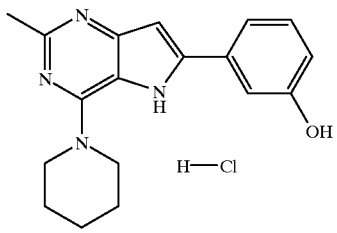

EXAMPLE 140
3-[2-Methyl-4-piperidylpyrrolo[4,5-d]pyrimidin-6-yl]phenol Hydrochloride Hydrate.

To a −78° C. solution of 1-[2,7-dimethyl-4-piperidylpyrrolo[4,5-d]pyrimidin-6-yl]-3-methoxybenzene (Example 139) (0.89 g, 2.76 mmol) in $CH_2Cl_2$ (40 mL) under a $N_2$ atmosphere was added 1 M $BBr_3$ (5.50 mL, 5.50 mmol). The reaction mixture was allowed to warm to room temperature. The mixture was stirred at room temperature for an additional 20 h. The reaction mixture was then poured onto ice-water (200 mL) and the pH of the aqueous solution was adjusted to pH 9 with the addition of $NEt_3$ (2 mL). $CH_2Cl_2$ (60 mL) added and the resulting mixture was stirred at room temperature for 2 h. The mixture was transferred to a separatory funnel. The organic solution was separated, washed with $H_2O$ (100 mL), saturated NaCl (100 mL), dried ($MgSO_4$), filtered and concentrated under reduced pressure to afford 0.90 g (100%) of 3-[2-methyl-4-piperidylpyrrolo[4,5-d]pyrimidin-6-yl]phenol as a beige colored solid. This compound (0.90 mg, 5.00 mmol) was dissolved in 5:1:1 EtOAc/MeOH/$CH_2Cl_2$ (40 mL) and heated to boiling. To the hot solution was added 1 M ethereal HCl (5.00 mL, 5.00 mmol). The solution was allowed to cool to room temperature. The resulting solid was collected by filtration, washed with EtOAc (2×10 mL), $Et_2O$ (3×5 mL) and dried under vacuum at 60° C. to give 525 mg (55%) of the title compound as white colored crystals. Mp: >280° C. $^1H$ NMR (DMSO-$d_6$; 400 MHz): δ 1.63 (br s, 6), 2.48 (s, 3), 3.97 (br s, 4), 6.73 (s, 1), 6.84–6.87 (m, 1), 7.24 (br s, 1), 7.27–7.28 (m, 2), 9.75 (s, 1), 11.61 (s, 1), 13.87 (s, 1). MS m/z: 309 (M+1 for free base). Anal. Calcd for $C_{18}H_{20}N_4O \cdot HCl \cdot 1.3H_2O$: C, 58.70; H, 6.46; N, 15.22; Cl, 9.63. Found: C, 59.09; H, 6.11; N, 14.91; Cl, 9.30.

EXAMPLE 141

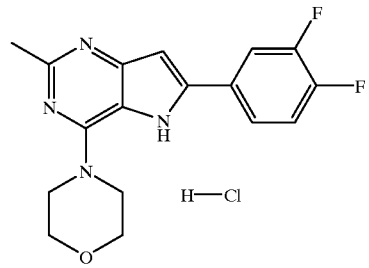

4-[6-(3,4-Difluorophenyl)-2-methylpyrrolo[2,3-e]pyrimidin-4-yl]morpholine Hydrochloride.

Using the method described in Example 30 by employing (1-(3,4-difluorophenyl)vinyl)pyrrolidine (freshly prepared before use from 3,4-difluoro acetophenone (Aldrich Chemical Company), pyrrolidine and $TiCl_4$ (2.04 g, 9.76 mmol), 2-methyl-4,6-dichloro-5-nitropyrimidine (Example 76(b)) (2.02 g, 9.76 mmol), N,N-diisopropylethylamine (1.7 mL, 9.76 mmol), morpholine (1.4 mL, 15.6 mmol), $NEt_3$ (1.5 mL) and $SnCl_2$ (29 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 0.78 g (24%) of 4-[6-(3,4-difluorophenyl)-2-methylpyrrolo[2,3-e]pyrimidin-4-yl]morpholine as a beige colored solid. This compound (780 mg, 3.00 mmol) was dissolved in 5:1 EtOAc/MeOH (40 mL) and heated to boiling. To the hot solution was added 1 M ethereal HCl (3.00 mL, 3.00 mmol). The solution was allowed to cool to room temperature. The resulting crystals were collected by filtration, washed with EtOAc (2×10 mL), $Et_2O$ (3×15 mL) and dried under vacuum at 60° C. to give 670 mg (15%) of the title compound as pale yellow colored crystals. Mp: >280° C. $^1H$ NMR (DMSO-$d_6$;

400 MHz): δ 2.37 (s, 3), 3.59 (br s, 4), 3.89 (br s, 4), 6.78 (s, 1), 7.40 (q, 1, J=8.8), 7.68 (br s, 1), 8.00 (t, 1, J=9.8), 11.94 (s, 1), 14.48 (s, 1). MS m/z: 331 (M+1 for free base). Anal. Calcd for $C_{17}H_{16}F_2N_4O \cdot HCl$: C, 55.66; H, 4.67; N, 15.28; Cl, 9.66. Found: C, 55.57; H, 4.77; N, 15.15; Cl, 9.61.

EXAMPLE 142

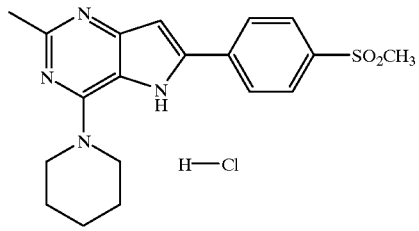

1-[2-Methyl-4-piperidylpyrrolo[4,5-d]pyrimidin-6-yl]-4-(methylsulfonyl)benzene Hydrochloride Monohydrate.

Using the method described in Example 30 by employing 1-(methylsulfonyl)-4-(1-pyrrolidinylvinyl) benzene (freshly prepared before use from 3-methyl sulfonylacetophenone (Acros Chemical Company), pyrrolidine and $TiCl_4$ (2.01 g, 8.00 mmol), 2-methyl-4,6-dichloro-5-nitropyrimidine (Example 76(b)) (1.71 g, 8.00 mmol), N,N-diisopropylethylamine (1.4 mL, 8.0 mmol), piperidine (1.3 mL, 12.8 mmol), $NEt_3$ (1.4 mL) and $SnCl_2$ (24 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 1.10 g (37%) of 1-[2-methyl-4-piperidyl pyrrolo[4,5-d]pyrimidin-6-yl]-4-(methylsulfonyl)benzene as a beige colored solid. This compound (1.10 g, 2.97 mmol) was dissolved in 4:1 EtOAc/MeOH (50 mL) and heated to boiling. To the hot solution was added 1 M ethereal HCl (3.00 mL, 3.00 mmol). The solution was allowed to cool to room temperature. The resulting crystals were collected by filtration, washed with EtOAc (2×10 mL), $Et_2O$ (3×15 mL) and dried under vacuum at 60° C. to give 1.05 g (32%) of the title compound as a beige colored solid. Mp: 279–281° C. $^1$H NMR (DMSO-$d_6$; 400 MHz): δ 1.65 (br s, 6), 2.51 (s, 3), 3.23 (s, 3), 4.01 (br s, 4), 7.02 (s, 1), 7.93, 8.27 (AB q, 4, J=8.3, 8.3), 12.14 (s, 1), 14.38 (s, 1). MS m/z: 371 (M+1 for free base). Anal. Calcd for $C_{19}H_{22}N_4O_2S \cdot HCl \cdot H_2O$: C, 53.70; H, 5.93; N, 13.19; Cl, 8.34. Found: C, 53.82; H, 5.94; N, 13.08; Cl, 8.49.

EXAMPLE 143

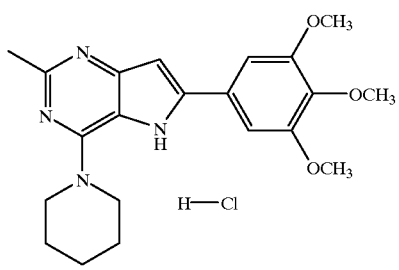

1,2,3-Trimethoxy-5-[2-methyl-4-piperidylpyrrolo[4,5-d]pyrimidin-6-yl]benzene Hydrochloride.

Using the method described in Example 30 by employing 1,2,3-trimethoxy-5-(1-pyrrolidinylvinyl) benzene (freshly prepared before use from 3,4,5-trimethoxyacetophenone (Aldrich Chemical Company), pyrrolidine and $TiCl_4$ (1.70 g, 6.46 mmol), 2-methyl-4,6-dichloro-5-nitropyrimidine (Example 76(b)) (1.35 g, 6.46 mmol), N,N-diisopropylethylamine (1.1 mL, 6.46 mmol), piperidine (1.0 mL, 10.3 mmol), $NEt_3$ (1.1 mL) and $SnCl_2$ (19 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 0.85 g (35%) of 1,2,3-trimethoxy-5-[2-methyl-4-piperidylpyrrolo[4,5-d]pyrimidin-6-yl]benzene as a beige colored solid. This compound (466 mg, 1.20 mmol) was dissolved in 1:3 EtOAc/MeOH (40 mL) and heated to boiling. To the hot solution was added 1 M ethereal HCl (1.20 mL, 1.20 mmol). The solution was allowed to cool to room temperature. The resulting crystals were collected by filtration, washed with EtOAc (2×10 mL), $Et_2O$ (3×15 mL) and dried under vacuum at 60° C. to give 409 mg (29%) of the title compound as white colored crystals. Mp: 275–277° C. $^1$H NMR (DMSO-$d_6$; 400 MHz): δ 1.64 (br s, 6), 2.52 (s, 3), 3.66 (s, 3), 3.39 (s, 6), 3.99 (br t, 4, J=5.2), 6.85 (s, 1), 7.75 (s, 2), 11.94 (s, 1), 14.28 (s, 1). MS m/z: 381 (M+1 for free base). Anal. Calcd for $C_{21}H_{26}N_4O_3 \cdot HCl$: C, 60.21; H, 6.50; N, 13.37; Cl, 8.46. Found: C, 60.24; H, 6.53; N, 13.37; Cl, 8.57.

EXAMPLE 144

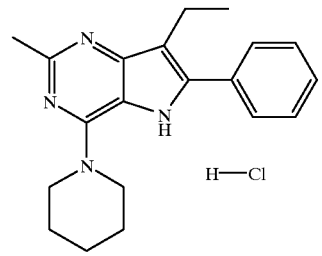

7-Ethyl-2-methyl-6-phenyl-4-piperidylpyrrolo[3,2-d]pyrimidine Hydrochloride Hydrate.

Using the method described in Example 30 by employing (1-phenylbut-1-enyl)pyrrolidine (freshly prepared before use from butyrophenone (Aldrich Chemical Company), pyrrolidine and $TiCl_4$ (1.63 g, 8.11 mmol), 2-methyl-4,6-dichloro-5-nitropyrimidine (Example 76(b)) (1.60 g, 8.11 mmol), N,N-diisopropylethylamine (1.4 mL, 8.11 mmol), piperidine (1.3 mL, 13.0 mmol), $NEt_3$ (1.3 mL) and $SnCl_2$ (24 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 100% EtOAc as eluant to give 0.42 g (16%) of 7-ethyl-2-methyl-6-phenyl-4-piperidylpyrrolo[3,2-d]pyrimidine as a beige colored solid. This compound (411 mg, 1.31 mmol) was dissolved in 5:1 EtOAc/MeOH (40 mL) and heated to boiling. To the hot solution was added 1 M ethereal HCl (1.30 mL, 1.30 mmol). The solution was allowed to cool to room temperature. The resulting crystals were collected by filtration, washed with EtOAc (2×10 mL), $Et_2O$ (3×15 mL) and dried under vacuum at 60° C. to give 34 mg (1%) of the title compound as a white colored solid. Mp: 261–263° C. $^1$H NMR (DMSO-$d_6$; 400 MHz): δ 1.05 (t, 3, J=7.5), 1.63 (br s, 6), 2.56 (s, 3), 2.69 (q, 2, J=7.2), 3.95 (br s, 4), 7.46–8.02 (m, 5), 11.90 (s, 1), 13.86 (s, 1). MS m/z: 321 (M+1 for free base). Anal. Calcd for $C_{20}H_{24}N_4 \cdot HCl \cdot 0.7H_2O$: C, 65.01; H, 7.20; N, 15.17; Cl, 9.59. Found: C, 65.09; H, 6.90; N, 14.98; Cl, 9.85.

EXAMPLE 145

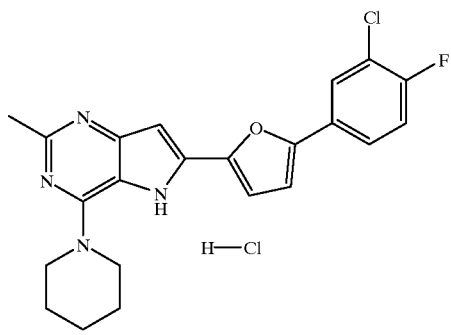

5-(3-Chloro-4-fluorophenyl)-2-[2-methyl-4-piperidyl pyrrolo[4,5-d]pyrimidin-6-yl]furan Hydrochloride Hydrate.

Using the method described in Example 30 by employing 5-(3-chloro-4-fluorophenyl)-2-(1-pyrrolidinyl vinyl)furan (freshly prepared before use from 1-[5-(3-chloro-4-fluorophenyl)-2-furyl]ethan-1-one (Maybridge Chemical Company), pyrrolidine and TiCl$_4$ (1.65 g, 5.67 mmol), 2-methyl-4,6-dichloro-5-nitropyrimidine (Example 76(b)) (1.20 g, 5.67 mmol), N,N-diisopropylethylamine (1.0 mL, 5.67 mmol), piperidine (0.9 mL, 9.1 mmol), NEt$_3$ (1.0 mL) and SnCl$_2$ (17 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 0.61 g (26%) of 5-(3-chloro-4-fluorophenyl)-2-[2-methyl-4-piperidylpyrrolo[4,5-d] pyrimidin-6-yl]furan as a beige colored solid. This compound (609 mg, 1.50 mmol) was dissolved in 10:1 EtOAc/MeOH (25 mL) and heated to boiling. To the hot solution was added 1 M ethereal HCl (1.50 mL, 1.50 mmol). The solution was allowed to cool to room temperature. The resulting crystals were collected by filtration, washed with EtOAc (2×10 mL), Et$_2$O (3×15 mL) and dried under vacuum at 60° C. to give 385 mg (15%) of the title compound as tan colored small needles. Mp: >280° C. $^1$H NMR (DMSO-d$_6$; 400 MHz): δ 1.65 (br s, 6), 2.51 (s, 3), 4.00 (br s, 4), 6.89 (s, 1), 7.26 (d, 1, J=3.7), 7.47 (d, 1, J=3.7), 7.50 (t, 1, J=9.0), 7.85–7.89 (m, 1), 8.10 (dd, 1, J=2.1, 7.1), 12.19 (s, 1), 14.31 (s, 1). MS m/z: 411 (M+1 for free base). Anal. Calcd for $C_{22}H_{20}ClFN_4O \cdot HCl \cdot 1.5H_2O$: C, 55.70; H, 5.10; N, 11.81; Cl, 14.95. Found: C, 55.80; H, 5.10; N, 11.72; Cl, 15.06.

EXAMPLE 146

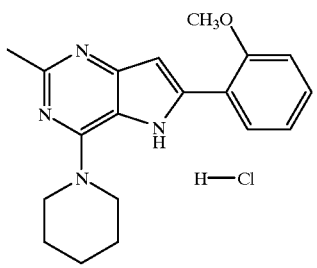

2-Methoxy-1-[2-methyl-4-piperidylpyrrolo[4,5-d] pyrimidin-6-yl]benzene Hydrochloride Monohydrate.

Using the method described in Example 30 by employing 2-methoxy-1-(1-pyrrolidinylvinyl)furan (freshly prepared before use from 2'-methoxy acetophenone (Aldrich Chemical Company), pyrrolidine and TiCl$_4$ (2.14 g, 10.5 mmol), 2-methyl-4,6-dichloro-5-nitropyrimidine (Example 76(b)) (2.25 g, 10.5 mmol), N,N-diisopropylethylamine (1.8 mL, 10.5 mmol), piperidine (1.7 mL, 16.8 mmol), NEt$_3$ (1.8 mL) and SnCl$_2$ (32 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 2.49 g (74%) of 2-methoxy-1-[2-methyl-4-piperidylpyrrolo[4,5-d]pyrimidin-6-yl] benzene as a beige colored foam. This compound (864 mg, 2.67 mmol) was dissolved in 10:1 EtOAc/MeOH (60 mL) and heated to boiling. To the hot solution was added 1 M ethereal HCl (2.70 mL, 2.70 mmol). The solution was allowed to cool to room temperature. The resulting crystals were collected by filtration, washed with EtOAc (2×10 mL), Et$_2$O (3×15 mL) and dried under vacuum at 60° C. to give 654 mg (50%) of the title compound as a pale yellow colored solid. Mp: 261–263° C. $^1$H NMR (DMSO-d$_6$; 400 MHz): δ 1.64 (br s, 6), 2.51 (s, 3), 3.83 (s, 3), 3.97 (br s, 4), 6.72 (s, 1), 7.07 (dt, 1, J=0.7, 7.4), 7.18 (d, 1, J=8.2), 7.44 (dt, 1, J=1.7, 7.1), 7.67 (dd, 1, J=1.3, 7.6), 11.74 (s, 1), 14.31 (s, 1). MS m/z: 411 (M+1 for free base). Anal. Calcd for $C_{19}H_{22}N_4O \cdot HCl \cdot H_2O$: C, 60.55; H, 6.69; N, 14.87; Cl, 9.41. Found: C, 60.68; H, 6.78; N, 14.82; Cl, 9.52.

EXAMPLE 147

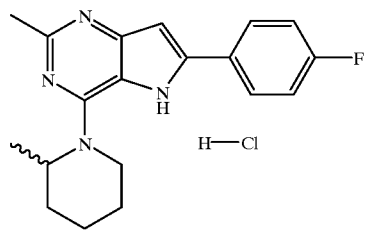

6-(4-Fluorophenyl)-2-methyl-4-(2-methylpiperidyl) pyrrolo[3,2-d]pyrimidine Hydrochloride Monohydrate.

Using the method described in Example 30 by employing [1-(4-fluorophenyl)vinyl]pyrrolidine (freshly prepared before use from 4'-fluoroacetophenone (Aldrich Chemical Company), pyrrolidine and TiCl$_4$ (2.17 g, 11.4 mmol), 2-methyl-4,6-dichloro-5-nitropyrimidine (Example 76(b)) (2.42 g, 11.4 mmol), N,N-diisopropylethylamine (2.0 mL, 11.4 mmol), 2-methylpiperidine (2.1 mL, 18.2 mmol), NEt$_3$ (2.0 mL) and SnCl$_2$ (34 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 0.88 g (24%) of 6-(4-fluorophenyl)-2-methyl-4-(2-methylpiperidyl)pyrrolo[3,2-d]pyrimidine as a beige colored solid. This compound (882 mg, 2.71 mmol) was dissolved in 10:1 EtOAc/MeOH (50 mL) and heated to boiling. To the hot solution was added 1 M ethereal HCl (2.70 mL, 2.70 mmol). The solution was allowed to cool to room temperature. The resulting crystals were collected by filtration, washed with EtOAc (2×10 mL), Et$_2$O (3×15 mL) and dried under vacuum at 60° C. to give 573 mg (14%) of the title compound as a white colored solid. Mp: 274–276° C. $^1$H NMR (DMSO-d$_6$; 400 MHz): δ 1.20 (d, 3, J=6.9), 1.40–1.73 (m, 6), 2.44 (s, 3), 3.35 (br s, 1), 4.48 (br s, 1), 5.13 (br s, 1), 6.75 (s, 1), 7.28 (t, 2, J=8.9), 7.89 (dd, 2, J=5.4, 5.4), 11.79 (s, 1), 14.04 (s, 1). MS m/z: 325 (M+1 for free base). Anal. Calcd for C$_{19}$H$_{21}$FN$_4$.HCl.H$_2$O: C, 60.23; H, 6.39; N, 14.79; Cl, 9.36. Found: C, 60.60; H, 6.28; N, 14.90; Cl, 9.35.

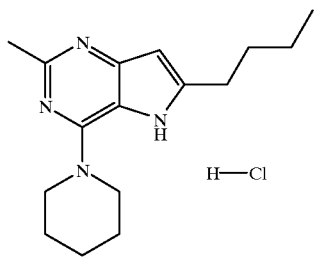

Example 148

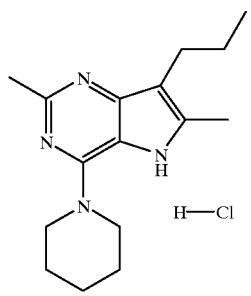

Example 149

EXAMPLE 148 AND EXAMPLE 149

6-Butyl-2-methyl-4-piperidylpyrrolo[3,2-d]pyrimidine Hydrochloride and 2,6-Dimethyl-4-piperidyl-7-propylpyrrolo[3,2-d]pyrimidine Hydrochloride.

Using the method described in Example 30 by employing a mixture of [1-butylvinyl]pyrrolidine and [1-methylpent-1-enyl]pyrrolidine (freshly prepared before use from 2-hexanone (Aldrich Chemical Company), pyrrolidine and TiCl$_4$ (1.75 g, 11.4 mmol), 2-methyl-4,6-dichloro-5-nitropyrimidine (Example 76(b)) (2.42 g, 11.4 mmol), N,N-diisopropylethylamine (2.0 mL, 11.4 mmol), piperidine (1.8 mL, 18.2 mmol), NEt$_3$ (2.0 mL) and SnCl$_2$ (34 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 0.71 g (23%) of 6-butyl-2-methyl-4-piperidylpyrrolo[3,2-d]pyrimidine as a beige colored foam and 326 mg (11%) of 2,6-dimethyl-4-piperidyl-7-propylpyrrolo[3,2-d]pyrimidine as a pale yellow colored solid.

Example 148

6-Butyl-2-methyl-4-piperidylpyrrolo[3,2-d]pyrimidine (0.71 g, 2.61 mmol) was dissolved in. 5:1 EtOAc/MeOH (30 mL) and heated to boiling. To the hot solution was added 1 M ethereal HCl (2.60 mL, 2.60 mmol). The solution was allowed to cool to room temperature. The resulting crystals were collected by filtration, washed with EtOAc (2×10 mL), Et$_2$O (3×15 mL) and dried under vacuum at 60° C. to give 525 mg (15%) of Example 148 as white colored cube shaped crystals. Mp: 246–248° C. $^1$H NMR (DMSO-d$_6$; 400 MHz): δ 1.17 (t, 3, J=7.4), 1.59 (quintet, 2, J=7.3), 1.87–1.94 (m, 8), 2.77 (s, 3), 3.06 (t, 2, J=7.8), 6.55 (s, 1), 12.08 (s, 1), 14.39 (s, 1). MS m/z: 273 (M+1 for free base). Anal. Calcd for C$_{16}$H$_{24}$N$_4$.HCl: C, 62.22; H, 8.16; N, 18.14; Cl, 11.48. Found: C, 62.31; H, 8.12; N, 18.18; Cl, 11.44.

Example 149

2,6-Dimethyl-4-piperidyl-7-propylpyrrolo[3,2-d]pyrimidine (326 mg, 1.20 mmol) was dissolved in 4:1 EtOAc/MeOH (30 mL) and heated to boiling. To the hot solution was added 1 M ethereal HCl (1.20 mL, 1.20 mmol). The solution was allowed to cool to room temperature. The resulting crystals were collected by filtration, washed with EtOAc (2×10 mL), Et$_2$O (3×15 mL) and dried under vacuum at 60° C. to give 218 mg (6%) of Example 149 as beige colored cube needles. Mp: 265–267.5° C. $^1$H NMR (DMSO-d$_6$; 400 MHz) δ 0.83 (t, 3, J=7.3), 1.40 (quintet, 2, J=7.3), 1.58 (m, 6), 2.35 (s, 3), 2.43 (m, 1), 2.56 (t, 2, J=7.1), 3.89 (s, 4), 11.79 (s, 1), 13.72 (s, 1). MS m/z: 273 (M+1 for free base). Anal. Calcd for C$_{16}$H$_{24}$N$_4$.HCl: C, 62.22; H, 8.16; N, 18.14; Cl, 11.48. Found: C, 61.98; H, 8.05; N, 18.02; Cl, 11.67.

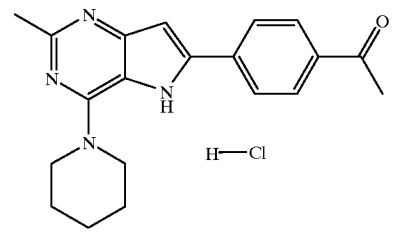

Example 150

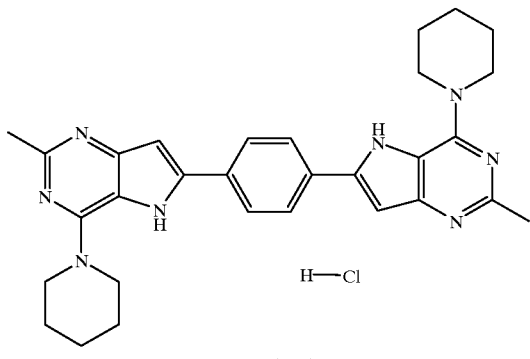

Example 151

EXAMPLE 150 AND EXAMPLE 151

1-[4-(2-Methyl-4-piperidylpyrrolo[4,5-d]pyrimidin-6-yl)phenyl]ethan-1-one Hydrochloride Hydrate and 2-Methyl-6-[4-(2-methyl-4-piperidylpyrrolo[4,5-d]pyrimidin-6-yl)phenyl]-4-piperidylpyrrolo[3,2-d]pyrimidine Hydrochloride hydrate.

Using the method described in Example 30 by employing a mixture of 1-[4-(1-pyrrolidinylvinyl) phenyl]ethan-1-one and [1-(4-(1-pyrrolidinylvinyl) phenyl)vinyl]pyrrolidine (freshly prepared before use from 1,4-diacetylbenzene (Aldrich Chemical Company), pyrrolidine and TiCl$_4$ (1.93 g, 7.20 mmol), 2-methyl-4,6-dichloro-5-nitropyrimidine (Example 76(b)) (2.90 g, 14.4 mmol), N,N-diisopropylethylamine (2.5 mL, 14.4 mmol), piperidine (2.2 mL, 23.0 mmol), NEt$_3$ (2.3 mL) and SnCl$_2$ (43 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 188 g (8%) of 1-[4-(2-methyl-4-piperidyl pyrrolo[4,5-d]pyrimidin-6-yl)phenyl]ethan-1-one as a brown colored solid and 76 mg (2%) of 2-methyl-6-[4-(2-methyl-4-piperidylpyrrolo[4,5-d]pyrimidin-6-yl)phenyl]-4-piperidylpyrrolo[3,2-d]pyrimidine as a yellow colored solid.

Example 150

1-[4-(2-Methyl-4-piperidylpyrrolo[4,5-d]pyrimidin-6-yl)phenyl]ethan-1-one (188 mg, 0.60 mmol) was dissolved in 5:1 EtOAc/MeOH (20 mL) and heated to boiling. To the hot solution was added 1 M ethereal HCl (0.60 mL, 0.60 mmol). The solution was allowed to cool to room temperature. The resulting solid was collected by filtration, washed with EtOAc (2×10 mL), Et$_2$O (3×15 mL) and dried under vacuum at 60° C. to give 104 mg (4%) of Example 150 as a yellow colored solid. Mp: 173.5–175° C. $^1$H NMR (DMSO-d$_6$; 400 MHz): δ 1.65 (br s, 6), 2.51 (s, 3), 2.57 (s, 3), 4.01 (br s, 4), 6.98 (s, 1), 8.05 (q, 4, J=4.5), 12.02 (s, 1), 14.31 (s, 1). MS m/z: 335 (M+1 for free base). Anal. Calcd for C$_{20}$H$_{22}$N$_4$O.HCl.1.75H$_2$O: C, 56.69; H, 6.64; N. 13.93; Cl, 8.81. Found: C, 59.78; H, 6.53; N, 14.00; Cl, 8.91.

Example 151

2-Methyl-6-[4-(2-methyl-4-piperidylpyrrolo[4,5-d]pyrimidin-6-yl)phenyl]-4-piperidylpyrrolo[3,2-d]pyrimidine (76 mg, 0.20 mmol) was dissolved in 5:2 EtOAc/MeOH (15 mL) and heated to boiling. To the hot solution was added 1 M ethereal HCl (0.40 mL, 0.40 mmol). The solution was allowed to cool to room temperature. The resulting crystals were collected by filtration, washed with EtOAc (2×5 mL), Et$_2$O (3×5 mL) and dried under vacuum at 60° C. to give 30 mg (1%) of Example 151 as a yellow colored powder. Mp: >280° C. $^1$H NMR (DMSO-d$_6$; 400 MHz): δ 1.66 (br s, 12), 2.52 (s, 6), 4.02 (br s, 8), 6.96 (s, 2), 8.05 (s, 4), 12.01 (s, 2), 14.21 (s, 2). MS m/z: 507 (M+1 for free base). Anal. Calcd for C$_{30}$H$_{34}$N$_8$.2HCl.4H$_2$O: C, 55.29; H, 6.81; N, 17.20; Cl, 10.88. Found: C, 54.96; H, 6.62; N, 16.74; Cl, 11.00.

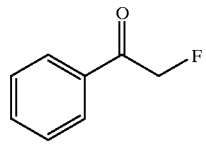

EXAMPLE 152

(a) 2-Fluoro-1-phenylethan-1-one.

A mixture of 2-bromoacetophenone (Aldrich Chemical Company) (5.42 g, 27.3 mmol), KF (6.32 g, 0.11 mol) and 18-crown-6 (3.61 g, 13.7 mmol) in CH$_3$CN (150 mL) was heated at 90° C. for 16 h under a N$_2$ atmosphere. Heating was discontinued and the mixture was allowed to cool to room temperature. The mixture was diluted with H$_2$O (300 mL) and EtOAc (400 mL) and transferred to a separatory funnel. The organic solution was separated, washed with H$_2$O (2×300 mL), saturated NaCl (300 mL), dried (MgSO$_4$), filtered and concentrated under reduced pressure. The resulting crude ketone (3.02 g) was used without further purification (see Gregory et al. *J. Med. Chem.* 1990, 33(9), 2569).

(b) 7-Fluoro-2-methyl-6-piperidylpyrrolo[3,2-d]pyrimidine Hydrochloride.

To a room temperature solution of [2-fluoro-1-phenylvinyl]pyrrolidine (freshly prepared before use from 2-fluoro-1-phenyl ethan-1-one (Example 152(a)), pyrrolidine and TiCl$_4$ (see Example 30) (2.44 g, 12.7 mmol) in anhydrous toluene (15 mL) was added N,N-diisopropylethylamine (Aldrich Chemical Company) (2.0 mL, 12.7 mmol) followed by 2-methyl-4,6-dichloro-5-nitropyrimidine (Example 76(b)) (2.61 g, 12.7 mmol). After stirring at room temperature for 2.5 h the reaction mixture was filtered through a fritted funnel. The residue was washed with hot toluene (2×30 mL) and the filtrate was concentrated under reduced pressure. The residue was dissolved with dioxane/toluene (20 mL:10 mL) and NEt$_3$ (Aldrich Chemical Company) (2.1 mL) and piperidine (Aldrich Chemical Company) (2.0 mL, 20.3 mmol) were added. The mixture was stirred at 80° C. for 2 h under a N$_2$ atmosphere. The SnCl$_2$ solution was added to the reaction mixture at 80° C. The mixture was stirred at 80° C. for an additional 16 h then the heating was discontinued and the mixture was allowed to cool to room temperature. The reaction mixture was poured onto a mixture of NaOH (5 g) and crushed ice (150 mL) and stirred for 1 h. The resulting slurry was filtered through a Celite® pad, the pad was rinsed with 10:1 EtOAc/MeOH (4×60 mL). The filtrate was transferred to a seperatory funnel. The organic solution was separated, washed with H$_2$O (3×350 mL), saturated NaCl (300 mL), dried (MgSO$_4$), filtered and concentrated under reduced pressure. The residue was purified by flash chromatography on silica gel with 50:50 EtOAc/hexanes as eluant to give 0.51 g (13%) of 7-fluoro-2-methyl-6-piperidylpyrrolo[3,2-d]pyrimidine as a brown colored foam. This compound (0.51 g, 1.60 mmol) was dissolved in 10:1 EtOAc/MeOH (35 mL) and heated to boiling. To the hot solution was added 1 M ethereal HCl (1.60 mL, 1.60 mmol). The solution was allowed to cool to room temperature. The resulting crystals were collected by filtration, washed with EtOAc (2×10 mL), Et$_2$O (3×15 mL) and dried under vacuum at 60° C. to give 270 mg (6%) of the title compound as pale green colored needles. Mp: >280° C. $^1$H NMR (DMSO-d$_6$; 400 MHz): δ 1.72 (br s, 6), 2.59 (s, 3), 4.07 (br s, 4), 7.53–7.57 (m, 1), 7.61 (t, 2, J=7.7), 7.87 (d, 2, J=7.5), 12.07 (s, 1), 14.56 (s, 1). MS m/z: 311 (M+1 for free base). Anal. Calcd for C$_{18}$H$_{19}$FN$_4$.HCl: C, 62.33; H, 5.81; N, 16.15; Cl, 10.22. Found: C, 62.04; H, 5.95; N, 16.08; Cl, 10.02.

EXAMPLE 153

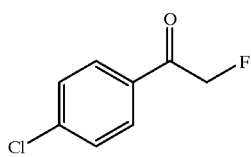

(a) 1-(4-Chlorophenyl)-2-fluoroethan-1-one.

Using the method described in Example 152(a) by employing 2-bromo-4'-chloroacetophenone (Aldrich Chemical Company) (4.06 g, 17.5 mmol), KF (4.1 g, 0.11 mol) and 18-crown-6 (3.61 g, 13.7 mmol). The resulting crude ketone was used without further purification.

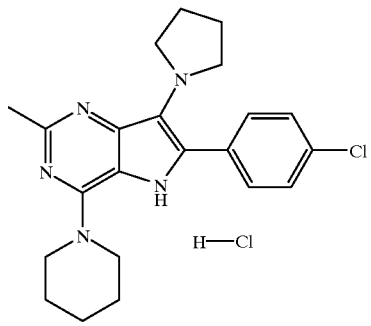

(b) 2-Methyl-6-phenyl-4-piperidyl-7-pyrrolidinyl pyrrolo[3,2-d]pyrimidine Hydrochloride Hydrate.

Using the method described in Example 30 by employing [1-(4-chlorophenyl)-2-fluorovinyl]pyrrolidine (freshly prepared before use from 1-(4-chlorophenyl)-2-fluoroethan-1-one (Example 153(a)), pyrrolidine and TiCl$_4$ (see Example 30) (3.00 g, 13.3 mmol), 2-methyl-4,6-dichloro-5-nitropyrimidine (Example 76(b)) (2.80 g, 13.3 mmol), N,N-diisopropylethylamine (2.3 mL, 13.3 mmol), piperidine (2.1 mL, 21.3 mmol), NEt$_3$ (2.2 mL) and SnCl$_2$ (40 mL of a 2 M soln in DMF). In this example, the SnCl$_2$ solution was added to the reaction mixture at 140° C. (Note: When both the piperidine displacement and the SnCl$_2$ reduction sequences are performed at 140° C. the pyrrolidine moiety is incorporated). The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 0.38 g (8%) of 2-methyl-6-phenyl-4-piperidyl-7-pyrrolidinylpyrrolo[3,2-d]pyrimidine as a brown colored solid. This compound (0.38 g, 1.00 mmol) was dissolved in 5:1 EtOAc/MeOH (20 mL) and heated to boiling. To the hot solution was added 1 M ethereal HCl (1.00 mL, 1.00 mmol). The solution was allowed to cool to room temperature. The resulting crystals were collected by filtration, washed with EtOAc (2×5 mL), Et$_2$O (3×5 mL) and dried under vacuum at 60° C. to give 162 mg (2%) of the title compound as a beige colored powder. Mp: >280° C. $^1$H NMR (DMSO-d$_6$; 400 MHz): 1.49 (br s, 2), 1.54 (br s, 4), 1.88 (br s, 2), 2.01 (br s, 2), 2.59 (s, 3), 2.92 (br s, 4), 3.72 (br s, 2), 4.04 (br s, 2), 7.57 (d, 2, J=8.5), 7.76 (d, 2, J=8.4), 11.44 (s, 1), 13.13 (s, 1). MS m/z: 396 (M+1 for free base). Anal. Calcd for C$_{22}$H$_{26}$ClN$_4$.HCl.0.5H$_2$O: C, 59.86; H, 6.39; N, 15.87; Cl, 16.06. Found: C, 59.56; H, 6.36; N, 15.70; Cl, 15.95.

EXAMPLE 154

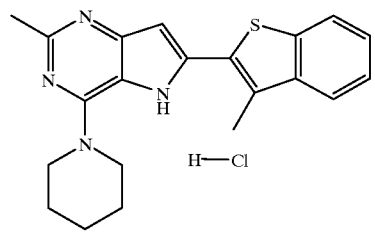

3-Methyl-2-[2-methyl-4-piperidylpyrrolo[4,5-d]pyrimidin-6-yl]benzo[b]thiophene Hydrochloride Hydrate.

Using the method described in Example 30 by employing 3-methyl-2-(1-pyrrolidinylvinyl)benzo[b]thiophene (freshly prepared before use from 2-acetyl-3-methylthianaphthene (Avocado Chemical Company), pyrrolidine and TiCl$_4$ (1.67 g, 6.88 mmol), 2-methyl-4,6-dichloro-5-nitropyrimidine (Example 76(b)) (1.43 g, 6.88 mmol), N,N-diisopropylethylamine (1.2 mL, 6.88 mmol), piperidine (1.1 mL, 11.0 mmol), NEt$_3$ (1.5 mL) and SnCl$_2$ (21 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl$_3$/MeOH as eluant to give 0.60 g (24%) of 3-methyl-2-[2-methyl-4-piperidylpyrrolo[4,5-d]pyrimidin-6-yl]benzo[b]thiophene as a beige colored solid. This compound (596 mg, 1.64 mmol) was dissolved in 5:1 EtOAc/MeOH (30 mL) and heated to boiling. To the hot solution was added 1 M ethereal HCl (1.70 mL, 1.70 mmol). The solution was allowed to cool to room temperature. The resulting crystals were collected by filtration, washed with EtOAc (2×10 mL), Et$_2$O (3×15 mL) and dried under vacuum at 60° C. to give 421 mg (16%) of the title compound as a pale yellow colored powder. Mp: >280° C. $^1$H NMR (DMSO-d$_6$; 400 MHz): δ 1.65 (br s, 6), 2.46 (s, 3), 2.51 (s, 3), 3.98 (br s, 4), 6.67 (s, 1), 7.41–7.47 (m, 2), 7.87 (dd, 1, J=1.7, 6.2), 7.99 (dd, 1, J=1.7, 6.4), 12.43 (s, 1), 14.38 (s, 1). MS m/z: 363 (M+1 for free base). Anal. Calcd for $C_{21}H_{22}N_4S \cdot HCl \cdot 0.4H_2O$: C, 62.10; H, 5.91; N, 13.80; Cl, 8.73. Found: C, 62.04; H, 5.92; N, 13.80; Cl, 8.83.

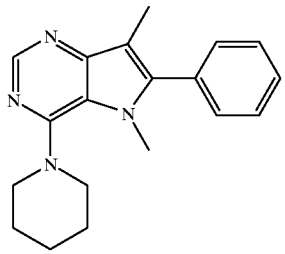

EXAMPLE 155

5,7-Dimethyl-6-phenyl-4-piperidylpyrrolo[3,2-d]pyrimidine.

To a 0° C. solution of 7-methyl-6-phenyl-4-piperidylpyrrolo[3,2-d]pyrimidine (Example 89) (177.3 mg, 0.61 mmol) in THF (10 mL) under a nitrogen atmosphere was added LiHMDS (1.0 M soln from Aldrich Chemical Company) (1.3 mL, 1.27 mmol). This mixture was stirred at 0° C. for 0.5 h then CH$_3$I (Aldrich Chemical Comapny) (41 mL, 0.67 mmol) was added. The 0° C. bath was removed and the solution stirred at room temperature for 2.5 h. The reaction mixture was poured into a separatory funnel containing EtOAc (35 mL) and H$_2$O (50 mL). The organic solution was collected washed with H$_2$O (3×40 mL), saturated NaCl (70 mL), dried (MgSO$_4$), filtered and concentrated under reduced pressure. The residue was purified via flash chromatography on silica gel 95:5 CHCl$_3$/MeOH as eluant to give 164 mg (86%) of the title compound as a beige colored solid. Mp: 123.0–125.0° C. $^1$H NMR (DMSO-d$_6$; 400 MHz): δ 1.68 (m, 2), 1.78 (m, 4), 2.30 (s, 3), 3.42 (br s, 4), 3.66 (s, 3), 7.44–7.54 (m, 5), 8.61 (s, 1). MS m/z: 307 (M+1).

EXAMPLE 156

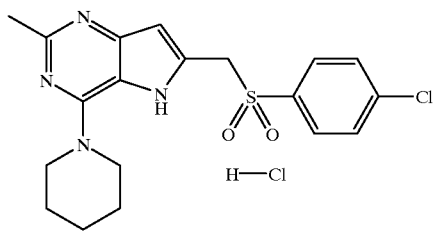

4-Chloro-1-[((2-methyl-4-piperidylpyrrolo[4,5-d]pyrimidin-6-yl)methyl)sulfonyl]benzene Hydrochloride Hydrate.

Using the method described in Example 30 by employing 1-[(2-pyrrolidinylprop-1-enyl)sulfonyl]- 4-chlorobenzene (freshly prepared before use from 4-chlorophenylsulfonylacetone (Lancaster Chemical Company), pyrrolidine and TiCl$_4$ (2.03 g, 7.10 mmol), 2-methyl-4,6-dichloro-5-nitropyrimidine (Example 76(b)) (1.47 g, 7.10 mmol), N,N-diisopropylethylamine (1.3 mL, 7.10 mmol), piperidine (1.1 mL, 11.4 mmol), NEt$_3$ (1.6 mL) and SnCl$_2$ (21 mL of a 2 M soln in DMF). In this example the mixture of enamine, 2-methyl-4,6-dichloro-5-nitropyrimidine and N,N-diisopropylethylamine was stirred at 100° C. for 20 h prior to piperidine addition. The SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 100% EtOAc as eluant to give 441 g (15%) of 4-chloro-1-[((2-methyl-4-piperidylpyrrolo[4,5-d]pyrimidin-6-yl)methyl)sulfonyl]benzene as a brown colored solid. This compound (0.44 g, 1.08 mmol) was dissolved in 5:1 EtOAc/MeOH (20 mL) and heated to boiling. To the hot solution was added 1 M ethereal HCl (1.10 mL, 1.10 mmol). The solution was allowed to cool to room temperature. The resulting crystals were collected by filtration, washed with EtOAc (2×10 mL), Et$_2$O (3×15 mL) and dried under vacuum at 60° C. to give 296 mg (9%) of the title compound as a white colored solid. Mp: 199–201° C. $^1$H NMR (DMSO-d$_6$; 400 MHz): δ 1.57 (m, 4), 1.65 (m, 2), 2.47 (s, 3), 3.85 (br s, 4), 5.02 (s, 2), 6.23 (s, 1), 7.65 (AB q, 4, J=6.2, 6.2), 12.20 (s, 1), 14.18 (s, 1). MS m/z: 405 (M+1 for free base). Anal. Calcd for $C_{19}H_{21}ClN_4O_2S \cdot HCl \cdot 0.9H_2O$: C, 49.87; H, 5.24; N, 12.25; Cl, 15.49. Found: C, 49.85; H, 5.17; N, 12.15; Cl, 15.61.

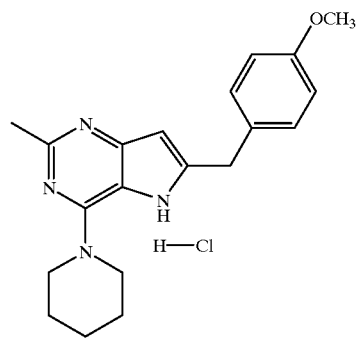

Example 157

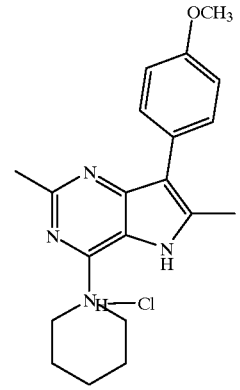

Example 158

EXAMPLE 157 AND EXAMPLE 158

4-Methoxy-1-[(2-methyl-4-piperidylpyrrolo[4,5-d]pyrimidin-6-yl)methyl]benzene Hydrochloride and 1-[2,6-Dimethyl-4-piperidylpyrrolo[3,2-d]pyrimidin-7-yl]-4-methoxybenzene Hydrochloride Hydrate.

Using the method described in Example 30 by employing 1-[2-pyrrolidinylprop-1-enyl]-4-methoxy benzene (freshly prepared before use from 4-methoxy phenylacetone (Aldrich Chemical Company), pyrrolidine and TiCl$_4$ (3.06 g, 14.10 mmol), 2-methyl-4,6-dichloro-5-nitropyrimidine (Example 76(b)) (2.92 g, 14.10 mmol), N,N-diisopropylethylamine (2.5 mL, 14.10 mmol), piperidine (2.2 mL, 22.6 mmol), NEt$_3$ (3.1 mL) and SnCl$_2$ (42 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 578 g (12%) of 4-methoxy-1-[(2-methyl-4-piperidylpyrrolo[4,5-d]pyrimidin-6-yl)methyl]benzene as a brown colored solid and 466 mg (10%) of 1-[2,6-dimethyl-4-piperidylpyrrolo[3,2-d]pyrimidin-7-yl]-4-methoxybenzene as a beige colored solid.

Example 157

4-Methoxy-1-[(2-methyl-4-piperidyl pyrrolo[4,5-d]pyrimidin-6-yl)methyl]benzene (574 mg, 1.71 mmol) was dissolved in 5:1 EtOAc/MeOH (40 mL) and heated to boiling. To the hot solution was added 1 M ethereal HCl (1.70 mL, 1.70 mmol). The solution was allowed to cool to room temperature. The resulting crystals were collected by filtration, washed with EtOAc (2×10 mL), Et$_2$O (3×15 mL) and dried under vacuum at 60° C. to give 488 mg (9%) of Example 157 as tan colored crystals. Mp: 263–267° C. $^1$H NMR (DMSO-d$_6$; 400 MHz): δ 1.73 (br s, 6), 3.75 (s, 3), 4.01 (br s, 4), 4.15 (s, 2), 6.19 (s, 1), 6.94 (d, 2, J=8.7), 7.27 (d, 2, J=8.6), 12.02 (s, 1), 13.93 (s, 1). MS m/z: 337 (M+1 for free base). Anal. Calcd for C$_{20}$H$_{24}$N$_4$O.HCl: C, 64.42; H, 6.76; N, 15.03; Cl, 9.51. Found: C, 64.41; H, 6.66; N, 15.00; Cl, 9.63.

Example 158

1-[2,6-Dimethyl-4-piperidylpyrrolo[3,2-d]pyrimidin-7-yl]-4-methoxybenzene (466 mg, 1.39 mmol) was dissolved in 5:1 EtOAc/MeOH (30 mL) and heated to boiling. To the hot solution was added 1 M ethereal HCl (1.40 mL, 1.40 mmol). The solution was allowed to cool to room temperature. The resulting crystals were collected by filtration, washed with EtOAc (2×10 mL), Et$_2$O (3×15 mL) and dried under vacuum at 60° C. to give 375 mg (7%) of Example 158 as a beige colored powder. Mp: 170° C. (dec). $^1$H NMR (DMSO-d$_6$; 400 MHz): δ 1.62 (br s, 6), 2.36 (s, 3), 2.46 (s, 3), 3.76 (s, 3), 3.95 (br s, 4), 7.03 (d, 2, J=8.7), 7.28 (d, 2, J=8.6), 12.11 (s, 1), 13.27 (s, 1). MS m/z: 337 (M+1 for free base). Anal. Calcd for C$_{20}$H$_{24}$N$_4$O.1.2HCl.0.9H$_2$O: C, 60.60; H, 6.87; N, 14.14; Cl, 10.73. Found: C, 60.74; H, 6.62; N, 14.01; Cl, 10.62.

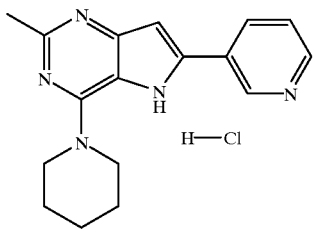

EXAMPLE 159
2-Methyl-4-piperidyl-6-(3-pyridyl)pyrrolo[3,2-d]pyrimidine Hydrochloride Hydrate.

Using the method described in Example 30 by employing 3-(1-pyrrolidinylvinyl)pyridine (freshly prepared before use from 3-acetylpyridine (Aldrich Chemical Company), pyrrolidine and TiCl$_4$ (1.95 g, 11.2 mmol), 2-methyl-4,6-dichloro-5-nitropyrimidine (Example 76(b)) (2.32 g, 11.2 mmol), N,N-diisopropylethylamine (2.0 mL, 11.2 mmol), piperidine (1.8 mL, 17.9 mmol), NEt$_3$ (2.5 mL) and SnCl$_2$ (34 mL of a 2 M soln in DMF). In this example the SnCl$_2$ solution was added to the reaction mixture at 140° C. The mixture was stirred at 140° C. for an additional 0.5 h then the heating was discontinued and the mixture was allowed to cool to room temperature. The mixture was stirred at room temperature an additional 4 d. The residue was purified by flash chromatography on silica gel with 95:5 CHCl$_3$/MeOH as eluant to give 0.90 mg (3%) of 2-methyl-4-piperidyl-6-(3-pyridyl)pyrrolo[3,2-d]pyrimidine as a beige colored solid. This compound (89 mg, 0.30 mmol) was dissolved in 10:1 EtOAc/MeOH (10 mL) and heated to boiling. To the hot solution was added 1 M ethereal HCl (0.30 mL, 0.30 mmol). The solution was allowed to cool to room temperature. The resulting crystals were collected by filtration, washed with EtOAc (2×5 mL), Et$_2$O (3×5 mL) and dried under vacuum at 60° C. to give 54 mg (2%) of the title compound as a brown colored solid. Mp: >280° C. $^1$H NMR (DMSO-d$_6$; 500 MHz): δ 1.65 (br s, 6), 2.51 (s, 3), 4.02 (t, 4, J=5.4), 6.96 (s, 1), 7.52 (dd, 1, J=7.9, 7.9), 8.32 (d, 1, J=8.0), 8.61 (d, 1, J=4.8), 9.11 (d, 1, J=2.1), 12.08 (s, 1), 14.29 (s, 1). MS m/z: 294 (M+1 for free base). Anal. Calcd for C$_{17}$H$_{19}$N$_5$.1.05HCl.1.5H$_2$O: C, 56.90; H, 6.48; N, 19.52; Cl, 10.37. Found: C, 57.20; H, 6.23; N, 19.50; Cl, 10.39.

EXAMPLE 160

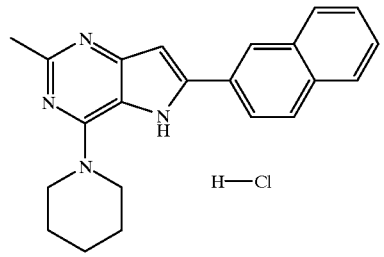

2-Methyl-6-(2-naphthyl)-4-piperidylpyrrolo[3,2-d]pyrimidine Hydrochloride Hydrate.

Using the method described in Example 30 by employing [1-(2-naphthyl)vinyl]pyrrolidine (freshly prepared before use from 21-acetylnaphthone (Aldrich Chemical Company), pyrrolidine and TiCl$_4$ (1.91 g, 8.60 mmol), 2-methyl-4,6-dichloro-5-nitropyrimidine (Example 76(b)) (1.78 g, 8.60 mmol), N,N-diisopropylethylamine (1.5 mL, 8.6 mmol), piperidine (1.4 mL, 13.8 mmol), NEt$_3$ (1.9 mL) and SnCl$_2$ (23 mL of a 2 M soln in DMF). In this example the SnCl$_2$ solution was added to the reaction mixture at 140° C. The mixture was stirred at 140° C. for an additional 2.5 h then the heating was discontinued and the mixture was allowed to cool to room temperature. The mixture was stirred at room temperature an additional 36 h. The residue was purified by flash chromatography on silica gel with 95:5 CHCl$_3$/MeOH as eluant to give 1.25 g (55%) of 2-methyl-6-(2-naphthyl)-4-piperidylpyrrolo[3,2-d]pyrimidine as a beige colored solid. This compound (1.25 g, 3.64 mmol) was dissolved in 5:1 EtOAc/MeOH (60 mL) and heated to boiling. To the hot solution was added 1 M ethereal HCl (3.60 mL, 3.60 mmol). The solution was allowed to cool to room temperature. The resulting crystals were collected by filtration, washed with EtOAc (2×10 mL), Et$_2$O (3×15 mL) and dried under vacuum at 60° C. to give 1.02 g (40%) of the title compound as a yellow colored powder. Mp: >280° C. $^1$H NMR (DMSO-d$_6$; 400 MHz): δ 1.67 (br s, 6), 2.52 (s, 3), 4.04 (t, 4, J=4.9), 6.98 (s, 1), 7.55 (m, 2), 7.94 (t, 1, J=4.0), 8.00 (d, 1, J=5.4), 8.02 (br s, 2), 8.50 (s, 1), 12.09 (s, 1), 14.27 (s, 1). MS m/z: 343 (M+1 for free base). Anal. Calcd for C$_{22}$H$_{22}$N$_4$.HCl.1.5H$_2$O: C, 65.09; H, 6.46; N, 13.81; Cl, 8.73. Found: C, 65.00; H, 66.45; N, 13.80; Cl, 8.76.

EXAMPLE 161

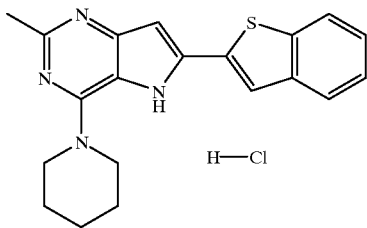

2-[2-Methyl-4-piperidylpyrrolo[4,5-d]pyrimidin-6-yl]benzo[b]thiophene Hydrochloride Hydrate.

Using the method described in Example 30 by employing 2-(1-pyrrolidinylvinyl)benzo[b]thiophene (freshly prepared before use from 2-acetylbenzo[b]thiophene (Avocado Chemical Company), pyrrolidine and $TiCl_4$ (1.71 g, 7.45 mmol), 2-methyl-4,6-dichloro-5-nitropyrimidine (Example 76(b)) (1.54 g, 7.45 mmol), N,N-diisopropylethylamine (1.3 mL, 7.45 mmol), piperidine (1.2 mL, 11.9 mmol), $NEt_3$ (1.7 mL) and $SnCl_2$ (22 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 1.04 g (40%) of 2-[2-methyl-4-piperidylpyrrolo[4,5-d]pyrimidin-6-yl]benzo[b]thiophene as a yellow colored powder. This compound (1.04 g, 2.98 mmol) was dissolved in 5:1 EtOAc/MeOH (50 mL) and heated to boiling. To the hot solution was added 1 M ethereal HCl (3.00 mL, 3.00 mmol). The solution was allowed to cool to room temperature. The resulting crystals were collected by filtration, washed with EtOAc (2×10 mL), $Et_2O$ (3×15 mL) and dried under vacuum at 60° C. to give 0.88 g (31%) of the title compound as a yellow colored powder. Mp: >280° C. $^1$H NMR (DMSO-$d_6$; 400 MHz): δ 1.66 (br s, 6), 2.51 (s, 3), 4.00 (br s, 4), 6.74 (s, 1), 7.39 (m, 2), 7.91 (t, 1, J=6.9), 8.00 (t, 1, J=4.0), 8.16 (s, 1), 12.22 (s, 1), 14.21 (s, 1). MS m/z: 349 (M+1 for free base). Anal. Calcd for $C_{20}H_{20}N_4S.HCl.0.70H_2O$: C, 60.42; H, 5.68; N, 14.10; Cl, 8.92. Found: C, 60.38; H, 5.56; N, 13.93; Cl, 9.03.

EXAMPLE 162

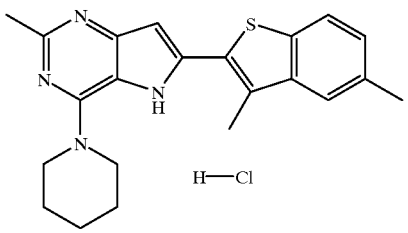

3,5-Dimethyl-2-[2-methyl-4-piperidylpyrrolo[4,5-d]pyrimidin-6-yl]benzo[b]thiophene Hydrochloride Monohydrate.

Using the method described in Example 30 by employing 3,5-dimethyl-2-(1-pyrrolidinylvinyl)benzo[b]thiophene (freshly prepared before use from 2-acetyl-3,5-dimethyl[b]thiophene (Avocado Chemical Company), pyrrolidine and $TiCl_4$ (1.81 g, 7.04 mmol), 2-methyl-4,6-dichloro-5-nitropyrimidine (Example 76(b)) (1.46 g, 7.04 mmol), N,N-diisopropylethylamine (1.2 mL, 7.04 mmol), piperidine (1.1 mL, 11.3 mmol), $NEt_3$ (1.5 mL) and $SnCl_2$ (21 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCl_3$/MeOH as eluant to give 0.53 g (20%) of 3,5-dimethyl-2-[2-methyl-4-piperidylpyrrolo[4,5-d]pyrimidin-6-yl]benzo[b]thiophene as a cream colored solid. This compound (530 mg, 1.41 mmol) was dissolved in 5:1 EtOAc/MeOH (30 mL) and heated to boiling. To the hot solution was added 1 M ethereal HCl (1.50 mL, 1.50 mmol). The solution was allowed to cool to room temperature. The resulting crystals were collected by filtration, washed with EtOAc (2×10 mL), $Et_2O$ (3×15 mL) and dried under vacuum at 60° C. to give 493 mg (17%) of the title compound as a yellow colored solid. Mp: >280° C. $^1$H NMR (DMSO-$d_6$; 400 MHz): δ 1.64 (br s, 6), 2.43 (s, 3), 2.44 (s, 3), 2.51 (s, 3), 3.98 (br s, 4), 6.65 (s, 1), 7.27 (d, 1, J=8.2), 7.66 (s, 1), 7.87 (d, 1, J=8.3), 12.31 (s, 1), 14.13 (s, 1). MS m/z: 377 (M+1 for free base). Anal. Calcd for $C_{22}H_{24}N_4S.HCl.H_2O$: C, 61.31; H, 6.31; N, 13.00; Cl, 8.23. Found: C, 61.26; H, 5.92; N, 12.91; Cl, 8.32.

EXAMPLE 163

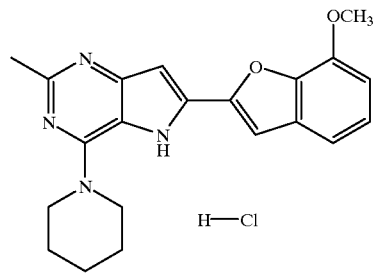

7-Methoxy-2-[2-methyl-4-piperidylpyrrolo[4,5-d]pyrimidin-6-yl]benzo[b]furan Hydrochloride Hydrate.

Using the method described in Example 30 by employing 7-methoxy-2-(1-pyrrolidinylvinyl)benzo[b]furan (freshly prepared before use from 2-acetyl-7-methoxybenzo[b]furan (Avocado Chemical Company), pyrrolidine and $TiCl_4$ (1.89 g, 7.77 mmol), 2-methyl-4,6-dichloro-5-nitropyrimidine (Example 76(b)) (1.61 g, 7.77 mmol), N,N-diisopropylethylamine (1.4 mL, 7.77 mmol), piperidine (1.2 mL, 12.4 mmol), $NEt_3$ (1.7 mL) and $SnCl_2$ (23 mL of a 2 M soln in DMF). In this example the $SnCl_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 $CHCL_3$/MeOH as eluant to give 0.27 g (10%) of 7-methoxy-2-[2-methyl-4-piperidylpyrrolo[4,5-d]pyrimidin-6-yl]benzo[b]furan as a brown colored powder. This compound (0.26 g, 0.72 mmol) was dissolved in 5:1 EtOAc/MeOH (30 mL) and heated to boiling. To the hot solution was added 1 M ethereal HCl (0.80 mL, 0.80 mmol). The solution was allowed to cool to room temperature. The resulting crystals were collected by filtration, washed with EtOAc (2×10 mL), $Et_2O$ (3×15 mL) and dried under vacuum at 60° C. to give 195 mg (7%) of the title compound as a yellow colored powder. Mp: >280° C. $^1$H NMR (DMSO-$d_6$; 400 MHz): δ 1.66 (br s, 6), 2.51 (s, 3), 3.92 (s, 3), 4.01 (br s, 4), 6.88 (s, 1), 6.98 (d, 1, J=9.6), 7.20 (t, 1, J=7.8), 7.28 (d, 1, J=7.7), 7.72 (s, 1), 12.31 (s, 1), 14.09 (s, 1). MS m/z:

363 (M+1 for free base). Anal. Calcd for C$_{21}$H$_{22}$N$_4$O$_2$.HCl.0.3H$_2$O: C, 62.38; H, 5.88; N, 13.86; Cl, 8.77. Found: C, 62.31; H, 5.81; N, 13.60; Cl, 8.82.

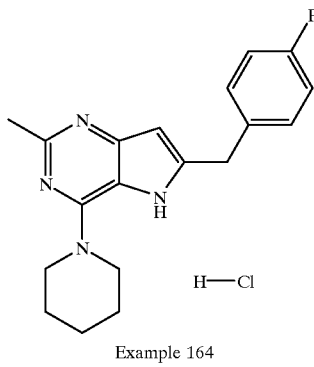

Example 164

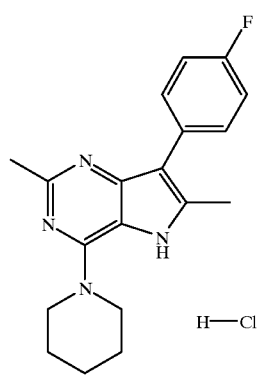

Example 165

EXAMPLE 164 AND EXAMPLE 165

6-[(4-Fluorophenyl)methyl]-2-methyl-4-piperidylpyrrolo[3,2-d]pyrimidine Hydrochloride and 7-(4-Fluorophenyl)-2,6-dimethyl-4-piperidylpyrrolo[3,2-d]pyrimidine Hydrochloride.

Using the method described in Example 30 by employing [2-(4-fluorophenyl)-1-methylvinyl]pyrrolidine (freshly prepared before use from (4-fluorophenyl) acetone (Aldrich Chemical Company), pyrrolidine and TiCl$_4$ (1.64 g, 8.00 mmol), 2-methyl-4,6-dichloro-5-nitropyrimidine (Example 76(b)) (1.66 g, 8.00 mmol), N,N-diisopropylethylamine (1.4 mL, 8.00 mmol), piperidine (1.3 mL, 12.8 mmol), NEt$_3$ (1.8 mL) and SnCl$_2$ (24 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 108 g (4%) of 6-[(4-fluorophenyl)methyl]-2-methyl-4-piperidylpyrrolo[3,2-d]pyrimidine as a white colored solid and 172 mg (7%) of 7-(4-fluorophenyl)-2,6-dimethyl-4-piperidyl pyrrolo[3,2-d] pyrimidine as a white colored solid.

Example 164

6-[(4-Fluorophenyl)methyl]-2-methyl-4-piperidylpyrrolo[3,2-d]pyrimidine (108 mg, 0.33 mmol) was dissolved in 5:1 EtOAc/MeOH (20 mL) and heated to boiling. To the hot solution was added 1 M ethereal HCl (0.40 mL, 0.40 mmol). The solution was allowed to cool to room temperature. The resulting solid was collected by filtration, washed with EtOAc (2×5 mL), Et$_2$O (3×5 mL) and dried under vacuum at 60° C. to give 97 mg (3%) of Example 164 as a white colored solid. Mp: 254–255° C. $^1$H NMR (DMSO-d$_6$; 400 MHz): δ 1.70 (br s, 6), 2.51 (s, 3), 3.98 (br s, 4), 6.21 (s, 1), 7.17 (t, 2, J=8.9), 7.35 (dd, 2, J=8.6, 8.5), 12.04 (s, 1), 13.90 (s, 1). MS m/z: 325 (M+1 for free base). Anal. Calcd for C$_{19}$H$_{21}$FN$_4$.HCl: C, 63.24; H, 6.15; N, 15.42; Cl, 9.93. Found: C, 63.26; H, 6.15; N, 15.42; Cl, 9.93.

Example 165

7-(4-Fluorophenyl)-2,6-dimethyl-4-piperidylpyrrolo[3,2-d]pyrimidine (162 mg, 0.50 mmol) was dissolved in 5:1 EtOAc/MeOH (15 mL) and heated to boiling. To the hot solution was added 1 M ethereal HCl (0.50 mL, 0.50 mmol). The solution was allowed to cool to room temperature. The resulting crystals were collected by filtration, washed with EtOAc (2×5 mL), Et$_2$O (3×5 mL) and dried under vacuum at 60° C. to give 122 mg (5%) of Example 165 as a beige colored solid. Mp: >280° C. $^1$H NMR (DMSO-d$_6$; 400 MHz): δ 1.63 (br s, 6), 2.37 (s, 3), 2.46 (s, 3), 3.95 (br s, 4), 7.30 (t, 2, J=8.8), 7.40 (dd, 2, J=8.5, 8.5), 12.10 (s, 1), 13.31 (s, 1). MS m/z: 325 (M+1 for free base). Anal. Calcd for C$_{19}$H$_{21}$FN$_4$.HCl: C, 63.24; H, 6.15; N, 15.53; Cl, 9.82. Found: C, 63.40; H, 6.22; N, 15.31; Cl, 9.94.

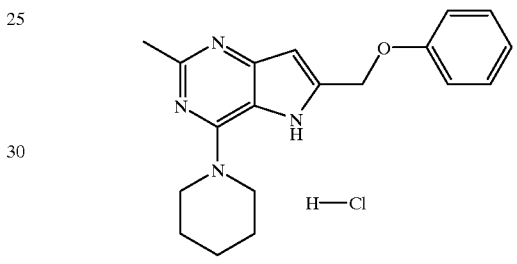

Example 166

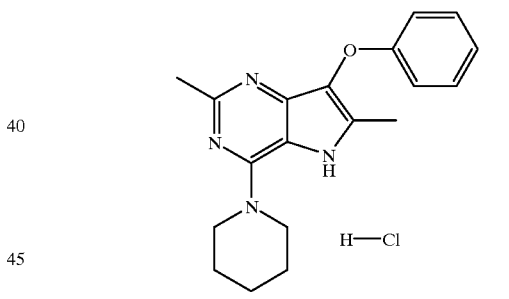

Example 167

EXAMPLE 166 AND EXAMPLE 167

[(2-Methyl-4-piperidylpyrrolo[4,5-d]pyrimidin-6-yl)methoxy]benzene hydrochloride and 2,6-Dimethyl-7-phenoxy-4-piperidylpyrrolo[3,2-d]pyrimidine Hydrochloride Hydrate.

Using the method described in Example 30 by employing [2-pyrrolidinylprop-2-enyloxy]benzene and [2-pyrrolidinylprop-1-enyloxy]benzene (freshly prepared before use from phenoxy-2-propanone (Aldrich Chemical Company), pyrrolidine and TiCl$_4$ (2.03 g, 13.50 mmol), 2-methyl-4,6-dichloro-5-nitropyrimidine (Example 76(b)) (2.79 g, 13.50 mmol), N,N-diisopropylethylamine (2.4 mL, 13.5 mmol), piperidine (2.2 mL, 21.6 mmol), NEt$_3$ (3.0 mL) and SnCl$_2$ (40 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 110 mg (3%) of [(2-methyl-4-piperidyl pyrrolo[4,5-d]pyrimidin-6-yl)methoxy]benzene as a brown colored gummy solid and 60 mg (1%) of 2,6-dimethyl-7-phenoxy-4-piperidylpyrrolo[3,2-d]pyrimidine as a yellow colored solid.

Example 166

[(2-Methyl-4-piperidylpyrrolo[4,5-d]pyrimidin-6-yl)methoxy]benzene (107 mg, 0.33 mmol) was dissolved in 5:1 EtOAc/MeOH (20 mL) and heated to boiling. To the hot solution was added 1 M ethereal HCl (0.40 mL, 0.40 mmol). The solution was allowed to cool to room temperature. The resulting solid was collected by filtration, washed with EtOAc (2×5 mL), Et$_2$O (3×5 mL) and dried under vacuum at 60° C. to give 66 mg (2%) of Example 166 as a white colored solid. Mp: 238–239° C. $^1$H NMR (DMSO-d$_6$; 400 MHz): δ 1.64 (br s, 6), 2.48 (s, 3), 3.94 (br s, 4), 5.22 (s, 2), 6.66 (s, 1), 6.92 (t, 1, J=7.3), 7.01 (d, 2, J=7.9), 7.26 (dt, 2, J=1.1, 7.4), 12.64 (s, 1), 14.18 (s, 1). MS m/z: 323 (M+1 for free base). Anal. Calcd for C$_{19}$H$_{22}$N$_4$O.HCl: C, 63.59; H, 6.46; N, 15.61; Cl, 9.88. Found: C, 63.48; H, 6.48; N, 15.51; Cl, 10.02.

Example 167

2,6-Dimethyl-7-phenoxy-4-piperidyl pyrrolo[3,2-d]pyrimidine (57 mg, 0.18 mmol) was dissolved in 5:1 EtOAc/MeOH (6 mL) and heated to boiling. To the hot solution was added 1 M ethereal HCl (0.20 mL, 0.20 mmol). The solution was allowed to cool to room temperature. The resulting crystals were collected by filtration, washed with EtOAc (2×5 mL), Et$_2$O (3×5 mL) and dried under vacuum at 60° C. to give 45 mg (1%) of Example 167 as a beige colored powder. Mp: >280° C. $^1$H NMR (DMSO-d$_6$; 400 MHz): δ 1.64 (br s, 6), 2.20 (s, 3), 2.43 (s, 3), 3.94 (br s, 4), 6.88 (d, 2, J=8.3), 7.01 (t, 1, J=7.0), 7.28 (t, 2, J=7.4), 12.01 (s, 1), 13.84 (s, 1). MS m/z: 323 (M+1 for free base). Anal. Calcd for C$_{19}$H$_{22}$N$_4$O.HCl.0.75H$_2$O: C, 61.28; H, 6.63; N, 15.05; Cl, 9.52. Found: C, 61.25; H, 6.31; N, 14.73; Cl, 9.44.

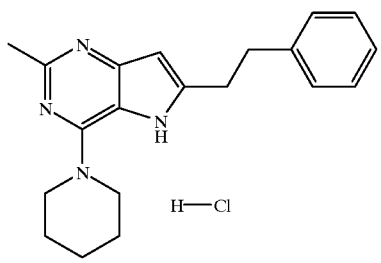

Example 168

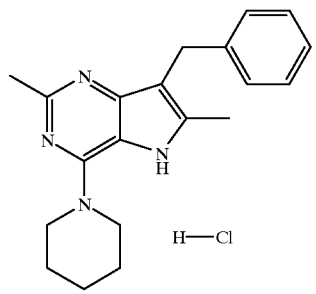

Example 169

EXAMPLE 168 AND EXAMPLE 169

2-Methyl-6-(2-phenylethyl)-4-piperidylpyrrolo[3,2-d]pyrimidine Hydrochloride Hydrate and 2,6-Dimethyl-7-benzyl-4-piperidylpyrrolo[3,2-d]pyrimidine Hydrochloride Hydrate.

Using the method described in Example 30 by employing [1-(2-phenylethyl)vinyl]pyrrolidine and [1-(3-phenylprop-1-enyl]pyrrolidine (freshly prepared before use from benzylacetone (Aldrich Chemical Company), pyrrolidine and TiCl$_4$ (2.23 g, 11.3 mmol), 2-methyl-4,6-dichloro-5-nitropyrimidine (Example 76(b)) (2.34 g, 11.3 mmol), N,N-diisopropylethylamine (2.0 mL, 11.3 mmol), piperidine (1.8 mL, 18.1 mmol), NEt$_3$ (2.5 mL) and SnCl$_2$ (34 mL of a 2 M soln in DMF). In this example the SnCl$_2$ solution was added to the reaction mixture at 140° C. The mixture was stirred at 140° C. for an additional 16 h then the heating was discontinued and the mixture was allowed to cool to room temperature. The residue was purified by flash chromatography on silica gel with 50:50 EtOAc/hexanes as eluant to give 500 mg (14%) of 2-methyl-6-(2-phenyl thyl)-4-piperidylpyrrolo[3,2-d]pyrimidine as a brown colored solid and 181 mg (5%) of 2,6-dimethyl-7-benzyl-4-piperidylpyrrolo[3,2-d]pyrimidine as a beige colored solid.

Example 168

2-Methyl-6-(2-phenylethyl)-4-piperidylpyrrolo[3,2-d]pyrimidine (481 mg, 1.50 mmol) was dissolved in 5:1 EtOAc/MeOH (40 mL) and heated to boiling. To the hot solution was added 1 M ethereal HCl (1.50 mL, 1.50 mmol). The solution was allowed to cool to room temperature. The resulting solid was collected by filtration, washed with EtOAc (2×5 mL), Et$_2$O (3×5 mL) and dried under vacuum at 60° C. to give 271 mg (7%) of Example 168 as a beige colored powder. Mp: 236–238° C. $^1$H NMR (DMSO-d$_6$; 400 MHz): δ 1.60 (br s, 6), 2.45 (s, 3), 2.95 (t, 2, J=8.4), 3.09 (t, 2, J=8.4), 3.92 (br s, 4), 6.24 (s, 1), 7.11–7.14 (m, 1), 7.16–7.25 (m, 4), 11.88 (s, 1), 14.06 (s, 1). MS m/z: 321 (M+1 for free base). Anal. Calcd for C$_{20}$H$_{24}$N$_4$.HCl.0.25H$_2$O: C, 66.46; H, 7.11; N, 15.51; Cl, 9.81. Found: C, 66.40; H, 7.12; N, 15.37; Cl, 9.91.

Example 169

2,6-Dimethyl-7-benzyl-4-piperidyl pyrrolo[3,2-d]pyrimidine (175 mg, 0.55 mmol) was dissolved in 5:1 EtOAc/MeOH (30 mL) and heated to boiling. To the hot solution was added 1 M ethereal HCl (0.60 mL, 0.60 mmol). The solution was allowed to cool to room temperature. The resulting crystals were collected by filtration, washed with EtOAc (2×5 mL), Et$_2$O (3×5 mL) and dried under vacuum at 60° C. to give 71 mg (2%) of Example 169 as a beige colored powder. Mp: >240° C. (dec). $^1$H NMR (DMSO-d$_6$; 400 MHz): δ 1.61 (br s, 6), 2.28 (s, 3), 2.52 (s, 3), 3.91 (br s, 4), 4.07 (s, 2), 7.08–7.13 (m, 3), 7.20 (t, 2, J=7.6), 11.99 (s, 1), 14.21 (s, 1). MS m/z: 321 (M+1 for free base). Anal. Calcd for C$_{20}$H$_{24}$N$_4$.HCl.0.4H$_2$o: C, 65.97; H, 7.14; N, 15.39; Cl, 9.74. Found: C, 66.04; H, 6.98; N, 15.37; Cl, 9.79.

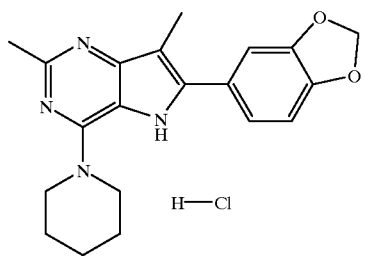

EXAMPLE 170

5-[2,7-Dimethyl-4-piperidylpyrrolo[4,5-d]pyrimidin-6-yl]-2H-benzo[d]1,3-dioxolane Hydrochloride Hydrate.

Using the method described in Example 30 by employing 5-(1-pyrrolidinylprop-1-enyl)-2H-benzo[d]1,3-dioxolene (freshly prepared before use from 3,4-methylenedioxypropiophenone (Lancaster Chemical Company), pyrrolidine and TiCl₄ (2.03 g, 8.78 mmol), 2-methyl-4,6-dichloro-5-nitropyrimidine (Example 76(b)) (1.82 g, 8.78 mmol), N,N-diisopropylethylamine (1.5 mL, 8.78 mmol), piperidine (1.4 mL, 14.1 mmol), NEt₃ (2.0 mL) and SnCl₂ (26 mL of a 2 M soln in DMF). In this example the SnCl₂ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl₃/MeOH as eluant to give 247 mg (8%) of 5-[2,7-dimethyl-4-piperidylpyrrolo[4,5-d]pyrimidin-6-yl]-2H-benzo[d]1,3-dioxolane as a beige colored solid. This compound (241 mg, 0.69 mmol) was dissolved in 5:1 EtOAc/MeOH (30 mL) and heated to boiling. To the hot solution was added 1 M ethereal HCl (0.70 mL, 0.70 mmol). The solution was allowed to cool to room temperature. The resulting crystals were collected by filtration, washed with EtOAc (2×10 mL), Et₂O (3×15 mL) and dried under vacuum at 60° C. to give 165 mg (5%) of the title compound as a beige colored powder. Mp: 268–269° C. ¹H NMR (DMSO-d₆; 400 MHz): δ 1.63 (br s, 6), 2.24 (s, 3), 2.54 (s, 3), 3.96 (br s, 4), 6.07 (s, 2), 7.05–7.11 (m, 2), 7.05 (d, 1, J=1.3), 11.76 (s, 1), 13.89 (s, 1). MS m/z: 351 (M+1 for free base). Anal. Calcd for $C_{20}H_{22}N_4O_2 \cdot HCl \cdot 0.4H_2O$: C, 60.95; H, 6.09; N, 14.22; Cl, 9.00. Found: C, 60.99; H, 5.88; N, 14.19; Cl, 9.09.

EXAMPLE 171

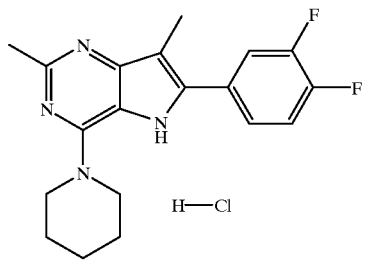

6-(3,4-Difluorophenyl)-2,7-dimethyl-4-piperidyl pyrrolo[3,2-d]pyrimidine Hydrochloride.

Using the method described in Example 30 by employing [1-(3,4-difluorophenyl)prop-1-enyl]pyrrolidine (freshly prepared before use from 3,4-difluoropropiophenone (Lancaster Chemical Company), pyrrolidine and TiCl₄ (2.27 g, 10.2 mmol), 2-methyl-4,6-dichloro-5-nitropyrimidine (Example 76(b)) (2.11 g, 10.2 mmol), N,N-diisopropylethylamine (1.8 mL, 10.2 mmol), piperidine (1.6 mL, 16.3 mmol), NEt₃ (2.3 mL) and SnCl₂ (31 mL of a 2 M soln in DMF). In this example the SnCl₂ solution was added to the reaction mixture at 140° C. The mixture was stirred at 140° C. for an additional 16 h then the heating was discontinued and the mixture was allowed to cool to room temperature. The residue was purified by flash chromatography on silica gel with 95:5 CHCl₃/MeOH as eluant to give 305 mg (9%) of 6-(3,4-difluorophenyl)-2,7-dimethyl-4-piperidylpyrrolo[3,2-d]pyrimidine as a brown colored oil. This compound (304 mg, 0.89 mmol) was dissolved in 5:1 EtOAc/MeOH (30 mL) and heated to boiling. To the hot solution was added 1 M ethereal HCl (0.90 mL, 0.90 mmol). The solution was allowed to cool to room temperature. The resulting crystals were collected by filtration, washed with EtOAc (2×10 mL), Et₂O (3×15 mL) and dried under vacuum at 60° C. to give 201 mg (5%) of the title compound as a beige colored powder. Mp: >280° C. ¹H NMR (DMSO-d₆; 400 MHz): δ 1.63 (br s, 6), 2.27 (s, 3), 2.56 (s, 3), 3.98 (br s, 4), 7.47–7.49 (m, 1), 7.61 (q, 1, J=8.6), 7.78 (dt, 1, J=1.4, 7.8), 11.96 (s, 1), 14.08 (s, 1). MS m/z: 343 (M+1 for free base). Anal. Calcd for $C_{19}H_{20}F_2N_4 \cdot 1.1HCl$: C, 59.64; H, 5.56; N, 14.65; Cl, 10.22. Found: C, 59.59; H, 5.56; N, 14.67; Cl, 10.02.

EXAMPLE 172

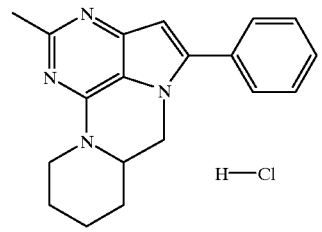

2-Methyl-5-phenyl-7,7a,8,9,10,11-hexahydro-1,3,11a-triaza-pyrrolo[3,2,1-de]phenanthridine Hydrochloride monohydrate.

A solution of 2-methyl-4-chloro-6-phenyl pyrrolo[3,2-d] pyrimidine (1.0 g, 4.1 mmol, Example 1e) and 2-hydroxymethyl piperidine (Aldrich Chemical Company) (0.49 g, 4.2 mmol) in N-methyl morpholine (10 mL) was heated at 110° C. for 12 h. The solvent was concentrated in vacuo and the residue was mixed with POCl₃ (5 mL, 54 mmol) and toluene (20 mL). The mixture was heated at reflux for 6.5 h before it was concentrated in vacuo. The residue was taken up in CH₂Cl₂ (50 mL)-H₂O (50 mL) and the pH of the aqueous phase was adjusted to pH~8 with NaOH solution (2 N). The organic phase was separated and the aqueous phase was extracted with CH₂Cl₂ (3×). The combinbed organic phase was dried over Na₂SO₄, concentrated in vacuo, and the resulting residue was purified by flash chromatography on silica gel (MeOH in CH₂Cl₂, 1–15%). The free base was treated with ethereal HCl to give the title compound as the HCl salt (0.18 g, 14%). Mp: >280° C. ¹H NMR (DMSO-d₆; 500 MHz): d 1.58–1.66 (m, 3), 1,85–1.91 (m, 2), 2.05 (d, 1, J=10), 2.55 (s, 3), 3.43 (t, 1, J=10), 4.22–4.25 (m, 2), 4.77 (t, 1, J=14), 4.86(d, 1, J=13), 7.10 (s, 1), 7.49–7.57 (m, 3), 8.02 (d, 2, J=8). MS m/z: 305 (M+1). Anal. Calcd for $C_{19}H_{20}N_4 \cdot 2HCl \cdot H_2O$: C, 57.72; H, 6.12; N, 14.18; Cl, 17.95. Found: C, 57.69; H, 6.24; N, 14.02; Cl, 17.79.

EXAMPLE 173

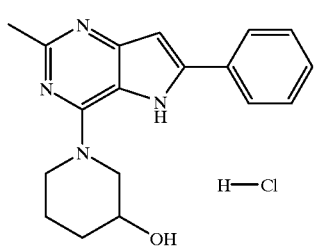

1-(2-Methyl-6-phenylpyrrollo[2,3-e]pyrimidine-4-yl)piperidin-3-ol Hydrochloride Hydrate.

A solution of 2-methyl-4-chloro-6-phenylpyrrolo[3,2-d]pyrimidine (0.6 g, 2.5 mmol, Example 1e), 3-hydroxy piperidine hydrogen chloride (Aldrich Chemical Company) (0.34 g, 2.5 mmol), and iso-Pr$_2$NEt (1.0 mL) in toluene was heated at reflux for 24 h. The mixture was allowed to cool to room temperature and was treated with aqueous NaOH (0.5 N, 10 mL). The slurry was filtered, and the solid was washed with CH$_2$Cl$_2$ (3×5 mL). The solid was dissolved in a mixture of CH$_2$Cl$_2$ (5 mL) plus a minimum amount of MeOH and the solution was treated with HCl (2 mL, 1 N in ether). The resulting mixture was filtered and the solid was trituated with hot EtOAc to afford the title compound as a white solid (0.54 g, 71%). $^1$H NMR (DMSO-d$_6$; 400 MHz): d 1.44–1.66 (m, 2), 1.74–1.80 (m, 2), 2.58 (s, 3), 3.76 (br s, 2), 3.99 (br s, 1), 4.30 (d, br d, J=12), 5.15 (br s, 0.5), 6.89 (s, 1), 7.44–7.57 (m, 3), 7.98 (d, 2, J=7.2), 11.90–11.98 (br s, 1). MS m/z: 308 (M+1). Anal. Calcd for C$_{18}$H$_{20}$N$_4$O.1.19HCl.0.34H$_2$O: C, 60.38; H, 6.16; N, 15.65; Cl, 11.80. Found: C, 60.38; H, 5.91; N, 15.61; Cl, 11.83.

EXAMPLE 174

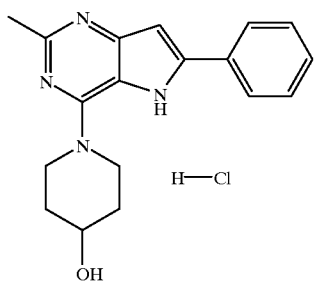

1-(2-Methyl-6-phenylpyrrolo[2,3-e]pyrimidine-4-yl)piperidin-4-ol Hydrochloride Hydrate.

The title compound was prepared according to the procedure described in Example 173, using 4-hydroxy piperidine (Aldrich Chemical Company) (0.26 g, 2.57 mmol) and 2-methyl-4-chloro-6-phenylpyrrolo[3,2-d]pyrimidine (Example 1e) (0.49 g, 2.0 mmol), as a white solid (0.30 g, 48%). $^1$H NMR (DMSO-d$_6$; 400 MHz) d 1.51–1.59 (m, 2), 2.58 (s, 3), 3.78–3.90 (m, 3), 4.34–4.37 (m, 2), 6.89 (s, 1), 7.49–7.57 (m, 3), 7.96 (d, 2, J=7.2), 11.8 (br s, 1). MS m/z: 308 (M+1). Anal. Calcd for C$_{18}$H$_{20}$N$_4$O.HCl.0.33H$_2$O: C, 61.62; H, 5.94; N, 15.97; Cl, 10.10. Found: C, 61.62; H, 5.91; N, 15.81; Cl, 10.28.

EXAMPLE 175

8-Aza-8-(2-Methyl-6-phenylpyrrolo[2,3-e]pyrimidine-4-yl)-1,4-dioxaspiro[4,5]decane Hydrochloride Hydrate.

The title compound was prepared according to the procedure described in Example 173, using 1,4-dioxa-8-azaspiro[4,5]decane (Aldrich Chemical Company) (0.35 g, 2.50 mmol) and 2-methyl-4-chloro-6-phenylpyrrolo[3,2-d]pyrimidine (Example 1e) (0.60 g, 2.47 mmol), as a white solid (0.46 g, 53%). $^1$H NMR (DMSO-d$_6$; 400 MHz) d 1.83 (br t, 4), 2.58 (s, 3), 3.97(s, 4), 4.12 (br t, 4), 6.93 (s, 1), 7.50–7.6 (m, 3), 7.96 (d, 2, J=6.8), 12.0 (br s, 1). MS m/z: 350 (M+1). Anal. Calcd for C$_{20}$H$_{22}$N$_4$O$_2$.1.01HCl.0.3H$_2$O: C, 61.18; H, 6.06; N, 14.27; Cl, 9.13. Found: C, 61.18; H, 5.76; N, 14.35; Cl, 9.36.

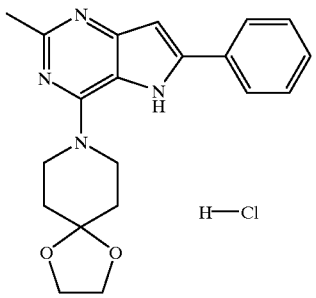

EXAMPLE 176

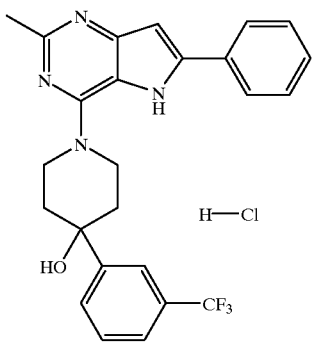

1-(2-Methyl-6-phenylpyrrolo[2,3-e]pyrmindine-4-yl)-4-[3-(trifluoromethyl)phenyl]piperidin-4-ol Hydrochloride Hydrate.

The title compound was prepared according to the procedure described in Example 173, using 4-[3-(trifluromethyl)phenyl]-4-piperidinol hydrochloride (Acros Organics) (0.6 g, 2.1 mmol) and 2-methyl-4-chloro-6-phenyl pyrrolo[3,2-d]pyrimidine (Example 1e) (0.42 g, 1.73 mmol), as a white solid (0.5 g, 59%). $^1$H NMR (DMSO-d$_6$; 400 MHz): d 1.83 (d, 2, J=13), 2.18 (t, 2, J=11), 2.59 (s, 3), 3.73 (br s, 2), 4.81 (br s, 2), 5.70 (s, 1), 6.93 (s, 1), 7.49–7.62 (m, 5), 7.83 (d, 1, J=7.6), 7.89 (s, 1), 7.97 (d, 2, J=7.6). MS m/z: 453 (M+1). Anal. Calcd for C$_{25}$H$_{23}$F$_3$N$_4$O.1.17HCl.0.17H$_2$O: C, 60.25; H, 4.96; N, 11.25; Cl, 8.33. Found: C, 60.25; H, 5.16; N, 10.88; Cl, 5 8.18.

EXAMPLE 177

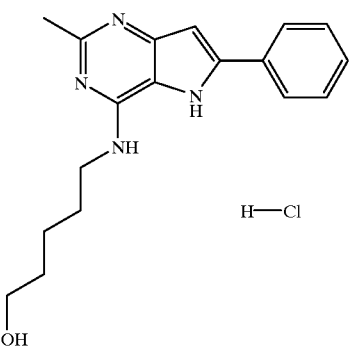

5-[(2-Methyl-6-phenylpyrrolo[2,3-e]pyrimidine-4-yl)amino]pentan-1-ol Hydrochloride Hydrate.

The title compound was prepared according to the procedure described in Example 173, using 5-amino-1-pentanol (Fluka Chemika) (0.35 g, 3.4 mmol) and 2-methyl-4-chloro-6-phenylpyrrolo[3,2-d]pyrimidine (Example 1e) (0.42 g, 1.73 mmol), as a white solid (0.36 g, 61%). $^1$H NMR (DMSO-d$_6$; 400 MHz): d 1.46 (br s, 4), 1.68 (bs, 2), 2.58 (s, 3), 3.62 (br s, 2), 4.40 (br s, 1), 6.93 (s, 1), 7.46–7.54 (m, 3), 8.05 (br, 2), 9.61 (s, 1), 13.47 (s, 1). MS m/z: 311 (M+1). Anal. Calcd for C$_{18}$H$_{22}$N$_4$O.HCl.0.28H$_2$O: C, 61.42; H, 6.75; N, 15.92; Cl, 10.07. Found: C, 61.42; H, 6.67; N, 15.75; Cl, 10.17.

EXAMPLE 178

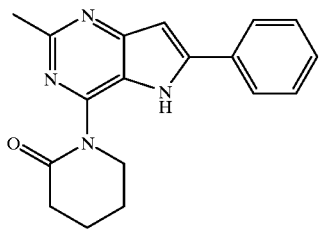

1-(2-Methyl-6-phenylpyrrolo[2,3-e]pyrimidine-4-yl)piperidin-2-one.

Phenyl-5-[(2-methyl-6-phenylpyrrolo[2,3-e]pyrimidine-4-yl)amino]pentanoate. A mixture of 2-methyl-4-chloro-6-phenylpyrrolo[3,2-d]pyrimidine (Example 1e) (1.0 g, 4.11 mmol), 5-aminovaleric acid (Aldrich Chemical Company) (0.78 g, 0.66 mmol), and phenol (1.0 g, 10.6 mmol) was heated at 150° C. for 24 h. The mixture was let cool to room temperature and was treated with 5 mL each of EtOAc and ether. The mixture was filtered and the solid was washed with ether (3x) to give a light yellow solid (1.15 g). A solution of this intermediate (0.2 g), EDCI-HCl (Aldrich Chemical Company) (0.32 g, 1.7 mmol), and a catalytic amount of 4-dimethylaminopyridine in CH$_2$Cl$_2$/DMF/pyridine (5:2:2 mL) was stirred at room temperature overnight. EtOAc (50 mL) was added and the resulting mixture was washed with H$_2$O (3x). The combined aqueous phase was back extracted with ether (1x) and the combined organic phase was washed with brine, dried over Na$_2$SO$_4$, and concentrated in vacuo. The resulting residue was purified by flash chromatography on silica gel with 6% NH$_3$ (2N solution in MeOH) in CH$_2$Cl$_2$ to give the title compound as a white solid (0.018 g, 8%). $^1$H NMR (CDCl$_3$; 400 MHz): d 1.96–2.13 (m, 4), 2.66–2.89 (m, 5), 4.17 (t, 2, J=5.6), 6.86(d, 1, J=2.0), 7.38D7.54 (m, 3), 7.74 (d, 2, J=8.0), 9.68 (s, 1). MS m/z: 307 (M+1). HPLC (H$_2$O/CH$_3$CN, 50:50): Rf 1.444, >97% pure.

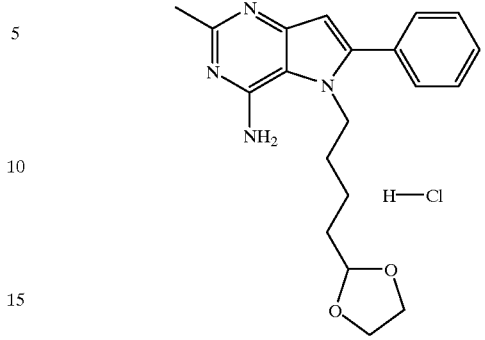

EXAMPLE 179

5-(4-(1,3-Dioxolan-2-yl)butyl)-2-methyl-6-phenyl pyrrolo[3,2-d]pyrimidine-4-ylamine Hydrochloride.

A solution of 2-methyl-4-amino-6-phenylpyrrolo[3,2-d]pyrimidine (Example 22) (0.079 g, 0.35 mmol), 2-(1-chlorobutyl)-1,3-dioxolane (Fluka Chemika) (0.14 g, 0.85 mmol), and iso-Pr$_2$NEt (0.3 mL, 1.7 mmol) in toluene/DMF (2.5:1.0 mL) was heated at reflux for 6 days. The mixture was allowed to cool to room temperature and purified by flash chromatography on silica gel with 5% NH$_3$ (2N in MeOH) 5% MeOH in CH$_2$Cl$_2$ to afford the product. The product was dissolved in CH$_2$Cl$_2$/EtOAc (1:1) and the solution was treated with a 2 M ethereal HCl (2 mL). The resulting slurry was filtered, and the solid was washed with hot EtOAc (3x) to give a yellow solid (29 mg, 23%). $^1$H NMR (DMSO-d$_6$; 400 MHz): d 1.53 (m, 2), 1.64 (m, 2), 1.84 (m, 2), 2.68 (s, 3), 3.86 (m, 2), 4.32 (br t, 2), 4.80 (t, 1), 7.34 (s, 1), 7.48–7.58 (m, 3), 8.11 (d, 2), 8.89 (s, 1), 9.17 (s, 1), 13.90 (s, 1). MS m/z: 353 (M+1). Anal. Calcd for C$_{20}$H$_{24}$N$_4$O$_2$.2HCl: C, 56.47; H, 6.16; N, 13.18. Found: C, 56.36; H, 6.08; N, 13.21.

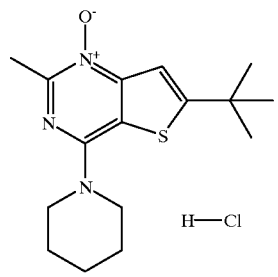

EXAMPLE 180

6-(tert-Butyl)-2-methyl-4-piperidylthiopheno[3,2-d]pyrimidin-1-ol Hydrochloride.

A solution of 6-(tert-butyl)-2-methyl-4-piperidyl thiopheno[3,2-d]pyrimidine (Example 34) (0.207 g, 0.716 mmol) in CH$_2$Cl$_2$ (5 mL) was treated with meta-chloro perbenzoic acid (Aldrich Chemical Company) (0.5 g, 2.9 mmol, 57–86% pure) and the reaction mixture was stirred at room temperature for 3 days. The reaction mixture was treated with aqueous NaOH (0.5 N, 10 mL) and the two layers were separated. The aqueous layer was extracted with CH$_2$Cl$_2$ (3x) and the combined organic phase was dried over Na$_2$SO$_4$, and concentrated in vacuo. The resulting residue was purified by flash chromatography on silica with MeOH in CH$_2$Cl$_2$ (0–10%) to give the product as a yellow solid (0.047 g, 21%). The product was dissolved in CH$_2$Cl$_2$ (1.0 mL) and the solution was treated with HCl (1 N in ether, 1.0 mL). The resulting solution was left capped at room temperature for 3 days whereby large yellow crystals were formed. The solvent was decanted and the crystals were washed with 1:1 EtOAc-hexanes (3×) to give the title compound (~15 mg). Mp: 202–203° C. (dec). $^1$H NMR (CDCl$_3$; 400 MHz): d 1.47 (s, 9), 1, 80 (br s, 6), 2.85 (s, 3), 4.05 (br s, 4), 7.46 (s, 1), 13.89 (br s, 1). MS m/z: 306 (M+1). Anal. Calcd for C$_{16}$H$_{23}$N$_3$OS.HCl: C, 56.2; H, 7.08; N, 12.29; S, 9.38. Found: C, 55.96; H, 6.99; N, 12.15; Cl, 15.51. The structure was confirmed by x-ray crystallography.

EXAMPLE 181

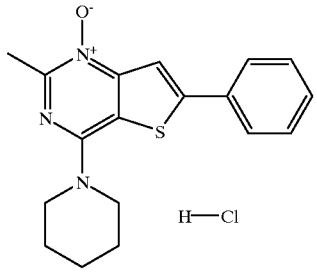

2-Methyl-6-phenyl-4-piperidylthiopheno[3,2-d]pyrimidin-1-ol Hydrochloride.

The oxidation was performed in a similar fashion as described in Example 180, using 240 mg (0.78 mmol) of 2-methyl-6-phenyl-4-piperidylthiopheno[3,2-d]pyrimidine (Example 32) and 240 mg (1.39 mmol, 57–86%) of meta-chloroperbenzoic acid to afford the product (76 mg, 30%). The product was dissolved in 2.0 mL of CH$_2$Cl$_2$ and the solution was treated with 0.3 mL of HCl (2N in ether). The solid was collected and was washed with hot EtOAc (3×) to give the title compound as a yellow solid (54 mg). $^1$H NMR (DMSO-d$_6$; 400 MHz) d 1.73 (s, 6), 2.69 (s, 3), 4.06 (br s, 4), 7.56 (br s, 3), 7.99 (br s, 2), 8.09 (s, 1). MS m/z: 326 (M+1).

EXAMPLE 182

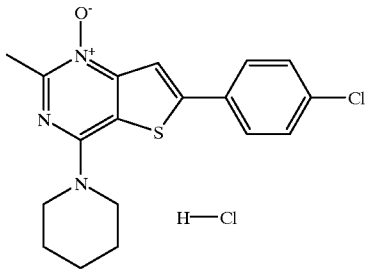

6-(4-Chloro-phenyl)-2-methyl-4-piperidylthiopheno[3,2-d]pyrimidin-1-ol Hydrochloride Hydrate.

The oxidation was performed in a similar fashion as described in Example 180, using 246 mg (0.72 mmol) of 6-(4-chloro-phenyl)-2-methyl-4-piperidylthiopheno[3,2-d]pyrimidine (Example 33) and 250 mg of meta-chloroperbenzoic acid (1.45 mmol, 57–80%), to afford the product (156 mg, 60%). A total of 226 mg of the product were dissolved in 2.5 mL of CH$_2$Cl$_2$ and the solution was treated with 0.3 mL of HCl (2N in ether). The solid was collected and washed with hot EtOAc (3×) to give the title compound as a yellow solid (87 mg). $^1$H NMR (DMSO-d$_6$; 400 MHz): d 1.73 (br s, 6), 2.69 (s, 3), 4.07 (br s, 4), 6.84 (s, 1), 763 (d, 2, J=8.4), 8.01 (d, 2, J=8.4), 8.15 (s, 1). MS m/z: 360, 362. Anal. Calcd for C$_{18}$H$_{18}$N$_3$ClOS.HCl.0.5H$_2$O: C, 53.33; H, 4.97; N, 10.37; S, 7.71; Cl, 17.49. Found: C, 53.00; H, 4.77; N, 10.21; S, 7.70; Cl, 15.51.

EXAMPLE 183

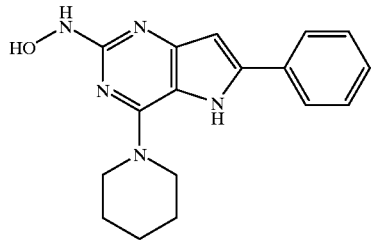

6-Phenyl-4-piperdyl)pyrrolo[3,2-d]pyrimidine-2-yl hydroxylamine Hydrochloride.

To a sealed 3-mL vial was 2-chloro-6-phenyl-4-piperidylpyrrolo[3,2-d]pyrimidine (Example 203(c)) (59 mg, 0.189 mmol), hydroxylamine hydrochloride (Aldrich Chemical Company) (52.5 mg, 0.754 mmol) and pyridine (1.0 mL). The solution was heated at 100° C. for 4 h. The reaction mixture was allowed to cool to room temperature and pyridine was removed in vacuo. The resulting residue was washed with sat. NaHCO$_3$, and extracted with CHCl$_3$ three times. The combined organic layers were dried over anhydrous Na$_2$SO$_4$, filtered and concentrated in vacuo. The resulting crude oil was purified by flash chromatography on silica gel with MeOH/CH$_2$Cl$_2$/NH$_4$OH(4:95:1) as eluant to afford 35 mg (60%) of a light-brown solid. The free base (35 mg, 0.113 mmol) was dissolved in hot MeOH (2 mL) and anhydrous ethereal HCl (0.113 mL of a 2 M soln, 0.226 mmol) was added dropwise. The precipitate was collected by filtration, washed with EtOAc/ether (1:1) (3×0.5 mL) and dried over vacuum to give 25 mg (58 %) of the title compound as a light brown solid. $^1$H NMR (DMSO-d$_6$; 400 MHz): d 1.40–1.50 (m, 6), 3.70–3.80 (m, 4), 6.48 (s, 1), 7.30–7.80 (m, 5), 9.72 (s, 0.5), 10.50 (s, 0.5), 11.46 (s, 0.5), 12.44 (s, 0.5). MS m/z : 310 (M+1). Anal. Calcd for C$_{17}$H$_{19}$N$_5$O.2HCl: C, 53.41; H, 5.54; N, 18.32. Found: C, 54.37; H, 6.16; N, 17.86.

EXAMPLE 184

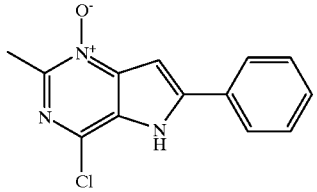

(a) 4-Chloro-2-methyl-6-phenylpyrrolo[3,2-d]pyrimidin-1-ol.

To a solution of 2-methyl-4-chloro-6-phenyl pyrrolo[3,2-d]pyrimidine (Example 1e) (0.30 g, 1.23 mmol) in CH$_2$Cl$_2$ (5 mL) was added meta-chloroperbenzoic acid (Aldrich Chemical Company) (0.48 g, 2.79 mmol, 57–86%). The mixture was stirred at room temperature for 12 h whereby it was filtered. The solid was further washed with ether (3×) to afford the product as a yellow solid. $^1$H NMR (MeOH-d$_4$; 400 MHz): d 2.60 (s, 3), 7.30 (s, 1), 7.47–7.56 (m, 3), 8.12 (d, 2, J=7.4), 12.4–13.1 (br s, 1). MS m/z: 259 (M+1).

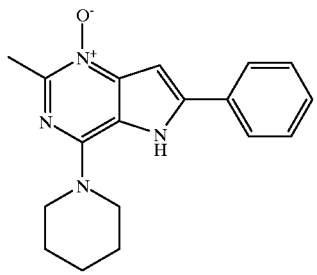

(b) 2-Methyl-6-phenyl-4-piperidylpyrrolo[3,2-d]pyrimidin-1-ol.

A solution of the chloride intermediate, prepared in Example 184(a), (0.178g, 0.69 mmol), and piperidine (0.50 mL, 5 mmol) in DMF (2.0 mL) was heated at 80° C . for 4 h. The solution was allowed to cool to room temperature and was diluted with EtOAc (~20 mL). The resulting mixture was washed with aqueous NaOH (0.5 M, 10 mL), dried over $Na_2SO_4$, and concentrated in vacuo. Purification by flash chromatography on silica gel with $NH_3$ (2 N in MeOH)-MeOH in $CH_2Cl_2$ (0–5%), followed by preparative TLC with $NH_3$ (2 N in MeOH)-MeOH in $CH_2Cl_2$ (2.5–5%), give the product (43 mg, 20%), which was crystallized from MeOH/EtOAc (1:4) as light yellow plates. Mp: 169–170° C.; $^1$H NMR (MeOH-$d_4$; 400 MHz): d 1.78 (s, 6), 2.65 (s, 3), 4.06 (br s, 4), 6.93 (s, 1), 7.32–7.54 (m, 3), 7.82 (d, 2, J=10.8). MS m/z: 309 (M+1). The structure was determined to be the monohydrate by x-ray crystallography.

EXAMPLE 185

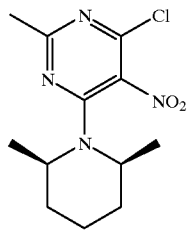

(a) 4-((6S,2R)-2,6-Dimethylpiperidyl)-6-chloro-2-methyl-5-nitropyrimidine.

To a solution of 4,6-dichloro-2-methyl-5-nitro pyrimidine (Example 76 (b)) (2.44 g, 11.78 mmol, 1.0 eq) and triethylamine (Aldrich Chemical Company, 2.38 g, 23.56 mmol, 2.0 eq) in THF (12 mL) was added a solution of cis-2,6-dimethylpiperidine (Aldrich Chemical Company, 1.59 g, 11.78 mmol, 1.0 eq) in THF (12 mL) slowly. The final reaction mixture was stirred at room temperature for 3 days. After the removal of solvent in vacuo, the crude material was purified by flash chromatography on silica gel with 0–10% EtOAc/hexanes as eluant to afford the title compound (2.80 g, 84%) as a brown solid. $^1$H NMR (CDCl$_3$, 500 MHz): d 1.29 (d, 6, J=7.0), 1.56 (m, 1), 1.60–1.63 (m, 2), 1.73 (m, 2), 1.84–1.90 (m, 1), 2.50 (s, 3), 4.42 (m, 2). MS m/z: 285 (M+H), m/z: 283 (M−H).

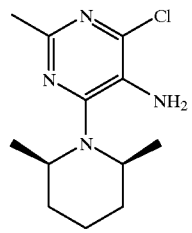

(b) 4-((6S,2R)-2,6-Dimethylpiperidyl)-6-chloro-2-methylpyrimidine-5-ylamine.

To a solution of 4-((6S,2R)-2,6-dimethyl piperidyl)-6-chloro-2-methyl-5-nitropyrimidine (Example 185(a)) (2.26 g, 7.94 mmol, 1.0 eq) in anhydrous diethyl ether (15 mL) was added a freshly prepared solution of $SnCl_2.H_2O$ (Aldrich Chemical Company, 32 mL, 2.0 M in concentrated aqueous HCl) slowly under $N_2$ at 0° C. The reaction mixture was stirred at room temperature for 3 h, and then was poured onto a ice bath containing NaOH (12 g). The aqueous phase was extracted with EtOAc (100 mL×4). The water phase was passed through a pad of Celite® and was extracted again with EtOAc (100 mL×3). The combined organic layers were dried over $Na_2SO_4$, filtered and concentrated in vacuo. The crude material was purified by flash chromatography on silica gel with 0–50% EtOAc/hexanes as eluant to afford the title compound (795 mg, 40%) as a yellow oil. $^1$H NMR (CDCl$_3$, 400 MHz): d 0.75 (d, 6, J=6.2), 1.31–1.34 (m, 2), 1.50–1.60 (m, 1), 1.72–1.76 (m, 3), 2.55 (s, 3), 3.03–3.07 (m, 2) 4.34 (br s, 2). MS m/z: 255 (M+H).

(c) 4-((6S,2R)-2,6-Dimethylpiperidyl-2-methyl-6-(2-phenylethynyl)pyrimidine-5-ylamine.

A mixture of 4-((6S,2R)-2,6-dimethylpiperidyl)-6-chloro-2-methylpyrimidine-5-ylamine (Example 185(b)) (347 mg, 1.36 mmol, 1.0 eq), phenylacetylene (Aldrich Chemical Company, 279 mg, 2.73 mmol, 2.0 eq), Pd(PPh$_3$)$_2$Cl$_2$ (Aldrich Chemical Company, 48 mg, 0.068 mmol, 0.05 eq) and CuI (Aldrich Chemical Company, 13 mg, 0.068 mmol, 0.05 eq) in triethylamine (3 mL) was stirred under $N_2$ at 70° C. overnight. Upon cooling to room temperature, the reaction mixture was diluted with CHCl$_3$ (50 mL), passed through a pad of Celite® and concentrated in vacuo. The crude material was purified by flash chromatography on silica gel with 0–8% EtOAc/hexanes as eluant to afford the title compound (412 mg, 95%) as a cherry colored semi-solid. $^1$H NMR (CDCl$_3$, 400 MHz): d 0.78 (d, 6, J=6.2), 1.25–1.40 (m, 2), 1.50–1.60 (m, 1), 1.74–1.77 (m, 3), 2.59 (s, 3), 4.57 (br s, 2), 7.38 (m, 3), 7.60 (m, 2). MS m/z: 321 (M+H).

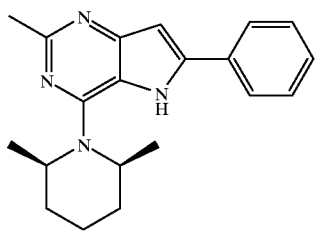

(d) 4-((6S,2R)-2,6-Dimethyl)-2-methyl-6-phenylpyrrolo[3,2-d]pyrimidine Hydrochloride.

A solution of 4-((6S,2R)-2,6-dimethylpiperidyl)-2-methyl-6-(2-phenylethynyl)pyrimidine-5-ylamine (Example 185 (c)) (387 mg, 1.21 mmol)) and CuI (Aldrich Chemical Company, 21 mg, 0.121 mmol, 0.1 eq) in anhydrous DMF (3 mL) was stirred under $N_2$ at 110° C. overnight. Upon cooling to the room temperature, the reaction mixture was diluted with $CH_2Cl_2$ (50 mL), passed through a pad of Celite® and concentrated under reduced pressure. The crude material was purified by flash chromatography on silica gel with 0–80% EtOAc/hexanes as eluant to afford the free base of the product as a brown solid (200 mg, 50%). Mp: 223–225° C. $^1$H NMR (CDCl$_3$, 400 MHz): d 1.28 (d, 6, J=6.8), 1.61–1.70 (m, 3), 1.81–1.96 (m, 3), 2.61 (s, 3), 4.63 (br s, 2), 6.78 (s, 1), 7.39 (t, 1, J=7.3), 7.48 (t, 2, J=7.3), 7.66 (d, 2, J=7.3), 8.39 (s, 1). MS m/z: 321 (M+H). The above material (195 mg, 0.61 mmol, 1.0 eq) was dissolved in diethyl ether (20 mL) and HCl (0.64 ml of a 1.0 M soln in ether, 0.64 mmol, 1.05 eq) was added dropwise. After stirring at room temperature for 10 min, the solution was concentrated in vacuo. Recrystallization from MeOH afforded the title compound (127 mg, 65%) as an off-white solid. Mp: >270° C. $^1$H NMR (DMSO-d$_6$, 400 MHz): d 1.34 (d, 6, J=6.7), 1.59 (m, 1), 1.78 (m, 4), 1.94 (m, 1), 2.61 (s, 3), 14 (br s, 2), 6.88 (s, 1), 7.51–7.59 (m, 3), 7.95 (d, 2, J=6.8), 11.60 (s, 1), 14.28 (s, 1). MS m/z: 321 (M+H). Anal. Calcd for $C_{20}H_{24}N_4$·HCl: C, 67.31; H, 7.06; N, 15.70. Found: C, 67.04; H, 6.97; N, 15.60.

EXAMPLE 186

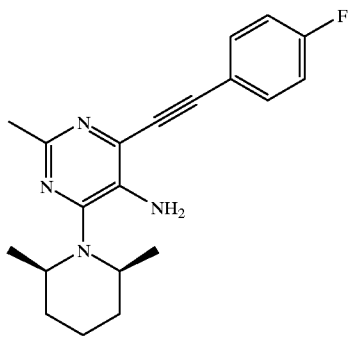

(a) 4-((6S,2R)-2,6-Dimethylpiperidyl)-6-[2-(4-fluorophenyl)ethynyl]-2-methylpyrimidine-5-ylamine.

This compound was synthesized by the method described in Example 185(c) from 4-((6S,2R)-2,6-dimethylpiperidyl)-6-chloro-2-methylpyrimidine-5-ylamine (Example 185(b)) (449 mg, 1.76 mmol, 1.0 eq) and 1-ethynyl-4-fluorobenzene (Aldrich Chemical Company, 500 mg, 4.16 mmol, 2.36 eq). The title compound was obtained as a brown solid (381 mg, 64%). Mp: 134–136° C. $^1$H NMR (CDCl$_3$, 400 MHz): d 0.78 (d, 6, J=6.2), 1.25–1.40 (m, 2), 1.50–1.60 (m, 1), 1.70–1.80 (m, 3), 2.59 (s, 3), 3.05–3.15 (m, 2), 4.55 (br s, 2), 7.05–7.09 (m, 2), 7.57–7.60 (m, 2). MS m/z: 339 (M+H).

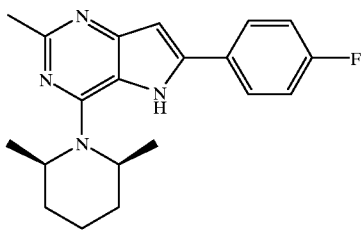

(b) 4-((6S,2R)-2,6-Dimethylpiperidyl)-6-(4-fluorophenyl)-2-methylpyrrolo[3,2-d]pyridine Hydrochloride Monohydrate.

This compound was synthesized by the method described in Example 185(d) from 4-((6S,2R)-2,6-dimethylpiperidyl)-6-[2-(4-fluorophenyl)ethynyl]-2-methylpyrimidine-5-ylamine (Example 186(a)) (335 mg, 0.99 mmol, 1.0 eq). The free base of the product was obtained as a brown solid (175 mg, 53%). Mp: 210–203° C. $^1$H NMR (CDCl$_3$, 400 MHz): d 1.27 (d, 6, J=6.8), 1.66–1.69 (m, 3), 1.81–1.96 (m, 3), 2.61 (s, 3), 4.61 (br s, 2), 6.71 (s, 1), 7.17 (t, 1, J=8.5), 7.63 (dd, 2, J=5.2, 8.5), 8.32 (s, 1). MS m/z: 339 (M+H). The above material (175 mg, 0.52 mmol, 1.0 eq) was used to prepare HCl salt by the method described in 185(d) to 86 mg (49%) of the title compound as a brown solid. Mp: >275° C. $^1$H NMR (DMSO-d$_6$, 400 MHz): d 1.34 (d, 6, J=6.7), 1.59 (m, 1), 1.78 (m, 4), 1.94 (m, 1), 2.61 (s, 3), 14 (br s, 2), 6.88 (s, 1), 7.51–7.59 (m, 3), 7.95 (d, 2, J=6.8), 11.60 (s, 1), 14.28 (s, 1). MS m/z: 339 (M+H), m/z: 337 (M−H). Anal. Calcd for $C_{20}H_{23}FN_4$·HCl·H$_2$O: C, 61.14; H, 6.67; N, 14.26. Found: C, 61.05; H, 6.78; N, 14.18.

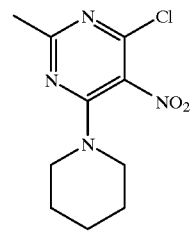

EXAMPLE 187

(a) 6-Chloro-2-methyl-5-nitro-4-piperidylpyrimidine.

To a solution of 4,6-dichloro-2-methyl-5-nitro pyrimidine (Example 76(b)) (8.00 g, 38.6 mmol, 1.00 eq) in THF (60 mL) was added a solution of piperidine (Aldrich Chemical Company, 3.29 g, 38.6 mmol, 1.00 eq) and diisopropylethylamine (Aldrich Chemical Company, 5.09 g, 39.4 mmol, 1.02 eq) dropwise through a additional funnel under $N_2$ at room temperature for 3 days. Diisopropylethylamine hydrogen chloride was filtered away as white solid, and the organic layer was concentrated in vacuo. The crude material was purified by flash chromatography on silica gel with 0–8% EtOAc/hexanes as eluant to afford the title compound (8.63 g, 87%) as a yellow solid. Mp: 62–64° C. $^1$H NMR (CDCl$_3$, 400 MHz): d 1.67 (m,6), 2.50 (s,3), 2.53 (m,4).

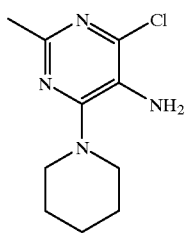

(b) 6-Chloro-2-methyl-4-piperidylpyrimidine-5-ylamine.

A solution of 6-chloro-2-methyl-5-nitro-4-piperidylpyrimidine (4.06 g, 15.8 mmol, 1.0 eq) in MeOH (68 mL) was hydrogenated in the presence of $PtO_2$ (Aldrich Chemical Company, 179 mg, 0.79 mmol, 0.05 eq) under $H_2$ (60 psi) at room temperature for 5 h. The reaction mixture was passed through a pad of Celite® and concentrated in vacuo. The crude material was purified by flash chromatography on silica gel with 0–15% EtOAc/hexanes as eluant to afford the title compound (1.86 g, 52%) as a orange oil. $^1$H NMR ($CDCl_3$, 400 MHz): d 1.67 (m, 6), 2.48 (s, 3), 3.25 (m, 4), 3.67 (br s, 2). MS m/z: 227 (M+H).

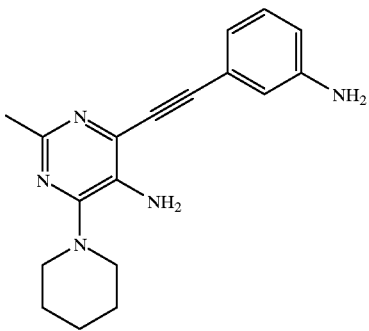

(c) 6-[2-(3-Aminophenyl)ethynyl]-2-methyl-4-piperidylpyrimidine-5-ylamine.

This compound was synthesized by the method described in example 1(c) from 6-chloro-2-methyl-4-piperidylpyrimidine-5-ylamine (Example 187(b)) (1.42 g, 6.26 mmol, 1.0 eq) and 3-ethylnylaniline (TCI America, 1.47 g, 12.5 mmol, 2.0 eq). The title compound was obtained as a red solid (625 mg, 33%). $^1$H NMR ($CDCl_3$, 400 MHz): d 1.69 (m, 6), 2.52 (s, 3), 3.27 (m, 4), 3.71 (s, 2), 3.92 (s, 2), 6.70 (d, 1, J=7.8), 6.90 (s, 1), 6.99 (d, 1, J=7.8) 7.14 (t, 1, J=7.8). MS m/z: 308 (M+H).

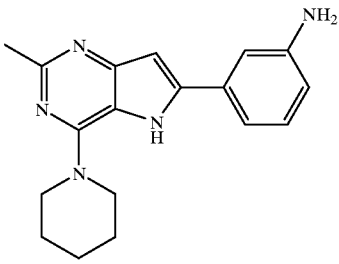

(d) 3-(2-Methyl-4-piperidylpyrrolo[4,5-d]pyrimidin-6-yl)phenylamine Hydrochloride Monohydrate.

This compound was synthesized by the method described in Example 185(d) from 6-[2-(3-aminophenyl) ethynyl]-2-methyl-4-piperidylpyrimidine-5-ylamine (Example 187(c)) (492 mg, 1.6 mmol, 1.0 eq). The free base of the product was obtained as an off-white solid (202 mg, 34%). $^1$H NMR (DMSO-$d_6$, 400 MHz): d 1.64 (br s, 6), 2.41 (s, 3), 3.72 9br s, 4), 5.21 (br s, 2), 6.53 (s, 1), 6.60 (d, 1, J=7.6), 7.00 (m, 2), 7.12 (t, 1, J=7.6), 10.97 (s, 1). MS m/z: 308 (M+H), m/z: 306 (M–H). The above material (202 mg, 0.66 mmol, 1.0 eq) was used to prepare HCl salt by the method described in Example 185(d) to give 80 mg (35%) of the title compound as a brown solid. Mp: >275° C. $^1$H NMR (DMSO-$d_6$, 400 MHz): d 1.70 (m, 6), 2.56 (s, 3), 4.04 (m, 4), 5.41 (br s, 2), 6.71 (m, 2), 7.03 (m, 2), 7.19 (m, 1), 11.95 (s, 1), 14.25 (s, 1). MS m/z: 308 (M+H), m/z: 306 (M–H). Anal. Calcd for $C_{18}H_{21}N_5 \cdot HCl \cdot H_2O$: C, 59.74; H, 6.69; N, 19.36. Found: C, 59.79; H, 6.58; N, 19.34.

EXAMPLE 188

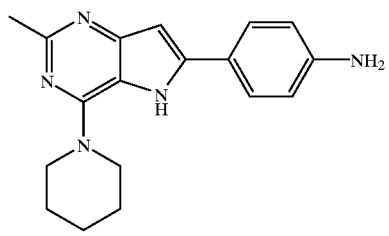

4-(2-Methyl-4-piperidylpyrrolo[4,5-d]pyrimidin-6-yl)phenylamine Hydrochloride.

A solution of 6-chloro-2-methyl-4-piperidyl pyrimidine-5-ylamine (Example 187(a)) (1.36 g, 6.0 mmol, 1.0 eq), $Pd_2(PPh_3)_2Cl_2$ (Aldrich Chemical Company, 210 mmg, 0.30 mmol, 0.05 eq), Cu(I)I (Aldrich Chemical Company, 57 mg, 0.30 mmol, 0.05 eq) in triethylamine (10 mL) was deoxygenated by bubbling $N_2$ for 10 min, and was heated to 70° C. A solution of 4-ethynylaniline (Lavastre, O; Cabioch, S.; Dixneuf, P. H. and Vohlidal, J. Tetrahedron, 1997, 53, 7595. 1.05 g, 9.0 mmol, 1.5 eq) in triethylamine (10 ml) deoxygenated by bubbling $N_2$ was transferred through a canula needle slowly. The final reaction mixture was stirred under $N_2$ at 70° C. for 48 h. Upon cooling to the room temperature, the reaction was diluted with $CH_2Cl_2$ (20 mL) and MeOH (20 mL), passed through a pad of Celite® and concentrated in vacuo. The crude material was purified by flash chromatography on silica gel with 10% DMF-0.5% Triethylamine-Toluene as eluant to afford the free base of the product (370 mg, 20%) as an orange solid. Mp: 239–242° C. $^1$H NMR (DMSO-$d_6$, 400 MHz): d 1.63 (br s, 6), 2.39 (s, 3), 3.65 (br s, 4), 5.42 (s, 2), 6.46 (s, 1), 6.46 (s, 1), 6.64 (d, 2, J=8.5), 7.56 (d, 2, J=8.5), 10.65 (s, 1). MS m/z: 308 (M+H). The above material (107 mg, 0.35 mmol, 1.0 eq) was used to prepare HCl salt by the method described in 1 (d) to give 47 mg (40%) of the title compound as a brown solid. Mp: >280° C. $^1$H NMR (DMSO-$d_6$, 400 MHz): d 1.68 (m, 6), 2.54 (s, 3), 4.00 (m, 4), 5.70 (br s, 2), 6.63 (s, 1), 6.67 (d, 2, J=8.5), 7.64 (d, 2, J=8.5), 11.55 (s, 1), 13.97 (s, 1). MS m/z: 308 (M+H), m/z: 306 (M–H). Anal. Calcd for $C_{18}H_{21}N_5 \cdot HCl$: C, 62.87; H, 6.45; Cl, 10.31; N, 20.37. Found: C, 62.66; H, 6.35; Cl, 10.56; N, 20.17.

EXAMPLE 189

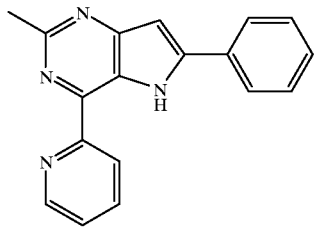

2-Methyl-6-phenyl-4-(2-pyridyl)pyrrolo[3,2-d]pyrimidine.

A mixture of 4-chloro-2-methyl-6-phenylpyrrolo[3,2-d]pyridine (150 mg, 0.61 mmol), 2-Pyridinyl tributylstannane (Maybridge, 270 mg, 0.73 mmol, 1.2 eq), tris(dibenzylideneacetone)dipalladium (0) (Aldrich Chemical Company, 14 mg, 0.015 mmol, 0.025 eq) and triphenylphosphine (Aldrich Chemical Company, 32 mg, 0.12 mmol, 0.2 eq) in anhydrous toluene was refluxed under $N_2$ for 48 h. Upon cooling to the room temperature, the reaction mixture was quenched with 5% HCl (30 mL), then neutralized with $Na_2CO_3$. The crude product was extracted with $CHCl_3$ (60 mL×3), washed with water (150 mL×1), saturated NaCl (150 mL×1), dried with $Na_2SO_4$ and concentrated in vacuo. Chromatography (silica gel, 0–0.5% $MeOH/CH_2Cl_2$) afforded 155 mg (yellow solid, 89%). Mp: 182–183° C. $^1$H NMR ($CDCl_3$, 400 MHz): d 2.90 (s, 3), 6.92 (d, 1, J=2.4), 7.4–7.5 (m, 2), 7.55 (t, 2, J=7.3), 7.67 (m, 1), 7.84 (d, 2, J=7.3), 7.94 (t, 1, J=7.9), 8.77 (d, 1, J=7.9), 8.82 (d, 1, J=4.2), 10.96 (s, 1). MS m/z: 287 (M+1), 285 (M−1).

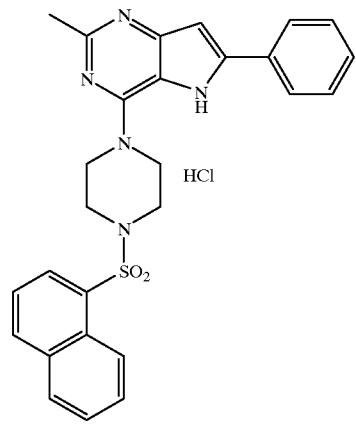

EXAMPLE 190
1-(2-Methyl-6-phenylpyrrolo[2,3-e]pyrimidin-4-yl)-4-naphthylsulfonyl) piperazine Hydrochloride Hydrate.

To an oven-dried, 50 ml round-bottomed flask was added 2-methyl-6-phenyl-4-piperazinylpyrrolo[3,2-d]pyrimidine (Example 26) (250 mg, 0.85 mmol), 1-naphthalenesulfonyl chloride (Aldrich Chemical Company) (232 mg, 1.02 mmol) and $CH_2Cl_2$ (25 ml). The slurry was stirred at room temperature under an $N_2$ as triethylamine (142 mL, 1.02 mmol) was added dropwise over 2 min. After 6 h the reaction was washed with saturated $NaHCO_3$ (3×20 ml) and then the aqueous layers were back extracted with $CH_2Cl_2$ (3×10 ml). The organic layers were combined, dried with $MgSO_4$, filtered and concentrated in vacuo to leave a solid. The white solid was dried under vacuum overnight to give 391 mg (95%) of the free base of the title compound. The free base (391 mg, 0.80 mmol) was dissolved in a mixture of hot $CH_2Cl_2$/EtOAc (20 ml) and anhydrous ethereal HCl (0.80 mL of a 1 M soln, 0.80 mmol) was added dropwise forming a precipitate immediately. After stirring at room temperature for 12 h the solution was filtered, solids collected, and dried in a vacuum oven at 60° C. overnight to give a quantitative yield of the title compound as light yellow solid. Mp: 195° C. (dec). $^1$H NMR (DMSO-$d_6$; 400 MHz): d 2.53 (s, 4), 4.11 (t, 4, J=4.7), 6.89 (s, 1), 7.53 (m, 3), 7.71 (m, 3), 7.94 (dd, 2, J=6.6, J=1.4), 8.11 (d, 1, J=8.0), 8.20 (dd, 1, J=6.6, J=0.6), 8.31 (d, 1, J=8.2), 8.72 (d, 1, J=8.6), 12.03 (s, 1). MS m/z: 484.5 (M+1). Anal. Calcd for $C_{27}H_{25}N_5O_2S \cdot HCl \cdot 2H_2O$: C, 58.53; H, 5.09; N, 12.64; Cl, 6.40. Found: C, 58.45; H, 5.28; N, 12.49; Cl, 6.51.

EXAMPLE 191

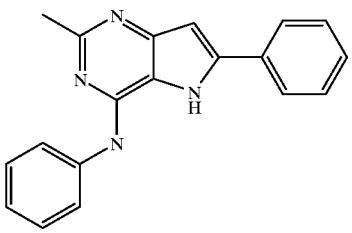

(2-Methyl-6-phenylpyrrolo[2,3-e]pyrimidin-4-yl) phenylamine Hydrochloride.

To a 5-mL, wheaton vial were added 4-chloro-2-methyl-6-phenylpyrrolo[3,2-d]pyrimidine (Example 1(e)) (100 mg, 0.41 mmol) and aniline (Aldrich Chemical Company) (0.37 mL, 4.1 mmol), followed by EtOH (1.5 mL). The reaction was heated at reflux for 4 h. The reaction mixture was allowed to cool to room temperature and the precipitate was collected by filtration, washed with hexanes, dried in a vacuum oven overnight to give 114 mg of a brown solid. The material was recrystallized from EtOH to give 57 mg (41%) of the title compound as an off-white solid. $^1$H NMR (DMSO-$d_6$; 400 MHz): d 2.67 (s, 3), 7.04 (s, 1), 7.21–7.23 (m, 1), 7.44–7.59 (m, 5), 8.03 (d, 2, J=8.0), 8.15 (d, 2, J=8.0), 11.61 (br s, 1), 13.84 (br s, 1). MS m/z: 301 (M+1).

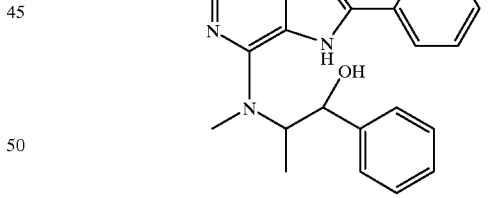

EXAMPLE 192
2-[Methyl(2-methyl-6-phenylpyrrolo[2,3-e]pyrimidin-4-yl)amino]-1-phenylpropan-1-ol.

To a 5-mL, Wheaton vial were added 4-chloro-2-methyl-6-phenylpyrrolo[3,2-d]pyrimidine (Example 1(e)) (100 mg, 0.41 mmol) and ephedrine hydrochloride (Aldrich Chemical Company) (410 mg, 2.1 mmol), followed by addition of a solution of potassium carbonate (0.71 g, 5.1 mmol) in water (2.5 mL). The reaction mixture was stirred at 120° C. for 20 h, allowed to cool to room temperature and extracted with $CH_2Cl_2$. The organic layer was dried over $Na_2SO_4$, concentrated in vacuo to give a brown residue, which was purified by flash chromatography on silica gel with 1:1 EtOAc/ hexanes as eluant to give 23 mg (15%) of the title compound as a tan solid. $^1$H NMR (DMSO-d$_6$; 400 MHz): d 1.21 (d, 3, J=6.8), 2.42 (s, 3), 3.21 (s, 3), 4.91 (m, 1), 5.02 (m, 1), 5.87 (br s, 1), 6.69 (s, 1), 7.18–7.85 (m, 10), 10.73 (br s, 1). MS m/z: 373 (M+1), 371 (M−1).

EXAMPLE 193

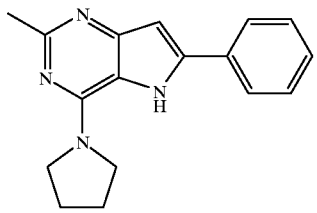

2-Methyl-6-phenyl-4-pyrrolidinylpyrrolo[3,2-d]pyrimidine Hydrochloride Monohydrate.

This compound was prepared according to the method described in Example 2 by employing 4-chloro-2-methyl-6-phenylpyrrolo[3,2-d]pyrimidine (Example 1(e)) (500 mg, 2.1 mmol), pyrrolidine (Aldrich Chemical Company) (0.86 mL, 10.3 mmol), and K$_2$CO$_3$ (2.83 g, 20.5 mmol) in H$_2$O (10 mL) to give 0.722 g of the free base as an off-white solid. To a solution of the above material in CHCl$_3$ (10 mL) and MeOH (0.5 mL) was added 1N ethereal HCl (Aldrich Chemical Company) (2.0 mL, 2.0 mmol). After stirring the reaction at room temperature for 40 min, the precipitate formed was collected by filtration, recrystallized in MeOH/H$_2$O to give 0.37 g (57%) of the title compound as off-white crystals. Mp: >296° C. $^1$H NMR (DMSO-d$_6$; 400 MHz): δ 1.99–2.08 (m, 4), 2.57 (s, 3), 3.81 (m, 2), 4.18 (m, 2), 6.88 (s, 1), 7.49–7.57 (m, 3), 7.96 (d, 2, J=6.9), 11.62 (br s, 1). MS m/z: 279 (M+1). Anal. Calcd for C$_{17}$H$_{18}$N$_4$.HCl.H$_2$O: C, 61.35; H, 6.36; N, 16.83; Cl, 10.65. Found: C, 61.55; H, 6.49; N, 16.75; Cl, 10.56.

EXAMPLE 194

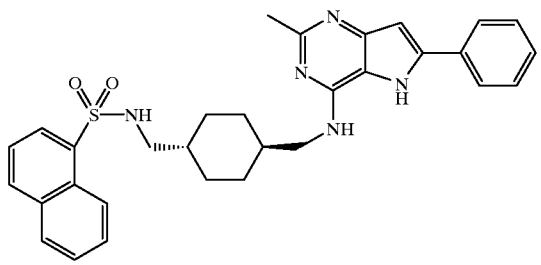

trans-[(4-{[(2-Methyl-6-phenylpyrrolo[2,3-e]pyrimidin-4-yl)amino]methyl}cyclohexyl)methyl](naphthylsulfonyl)amine Hydrochloride Hydrate.

This compound was prepared according to the method described in Example 2 by employing 4-chloro-2-methyl-6-phenylpyrrolo[3,2-d]pyrimidine (Example 1(e)) (300 mg, 1.2 mmol), trans-{[4-(aminomethyl)cyclohexyl]methyl}(naphthylsulfonyl)amine (Rueger, H. et al WO 97/20823) (2.0 g, 6.1 mmol), and K$_2$CO$_3$ (1.7 g, 12.3 mmol) in H$_2$O (8 mL). The residue was purified by flash chromatography on silica gel with 100:5 CHCl$_3$/MeOH as eluant to give 473 mg (71%) of the free base as an off-white solid. To a solution of the above material in MeOH (5 mL) was added 1N ethereal HCl (Aldrich Chemical Company) (0.9 mL, 0.9 mmol). After stirring the reaction at room temperature for 30 min, the precipitate formed was collected by filtration, recrystallized in MeOH/H$_2$O to give 0.19 g of the title compound as off-white crystals. Mp: 165–170° C. $^1$H NMR (DMSO-d$_6$; 400 MHz): δ 0.71–0.88 (m, 4), 1.25 (m, 1), 1.53 (m, 1), 1.63–1.66 (m, 2), 1.76–1.78 (m, 2), 2.57 (s, 3), 2.63 (m, 2), 3.46 (m, 2), 6.93 (s, 1), 7.47–8.22 (m, 12), 8.68 (br s, 1), 9.28 (br s, 1), 13.23 (br s, 1), 14.04 (br s, 1). MS m/z: 540 (M+1). Anal. Calcd for C$_{31}$H$_{33}$N$_5$O$_2$S.HCl.2H$_2$O: C, 60.82; H, 6.26; N, 11.44; Cl, 5.79; S, 5.24. Found: C, 60.73; H, 6.16; N, 11.35; Cl, 5.91; S, 5.16.

EXAMPLE 195

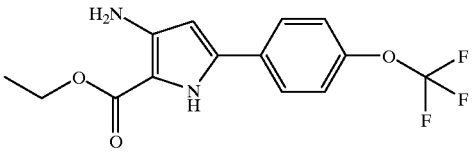

(a) Ethyl 3-amino-5-[4-(trifluoromethoxy)phenyl]pyrrole-2-carboxylate.

To a 250-mL, round-bottomed flask were added 4-trifluoromethoxybenzoyl acetonitrile (5.00 g, 21.8 mmol), p-toluenesulfonic anhydride (8.55 g, 26.2 mmol) and CH$_2$Cl$_2$ (100 mL). To the above solution was then added Et$_3$N (4.6 mL, 32.7 mmol) dropwise. After 16 h of stirring at ambient temperature, the reaction mixture was partitioned between H$_2$O and CH$_2$Cl$_2$. The organic layer was separated, and the aqueous layer was extracted with CH$_2$Cl$_2$ (3×). The combined organic layers were dried over Na$_2$SO$_4$ and concentrated in vacuo to give an orange solid. Sodium ethoxide was prepared freshly from Na° (1.76 g, 76.3 mmol) and absolute ethanol (50 mL) in an oven-dried, 250-mL, round-bottomed flask equipped with a positive flow of N$_2$ gas. To the above solution was then added a solution of the crude orange solid and diethyl aminomalonate hydrochloride (5.54 g, 26.2 mmol) in ethanol (85 mL) and THF (7 mL) dropwise through an addition funnel. After the addition was completed, the reaction mixture was stirred at ambient temperature for 3 h and concentrated in vacuo. Water and EtOAc were added, and the aqueous layer was back extracted with EtOAc (3×). The combined EtOAc layers were dried over Na$_2$SO$_4$ and concentrated in vacuo to give a dark-red solid. This material was purified by flash chromatography on silica gel with 1:9 EtOAc/hexanes as eluant to give 2.58 g (38%) of the title compound as an off-white solid. Mp: 175.0–178.0° C. $^1$H NMR (DMSO-d$_6$; 500 MHz) d 1.30 (t, 3H, J=7.0), 4.24 (q, 2H, J=7.0), 5.12 (br s, 2H), 6.04 (d, 1H, J=2.3), 7.35 (d, 2H, J=8.6), 7.88 (d, 2H, J=8.6), 10.86 (br s, 1H); MS m/z: 314 (M+1); IR (Nujol, cm$^{-1}$): 3446, 3313, 1669; Anal. Calcd for C$_{14}$H$_{13}$F$_3$N$_2$O$_3$: C, 53.51; H, 4.17; N, 8.91. Found: C, 53.24; H, 4.28; N, 8.81.

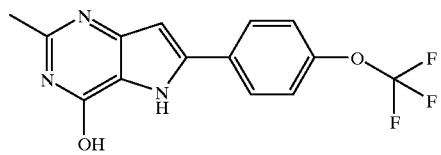

(b) 2-Methyl-6-[4-(trifluoromethoxy)phenyl]pyrrolo[3,2-d]pyrimidin-4-ol.

This compound was prepared according to the method described in Example 68(a) by employing ethyl 3-amino-5-[4-(trifluoromethoxy)phenyl]pyrrole-2-carboxylate (Example 195(a)) (2.24 g, 7.1 mmol), dry HCl gas in acetonitrile (60 mL) and then 6% aqueous sodium hydroxide (30 mL) and ethanol (50 mL) to give 1.68 g (76%) of the title compound as off-white solid. $^1$H NMR (DMSO-$d_6$; 500 MHz): d 2.31 (s, 3), 6.81 (s, 1), 7.43 (d, 2, J=8.6), 8.05 (d, 2, J=8.6), 11.81 (br s, 1), 12.36 (br s, 1). MS m/z: 310 (M+1), 308 (M−1).

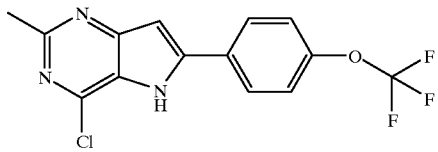

(c) [4-(4-Chloro-2-methylpyrrolo[4,5-d]pyrimidin-6-yl) phenoxy]trifluoromethane.

This compound was prepared according to the method described in Example 68 (b) by employing 2-methyl-6-[4-(trifluoromethoxy)phenyl]pyrrolo[3,2-d]pyrimidin-4-ol (Example 195(b)) (1.67 g, 5.4 mmol) and POCl$_3$ (12.6 mL, 135 mmol) to give 1.32 g (75%) of the title compound as brown solid. $^1$H NMR (CDCl$_3$; 500 MHz): d 2.80 (s, 3), 6.93 (s, 1), 7.38 (d, 2, J=8.5), 7.80 (d, 2, J=8.5). MS m/z: 328, 330 (M+1); 326, 328 (M−1).

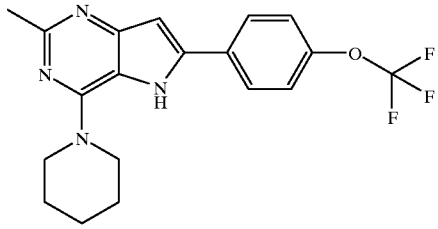

(d) Trifluoro[4-(2-methyl-4-piperidylpyrrolo[4,5-d] pyrimidin-6-yl)phenoxy]methane Hydrochloride Monohydrate.

This compound was prepared according to the method described in Example 2 by employing [4-(4-chloro-2-methylpyrrolo[4,5-d]pyrimidin-6-yl)phenoxy]trifluoro methane (Example 195(c)) (650 mg, 2.0 mmol), piperidine (Aldrich Chemical Company) (1.0 mL, 9.9 mmol), and K$_2$CO$_3$ (2.7 g, 20 mmol) in H$_2$O (15 mL) to give 351 mg (47%) of the free base as a tan solid. To a solution of the above material in CHCl$_3$ (10 mL) was added 1N ethereal HCl (Aldrich Chemical Company) (1.0 mL, 1.0 mmol). After stirring the reaction at room temperature for 30 min, the solvent was evaporated in vacuo and the solid obtained was recrystallized in MeOH/H$_2$O to give 0.156 g of the title compound as off-white crystals. $^1$H NMR (DMSO-$d_6$; 500 MHz): d 1.70–1.72 (m, 6), 2.57 (s, 3), 4.06–4.07 (m, 4), 6.93 (s, 1), 7.56 (d, 2, J=8.6), 8.13 (d, 2, J=8.6), 12.01 (br s, 1), 14.21 (br s, 1). MS m/z: 377 (M+1). Anal. Calcd for C$_{19}$H$_{19}$F$_3$N$_4$O.HCl.H$_2$O: C, 52.97; H, 5.15; N, 13.00; Cl, 8.23. Found: C, 53.01; H, 5.13; N, 12.90; Cl, 8.34.

EXAMPLE 196

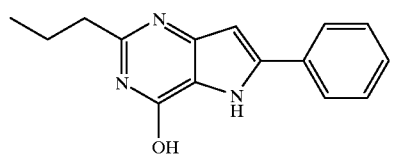

(a) 6-Phenyl-2-propylpyrrolo[3,2-d]pyrimidin-4-ol.

This compound was prepared according to the method described in Example 68(a) by employing ethyl 3-amino-5-phenylpyrrole-2-carboxylate (Example 66(b)) (2.05 g, 8.9 mmol), dry HCl gas in butyronitrile (70 mL) and then 6% aqueous sodium hydroxide (30 mL) and ethanol (50 mL) to give 2.12 g (94%) of the title compound as a gray solid. $^1$H NMR (DMSO-$d_6$; 400 MHz): d 0.92 (t, 3, J=7.4), 1.67–1.77 (m, 2), 2.55 (t, 2, J=7.4), 6.80 (s, 1), 7.32–7.46 (m, 3), 7.93 (d, 2, J=7.6), 11.77 (br s, 1), 12.29 (br s, 1). MS m/z: 254 (M+1).

(b) 4-Chloro-6-phenyl-2-propylpyrrolo[3,2-d]pyrimidine.

This compound was prepared according to the method described in Example 68 (b) by employing 6-phenyl-2-propylpyrrolo[3,2-d]pyrimidin-4-ol (Example 196(a)) (2.12 g, 8.4 mmol) and POCl$_3$ (15.7 mL, 168 mmol) to give 1.46 g (64%) of the title compound as a tan solid. $^1$H NMR (CDCl$_3$; 500 MHz): d 1.01 (t, 3, J=7.4), 1.85–1.94 (m, 2), 2.99 (t, 2, J=7.7), 6.95 (s, 1), 7.45–7.53 (m, 3), 7.76 (d, 2, J=7.9), 8.95 (br s, 1).

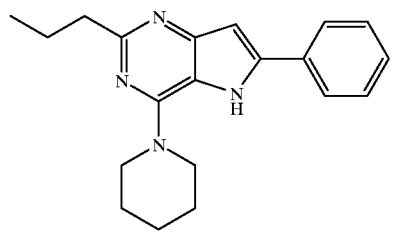

(c) 6-Phenyl-4-piperidyl-2-propylpyrrolo[3,2-d]pyrimidine Hydrochloride Monohydrate.

This compound was prepared according to the method described in Example 2 by employing 4-chloro-6-phenyl-2-propylpyrrolo[3,2-d]pyrimidine (Example 196 (b)) (500 mg, 1.8 mmol), piperidine (Aldrich Chemical Company) (0.91 mL, 9.2 mmol), and K$_2$CO$_3$ (2.54 g, 18 mmol) in H$_2$O (15 mL) to give 534 mg (91%) of the free base as a tan solid. To a solution of the above material in CHCl$_3$ (10 mL) was added 1N ethereal HCl (Aldrich Chemical Company) (1.7 mL, 1.7 mmol). After stirring the reaction at room temperature for 30 min, the solvent was evaporated in vacuo and the solid obtained was recrystallized in MeOH/H$_2$O to give 0.324 g of the title compound as off-white crystals. Mp: 258.0–262.5° C. $^1$H NMR (DMSO-$d_6$; 400 MHz): d 0.92 (t, 3, J=7.4), 1.67 (m, 6), 1.72–1.81 (m, 2), 2.77 (t, 2, J=7.4), 4.02–4.03 (m, 4), 6.86 (s, 1), 7.45–7.53 (m, 3), 7.91 (d, 2, J=7.0), 12.00 (br s, 1). MS m/z: 321 (M+1). Anal. Calcd for $C_{20}H_{24}N_4 \cdot HCl \cdot H_2O$: C, 64.07; H, 7.26; N, 14.96; Cl, 9.46. Found: C, 64.16; H, 7.31; N, 15.01; Cl, 9.57.

EXAMPLE 197

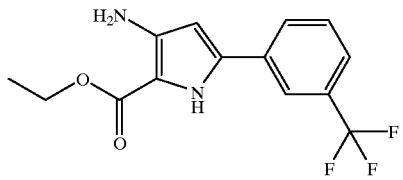

(a) Ethyl 3-amino-5-[3-(trifluoromethyl)phenyl]pyrrole-2-carboxylate.

This compound (5.22 g, 37%) was prepared according to the method described in Example 195(a) by employing 3-trifluoromethylbenzoyl acetonitrile (10 g, 46.9 mmol) and was recrystallized from toluene. Mp: 181.5–182.0° C. $^1$H NMR (DMSO-$d_6$; 500 MHz) d 1.31 (t, 3H, J=7.0), 4.25 (q, 2H, J=7.0), 5.12 (br s, 2H), 6.15 (d, 1H, J=2.6), 7.58 (d, 2H, J=8.1), 8.00–8.01 (m, 1H), 8.22 (s, 1H), 11.06 (br s, 1H); MS m/z: 298 (M+1); IR (Nujol, cm$^{-1}$): 3441, 3356, 1641; Anal. Calcd for $C_{14}H_{13}F_3N_2O_2$: C, 56.38; H, 4.39; N, 9.39. Found: C, 56.10; H, 4.48; N, 9.14.

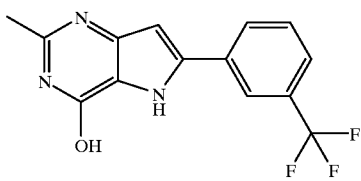

(b) 2-Methyl-6-[3-(trifluoromethyl)phenyl]pyrrolo[3,2-d]pyrimidin-4-ol.

This compound was prepared according to the method described in Example 68(a) by employing ethyl 3-amino-5-[3-(trifluoromethyl)phenyl]pyrrole-2-carboxylate (Example 197(a)) (5.05 g, 17.0 mmol), dry HCl gas in acetonitrile (120 mL) and then 6% aqueous sodium hydroxide (70 mL) and ethanol (120 mL) to give 2.82 g (57%) of the title compound as an off-white solid. $^1$H NMR (DMSO-$d_6$; 500 MHz): d 2.32 (s, 3), 6.94 (s, 1), 7.65–7.67 (m, 2), 8.21–8.22 (m, 1), 8.37 (s, 1), 11.83 (br s, 1), 12.50 (br s, 1). MS m/z: 294 (M+1).

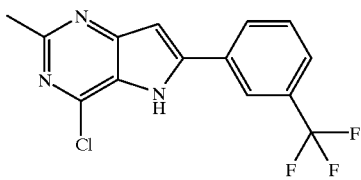

(c) 4-Chloro-2-methyl-6-[3-(trifluoromethyl)phenyl]pyrrolo[3,2-d]pyrimidine.

This compound was prepared according to the method described in Example 68 (b) by employing 2-methyl-6-[3-(trifluoromethyl)phenyl]pyrrolo[3,2-d]pyrimidin-4-ol (Example 197(b)) (2.82 g, 9.6 mmol) and POCl$_3$ (18 mL, 192 mmol) to give 1.33 g (45%) of the title compound as a tan solid. $^1$H NMR (CDCl$_3$; 400 MHz): d 2.79 (s, 3), 6.99 (s, 1), 7.63–7.73 (m, 2), 8.14 (d, 1, J=7.6), 8.40 (s, 1).

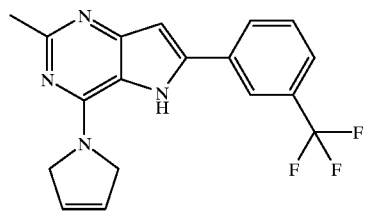

(d) 2-Methyl-4-(3-pyrrolinyl)-6-[3-(trifluoromethyl)phenyl]pyrrolo[3,2-d]pyrimidine Hydrochloride Monohydrate.

This compound was prepared according to the method described in Example 2 by employing 4-chloro-2-methyl-6-[3-(trifluoromethyl)phenyl]pyrrolo[3,2-d]pyrimidine (Example 197(c)) (400 mg, 1.3 mmol), 3-pyrroline (Aldrich Chemical Company) (0.49 mL, 6.4 mmol), and K$_2$CO$_3$ (1.78 g, 12.8 mmol) in H$_2$O (10 mL) to give 422 mg (96%) of the free base as a tan solid. To a solution of the above material in CHCl$_3$ (10 mL) was added 1N ethereal HCl (Aldrich Chemical Company) (1.3 mL, 1.3 mmol). After stirring the reaction at room temperature for 30 min, the solvent was evaporated in vacuo and the solid obtained was recrystallized in MeOH/H$_2$O to give 0.226 g of the title compound as off-white crystals. Mp: >270° C. $^1$H NMR (DMSO-$d_6$; 400 MHz): d 2.61 (s, 3), 4.61 (m, 2), 5.06 (m, 2), 6.16 (d, 2, J=18), 7.11 (s, 1), 7.79–7.83 (m, 1), 7.89 (d, 1, J=7.9), 8.29 (d, 1, J=7.9), 8.35 (s, 1), 11.74 (br s, 1). MS m/z: 345 (M+1). Anal. Calcd for $C_{18}H_{17}F_3N_4 \cdot HCl \cdot H_2O$: C, 54.21; H, 4.55; N, 14.05; Cl, 8.89. Found: C, 54.21; H, 4.39; N, 13.80; Cl, 8.75.

EXAMPLE 198

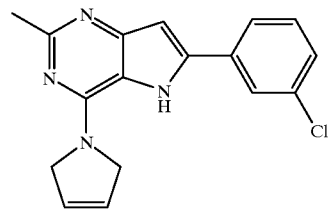

6-(3-Chlorophenyl)-2-methyl-4-(3-pyrrolinyl)pyrrolo[3,2-d]pyrimidine Hydrochloride Hydrate.

This compound was prepared according to the method described in Example 2 by employing 4-chloro-2-methyl-6-(3-chlorophenyl)pyrrolo[3,2-d]pyrimidine (Example (70 (d)) (474 mg, 1.7 mmol), 3-pyrroline (Aldrich Chemical Company) (0.65 mL, 8.5 mmol), and K$_2$CO$_3$ (2.35 g, 17 mmol) in H$_2$O (10 mL) to give the free base as a tan solid. To a solution of the above material in CHCl$_3$ (10 mL) was added 1N ethereal HCl (Aldrich Chemical Company) (1.7 mL, 1.7 mmol). After stirring the reaction at room temperature for 30 min, the solvent was evaporated in vacuo and the solid obtained was recrystallized in MeOH/H$_2$O to give 0.317 g (54%) of the title compound as off-white crystals. Mp: 287.5–293.0° C. $^1$H NMR (DMSO-$d_6$; 400 MHz): d 2.60 (s, 3), 4.60 (m, 2), 5.06 (m, 2), 6.14 (d, 2, J=14), 7.04 (s, 1), 7.57–7.60 (m, 2), 7.95–7.98 (m, 1), 8.13 (s, 1), 11.64 (br s, 1). MS m/z: 311 (M+1). Anal. Calcd for $C_{17}H_{15}ClN_4 \cdot HCl \cdot 1.25H_2O$: C, 55.24; H, 5.04; N, 15.16; Cl, 19.18. Found: C, 55.24; H, 4.92; N, 15.02; Cl, 18.98.

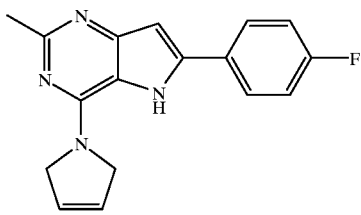

EXAMPLE 199
6-(4-Fluorophenyl)-2-methyl-4-(3-pyrrolinyl)pyrrolo[3,2-d]pyrimidine Hydrochloride Hydrate.

This compound was prepared according to the method described in Example 2 by employing 4-chloro-2-methyl-6-(4-fluorophenyl)pyrrolo[3,2-d]pyrimidine (example 73(c)) (413 mg, 1.6 mmol), 3-pyrroline (Aldrich Chemical Company) (0.61 mL, 7.9 mmol), and $K_2CO_3$ 2.18 g, 15.8 mmol) in $H_2O$ (10 mL) to give the free base as a tan solid. To a solution of the above material in $CHCl_3$ (10 mL) was added 1N ethereal HCl (Aldrich Chemical Company) (1.6 mL, 1.6 mmol). After stirring the reaction at room temperature for 30 min, the solvent was evaporated in vacuo and the solid obtained was recrystallized in $MeOH/H_2O$ to give 0.334 g (64%) of the title compound as tan crystals. $^1$H NMR (DMSO-$d_6$; 400 MHz): d 2.60 (s, 3), 4.58 (m, 2), 5.05 (m, 2), 6.13 (d, 2, J=12), 6.92 (s, 1), 7.37–7.44 (m, 2), 8.03–8.09 (m, 2), 11.65 (br s, 1). MS m/z: 295 (M+1). Anal. Calcd for $C_{17}H_{15}FN_4 \cdot HCl \cdot 1.25H_2O$: C, 57.82; H, 5.27; N, 15.87; Cl, 10.04. Found: C, 57.82; H, 5.29; N, 15.71; Cl, 9.94.

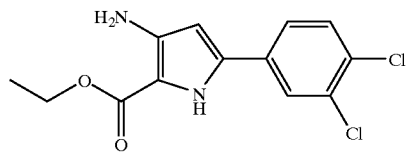

EXAMPLE 200
(a) Ethyl 3-amino-5-(3,4-dichlorophenyl)pyrrole-2-carboxylate.

The title compound (2.43 g, 31%) was prepared according to the method described in Example 195(a) by employing 3,4-dichlorobenzoyl acetonitrile (5.57 g, 26.0 mmol) and was recrystallized from toluene. Mp: 184.0–185.0° C. $^1$H NMR (DMSO-$d_6$; 500 MHz) d 1.30 (t, 3H, J=7.0), 4.24 (q, 2H, J=7.0), 5.12 (br s, 2H), 6.11 (s, 1H), 7.60 (d, 1H, J=8.5), 7.72 (d, 1H, J=8.5), 8.14 (s, 1H), 10.95 (br s, 1H); MS m/z: 299 (M+1); IR (Nujol, cm$^{-1}$): 3440, 3337, 1638; Anal. Calcd for $C_{13}H_{12}Cl_2N_2O_2$: C, 52.19; H, 4.04; N, 9.36; Cl, 23.70. Found: C, 52.20; H, 4.12; N, 9.23; Cl, 23.53.

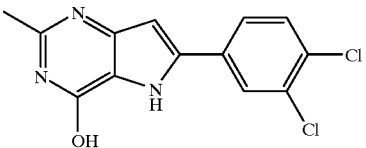

(b) 6-(3,4-Dichlorophenyl)-2-methylpyrrolo[3,2-d]pyrimidin-4-ol.

This compound was prepared according to the method described in Example 68(a) by employing ethyl 3-amino-5-(3,4-dichlorophenyl)pyrrole-2-carboxylate (Example 200 (a)) (2.35 g, 7.9 mmol), dry HCl gas in acetonitrile (60 mL) and then 6% aqueous sodium hydroxide (35 mL) and ethanol (60 mL) to give 2.25 g (97%) of the title compound as a tan solid. $^1$H NMR (DMSO-$d_6$; 500 MHz): d 2.31 (s, 3), 6.91 (s, 1), 7.69 (d, 1, J=8.4), 7.91–7.93 (m,1), 8.27 (s,1), 11.84 (br s,1), 12.50 (br s,1).

(c) 6-(3,4-Dichlorophenyl)-4-chloro-2-methylpyrrolo[3,2-d]pyrimidine.

This compound was prepared according to the method described in Example 68 (b) by employing 6-(3,4-dichlorophenyl)-2-methylpyrrolo[3,2-d]pyrimidin-4-ol (Example 200(b)) (2.25 g, 7.7 mmol) and $POCd_3$ (18 mL, 191 mmol) to give 1.07 g (45%) of the title compound as a tan solid. $^1$H NMR (CDCl$_3$; 400 MHz): d 2.80 (s, 3), 6.93 (s, 1), 7.58 (m, 2), 7.84 (s, 1), 8.71 (br s, 1).

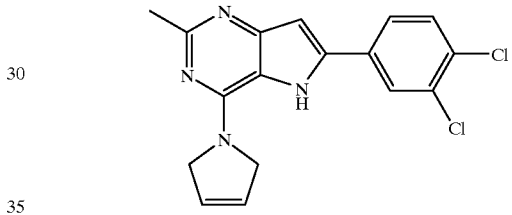

(d) 6-(3,4-Dichlorophenyl)-2-methyl-4-(3-pyrrolinyl)pyrrolo[3,2-d]pyrimidine Hydrochloride Hydrate.

This compound was prepared according to the method described in Example 2 by employing 4-chloro-2-methyl-6-(3,4-dichlorophenyl)pyrrolo[3,2-d]pyrimidine (Example 200(c)) (400 mg, 1.3 mmol), 3-pyrroline (Aldrich Chemical Company) (0.49 mL, 6.4 mmol), and $K_2CO_3$ (1.77 g, 13 mmol) in $H_2O$ (10 mL) to give 381 mg (86%) of the free base as a tan solid. To a solution of the above material in $CHCl_3$ (10 mL) was added 1N ethereal HCl (Aldrich Chemical Company) (1.1 mL, 1.1 mmol). After stirring the reaction at room temperature for 30 min, the solvent was evaporated in vacuo and the solid obtained was recrystallized in MeOH to give 0.121 g of the title compound as tan crystals. $^1$H NMR (DMSO-$d_6$; 400 MHz): d 2.37 (s, 3), 4.37 (m, 2), 4.82 (m, 2), 5.92 (d, 2, J=17), 6.85 (s, 1), 7.62 (d, 1, J=8.5), 7.77–7.79 (m, 1), 8.12 (s, 1), 11.40 (br s, 1). MS m/z: 346 (M+1). Anal. Calcd for $C_{17}H_{14}Cl_2N_4 \cdot HCl \cdot 1.75H_2O$: C, 49.39; H, 4.52; N, 13.56; Cl, 25.76. Found: C, 49.39; H, 4.41; N, 13.46; Cl, 25.84.

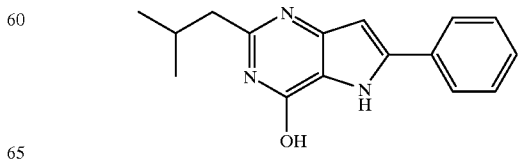

EXAMPLE 201

(a) 2-(2-Mothylpropyl)-6-phenylpyrrolo[3,2-d]pyrimidin-4-ol.

This compound was prepared according to the method described in Example 68(a) by employing ethyl 3-amino-5-phenylpyrrole-2-carboxylate ((Example 66(b)) (2.50 g, 10.9 mmol), dry HCl gas in isovaleronitrile (50 g) and then 6% aqueous sodium hydroxide (35 mL) and ethanol (50 mL) to give 1.77 g (61%) of the title compound as a brown solid. $^1$H NMR (DMSO-d$_6$; 500 MHz): d 0.92 (d, 6, J=7.0), 2.13–2.16 (m, 1), 2.44 (d, 2, J=7.0), 6.79 (s,1), 7.32–7.49 (m 3), 7.93 (d, 2, J=7.8), 11.74 (br s,1), 12.28 (br s,1). MS m/z: 268 (M+1), 266 (M−1).

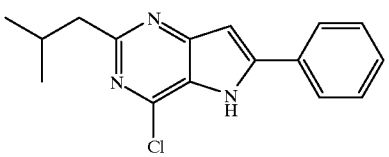

(b) 4-Chloro-2-(2-methylpropyl)-6-phenylpyrrolo[3,2-d]pyrimidine.

This compound was prepared according to the method described in Example 68 (b) by employing 2-(2-methylpropyl)-6-phenylpyrrolo[3,2-d]pyrimidin-4-ol (Example 201(a)) (1.77 g, 6.6 mmol) and POCl$_3$ (15.5 mL, 165 mmol) to give 0.59 g (31%) of the title compound as a tan solid. $^1$H NMR (CDCl$_3$; 500 MHz): d 0.99 (d, 6, J=6.2), 2.34 (m, 1), 2.93 (d, 2, J=6.2), 6.99 (s, 1), 7.27–7.42 (m 3), 7.80 (m, 2).

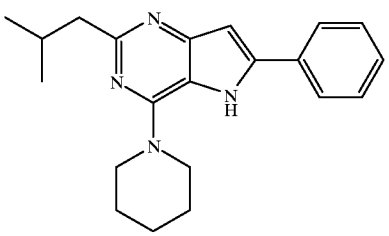

(c) 2-(2Methylpropyl)-6-phenyl-4-piperidylpyrrolo[3,2-d]pyrimidine Hydrochloride Monohydrate.

This compound was prepared according to the method described in Example 2 by employing 4-chloro-2-(2-methylpropyl)-6-phenylpyrrolo[3,2-d]pyrimidine (Example 201(b)) (588 mg, 2.1 mmol), piperidine (Aldrich Chemical Company) (1.0 mL, 10.3 mmol), and K$_2$CO$_3$ (2.85 g, 21 mmol) in H$_2$O (15 mL) to give the free base as a tan solid. To a solution of the above material in CHCl$_3$ (10 mL) was added 1N ethereal HCl (Aldrich Chemical Company) (2.0 mL, 2.0 mmol). After stirring the reaction at room temperature for 30 min, the solvent was evaporated in vacuo and the solid obtained was recrystallized in MeOH/H$_2$O to give 0.313 g (40%) of the title compound as orange crystals. Mp: 226.0–229.5° C. $^1$H NMR (DMSO-d$_6$; 400 MHz): d 1.19 (d, 6, J=7.0), 1.93 (m, 6), 2.40–2.50 (m, 1), 2.92 (d, 2, J=7.0), 4.28–4.30 (m, 4), 7.13 (s, 1), 7.72–7.81 (m, 3), 8.18 (d, 2, J=8.3), 12.25 (br s, 1). MS m/z: 335.5 (M+1). Anal. Calcd for C$_{21}$H$_{26}$N$_4$.HCl.H$_2$O: C, 64.85; H, 7.52; N, 14.41. Found: C, 65.12; H, 7.32; N, 14.18.

EXAMPLE 202

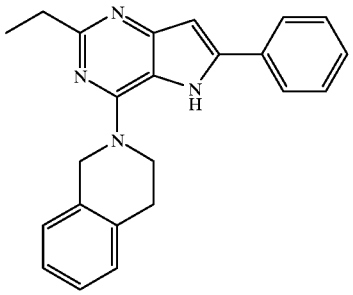

2-Ethyl-6-phenyl-4-(2-1,2,3,4-tetrahydroisoquinolyl)pyrrolo[3,2-d]pyrimidine Hydrochloride Monohydrate.

This compound was prepared according to the method described in Example 2 by employing 2-ethyl-4-chloro-6-phenylpyrrolo[3,2-d]pyrimidine (example (68b)) (500 mg, 1.7 mmol), 1,2,3,4-tetrahydroisoquinoline (Aldrich Chemical Company) (1.1 mL, 8.5 mmol), and K$_2$CO$_3$ (2.35 g, 17 mmol) in H$_2$O (15 mL) to give 410 mg (68%) of the free base as a tan solid. To a solution of the above material in CHCl$_3$ (10 mL) was added 1N ethereal HCl (Aldrich Chemical Company) (1.2 mL, 1.2 mmol). After stirring the reaction at room temperature for 30 min, the solvent was evaporated in vacuo and the solid obtained was recrystallized in MeOH/H$_2$O to give 0.42 g of the title compound as tan crystals. Mp: 170.0–171.5° C. $^1$H NMR (DMSO-d$_6$; 500 MHz): d 1.36 (t, 3, J=7.5), 2.91 (t, 2, J=7.5), 3.08 (t, 2, J=5.8), 4.32 (t, 2, J=5.8), 5.29 (s, 2), 6.92 (s, 1), 7.27–7.41 (m, 4), 7.53–7.60 (m, 3), 8.00 (d, 2, J=7.3), 11.97 (br s, 1), 14.42 (br s, 1). MS m/z: 355.5 (M+1). Anal. Calcd for C$_{23}$H$_{22}$N$_4$.HCl.H$_2$O: C, 67.56; H, 6.16; N, 13.70. Found: C, 67.27; H, 6.10; N, 13.47.

EXAMPLE 203

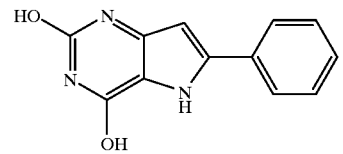

(a) 6-Phenylpyrrolo[3,2-d]pyrimidine-2,4-diol.

In a 1-1 round-bottomed flask was added ethyl 3-amino-5-phenylpyrrole-2-carboxylate (Example 66 (b)) (20 g, 87 mmol), followed by acetic acid (435 mL) and H$_2$O (44 mL). Potassium cyanate (21.2 g, 261 mmol) dissolved in 70 mL of H$_2$O was then added dropwise through an addition funnel. The reaction mixture was stirred at room temperature for 15 h. The precipitate formed was collected by filtration, washed with H$_2$O and ether, dried to give a white solid. To the above solid in a 1-L round-bottomed flask was added 6% aqueous sodium hydroxide (435 mL). The suspension was heated at reflux for 2 h. The reaction mixture was acidified using 12 N HCl to pH 6. The precipitate formed was filtered, washed with H$_2$O, dried in a vacuum oven overnight to give 15.2 g (77%) of the title compound as a white solid. $^1$H NMR (DMSO-d$_6$; 500 MHz): d 6.29 (s,1), 7.33–7.43 (m,3), 7.85 (d,2, J=7.3), 10.62 (br s, 1), 10.85 (br s, 1), 12.19 (br s,1). MS m/z: 226 (M−1).

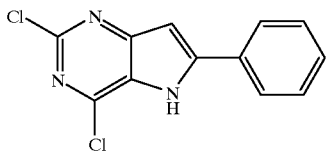

(b) 2,4-Dichloro-6-phenylpyrrolo[3,2-d]pyrimidine.

A mixture of 6-phenylpyrrolo[3,2-d]pyrimidine-2,4-diol (Example 203(a)) (6.0 g, 26.6 mmol) and POCl$_3$ (210 mL, 229 mmol) in a 500-mL, round-bottomed flask was heated at 120° C. for 60 h. POCl$_3$ was removed in vacuo to give a dark-red residue. Ice-water was added, and the pH of the reaction mixture was adjusted to pH 6 by the addition of aqueous NH$_3$ at 0° C. The resulting mixture was extracted three times with EtOAc. Combined organic layer were washed with brine, dried over Na$_2$SO$_4$, concentrated in vacuo and dried in a vacuum oven overnight to give 2.84 g (40%) of the title compound as an orange solid. $^1$H NMR (DMSO-d$_6$; 400 MHz): d 6.95 (s, 1), 7.50–7.66 (m,3), 7.77 (d,2, J=8.1), 8.88 (br s,1).

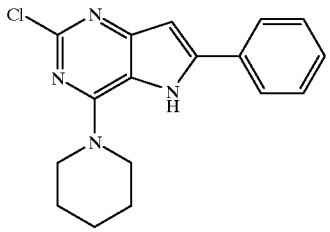

(c) 2-Chloro-6-phenyl-4-piperidylpyrrolo[3,2-d]pyrimidine.

This compound was prepared according to the method described in Example 2 by employing 2,4-dichloro-6-phenylpyrrolo[3,2-d]pyrimidine (Example 203(b)) (2.84 g, 10.8 mmol), piperidine (Aldrich Chemical Company) (5.3 mL, 53.8 mmol), and K$_2$CO$_3$ (14.9 g, 108 mmol) in H$_2$O (100 mL) to give 3.23 g (96%) of the title compound as an orange solid. $^1$H NMR (DMSO-d$_6$; 400 MHz): d 1.77 (m, 6), 3.83 (m, 4), 6.75 (s, 1), 7.37–7.55 (m, 3), 7.64 (d, 2, J=7.3), 8.21 (br s, 1). MS m/z: 313, 315 (M+1); 311, 313 (M−1).

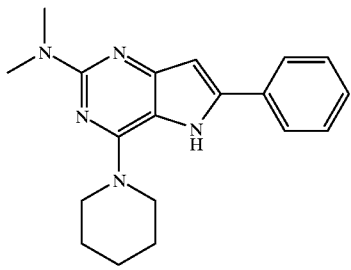

(d) Dimethyl(6-phenyl-4-piperidylpyrrolo[3,2-d]pyrimidin-2-yl)amine Hydrochloride Hydrate.

A mixture of 2-chloro-6-phenyl-4-piperidylpyrrolo[3,2-d] pyrimidine (Example 203(c)) (313 mg, 1 mmol), aqueous dimethylamine (Aldrich Chemical Company) (40 wt. %, 1.5 mL, 12 mmol), 5 mL of n-butanol and 0.2 mL of 12 N HCl in a 25-mL, round-bottomed flask was heated at reflux for 32 h under a stream of N$_2$. After cooling to room temperature, the precipitate was collected by filtration, washed with hexanes and dried in a vacuum oven overnight to give 239 mg (74%) of the title compound as orange crystals. Mp: >300° C. $^1$H NMR (DMSO-d$_6$; 500 MHz): d 1.68 (m, 6), 3.19 (s, 6), 3.95 (m, 4), 6.70 (s, 1), 7.45–7.54 (m, 3), 7.86 (d, 2, J=7.4), 11.58 (br s, 1), 12.22 (br s, 1). MS m/z: 322.5 (M+1). Anal. Calcd for C$_{19}$H$_{23}$N$_5$.1.2HCl.1.75H$_2$O: C, 57.68; H, 7.04; N, 17.71; Cl, 10.61. Found: C, 57.68; H, 6.99; N, 17.77; Cl, 10.85.

EXAMPLE 204

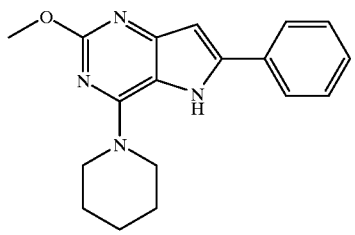

2-Methoxy-6-phenyl-4-piperidylpyrrolo[3,2-d]pyrimdine Hydrochloride Monohydrate.

A mixture of 2-chloro-6-phenyl-4-piperidylpyrrolo[3,2-d] pyrimidine (Example 203(c)) (626 mg, 2 mmol), sodium methoxide (Aldrich Chemical Company) (25 wt. %, 0.78 mL, 4.5 mmol) and 2 mL of DMSO in a 15-mL, round-bottomed flask was heated at reflux for 72 h under a stream of N$_2$. After cooling to room temperature, the residue was partitioned between H$_2$O and CH$_2$Cl$_2$. The aqueous layer was extracted with CH$_2$Cl$_2$ and the combined CH$_2$Cl$_2$ layers were dried over Na$_2$SO$_4$, concentrated in vacuo and purified by flash chromatography on silica gel with 1:5 to 1:2 EtOAc/hexanes as eluant to give 217 mg (35%) of the free base as a purple solid. To a solution of the above material in CHCl$_3$ (10 mL) was added 1N ethereal HCl (Aldrich Chemical Company) (0.75 mL, 0.75 mmol). After stirring the reaction at room temperature for 30 min, the solvent was evaporated in vacuo and the solid obtained was recrystallized in MeOH/H$_2$O to give 0.117 g of the title compound as a light-green crystals. Mp: 270–276° C. $^1$H NMR (DMSO-d$_6$; 500 MHz): d 1.73 (m, 6), 4.05 (m, 7), 6.75 (s, 1), 7.48–7.56 (m, 3), 7.92 (d, 2, J=8.3), 11.87 (br s, 1), 13.87 (br s, 1). MS m/z: 309 (M+1). Anal. Calcd for C$_{18}$H$_{20}$N$_4$O.HCl.H$_2$O: C, 59.58; H, 6.39; N, 15.44; Cl, 9.77. Found: C, 59.59; H, 6.49; N, 15.47; Cl, 9.90.

EXAMPLE 205

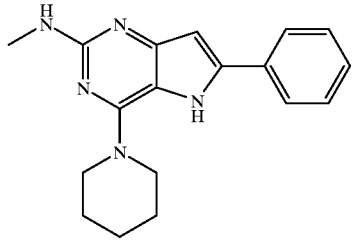

Methyl(6-phenyl-4-piperidylpyrrolo[3,2-d]pyrimidin-2-yl) amine Hydrochloride Monohydrate.

A mixture of 2-chloro-6-phenyl-4-piperidylpyrrolo[3,2-d] pyrimidine (Example 203(c)) (626 mg, 2 mmol), aqueous methylamine (Aldrich Chemical Company) (40 wt. %, 3.1 mL, 35 mmol), 10 mL of n-butanol and 0.4 mL of 12 N HCl in a 25-mL, round-bottomed flask was heated at reflux for 48 h under a stream of N$_2$. After cooling to room temperature, the solvent was evaporated in vacuo and the residue was partitioned between 5% NaHCO₃ and CH₂Cl₂. The aqueous layer was extracted with CH₂Cl₂ and the combined CH₂Cl₂ layers were dried over Na₂SO₄, concentrated in vacuo and purified by flash chromatography on silica gel with 100:2 to 100:5 CHCl₃/MeOH as eluant to give 30 mg (5%) of the free base. ¹H NMR (DMSO-d₆; 500 MHz): d 1.68 (m, 6), 3.19 (s, 6), 3.95 (m, 4), 6.70 (s, 1), 7.45–7.54 (m, 3), 7.86 (d, 2, J=7.4), 11.58 (br s, 1), 12.22 (br s, 1). To a solution of the above material in CHCl₃ (5 mL) was added 1N ethereal HCl (Aldrich Chemical Company) (0.1 mL, 0.1 mmol). After stirring the reaction at room temperature for 30 min, the solvent was evaporated in vacuo and the solid obtained was recrystallized in MeOH/H₂O to give 15 mg of the title compound as orange crystals. Mp: 195–200° C. MS m/z: 308.5 (M+1). Anal. Calcd for C₁₉H₂₃N₅.HCl.H₂O: C, 59.74; H, 6.68; N, 19.35. Found: C, 59.34; H, 6.69; N, 18.93.

EXAMPLE 206

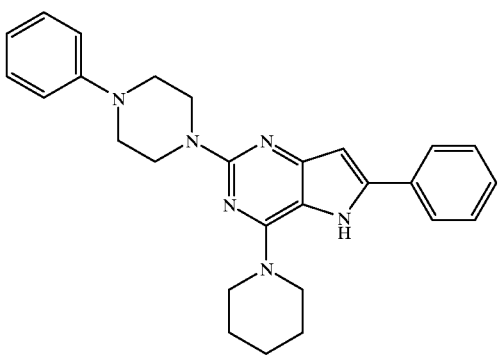

6-Phenyl-2-(4-phenylpiperazinyl)-4-piperidylpyrrolo[3,2-d]pyrimidine Hydrochloride Hydrate.

To the mixture of 2-chloro-6-phenyl-4-piperidyl pyrrolo [3,2-d]pyrimidine (Example 203(c)) (200 mg, 0.64 mmol) and 1-phenylpiperazine (Aldrich Chemical Company) (0.49 mL, 3.2 mmol) in a 50-mL, round-bottomed flask was added a solution of K₂CO₃ (0.89 g, 6.4 mmol) in 10 mL of H₂O. The reaction mixture was heated at reflux for 72 h under a stream of N₂. After cooling to room temperature, the mixture was partitioned between H₂O and CH₂Cl₂. The aqueous layer was extracted with CH₂Cl₂ and the combined CH₂Cl₂ layers were dried over Na₂SO₄, concentrated in vacuo and purified by flash chromatography on silica gel with 1:5 to 1:4 EtOAc/hexanes as eluant to give 107 mg (38%) of the free base as white solids. To a solution of the above material in CHCl₃ (5 mL) was added 1N ethereal HCl (Aldrich Chemical Company) (0.24 mL, 0.24 mmol). After stirring the reaction at room temperature for 30 min, the solvent was evaporated in vacuo and the foam obtained was recrystallized in MeOH/H₂O to give 54 mg of the title compound as off-white solids. Mp: 267.5–270.0° C. MS m/z: 439.5 (M+1). ¹H NMR (DMSO-d₆; 500 MHz): d 1.88 (m, 6), 4.07–4.15 (m, 12), 6.89 (s, 1), 7.00–7.02 (m, 2), 7.19 (d, 2, J=8.0), 7.42–7.45 (m, 2), 7.63–7.72 (m, 3), 8.05 (d, 2, J=7.6), 11.81 (br s, 1), 12.73 (br s, 1). Anal. Calcd for C₂₈H₃₂N₆.1.5HCl.1.25H₂O: C, 62.82; H, 6.63; N, 16.28; Cl, 10.51. Found: C, 62.82; H, 6.68; N, 16.26; Cl, 10.63.

EXAMPLE 207

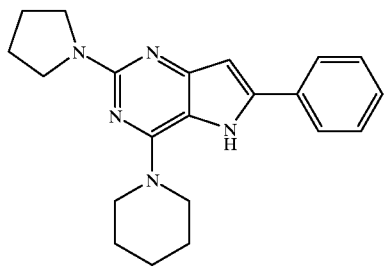

6-Phenyl-4-piperidyl-2-pyrrolidinylpyrrolo[3,2-d]pyrimidine Hydrochloride Monohydrate.

To the solution of 2-chloro-6-phenyl-4-piperidyl pyrrolo [3,2-d]pyrimidine (Example 203(c)) (250 mg, 0.80 mmol) in 2 mL of dioxane in a 5-mL, Wheaton vial was added pyrrolidine (0.33 mL, 4.0 mmol). The vial was capped and heated at 110° C. for 44 h. After cooling to room temperature, the precipitate was collected by filtration, washed with hexanes and dried in air to give 225 mg (81%) of the free base as light-yellow solids. To a solution of the above material in CHCl₃ (5 mL) was added 1N ethereal HCl (Aldrich Chemical Company) (0.63 mL, 0.63 mmol). After stirring the reaction at room temperature for 30 min, the solvent was evaporated in vacuo and the foam obtained was recrystallized in MeOH/H₂O to give 100 mg of the title compound as light-yellow crystals. Mp: >272° C. ¹H NMR (DMSO-d₆; 400 MHz): d 1.68–1.70 (m, 6), 2.00 (m, 4), 3.57 (m, 4), 3.96–3.97 (m, 4), 6.67 (s, 1), 7.46–7.56 (m, 3), 7.88 (d, 2, J=8.5), 11.57 (br s, 1), 12.11 (br s, 1). Anal. Calcd for C₂₁H₂₅N₅.HCl.H₂O: C, 62.75; H, 7.02; N, 17.42; Cl, 8.82. Found: C, 62.85; H, 6.93; N, 17.36; Cl, 8.70.

EXAMPLE 208

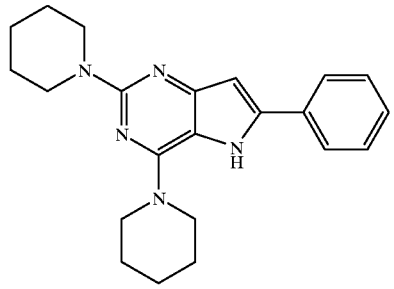

6-Phenyl-2,4-dipiperidylpyrrolo[3,2-d]pyrimidine Hydrochloride.

This compound was prepared according to the method described in Example 207 by employing 2-chloro-6-phenyl-4-piperidylpyrrolo[3,2-d]pyrimidine (Example 203(c)) (250 mg, 0.8 mmol), piperidine (Aldrich Chemical Company) (0.39 mL, 4.0 mmol) and dioxane (2 mL) to give 198 mg (69%) of the free base as a tan solid. To a solution of the above material in CHCl₃ (10 mL) was added 1N ethereal HCl (Aldrich Chemical Company) (0.54 mL, 0.54 mmol). After stirring the reaction at room temperature for 30 min, the solvent was evaporated in vacuo and the solid obtained was recrystallized in MeOH/H₂O to give 38 mg of the title compound as light-yellow crystals. Mp: >272° C. ¹H NMR (DMSO-d₆; 400 MHz): d 1.61–1.70 (m, 6), 3.74 (m, 4), 3.94 (m, 4), 6.71 (s, 1), 7.45–7.55 (m, 3), 7.87 (d, 2, J=7.3), 11.61 (br s, 1), 12.44 (br s, 1). Anal. Calcd for C₂₂H₂₇N₅.HCl: C,

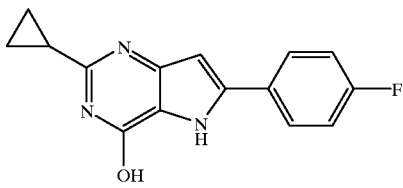

66.40; H, 7.09; N, 17.60; Cl, 8.91. Found: C, 66.25; H, 7.21; N, 17.48; Cl, 9.03.

EXAMPLE 209

(a) 2-Cyclopropyl-6-(4-fluorophenyl)pyrrolo[3,2-d]pyrimidin-4-ol.

This compound was prepared according to the method described in Example 68(a) by employing ethyl 3-amino-5-(4-fluorophenyl)pyrrole-2-carboxylate (Example 73(a)) (1.05 g, 4.2 mmol), dry HCl gas in cyclopropylcyanide (40 g) and then 6% aqueous sodium hydroxide (30 mL) and ethanol (70 mL) to give 1.41 g of the title compound as an off-white solid. H NMR (DMSO-$d_6$; 400 MHz): d 0.77–0.83 (m, 4), 1.32 (m, 1), 1.75 (m, 1), 6.54 (s, 1), 7.09–7.14 (m, 2), 7.77–7.81 (m, 2), 11.85 (br s, 1), 12.04 (br s, 1). MS m/z: 270.5 (M+1).

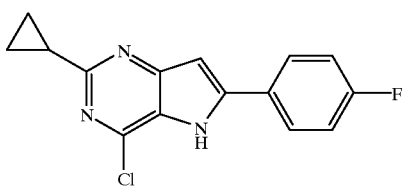

(b) 4-Chloro-2-cyclopropyl-6-(4-fluorophenyl)pyrrolo[3,2-d]pyrimidine.

This compound was prepared according to the method described in Example 68 (b) by employing 2-cyclopropyl-6-(4-fluorophenyl)pyrrolo[3,2-d]pyrimidin-4-ol (Example 209(a)) (1.14 g, 4.23 mmol), POCl$_3$ (8 mL, 85 mmol) and benzyltriethylammonium chloride (0.48 g, 2.1 mmol) to give 0.97 g (80%) of the title compound as an orange solid. $^1$H NMR (DMSO-$d_6$; 400 MHz): d 1.06–1.11 (m, 2), 1.18–1.22 (m, 2), 2.31–2.35 (m, 1), 6.83 (s, 1), 7.17–7.22 (m, 2), 7.74–7.77 (m, 2), 9.15 (br s, 1).

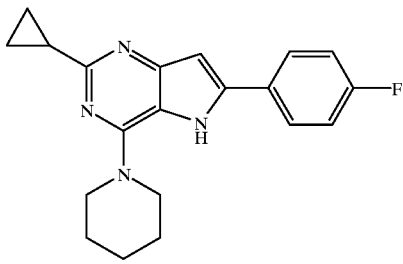

(c) 2-Cyclopropyl-6-(4-fluorophenyl)-4-piperidyl pyrrolo[3,2-d]pyrimidine Hydrochloride Hydrate.

This compound was prepared according to the method described in Example 2 by employing 4-chloro-2-cyclopropyl-6-(4-fluorophenyl)pyrrolo[3,2-d]pyrimidine (Example 209(b)) (437 mg, 1.5 mmol), piperidine (Aldrich Chemical Company) (0.75 mL, 7.6 mmol), and K$_2$CO$_3$ (1.05 g, 7.6 mmol) in H$_2$O (10 mL) to give 399 mg (78%) of the free base as a beige solid. To a solution of the above material in CHCl$_3$ (10 mL) was added 1N ethereal HCl (Aldrich Chemical Company) (1.2 mL, 1.2 mmol). After stirring the reaction at room temperature for 30 min, the solvent was evaporated in vacuo and the solid obtained was recrystallized in MeOH/H$_2$O to give 0.14 g of the title compound as off-white crystals. Mp: >280° C. $^1$H NMR (DMSO-$d_6$; 400 MHz): d 1.34–1.41 (m, 4), 1.88 (m, 6), 2.37–2.41 (m, 1), 4.18 (m, 4), 7.09 (s, 1), 7.62 (t, 2, J=8.8), 8.21–8.25 (m, 2), 12.14 (br s, 1). MS m/z: 337 (M+1). Anal. Calcd for C$_{20}$H$_{21}$FN$_4$.HCl.0.25H$_2$O: C, 63.80; H, 6.00; N, 14.88; Cl, 9.42. Found: C, 63.82; H, 5.97; N, 14.91; Cl, 9.70.

EXAMPLE 210

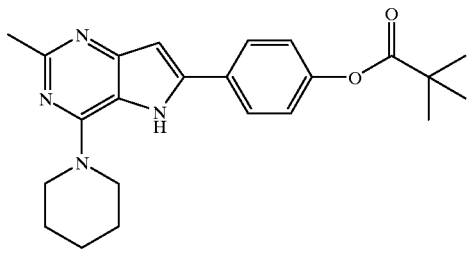

4-(2-Methyl-4-piperidylpyrrolo[4,5-d]pyrimidin-6-yl) phenyl 2,2-dimethylpropanoate.

To the mixture of 2-methyl-4-piperidyl-6-(4-hydroxyphenyl)pyrrolo[3,2-d]pyrimidine (example 72) (385 mg, 1.25 mmol) and pyridine (5 mL) in a 25-mL, round-bottomed flask was added trimethylacetic anhydride (Aldrich Chemical Company) (0.3 mL, 1.5 mmol). The reaction mixture was heated at reflux for 24 h under a stream of N$_2$. After cooling to room temperature, the solvent was evaporated in vacuo and the residue was partitioned between H$_2$O and CH$_2$Cl$_2$. The aqueous layer was extracted with CH$_2$Cl$_2$ and the combined CH$_2$Cl$_2$ layers were dried over Na$_2$SO$_4$, concentrated in vacuo and purified by flash chromatography on silica gel with 100:2.5 CHCl$_3$/MeOH as eluant to give 417 mg (85%) of a brown solid. It was recrystallized in EtOH to give 87 mg of the title compound as white solids. Mp: 272–274° C. MS m/z: 393.0 (M+1). $^1$H NMR (CDCl$_3$; 400 MHz): d 1.38 (s, 9), 1.76 (m, 6), 2.60 (s, 3), 3.79 (m, 4), 6.72 (s, 1), 7.17 (d, 2, J=8.6), 7.65 (d, 2, J=8.6), 8.06 (br s, 1). Anal. Calcd for C$_{23}$H$_{28}$N$_4$O$_2$: C, 70.38; H, 7.19; N, 14.27. Found: C, 70.52; H, 7.20; N, 14.32.

EXAMPLE 211

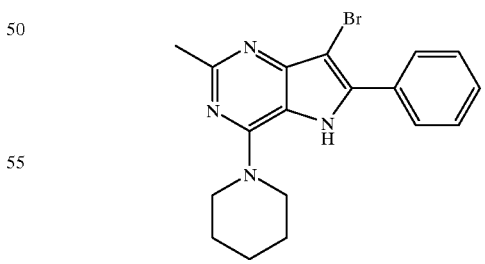

7-Bromo-2-methyl-6-phenyl-4-piperidylpyrrolo[3,2-d]pyrimidine Hydrochloride.

To an oven-dried, 50-mL, round-bottomed flask was added 2-methyl-6-phenyl-4-(piperidinyl)pyrrolo[3,2-d]pyrimidine (Example 35)) (500 mg, 1.71 mmol) which was dissolved in glacial AcOH (15 mL). To this solution was added Br$_2$ (Aldrich Chemical Company) (90.0 mL, 1.8 mmol) dropwise over 2 min. The resulting dark mixture was diluted with H₂O (10 mL) and the mixture was warmed to 45° C. and stirred for 2 h. The reaction was allowed to cool to room temperature and the crude material was extracted with EtOAc (50 mL) and washed with saturated NaHCO₃ (3×50 mL). The organic layer was washed with brine (50 mL), dried over MgSO₄, filtered and evaporated in vacuo to give an oily residue. The residue was purified by silica gel chromatography with 50% EtOAc/hexanes as eluant to give 500 mg (79.4% yield) of a yellow solid. Mp: 239–240 ° C. ¹H NMR (DMSO-d₆; 400 MHz): d 1.74 (s, 6), 2.63 (s, 3), 3.83 (s, 4), 7.44 (t, 1, J=2.4), 7.5 (t, 2, J=7.0), 7.80 (d, 2, J=7.1). MS m/z: 373.0 (M+1); 369.0, 371.0 (M−1).

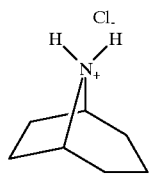

EXAMPLE 212

(a) 8-Azabicyclo[3.2.1]octane Hydrochloride.

To an oven-dried, 100-mL, round-bottomed flask was added tropane (2.5 g, 19.96 mmol) followed by toluene (20 mL), and a-chloro-ethyl chloroformate (3.2 mL, 30 mmol). The flask was purged with N₂ and the mixture was heated at 120° C. for 16 h. The reaction was allowed to cool to room temperature and the solvent was evaporated in vacuo. The resulting residue was dissolved in MeOH (20 mL) and heated to reflux at 85° C. for 3 h. The solvent was evaporated in vacuo and the product dried under vacuum to give 2.90 g (98% yield) of a light brown solid. MS m/z: 112.0 (M+1). ¹H NMR (DMSO-d₆; 400 MHz): d 1.64 (m, 4), 1.95 (m, 6), 3.92 (s, 2), 9.24 (br d, 2, J=7.3).

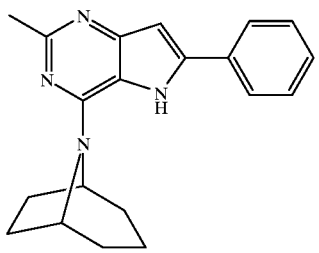

(b) 4-(8-azabicyclo[3.2.1]oct-8-yl)-2-methyl-6-phenyl pyrrolo[3,2-d]pyrimidine Hydrochloride.

To an oven-dried, 50-mL, round-bottomed flask was added NaOCH₃ (250 mg, 1.03 mmol) and 8-azabicyclo [3.2.1]octane hydrochloride (Example 212(a)) (152 mg, 1.03 mmol) and the resulting mixture was stirred at room temperature for 30 min. To this mixture was added 4-chloro-2-methyl-6-phenylpyrrolo[3,2-d]pyrimidine (Example 1(e)) (125 mg, 0.513 mmol) and the mixture was heated to 180° C. for 4 h. The reaction was allowed to cool to room temperature and the crude material was purified by silica gel chromatography with 50% EtOAc/hexanes as eluant to give 95 mg (60% yield) of light brown solid. The free base (88.0 mg, 0.277 mmol) was dissolved in hot EtOAc (10 mL) and anhydrous ethereal HCl (0.28 mL, of a 1.0 M soln, 0.28 mmol) was added dropwise. The mixture was stirred for 2 h and allowed to cool to room temperature. The resulting solid was filtered and dried under high vacuum to give 65 mg (66% yield) of the title compound as a light brown solid. Mp: >300° C. ¹H NMR (DMSO-d₆; 400 MHz): d 1.32 (m, 4), 2.63 (s, 3), 3.37 (s, 6), 5.26 (s, 2), 6.94 (s, 1), 7.61 (m, 3), 8.0 (d, J=7.0, 2), 11.84 (s, 1), 14.2 (s, 1). MS m/z: 387.5 (M+1); 385.5 (M−1).

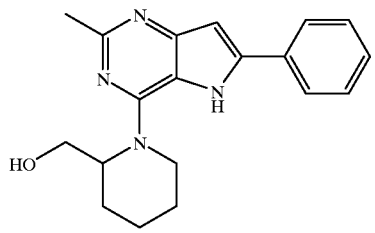

EXAMPLE 213

(1-[2-Methyl-6-phenylpyrrolo[2,3-e]pyrimidin-4-yl)-2-piperidyl)methan-1-ol Hydrochloride.

To an oven-dried, 50-mL, round-bottomed flask was added 4-chloro-2-methyl-6-phenylpyrrolo[3,2-d]pyrimidine (Example 1(e)) (250 mg, 1.03 mmol) and 2-hydroxymethyl piperidine (Aldrich Chemical Company) (237 mg, 2.06 mmol). The flask was purged with N₂ and the mixture was heated to 180° C. for 16 h. The reaction was allowed to cool to room temperature and the crude material was purified by silica gel chromatography with EtOAc as eluant to give 125 mg (38% yield) of an off white solid. ¹H NMR (CDCl₃; 400 MHz); d 1.74 (m, 6), 2.59 (s, 3), 3.1 (m, 1), 3.8 (m, 1), 4.35 (t, 1, J=10.9), 4.55 (m, 2), 6.72 (s, 1), 7.44 (m, 3), 7.65 (d, J=7.3), 9.9 (br, 1). MS m/z: 323.5 (M+1); 321.5 (M−1).

EXAMPLE 214

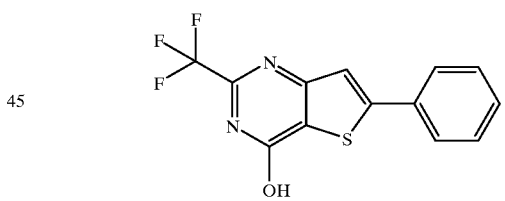

(a) 6-Phenyl-2-(trifluoromethyl)thiophene[3,2-d]pyrimidin-4-ol.

To an oven-dried, 100-mL, round-bottomed flask was added methyl 3-amino-5-phenylthiophene-2-carboxylate (Maybridge Chemical Company) (1.00 g, 4.29 mmol) along with trifluoroacetamidine (560 mg, 5 mmol) and the mixture was heated to 190° C. for 16 h. A solid formed in the reaction and as the mixture was allowed to cool to room temperature. Ethanol (50 mL) was added to the reaction mixture and the solid filtered off and dried under vacuum to give 420 mg (33% yield) of a white solid. Mp: 245–246° C. ¹H NMR (CDCl₃; 400 MHz): d 7.38 (m, 1), 7.48 (m, 2), 7.58 (dd, 1, J=1, 6.8), 7.67 (s, 1), 7.72 (dd, 2, J=1.2, 6.4). MS m/z: 297.0 (M+1); 295.0 (M−1).

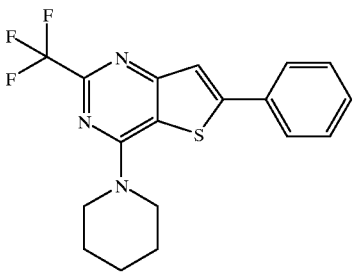

(b) 6-Phenyl-4-piperidyl-2-(trifluoromethyl)thiophene [3,2-d]pyrimidine Hydrochloride.

To an oven-dried, 50-mL, round-bottomed flask was added methanesulfonylimidazole (prepared by the method described by J. Michalski and co-workers Phosphorus and Sulfur 1986, 26, 321.) (67 mg, 0.372 mmol) and THF (10 mL), which was cooled to 0° C. with stirring under $N_2$. To this solution was added methyl triflate (Aldrich Chemical Company) (42 mL, 0.375 mmol) dropwise. The resulting mixture was stirred at 0° C. for 30 min before a solution of 6-phenyl-2-(trifluoromethyl)thiophene [3,2-d]pyrimidin-4-ol (Example 214(a)) (100 mg, 0.338 mmol) and 1-methylimidazole (22 mL, 0.281 mmol) dissolved in THF (5 mL) was added. The resulting solution was allowed to warm to room temperature over the course of 2 h, and piperidine (0.25 mL. 2.5 mmol) was added dropwise. The mixture was stirred for 30 min and then dissolved in $CHCl_3$ (50 mL). The organic layer was washed with brine (3×50 mL), dried over $MgSO_4$, filtered, and evaporated to give a residue. The residue was purified by silica gel chromatography with 20% EtOAc/hexanes as eluant to give 80 mg (67% yield) as a light yellow solid. The free base (48 mg, 0.132 mmol) was dissolved in hot $CH_2Cl_2$ (5 mL) and anhydrous ethereal HCl (0.132 mL, of an 1.0 M soln, 0.132 mmol) was added. The solid was filtered off and dried under vacuum to give 50 mg (95% yield) of a yellow solid. Mp: 168–169° C. $^1$H NMR (DMSO-$d_6$; 400 MHz): d 1.7 (br, s, 6), 4.0 (s, 4), 7.52 (m, 3H), 7.91 (d, 2, J=7.16), 8.03 (s, 1). MS m/z: 323.5 (M+1); 321.5 (M−1).

EXAMPLE 215

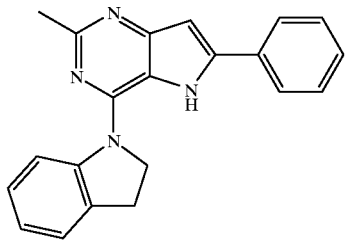

4-Indolinyl-2-methyl-6-phenylpyrrolo[3,2-d]pyrimidine Hydrochloride Hydrate.

To an oven-dried, 50-mL, round-bottomed flask was added 4-chloro-2-methyl-6-phenylpyrrolo[3,2-d]pyrimidine (Example 1(e)) (350 mg, 1.44 mmol) and indoline (Aldrich Chemical Company) (350 mg, 2.94 mmol). The flask was purged with $N_2$ and the mixture was heated to 180° C. for 1 h. The reaction was allowed to cool to room temperature and the crude material was purified by silica gel chromatography with 33% EtOAc/hexanes to give 250 mg (53% yield) of an off white solid. The free base (221 mg, 0.677 mmol) was dissolved in hot EtOAc (15 mL)and MeOH (2 mL) and anhydrous ethereal HCl (0.677 mL, of a 1.0 M soln, 0.677 mmol) was added dropwise. The mixture was stirred for 2 h and allowed to cool to room temperature. The resulting solid was filtered and dried under high vacuum to give 239 mg (97% yield) of the title compound as a light yellow solid. Mp: >300° C. $^1$H NMR (DMSO-$d_6$; 400 MHz): d 2.7 (s, 3), 4.87 (t, 2, J=8.2), 7.0 (s, 1), 7.17 (t, 1, J=7.5), 7.32 (t, 1, J=7.6), 7.58 (m, 3), 8.0 (d, 2, J=6.9), 8.53 (d, 1, J=3.3), 11.7 (br, 1), 14.55 (br, 1). MS m/z: 327.0 (M+1); 325 (M−1). Anal. Calcd for $C_{21}H_{18}$ $N_4$. 1.0HCl. 1.25$H_2O$: C, 65.45; H, 5.62; N, 14.54. Found: C, 65.62; H, 5.62; N, 14.49.

EXAMPLE 216

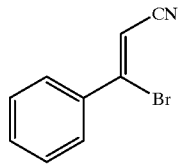

(a) (2Z)-3-Bromo-3-phenylprop-2-enenitrile.

To an oven-dried, 250-mL, round-bottomed flask was added benzolyacetonitrile (Avocado Chemical Company) (5.00 g, 34.4 mmol) and $PBr_3$ (100 mL), and the resulting mixture was heated at 170° C. with stirring under $N_2$. After 48 h, the mixture was allowed to cool to room temperature and was carefully poured into ice (500 g) and $CHCl_3$ (250 mL) was added. The mixture was stirred for 1 h. The layers were separated and the aqueous layer was extracted with $CHCl_3$ (125 mL). The organic layers were combined and washed with saturated $NaHCO_3$ (3×200 mL) and brine (250 mL). The organic layer was dried over $MgSO_4$, filtered, and evaporated in vacuo to give 8.00 g (98% yield) of a black oil. $^1$H NMR ($CDCl_3$; 400 MHz): d 6.35 (s,1), 7.6 (d, J=6.3,2), 7.4 (m,3).

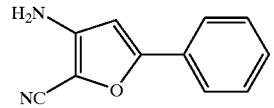

(b) 3-Amino-5-phenylfuran-2-carbonitrile.

To an oven-dried, 150-mL, round-bottomed flask was added glycolonitrile (Aldrich Chemical Company) (4.6 g, 55 wt. % in $H_2O$, 24.04 mmol), followed by THF (100 mL), and $MgSO_4$ (10 g). The mixture was stirred for 1 h before a soln of (2Z)-3-bromo-3-phenylprop-2-enenitrile (Example 216 (a)) (2.5 g, 12.04 mmol) was added. The mixture was stirred rapidly at room temperature as NaH (1.0 g, 60% in mineral oil, 25 mmol) was carefully added in portions over 1 h. The mixture was poured into ice (100 g) and stirred for 10 min. The reaction was extracted with a mixture of 3:1 of $CHCl_3$:i-PrOH (3×75 mL). The combined organic layers were washed with brine (200 mL), dried over $MgSO_4$, filtered and evaporated to give 2.0 g (90.5% yield) of an oil. $^1$H NMR ($CDCl_3$; 400 MHz): d 4.01 (br, 2), 6.35 (s, 1), 7.4 (m, 3), 7.63 (d, 2, J=7.1).

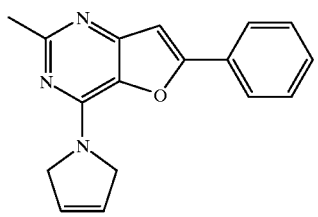

(c) 2-Methyl-6-phenyl-4-(3-pyrrolinyl)furano[3,2-d]pyrimidine Hydrochloride Hydrate.

To an oven-dried, 150-mL, round-bottomed flask was added N,N-dimethylacetamide (1.02 mL, 11 mmol) followed by POCl$_3$ (50 mL). the mixture was stirred at room temperature for 1 h. To this mixture was added 3-amino-5-phenylfuran-2-carbonitrile (Example 216 (b)) (677 mg, 3.68 mmol). The resulting mixture was heated at 160° C. for 36 h. The solvent was evaporated in vacuo and toluene (50 mL) was added. The solvent was again evaporated in vacuo and to the crude residue was added 3-pyrroline (Aldrich Chemical Company) (2.00 g, 28.9 mmol). The reaction was then heated to 120° C. for 1 h and then allowed to cool to room temperature. The crude material was dissolved in CHCl$_3$ (100 mL) and washed with saturated NaHCO$_3$ (3×100 mL), brine (100 mL), and dried over MgSO$_4$. The organic layer was filtered, and evaporated in vacuo to give a residue which was purified by silica gel chromatography with 50% EtOAc/hexanes as eluant. The product was isolated in 550 g (54% yield) as a light yellow solid. The free base (510 mg, 1.84 mmol) was dissolved in hot EtOAc (20 mL) and anhydrous ethereal HCl (1.85 mL, 1.0 M soln, 1.85 mmol) was added dropwise. A precipitate formed immediately and the mixture was allowed to cool to room temperature. The solid was filtered and dried under vacuum to give 565 mg (95% yield) of the title compound. Mp: 279–280° C. $^1$H NMR (DMSO-d$_6$; 500 MHz): d 2.65 (s, 3), 4.58 (s, 2), 5.01 (s, 2), 6.13 (d, 2, J=20), 7.59 (m, 3), 7.65 (s, 1), 8.13 (d, 2, J=5.9). MS m/z: 278.0 (M+1). Anal. Calcd for C$_{17}$H$_{15}$N$_3$O.1.10HCl.1.1H$_2$O: C, 60.54; H, 5.47; N, 12.46; Cl, 11.56. Found: C, 60.58; H, 5.41; N, 12.44; Cl, 11.38.

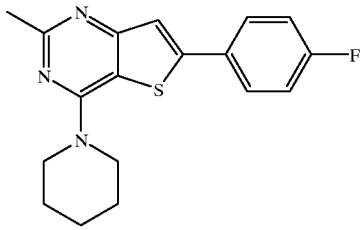

EXAMPLE 217
6-(4-Fluorophenyl)-2-methyl-4-piperidylthiopheno[3,2-d]pyrimidine Hydrochloride Hydrate.

To an oven-dried, 150-mL, round-bottomed flask was added N,N-dimethylacetamide (1.07 mL, 11.5 mmol) followed by POCl$_3$ (50 mL). The mixture was stirred at room temperature for 1 h. To this mixture was added 3-amino-2-cyano-5-(4-fluorophenyl)thiophene (Maybridge Chemical Company) (2.5 g, 11.45 mmol) and the resulting mixture was heated at reflux for 36 h. The reaction was allowed to cool to room temperature and the solvent was evaporated in vacuo. The residue was suspended in toluene (50 mL) and again the solvent was evaporated at reduced pressure. Approximately 500 mg of residue was removed and added to an oven-dried, 50-mL, round-bottomed flask, followed by piperidine (10 mL). The flask was purged with N$_2$, and heated to 160° C. for 2 h. The flask was allowed to cool to room temperature and the crude material was purified by silica gel chromatography with 33% EtOAc/hexanes to give 250 mg of a light yellow solid. The free base (223 mg, 0.681 mmol) was dissolved in hot EtOAc (10 mL) and anhydrous ethereal HCl (0.68 mL, 1.0 M soln, 0.68 mmol) was added dropwise. A precipitate formed immediately and the reaction was allowed to cool to room temperature and was stirred for an additional 1 h. The light yellow solid was filtered off and dried under vacuum overnight to give 240 mg (97% yield) of a light yellow solid. Mp: 285–287° C. $^1$H NMR (DMSO-d$_6$; 400 MHz): d 1.76 (s,6), 2.63 (s,3), 4.13 (s,4), 7.43 (t,2, J=8.8), 7.8 (s,1), 8.01 (m,2). MS m/z: 328.0 (M+1). Anal. Calcd for C$_{18}$H$_{18}$FN$_3$S. 1.25HCl.0.5H$_2$O: C, 65.48; H, 5.35; N, 10.98; Cl, 11.64. Found: C, 56.48; H, 5.40; N, 10.94; Cl, 11.64.

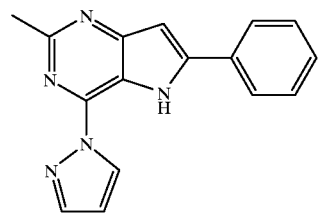

EXAMPLE 218

2-Methyl-6-phenyl-4-pyrazolypyrrolo[3,2-d]pyrimidine Hydrochloride Hydrate.

To an oven-dried, 50-mL, round-bottomed flask was added 4-chloro-2-methyl-6-phenylpyrrolo[3,2-d]pyrimidine (Example 1(e)) (350 mg, 1.44 mmol) followed by pyrazole (Aldrich Chemical Company) (196 mg, 2.88 mmol) and solid Na$_2$CO$_3$ (610 mg, 5.76 mmol). The flask was purged with N$_2$ and heated to 190–200° C. for 4 h. The reaction was allowed to cool to room temperature and the residue was dissolved in MeOH (25 mL). The remaining salts were filtered off and the organic layer evaporated under reduced pressure. The residue was purified by silica gel chromatography with EtOAc as eluant to give 245 mg (62% yield) of an off white solid. The free base (238 mg, 0.865 mmol) was dis-solved in hot EtOAc (15 mL) and anhydrous ethereal HCl (0.87 mL, 1.0 M soln, 0.87 mmol) was added dropwise. A precipitate formed and the reaction was allowed to cool to room temperature and stirred for 1 h. The solid was filtered off and dried under vacuum at 60° C. overnight to give 250 mg (93% yield) of an off white solid. Mp: 253–254° C. $^1$H NMR (DMSO-d$_6$; 400MHz): d 2.8 (s, 3), 6.83 (s, 1), 7.23 (s, 1), 7.58 (m, 3), 8.12 (d, 2, J=6.4), 8.22 (s, 1), 8.88 (d, 1, J=2.5), 12.0 (br s, 1). MS m/z: 276.0 (M+1). Anal. Calcd for C$_{16}$H$_{13}$N$_5$.1.11HCl.0.9H$_2$O: C, 57.86; H, 4.83; N, 21.09; Cl, 11.88. Found: C, 58.01; H, 4.88; N, 20.79; Cl, 11.88.

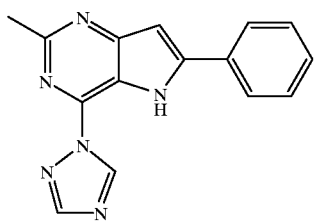

EXAMPLE 219
2-Methyl-6-phenyl-4-[1,2,4-triazolyl]pyrrolo[3,2-d]pyrimidine Hydrochloride.

To an oven-dried, 50-mL, round-bottomed flask was added 4-chloro-2-methyl-6-phenylpyrrolo[3,2-d]pyrimidine (Example 1(e)) (350 mg, 1.44 mmol) followed by 1,2,4-triazole (Aldrich Chemical Company) (200 mg, 2.88 mmol) and solid $Na_2CO_3$ (610 mg, 5.76 mmol). The flask was purged with $N_2$ and heated to 190–200° C. for 4 h. The reaction was allowed to cool to room temperature and the residue was dissolved in MeOH (25 mL). The remaining salts were filter off and the organic layer evaporated under reduced pressure. The residue was purified by silica gel chromatography with 50% EtOAc/hexanes as eluant to give 180 mg (45% yield) of an off white solid. The free base (168 mg, 0.608 mmol) was dissolved in hot EtOAc (15 mL) and anhydrous ethereal HCl (0.61 mL, 1.0 M soln, 0.61 mmol) was added dropwise. A precipitate formed and the reaction was allowed to cool to room temperature and stirred for 1 h. The solid was filtered off and dried under vacuum at 60° C. overnight to give 182 mg (96% yield) of an off white solid. Mp: 264–265° C. $^1$H NMR (DMSO-$d_6$; 400 MHz): d 2.77 (s, 3), 7.22 (s, 1), 7.57 (m, 3), 8.10 (d, 2, J=5.5), 8.6 (d, 1, J=3.4), 9.64 (d, 1, J=4.2), 11.87 (br m, 1). MS m/z: 277.0 (M+1); 275 (M−1).

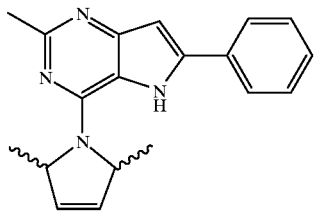

EXAMPLE 220
4-(2,5-Dimethyl(3-pyrrolinyl)-2-methyl-6-phenylpyrrolo[3,2-d]pyrimidine Hydrochloride Hydrate.

To an oven-dried, 50-mL, round-bottomed flask was added 4-chloro-2-methyl-6-phenylpyrrolo[3,2-d]pyrimidine (Example 1(e)) (600 mg, 2.46 mmol) and a cis and trans mixture of 2,5-dimethyl-3-pyrroline (Aldrich Chemical Company) (717 mg, 7.38 mmol). The flask was purged with $N_2$ and the mixture was heated to 180° C. for 1 h. The reaction was allowed to cool to room temperature and the crude material triturated with MeOH to give 550 mg (73% yield) of an off white solid. The free base (500 mg, 1.64 mmol) was dissolved in hot EtOAc (15 mL) and MeOH (2 mL) and anhydrous ethereal HCl (1.64 mL, of a 1.0 M soln, 1.64 mmol) was added dropwise. The mixture was stirred for 2 h and allowed to cool to room temperature. The resulting solid was filtered and dried under high vacuum to give 550 mg (98% yield) of the title compound as a light yellow solid. Mp: 242–243° C. $^1$H NMR (DMSO-$d_6$; 400 MHz): d 1.42 (d, 6, J=6.3), 2.54 (s, 3), 5.14 (br, 1), 5.65 (br, 1), 6.00 (s, 2), 6.84 (s, 1), 7.5 (m, 3), 7.85 (d, 2, J=7.0). MS m/z: 358 (M+1). Anal. Calcd for $C_{19}H_{20}N_4 \cdot 1.0$ HCl$\cdot 0.90$ $H_2O$: C, 63.91; H, 6.44; N, 15.69; Cl, 9.93. Found: C, 64.01; H, 6.20; N, 15.5; Cl, 9.78.

EXAMPLE 221

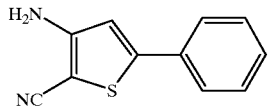

(a) 3-Amino-5-phenylthiophene-2-carbonitrile.

To an oven-dried, 50-mL, round-bottomed flask was added acetylmercaptoacetonitrile (Maybridge Chemical Company) (2.00 g, 17.37 mmol), followed by anhydrous EtOH (50 mL) and the dropwise addition of $NaOCH_3$ (5.64 g, 21 wt. %, 17.37 mmol). The resulting mixture was stirred for 1 h at room temperature, and then cooled to −78° C. with a dry ice/acetone bath. To this solution was added an ethanolic solution of vinyl bromide example 33 a (3.8 g, 18.26 mmol) in anhydrous EtOH (10 mL) at −78° C. After stirring for 1 h at this temperature, the reaction was allowed to warm to room temperature and was stirred for an additional 2 h. The solvent was evaporated under reduced pressure to leave a residue. The residue was dissolved in $CHCl_3$ (100 mL) and washed with 2.0 N NaOH (3×75 mL), and brine (100 mL). The organic layer was dried over $MgSO_4$, filtered, and evaporated to give a brown solid in 3.4 g (98% yield). $^1$H NMR (DMSO-$d_6$; 400 MHz): d 4.48 (br, 2), 6.75 (s, 1), 7.39 (m, 3), 7.53 (dd, 2, J=2, 6). MS m/z: 201 (M+1).

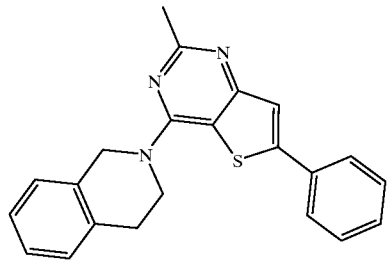

(b) 2-Methyl-6-phenyl-4-[2-1,2,3,4-tetrahydro isoquinolyl)thiopheno(3,2-d]pyrimidine Hydrochloride Hydrate.

To an oven-dried, 150-mL, round-bottomed flask was added N,N-dimethylacetamide (Aldrich Chemical Company) (1.07 mL, 11.5 mmol) followed by $POCl_3$ (50 mL). The mixture was stirred at room temperature for 1 h. To this mixture was added 3-amino-2-cyano-5-phenyl thiophene (Example 221(a)) (2.5 g, 11.45 mmol) and the resulting mixture was heated at reflux for 36 h. The reaction was allowed to cool to room temperature and the solvent was evaporated in vacuo. The residue was suspended in toluene (50 mL) and again the solvent was evaporated at reduced pressure. Approximately 750 mg of residue was removed and added to an oven-dried, 50-mL, round-bottomed flask, followed by 1,2,3,4-tetrahyrdoisoquinoline (4.0 mL, 31.9 mmol). The flask was purged with $N_2$, and heated to 160° C. for 2 h. The flask was allowed to cool to room temperature and the crude material was purified by silica gel chromatography with 25% EtOAc/hexanes to give 250 mg of a light yellow solid. The free base (500 mg, 1.4 mmol) was dissolved in hot EtOAc (20 mL) and anhydrous ethereal HCl (1.4 mL, 1.0 M soln, 1.4 mmol) was added dropwise. A precipitate formed immediately and the reaction was allowed to cool to room temperature and was stirred for an additional 1 h. The light yellow solid was filtered off and dried under vacuum overnight to give 540 mg (98% yield) of a light orange solid. Mp: 263–265° C. $^1$H NMR (DMSO-$d_6$; 400 MHz): d 2.55 (s, 3), 3.00 (s, 2), 4.19 (t, 2, J=5.7), 5.15 (s, 2), 7.17 (m, 3), 7.28 (d, 1, J=4.0), 7.45 (m, 3), 7.71 (s, 1), 7.80 (m, 2). MS m/z: 375.0 (M+1). Anal. Calcd for $C_{22}H_{19}N_3S.1.0HCl.0.88H_2O$: C, 64.38; H, 5.35; N, 10.24; Cl, 8.77. Found: C, 64.38; H, 5.10; N, 10.14; Cl, 8.76.

EXAMPLE 222

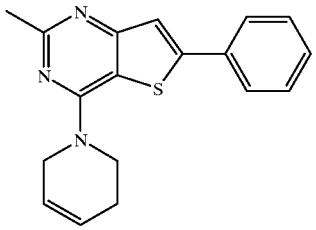

2-Methyl-6-phenyl-4-(1,2,5,6-tetrahydropyridyl) thiopheno[3,2-d]pyrimidine Hydrochloride Hydrate.

To an oven-dried, 150-mL, round-bottomed flask was added N,N-dimethylacetamide (Aldrich Chemical Company) (1.07 mL, 11.5 mmol) followed by POCl$_3$ (50 mL). The mixture was stirred at room temperature for 1 h. To this mixture was added 3-amino-2-cyano-5-phenyl thiophene (Example 221(a)) (2.5 g, 11.45 mmol) and the resulting mixture was heated at reflux for 36 h. The reaction was allowed to cool to room temperature and the solvent was evaporated in vacuo. The residue was suspended in toluene (50 mL) and again the solvent was evaporated at reduced pressure. Approximately 750 mg of residue was removed and added to an oven-dried, 50-mL, round-bottomed flask, followed by 1,2,3,6-tetrahyrdopyridine (3.0 mL, 32.9 mmol). The flask was purged with $N_{21}$, and heated to 160° C. for 2 h. The flask was allowed to cool to room temperature and the crude material was purified by silica gel chromatography with 25% EtOAc/hexanes to give 325 mg of a light yellow solid. The free base (300 mg, 0.976 mmol) was dissolved in hot EtOAc (15 mL) and anhydrous ethereal HCl (1.0 mL, 1.0 M soln, 1.0 mmol) was added dropwise. A precipitate formed immediately and the reaction was allowed to cool to room temperature and was stirred for an additional 1 h. The light yellow solid was filtered off and dried under vacuum overnight to give 320 mg (95.5% yield) of a light yellow solid. Mp: 279–281° C. $^1$H NMR (DMSO-$d_6$; 400 MHz): d 2.59 (br s, 2), 2.85 (s, 3), 4.42 (t, 2, J=5.7), 4.87 (s, 2), 6.09 (d, 1, J=10), 6.23 (d, 1, J=9.9), 7.78 (m, 3), 8.04 (s, 1), 8.15 (m, 2). MS m/z: 308.0 (M+1). Anal. Calcd for $C_{18}H_{17}N_3S.1.0HCl.0.65H_2O$: C, 60.73; H, 5.47; N, 11.81; Cl, 10.05. Found:C, 60.73; H, 5.32; N, 11.61; Cl, 9.95.

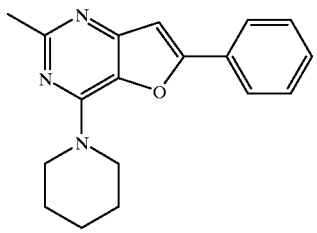

EXAMPLE 223

2-Methyl-6-phenyl-4-piperidylfurano[3,2-d]pyrimidine Hydrochloride Hydrate.

To an oven-dried, 150-mL, round-bottomed flask was added N,N-dimethylacetamide (1.02 mL, 11 mmol) followed by POCl$_3$ (50 mL). The mixture was stirred at room temperature for 1 h. To this mixture was added 3-amino-5-phenylfuran-2-carbonitrile (Example 216(b)) (677 mg, 3.68 mmol). The resulting mixture was heated at 160° C. for 36 h. The solvent was evaporated in vacuo and toluene (50 mL) was added. The solvent was again evaporated in vacuo and to the crude residue was added piperidine (Aldrich Chemical Company) (3.00 mL, 30.3 mmol). The reaction was then heated to 160° C. for 1 h and then allowed to cool to room temperature. The crude material was dissolved in CHCl$_3$ (100 mL) and washed with saturated NaHCO$_3$ (3×100 mL), brine (100 mL), and dried over MgSO$_4$. The organic layer was filtered, and evaporated in vacuo to give a residue which was purified by silica gel chromatography with 50% EtOAc/hexanes as eluant. The product was isolated in 200 mg (19% yield) as a light yellow solid. The free base (181 mg, 0.617 mmol) was dissolved in hot EtOAc (20 mL) and anhydrous ethereal HCl (0.617 mL, 1.0 M soln, 0.617 mmol) was added dropwise. A precipitate formed immediately and the mixture was allowed to cool to room temperature. The solid was filtered and dried under vacuum to give 198 mg (97% yield) of the title compound. Mp: >290° C. $^1$H NMR (DMSO-$d_6$; 400 MHz): d 1.75 (br s, 6), 2.58 (s, 3), 4.16 (s, 4), 7.61 (m, 4), 8.08 (d, 2, J=6.8). MS m/z: 294.0 (M+1). Anal. Calcd for $C_{18}H_{19}N_3O.1.08 HCl.1.82 H_2O$. C, 59.11; H, 6.54; N, 11.49; Cl, 10.51. Found:C, 59.11; H, 6.19; N, 11.42; Cl, 10.62.

EXAMPLE 224

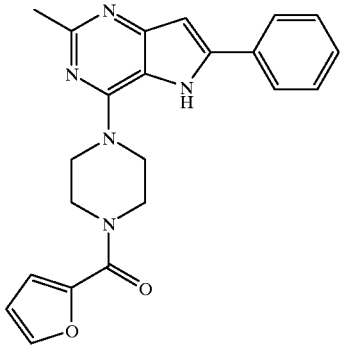

1-(2-Furanylcarbonyl)-4-(2-methyl-6-phenylpyrrolo[2,3-e]pyrimidin-4-yl)piperazine Hydrochloride Monohydrate.

To an oven-dried, 50-mL, round-bottomed flask was added 4-chloro-2-methyl-6-phenylpyrrolo[3,2-d]pyrimidine (Example 1(e)) (500 mg, 2.05 mmol) and the 1-(2-furoyl) piperazine (Avocado Chemical Company) (810 mg, 4.10 mmol). The flask was purged with $N_2$ and the mixture was heated to 180° C. for 30 min. The reaction was allowed to cool to room temperature and the crude material was purified by flash chromatography on silica gel with 50% EtOAc/$CHCl_3$ as eluant to give 500 mg (63% yield) of an off white solid. The free base (200 mg, 0.52 mmol) was dissolved in hot EtOAc (10 mL) and anhydrous ethereal HCl (0.52 mL, of a 1.0 M soln, 0.52 mmol) was added dropwise. The mixture was stirred for 2 h and allowed to cool to room temperature. The resulting solid was filtered and dried under high vacuum to give 205 mg (96% yield) of the title compound as a light yellow solid. Mp: 192–193° C. $^1$H NMR (DMSO-$d_6$; 400 MHz): d 2.54 (s, 3), 3.89 (br s, 4), 4.17 (t, 4, J=4.3), 6.62 (q, 1, J=1.7), 6.9 (s, 1), 7.05 (d, 1, J=3.4), 7.4 (m, 3), 7.85 (s, 1), 7.93 (d, 2, J=6.92). MS m/z: 388 (M+1). Anal. Calcd for $C_{22}H_{21}N_5O_2 \cdot HCl \cdot H_2O$: C, 59.79; H, 5.47; N, 15.85; O, 10.86; Cl, 8.02. Found: C, 59.99; H, 5.33; N, 15.79; Cl, 8.06.

EXAMPLE 225

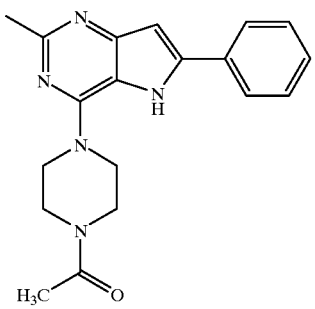

1-Acetyl-4-(2-methyl-6-phenylpyrrolo[2,3-e]pyrimidin-4-yl)piperazine Hydrochloride.

To an oven-dried, 50-mL, round-bottomed flask was added 4-chloro-2-methyl-6-phenylpyrrolo[3,2-d]pyrimidine (Example 1(e)) (500 mg, 2.05 mmol) and 1-acetyl-piperazine (Aldrich Chemical Company) (525 mg, 4.10 mmol). The flask was purged with $N_2$ and the mixture was heated to 180° C. for 30 min. The reaction was allowed to cool to room temperature and the crude material was purified by flash chromatography on silica gel with 10% MeOH/EtOAc as eluant to give 600 mg (87% yield) of an off white solid. The free base (400 mg, 1.2 mmol) was dissolved in hot EtOAc (10 mL) and anhydrous ethereal HCl (1.2 mL, of a 1.0 M soln, 1.2 mmol) was added dropwise. The mixture was stirred for 2 h and allowed to cool to room temperature. The resulting solid was filtered and dried under high vacuum to give 205 mg (96% yield) of the title compound as a light yellow solid. Mp: 282–283° C. $^1$H NMR (DMSO-$d_6$; 400 MHz): d 2.09 (s, 3), 2.61 (s, 3), 3.7 (s, 4), 4.14 (dt, J=5.3, 14), 6.95 (s, 1), 7.54 (m, 3), 8.00 (d, 2, J=6.88). MS m/z: 366 (M+1); 364 (M−1). Anal. Calcd for $C_{19}H_{21}N_5O \cdot HCl$: C, 60.76; H, 5.95; N, 18.65; O, 4.45; Cl, 10.19. Found: C, 60.76; H, 5.90; N, 18.64; Cl, 10.15.

EXAMPLE 226

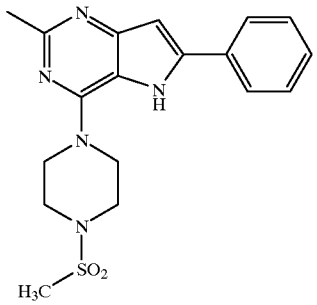

1-(2-Methyl-6-phenylpyrrolo[2,3-e]pyrimidin-4-yl)-4-(methylsulfonyl)piperazine Hydrochloride Monohydrate.

To an oven-dried, 50-mL, round-bottomed flask was added 2-methyl-6-phenyl-4-piperazinylpyrrolo[3,2-d]pyrimidine (Example 26) (400 mg, 1.36 mmol) was suspended in anhydrous THF (20 mL) and $Et_3N$ (0.4 mL, 2.8 mmol) was added. The mixture was cooled to 0° C. and methanesulfonyl chloride (Aldrich Chemical Company) (0.12 mL, 1.5 mmol) was added dropwise and allowed to warm to room temperature over 30 min. EtOAc (50 mL) was added to the mixture which was extracted with saturated $NaHCO_3$ (3×50 mL). The organic layer was washed with saturated NaCl (75 mL), dried over $MgSO_4$, filtered and evaporated in vacuo to give 450 mg (89% yield) as a light yellow solid. The free base (440 mg, 1.2 mmol) was dissolved in hot EtOAc (20 mL) and anhydrous ethereal HCl (1.18 mL, of a 1.0 M soln, 1.18 mmol) was added dropwise. The mixture was stirred for 2 h and allowed to cool to room temperature. The resulting solid was filtered and dried under high vacuum to give 460 mg (95.6% yield) of the title compound as a light yellow solid. Mp: 280–282° C. $^1$H NMR (DMSO-$d_6$; 400 MHz); d 2.54 (s, 3), 2.88 (s, 3), 3.29 (s, 4), 4.13 (t, 4, J=4.62), 6.9 (s, 1), 7.51 (m, 3), 7.94 (d, 2, J=6.85). MS ml/z: 372 (M+1); 370 (M−1). Anal. Calcd for $C_{18}H_{21}N_5O_2S \cdot HCl \cdot H_2O'$.: C, 50.46; H, 5.70; N, 16.35; Cl, 8.41. Found: C, 50.71; H, 5.60; N, 16.22; Cl, 8.45.

EXAMPLE 227

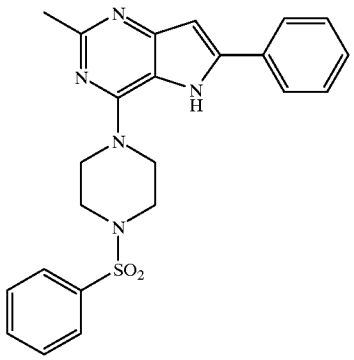

1-(2-Methyl-6-phenylpyrrolo[2,3-e]pyrimidin-4-yl(phenyl sulfonyl)piperazine Hydrochloride Monohydrate.

To an oven-dried, 50-mL, round-bottomed flask was added 2-methyl-6-phenyl-4-piperazinylpyrrolo[3,2-d]pyrimidine (Example 26) (400 mg, 1.36 mmol) was suspended in anhydrous THF (20 mL) and $Et_3N$ (0.4 mL, 2.8 mmol) was added. The mixture was cooled to 0° C. and benzenesulfonyl chloride (Aldrich Chemical Company)

(0.19 mL, 1.5 mmol) was added dropwise and allowed to warm to room temperature over 30 min. EtOAc (50 mL) was added to the mixture which was extracted with saturated NaHCO₃ (3×50 mL). The organic layer was washed with saturated NaCl (75 mL), dried over MgSO₄, filtered and evaporated in vacuo to give 450 mg (89% yield) as a light yellow solid. The free base (500 mg, 1.15 mmol) was dissolved in hot EtOAc (20 mL) and anhydrous ethereal HCl (1.15 mL, of a 1.0 M soln, 1.15 mmol) was added dropwise. The mixture was stirred for 2 h and allowed to cool to room temperature. The resulting solid was filtered and dried under high vacuum to give 510 mg (94.1% yield) of the title compound as a light yellow solid. Mp: 242–243° C. ¹H NMR (DMSO-d₆; 400 MHz); d 2.4 (s, 3), 2.98 (t, 4, J=4.6), 4.00 (t, 4, J=4.7), 6.75 (s, 1), 7.37 (m, 3), 7.49 (t, 2, J=7.8), 7.57 (t, 1, J=7.5), 7.62 (d, 2, J=7.2), 7.81 (d, 2, J=6.7). MS m/z: 434 (M+1); 432 (M−1). Anal. Calcd for C₂₃H₂₄N₅O₂S.HCl.H₂O: C, 56.63; H, 5.37; N, 14.36; Cl, 7.27. Found: C, 56.63; H, 5.37; N, 14.27; Cl, 7.41.

EXAMPLE 228

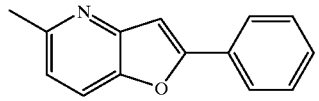

(a) 5-Methyl-2-phenylfurano[3,2-b]pyridine.

A mixture of 6-iodo-2-picolin-5-ol (Aldrich Chemical Company) (1.00 g, 4.29 mmol), phenylacetylene (Aldrich Chemical Company) (0.66 mL, 6.01 mmol), Cl₂Pd(PPh₃)₂ (15.1 mg, 0.21 mmol) and CuI (41.0 mg, 0.21 mmol) in Et₃N (20 mL) was heated under reflux (100° C.) for 16 h. Heating was discontinued and after cooling the mixture was diluted with CH₂Cl₂ (100 mL) and NH₄Cl (50 mL). The mixture was transferred to a separatory funnel. The organic solution was collected, washed with saturated NH₄Cl (50 mL) and saturated NaCl (50 mL). The organic solution was collected, dried over MgSO₄, filtered and concentrated under reduced pressure. The residue was purified by flash chromatography on silica gel with 50:50 EtOAc:hexanes as elutant to give 821 mg (91%) of the title compound as a white colored solid. ¹H NMR (CDCl₃; 400 MHz): δ 2.63 (s, 3), 7.07 (d, 1, J=8.4), 7.15 (s, 1), 7.40 (dt, 1, J=2.1, 7.4), 7.47 (t, 2, J=7.8), 7.67 (d, 1, J=8.6), 7.90 (dd, 2, J=1.5, 7.2). MS m/z : 210 (M+1).

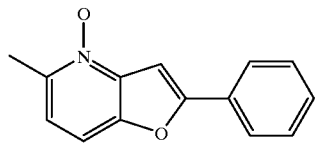

(b) 5-Methyl-2-phenylfurano[3,2-b]pyridine N-oxide.

A mixture of 5-methyl-2-phenylfurano[3,2-b]pyridine (Example 228(a)) (507 mg, 2.43 mmol) and m-chloroperbenzoic acid (0.84 g, purity 60%, 2.91 mmol) in CHCl₃ (20 mL) was stirred at 25° C. for 18 h. The mixture was filtered slowly through a fritted funnel with a basic alumina (20 g) pad. The pad was washed with CHCl₃ (50 mL) and the organic solutions were combined and concentrated under reduced pressure to afford 517 mg (95%) of the title compound as a white colored solid. ¹H NMR (CDCl₃; 400 MHz): δ 2.64 (s, 3), 7.15 (d, 1, J=8.4), 7.40 (d, 1, J=8.4), 7.43–7.51 (m, 4), 7.89 (dd, 2, J=1.4, 7.0). MS m/z: 226 (M+1).

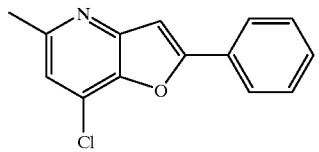

(c) 7-Chloro-5-methyl-2-phenylfurano[3,2-b]pyridine.

To a mixture of 5-methyl-2-phenylfurano[3,2-b]pyridine N-oxide (Example 228(b)) (302 mg, 1.33 mmol) in CHCl₃ (4 mL) was added POCl₃ (1.3 mL, 13.3 mmol). The mixture was heated to 60° C. where it was stirred for 16 h. After cooling the reaction mixture was poured onto crushed ice (50 mL). The pH of the mixture was adjusted to pH 8 with the slow addition of saturated NaHCO₃ (15 mL). CHCl₃ (30 mL) was added and the mixture was transferred to a separatory funnel. The organic solution was collected and the aqueous solution washed with CHCl₃ (2×30 mL). The organic solutions were combined, dried over MgSO₄, filtered and concentrated under reduced pressure. The residue was purified by flash chromatography on silica gel with 25:75 EtOAc:hexanes as elutant to give 220 mg (68%) of the title compound as a white solid. ¹H NMR (CDCl₃; 400 MHz): δ 2.63 (s, 3), 7.10 (s, 1), 7.15 (s, 1), 7.43 (t, 1, J=7.3), 7.49 (t, 2, J=7.8), 7.93 (d, 2, J=7.9). MS m/z : 244 (M+1).

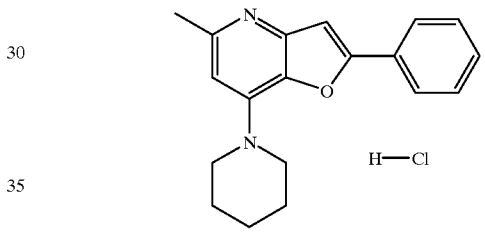

(d) 5-Methyl-2-phenyl-7-piperidylfurano[3,2-b]pyridine hydrochloride.

To a mixture of 7-chloro-5-methyl-2-phenylfurano [3,2-b]pyridine (Example 228(c)) (365 mg, 1.50 mmol) and piperidine (5 mL, 50.5 mmol) was added DMF (2 mL). Mixture stirred at 120° C. under N₂ for 26 h. After cooling, the reaction mixture was concentrated. The residue was diluted with H₂O (70 mL) and Et₂O (50 mL). The mixture was transferred to a separatory funnel and the organic solution was collected. The aqueous solution was washed with Et₂O (2×40 mL). The organic solutions were combined, washed with H₂O (50 mL), saturated NaCl (70 mL), dried over MgSO₄, filtered and concentrated under reduced pressure. The residue was purified by flash chromatography on silica gel with 50:50 EtOAc:hexanes as elutant to give 300 mg (68%) of 5-methyl-2-phenyl-7-piperidylfurano[3,2-b] pyridine as a cream colored solid. This material (298 mg, 1.02 mmol) was dissolved in EtOAc (20 mL) and heated to boiling. To the hot solution was added 1M etheral HCl (1.00 mL, 1.00 mmol). The solution was left to cool to 25° C. The resulting solid was collected by filtration, washed with EtOAc (2×5 mL), Et₂O (3×5 mL) and dried under vacuum at 25° C. to give 290 mg (59%) of the title compound as a white colored powder. Mp: >280° C. ¹H NMR (DMSO-d₆; 400 MHz): δ 1.67 (br s, 6), 2.49 (s, 3), 3.94 (br s, 4), 6.93 (s, 1), 7.46–7.54 (m, 4), 7.98 (dd, 2, J=1.5, 7.6), 14.14 (s, 1). MS m/z: 293 (M+1 for free base). Anal. Calcd for C₁₉H₂₀N₂O.HCl.0.25H₂O: C, 68.46; H, 6.50; N, 8.41; Cl, 10.64. Found C, 68.60; H, 6.44; N, 8.43; Cl, 10.56.

EXAMPLE 229

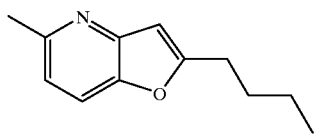

(a) 2-Butyl-5-methylfurano[3,2-b]pyridine.

A mixture of 6-iodo-2-picolin-5-ol (Aldrich Chemical Company) (1.49 g, 6.33 mmol), 1-hexyne (Aldrich Chemical Company) (1.02 mL, 8.86 mmol), $Cl_2Pd(PPh_3)_2$ (220 mg, 0.32 mmol) and CuI (60.0 mg, 0.32 mmol) in $Et_3N$ (25 mL) was heated under reflux (90° C.) for 18 h. Heating was discontinued and after cooling the mixture was diluted with $CH_2Cl_2$ (100 mL) and $NH_4Cl$ (50 mL). The mixture was transferred to a separatory funnel. The organic solution was collected, washed with saturated $NH_4Cl$ (50 mL) and saturated NaCl (50 mL). The organic solution was collected, dried over $MgSO_4$, filtered and concentrated under reduced pressure. The residue was purified by flash chromatography on silica gel with 50:50 EtOAc:hexanes as elutant to give 1.08 g (92%) of the title compound as a yellow colored oil. $^1$H NMR ($CDCl_3$; 400 MHz): δ 0.94 (t, 3, J=7.4), 1.43 (hextet, 2, J=7.5), 1.74 (quintet, 2, J=7.6), 2.62 (s, 3), 2.79 (t, 2, J=7.6), 6.52 (s, 1), 6.99 (d, 1, J=8.4), 7.53 (d, 1, J=8.4). MS m/z: 190 (M+1).

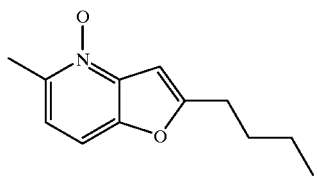

(b) 2-Butyl-5-methylfurano[3,2-b]pyridine N-oxide.

A mixture of 2-butyl-5-methylfurano[3,2-b]pyridine (Example 229(a)) (1.06 g, 5.61 mmol) and m-chloroperbenzoic acid (1.94 g, purity 60%, 6.73 mmol) in $CHCl_3$ (50 mL) was stirred at 25° C. for 18 h. The mixture was filtered slowly through a fritted funnel with a basic alumina (30 g) pad. The pad was washed with $CHCl_3$ (50 mL) and the organic solutions were combined and concentrated under reduced pressure to afford 1.14 g (99%) of the title compound as a yellow colored oil. $^1$H NMR ($CDCl_3$; 400 MHz): δ 0.95 (t, 3, J=7.3), 1.41 (hextet, 2, J=7.4), 1.74 (quintet, 2, J=7.5), 2.60 (s, 3), 2.81 (t, 2, J=7.5), 6.86 (s, 1), 7.07 (d, 1, J=8.4), 7.26 (d, 1, J=8.4). MS m/z: 207 (M+1).

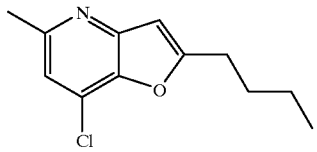

(c) 2-Butyl-7-chloro-5-methylfurano[3,2-b]pyridine.

To a mixture of 2-butyl-5-methylfurano[3,2-b]pyridine N-oxide (Example 229(b)) (1.13 g, 5.51 mmol) in $CHCl_3$ (3 mL) was added $POCl_3$ (5.1 mL, 55.1 mmol). The mixture was heated to 80° C. where it was stirred for 16 h. After cooling the reaction mixture was poured onto crushed ice (100 mL). The pH of the mixture was adjusted to pH 8 with the slow addition of saturated $NaHCO_3$ (150 mL). $CHCl_3$ (150 mL) was added and the mixture was transferred to a separatory funnel. The organic solution was collected and the aqueous solution washed with $CHCl_3$ (2×70 mL). The organic solutions were combined, dried over $MgSO_4$, filtered and concentrated under reduced pressure. The residue was purified by flash chromatography on silica gel with 10:90 EtOAc:hexanes as elutant to give 671 mg (54%) of the title compound as a white colored solid. $^1$H NMR ($CDCl_3$; 400 MHz): δ 0.96 (t, 3, J=7.4), 1.43 (hextet, 2, J=7.4), 1.76 (quintet, 2, J=7.5), 2.60 (s, 3), 2.83 (t, 2, J=7.7), 6.54 (s, 1), 7.02 (s, 1). MS m/z: 224 (M+1).

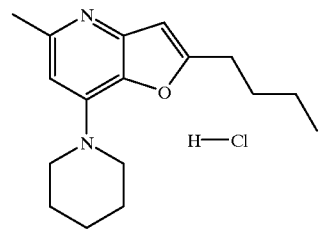

(d) 2-Butyl-5-methyl-7-piperidylfurano[3,2-b]pyridine hydrochloride.

To a mixture of 2-butyl-7-chloro-5-methylfurano [3,2-b] pyridine (Example 229(c)) (329 mg, 1.45 mmol) and piperidine (3 mL, 30.4 mmol) was added a mixture of $K_2CO_3$ (0.85 g, 5.8 mmol) in $H_2O$ (1 mL). Mixture stirred at 100° C. under $N_2$ for 16 h. After cooling, the reaction mixture was concentrated. The residue was diluted with $H_2O$ (70 mL) and $Et_2O$ (50 mL). The mixture was transferred to a separatory funnel and the organic solution was collected. The aqueous solution was washed with $Et_2O$ (2×40 mL). The organic solutions were combined, washed with $H_2O$ (50 mL), saturated NaCl (70 mL), dried over $MgSO_4$, filtered and concentrated under reduced pressure. The residue was purified by flash chromatography on silica gel with 50:50 EtOAc:hexanes as elutant to give 310 mg (77%) of 2-butyl-5-methyl-7-piperidylfurano[3,2-b]pyridine as a cream colored solid. This material (310 mg, 1.12 mmol) was dissolved in EtOAc (10 mL) and heated to boiling. To the hot solution was added 1M etheral HCl (1.20 mL, 1.20 mmol). The solution was left to cool to 25° C. The resulting solid was collected by filtration, washed with EtOAc (2×5 mL), $Et_2O$ (3×5 mL) and dried under vacuum at 25° C. to give 311 mg (69%) of the title compound as a white colored powder. Mp: 172–173° C. $^1$H NMR ($CDCl_3$; 400 MHz): δ 0.95 (t, 3, J=7.4), 1.42 (hextet, 2, J=7.3), 1.69 (quintet, 2, J=7.7), 1.79 (br s, 6), 2.71 (s, 3), 2.79 (t, 2, J=7.5), 3.85 (br, 4), 6.29 (s, 1), 7.01 (s, 1), 15.56 (s, 1). MS m/z: 2793 (M+1 for free base). Anal. Calcd for $C_{17}H_{24}N_2O\cdot HCl\cdot 0.5H_2O$: C, 64.24; H, 8.25; N, 8.82; Cl, 11.15. Found C, 64.42; H, 8.23; N, 8.75; Cl, 11.26.

EXAMPLE 230 AND EXAMPLE 231

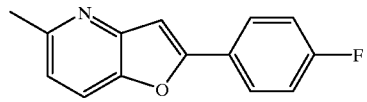

(a) 2-(4-Fluorophenyl)-5-mothylfurano[3,2-b]pyridine.

A mixture of 6-iodo-2-picolin-5-ol (Aldrich Chemical Company) (1.38 g, 5.86 mmol), 1-ethynyl-4-fluorobenzene (Aldrich Chemical Company) (0.99 g, 8.21 mmol), $Cl_2Pd$ $(PPh_3)_2$ (205 mg, 0.29 mmol) and CuI (56 mg, 0.29 mmol) in $Et_3N$ (25 mL) was heated under reflux (90° C.) for 16 h. Heating was discontinued and after cooling the mixture was diluted with CH₂Cl₂ (100 mL) and NH₄Cl (50 mL). The mixture was transferred to a separatory funnel. The organic solution was collected, washed with saturated NH₄Cl (50 mL) and saturated NaCl (50 mL). The organic solution was collected, dried over MgSO₄, filtered and concentrated under reduced pressure. The residue was purified by flash chromatography on silica gel with 50:50 EtOAc:hexanes as elutant to give 1.17 g (88%) of the title compound as a white colored solid. ¹H NMR (CDCl₃; 400 MHz): δ 2.66 (s, 3), 7.08 (s, 1), 7.17 (t, 2, J=6.7), 7.66 (d, 1, J=8.3), 7.84–7.89 (m, 2). MS m/z: 228 (M+1).

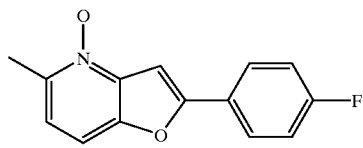

(b) 2-(4-Fluorophenyl)-5-methylfurano[3,2-b]

A mixture of 2-(4-fluorophenyl)-5-methylfurano [3,2-b] pyridine (Example 230(a)) (1.15 g, 5.07 mmol) and m-chloroperbenzoic acid (1.75 g, purity 60%, 6.08 mmol) in CHCl₃ (40 mL) was stirred at 25° C. for 18 h. The mixture was filtered slowly through a fritted funnel with a basic alumina (40 g) pad. The pad was washed with CHCl₃ (2×50 mL) and the organic solutions were combined and concentrated under reduced pressure to afford 1.23 mg (95%) of the title compound as a white solid. ¹H NMR (CDCl₃; 400 MHz): δ 2.63 (s, 3), 7.13–7.21 (m, 3), 7.39 (d, 1, J=8.4), 7.41 (s, 1), 7.85–7.89 (m, 2). MS m/z: 244 (M+1).

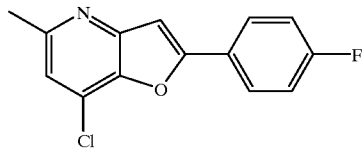

(c) 7-Chloro-2-(4-fluorophenyl)-5-methylfurano[3,2-b]pyridine.

To a mixture of 2-(4-fluorophenyl)-5-methylfurano [3,2-b]pyridine N-oxide (Example 230(b)) (1.22 g, 5.02 mmol) in CHCl₃ (2 mL) was added POCl₃ (5.0 mL, 50.2 mmol). The mixture was heated to 100° C. where it was stirred for 8 h. After cooling the reaction mixture was poured onto crushed ice (50 mL). The pH of the mixture was adjusted to pH 8 with the slow addition of saturated NaHCO₃ (100 mL). CHCl₃ (100 mL) was added and the mixture was transferred to a separatory funnel. The organic solution was collected and the aqueous solution washed with CHCl₃ (2×70 mL). The organic solutions were combined, dried over MgSO₄, filtered and concentrated under reduced pressure. The residue was purified by flash chromatography on silica gel with 50:50 EtOAc:hexanes as elutant to give 775 mg (59%) of the title compound as a white colored solid. ¹H NMR (CDCl₃; 400 MHz): δ 2.63 (s, 3), 7.09 (s, 1), 7.11 (s, 1), 7.18 (t, 2, J=8.6), 7.89–7.93 (m, 2). MS m/z: 262 (M+1).

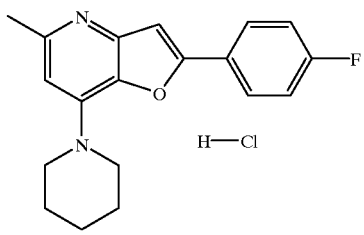

Example 230

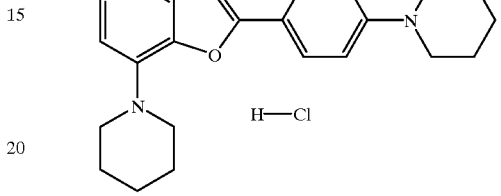

Example 231

(d) 2-(4-Fluorophenyl)-5-methyl-7-piperidylfurano[3,2-b]pyridine hydrochloride (Example 230) and 5-Methyl-7-piperidyl-2-(4-piperidylphenyl)furano[3,2-b]pyridine hydrochloride (Example 231).

To a mixture of 7-chloro-5-methyl-2-phenylfuranо [3,2-b]pyridine (Example 230(c)) (370 mg, 1.43 mmol) and piperidine (5 mL, 50.5 mmol) was added DMF (2 mL). Mixture stirred at 120° C. under N₂ for 24 h. After cooling, the reaction mixture was concentrated. The residue was diluted with H₂O (70 mL) and Et₂O (50 mL). The mixture was transferred to a separatory funnel and the organic solution was collected. The aqueous solution was washed with Et₂O (2×40 mL). The organic solutions were combined, washed with H₂O (50 mL), saturated NaCl (70 mL), dried over MgSO₄. filtered and concentrated under reduced pressure. The residue was purified by flash chromatography on silica gel with 50:50 EtOAc:hexanes as elutant to give 132 mg (30%) of 2-(4-fluorophenyl)-5-methyl-7-piperidylfurano[3,2-b]pyridine as a cream colored solid and 35 mg (7%) of 5-methyl-7-piperidyl-2-(4-piperidylphenyl)furano[3,2-b]pyridine as a tan colored solid.

Example 230

2-(4-Fluorophenyl)-5-methyl-7-piperidylfurano[3,2-b]pyridine (132 mg, 0.42 mmol) was dissolved in EtOAc (5 mL) and heated to boiling. To the hot solution was added 1M etheral HCl (0.50 mL, 0.5 mmol). The solution was left to cool to 25° C. The resulting solid was collected by filtration, washed with EtOAc (2×2 mL), Et₂O (3×5 mL) and dried under vacuum at 25° C. to give 130 mg (27%) of the title compound as a cream colored powder. Mp: >280° C. ¹H NMR (DMSO-d₆; 400 MHz): δ 1.68 (br s, 6), 2.48 (s, 3), 3.94 (br s, 4), 6.95 (s, 1), 7.39 (t, 2, J=8.6), 7.50 (s, 1), 8.07 (m, 2), 13.85 (s, 1). MS m/z: 311 (M+1 for free base). Anal. Calcd for C₁₉H₁₉FN₂O.HCl.0.25H₂O: C, 64.95; H, 5.88; N, 7.98; Cl, 10.09. Found C, 65.18; H, 5.86; N, 7.93; Cl, 10.13.

Example 231

5-Methyl-7-piperidyl-2-(4-piperidyl phenyl)furano[3,2-b]pyridine (31.0 mg, 0.08 mmol) was dissolved in EtOAc (5 mL) and heated to boiling. To the hot solution was added 1M etheral HCl (0.20 mL, 0.20 mmol). The solution was left to cool to 25° C. The resulting solid was collected by filtration, washed with EtOAc (2×2 mL), Et₂O (3×5 mL) and dried under vacuum at 25° C. to give 30 mg (6%) of the title compound as a brown colored solid. Mp: decomposition >170° C. ¹H NMR (DMSO-d₆; 400 MHz): δ 1.54 (br s, 6), 1.64 (br s, 6), 2.43 (s, 3), 3.29 (br s, 4), 3.89 (br s, 4), 6.85 (s, 1), 7.10 (m, 1), 7.22 (s, 1), 7.80 (m, 2), 13.75 (s, 1). MS m/z: 376 (M+1 for free base). Anal. Calcd for C₂₄H₂₉N₃O.2HCl.2.5H₂O: C, 58.41; H, 7.35; N, 8.52; Cl, 14.37. Found C, 58.30; H, 7.28; N, 8.38; Cl, 14.18.

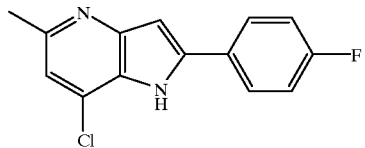

EXAMPLE 232

(a) 7-Chloro-5-methyl-2-(4-fluorophenyl)pyrrolo-[3,2-b] pyridine.

To a solution of 3-amino-2,4-dichloro-6-methyl pyridine (5.3 g, 28.2 mmol) in NEt₃ (190 mL), was added (PPh₃)₂PdCl₂ (1.4 g, 2.1 mmol), and CuI (400 mg, 2.2 mmol). The mixture was cooled to 0° C. and a solution of 4-fluorophenylacetylene (4.5 g, 37.5 mmol) in 10 mL of DMF was added slowly via syringe. The mixture was allowed to warm to room temperature then heated at 80° C. for 96 h. The mixture was allowed to cool to room temperature and filtered through a short pad of celite. The celite was rinsed with NEt₃ and the filtrate was concentrated in vacuo. The crude material was purified by flash chromatography on silica gel with 1:4 EtOAc:hexanes to afford 2.91 g (40%) of starting material followed by 2.97 g (55%, 91% based on recovered starting material) of 3-Amino-4-chloro-6-methyl-2-(2-phenylethynyl)pyridine as a dark brown solid. MS m/z: 243 (M+1). The crude intermediate (2.90 g, 11.1 mmol) was dissolved in anhydrous DMF (250 mL), CuI (310 mg, 16.3 mmol) was added and the mixture was heated at 95° C. for 19 h. The reaction mixture was cooled to room temperature and the crude product was collected by filtration. Chromatography on silica with 8:1 CHCl₃:MeOH gave 1.6 g (54%, 30% over two steps) of 7-chloro-5-methyl-2-(4-fluorophenyl)pyrrolo-[3,2-b]pyridine. ¹H NMR (DMSO-d₆; 500 MHz): d 2.50 (s, 3), 6.99 (s, 1), 7.11 (s,1), 7.32 (t, 2, J=8.8), 8.05 (m, 2), 11.78 (s, 1). MS m/z: 262 (M+H).

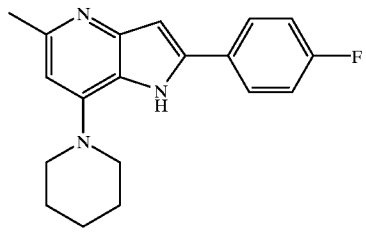

(b) 5-Methyl-2-(4-fluorophenyl)-7-piperidylpyrrolo[3,2-b] pyridine.

A mixture of 7-chloro-5-methyl-2-(4-fluorophenyl) pyrrolo[3,2-b]pyridine (1.5 g, 5.9 mmol) in 3:1 o-xylene/piperidine (20 mL) was heated at 140° C. in a Teflon-capped pressure tube for 5 d. The mixture was allowed to cool to room temperature, diluted with 5 mL of a 5:1 mixture of CHCl₃:MeOH and run through a short column of silica eluting with 10:1 CHCl₃:MeOH. The filtrate was concentrated in vacuo, the crude product was dissolved in 20 mL of CHCl₃ and 1M HCl in ether (8.0 mL, 8.0 mmol) was added slowly via syringe. The mixture was dried by rotary evaporation and triturated with a 1:5 mixture of EtOH:EtOAc. Filtration and drying under high vacuum for 24 h gave 1.45 g (70%) of the title compound as a yellow solid. ¹H NMR (DMSO-d₆; 500 MHz): d 1.72 (b s, 6), 2.55 (s, 3), 3.76 (s, 4), 6.80 (s, 1), 6.89 (s,1), 7.40 (t, 2, J=8.8), 8.02 (m, 2), 11.82 (s, 1), 13.79 (s, 1). Anal. Calcd for C₁₉H₂₀F₁N₃.HCl.0.5H₂O: C, 64.31; H, 6.25; N, 11.84. Found: C, 63.95; H, 6.15; N, 12.21.

EXAMPLE 233

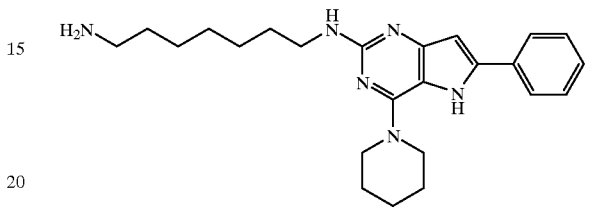

(7-Aminoheptyl)-(6-phenyl-4-piperidylpyrrolo[3,2-d] pyrimidin-2-yl)amine Hydrochloride Hydrate.

To a sealed 5-mL vial was added 2-chloro-6-phenyl-4-piperidylpyrrolo[3,2-d]pyrimidine (Example 203(c)) (55 mg, 0.176 mmol), 1,7-diaminoheptane (Aldrich Chemical Company) (92 mg, 0.703 mmol) and pyridine (1.5 mL). The solution was heated at 150° C. for 3 h. The reaction mixture was allowed to cool to room temperature and pyridine was removed in vacuo. The resulting residue was washed with sat. NaHCO₃, and extracted with CHCl₃ three times. The combined organic layers were dried over anhydrous Na₂SO₄, filtered and concentrated in vacuo. The resulting crude oil was purified by flash chromatography on silica gel with MeOH/CH₂Cl₂/NH₄OH(4:95:1) as eluant to afford 30 mg (42%) of a light-brown solid. The free base (30 mg, 0.074 mmol) was dissolved in CH₂Cl₂ (2 mL) and anhydrous ethereal HCl (0.11 mL of a 2 M soln, 0.22 mmol) was added dropwise. The precipitate was collected by filtration, washed with EtOAc/ether (1:1) (3×1 mL) and dried over vacuum to give 25 mg (66%) of the title compound as a light brown solid. ¹H NMR (DMSO-d₆;400 MHz): d 1.30–1.20 (m, 16), 2.90–2.95 (m, 2), 3.55–3.60 (m, 2), 4.11 (s, 4), 6.83 (s, 1), 7.60–8.30 (m, 9). MS m/z: 407 (M+1). Anal. Calcd for C₂₄H₃₄N₆.3HCl.H₂O: C, 54.00; H, 7.36; N, 15.74. Found: C, 54.20; H, 7.02; N, 14.46.

EXAMPLE 234

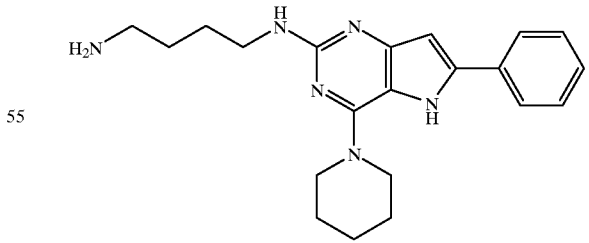

(4-Aminobutyl)-(6-phenyl-4-piperidylpyrrolo[3,2-d] pyrimidin-2-yl)amine Hydrochloride Hydrate.

To a sealed 3-mL vial was added 2-chloro-6-phenyl-4-piperidylpyrrolo[3,2-d]pyrimidine (Example 203(c)) (56 mg, 0.18 mmol), 1,4-diaminobutane(Aldrich Chemical Company) (158 mg, 1.80 mmol) and pyridine (0.5 mL). The solution was heated at 150° C. for 6 h. The reaction mixture was allowed to cool to room temperature and pyridine was removed in vacuo. The resulting residue was washed with sat. NaHCO$_3$, and extracted with CHCl$_3$ three times. The combined organic layers were dried over anhydrous Na$_2$SO$_4$, filtered and concentrated in vacuo. The resulting crude oil was purified by flash chromatography on silica gel with MeOH/CH$_2$Cl$_2$/NH$_4$OH (4:95:1) as eluant to afford 25 mg (38%) of a light-brown solid. The free base (30 mg, 0.074 mmol) was dissolved in CH$_2$Cl$_2$ (2 mL) and anhydrous ethereal HCl (0.10 mL of a 2 M soln, 0.20 mmol) was added dropwise. The precipitate was collected by filtration, washed with EtOAc/ether (1:1) (3×0.5 mL) and dried over vacuum to give 25 mg (77%) of the title compound as a light brown solid. $^1$H NMR (MeOH-d$_6$; 400 MHz): d 1.90–2.10 (m,10), 3.20–3.20 (m,2), 3.70–3.80 (m,2), 4.20–4.30 (m,4), 6.84 (s,1), 7.70–8.20 (m,5). MS m/z: 365 (M+1). Anal. Calcd for C$_{21}$H$_{28}$N$_6$.3HCl.H$_2$O: C, 51.28; H, 6.76; N, 17.08. Found: C, 52.00; H, 6.81; N, 15.01.

Biological Studies

Feeding Studies in Mice

Protocol For Icv Administration Of Compounds In Ad-Lib Fed OB/OB Female Mice.

Eight week old (approx. 50 g) OB/OB female mice were obtained from Jackson Laboratories (Bar Harbor, Me.) and given one week to acclimate to the animal facility before the experiment. Animals were housed 10 per cage and were provided with food and water ad-lib. Immediately prior to injection, animals were removed from group housing and lightly anesthetized using 4% isofluorane vapor. Freehand intracerebroventricular ("icv") injection of compounds was done in a 100% DMSO vehicle in a volume of 5 µl. Immediately following the injection, animals were placed in individual cages and were provided with a pre-weighed portion of regular chow pellets. Total amount of food consumed was measured at 1, 2, 4 and 24 hours post-injection.

The results show a statistically significant decrease in food intake in obese animals:

| I.C.V. treatment | 4 hr food intake (g ± S.E.M.) |
| --- | --- |
| vehicle | 0.61 ± 0.10 |
| Example 35 | 0.29 ± 0.11* |

*significantly different from vehicle, p < 0.05

Protocol for Mice Studies

Protocol For IP Administration Of Compounds In Male BALB-C Mice.

Male BALB-C mice (20–25 g)were obtained from Charles Rivers (Wilmington, Mass.) and were given at least a one week acclimation period to Amgen's animal care facilities. Animals were housed 10/cage and were provided ad libitum food and water. For testing, mice were fasted for 18–20 hr (overnight) prior to the start of the experiment. On the day of the experiment, mice were removed from group housing and placed into individual cages (without food). Test compounds or vehicle was then administered via the intraperitoneal (i.p.) route of administration. Test compounds were suspended in a 2% tween solution; the 2% tween solution was used as the vehicle treatment (control group). Group sizes for each treatment were 6–8 animals. After 30 min, premeasured food was placed into the cages. Two hours later, the food was weighed again. The difference between 2 hr weight and the premeasured weight was taken as 2 hr food intake. The following compounds showed at least a 10% inhibition of feeding in the mouse model at 30 mg/kg (ip): Examples 9, 30, 32, 33, 35, 61, 63, 64, 65, 66e, 68c, 69c, 71e, 72, 73a, 76c, 77, 80d, 81d, 85, 92d, 93, 95c, 96, 97, 98, 101, 103, 107, 108, 111, 114, 116, 118, 119, 121, 122, 123, 124, 125, 130, 131, 194, 195d, 196c, 197, 198, 199, 215, 217, 218 and 232b.

Feeding Studies in Rats

Protocol For Icv Administration Of Compounds In Food-Deprived Long-Evans Male Rats Adult male Long-Evans rats (approx. 275 g) were obtained from Charles River Laboratories (Wilmington, Mass.) and given one week to acclimate to the animal facility. Animals were housed individually and given ad-lib access to food and water. After acclimation, animals were anesthetized (75 mg/kg Sodium Nembutal) and implanted with 23 g cannulas (Plastics One, Roanoke, Va.) into the right lateral cerebral ventricle. All animals were given at least 1 week post-operative recover before any experiment.

Animals were food deprived for 16 hours prior to injections. Intracerebroventricular injection of compounds was done in awake, unrestrained animals in a DMSO vehicle in a volume of 20 µl. Immediately following the injection, the animals were returned to their home cage and were provided with a pre-weighed portion of regular rat chow pellets. Total food consumed was measured at 2 and 4 hours post-injection.

The results show a statistically significant decrease in food intake in food deprived animals:

| I.C.V. treatment | 4 hr food intake (g ± S.E.M.) |
| --- | --- |
| vehicle | 8.69 ± 0.53 |
| Example 1f | 5.13 ± 1.40* |

*significantly different from vehicle, p < 0.05

Protocol For Icv Administration Of NPY Antagonists Against pNPY Induced Feeding In Satiated Long-Evans Male Rats Adult male Long-Evans rats (approx. 275 g) were obtained from Charles River Laboratories (Wilmington, Mass.) and given one week to acclimate to the animal facility. Animals were housed individually and given ad-lib access to food and water. After acclimation, animals were anesthetized (75 mg/kg Sodium Nembutal) and implanted with 23 g cannulas (Plastics One, Roanoke, Va.) into the right lateral cerebral ventricle. All animals were given at least 1 week post-operative recover before any experiment.

Approximately 16 hours prior to injection, animals were provided with access to 30 grams of a sucrose/condensed milk/rat chow mash along with their regular chow. Ninety minutes prior to injections, regular chow was removed from the cages and animals were provided with a fresh portion of the high sucrose mash. Intracerebroventricular injection of antagonist or vehicle was done in awake, unrestrained animals in a DMSO vehicle in a volume of 20 µl. Approximately 15 minutes after the administration of the antagonist or vehicle, animals were given a second 5 µl injection of either water or pNPY. After the second injection, the portion of high sucrose mash was weighed and total food consumed was measured at 2 and 4 hours post-injection.

The results show the ability of the compounds of the invention to significantly inhibit NPY induced feeding behavior in animals:

| I.C.V. treatment | 4 hr food intake (g ± S.E.M.) |
| --- | --- |
| vehicle | 5.29 ± 0.97 |
| Example 2 | 3.35 ± 0.62* |

*significantly different from vehicle, p < 0.05

Protocol For IP Administration Of Compounds In Fasted Long-Evans Male Rats

Male Long Evans rats (85–100 g)were obtained from Harlan (Indianapolis, Ind.) and were given at least a one week acclimation period to Ambients animal care facilities. Animals were individually housed and were provided ad libitum food and water. For testing, rats were fasted for 18–20 hr (overnight) prior to the start of the experiment. On the test day, test compounds or vehicle was administered via the intraperitoneal (i.p.) route of administration. Test compounds were suspended in a 2% tween solution; the 2% tween solution was used as the vehicle treatment (control group). Group sizes for each treatment were 6–8 animals. After 30 min, premeasured food was placed into the cages. Two hours later, the food was weighed again. The difference between 2 hr weight and the premeasured weight was taken as 2 hr food intake. The following compounds showed at least a 10% inhibition of feeding in the mouse model at 30 mg/kg (ip): Examples 32, 33, 35, 61, 63, 65, 66e, 68c, 69c, 70e, 71e, 72, 76c, 80d, 85, 90, 95c, 96, 97, 101, 102, 104, 108, 111, 116, 118, 119, 121, 122, 123, 124, 126, 127, 134, 137, 141, 142, 143, 148, 150, 160, 168, 194, 195, 196c, 197d, 198, 200d, 202, 203, 209c, 216c, 217 and 232b.

Protocol For MCP-1 Inhibition Assay

Compounds of this invention may be shown to inhibit monocyte chemoattractant protein 1 (MCP-1) binding using the methods described in WO 98/06703 (incorporated herein by reference in its entirety). Membranes for use the MCP-1 inhibition assay can be prepared as follows. Human monocytic leukemia cell line, THP-1, cells are centrifuged, washed twice in ice-cold PBS (phosphate-buffered saline), resuspended in ice-cold lysis buffer (5mM HEPES (N-(2-hydroxyethyl)piperazine-N'-(2-ethanesulfonic acid)), pH 7.5, 2 mM EDTA, 5 ug/mL aprotinin, 5 ug/mL aprotinin, 5 ug/mL chymostatin and 100 ug/mL phenylmethanesulfonyl fluoride) at a concentration of about $5\times10^7$ cells/mL. The cell suspension is dounced 10–15 times using a B pestle (e.g., small pestle tissue grinder of 0.07 mm clearance) on ice. Nuclei and debris are removed by centrifugation at 500–1000×g for about 10 minutes at about 4° C. The supernatant is transferred to a fresh tube and centrifuged at 25,000×g for about 30 minutes at about 4° C. The supernatant is aspirated and the pellet is resuspended in buffer (10 mM HEPES, pH 7.5, 300 mM sucrose, 1 ug/mL leupeptin, 1 ug/mL aprotinin, 1 ug/mL chymostatin and 10 ug/mL phenylmethanesulfonyl fluoride) using a minihomogenizer until all clumps are resolved. Membranes are aliquoted and frozen at about −70° C. until needed. The total membrane protein can be determined with a standard protein assay, such as Bradford protein assay, BioRad, Richmond, Calif.

Assays typically involve mixing about 10–20 ug of total membrane protein, a test compound in DMSO and about 0.2 nM $I^{125}$-labeled MCP-1 (Amersham, Arlington Heights, Ill.) in assay buffer (10 mM HEPES, pH 7.2, 1 mM $CaCl_2$, 5 mM $MgCl_2$ and 0.5% BSA) at a final volume of about 100 $\mu$l. After about 30–60 minutes at room temperature, the assay is filtered with GF/C filters (Whatman glass fiber filters, Type C) or GF/B unifilter plates (Packard) pre-soaked in 0.3% polyethyleneimine and washed twice with assay buffer containing about 0.5 M NaCl. The filters are dried and counted in a scintillation counter using standard scintillation fluid. Typically, the final concentration of compound in the assay ranges from about 0.05 $\mu$M to about 100 $\mu$M. Negative controls contain the same concentration of DMSO present in assays containing compound. Positive controls contain about 250–500 nM cold MCP-1 (Peprotech, Rocky Hill, N.J.) in DMSO. IC50 values can be calculated for each compound using a non-linear 3-parameter logistic curve fit. Any observed non-specific binding is subtracted from all data prior to analysis.

Protocols For CRF Antagonist and CRH Binding Protein inhibition Activity Determination Compounds of this invention may be shown to antagonize CRF and/or inhibit binding of CRH binding protein using the methods described in WO 98/05661, WO 98/08846 and WO 98/08847 (each of which is incorporated herein by reference in its entirety).

Protocol For Corticotropin Releasing Factor Antagonist Activity Determination

Compounds of this invention may be shown to be antagonists of CRF activity using the methods described in Endocrinology 116:1653–1659 (1985) and Peptides 10:179–188 (1985) (each of which are incorporated herein by reference in their entirety).

Protocol For Corticotropin Releasing Factor Hormone Binding Protein Inhibition Activity Determination Compounds of this invention may be shown to inhibit CRH binding protein activity using the methods described in Brain Research 745:248–255 (1997) (incorporated herein by reference in its entirety).

Protocols For Protein Kinase Inhibition Activity Determination

Compounds of this invention may be shown to inhibit protein kinases and cell growth using the methods described in WO 98/07726 (incorporated herein by reference in its entirety).

Protocols For EGF-R-PTK Inhibition Activity Determination

The inhibition of EGF-receptor-specific protein tyrosine kinase (EGF-R-PTK) can be demonstrated using the recombinant intracellular domain of the EGF receptor described in E. McGlynn et al., Europ. J. Biochem. 207:265–275 (1992). Inhibition of EGF-stimulated cellular tyrosine phosphorylation in the EGF-receptor can be shown in the human A431 epithelial carcinoma cell line by means of an ELISA which is described in U. Trinks et al., J. Med. Chem. 37:7, 1015–1027 (1994). U. Trinks et al. also describe a method for testing the inhibition EGF stimulation of quiescent BALB/c3T3 cells to rapidly induce the expression of c-fos mRNA which involves pretreating the cells with test compound A method (Meyer et al., Int. J. Cancer 43:851 (1989)) for screening compounds for inhibition of the cell growth of EGF-dependent cell lines, such as the epidermoid BALB/c mouse keratinocyte cell line (Weissmann, and Aaronson, Cell 32:599 (1983)), the A431 cell line, a standard source of EGF-dependent epithelial cells (Carpenter and Zendegni, J. Anal. Biochem. 153:279–282 (1985)) and the like, is as follows: BALB/MK cells (about 10,000/microtitre plate well) are transferred to 96-well microtitre plates. A test compound (dissolved in DMSO) is added in a dilution series of concentrations such that the final concentration of DMSO does not exceed 1% (v/v). The plates are incubated for about three days during which the control cultures without test compound are able to undergo at least three cell-division cycles. The growth of the MK cells is measured by means of Methylene Blue staining (the cells are fixed with glutaraldehyde, washed with water and stained with 0.05% Methylene Blue). After washing, the stain is eluted with 3% HCl and the optical density per well of the microtitre plate is measured, such as with a Titertek Multiscan, at 665 nm. The $IC_{50}$ of the test compound is calculated based on the cell counts.

A method for in vivo screening of compounds for inhibition of the growth of tumour cells, such as the human epidermoid carcinoma A431 (ATCC No. CRL 1555; American Type Culture Collection, Rockville, Md., USA; Santon et al., Cancer Research 46:4701–4705 (1986); and Ozawa et al., Int. J. Cancer 40:706–710 (1987)) is as follows. The human epidermoid carcinoma A431 is transplanted into female BALB/c nude mice (Bomholtgard, Denmark). This carcinoma has been reported to exhibit a growth that correlates with the extent of the expression of the EGF-receptor. Tumours having a volume of approximately 1 cm$^3$ cultured in vivo are surgically removed from experimental animals under sterile conditions. These tumours are comminuted and suspended in 10 volumes (w/v) of phosphate-buffered saline. The suspension is injected s.c. (0.2 ml/mouse in phosphate-buffered saline) into the left flank of the animals. Alternatively, 1×10$^6$ cells from an in vitro culture in 0.2 ml of phosphate-buffered saline can be injected. Treatment with a test compound is started 5 or 7 days after transplantation, when the tumours have reached a diameter of 4–5 mm. The test compound is administered, at different doses for different animal groups, once a day for 15 successive days. The tumour growth is determined by measuring the diameter of the tumours along three axes that are perpendicular to each other. The tumour volumes can be calculated using the formula p×L×D$^2$/6 (Evans et al., Brit. J. Cancer 45:466–8 (1982)).

Protocols For Determination of Activity Inhibition of Other Protein Kinases

Methods for screening compounds for inhibition of other protein tyrosine kinases that are involved in signal transmission mediated by trophic factors, for example abl kinase (v-abl kinase), kinases from the family of the src kinases (c-src kinase and c-erbB2 kinase (HER-2)), and serine/threonine kinases (protein kinase C), all of which are involved in growth regulation and transformation in mammalian cells, including human cells, are as follows. Inhibition of v-abl tyrosine can be determined using [Val$^5$]-angiotensin II and [γ-$^{32}$P]-ATP substrates in the methods of Lydon et al. (Oncogene Research 5:161–173 (1990)) and Geissler et al. (Cancer Research 52:4492–4498 (1992)). The inhibition of c-erbB2 tyrosine kinase (HER-2) can be determined using an analogous method to the above described EGF-R-TPK method (House et al., Europ. J. Biochem. 140:363–367 (1984)). Alternatively, the activity of isolated c-erbB2 kinase can be determined (Akiyama et al., Science 232:1644 (1986)).

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound of formula

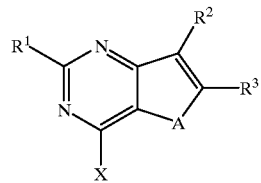

or a pharmaceutically acceptable salt, ester, solvate or N-oxide thereof, wherein A is N—H or N—R$^4$;

$R^1$ is a hydrogen, halo, —OH, —NO$_2$, —NHOH, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical;

$R^2$ is a hydrogen, halo, —OH, —NO$_2$, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical, provided that R$^2$ is not an optionally substituted phenyl, thienyl, pyridyl, pyrazinyl, pyrimidyl or pyridazinyl radical;

$R^3$ is a (C$_3$–C$_{10}$)cycloalkyl, (C$_1$–C$_8$)alkyl, —((C$_1$–C$_8$)alkyl)OH, (C$_1$–C$_8$)alkoxy-(C$_1$–C$_8$)alkyl-, -((C$_1$–C$_8$)alkyl)N(R$^5$)$_2$, -((C$_1$–C$_8$)alkyl)S(O)$_p$((C$_1$–C$_8$)alkyl), —(CH$_2$)((C$_3$–C$_{10}$)cycloalkyl)$_k$(CH$_2$)$_m$OH, —(CH$_2$)$_m$((C$_3$–C$_{10}$)cycloalkyl)(CH$_2$)$_m$OH, —(CH$_2$)$_m$((C$_3$–C$_{10}$)cycloalkyl)$_k$(CH$_2$)OH, —(CH$_2$)((C$_3$–C$_{10}$)cycloalkyl)$_k$(CH$_2$)$_m$(C$_1$–C$_8$)alkoxy, —(CH$_2$)$_m$((C$_3$–C$_{10}$)cycloalkyl)(CH$_2$)$_m$(C$_1$–C$_8$)alkoxy, —(CH$_2$)$_m$((C$_3$–C$_{10}$)cycloalkyl)$_k$(CH$_2$)(C$_1$–C$_8$)alkoxy, —(CH$_2$)((C$_3$–C$_{10}$)cycloalkyl)$_k$(CH$_2$)$_m$N(R$^5$)$_2$, —(CH$_2$)$_m$((C$_3$–C$_{10}$)cycloalkyl)(CH$_2$)$_m$N(R$^5$)$_2$, —(CH$_2$)$_m$((C$_3$–C$_{10}$)cycloalkyl)$_k$(CH$_2$)N(R$^5$)$_2$, —(CH$_2$)$_m$((C$_3$–C$_{10}$)cycloalkyl)(CH$_2$)$_m$S(O)$_p$R$^5$, —D'(S(O)$_q$R$^5$), —D'(aryloxy), —D'(aryl), —D' (heteroaryl), —D'((C$_3$–C$_{10}$)cycloalkyl), —D' (NR$^5$SO$_2$R$^5$), —D'(CON(R$^5$)$_2$), —D'(CO$_2$R$^5$), —D' (NR$^5$CON(R$^5$)$_2$), —D'(NR$^5$(CO)R$^5$), —D' (NR$^5$CO$_2$R$^5$), —D'(COR$^5$), —D'(Q), —D(aryloxy), —D(aryl), —D(heteroaryl), —D((C$_3$–C$_{10}$)cycloalkyl), —D(NR$^5$SO$_2$R$^5$), —D(CON(R$^5$)$_2$), —D(CO$_2$R$^5$), —D(S(O)$_q$R$^5$), —D(NR$^5$CON(R$^5$)$_2$), —D(NR$^5$(CO) R$^5$), —D(NR$^5$CO$_2$R$^5$), —D(COR$^5$) or —(NR$^5$)$_k$— D—Q radical;

$R^4$ is a (C$_1$–C$_8$)alkyl, (C$_3$–C$_{10}$)cycloalkyl, —Z((C$_1$–C$_8$) alkoxy), —Z(aryloxy), —Z(aryl), —Z(heteroaryl), —Z((C$_3$–C$_{10}$)cycloalkyl), —Z(NR$^5$SO$_2$R$^5$), —Z(CON (R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical;

X is a (C$_1$–C$_8$)alkyl, (C$_3$–C$_{10}$)cycloalkyl, —(NR$^5$)$_k$ ((C$_1$–C$_8$)alkyl) (C$_1$–C$_8$)alkoxy, —(NR$^5$)$_k$((C$_1$–C$_8$) alkyl)aryloxy, —(NR$^5$)((C$_1$–C$_8$)alkyl)$_k$S(O)$_p$R$^5$, —(NR$^5$)$_k$((C$_1$–C$_8$)alkyl)S(O)$_p$R$^5$, —(NR$^5$)D(C$_1$–C$_8$) alkoxy, —(NR$^5$)(CH$_2$)$_m$((C$_3$–C$_{10}$)cycloalkyl)$_k$(CH$_2$) (C$_1$–C$_8$)alkoxy, —(NR$^5$)$_k$(CH$_2$)((C$_3$–C$_{10}$)cycloalkyl)$_k$ (CH$_2$)$_m$(C$_1$–C$_8$)alkoxy, —(NR$^5$)$_k$(CH$_2$)$_m$((C$_3$–C$_{10}$) cycloalkyl)(CH$_2$)$_m$(C$_1$–C$_8$)alkoxy, —(NR$^5$)(CH$_2$)$_m$ ((C$_3$–C$_{10}$)cycloalkyl)$_k$(CH$_2$)aryloxy, —(NR$^5$)$_k$(CH$_2$)

$((C_3-C_{10})$cycloalkyl$)_k(CH_2)_m$aryloxy, —$(NR^5)_k(CH_2)_m((C_3-C_{10})$cycloalkyl$)(CH_2)_m$aryloxy, —$Z(S(O)_qR^5)$, —$Z($aryl$)$, —$Z($heteroaryl$)$, —$Z((C_3-C_{10})$cycloalkyl$)$, —$Z(NR^5SO_2R^5)$, —$Z(CON(R^5)_2)$, —$Z(CO_2R^5)$, —$Z(N(R^5)_2)$, —$Z(NR^5CON(R^5)_2)$, —$Z(NR^5(CO)R^5)$, —$Z(NR^5CO_2R^5)$, —$Z(COR^5)$ or —$Z(Q)$ radical;

Q and Q' are each independently a 4-membered to 10-membered heterocyclyl or heteroaryl radical;

each $R^5$ is independently a hydrogen, —OH, $(C_1-C_8)$ alkoxy, aryl, —$NH_2$, —$NH((C_1-C_8)$alkyl$)$, —$N((C_1-C_8)$alkyl$)_2$, $(C_1-C_8)$alkyl or $(C_3-C_{10})$ cycloalkyl radical;

D is —$(CH_2)_m((C_3-C_{10})$cycloalkyl$)_k(CH_2)_m$— and D' is -$((C_1-C_8)$alkyl$)_k$—;

Z is $D(NR^5)_k$, $D'(NR^5)_k$, $(NR^5)_kD$ or $(NR^5)_kD'$;

each k is independently 0 or 1;

each m is independently an integer between 0 and 6;

each p is independently an integer between 0 and 2; and each q is independently 1 or 2; and wherein each alkyl, aryl, heteroaryl, cycloalkyl, Q, alkoxy or aryloxy moiety of any of X, $R^1$, $R^2$, $R^3$, $R^4$ and $R^5$ is optionally substituted with 1–3 radicals of halo and 1–2 radicals of —$CF_3$, —$OCF_3$, —$Z(COOH)$, —$Z(OH)$, —$Z(NO_2)$, —$Z(SH)$, -$(C_1-C_8)$alkyl, -$(C_1-C_8)$acyloxy, -$(C_3-C_{10})$cycloalkyl, —$S$-$((C_1-C_8)$alkyl$)_k$-aryl, $((C_1-C_8)$alkyl$)_k$—$SO_2NH$-aryl, —$S$-$(C_1-C_8)$alkyl, —$Z((C_1-C_8)$alkoxy$)$, —$Z($aryloxy$)$, —$Z($aryl$)$, —$Z($heteroaryl$)$, —$Z((C_3-C_{10})$cycloalkyl$)$, —$Z(NR^9SO_2R^9)$, —$Z(CON(R^9)_2)$, —$Z(CO_2R^9)$, —$Z(N(R^9)_2)$, —$Z(NR^9CON(R^9)_2)$, —$Z(NR^9(CO)R^9)$, —$Z(NR^9CO_2R^9)$, —$Z(COR^9)$, —$Z(S(O)_pR^9)$ or —$Z(Q')$, wherein such aryl, heteroaryl, cycloalkyl and Q' substituents are optionally substituted with 1–3 radicals of halo, —$NO_2$, —$CF_3$, —$OCF_3$, —$N(R^9)_2$, —$C(O)R^9$, —$CO_2R^9$, —$OR^9$, —$SR^9$ or $(C_1-C_8)$alkyl; and wherein each $R^9$ is independently a hydrogen or $(C_1-C_8)$alkyl radical; and provided that the total number of aryl, heteroaryl, cycloalkyl, heterocyclyl, Q and Q' moieties in A, X, $R^1$, $R^2$ and $R^3$ is 0–4; and provided that:

(a) when A is NH, $R^1$ is H, methyl or phenyl, and $R^3$ is methyl, ethyl or phenyl, then (1) when $R^2$ is H, X is not —$NH_2$, —$N(CH_2CH_3)_2$, —$NHCH_2CH_2N(CH_2CH_2)_2$, —$NHCH_2CH_2CH_2CO_2H$, —$NHCH_2CH_2OH$, —$NH$-phenyl, —$NHCH_2CH_2$-phenyl, —$NH$—$CH(CH_3)CH_2$-phenyl, —$NH$-(methoxyphenyl), —$NHCH_2CH_2$-(dimethoxyphenyl), —$NHCH_2CH_2$-imidazolyl, —$NHCH_2CH_2$-(methylthioimidazolyl), —$NHCH_2CH_2$-cyclohexyl, —$NH$-cyclohexyl, piperidinyl, morpholinyl, —$NHNH_2$, —$NHCH(CH_3)_2$, —$NH$-butyl, —$NH$—$CH(CH_3)(CH_2)_4CH_3$, —$NH(CH_2)_2$cyclohexenyl, —$NH$—$(CH_2)_5CH_3$, —$NHCH_2CH$=$CH_2$, —$NH$—$CH_2$-phenyl, 4-methylpiperazine, —$NHSO_2$(4-aminophenyl) or —$NH$-(4-methylpiperazine); (2) when $R^2$ is —$CH_2N(CH_2CH_3)_2$, —$CH_2NH$-butyl, —$CH_2NHCH_2CH_2$-cyclohexenyl or —$CH_2NHCH_2CH_2COOH$, X is not —$NH(CH_2)_2$cyclohexenyl; and (3) when $R^2$ is methyl, acetyl or —$COOCH_2CH_3$, X is not —$NH_2$ or —$NH(C(O)CH_3)$;

(b) when $R^1$ is ethoxy, $R^2$ is H, $R^3$ is —$COOCH_2CH_3$ and A is NH, then X is not —$NH_2$;

(c) when A is N-$C_1$-$C_6$ alkyl, $R^1$ and $R^3$ are hydrogen, halo, alkyl, alkoxy or alkylthio, then $R^2$ is not thienyl optionally substituted with 1–3 halo, hydroxy, alkyl or alkoxy radicals;

(f) when A is N—H or N—$R^4$ and $R^3$ is aryl or heteroaryl, then $R^2$ is not aryl or heteroaryl;

(g) when A is N—$R^4$, $R^1$ is H and $R^3$ is alkyl, then X is not —$NH_2$; and (h) when A is N—H or N—$R^4$ and $R^2$ is H, then $R^3$ is not optionally substituted phenyl which is substituted by —$N(R^5)$-$(C_2-C_6$ alkyl$)$—$N(R^5)_2$ or —$N(R^5)$-$(C_2-C_6$ alkyl$)$-Q.

2. A compound of claim 1 or a pharmaceutically acceptable salt, ester, solvate or N-oxide thereof, wherein A is N—H or N—$R^4$;

$R^1$ is a hydrogen, halo, —OH, —$NO_2$, —NHOH, —$CF_3$, —$OCF_3$, $(C_1-C_8)$alkyl, $(C_3-C_{10})$cycloalkyl, —$Z((C_1-C_8)$alkoxy$)$, —$Z($aryloxy$)$, —$Z($aryl$)$, —$Z($heteroaryl$)$, —$Z((C_3-C_{10})$cycloalkyl$)$, —$Z(NR^5SO_2R^5)$, —$Z(CON(R^5)_2)$, —$Z(CO_2R^5)$, —$Z(N(R^5)_2)$, —$Z(NR^5CON(R^5)_2)$, —$Z(NR^5(CO)R^5)$, —$Z(NR^5CO_2R^5)$, —$Z(COR^5)$, —$Z(S(O)_pR^5)$ or —$Z(Q)$ radical, provided $R^1$ is not an optionally substituted aryl or heteroaryl radical;

$R^2$ is a hydrogen, halo, —OH, —$NO_2$, —$CF_3$, —$OCF_3$, $(C_1-C_8)$alkyl, $(C_3-C_{10})$cycloalkyl, —$Z((C_1-C_8)$ alkoxy$)$, —$Z($aryloxy$)$, —$Z($aryl$)$, —$Z($heteroaryl$)$, —$Z((C_3-C_{10})$cycloalkyl$)$, —$Z(NR^5SO_2R^5)$, —$Z(CON(R^5)_2)$, —$Z(N(R^5)_2)$, —$Z(NR^5CON(R^5)_2)$, —$Z(NR^5(CO)R^5)$, —$Z(NR^5CO_2R^5)$, —$Z(COR^5)$, —$Z(S(O)_pR^5)$ or —$Z(Q)$ radical, provided that $R^2$ is not an optionally substituted aryl or heteroaryl radical;

$R^3$ is a $(C_3-C_{10})$cycloalkyl, $(C_1-C_8)$alkyl, -$((C_1-C_8)$alkyl$)$OH, $(C_1-C_8)$alkoxy-$(C_1-C_8)$alkyl-, -$((C_1-C_8)$alkyl$)$N$(R^5)_2$, -$((C_1-C_8)$alkyl$)$S$(O)_p((C_1-C_8)$alkyl$)$, —$(CH_2)((C_3-C_{10})$cycloalkyl$)_k(CH_2)_m$OH, —$(CH_2)_m((C_3-C_{10})$cycloalkyl$)(CH_2)_m$OH, —$(CH_2)_m((C_3-C_{10})$cycloalkyl$)_k(CH_2)$OH, —$(CH_2)((C_3-C_{10})$cycloalkyl$)_k(CH_2)_m(C_1-C_8)$alkoxy, —$(CH_2)_m((C_3-C_{10})$cycloalkyl$)(CH_2)_m(C_1-C_8)$alkoxy, —$(CH_2)_m((C_3-C_{10})$cycloalkyl$)_k(CH_2)(C_1-C_8)$alkoxy, —$(CH_2)_m((C_3-C_{10})$cycloalkyl$)_k(CH_2)_m N(R^5)_2$, —$(CH_2)_m((C_3-C_{10})$cycloalkyl$)(CH_2)_m N(R^5)_2$, —$(CH_2)_m((C_3-C_{10})$cycloalkyl$)_k(CH_2)_m N(R^5)_2$, —$(CH_2)_m((C_3-C_{10})$cycloalkyl$)(CH_2)_m S(O)_pR^5$, —D'$(S(O)_qR^5)$, —$(CH_2)_m((C_3-C_{10})$cycloalkyl$))(CH_2)_m(COR^5)$ -$((C_1-C_8)$ alkyl$)(CO_2R^5)$, -$((C_1-C_8)$alkyl$)(COR^5)$, —D'$(S(O)_qR_5)$ —D'$($aryloxy$)$, —D'$($aryl$)$, —D'$($heteroaryl$)$, —D'$((C_3-C_{10})$cycloalkyl$)$, —D'$(NR^5SO_2R^5)$, —D'$(CON(R^5)_2)$, —D'$(NR^5CON(R^5)_2)$, —D'$(NR^5(CO)R^5)$, —D'$(NR^5CO_2R^5)$, —D'$(Q)$, —D$($aryloxy$)$, —D$($aryl$)$, —D$($heteroaryl$)$, —D$((C_3-C_{10})$cycloalkyl$)$, —D$(NR^5SO_2R^5)$, —D$(CON(R^5)_2)$, or —$(NR^5)_k$—D—Q radical, provideed $R^3$ is not —$SO_2NH_2$;

$R^4$ is a $(C_1-C_8)$alkyl, $(C_3-C_{10})$cycloalkyl, —$Z((C_1-C_8)$ alkoxy$)$, —$Z($aryloxy$)$, —$Z($aryl$)$, —$Z($heteroaryl$)$, —$Z((C_3-C_{10})$cycloalkyl$)$, —$Z(NR^5SO_2R^5)$, —$Z(CON(R^5)_2)$, —$Z(CO_2R^5)$, —$Z(N(R^5)_2)$, —$Z(NR^5CON(R^5)_2)$, —$Z(NR^5(CO)R^5)$, —$Z(NR^5CO_2R^5)$, —$Z(COR^5)$, —$Z(S(O)_pR^5)$ or —$Z(Q)$ radical;

X is a —$(NR^5)_k((C_1-C_8)$alkyl$)$ $(C_1-C_8)$alkoxy, —$(NR^5)_k((C_1-C_8)$alkyl$)$aryloxy, —$(NR^5)((C_1-C_8)$ alkyl$)_kS(O)_pR^5$, —$(NR^5)_k((C_1-C_8)$alkyl$)S(O)_pR^5$, —$(NR^5)D(C_1-C_8)$alkoxy, —$(NR^5)(CH_2)_m((C_3-C_{10})$ cycloalkyl$)_k(CH_2)(C_1-C_8)$alkoxy, —$(NR^5)_k(CH_2)$ $((C_3-C_{10})$cycloalkyl$)_k(CH_2)_m(C_1-C_8)$alkoxy, —$(NR^5)_k(CH_2)_m$

221

$((C_3-C_{10})$cycloalkyl$)(CH_2)_m(C_1-C_8)$alkoxy, $-(NR^5)$ $(CH_2)_m((C_3-C_{10})$cycloalkyl$)_k(CH_2)$aryloxy, $-(NR^5)_k$ $(CH_2)((C_3-C_{10})$cycloalkyl$)_k(CH_2)_m$aryloxy, $-(NR^5)_k$ $(CH_2)_m((C_3-C_{10})$cycloalkyl$)(CH_2)_m$aryloxy, $-Z(S(O)_qR^5)$, $-Z$(aryl), $-Z$(heteroaryl), $-Z((C_3-C_{10})$cycloalkyl$)$, $-Z(NR^5SO_2R^5)$, $-Z(CON(R^5)_2)$, $-Z(CO_2R^5)$, $-Z(N(R^5)_2)$, $-Z(NR^5CON(R^5)_2)$, $-Z(NR^5(CO)R^5)$, $-Z(NR^5CO_2R^5)$, $-Z(COR^5)$ or $-Z(Q)$ radical;

Q and Q' are each independently a 4-membered to 10-membered heterocyclyl or heteroaryl radical;

each $R^5$ is independently a hydrogen, $-OH$, $(C_1-C_8)$ alkoxy, aryl, $-NH_2$, $-NH((C_1-C_8)$alkyl$)$, $-N((C_1-C_8)$alkyl$)_2$, $(C_1-C_8)$alkyl or $(C_3-C_{10})$ cycloalkyl radical;

D is $-(CH_2)_m((C_3-C_{10})$cycloalkyl$)_k(CH_2)_m-$ and D' is $-((C_1-C_8)$alkyl$)_k-$;

Z is $D(NR^5)_k$, $D'(NR^5)_k$, $(NR^5)_kD$ or $(NR^5)_kD'$;

each k is independently 0 or 1;

each m is independently an integer between 0 and 6;

each p is independently an integer between 0 and 2; and each q is independently 1 or 2; and wherein each alkyl, aryl, heteroaryl, cycloalkyl, Q, alkoxy or aryloxy moiety of any of X, $R^1$, $R^2$, $R^3$, $R^4$ and $R^5$ is optionally substituted with 1–3 radicals of halo and 1–2 radicals of $-CF_3$, $-OCF_3$, $-Z(COOH)$, $-Z(OH)$, $-Z(NO_2)$, $-Z(SH)$, $-(C_1-C_8)$alkyl, $-(C_1-C_8)$acyloxy, $-(C_3-C_{10})$cycloalkyl, $-S-((C_1-C_8)$alkyl$)_k$-aryl, $-((C_1-C_8)$alkyl$)_k-SO_2NH$-aryl, $-S-(C_1-C_8)$alkyl, $-Z((C_1-C_8)$alkoxy$)$, $-Z$(aryloxy), $-Z$(aryl), $-Z$(heteroaryl), $-Z((C_3-C_{10})$cycloalkyl$)$, $-Z(NR^9SO_2R^9)$, $-Z(CON(R^9)_2)$, $-Z(CO_2R^9)$, $-Z(N(R^9)_2)$, $-Z(NR^9CON(R^9)_2)$, $-Z(NR^9(CO)R^9)$, $-Z(NR^9CO_2R^9)$, $-Z(COR^9)$, $-Z(S(O)_pR^9)$ or $-Z(Q')$, wherein such aryl, heteroaryl, cycloalkyl and Q' substituents are optionally substituted with 1–3 radicals of halo, $-NO_2$, $-CF_3$, $-OCF_3$, $-N(R^9)_2$, $-C(O)R^9$, $-CO_2R^9$, $-OR^9$, $-SR^9$ or $(C_1-C_8)$alkyl; and wherein each $R^9$ is independently a hydrogen or $(C_1-C_8)$alkyl radical.

3. The compound of claim 2 or a pharmaceutically acceptable salt, ester, solvate or N-oxide thereof, wherein A is N—H or N—$R^4$;

$R^1$ is a hydrogen, halo, $-OH$, $-NO_2$, $-NHOH$, $-CF_3$, $-OCF_3$, $(C_1-C_8)$alkyl, $(C_3-C_6)$cycloalkyl, $-Z((C_1-C_8)$alkoxy$)$, $-Z((C_3-C_6)$cycloalkyl$)$, $-Z(NR^{10}SO_2R^5)$, $-Z(N(R^5)_2)$ or $-Z(Q)$ radical;

$R^2$ is a hydrogen, halo, $-OH$, $-NO_2$, $-CF_3$, $-OCF_3$, $(C_1-C_8)$alkyl, $(C_3-C_{10})$cycloalkyl, $-Z((C_1-C_8)$alkoxy$)$, $-Z$(aryloxy), $-Z$(aryl), $-Z$(heteroaryl), $-Z((C_3-C_{10})$cycloalkyl$)$, $-Z(NR^{10}SO_2R^5)$, $-Z(CON(R^5)_2)$, $-Z(N(R^5)_2)$, $-Z(NR^{10}CON(R^5)_2)$, $-Z(NR^{10}(CO)R^5)$, $-Z(NR^{10}CO_2R^5)$, $-Z(S(O)_pR^5)$ or $-Z(Q)$ radical, provided that $R^2$ is not an optionally substituted aryl or heteroaryl radical;

$R^3$ is a $(C_3-C_{10})$cycloalkyl, $(C_3-C_8)$alkyl, $-((C_1-C_8)$alkyl$)OH$, $(C_1-C_8)$alkoxy-$(C_1-C_8)$ alkyl-, $-((C_1-C_8)$alkyl$)N(R^5)_2$, $-((C_1-C_8)$alkyl$)S(O)_p((C_1-C_8)$alkyl$)$, $-(CH_2)_m((C_3-C_{10})$cycloalkyl$)(CH_2)_mOH$, $-(CH_2)_m((C_3-C_{10})$cycloalkyl$)(CH_2)_mOH$, $-(CH_2)_m((C_3-C_{10})$ cycloalkyl$)_k(CH_2)OH$, $-(CH_2)((C_3-C_{10})$cycloalkyl$)_k (CH_2)_m(C_1-C_8)$alkoxy, $-(CH_2)_m((C_3-C_{10})$cycloalkyl$)(CH_2)_m(C_1-C_8)$alkoxy, $-(CH_2)_m((C_3-C_{10})$cycloalkyl$)_k(CH_2)(C_1-C_8)$alkoxy, $-(CH_2)((C_3-C_{10})$cycloalkyl$)_k(CH_2)_mN(R^5)_2$, $-(CH_2)_m((C_3-C_{10})$cycloalkyl$)$

222

$(CH_2)_mN(R^5)_2$, $-(CH_2)_m((C_3-C_{10})$cycloalkyl$)_k(CH_2) N(R^5)_2$, $-(CH_2)_m((C_3-C_{10})$cycloalkyl$)(CH_2)_m S(O)_pR^5$, $-(CH_2)_m((C_3-C_{10})$cycloalkyl$)(CH_2)_m (CO_2R^5)$, $-(CH_2)_m((C_3-C_{10})$cycloalkyl$)(CH_2)_m(CO R^5)$, $-((C_1-C_8)$alkyl$)(CO_2R^5)$, $-((C_1-C_8)$alkyl$)(COR^5)$, $-D'(S(O)_qR^5)$, $-D'$(aryloxy), $-D'$(aryl), $-D'$(heteroaryl), $-D'((C_3-C_{10})$cycloalkyl$)$, $-D'(NR^{10}SO_2R^5)$, $-D'(CON(R^5)_2)$, $-D'(NR^{10}CON(R^5)_2)$, $-D'(NR^{10}(CO)R^5)$, $-D'(NR^{10}CO_2R^5)$, $-D'(Q)$, $-D$(aryloxy), $-D$(aryl), $-D$(heteroaryl), $-D((C_3-C_{10}))$cycloalkyl$)$, $-D(NR^{10}SO_2R^5)$, $-D(CON(R^5)_2)$, $-D(S(O)_qR^5)$, $-D(NR^{10}CON(R^5)_2)$, $-D(NR^{10}(CO)R^5)$, $-D(NR^{10}CO_2R^5)$ or $-(NR^{10})_k-D-Q$ radical, provided $R^3$ is not $-SO_2NH_2$;

$R^4$ is a $(C_1-C_4)$alkyl, $(C_3-C_6)$cycloalkyl, $-N(R^5)_2$ or $-Z(Q)$ radical;

X is a $-(NR^{10})((C_1-C_8)$alkyl$)(C_1-C_8)$alkoxy, $-(NR^{10})((C_1-C_8)$alkyl$)$aryloxy, $-(NR^{10})S(O)_pR^5$, $-(NR^{10})((C_1-C_8)$alkyl$)S(O)_pR^5$, $-(NR^{10})D(C_1-C_8)$alkoxy, $-(NR^{10})(CH_2)_m((C_3-C_{10})$cycloalkyl$)_k(CH_2)(C_1-C_8)$ alkoxy, $-(NR^{10})(CH_2)((C_3-C_{10})$cycloalkyl$)_k(CH_2)_m (C_1-C_8)$alkoxy, $-(NR^{10})(CH_2)_m((C_3-C_{10})$cycloalkyl$)(CH_2)_m(C_1-C_8)$alkoxy, $-(NR^{10})(CH_2)_m((C_3-C_{10})$ cycloalkyl$)_k(CH_2)$aryloxy, $-(NR^{10})(CH_2)((C_3-C_{10})$ cycloalkyl$)_k(CH_2)$aryloxy, $-(NR^{10})(CH_2)_m((C_3-C_{10})$ cycloalkyl$)(CH_2)_m$aryloxy, $-(NR^{10})D(S(O)_qR^5)$, $-(NR^{10})D'(S(O)_qR^5)$, $-(NR^{10})D$(aryl), $-(NR^{10})D'$ (aryl), $-(NR^{10})D$(heteroaryl), $-(NR^{10})D'$ (heteroaryl), $-(NR^{10})D((C_3-C_{10})$cycloalkyl$)$, $-(NR^{10})D'((C_3-C_{10})$cycloalkyl$)$, $-(NR^{10})D (NR^{10}SO_2R^5)$, $-(NR^{10})D'(NR^{10}SO_2R^5)$, $-(NR^{10})D (CON(R^5)_2)$, $-(NR^{10})D'(CON(R^5)_2)$, $-(NR^{10})D (CO_2R^5)$, $-(NR^{10})D'(CO_2R^5)$, $-(NR^{10})D(N(R^5)_2)$, $-N(R^5)_2$, $-(NR^{10})D'(N(R^5)_2)$, $-(NR^{10})D (NR^{10}CON(R^5)_2)$, $-(NR^{10})D'(NR^{10}CON(R^5)_2)$, $-(NR^{10})D(NR^{10}(CO)R^5)$, $-(NR^{10})D'(NR^{10}(CO)R^5)$, $-(NR^{10})D(NR^{10}CO_2R^5)$, $-(NR^{10})D'(NR^{10}CO_2R^5)$, $-(NR^{10})D(COR^5)$, $-(NR^{10})D'(COR^5)$, $-(NR^{10})D-Q$, $-(NR^{10})D'-Q$ or Q radical;

wherein each $R^{10}$ is independently a hydrogen or $(C_1-C_4)$ alkyl radical;

each Q and Q' are each independently a 4-membered to 10-membered heterocyclyl or heteroaryl radical;

each $R^5$ is independently a hydrogen, $-OH$, $(C_1-C_4)$ alkoxy, $-NH_2$, $-NH((C_1-C_4)$alkyl$)$, $-N((C_1-C_4)$ alkyl$)_2$, $(C_1-C_4)$alkyl or $(C_3-C_6)$cycloalkyl radical;

D is $-(CH_2)_m((C_3-C_{10})$cycloalkyl$)_k(CH_2)_m-$ and D' is $-((C_1-C_8)$alkyl$)_k-$;

Z is $D(NR^{10})_k$, $D'(NR^{10})_k$, $(NR^{10})_kD$ or $(NR^{10})_kD'$, each k is independently 0 or 1;

each m is independently an integer between 0 and 4;

each p is independently an integer between 0 and 2; and each q is independently 1 or 2; and wherein each aryl, heteroaryl, cycloalkyl, Q or aryloxy moiety of any of X, $R^1$, $R^2$, $R^3$, $R^4$ and $R^5$ is optionally substituted with 1–3 radicals of halo and 1–2 radicals of $-CF_3$, $-OCF_3$, $-OR^9$, $-SR^9$, $-NO_2$, $-(C_1-C_4)$ alkyl, $-(C_1-C_4)$acyloxy, $-(C_3-C_6)$cycloalkyl, $-S-((C_1-C_4)$alkyl$)_k$-aryl, $-((C_1-C_4)$alkyl$)_k-SO_2NH$-aryl, aryloxy, aryl, $-NR^9SO_2R^9$, $-CON(R^9)_2$, $-CO_2R^9$, $-N(R^9)_2$, $-NR^9CON(R^9)_2$, $-NR^9(CO)R^9$, $-NR^9CO_2R^9$, $-COR^9$, $-S(O)_2(C_1-C_4)$alkyl or Q', wherein such aryl, heteroaryl, cycloalkyl and Q' substituents are optionally substituted with 1–2 radicals of halo, $-NO_2$, $-CF_3$, $-OCF_3$, $-N(R^9)_2$, $-C(O)R^9$, $-CO_2R^9$, $-OR^9$, $-SR^9$ or $(C_1-C_4)$alkyl; and wherein each $R^9$ is independently a hydrogen or $(C_1-C_4)$ alkyl radical; and provided that the total number of aryl, heteroaryl, cycloalkyl, heterocyclyl, Q and Q' moieties in A, X, $R^1$, $R^2$ and $R^3$ is 0–3.

4. The compound of claim 3 or a pharmaceutically acceptable salt, ester, solvate or N-oxide thereof, wherein A is N—H or N—$R^4$;

$R^1$ is a hydrogen, halo, —OH, —$NO_2$, —NHOH, —$CF_3$, —$OCF_3$, $(C_1-C_4)$alkyl, $(C_1-C_4)$alkoxy, —$(NR^{10})_k$ $((C_1-C_2)$alkyl$)_k$-cyclopropyl or —$(NR^{10})_k((C_1-C_2)$alkyl$)_k$—$N(R^{10})_2$ radical;

$R^2$ is a hydrogen, chloro, fluoro, —$CF_3$, —$OCF_3$, $(C_1-C_4)$ alkyl, $(C_3-C_6)$cycloalkyl, —$(NR^{10})_k((C_1-C_2)$alkyl$)_k$-$(C_1-C_4)$alkoxy, —$(NR^{10})_k((C_1-C_2)$alkyl$)_k$—$(CON(R^5)_2)$, —$(NR^{10})_k((C_1-C_2)$alkyl$)_k$—$(N(R^5)_2)$, —$(NR^{10})_k((C_1-C_2)$alkyl$)_k$—$(S(O)_pR^5)$ or —$(NR^{10})_k$ $((C_1-C_2)$alkyl$)_k$—Q radical;

$R^3$ is a $(C_3-C_6)$cycloalkyl, $(C_3-C_6)$alkyl, -$((C_1-C_4)$alkyl) OH, $(C_1-C_4)$alkoxy-$(C_1-C_4)$alkyl-, -$((C_1-C_4)$alkyl)N $(R^5)_2$, —$(CH_2)(C_3-C_6)$cycloalkyl$)_k(CH_2)_m$OH, —$(CH_2)_m((C_3-C_6)$cycloalkyl$)(CH_2)_m$OH, —$(CH_2)_m$ $((C_3-C_6)$cycloalkyl$)_k(CH_2)$OH, —$(CH_2)((C_3-C_6)$ cycloalkyl$)_k(CH_2)_m(C_1-C_4)$alkoxy, —$(CH_2)_m((C_3-C_6)$ cycloalkyl$)(CH_2)_m(C_1-C_4)$alkoxy, —$(CH_2)_m((C_3-C_6)$ cycloalkyl$)_k(CH_2)(C_1-C_4)$alkoxy, —$(CH_2)((C_3-C_6)$ cycloalkyl$)_k(CH_2)_mN(R^5)_2$, —$(CH_2)_m((C_3-C_6)$ cycloalkyl$)(CH_2)_mN(R^5)_2$, —$(CH_2)_m((C_3-C_6)$ cycloalkyl$)_k(CH_2)N(R^5)_2$, —$(CH_2)_m((C_3-C_6)$ cycloalkyl$)(CH_2)_mS(O)_pR^5$, —$(CH_2)_m((C_3-C_6)$ cycloalkyl$)(CH_2)_m(CO_2R^5)$, —$(CH_2)_m((C_3-C_6)$ cycloalkyl$)(CH_2)_m(COR^5)$, —D'$(S(O)_qR^5)$, —D' (aryloxy), —D'(aryl), —D'(heteroaryl), —D'$((C_3-C_{10})$ cycloalkyl), —D'(Q), —D(aryloxy), —D(aryl), —D(heteroaryl), —D$(NR^{10}SO_2R^5)$, —D$(CON(R^5)_2)$, —D$(S(O)_qR^5)$, —D$(NR^{10}CON(R^5)_2)$, —D$(NR^{10}(CO)$ $R^5)$, —D$(NR^{10}CO_2R^5)$ or —$(NR^{10})_k$—D—Q radical, provided $R^3$ is not —$SO_2NH_2$;

$R^4$ is a $(C_1-C_4)$alkyl radical;

X is a —$(N((C_1-C_4)$alkyl$))$-$((C_1-C_4)$alkyl)aryloxy, —$(N$ $((C_1-C_4)$alkyl$))$—$(CH_2)_m((C_3-C_6)$cycloalkyl$)_k(CH_2)$ $(C_1-C_4)$alkoxy, —$(N((C_1-C_4)$alkyl$))$—$(CH_2)((C_3-C_6)$ cycloalkyl$)_k(CH_2)_m(C_1-C_4)$alkoxy, —$(N((C_1-C_4)$ alkyl$))$—$(CH_2)_m((C_3-C_6)$cycloalkyl$)(CH_2)_m(C_1-C_4)$ alkoxy, —$(N((C_1-C_4)$alkyl$))$—$(CH_2)_m((C_3-C_6)$ cycloalkyl$)_k(CH_2)$aryloxy, —$(N((C_1-C_4)$alkyl$))$— $(CH_2)((C_3-C_6)$cycloalkyl$)_k(CH_2)_m$aryloxy, —$(N$ $((C_1-C_4)$alkyl$))$—$(CH_2)_m(C_3-C_6)$cycloalkyl$)$ $(CH_2)_m$aryloxy, —$(N((C_1-C_4)$alkyl$))$-D(aryl), —$(N$ $((C_1-C_4)$alkyl$))$-D'(aryl), —$(N((C_1-C_4)$alkyl$))$-D (heteroaryl), —$(N((C_1-C_4)$alkyl$))$-D'(heteroaryl), —$(N$ $((C_1-C_4)$alkyl$))$-D$(NR^{10}SO_2R^5)$, —$(N((C_1-C_4)$alkyl$))$- D$(CON(R^5)_2)$, —$(N((C_1-C_4)$alkyl$))$-D$(CO_2R^5)$, —$(N$ $((C_1-C_4)$alkyl$))$-D$(N(R^5)_2)$, —$N(R^5)_2$, —$(N((C_1-C_4)$ alkyl$))$-D$(NR^{10}CON(R^5)_2)$, —$(N((C_1-C_4)$alkyl$))$-D $(NR^{10}(CO)R^5)$, —$(N((C_1-C_4)$alkyl$))$-D$(NR^{10}CO_2R^5)$, —$(N((C_1-C_4)$alkyl$))$-D$(COR^5)$, —$(N((C_1-C_4)$alkyl$))$- D—Q, —$(N((C_1-C_4)$alkyl$))$-D'—Q or Q radical;

wherein each $R^{10}$ is independently a hydrogen or $(C_1-C_4)$ alkyl radical;

each Q is independently a 4-membered to 10-membered heterocyclyl or heteroaryl radical;

each $R^5$ is independently a hydrogen, —OH, $(C_1-C_4)$ alkoxy, —$NH_2$, —$NH((C_1-C_4)$alkyl), —$N((C_1-C_4)$ alkyl$)_2$ or $(C_1-C_4)$alkyl radical;

D is —$(CH_2)_m((C_3-C_6)$cycloalkyl$)_k(CH_2)_m$— and D' is -$((C_1-C_4)$alkyl$)_k$-;

Z is $(NR^{10})_k$D or $(NR^{10})_k$D';

each k is independently 0 or 1;

each m is independently an integer between 0 and 3;

each p is independently an integer between 0 and 2; and each q is independently 1 or 2; and wherein each aryl, heteroaryl, cycloalkyl, Q or aryloxy moiety of any of X, $R^2$ and $R^3$ is optionally substituted with 1–2 radicals of halo, —$CF_3$, —$OCF_3$, —$OR^9$, —$SR^9$, —$NO_2$, $(C_1-C_4)$alkyl, $(C_1-C_4)$acyloxy, —$NR^9SO_2R^9$, —$CON(R^9)_2$, —$CO_2R^9$, —$N(R^9)_2$, —$NR^9CON(R^9)_2$, —$NR^9(CO)R^9$, —$NR^9CO_2R^9$, —$COR^9$ or —$S(O)_2(C_1-C_4)$alkyl; and wherein each $R^9$ is independently a hydrogen or $(C_1-C_4)$alkyl radical; and provided that the total number of aryl, heteroaryl, cycloalkyl, heterocyclyl and Q moieties in A, X, $R^1$, $R^2$ and $R^3$ is 1–3.

5. The compound of claim 4 or a pharmaceutically acceptable salt, ester, solvate or N-oxide thereof, wherein A is N—H;

$R^1$ is a bromo, chloro, fluoro, —OH, —$NO_2$, —NHOH, —$CF_3$, —$OCF_3$, $(C_1-C_2)$alkyl, $(C_1-C_2)$alkoxy, —$(NR^{10})_k((C_1-C_2)$alkyl$)_k$-cyclopropyl, —$NH_2$ or —$NH((C_1-C_2)$alkyl) radical;

$R^2$ is a hydrogen, chloro, fluoro, —$CF_3$, —$OCF_3$, $(C_1-C_2)$ alkyl or $(C_1-C_2)$alkoxy radical;

$R^3$ is a $(C_3-C_6)$cycloalkyl, $(C_3-C_6)$alkyl, -$((C_1-C_4)$alkyl) OH, $(C_1-C_4)$alkoxy-$(C_1-C_4)$alkyl-, -$((C_1-C_4)$alkyl)N $(R^5)_2$, —$(CH_2)(C_5-C_6)$cycloalkyl$)_k(CH_2)_m$OH, —$(CH_2)_m((C_5-C_6)$cycloalkyl$)(CH_2)_m$OH, —$(CH_2)_m$ $((C_5-C_6)$cycloalkyl$)_k(CH_2)$OH, —$(CH_2)((C_5-C_6)$ cycloalkyl$)_k(CH_2)_m(C_1-C_2)$alkoxy, —$(CH_2)_m((C_3-C_6)$ cycloalkyl$)(CH_2)_m(C_1-C_2)$alkoxy, —$(CH_2)_m((C_5-C_6)$ cycloalkyl$)_k(CH_2)(C_1-C_2)$alkoxy, —$(CH_2)((C_5-C_6)$ cycloalkyl$)_k(CH_2)_mN(R^5)_2$, —$(CH_2)_m((C_5-C_6)$ cycloalkyl$)(CH_2)_mN(R^5)_2$, —$(CH_2)_m((C_5-C_6)$ cycloalkyl$)_k(CH_2)N(R^5)_2$, —$(CH_2)_m((C_5-C_6)$ cycloalkyl$)(CH_2)_mS(O)_pR^5$, —$(CH_2)_m((C_5-C_6)$ cycloalkyl$)(CH_2)_m(CO_2R^5)$, —$(CH_2)_m((C_5-C_6)$ cycloalkyl$)(CH_2)_m(COR^5)$, —D'$(S(O)_qR^5)$, —D' (aryloxy), —D'(aryl), —D'(heteroaryl), —D'$((C_3-C_6)$ cycloalkyl), —D'(Q), —D(aryloxy), —D(aryl), —D(heteroaryl), —D$(NR^{10}SO_2R^5)$, —D$(CON(R^5)_2)$, —D$(S(O)_qR^5)$, —D$(NR^{10}CON(R^5)_2)$, —D$(NR^{10}(CO)$ $R^5)$, —D$(NR^{10}CO_2R^5)$ or —$(NR^{10})_k$—D—Q radical, provided $R^3$ is not —$SO_2NH_2$;

X is a —$N((C_1-C_4)$alkyl$)_2$ or Q radical;

wherein each $R^{10}$ is independently a hydrogen or $(C_1-C_2)$ alkyl radical;

each Q is independently a 4-membered to 10-membered heterocyclyl or heteroaryl radical;

each $R^5$ is independently a hydrogen, —OH, $(C_1-C_2)$ alkoxy, —$NH_2$, —$NH((C_1-C_2)$alkyl), —$N((C_1-C_2)$ alkyl$)_2$ or $(C_1-C_2)$alkyl radical;

D is —$(CH_2)_m((C_5-C_6)$cycloalkyl$)_k(CH_2)_m$— and D' is -$((C_1-C_4)$alkyl$)_k$-;

Z is $(NR^{10})_k$D or $(NR^{10})_k$D';

each k is independently 0 or 1;

each m is independently an integer between 0 and 2;

each p is independently an integer between 0 and 2; and each q is independently 1 or 2; and wherein each aryl, heteroaryl, cycloalkyl, Q or aryloxy moiety of any of X, $R^2$ and $R^3$ is optionally substituted with 1–2 radicals of halo, —CF₃, —OCF₃, —OR⁹, —SR⁹, —NO₂, (C₁–C₄)alkyl, (C₁–C₄)acyloxy, —NR⁹SO₂R⁹, —CON(R⁹)₂, —CO₂R⁹, —N(R⁹)₂, —NR⁹CON(R⁹)₂, —NR⁹(CO)R⁹, —NR⁹CO₂R⁹, —COR⁹ or —S(O)₂(C₁–C₄)alkyl; and wherein each R⁹ is independently a hydrogen or (C₁–C₂)alkyl radical; and provided that the total number of aryl, heteroaryl, cycloalkyl, heterocyclyl and Q moieties in A, X, R¹, R² and R³ is 1–3.

6. The compound of claim 1 which is:

2-Methyl-6-phenyl-4-(2-1,2,3,4-tetrahydroquinolino-2-yl)pyrrolo[3,2-d]pyrimidine;

(S)-[1-(2-methyl-6-phenylpyrrolo[2,3-e]pyrimidin-4-yl)pyrrolidin-2-yl]methan-1-ol;

1-(2-methyl-6-phenylpyrrolo[2,3-e]pyrimidin-4-yl)pyrrolidin-3-ol;

4-Homopiperidyl-2-methyl-6-phenylpyrrolo[3,2-d]pyrimidine;

2-Methyl-6-phenyl-4-pyrrolidinylpyrrolo[3,2-d]pyrimidine;

2-Methyl-6-(4-methylphenyl)-4-piperidylpyrrolo[3,2-d]pyrimidine;

Dimethyl[1-(2-methyl-6-phenylpyrrolo[2,3-e]pyrimidin-4-yl)(4-piperidyl)]amine;

Dimethyl{[1-(2-methyl-6-phenylpyrrolo[2,3-e]pyrimidin-4-yl)(2-piperidyl)]methyl}amine;

2-Isopropyl-6-phenyl-4-piperidylpyrrolo[3,2-d]pyrimidine;

cis/trans-4-(3,5-dimethylpiperidinyl)-2-methyl-6-phenylpyrrolo[3,2-d]pyrimidine;

[1-(2-methyl-6-phenylpyrrolo[2,3-e]pyrimidin-4-yl)-3-piperidyl]methan-1-ol;

2,5-Dimethyl-6-phenyl-4-piperidylpyrrolo[3,2-d]pyrimidine;

2-(2-Methyl-6-phenylpyrrolo[2,3-e]pyrimidin-4-yl)thiophene;

2-Methyl-6-phenyl-4-(3-pyridinyl)pyrrolo[3,2-d]pyrimidine;

2-(2-Methyl-6-phenylpyrrolo[2,3-e]pyrimidin-4-yl)-1,3-thiazole;

2-Methyl-4-(2-methylpyrrolidin-1-yl)-6-phenylpyrrolo[3,2-d]pyrimidine;

2-Methyl-6-phenyl-4-(pyrrolinyl)pyrrolo[3,2-d]pyrimidine;

2-Methyl-6-phenyl-4-(2-piperidineethanolyl)pyrrolo[3,2-d]pyrimidine;

2-Methyl-6-phenyl-4-(2-methylpiperidinyl)pyrrolo[3,2-d]pyrimidine;

2-Methyl-6-phenyl-4-(2-ethylpiperidinyl)pyrrolo[3,2-d]pyrimidine;

2-Methyl-6-phenyl-4-(1,2,3,6-tetrahydropyridinyl)pyrrolo[3,2-d]pyrimidine;

6-Phenyl-4-piperidylpyrrolo[3,2-d]pyrimidine-2-ylamine;

2-Methylthio-6-phenyl-4-piperidylpyrrolo[3,2-d]pyrimidine;

2-Ethyl-6-phenyl-4-piperidylpyrrolo[3,2-d]pyrimidine;

2-Cyclopropyl-6-phenyl-4-piperidylpyrrolo[3,2-d]pyrimidine;

6-(3-Chlorophenyl)-2-methyl-4-piperidylpyrrolo[3,2-d]pyrimidine;

4-Methoxy-1-(2-methyl-4-piperidylpyrrolo[4,5-d]pyrimidin-6-yl)benzene;

4-(2-Methyl-4-piperidylpyrrolo[4,5-d]pyrimidin-6-yl)phenol;

6-(4-Fluorophenyl)-2-methyl-4-piperidylpyrrolo[3,2-d]pyrimidine;

4-Azetidinyl-2-methyl-6-phenylpyrrolo[3,2-d]pyrimidine;

2-(2-Methyl-4-piperidylpyrrolo[4,5-d]pyrimidin-6-yl)thiophene;

2-Methyl-4-piperidyl-6-(2-pyridyl)pyrrolo[3,2-d]pyrimidine;

6-Adamantanyl-2-methyl-4-piperidylpyrrolo[3,2-d]pyrimidine;

2-Methyl-4-piperidyl-6-pyrazin-2-ylpyrrolo[3,2-d]pyrimidine;

2-(2-Methyl-4-piperidylpyrrolo[4,5-d]pyrimidin-6-yl)benzo[b]furan;

2,7-Dimethyl-6-phenyl-4-piperidylpyrrolo[3,2-d]pyrimidine;

6-Phenyl-4-piperidyl-2-(trifluoromethyl)pyrrolo[3,2-d]pyrimidine;

6-(4-Chlorophenyl)-2-methyl-4-piperidylpyrrolo[3,2-d]pyrimidine;

(6-Phenyl-4-piperidylpyrrolo[3,2-d]pyrimidine-2-yl) propylamine;

6-(tert-Butyl)-2-methyl-4-piperidylpyrrolo[3,2-d]pyrimidine;

2-Methyl-6-(2-methylcyclopent-1-eneyl)-4-piperidylpyrrolo[3,2-d]pyrimidine;

2,5-Dimethyl-3-(2-methyl-4-piperidylpyrrolo[4,5-d]pyrimidin-6-yl)thiophene;

2-Methyl-6-(4-phenylphenyl)-4-piperidylpyrrolo[3,2-d]pyrimidine;

3-(2-Methyl-4-piperidylpyrrolo[4,5-d]pyrimidin-6-yl)-1-(phenylsulfonyl)pyrrole;

6-(2-Fluorophenyl)-2-methyl-4-piperidylpyrrolo[3,2-d]pyrimidine;

6-(3-Fluorophenyl)-2-methyl-4-piperidylpyrrolo[3,2-d]pyrimidine;

2-Methyl-6-phenyl-4-(4-phenylpiperazinyl)pyrrolo[3,2-d]pyrimidine;

2-Methyl-4-piperidyl-6-(3-(trifluoromethyl)phenyl)pyrrolo[3,2-d]pyrimidine;

6-(2,6-Difluorophenyl)-2-methyl-4-piperidylpyrrolo[3,2-d]pyrimidine;

6-(2,5-Difluorophenyl)-2-methyl-4-piperidylpyrrolo[3,2-d]pyrimidine;

2-Methyl-4-piperidyl-6-(4-(trifluoromethyl)phenyl)pyrrolo[3,2-d]pyrimidine;

2-Methyl-4-piperidyl-6-(2,3,4-trichlorophenyl)pyrrolo[3,2-d]pyrimidine;

5-[2-Methyl-4-piperidylpyrrolo[4,5-d]pyrimidin-6-yl]-2H-benzo[d]1,3-dioxolane;

2-Methyl-4-piperidyl-6-(3,4,5-trifluorophenyl)pyrrolo[3,2-d]pyrimidine;

6-(3,5-Difluorophenyl)-2-methyl-4-piperidylpyrrolo[3,2-d]pyrimidine;

6-(3,4-Dichlorophenyl)-2-methyl-4-piperidylpyrrolo[3,2-d]pyrimidine;

2-Fluoro-1-methoxy-4-[2-methyl-4-piperidylpyrrolo[4,5-d]pyrimidin-6-yl]benzene;

2-Fluoro-4-[2-methyl-4-pyridylpyrrolo[4,5-d]pyrimidin-6-yl]phenol;

6-((3,5-bis(Trifluoromethyl)phenyl)-2-methyl-4-piperidylpyrrolo[3,2-d]pyrimidine;

Trifluoro[4-(2-methyl-4-piperidylpyrrolo[4,5-d]pyrimidin-6-yl)phenylthio]methane;

6-(3,4-Dimethylphenyl)-2-methyl-4-piperidylpyrrolo[3,2-d]pyrimidine;

6-(2-Methyl-4-piperidylpyrrolo[4,5-d]pyrimidin-6-yl)-2H,3H-benzo[e]1,4-dioxane;

1,2-Dimethoxy-4-(2-methyl-4-piperidylpyrrolo[4,5-d]pyrimidin-6-yl)benzene;

6-Fluoren-2-yl-2-methyl-4-piperidylpyrrolo[3,2-d]pyrimidine;

2-Methyl-4-piperidyl-6-(2–5,6,7,8-tetrahydronaphthyl)pyrrolo[3,2-d]pyrimidine;

2-Methyl-6-(5-methyl-1-phenylpyrazol-4-yl)-4-piperidyl pyrrolo[3,2-d]pyrimidine;

6-Indan-5-yl-2-methyl-4-piperidylpyrrolo[3,2-d]pyrimidine;

5-[2-Methyl-4-piperidylpyrrolo[4,5-d]pyrimidin-6-yl]-2,3-dihydrobenzo[b]furan;

2,4-Dimethyl-5-[2-methyl-4-piperidylpyrrolo[4,5-d]pyrimidin-6-yl]-1,3-thiazole;

2,7-Dimethyl-4-piperidyl-6-((4-trifluoromethyl)phenyl)pyrrolo[3,2-d]pyrimidine;

6-(4-Fluorophenyl)-2,7-dimethyl-4-piperidylpyrrolo[3,2-d]pyrimidine;

6-(3,4-Dichlorophenyl)-2,7-dimethyl-4-piperidyl pyrrolo[3,2-d]pyrimidine;

1-(2,7-Dimethyl-4-piperidylpyrrolo[4,5-d]pyrimidin-6-yl)-4-methoxybenzene;

4-(2,7-Dimethyl-4-piperidylpyrrolo[4,5-d]pyrimidin-6-yl)phenol;

6-(3,5-Difluorophenyl)-2,7-dimethyl-4-piperidyl pyrrolo[3,2-d]pyrimidine;

1-(2,7-Dimethyl-4-piperidylpyrrolo[4,5-d]pyrimidin-6-yl)-3-methoxybenzene;

4-(6-(3,4-Difluorophenyl)-2-methylpyrrolo[2,3-e]pyrimidin-4-yl)morpholine;

1-(2-Methyl-4-piperidylpyrrolo[4,5-d]pyrimidin-6-yl)-4-(methylsulfonyl)benzene;

1,2,3-Trimethoxy-5-(2-methyl-4-piperidylpyrrolo[4,5-d]pyrimidin-6-yl)benzene;

7-Ethyl-2-methyl-6-phenyl-4-piperidylpyrrolo[3,2-d]pyrimidine;

5-(3-Chloro-4-fluorophenyl)-2-(2-methyl-4-piperidylpyrrolo[4,5-d]pyrimidin-6-yl)furan;

6-(4-Fluorophenyl)-2-methyl-4-(2-methylpiperidyl)pyrrolo[3,2-d]pyrimidine;

6-Butyl-2-methyl-4-piperidylpyrrolo[3,2-d]pyrimidine;

2,6-Dimethyl-4-piperidyl-7-propylpyrrolo[3,2-d]pyrimidine;

1-(4-(2-Methyl-4-piperidylpyrrolo[4,5-d]pyrimidin-6-yl)phenyl)ethan-1-one;

7-Fluoro-2-methyl-6-piperidylpyrrolo[3,2-d]pyrimidine;

2-Methyl-6-phenyl-4-piperidyl-7-pyrrolidinyl pyrrolo[3,2-d]pyrimidine;

3-Methyl-2-(2-methyl-4-piperidylpyrrolo[4,5-d]pyrimidin-6-yl)benzo[b]thiophene;

4-Chloro-1-(((2-methyl-4-piperidylpyrrolo[4,5-d]pyrimidin-6-yl)methyl)sulfonyl)benzene;

4-Methoxy-1-((2-methyl-4-piperidylpyrrolo[4,5-d]pyrimidin-6-yl)methyl)benzene;

1-(2,6-Dimethyl-4-piperidylpyrrolo[3,2-d]pyrimidin-7-yl)-4-methoxybenzene;

2-Methyl-6-(2-naphthyl)-4-piperidylpyrrolo[3,2-d]pyrimidine;

3,5-Dimethyl-2-(2-methyl-4-piperidylpyrrolo[4,5-d]pyrimidin-6-yl)benzo[b]thiophene;

7-Methoxy-2-(2-methyl-4-piperidylpyrrolo[4,5-d]pyrimidin-6-yl)benzo[b]furan;

6-((4-Fluorophenyl)methyl)-2-methyl-4-piperidyl pyrrolo[3,2-d]pyrimidine;

7-(4-Fluorophenyl)-2,6-dimethyl-4-piperidylpyrrolo[3,2-d]pyrimidine;

((2-Methyl-4-piperidylpyrrolo[4,5-d]pyrimidin-6-yl)methoxy)benzene;

2,6-Dimethyl-7-phenoxy-4-piperidylpyrrolo[3,2-d]pyrimidine;

2-Methyl-6-(2-phenylethyl)-4-piperidylpyrrolo[3,2-d]pyrimidine;

2,6-Dimethyl-7-benzyl-4-piperidylpyrrolo[3,2-d]pyrimidine;

5-(2,7-Dimethyl-4-piperidylpyrrolo[4,5-d]pyrimidin-6-yl)-2H-benzo[d]1,3-dioxolane;

6-(3,4-Difluorophenyl)-2,7-dimethyl-4-piperidylpyrrolo[3,2-d]pyrimidine;

1-(2-Methyl-6-phenylpyrrolo[2,3-e]pyrimidine-4-yl)piperidin-3-ol;

1-(2-Methyl-6-phenylpyrrolo[2,3-e]pyrimidine-4-yl)piperidin-4-ol;

8-Aza-8-(2-Methyl-6-phenylpyrrolo[2,3-e]pyrimidine-4-yl)-1,4-dioxaspiro[4,5]decane;

1-(2-Methyl-6-phenylpyrrolo[2,3-e]pyrimidine-4-yl)-4-(3-(trifluoromethyl)phenyl)piperidin-4-ol;

1-(2-Methyl-6-phenylpyrrolo[2,3-e]pyrimidine-4-yl)piperidin-2-one;

2-Methyl-6-phenyl-4-piperidylpyrrolo[3,2-d]pyrimidin-1-ol;

4-((6S,2R)-2,6-Dimethyl)-2-methyl-6-phenylpyrrolo[3,2-d]pyrimidine;

3-(2-Methyl-4-piperidylpyrrolo[4,5-d]pyrimidin-6-yl)phenylamine;

4-(2-Methyl-4-piperidylpyrrolo[4,5-d]pyrimidin-6-yl)phenylamine;

1-(2-Methyl-6-phenylpyrrolo[2,3-e]pyrimidin-4-yl)-4-naphthylsulfonyl)piperazine;

2-Methyl-6-phenyl-4-pyrrolidinylpyrrolo[3,2-d]pyrimidine;

Trifluoro(4-(2-methyl-4-piperidylpyrrolo[4,5-d]pyrimidin-6-yl)phenoxy)methane;

6-Phenyl-4-piperidyl-2-propylpyrrolo[3,2-d]pyrimidine;

2-Methyl-4-(3-pyrrolinyl)-6-(3-(trifluoromethyl)phenyl)pyrrolo[3,2-d]pyrimidine;

6-(3-Chlorophenyl)-2-methyl-4-(3-pyrrolinyl)pyrrolo[3,2-d]pyrimidine;

6-(4-Fluorophenyl)-2-methyl-4-(3-pyrrolinyl)pyrrolo[3,2-d]pyrimidine;

6-Phenyl-4-piperidyl)pyrrolo[3,2-d]pyrimidine-2-yl hydroxylamine;

6-(3,4-Dichlorophenyl)-2-methyl-4-(3-pyrrolinyl)pyrrolo[3,2-d]pyrimidine;

2-(2-Methylpropyl)-6-phenyl-4-piperidylpyrrolo[3,2-d]pyrimidine;

2-Ethyl-6-phenyl-4-(2-1,2,3,4-tetrahydroisoquinolyl)pyrrolo[3,2-d]pyrimidine;

2-Chloro-6-phenyl-4-piperidylpyrrolo[3,2-d]pyrimidine;

Dimethyl(6-phenyl-4-piperidylpyrrolo[3,2-d]pyrimidin-2-yl)amine;

2-Methoxy-6-phenyl-4-piperidylpyrrolo[3,2-d]pyrimidine;

Methyl(6-phenyl-4-piperidylpyrrolo[3,2-d]pyrimidin-2-yl)amine;

6-Phenyl-2-(4-phenylpiperazinyl)-4-piperidylpyrrolo[3,2-d]pyrimidine;

2-Cyclopropyl-6-(4-fluorophenyl)-4-piperidylpyrrolo[3,2-d]pyrimidine;

4-(2-Methyl-4-piperidylpyrrolo[4,5-d]pyrimidin-6-yl)phenyl 2,2-dimethylpropanoate;

7-Bromo-2-methyl-6-phenyl-4-piperidylpyrrolo[3,2-d]pyrimidine;

4-(8-azabicyclo[3.2.1]oct-8-yl)-2-methyl-6-phenyl pyrrolo[3,2-d]pyrimidine;

(1-[2-Methyl-6-phenylpyrrolo[2,3-e]pyrimidin-4-yl)-2-piperidyl)methan-1-ol;

4-Indolinyl-2-methyl-6-phenylpyrrolo[3,2-d]pyrimidine;

2-Methyl-6-phenyl-4-pyrazolypyrrolo[3,2-d]pyrimidine;

2-Methyl-6-phenyl-4-[1,2,4-triazolyl]pyrrolo[3,2-d]pyrimidine;

4-(2,5-Dimethyl(3-pyrrolinyl)-2-methyl-6-phenyl pyrrolo[3,2-d]pyrimidine;

1-(2-Furanylcarbonyl)-4-(2-methyl-6-phenylpyrrolo[2,3-e]pyrimidin-4-yl)piperazine;

1-Acetyl-4-(2-methyl-6-phenylpyrrolo[2,3-e]pyrimidin-4-yl)piperazine;

1-(2-Methyl-6-phenylpyrrolo[2,3-e]pyrimidin-4-yl)-4-(methylsulfonyl)piperazine;

1-(2-Methyl-6-phenylpyrrolo[2,3-e]pyrimidin-4-yl(phenylsulfonyl)piperazine;

(7-Aminoheptyl)-(6-phenyl-4-piperidylpyrrolo[3,2-d]pyrimidin-2-yl)amine; or (4-Aminobutyl)-(6-phenyl-4-piperidylpyrrolo[3,2-d]pyrimidin-2-yl)amine; or a pharmaceutically acceptable salt thereof.

7. A pharmaceutical composition comprising a compound according to any of claims 1 to 6 and a pharmaceutically acceptable carrier.

8. A method for modulating feeding behavior which comprises administering to a warm blood animal an effective amount of a compound according to any of claims 1 to 6.

9. A method for the prophylaxis or treatment of obesity which comprises administering to a warm blood animal an effective amount of a compound according to any of claims 1 to 6.

10. A method for the prophylaxis or treatment of diabetes which comprises administering to a warm blood animal an effective amount of a compound according to any of claims 1 to 6.

11. A method for the prophylaxis or treatment of a tumor disease in a warm blooded animal comprising administering to the warm blooded animal an effective amount of a compound according to any of claims 1 to 6.

12. A method for the prophylaxis or treatment of an inflammatory disease or disorder comprising administering to the warm blood animal an effectivv amount of a compound according to any of claims 1 to 6.

13. A method for the prophylaxis or treatment of a diseases or disorder which can be effected or facilitated by modulating CRF in a warm blooded animal comprising administering to the warm blood animal an effective amount of a compound according to any of claims 1 to 6.

14. The method of claim 13 wherein the disease or disorder is rheumatoid arthritis; osteoarthritis; pain; asthma; psoriasis; allergies; generalized anxiety disorder; panic; phobias; obsessive-compulsive disorder; post-traumatic stress disorder; sleep disorders; stress-induced psychotic episodes; pain perception; fibromyalgia; mood disorders; depression; dysthemia; bipolar disorders; cyclothymia; chronic fatigue syndrome; stress-induced headache; cancer; irritable bowel syndrome; Crohn's disease; spastic colon; post operative ileus; ulcer; diarrhea; fever; human immunodeficiency virus (HIV) infections; neurodegenerative diseases; Alzheimer's disease; Parkinson's disease; Huntington's disease; gastrointestinal diseases; eating disorders; anorexia; bulimia nervosa; hemorrhagic stress; chemical dependencies; addictions; drug or alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage; excitotoxic neuronal damage; epilepsy; stroke; immune dysfunctions; muscular spasms; urinary incontinence; senile dementia of the Alzheimer's type; multiinfarct dementia; amyotrophic lateral sclerosis; hypertension; tachycardia; congestive heart failure; osteoporosis; premature birth; hypoglycemia; diarrhea; or colonic hypersensitivity.

15. A method for modulating feeding behavior, obesity or diabetes, or another disease state associated with the same or related pathway which modulates feeding behavior, obesity or diabetes which comprises administering to a warm blood animal an effective amount of a compound of formula

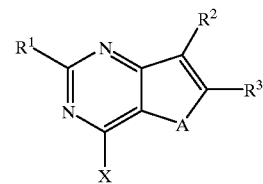

or a pharmaceutically acceptable salt, ester, solvate or N-oxide thereof, wherein A is N—H or N—R$^4$;

R$^1$ and X are each independently a hydrogen, halo, —OH, —NO$_2$, —NHOH, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical;

R$^2$ and R$^3$ are each independently a hydrogen, halo, —OH, —NO$_2$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q); provided R$^2$ is not an optionally substituted aryl or heteroaryl radical;

R$^4$ is a hydrogen, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical;

each R$^5$ is independently a hydrogen, —OH, (C$_1$–C$_8$) alkoxy, aryl, —NH$_2$, —NH((C$_1$–C$_8$)alkyl), —N((C$_1$–C$_8$)alkyl)$_2$, (C$_1$–C$_8$)alkyl or (C$_3$–C$_{10}$) cycloalkyl radical;

Q and Q' are each independently a 4-membered to 10-membered heterocyclyl or heteroaryl radical;

Z is D(NR$^5$)$_k$, D'(NR$^5$)$_k$, (NR$^5$)$_k$D or (NR$^5$)$_k$D';

D is —(CH$_2$)$_m$((C$_3$–C$_{10}$)cycloalkyl)$_k$(CH$_2$)$_m$—; and D' is -((C$_1$–C$_8$)alkyl)$_k$-;

each k is independently 0 or 1;

each m is independently an integer between 0 and 6;

each p is independently an integer between 0 and 2; and each q is independently 1 or 2; and wherein each alkyl, aryl, heteroaryl, cycloalkyl, Q, alkoxy or aryloxy moiety of any of X, R$^1$, R$^2$, R$^3$, R$^4$ and R$^5$ is optionally substituted with 1–3 radicals of halo and 1–2 radicals of —CF$_3$, —OCF$_3$, —Z(COOH), —Z(OH), —Z(NO$_2$), —Z(SH), -(C$_1$–C$_8$)alkyl, -(C$_1$–C$_8$)acyloxy, -(C$_3$–C$_{10}$)cycloalkyl, —S-((C$_1$–C$_8$)alkyl)$_k$-aryl, -((C$_1$–C$_8$)alkyl)$_k$—SO$_2$NH-aryl, —S-(C$_1$–C$_8$)alkyl, —Z((C$_1$–C$_8$)alkoxy), —Z(aryloxy), —Z(aryl), —Z(heteroaryl), —Z((C$_3$–C$_{10}$)cycloalkyl), —Z(NR$^9$SO$_2$R$^9$), —Z(CON(R$^9$)$_2$), —Z(CO$_2$R$^9$), —Z(N(R$^9$)$_2$), —Z(NR$^9$CON(R$^9$)$_2$), —Z(NR$^9$(CO)R$^9$), —Z(NR$^9$CO$_2$R$^9$), —Z(COR$^9$), —Z(S(O)$_p$R$^9$) or —Z(Q'), wherein such aryl, heteroaryl, cycloalkyl and Q' substitutents are optionally substituted with 1–3 radicals of halo, —NO$_2$, —CF$_3$, —OCF$_3$, —N(R$^9$)$_2$, —C(O)R$^9$, —CO$_2$R$^9$, —OR$^9$, —SR$^9$ or (C$_1$–C$_8$)alkyl; and wherein each R$^9$ is independently a hydrogen or (C$_1$–C$_8$)alkyl radical; and provided that the total number of aryl, heteroaryl, cycloalkyl, heterocyclyl, Q and Q' moieties in A, X, R$^1$, R$^2$ and R$^3$ is 0–4.

16. The method of claim 15, wherein A is N—H or N—R$^4$;

R$^1$ is a hydrogen, halo, —OH, —NO$_2$, —NHOH, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical, provided R$^1$ is not an optionally substituted aryl or heteroaryl radical;

R$^2$ is a hydrogen, halo, —OH, —NO$_2$, —CF$_3$, —OCF$_3$, (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical, provided that R$^2$ is not an optionally substituted aryl or heteroaryl radical;

R$^3$ is a (C$_3$–C$_{10}$)cycloalkyl, (C$_1$–C$_8$)alkyl, -((C$_1$–C$_8$)alkyl)OH, (C$_1$–C$_8$)alkoxy-(C$_1$–C$_8$)alkyl-, -((C$_1$–C$_8$)alkyl)N(R$^5$)$_2$, -((C$_1$–C$_8$)alkyl)S(O)$_p$((C$_1$–C$_8$)alkyl), —(CH$_2$)((C$_3$–C$_{10}$)cycloalkyl)$_k$(CH$_2$)$_m$OH, —(CH$_2$)$_m$((C$_3$–C$_{10}$)cycloalkyl)(CH$_2$)$_m$OH, —(CH$_2$)$_m$((C$_3$–C$_{10}$)cycloalkyl)$_k$(CH$_2$)OH, —(CH$_2$)((C$_3$–C$_{10}$)cycloalkyl)$_k$(CH$_2$)$_m$(C$_1$–C$_8$)alkoxy, —(CH$_2$)$_m$((C$_3$–C$_{10}$)cycloalkyl) (CH$_2$)$_m$(C$_1$–C$_8$)alkoxy, —(CH$_2$)$_m$((C$_3$–C$_{10}$)cycloalkyl)$_k$(CH$_2$)(C$_1$–C$_8$)alkoxy, —(CH$_2$)((C$_3$–C$_{10}$)cycloalkyl)$_k$(CH$_2$)$_m$N(R$^5$)$_2$, —(CH$_2$)$_m$((C$_3$–C$_{10}$)cycloalkyl) (CH$_2$)$_m$N(R$^5$)$_2$, —(CH$_2$)$_m$((C$_3$–C$_{10}$)cycloalkyl)$_k$(CH$_2$)N(R$^5$)$_2$, —(CH$_2$)$_m$((C$_3$–C$_{10}$)cycloalkyl)(CH$_2$)$_m$S(O)$_p$R$^5$, —D'(S(O)$_q$R$^5$), —D'(aryloxy), —D'(aryl), —D'(heteroaryl), —D'((C$_3$–C$_{10}$)cycloalkyl), —D'(NR$^5$SO$_2$R$^5$), —D'(CON(R$^5$)$_2$), —D'(CO$_2$R$^5$), —D'(NR$^5$CON(R$^5$)$_2$), —D'(NR$^5$(CO)R$^5$), —D'(NR$^5$CO$_2$R$^5$), —D'(COR$^5$), —D'(Q), —D(aryloxy), —D(aryl), —D(heteroaryl), —D((C$_3$–C$_{10}$)cycloalkyl), —D(NR$^5$SO$_2$R$^5$), —D(CON(R$^5$)$_2$), —D(CO$_2$R$^5$), —D(S(O)$_q$R$^5$), —D(NR$^5$CON(R$^5$)$_2$), —D(NR$^5$(CO)R$^5$), —D(NR$^5$CO$_2$R$^5$), —D(COR$^5$) or —(NR$^5$)$_k$—D—Q radical;

R$^4$ is a (C$_1$–C$_8$)alkyl, (C$_3$–C$_{10}$)cycloalkyl, —Z((C$_1$–C$_8$)alkoxy), —Z(aryloxy), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$), —Z(S(O)$_p$R$^5$) or —Z(Q) radical;

X is a (C$_1$–C$_8$)alkyl, (C$_3$–C$_{10}$)cycloalkyl, —(NR$^5$)$_k$((C$_1$–C$_8$)alkyl)(C$_1$–C$_8$)alkoxy, —(NR$^5$)$_k$((C$_1$–C$_8$)alkyl)aryloxy, —(NR$^5$)((C$_1$–C$_8$)alkyl)$_k$S(O)$_p$R$^5$, —(NR$^5$)$_k$((C$_1$–C$_8$)alkyl)S(O)$_p$R$^5$, —(NR$^5$)D(C$_1$–C$_8$)alkoxy, —(NR$^5$)(CH$_2$)$_m$((C$_3$–C$_{10}$)cycloalkyl)$_k$(CH$_2$)(C$_1$–C$_8$)alkoxy, —(NR$^5$)$_k$(CH$_2$)((C$_3$–C$_{10}$)cycloalkyl)$_k$(CH$_2$)$_m$(C$_1$–C$_8$)alkoxy, —(NR$^5$)$_k$(CH$_2$)$_m$((C$_3$–C$_{10}$)cycloalkyl)(CH$_2$)$_m$(C$_1$–C$_8$)alkoxy, —(NR$^5$)(CH$_2$)$_m$((C$_3$–C$_{10}$)cycloalkyl)$_k$(CH$_2$)aryloxy, —(NR$^5$)$_k$(CH$_2$)((C$_3$–C$_{10}$)cycloalkyl)$_k$(CH$_2$)$_m$aryloxy, —(NR$^5$)$_k$(CH$_2$)$_m$((C$_3$–C$_{10}$)cycloalkyl)(CH$_2$)$_m$aryloxy, —Z(S(O)$_q$R$^5$), —Z(aryl), —Z(heteroaryl), —Z((C$_3$–C$_{10}$)cycloalkyl), —Z(NR$^5$SO$_2$R$^5$), —Z(CON(R$^5$)$_2$), —Z(CO$_2$R$^5$), —Z(N(R$^5$)$_2$), —Z(NR$^5$CON(R$^5$)$_2$), —Z(NR$^5$(CO)R$^5$), —Z(NR$^5$CO$_2$R$^5$), —Z(COR$^5$) or —Z(Q) radical;

Q and Q' are each independently a 4-membered to 10-membered heterocyclyl or heteroaryl radical;

each R$^5$ is independently a hydrogen, —OH, (C$_1$–C$_8$) alkoxy, aryl, —NH$_2$, —NH((C$_1$–C$_8$)alkyl), —N((C$_1$–C$_8$)alkyl)$_2$, (C$_1$–C$_8$)alkyl or (C$_3$–C$_{10}$) cycloalkyl radical;

D is —(CH$_2$)$_m$((C$_3$–C$_{10}$)cycloalkyl)$_k$(CH$_2$)$_m$— and D' is -((C$_1$–C$_8$)alkyl)$_k$-;

Z is D(NR$^5$)$_k$, D'(NR$^5$)$_k$, (NR$^5$)$_k$D or (NR$^5$)$_k$D';

each k is independently 0 or 1;

each m is independently an integer between 0 and 6;

each p is independently an integer between 0 and 2; and each q is independently 1 or 2; and wherein each alkyl, aryl, heteroaryl, cycloalkyl, Q, alkoxy or aryloxy moiety of any of X, R$^1$, R$^2$, R$^3$, R$^4$ and R$^5$ is optionally substituted with 1–3 radicals of halo and 1–2 radicals of —CF$_3$, —OCF$_3$, —Z(COOH), —Z(OH), —Z(NO$_2$), —Z(SH), -(C$_1$–C$_8$)alkyl, -(C$_1$–C$_8$)acyloxy, -(C$_3$–C$_{10}$)cycloalkyl, —S-((C$_1$–C$_8$)alkyl)$_k$-aryl, -((C$_1$–C$_8$)alkyl)$_k$—SO$_2$NH-aryl, —S-(C$_1$–C$_8$)alkyl, —Z((C$_1$–C$_8$)alkoxy), —Z(aryloxy), —Z(aryl), —Z(heteroaryl), —Z((C$_3$–C$_{10}$)cycloalkyl), —Z(NR$^9$SO$_2$R$^9$), —Z(CON(R$^9$)$_2$), —Z(CO$_2$R$^9$), —Z(N(R$^9$)$_2$), —Z(NR$^9$CON(R$^9$)$_2$), —Z(NR$^9$(CO)R$^9$), —Z(NR$^9$CO$_2$R$^9$), —Z(COR$^9$), —Z(S(O)$_p$R$^9$) or —Z(Q'), wherein such aryl, heteroaryl, cycloalkyl and Q' substituents are optionally substituted with one or more radicals of halo, —NO$_2$, —CF$_3$, —OCF$_3$, —N(R$^9$)$_2$, —C(O)R$^9$, —CO$_2$R$^9$, —OR$^9$, —SR$^9$ or ($C_1$–$C_8$)alkyl; and wherein each $R^9$ is independently a hydrogen or ($C_1$–$C_8$)alkyl radical;

or a pharmaceutically acceptable salt, ester, solvate or N-oxide thereof.

17. The method of claim 16, wherein A is N—H or N—$R^4$;

$R^1$ is a hydrogen, halo, —OH, —$NO_2$, —NHOH, —$CF_3$, —$OCF_3$, ($C_1$–$C_8$)alkyl, ($C_3$–$C_{10}$)cycloalkyl, —Z(($C_1$–$C_8$)alkoxy), —Z(aryloxy), —Z(aryl), —Z(heteroaryl), —Z(($C_3$–$C_{10}$)cycloalkyl), —Z($NR^5SO_2R^5$), —Z($CON(R^5)_2$), —Z($CO_2R^5$), —Z($N(R^5)_2$), —Z($NR^5CON(R^5)_2$), —Z($NR^5(CO)R^5$), —Z($NR^5CO_2R^5$), —Z($COR^5$), —Z($S(O)_pR^5$) or —Z(Q) radical;

$R^2$ is a hydrogen, halo, —OH, —$NO_2$, —$CF_3$, —$OCF_3$, ($C_1$–$C_8$)alkyl, ($C_3$–$C_{10}$)cycloalkyl, —Z(($C_1$–$C_8$) alkoxy), —Z(aryloxy), —Z(aryl), —Z(heteroaryl), —Z(($C_3$–$C_{10}$)cycloalkyl), —Z($NR^5SO_2R^5$), —Z(CON($R^5$)$_2$), —Z($N(R^5)_2$), —Z($NR^5(CO)R^5$), —Z($NR^5(CO)R^5$), —Z($NR^5CO_2R^5$), —Z($S(O)_pR^5$) or —Z(Q) radical, provided that $R^2$ is not an optionally substituted aryl or heteroaryl radical;

$R^3$ is a ($C_3$–$C_{10}$)cycloalkyl, ($C_3$–$C_8$)alkyl, -(($C_1$–$C_8$)alkyl)OH, ($C_1$–$C_8$)alkoxy-($C_1$–$C_8$)alkyl-, -(($C_1$–$C_8$)alkyl)N($R^5$)$_2$, —(($C_1$–$C_8$)alkyl)S(O)$_p$(($C_1$–$C_8$)alkyl), —($CH_2$)(($C_3$–$C_{10}$)cycloalkyl)$_k$($CH_2$)$_m$OH, —($CH_2$)$_m$ (($C_3$–$C_{10}$)cycloalkyl)($CH_2$)$_m$OH, —($CH_2$)$_m$(($C_3$–$C_{10}$)cycloalkyl)($CH_2$)OH, —($CH_2$)(($C_3$–$C_{10}$)cycloalkyl)$_k$($CH_2$)$_m$($C_1$–$C_8$)alkoxy, —($CH_2$)$_m$(($C_3$–$C_{10}$)cycloalkyl)($CH_2$)$_m$($C_1$–$C_8$)alkoxy, —($CH_2$)$_m$(($C_3$–$C_{10}$)cycloalkyl)$_k$($CH_2$)($C_1$–$C_8$)alkoxy, —($CH_2$)(($C_3$–$C_{10}$)cycloalkyl)$_k$($CH_2$)$_m$N($R^5$)$_2$, —($CH_2$)$_m$(($C_3$–$C_{10}$)cycloalkyl)($CH_2$)$_m$N($R^5$)$_2$, —($CH_2$)$_m$(($C_3$–$C_{10}$)cycloalkyl)$_k$($CH_2$)N($R^5$)$_2$, —($CH_2$)$_m$(($C_3$–$C_{10}$)cycloalkyl)($CH_2$)$_m$S(O)$_p R^5$, —D'(S(O)$_q R^5$), —D'(aryloxy), —D'(aryl), —D'(heteroaryl), —D'(($C_3$–$C_{10}$)cycloalkyl), —D'($NR^5SO_2R^5$), —D'($CON(R^5)_2$), —D'($NR^5CON(R^5)_2$), —D'($NR^5(CO)R^5$), —D'($NR^5CO_2R^5$), —D'(Q), —D(aryloxy), —D(aryl), —D(heteroaryl), —D(($C_3$–$C_{10}$)cycloalkyl), —D($NR^5SO_2R^5$), —D(CON($R^5$)$_2$), —D(S(O)$_q R^5$), —D($NR^5CON(R^5)_2$), —D($NR^5(CO)R^5$), —D($NR^5CO_2R^5$), or —($NR^5$)$_k$—D—Q radical;

$R^4$ is a ($C_1$–$C_8$)alkyl, ($C_3$–$C_{10}$)cycloalkyl, —Z(($C_1$–$C_8$)alkoxy), —Z(aryloxy), —Z(aryl), —Z(heteroaryl), —Z(($C_3$–$C_{10}$)cycloalkyl), —Z($NR^5SO_2R^5$), —Z(CON($R^5$)$_2$), —Z($CO_2R^5$), —Z($N(R^5)_2$), —Z($NR^5CON(R^5)_2$), —Z($NR^5(CO)R^5$), —Z($NR^5CO_2R^5$), —Z($COR^5$), —Z($S(O)_p R^5$) or —Z(Q) radical;

X is a —($NR^5$)$_k$(($C_1$–$C_8$)alkyl)($C_1$–$C_8$)alkoxy, —($NR^5$)$_k$ (($C_1$–$C_8$)alkyl)aryloxy, —($NR^5$)(($C_1$–$C_8$)alkyl)$_k$ S(O)$_p R^5$, —($NR^5$)$_k$(($C_1$–$C_8$)alkyl)S(O)$_p R^5$, —($NR^5$)D ($C_1$–$C_8$)alkoxy, —($NR^5$)($CH_2$)$_m$(($C_3$–$C_{10}$)cycloalkyl)$_k$ ($CH_2$)($C_1$–$C_8$)alkoxy, —($NR^5$)$_k$($CH_2$)(($C_3$–$C_{10}$) cycloalkyl)$_k$($CH_2$)$_m$($C_1$–$C_8$)alkoxy, —($NR^5$)$_k$($CH_2$)$_m$ (($C_3$–$C_{10}$)cycloalkyl)($CH_2$)$_m$($C_1$–$C_8$)alkoxy, —($NR^5$) ($CH_2$)$_m$(($C_3$–$C_{10}$)cycloalkyl)$_k$($CH_2$)aryloxy, —($NR^5$)$_k$ ($CH_2$)(($C_3$–$C_{10}$)cycloalkyl)$_k$($CH_2$)$_m$aryloxy, —($NR^5$)$_k$ ($CH_2$)$_m$(($C_3$–$C_{10}$)cycloalkyl)($CH_2$)$_m$aryloxy, —Z(S(O)$_q R^5$), —Z(aryl), —Z(heteroaryl), —Z(($C_3$–$C_{10}$)cycloalkyl), —Z($NR^5SO_2R^5$), —Z(CON ($R^5$)$_2$), —Z($CO_2R^5$), —Z($N(R^5)_2$), —Z($NR^5CON(R^5)_2$), —Z($NR^5(CO)R^5$), —Z($NR^5CO_2R^5$), —Z($COR^5$) or —Z(Q) radical; and Q and Q' are each independently a 4-membered to 10-membered heterocyclyl or heteroaryl radical;

each $R^5$ is independently a hydrogen, —OH, ($C_1$–$C_8$) alkoxy, aryl, —$NH_2$, —NH(($C_1$–$C_8$)alkyl), —N(($C_1$–$C_8$)alkyl)$_2$, ($C_1$–$C_8$)alkyl or ($C_3$–$C_{10}$) cycloalkyl radical;

D is —($CH_2$)$_m$(($C_3$–$C_{10}$)cycloalkyl)$_k$($CH_2$)$_m$— and D' is -(($C_1$–$C_8$)alkyl)$_k$-;

Z is D($NR^5$)$_k$, D'($NR^5$)$_k$, ($NR^5$)$_k$D or ($NR^5$)$_k$D';

each k is independently 0 or 1;

each m is independently an integer between 0 and 6;

each p is independently an integer between 0 and 2; and each q is independently 1 or 2; and wherein each alkyl, aryl, heteroaryl, cycloalkyl, Q, alkoxy or aryloxy moiety of any of X, $R^1$, $R^2$, $R^3$, $R^4$ and $R^5$ is optionally substituted with 1–3 radicals of halo and 1–2 radicals of —$CF_3$, —$OCF_3$, —Z(COOH), —Z(OH), —Z($NO_2$), —Z(SH), -($C_1$–$C_8$)alkyl, -($C_1$–$C_8$)acyloxy, -($C_3$–$C_{10}$)cycloalkyl, —S-(($C_1$–$C_8$) alkyl)$_k$-aryl, -(($C_1$–$C_8$)alkyl)$_k$SO$_2$NH-aryl, —S-($C_1$–$C_8$)alkyl, —Z(($C_1$–$C_8$)alkoxy), —Z(aryloxy), —Z(aryl), —Z(heteroaryl), —Z(($C_3$–$C_{10}$)cycloalkyl), —Z($NR^9SO_2R^9$), —Z($CON(R^9)_2$), —Z($CO_2R^9$), —Z($N(R^9)_2$), —Z($NR^9CON(R^9)_2$), —Z($NR^9(CO)R^9$), —Z($NR^9CO_2R^9$), —Z($COR^9$), —Z($S(O)_p R^9$) or —Z(Q'), wherein such aryl, heteroaryl, cycloalkyl and Q' substitutents are optionally substituted with 1–3 radicals of halo, —$NO_2$, —$CF_3$, —$OCF_3$, —$N(R^9)_2$, —C(O)$R^9$, —$CO_2R^9$, —$OR^9$, —$SR^9$ or ($C_1$–$C_8$)alkyl; and wherein each $R^9$ is independently a hydrogen or ($C_1$–$C_8$)alkyl radical;

or a pharmaceutically acceptable salt, ester, solvate or N-oxide thereof.

18. The method of claim 17, wherein A is N—H or N—$R^4$;

$R^1$ is a hydrogen, halo, —OH, —$NO_2$, —NHOH, —$CF_3$, —$OCF_3$, ($C_1$–$C_8$)alkyl, ($C_3$–$C_6$)cycloalkyl, —Z(($C_1$–$C_8$)alkoxy), —Z(($C_3$–$C_6$)cycloalkyl), —Z($NR^{10}SO_2R^5$), —Z($N(R^5)_2$) or —Z(Q) radical;

$R^2$ is a hydrogen, halo, —OH, —$NO_2$, —$CF_3$, —$OCF_3$, ($C_1$–$C_8$)alkyl, ($C_3$–$C_{10}$)cycloalkyl, —Z(($C_1$–$C_8$) alkoxy), —Z(aryloxy), —Z(aryl), —Z(heteroaryl), —Z(($C_3$–$C_{10}$)cycloalkyl), —Z($NR^{10}SO_2R^5$), —Z(CON($R^5$)$_2$), —Z($N(R^5)_2$), —Z($NR^{10}CON(R^5)_2$), —Z($NR^{10}(CO)R^5$), —Z($NR^{10}CO_2R^5$), —Z($S(O)_p R^5$) or —Z(Q) radical, provided that $R^2$ is not an optionally substituted aryl or heteroaryl radical;

$R^3$ is a ($C_3$–$C_{10}$)cycloalkyl, ($C_3$–$C_8$)alkyl, —(($C_1$–$C_8$) alkyl)OH, ($C_1$–$C_8$)alkoxy-($C_1$–$C_8$) alkyl-, -(($C_1$–$C_8$) alkyl)N($R^5$)$_2$, —(($C_1$–$C_8$)alkyl)S(O)$_p$(($C_1$–$C_8$)alkyl), —($CH_2$)(($C_3$–$C_{10}$)cycloalkyl)$_k$($CH_2$)$_m$OH, —($CH_2$)$_m$ (($C_3$–$C_{10}$)cycloalkyl)($CH_2$)$_m$OH, —($CH_2$)$_m$(($C_3$–$C_{10}$) cycloalkyl)$_k$($CH_2$)OH, —($CH_2$)(($C_3$–$C_{10}$)cycloalkyl)$_k$ ($CH_2$)$_m$($C_1$–$C_8$)alkoxy, —($CH_2$)$_m$(($C_3$–$C_{10}$)cycloalkyl) ($CH_2$)$_m$($C_1$–$C_8$)alkoxy, —($CH_2$)$_m$(($C_3$–$C_{10}$)cycloalkyl)$_k$($CH_2$)($C_1$–$C_8$)alkoxy, —($CH_2$)(($C_3$–$C_{10}$) cycloalkyl)$_k$($CH_2$)$_m$N($R^5$)$_2$, —($CH_2$)$_m$(($C_3$–$C_{10}$) cycloalkyl)($CH_2$)$_m$N($R^5$)$_2$, —($CH_2$)$_m$(($C_3$–$C_{10}$) cycloalkyl)$_k$($CH_2$) N($R^5$)$_2$, —($CH_2$)$_m$(($C_3$–$C_{10}$)cycloalkyl)($CH_2$)$_m$S(O)$_p R^5$, —($CH_2$)$_m$(($C_3$–$C_{10}$)cycloalkyl)($CH_2$)$_m$($CO_2R^5$), —($CH_2$)$_m$(($C_3$–$C_{10}$)cycloalkyl)($CH_2$)$_m$($COR^5$), —(($C_1$–$C_8$)alkyl)($CO_2R^5$), —(($C_1$–$C_8$)alkyl)($COR^5$), —D'(S(O)$_q R^5$), —D'(aryloxy), —D'(aryl), —D'(heteroaryl), —D'(($C_3$–$C_{10}$)cycloalkyl), —D'($NR^{10}SO_2R^5$), —D'(CON($R^5$)$_2$), —D'($NR^{10}CON(R^5)_2$), —D'($NR^{10}(CO)R^5$), —D'($NR^{10}CO_2R^5$), —D'(Q), —D(aryloxy), —D(aryl), —D(heteroaryl), —D(($C_3$–$C_{10}$))cycloalkyl), —D($NR^{10}SO_2R^5$), —D(CON($R^5$)$_2$), —D(S(O)$_qR^5$), —D($NR^{10}$CON($R^5$)$_2$), —D($NR^{10}$(CO)$R^5$), —D($NR^{10}CO_2R^5$) or —($NR^{10}$)$_k$—D—Q radical;

$R^4$ is a ($C_1$–$C_4$)alkyl, ($C_3$–$C_6$)cycloalkyl, —N($R^5$)$_2$ or —Z(Q) radical;

X is a —($NR^{10}$)(($C_1$–$C_8$)alkyl)($C_1$–$C_8$)alkoxy, —($NR^{10}$)(($C_1$–$C_8$)alkyl)aryloxy, —($NR^{10}$)S(O)$_pR^5$, —($NR^{10}$)(($C_1$–$C_8$)alkyl)S(O)$_pR^5$, —($NR^{10}$)D($C_1$–$C_8$)alkoxy, —($NR^{10}$)($CH_2$)$_m$(($C_3$–$C_{10}$)cycloalkyl)$_k$($CH_2$)($C_1$–$C_8$) alkoxy, —($NR^{10}$)($CH_2$)$_m$(($C_3$–$C_{10}$)cycloalkyl)$_k$($CH_2$)$_m$ ($C_1$–$C_8$)alkoxy, —($NR^{10}$)($CH_2$)$_m$(($C_3$–$C_{10}$)cycloalkyl) ($CH_2$)$_m$($C_1$–$C_8$)alkoxy, —($NR^{10}$)($CH_2$)$_m$(($C_3$–$C_{10}$)cycloalkyl)$_k$($CH_2$)$_m$aryloxy, —($NR^{10}$)($CH_2$)(($C_3$–$C_{10}$)cycloalkyl)$_k$($CH_2$)$_m$aryloxy, —($NR^{10}$)($CH_2$)$_m$(($C_3$–$C_{10}$)cycloalkyl)($CH_2$)$_m$aryloxy, —($NR^{10}$)D(S(O)$_qR^5$), —($NR^{10}$)D'(S(O)$_qR^5$), —($NR^{10}$)D(aryl), —($NR^{10}$)D' (aryl), —($NR^{10}$)D(heteroaryl), —($NR^{10}$)D' (heteroaryl), —($NR^{10}$)D(($C_3$–$C_{10}$)cycloalkyl), —($NR^{10}$)D'(($C_3$–$C_{10}$)cycloalkyl), —($NR^{10}$)D ($NR^{10}SO_2R^5$), —($NR^{10}$)D'($NR^{10}SO_2R^5$), —($NR^{10}$)D (CON($R^5$)$_2$), —($NR^{10}$)D'(CON($R^5$)$_2$), —($NR^{10}$)D ($CO_2R^5$), —($NR^{10}$)D'($CO_2R^5$), —($NR^{10}$)D(N($R^5$)$_2$), —N($R^5$)$_2$, —($NR^{10}$)D'(N($R^5$)$_2$), —($NR^{10}$)D ($NR^{10}$CON($R^5$)$_2$), —($NR^{10}$)D'($NR^{10}$CON($R^5$)$_2$), —($NR^{10}$)D($NR^{10}$(CO)$R^5$), —($NR^{10}$)D'($NR^{10}$(CO)$R^5$), —($NR^{10}$)D($NR^{10}CO_2R^5$), —($NR^{10}$)D'($NR^{10}CO_2R^5$), —($NR^{10}$)D(COR$^5$), —($NR^{10}$)D'(COR$^5$), —($NR^{10}$)D—Q, —($NR^{10}$)D'—Q or Q radical;

wherein each $R^{10}$ is independently a hydrogen or ($C_1$–$C_4$) alkyl radical;

each Q and Q' are each independently a 4-membered to 10-membered heterocyclyl or heteroaryl radical;

each $R^5$ is independently a hydrogen, —OH, ($C_1$–$C_4$) alkoxy, —$NH_2$, —NH(($C_1$–$C_4$)alkyl), —N(($C_1$–$C_4$)alkyl)$_2$, ($C_1$–$C_4$)alkyl or ($C_3$–$C_6$)cycloalkyl radical;

D is —($CH_2$)$_m$(($C_3$–$C_{10}$)cycloalkyl)$_k$($CH_2$)$_m$— and D' is -(($C_1$–$C_8$)alkyl)$_k$-;

Z is D($NR^{10}$)$_k$, D'($NR^{10}$)$_k$, ($NR^{10}$)$_k$D or ($NR^{10}$)$_k$D';

each k is independently 0 or 1;

each m is independently an integer between 0 and 4;

each p is independently an integer between 0 and 2; and each q is independently 1 or 2; and wherein each aryl, heteroaryl, cycloalkyl, Q or aryloxy moiety of any of X, $R^1$, $R^2$, $R^3$, $R^4$ and $R^5$ is optionally substituted with 1–3 radicals of halo and 1–2 radicals of —$CF_3$, —$OCF_3$, —$OR^9$, —$SR^9$, —$NO_2$, -($C_1$–$C_4$)alkyl, -($C_1$–$C_4$)acyloxy, -($C_3$–$C_6$)cycloalkyl, —S-(($C_1$–$C_4$)alkyl)$_k$-aryl, -(($C_1$–$C_4$)alkyl)$_k$—$SO_2$NH-aryl, aryloxy, aryl, —$NR^9SO_2R^9$, —CON($R^9$)$_2$, —$CO_2R^9$, —N($R^9$)$_2$, —$NR^9$CON($R^9$)$_2$, —$NR^9$(CO)$R^9$, —$NR^9CO_2R^9$, —COR$^9$, —S(O)$_2$($C_1$–$C_4$)alkyl or Q', wherein such aryl, heteroaryl, cycloalkyl and Q' substituents are optionally substituted with 1–2 radicals of halo, —$NO_2$, —$CF_3$, —$OCF_3$, —N($R^9$)$_2$, —C(O)$R^9$, —$CO_2R^9$, —$OR^9$, —$SR^9$ or ($C_1$–$C_4$)alkyl; and wherein each $R^9$ is independently a hydrogen or ($C_1$–$C_4$)alkyl radical; and provided that the total number of aryl, heteroaryl, cycloalkyl, heterocyclyl, Q and Q' moieties in A, X, $R^1$, $R^2$ and $R^3$ is 0–3;

or a pharmaceutically acceptable salt, ester, solvate or N-oxide thereof.

19. The method of claim 18, wherein A is N—H or N—$R^4$;

$R^1$ is a hydrogen, halo, —OH, —$NO_2$, —NHOH, —$CF_3$, —$OCF_3$, ($C_1$–$C_4$)alkyl, ($C_1$–$C_4$)alkoxy, —($NR^{10}$)$_k$ (($C_1$–$C_2$)alkyl)$_k$-cyclopropyl or —($NR^{10}$)$_k$(($C_1$–$C_2$)alkyl)$_k$—N($R^{10}$)$_2$ radical;

$R^2$ is a hydrogen, chloro, fluoro, —$CF_3$, —$OCF_3$, ($C_1$–$C_4$) alkyl, ($C_3$–$C_6$)cycloalkyl, —($NR^{10}$)$_k$(($C_1$–$C_2$)alkyl)$_k$-($C_1$–$C_4$)alkoxy), —($NR^{10}$)$_k$(($C_1$–$C_2$)alkyl)$_k$—(CON ($R^5$)$_2$), —($NR^{10}$)$_k$(($C_1$–$C_2$)alkyl)$_k$—(N($R^5$)$_2$), —($NR^{10}$)$_k$(($C_1$–$C_2$)alkyl)$_k$—(S(O)$_pR^5$) or —($NR^{10}$)$_k$ (($C_1$–$C_2$)alkyl)$_k$—Q radical;

$R^3$ is a ($C_3$–$C_6$)cycloalkyl, ($C_3$–$C_6$)alkyl, -(($C_1$–$C_4$)alkyl) OH, ($C_1$–$C_4$)alkoxy-($C_1$–$C_4$)alkyl-, -(($C_1$–$C_4$)alkyl)N ($R^5$)$_2$, —($CH_2$)(($C_3$–$C_6$)cycloalkyl)$_k$($CH_2$)$_m$OH, —($CH_2$)$_m$(($C_3$–$C_6$)cycloalkyl)($CH_2$)$_m$OH, —($CH_2$)$_m$ (($C_3$–$C_6$)cycloalkyl)$_k$($CH_2$)OH, —($CH_2$)(($C_3$–$C_6$) cycloalkyl)$_k$($CH_2$)$_m$($C_1$–$C_4$)alkoxy, —($CH_2$)$_m$(($C_3$–$C_6$) cycloalkyl)($CH_2$)$_m$($C_1$–$C_4$)alkoxy, —($CH_2$)$_m$(($C_3$–$C_6$) cycloalkyl)$_k$($CH_2$)($C_1$–$C_4$)alkoxy, —($CH_2$)(($C_3$–$C_6$) cycloalkyl)$_k$($CH_2$)$_m$N($R^5$)$_2$, —($CH_2$)$_m$(($C_3$–$C_6$) cycloalkyl)($CH_2$)$_m$N($R^5$)$_2$, —($CH_2$)$_m$(($C_3$–$C_6$) cycloalkyl)$_k$($CH_2$)N($R^5$)$_2$, —($CH_2$)$_m$(($C_3$–$C_6$) cycloalkyl)($CH_2$)$_m$S(O)$_pR^5$, —($CH_2$)$_m$(($C_3$–$C_6$) cycloalkyl)($CH_2$)$_m$($CO_2R^5$), —($CH_2$)$_m$(($C_3$–$C_6$) cycloalkyl)($CH_2$)$_m$(COR$^5$), —D'(S(O)$_qR^5$), —D' (aryloxy), —D'(aryl), —D'(heteroaryl), —D'(($C_3$–$C_{10}$) cycloalkyl), —D'(Q), —D(aryloxy), —D(aryl), —D(heteroaryl), —D($NR^{10}SO_2R^5$), —D(CON($R^5$)$_2$), —D(S(O)$_qR^5$), —D($NR^{10}$CON($R^5$)$_2$), —D($NR^{10}$(CO) $R^5$), —D($NR^{10}CO_2R^5$) or —($NR^{10}$)$_k$—D—Q radical:

X is a —(N(($C_1$–$C_4$)alkyl))-(($C_1$–$C_4$)alkyl)aryloxy, —(N (($C_1$–$C_4$)alkyl))—($CH_2$)$_m$($C_3$–$C_6$)cycloalkyl)$_k$($CH_2$) ($C_1$–$C_4$)alkoxy, —(N(($C_1$–$C_4$)alkyl))—($CH_2$)(($C_3$–$C_6$) cycloalkyl)$_k$($CH_2$)$_m$(($C_1$–$C_4$)alkoxy, —(N(($C_1$–$C_4$) alkyl))—($CH_2$)$_m$(($C_3$–$C_6$)cycloalkyl)($CH_2$)$_m$($C_1$–$C_4$) alkoxy, —(N(($C_1$–$C_4$)alkyl))—($CH_2$)$_m$($C_3$–$C_6$) cycloalkyl)$_k$($CH_2$)aryloxy, —(N(($C_1$–$C_4$)alkyl))—($CH_2$)(($C_3$–$C_6$)cycloalkyl)$_k$($CH_2$)$_m$aryloxy, —(N (($C_1$–$C_4$)alkyl))—($CH_2$)$_m$(($C_3$–$C_6$)cycloalkyl) ($CH_2$)$_m$aryloxy, —(N(($C_1$–$C_4$)alkyl))-D(aryl), —(N (($C_1$–$C_4$)alkyl))-D'(aryl), —(N(($C_1$–$C_4$)alkyl))-D (heteroaryl), —(N(($C_1$–$C_4$)alkyl))-D'(heteroaryl), —(N (($C_1$–$C_4$)alkyl))-D($NR^{10}SO_2R^5$), —(N(($C_1$–$C_4$)alkyl))-D(CON($R^5$)$_2$), —(N(($C_1$–$C_4$)alkyl))-D($CO_2R^5$), —(N (($C_1$–$C_4$)alkyl))-D(N($R^5$)$_2$), —N($R^5$)$_2$, —(N(($C_1$–$C_4$) alkyl))-D($NR^{10}$CON($R^5$)$_2$), —(N(($C_1$–$C_4$)alkyl))-D ($NR^{10}$(CO)$R^5$), —(N(($C_1$–$C_4$)alkyl))-D($NR^{10}CO_2R^5$), —(N(($C_1$–$C_4$)alkyl))-D(COR$^5$), —(N(($C_1$–$C_4$)alkyl))-D—Q, —(N(($C_1$–$C_4$)alkyl))-D'—Q or Q radical;

wherein each $R^{10}$ is independently a hydrogen or ($C_1$–$C_4$) alkyl radical;

each Q is independently a 4-membered to 10-membered heterocyclyl or heteroaryl radical;

each $R^5$ is independently a hydrogen, —OH, ($C_1$–$C_4$) alkoxy, —$NH_2$, —NH(($C_1$–$C_4$)alkyl), —N(($C_1$–$C_4$) alkyl)$_2$ or ($C_1$–$C_4$)alkyl radical;

D is —($CH_2$)$_m$(($C_3$–$C_6$)cycloalkyl)$_k$($CH_2$)$_m$— and D' is -(($C_1$–$C_4$)alkyl)$_k$-;

Z is ($NR^{10}$)$_k$D or ($NR^{10}$)$_k$D';

each k is independently 0 or 1;

each m is independently an integer between 0 and 3;

each p is independently an integer between 0 and 2; and each q is independently 1 or 2; and wherein each aryl, heteroaryl, cycloalkyl, Q or aryloxy moiety of any of X, $R^2$ and $R^3$ is optionally substituted with 1–2 radicals of halo, —$CF_3$, —$OCF_3$, —$OR^9$, —$SR^9$, —$NO_2$, ($C_1$–$C_4$)alkyl, ($C_1$–$C_4$)acyloxy, —$NR^9SO_2R^9$, —$CON(R^9)_2$, —$CO_2R^9$, —$N(R^9)_2$, —$NR^9CON(R^9)_2$, —$NR^9(CO)R^9$, —$NR^9CO_2R^9$, —$COR^9$ or —$S(O)_2$($C_1$–$C_4$)alkyl; and wherein each $R^9$ is independently a hydrogen or ($C_1$–$C_4$)alkyl radical; and provided that the total number of aryl, heteroaryl, cycloalkyl, heterocyclyl and Q moieties in A, X, $R^1$, $R^2$ and $R^3$ is 1–3;

or a pharmaceutically acceptable salt, ester, solvate or N-oxide thereof.

20. The method of claim 19, wherein A is N—H;

$R^1$ is a bromo, chloro, fluoro, —OH, —$NO_2$, —NHOH, —$CF_3$, —$OCF_3$, ($C_1$–$C_2$)alkyl, ($C_1$–$C_2$)alkoxy, —$(NR^{10})_k$(($C_1$–$C_2$)alkyl)$_k$-cyclopropyl, —$NH_2$ or —NH(($C_1$–$C_2$)alkyl) radical;

$R^2$ is a hydrogen, chloro, fluoro, —$CF_3$, —$OCF_3$, ($C_1$–$C_2$) alkyl or ($C_1$–$C_2$)alkoxy radical;

$R^3$ is a ($C_3$–$C_6$)cycloalkyl, ($C_3$–$C_6$)alkyl, -(($C_1$–$C_4$)alkyl)OH, ($C_1$–$C_4$)alkoxy-($C_1$–$C_4$)alkyl-, -(($C_1$–$C_4$)alkyl)N($R^5$)$_2$, —$(CH_2)$(($C_5$–$C_6$)cycloalkyl)$_k$($CH_2$)$_m$OH, —$(CH_2)_m$(($C_5$–$C_6$)cycloalkyl)($CH_2$)$_m$OH, —$(CH_2)_m$(($C_5$–$C_6$)cycloalkyl)$_k$($CH_2$)OH, —$(CH_2)$(($C_5$–$C_6$)cycloalkyl)$_k$($CH_2$)$_m$($C_1$–$C_2$)alkoxy, —$(CH_2)_m$(($C_5$–$C_6$)cycloalkyl)($CH_2$)$_m$($C_1$–$C_2$)alkoxy, —$(CH_2)_m$(($C_5$–$C_6$)cycloalkyl)$_k$($CH_2$)($C_1$–$C_2$)alkoxy, —$(CH_2)$(($C_5$–$C_6$)cycloalkyl)$_k$($CH_2$)$_m$N($R^5$)$_2$, —$(CH_2)_m$(($C_5$–$C_6$)cycloalkyl)($CH_2$)$_m$N($R^5$)$_2$, —$(CH_2)_m$(($C_5$–$C_6$)cycloalkyl)$_k$($CH_2$)N($R^5$)$_2$, —$(CH_2)_m$(($C_5$–$C_6$)cycloalkyl)($CH_2$)$_m$S(O)$_p$$R^5$, —$(CH_2)_m$(($C_5$–$C_6$)cycloalkyl)($CH_2$)$_m$(CO$_2$$R^5$), —$(CH_2)_m$(($C_5$–$C_6$)cycloalkyl)($CH_2$)$_m$(COR$^5$), —D'(S(O)$_q$$R^5$), —D'(aryloxy), —D'(aryl), —D'(heteroaryl), —D'(($C_3$–$C_6$)cycloalkyl), —D'(Q), —D(aryloxy), —D(aryl), —D(heteroaryl), —D(NR$^{10}$SO$_2$$R^5$), —D(CON($R^5$)$_2$), —D(S(O)$_q$$R^5$), —D(NR$^{10}$CON($R^5$)$_2$), —D(NR$^{10}$(CO)$R^5$), —D(NR$^{10}$CO$_2$$R^5$) or —(NR$^{10}$)$_k$—D—Q radical;

X is a —N(($C_1$–$C_4$)alkyl)$_2$ or Q radical;

wherein each $R^{10}$ is independently a hydrogen or ($C_1$–$C_2$) alkyl radical; or each Q is independently a 4-membered to 10-membered heterocyclyl or heteroaryl radical;

each $R^5$ is independently a hydrogen, —OH, ($C_1$–$C_2$) alkoxy, —$NH_2$, —NH(($C_1$–$C_2$)alkyl), —N(($C_1$–$C_2$) alkyl)$_2$ or ($C_1$–$C_2$)alkyl radical;

D is —$(CH_2)_m$(($C_5$–$C_6$)cycloalkyl)$_k$($CH_2$)$_m$— and D' is -(($C_1$–$C_4$)alkyl)$_k$-;

Z is (NR$^{10}$)$_k$D or (NR$^{10}$)$_k$D';

each k is independently 0 or 1;

each m is independently an integer between 0 and 2;

each p is independently an integer between 0 and 2; and each q is independently 1 or 2; and wherein each aryl, heteroaryl, cycloalkyl, Q or aryloxy moiety of any of X, $R^2$ and $R^3$ is optionally substituted with 1–2 radicals of halo, —$CF_3$, —$OCF_3$, —$OR^9$, —$SR^9$, —$NO_2$, ($C_1$–$C_4$)alkyl, ($C_1$–$C_4$)acyloxy, —$NR^9SO_2R^9$, —$CON(R^9)_2$, —$CO_2R^9$, —$N(R^9)_2$, —$NR^9CON(R^9)_2$, —$NR^9(CO)R^9$, —$NR^9CO_2R^9$, —$COR^9$ or —$S(O)_2$($C_1$–$C_4$)alkyl; and wherein each $R^9$ is independently a hydrogen or ($C_1$–$C_2$)alkyl radical; and provided that the total number of aryl, heteroaryl, cycloalkyl, heterocyclyl and Q moieties in X, $R^1$, $R^2$ and $R^3$ is 1–2;

or a pharmacuetically acceptable salt, ester, solvate or N-oxide thereof.

* * * * *